United States Patent
Ren et al.

(10) Patent No.: US 8,703,777 B2
(45) Date of Patent: Apr. 22, 2014

(54) CERTAIN CHEMICAL ENTITIES, COMPOSITIONS AND METHODS

(75) Inventors: Pingda Ren, San Diego, CA (US); Yi Liu, San Diego, CA (US); Troy Edward Wilson, San Marino, CA (US); Katrina Chan, San Diego, CA (US); Christian Rommel, La Jolla, CA (US); Liansheng Li, San Diego, CA (US)

(73) Assignee: Intellikine LLC, La Jolla, CA (US)

( * ) Notice: Subject to any disclaimer, the term of this patent is extended or adjusted under 35 U.S.C. 154(b) by 446 days.

(21) Appl. No.: 12/811,695

(22) PCT Filed: Jan. 5, 2009

(86) PCT No.: PCT/US2009/000042
§ 371 (c)(1),
(2), (4) Date: Nov. 11, 2010

(87) PCT Pub. No.: WO2009/088990
PCT Pub. Date: Jul. 16, 2009

(65) Prior Publication Data
US 2011/0046165 A1    Feb. 24, 2011

Related U.S. Application Data

(63) Continuation-in-part of application No. PCT/US2009/000038, filed on Jan. 5, 2009.

(60) Provisional application No. 61/009,971, filed on Jan. 4, 2008, provisional application No. 61/194,294, filed on Sep. 26, 2008, provisional application No. 61/201,146, filed on Dec. 5, 2008.

(51) Int. Cl.
| C07D 487/04 | (2006.01) |
| A61K 31/519 | (2006.01) |
| A61K 31/52 | (2006.01) |
| C07D 473/34 | (2006.01) |
| A61P 35/00 | (2006.01) |
| A61P 29/00 | (2006.01) |

(52) U.S. Cl.
USPC ........ 514/262.1; 544/262; 544/277; 544/255; 514/263.22; 514/260.1

(58) Field of Classification Search
USPC ............ 544/262, 255, 118; 514/262.1, 260.1, 514/234.2
See application file for complete search history.

(56) References Cited

U.S. PATENT DOCUMENTS

| 4,547,508 A | 10/1985 | Konz et al. |
| 4,656,159 A | 4/1987 | McPherson et al. |
| 4,704,381 A | 11/1987 | Schaumann et al. |
| 4,795,627 A | 1/1989 | Fisher et al. |
| 5,240,941 A | 8/1993 | Bruneau |
| 5,294,612 A | 3/1994 | Bacon et al. |
| 5,310,731 A | 5/1994 | Olsson et al. |
| 5,364,862 A | 11/1994 | Spada et al. |
| 5,420,419 A | 5/1995 | Wood |
| 5,428,125 A | 6/1995 | Hefner, Jr. et al. |
| 5,442,039 A | 8/1995 | Hefner, Jr. et al. |
| 5,504,103 A | 4/1996 | Bonjouklian et al. |
| 5,506,347 A | 4/1996 | Erion et al. |
| 5,561,134 A | 10/1996 | Spada et al. |
| 5,563,257 A | 10/1996 | Zilch et al. |
| 5,593,997 A | 1/1997 | Dow et al. |
| 5,646,128 A | 7/1997 | Firestein et al. |
| 5,652,366 A | 7/1997 | Spada et al. |
| 5,654,307 A | 8/1997 | Bridges et al. |
| 5,665,721 A | 9/1997 | Bhagwat et al. |
| 5,674,998 A | 10/1997 | Boyer et al. |
| 5,686,455 A | 11/1997 | Adams et al. |
| 5,736,554 A | 4/1998 | Spada et al. |
| 5,747,235 A | 5/1998 | Farid et al. |
| 5,756,711 A | 5/1998 | Zilch et al. |
| 5,763,596 A | 6/1998 | Boyer et al. |

(Continued)

FOREIGN PATENT DOCUMENTS

| CA | 1338379 C | 6/1996 |
| CN | 101602768 A | 12/2009 |

(Continued)

OTHER PUBLICATIONS

Abraham, T. (Journal of Polymer Science, 1982, 20(7), 1953-1957).*
Campora, et al. Binuclear complexes of nickel bridged by hydrocarbon ligands. Isocyanide insertion chemistry and amide formation by intramolecular coupling of acyl and imidoyl functionalities. Organometallics. Jan. 1992; 11(1): 11-13.
Campora, et al. Isocyanide insertion chemistry. Synthesis and structural characterization of bridging imidoyl complexes of nichel and amide formation by intramolecular coupling of acyl and imidoyl functionalities. Organometallics. Oct. 1993;12(10):4025-31.

(Continued)

*Primary Examiner* — Susanna Moore
(74) *Attorney, Agent, or Firm* — Jones Day

(57) ABSTRACT

Provided herein are substituted bicyclic compounds, e.g., compounds of Formula IV, methods of their synthesis, pharmaceutical compositions comprising the compounds, and methods of their use. The compounds provided herein are useful for inhibiting phosphatidyl inositol-3 kinase (PI3 kinase), e.g., for the treatment of various diseases and conditions associated with PI3 kinase activity, including but not limited to, cancer, inflammatory disease, immune disease, and respiratory disease.

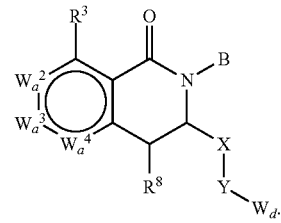

Formula IV

35 Claims, 11 Drawing Sheets

(56) References Cited

U.S. PATENT DOCUMENTS

| | | |
|---|---|---|
| 5,763,597 A | 6/1998 | Ugarkar et al. |
| 5,763,885 A | 6/1998 | Murphy et al. |
| 5,795,977 A | 8/1998 | Ugarkar et al. |
| 5,811,454 A | 9/1998 | Springer |
| 5,824,492 A | 10/1998 | Hiles et al. |
| 5,858,753 A | 1/1999 | Chantry et al. |
| 5,914,488 A | 6/1999 | Sone |
| 5,919,808 A | 7/1999 | Petrie et al. |
| 5,922,753 A | 7/1999 | Petrie et al. |
| 5,948,776 A | 9/1999 | Petrie et al. |
| 5,965,573 A | 10/1999 | Petrie et al. |
| 5,977,061 A | 11/1999 | Holy et al. |
| 5,981,533 A | 11/1999 | Traxler et al. |
| 5,985,589 A | 11/1999 | Chantry et al. |
| 5,990,169 A | 11/1999 | Petrie et al. |
| 5,994,358 A | 11/1999 | Petrie et al. |
| 6,001,839 A | 12/1999 | Calderwood et al. |
| 6,057,305 A | 5/2000 | Holy et al. |
| 6,084,095 A | 7/2000 | Bridges et al. |
| 6,093,737 A | 7/2000 | Anthony et al. |
| 6,127,121 A | 10/2000 | Meyer, Jr. et al. |
| 6,153,631 A | 11/2000 | Petrie et al. |
| 6,191,170 B1 | 2/2001 | Medina |
| 6,251,901 B1 | 6/2001 | Petrie et al. |
| 6,265,410 B1 | 7/2001 | Bridges et al. |
| 6,268,370 B1 | 7/2001 | Adams et al. |
| 6,312,894 B1 | 11/2001 | Hedgpeth et al. |
| 6,323,201 B1 | 11/2001 | Carson et al. |
| 6,342,514 B1 | 1/2002 | Petrie et al. |
| 6,350,741 B1 | 2/2002 | Golec et al. |
| 6,383,790 B1 | 5/2002 | Shokat |
| 6,384,039 B1 | 5/2002 | Fossa |
| 6,387,894 B1 | 5/2002 | Fossa |
| 6,390,821 B1 | 5/2002 | Shokat |
| 6,455,534 B2 | 9/2002 | Bridges et al. |
| 6,472,153 B1 | 10/2002 | Dempcy et al. |
| 6,482,623 B1 | 11/2002 | Vanhaesebroeck et al. |
| 6,485,906 B2 | 11/2002 | Meyer, Jr. et al. |
| 6,492,346 B1 | 12/2002 | Hedgpeth et al. |
| 6,506,769 B2 | 1/2003 | Snow et al. |
| 6,518,277 B1 | 2/2003 | Sadhu et al. |
| 6,521,417 B1 | 2/2003 | Shokat |
| 6,521,620 B1 | 2/2003 | Bridges et al. |
| 6,531,491 B1 | 3/2003 | Kania et al. |
| 6,534,524 B1 | 3/2003 | Kania et al. |
| 6,545,005 B1 | 4/2003 | Baxter et al. |
| 6,552,192 B1 | 4/2003 | Hanus et al. |
| 6,562,819 B2 | 5/2003 | Carson et al. |
| 6,583,161 B1 | 6/2003 | Medina |
| 6,613,798 B1 | 9/2003 | Porter et al. |
| 6,630,495 B1 | 10/2003 | Cooke et al. |
| 6,632,789 B1 | 10/2003 | June |
| 6,645,989 B2 | 11/2003 | Adams et al. |
| 6,649,631 B1 | 11/2003 | Orme et al. |
| 6,653,296 B1 | 11/2003 | Holy et al. |
| 6,653,306 B1 | 11/2003 | Alexander et al. |
| 6,660,744 B1 | 12/2003 | Hirst et al. |
| 6,660,845 B1 | 12/2003 | Gall et al. |
| 6,664,269 B2 | 12/2003 | Martin et al. |
| 6,667,300 B2 | 12/2003 | Sadhu et al. |
| 6,690,583 B1 | 2/2004 | Bergstedt et al. |
| 6,713,484 B2 | 3/2004 | Bridges et al. |
| 6,720,344 B2 | 4/2004 | Kerwin et al. |
| 6,734,187 B1 | 5/2004 | Tanaka et al. |
| 6,770,639 B2 | 8/2004 | Snow et al. |
| 6,777,425 B2 | 8/2004 | Burli et al. |
| 6,777,439 B2 | 8/2004 | Durden |
| 6,790,844 B2 | 9/2004 | Ueno et al. |
| 6,800,620 B2 | 10/2004 | Sadhu et al. |
| 6,849,420 B2 | 2/2005 | Vanhaesebroeck et al. |
| 6,849,713 B2 | 2/2005 | Zhang et al. |
| 6,852,727 B2 | 2/2005 | Goulet et al. |
| 6,906,103 B2 | 6/2005 | Zhang et al. |
| 6,916,949 B2 | 7/2005 | Springer et al. |
| 6,919,332 B2 | 7/2005 | Noe et al. |
| 6,921,763 B2 | 7/2005 | Hirst et al. |
| 6,949,535 B2 | 9/2005 | Sadhu et al. |
| 7,026,461 B1 | 4/2006 | Shokat |
| 7,041,676 B2 | 5/2006 | McDonald et al. |
| 7,049,116 B2 | 5/2006 | Shokat |
| 7,049,312 B1 | 5/2006 | Rafferty et al. |
| 7,064,218 B2 | 6/2006 | Dyatkina et al. |
| 7,071,355 B2 | 7/2006 | Leban et al. |
| 7,115,627 B2 | 10/2006 | Pinto et al. |
| 7,115,653 B2 | 10/2006 | Baxter et al. |
| 7,144,903 B2 | 12/2006 | Collins et al. |
| 7,157,487 B2 | 1/2007 | Nakayama et al. |
| 7,166,293 B2 | 1/2007 | Teng et al. |
| 7,208,601 B2 | 4/2007 | Mjalli et al. |
| 7,217,794 B2 | 5/2007 | Abdel-Meguid et al. |
| 7,235,585 B2 | 6/2007 | Springer et al. |
| 7,244,741 B2 | 7/2007 | Simon et al. |
| 7,247,736 B2 | 7/2007 | Leban et al. |
| 7,262,204 B2 | 8/2007 | Collins et al. |
| 7,265,111 B2 | 9/2007 | Bigot et al. |
| 7,265,131 B2 | 9/2007 | Johnson et al. |
| 7,329,765 B2 | 2/2008 | Burli et al. |
| 7,332,497 B2 | 2/2008 | Hirst et al. |
| 7,348,427 B2 | 3/2008 | Burli et al. |
| 7,365,094 B2 | 4/2008 | Leban et al. |
| 7,384,967 B2 | 6/2008 | Polisetti et al. |
| 7,396,836 B2 | 7/2008 | Harada et al. |
| 7,414,036 B2 | 8/2008 | Sevillano et al. |
| 7,429,596 B2 | 9/2008 | Tanaka et al. |
| 7,439,254 B2 | 10/2008 | Bergnes |
| 7,449,477 B2 | 11/2008 | Barda et al. |
| 7,459,462 B2 | 12/2008 | Simon et al. |
| 7,459,472 B2 | 12/2008 | Mjalli et al. |
| 7,470,721 B2 | 12/2008 | Durden |
| 7,501,538 B2 | 3/2009 | Mjalli et al. |
| 7,534,797 B2 | 5/2009 | Arnold et al. |
| 7,541,373 B2 | 6/2009 | Polisetti et al. |
| 7,569,571 B2 | 8/2009 | Dong et al. |
| 7,572,913 B2 | 8/2009 | McKerracher et al. |
| 7,579,348 B2 | 8/2009 | Wang et al. |
| 7,585,868 B2 | 9/2009 | Knight et al. |
| 7,608,594 B2 | 10/2009 | Blagg et al. |
| 7,615,552 B2 | 11/2009 | Ono et al. |
| 7,622,451 B2 | 11/2009 | Blagg et al. |
| 7,678,803 B2 | 3/2010 | Huang et al. |
| 7,700,607 B2 | 4/2010 | Hu et al. |
| 7,745,485 B2 | 6/2010 | Durden |
| 7,932,260 B2 | 4/2011 | Fowler et al. |
| 8,106,146 B2 | 1/2012 | Benz et al. |
| 8,193,182 B2 | 6/2012 | Ren et al. |
| 2001/0019829 A1 | 9/2001 | Nelson et al. |
| 2001/0027197 A1 | 10/2001 | Bridges et al. |
| 2002/0016460 A1 | 2/2002 | Snow et al. |
| 2002/0016976 A1 | 2/2002 | Shokat |
| 2002/0037856 A1 | 3/2002 | Zhang et al. |
| 2002/0102590 A1 | 8/2002 | Taing et al. |
| 2002/0127625 A1 | 9/2002 | Oxelius |
| 2002/0146690 A1 | 10/2002 | Meyer et al. |
| 2002/0147160 A1 | 10/2002 | Bhat et al. |
| 2002/0156081 A1 | 10/2002 | Hirst et al. |
| 2002/0161014 A1 | 10/2002 | Sadhu et al. |
| 2002/0173524 A1 | 11/2002 | Collins et al. |
| 2003/0001141 A1 | 1/2003 | Sun et al. |
| 2003/0008896 A1 | 1/2003 | Martin et al. |
| 2003/0018022 A1 | 1/2003 | Collins et al. |
| 2003/0022344 A1 | 1/2003 | Williams et al. |
| 2003/0064997 A1 | 4/2003 | Adams et al. |
| 2003/0073218 A1 | 4/2003 | Shokat |
| 2003/0083268 A1 | 5/2003 | Burli et al. |
| 2003/0113765 A1 | 6/2003 | Dempcy et al. |
| 2003/0119479 A1 | 6/2003 | Arima et al. |
| 2003/0119791 A1 | 6/2003 | Kerwin et al. |
| 2003/0139427 A1 | 7/2003 | Castelhano et al. |
| 2003/0143602 A1 | 7/2003 | Meyer et al. |
| 2003/0166929 A1 | 9/2003 | Snow et al. |
| 2003/0180924 A1 | 9/2003 | DeSimone |
| 2003/0186987 A1 | 10/2003 | Bridges et al. |
| 2003/0187001 A1 | 10/2003 | Calderwood et al. |
| 2003/0195211 A1 | 10/2003 | Sadhu et al. |

(56) References Cited

U.S. PATENT DOCUMENTS

| | | |
|---|---|---|
| 2003/0199516 A1 | 10/2003 | Moser et al. |
| 2003/0208800 A1 | 11/2003 | Eby et al. |
| 2003/0212113 A1 | 11/2003 | Dyatkina et al. |
| 2003/0232849 A1 | 12/2003 | Noe et al. |
| 2003/0235822 A1 | 12/2003 | Lokhov et al. |
| 2004/0039035 A1 | 2/2004 | Collins et al. |
| 2004/0043959 A1 | 3/2004 | Bloom et al. |
| 2004/0043983 A1 | 3/2004 | Li |
| 2004/0067901 A1 | 4/2004 | Bhat et al. |
| 2004/0067915 A1 | 4/2004 | McMahon et al. |
| 2004/0072766 A1 | 4/2004 | June |
| 2004/0072788 A1 | 4/2004 | Bhat et al. |
| 2004/0102423 A1 | 5/2004 | MacLaughlan et al. |
| 2004/0102437 A1 | 5/2004 | Takami et al. |
| 2004/0110717 A1 | 6/2004 | Carroll et al. |
| 2004/0110945 A1 | 6/2004 | Nakayama et al. |
| 2004/0116689 A1 | 6/2004 | Gall et al. |
| 2004/0122235 A1 | 6/2004 | Polisetti et al. |
| 2004/0127434 A1 | 7/2004 | Bigot et al. |
| 2004/0176458 A1 | 9/2004 | Leban et al. |
| 2004/0176601 A1 | 9/2004 | Goulet et al. |
| 2004/0192758 A1 | 9/2004 | Leban et al. |
| 2004/0266780 A1 | 12/2004 | Sadhu et al. |
| 2005/0004149 A1 | 1/2005 | Harada et al. |
| 2005/0043239 A1 | 2/2005 | Douangpanya et al. |
| 2005/0049310 A1 | 3/2005 | Mjalli et al. |
| 2005/0054614 A1 | 3/2005 | Diacovo et al. |
| 2005/0059713 A1 | 3/2005 | Mjalli et al. |
| 2005/0085472 A1 | 4/2005 | Tanaka et al. |
| 2005/0101551 A1 | 5/2005 | Sevillano et al. |
| 2005/0124637 A1 | 6/2005 | Cheng et al. |
| 2005/0143317 A1 | 6/2005 | Abdel-Meguid et al. |
| 2005/0153997 A1 | 7/2005 | Simon et al. |
| 2005/0171148 A1 | 8/2005 | Mjalli et al. |
| 2005/0182045 A1 | 8/2005 | Nagase et al. |
| 2005/0187418 A1 | 8/2005 | Small et al. |
| 2005/0197340 A1 | 9/2005 | Arora et al. |
| 2005/0214310 A1 | 9/2005 | Toki et al. |
| 2005/0215579 A1 | 9/2005 | Simon et al. |
| 2005/0239809 A1 | 10/2005 | Watts et al. |
| 2005/0250770 A1 | 11/2005 | Ono et al. |
| 2005/0256066 A1 | 11/2005 | Abel et al. |
| 2005/0261317 A1 | 11/2005 | Sadhu et al. |
| 2005/0272751 A1 | 12/2005 | McKerracher et al. |
| 2006/0019988 A1 | 1/2006 | McDonald et al. |
| 2006/0069034 A1 | 3/2006 | Burli et al. |
| 2006/0079538 A1 | 4/2006 | Hallahan et al. |
| 2006/0106038 A1 | 5/2006 | Bouscary et al. |
| 2006/0116326 A1 | 6/2006 | Burli et al. |
| 2006/0135790 A1 | 6/2006 | Hyett et al. |
| 2006/0156485 A1 | 7/2006 | Lim |
| 2006/0183783 A1 | 8/2006 | Polisetti et al. |
| 2006/0199776 A1 | 9/2006 | Blagg et al. |
| 2006/0205694 A1 | 9/2006 | Alonso et al. |
| 2006/0235031 A1 | 10/2006 | Arnold et al. |
| 2006/0276470 A1 | 12/2006 | Jackson et al. |
| 2006/0287295 A1 | 12/2006 | Barlaam et al. |
| 2006/0293274 A1 | 12/2006 | Wu |
| 2007/0015773 A1 | 1/2007 | Bergeron et al. |
| 2007/0017915 A1 | 1/2007 | Weder et al. |
| 2007/0027193 A1 | 2/2007 | Leban et al. |
| 2007/0032640 A1 | 2/2007 | Varghese et al. |
| 2007/0054915 A1 | 3/2007 | Arora et al. |
| 2007/0072897 A1 | 3/2007 | Mahaney et al. |
| 2007/0099871 A1 | 5/2007 | Davis et al. |
| 2007/0142405 A1 | 6/2007 | Dong et al. |
| 2007/0179151 A1 | 8/2007 | Chen et al. |
| 2007/0224672 A1 | 9/2007 | Leban et al. |
| 2007/0249598 A1 | 10/2007 | Wang et al. |
| 2007/0270452 A1 | 11/2007 | Blagg et al. |
| 2008/0032960 A1 | 2/2008 | Knight et al. |
| 2008/0058521 A1 | 3/2008 | Krishnan et al. |
| 2008/0070935 A1 | 3/2008 | Huang et al. |
| 2008/0119454 A1 | 5/2008 | Polisetti et al. |
| 2008/0119455 A1 | 5/2008 | Polisetti et al. |
| 2008/0119461 A1 | 5/2008 | Sin et al. |
| 2008/0200465 A1 | 8/2008 | Burli et al. |
| 2008/0249090 A1 | 10/2008 | Hu et al. |
| 2008/0261956 A1 | 10/2008 | Choi et al. |
| 2008/0287469 A1 | 11/2008 | Diacovo et al. |
| 2008/0292626 A1 | 11/2008 | Wang et al. |
| 2008/0293674 A1 | 11/2008 | Schwarz et al. |
| 2008/0306053 A1 | 12/2008 | Tachdjian et al. |
| 2008/0306093 A1 | 12/2008 | Servant et al. |
| 2008/0312180 A1 | 12/2008 | Liang et al. |
| 2008/0318942 A1 | 12/2008 | Simon et al. |
| 2009/0030023 A1 | 1/2009 | Harada et al. |
| 2009/0053192 A1 | 2/2009 | Millan et al. |
| 2009/0088452 A1 | 4/2009 | Coleman et al. |
| 2009/0099214 A1 | 4/2009 | Fairhurst et al. |
| 2009/0105233 A1 | 4/2009 | Chua et al. |
| 2009/0118283 A1 | 5/2009 | Defert et al. |
| 2009/0124638 A1 | 5/2009 | Shokat et al. |
| 2009/0124654 A1 | 5/2009 | Mjalli et al. |
| 2009/0137581 A1 | 5/2009 | Chen et al. |
| 2009/0163481 A1 | 6/2009 | Murphy et al. |
| 2009/0163709 A1 | 6/2009 | Blagg |
| 2009/0170879 A1 | 7/2009 | Szucova et al. |
| 2009/0181920 A1 | 7/2009 | Watkins et al. |
| 2009/0181988 A1 | 7/2009 | Tanaka et al. |
| 2009/0187014 A1 | 7/2009 | Blagg |
| 2009/0203689 A1 | 8/2009 | Dhalla et al. |
| 2009/0232768 A1 | 9/2009 | Birkus et al. |
| 2009/0247513 A1 | 10/2009 | Burli et al. |
| 2009/0253694 A1 | 10/2009 | Ono et al. |
| 2009/0264409 A1 | 10/2009 | Dong et al. |
| 2009/0264423 A2 | 10/2009 | Chua et al. |
| 2009/0270426 A1 | 10/2009 | Knight et al. |
| 2009/0270567 A1 | 10/2009 | Small et al. |
| 2009/0312319 A1 | 12/2009 | Ren et al. |
| 2009/0312406 A1 | 12/2009 | Hsieh et al. |
| 2009/0318411 A1 | 12/2009 | Castanedo et al. |
| 2009/0325967 A1 | 12/2009 | Fairhurst et al. |
| 2010/0009963 A1 | 1/2010 | Knight et al. |
| 2010/0022585 A1 | 1/2010 | deLong et al. |
| 2010/0029658 A1 | 2/2010 | Gavish et al. |
| 2010/0029693 A1 | 2/2010 | Douangpanya et al. |
| 2010/0048540 A1 | 2/2010 | Boyle et al. |
| 2010/0048882 A1 | 2/2010 | Blagg et al. |
| 2010/0056494 A1 | 3/2010 | Winzeler et al. |
| 2010/0105630 A1 | 4/2010 | Blagg |
| 2010/0168153 A1 | 7/2010 | Stowasser et al. |
| 2010/0179167 A1 | 7/2010 | Xu et al. |
| 2010/0190749 A1 | 7/2010 | Ren et al. |
| 2011/0046165 A1 | 2/2011 | Ren et al. |
| 2011/0124641 A1 | 5/2011 | Ren et al. |
| 2011/0144134 A1 | 6/2011 | Shokat et al. |
| 2011/0172228 A1 | 7/2011 | Ren et al. |
| 2011/0224223 A1 | 9/2011 | Shokat et al. |
| 2011/0269779 A1 | 11/2011 | Wilson et al. |
| 2011/0281866 A1 | 11/2011 | Ren et al. |
| 2011/0301144 A1 | 12/2011 | Knight et al. |
| 2012/0059000 A1 | 3/2012 | Ren et al. |
| 2012/0065154 A1 | 3/2012 | Tanaka et al. |
| 2012/0122838 A1 | 5/2012 | Ren et al. |
| 2012/0149701 A1 | 6/2012 | Ren et al. |
| 2012/0184568 A1 | 7/2012 | Ren et al. |
| 2012/0202784 A1 | 8/2012 | Aronov et al. |
| 2012/0245169 A1 | 9/2012 | Ren et al. |
| 2012/0329776 A1 | 12/2012 | Ren et al. |
| 2013/0029982 A1 | 1/2013 | Castro et al. |
| 2013/0029984 A1 | 1/2013 | Castro et al. |
| 2013/0053362 A1 | 2/2013 | Castro et al. |

FOREIGN PATENT DOCUMENTS

| | | |
|---|---|---|
| DE | 2139107 | 2/1973 |
| EP | 773023 A1 | 5/1997 |
| EP | 1020445 A1 | 7/2000 |
| GB | 812366 A | 4/1959 |
| GB | 937725 A | 9/1963 |
| JP | 61-109797 A | 5/1986 |
| JP | 05-256693 A | 10/1993 |
| JP | 08295667 A | 11/1996 |

(56) References Cited

FOREIGN PATENT DOCUMENTS

| | | | |
|---|---|---|---|
| JP | 09143163 A | 6/1997 |
| JP | 10206995 A | 8/1998 |
| JP | 2000072773 A | 3/2000 |
| JP | 2002131859 A | 5/2002 |
| JP | 2003073357 A | 3/2003 |
| JP | 2004161716 A | 6/2004 |
| WO | 83/01446 A1 | 4/1983 |
| WO | 91/17161 A1 | 11/1991 |
| WO | 92/14733 A1 | 9/1992 |
| WO | 93/16091 A1 | 8/1993 |
| WO | 93/16092 A1 | 8/1993 |
| WO | 93/18035 A1 | 9/1993 |
| WO | 9319767 A1 | 10/1993 |
| WO | WO 93/22443 A1 | 11/1993 |
| WO | 9413677 A1 | 6/1994 |
| WO | 9417803 A1 | 8/1994 |
| WO | 9429436 A1 | 12/1994 |
| WO | 9510628 A2 | 4/1995 |
| WO | 9512588 A1 | 5/1995 |
| WO | 9529673 A1 | 11/1995 |
| WO | 95/32984 A1 | 12/1995 |
| WO | 9510628 A3 | 9/1996 |
| WO | 9640706 A1 | 12/1996 |
| WO | 97/28133 A1 | 8/1997 |
| WO | WO 97/28161 A1 | 8/1997 |
| WO | WO 98/41525 A1 | 9/1998 |
| WO | 98/52611 A1 | 11/1998 |
| WO | 98/57952 A1 | 12/1998 |
| WO | WO 00/17202 A1 | 3/2000 |
| WO | WO 01/02369 A2 | 1/2001 |
| WO | 0116114 A2 | 3/2001 |
| WO | 200116114 A3 | 3/2001 |
| WO | WO 01/19829 A2 | 3/2001 |
| WO | 0125238 A2 | 4/2001 |
| WO | 0131063 A1 | 5/2001 |
| WO | 0138584 A2 | 5/2001 |
| WO | 0155140 A1 | 8/2001 |
| WO | WO 01/56988 A1 | 8/2001 |
| WO | WO 01/19829 A3 | 9/2001 |
| WO | 0125238 A3 | 10/2001 |
| WO | 0138584 A3 | 10/2001 |
| WO | 0181346 A2 | 11/2001 |
| WO | 200181346 A3 | 11/2001 |
| WO | 0206192 A1 | 1/2002 |
| WO | 0230944 A2 | 4/2002 |
| WO | WO 01/02369 A3 | 4/2002 |
| WO | 02057425 A2 | 7/2002 |
| WO | 02076986 A1 | 10/2002 |
| WO | 02080926 A1 | 10/2002 |
| WO | 02083143 A1 | 10/2002 |
| WO | 02090334 A1 | 11/2002 |
| WO | WO 02/088025 A1 | 11/2002 |
| WO | 02030944 A3 | 1/2003 |
| WO | 03000187 A2 | 1/2003 |
| WO | WO 03/016275 A1 | 2/2003 |
| WO | WO 03/020880 A2 | 3/2003 |
| WO | WO 03/024969 A1 | 3/2003 |
| WO | 03028341 A2 | 4/2003 |
| WO | 03035075 A1 | 5/2003 |
| WO | 03059884 A1 | 7/2003 |
| WO | WO 03/020880 A3 | 10/2003 |
| WO | WO 03/082341 A1 | 10/2003 |
| WO | 03106426 A1 | 12/2003 |
| WO | 2004006906 A3 | 1/2004 |
| WO | 2004039774 A3 | 1/2004 |
| WO | WO 04/006906 A2 | 1/2004 |
| WO | 2003000187 A3 | 3/2004 |
| WO | WO 2004/018058 A2 | 3/2004 |
| WO | 2004031177 A1 | 4/2004 |
| WO | WO 2004/039774 A2 | 5/2004 |
| WO | 2004018058 A3 | 7/2004 |
| WO | 2004058717 A1 | 7/2004 |
| WO | WO 2004/087053 A2 | 10/2004 |
| WO | WO 2004/111014 A1 | 12/2004 |
| WO | 2005002585 A1 | 1/2005 |
| WO | 2005007085 A2 | 1/2005 |
| WO | 2005012323 A2 | 2/2005 |
| WO | 2005016348 A1 | 2/2005 |
| WO | 2005016349 A1 | 2/2005 |
| WO | 2005016528 A2 | 2/2005 |
| WO | 2005021533 A1 | 3/2005 |
| WO | 2002057425 A3 | 4/2005 |
| WO | 2005012323 A3 | 5/2005 |
| WO | 2005016528 A3 | 5/2005 |
| WO | 2005047289 A1 | 5/2005 |
| WO | WO 2005/044181 A2 | 5/2005 |
| WO | 2005061460 A1 | 7/2005 |
| WO | 2005067901 A2 | 7/2005 |
| WO | WO 2005/063258 A1 | 7/2005 |
| WO | WO 2005/074603 A2 | 8/2005 |
| WO | 2005007085 A3 | 9/2005 |
| WO | WO 2005/097800 A1 | 10/2005 |
| WO | 2005105760 A1 | 11/2005 |
| WO | 2005067901 A3 | 12/2005 |
| WO | 2005112935 A1 | 12/2005 |
| WO | 2005113556 A1 | 12/2005 |
| WO | 2005117889 A1 | 12/2005 |
| WO | 2005120511 A1 | 12/2005 |
| WO | 2005044181 A3 | 3/2006 |
| WO | 2006030032 A1 | 3/2006 |
| WO | 2006038865 A1 | 4/2006 |
| WO | 2006050501 A2 | 5/2006 |
| WO | 2006050946 A1 | 5/2006 |
| WO | WO 2006/068760 A2 | 6/2006 |
| WO | 2004087053 A3 | 8/2006 |
| WO | 2006089106 A2 | 8/2006 |
| WO | 2006108107 A1 | 10/2006 |
| WO | WO 2006/112666 A1 | 10/2006 |
| WO | 2005074603 A3 | 11/2006 |
| WO | 2006114064 A2 | 11/2006 |
| WO | 2006114065 A2 | 11/2006 |
| WO | 2006068760 A3 | 12/2006 |
| WO | 2006089106 A3 | 12/2006 |
| WO | 2007006547 A1 | 1/2007 |
| WO | WO 2007/002293 A2 | 1/2007 |
| WO | 2007020046 A1 | 2/2007 |
| WO | 2007002293 A3 | 3/2007 |
| WO | WO 2007/025090 A2 | 3/2007 |
| WO | 2006050501 A3 | 5/2007 |
| WO | WO 2007/061737 A2 | 5/2007 |
| WO | 2006114064 A3 | 6/2007 |
| WO | 2006114065 A3 | 6/2007 |
| WO | 2007025090 A3 | 6/2007 |
| WO | WO 2007/075554 A2 | 7/2007 |
| WO | WO 2007/079164 A2 | 7/2007 |
| WO | 2007079164 A3 | 9/2007 |
| WO | WO 2007/103308 A2 | 9/2007 |
| WO | 2007114926 A2 | 10/2007 |
| WO | 2007121453 A2 | 10/2007 |
| WO | WO 2007/112005 A2 | 10/2007 |
| WO | 2007121920 A2 | 11/2007 |
| WO | 2007121924 A2 | 11/2007 |
| WO | 2007135398 A1 | 11/2007 |
| WO | WO 2007/124854 A1 | 11/2007 |
| WO | WO 2007/125310 A2 | 11/2007 |
| WO | WO 2007/125315 A2 | 11/2007 |
| WO | WO 2007/126841 A2 | 11/2007 |
| WO | WO 2007/134828 A1 | 11/2007 |
| WO | WO 2007/135380 A2 | 11/2007 |
| WO | 2007061737 A3 | 12/2007 |
| WO | 2007125315 A3 | 12/2007 |
| WO | 2007121920 A3 | 1/2008 |
| WO | 2008012326 A1 | 1/2008 |
| WO | WO 2008/001236 A2 | 1/2008 |
| WO | 2007103308 A3 | 2/2008 |
| WO | 2007112005 A3 | 2/2008 |
| WO | 2007125310 A3 | 3/2008 |
| WO | 2008025755 A1 | 3/2008 |
| WO | 2008047821 A1 | 4/2008 |
| WO | 2008063625 A2 | 5/2008 |
| WO | 2008064018 A1 | 5/2008 |
| WO | 2007121453 A3 | 7/2008 |
| WO | 2008079028 A1 | 7/2008 |
| WO | 2008082487 A2 | 7/2008 |

(56) References Cited

FOREIGN PATENT DOCUMENTS

| | | |
|---|---|---|
| WO | 2008094737 A2 | 8/2008 |
| WO | 2007121924 A3 | 9/2008 |
| WO | 2008112715 A2 | 9/2008 |
| WO | 2007114926 A3 | 10/2008 |
| WO | 2008125014 A1 | 10/2008 |
| WO | 2008125207 A1 | 10/2008 |
| WO | 2008127226 A2 | 10/2008 |
| WO | WO 2008/118454 A2 | 10/2008 |
| WO | WO 2008/118455 A1 | 10/2008 |
| WO | WO 2008/118468 A1 | 10/2008 |
| WO | 2007126841 A3 | 11/2008 |
| WO | 2008112715 A3 | 11/2008 |
| WO | 2008118454 A3 | 11/2008 |
| WO | 2008136457 A1 | 11/2008 |
| WO | 2008082487 A3 | 12/2008 |
| WO | 2008127226 A3 | 12/2008 |
| WO | 2009000412 A1 | 12/2008 |
| WO | 2008112715 A3 | 1/2009 |
| WO | 2009004621 A1 | 1/2009 |
| WO | 2009010925 A2 | 1/2009 |
| WO | 2009010925 A3 | 1/2009 |
| WO | 2009023718 A2 | 2/2009 |
| WO | 2008094737 A3 | 3/2009 |
| WO | 2009023718 A3 | 4/2009 |
| WO | 2009044707 A1 | 4/2009 |
| WO | 2009050506 A2 | 4/2009 |
| WO | 2009064802 A2 | 5/2009 |
| WO | 2009010925 A3 | 7/2009 |
| WO | 2009064802 A3 | 7/2009 |
| WO | 2009088986 A1 | 7/2009 |
| WO | 2009088990 A1 | 7/2009 |
| WO | 2009100406 A2 | 8/2009 |
| WO | 2009117157 A1 | 9/2009 |
| WO | 2009050506 A3 | 11/2009 |
| WO | 2009100406 A3 | 11/2009 |
| WO | 2010006086 A2 | 1/2010 |
| WO | 2010009207 A1 | 1/2010 |
| WO | 2010019210 A2 | 2/2010 |
| WO | 2010036380 A1 | 4/2010 |
| WO | 2010039534 A2 | 4/2010 |
| WO | 2010019210 A3 | 5/2010 |
| WO | 2010039534 A3 | 8/2010 |
| WO | WO 2011/008302 A1 | 1/2011 |
| WO | 2011146882 A1 | 11/2011 |
| WO | WO 2011/146882 A1 | 11/2011 |
| WO | WO 2012/064973 A2 | 5/2012 |
| WO | WO 2012/097000 A1 | 7/2012 |

OTHER PUBLICATIONS

Chaisuparat, et al. Dual Inhibition of P13K(alpha) and mTOR as an Alternative Treatment for Kaposi's Sarcoma. Cancer Research. 2008;68:8361.

Chappelow, et al. Neovascular Age-Related Macular Degeneration: Potential Therapies. Drugs. 2008;68 (8):1029-1036.

Davis, et al. The preperation of Substituted 1(2H)-Isoquinolinones from Dilithiated 2-Methyl-N-arylbenzamides, 2-Methyl-N-(arylmethyl)-benzamides, or 2-Methylbenzoic Acid, 2, 2-Dimethylhydrazide. Synthetic Communications. Sep. 1997;27(17):2961-9.

Dijksman, et al. 271.1 : 2-Dihydro-2-thianaphthalene derivatives. Part I. Preperation and reactions of 1 : 2- Dihydro-1-keto-2-thianaphthalenes. J. Chem. Soc. 1951:1213-18.

Donati, et al. Emerging Therapies for Neovascular Age-Related Macular Degeneration: State of Art. Ophthalmologica. 2007;221:366-377.

Graupera, et al. Angiogenesis selectively requires the p110 isoform of P13K to control endothelial cell lmigration. Nature. 2008;453:662-666.

Hellwinkel, et al. Heterocyclensynthesen mit MF/A1203-Basensystemen; 2- Arylbenzofurane and 2,3- Diarylisochinolin-1(2H)-one. Synthesis. 1995;1995(9):1135-41.

International Search Report dated Mar. 23, 2009 for PCT Application dated US2009/00042.

International Search Report dated Mar. 11, 2009 for PCT Application No. US2009/00038.

Kajita, et al. Nickel-catalyzed decarbonylative addition of phthalimides to alkynes. J. Am. Chem.Soc. May 14, 2008;130(19):6058-9.

Kundu, et al. Palladium-Catalysed Heteroannualation with Terminal Alkynes; a Highly Regio-and Stereoselective Synthesis of (Z)-3-Aryl(alykl)idene Isoindolin-1-ones1. Tetrahedron. Jun. 30, 2000;56(27):4777-92.

Lee, et al. All Roads lead to mTOR integrating inflammation and tumor angiogenesis. Cell Cycle. 2007;6 (24):3011-3014.

Majumder, et al. mTOR inhibition reverses Akt-dependent prostate intraepithelial neoplasia through regulation of apoptic and HIF-1-dependent pathways. Nature Medicine. 2004;10:594-601.

Mellinghoff, et al. TORward AKTually useful mouse models. Nature Medicine. 2004;10:579-580.

Modi, et al. Isoquinolones; Part IV-Synthesis of Methyl, 3-Formyl & Other 3-Substituted N-Arylisoquinolones, Indian J. Chem. 1979;18B:304-306.

Nemazanyi, et al. 3-Amino-4aryl-1(2H)-isoquinolones. Chemistry of Heterocyclic Compounds. Mar. 1991;27 (3):307-8.

Oda, et al. PIK3CA Cooperates with Other Phosphatidylinositol 3'-Kinase Pathway Mutations to Effect Oncogenic Transformation. Cancer Research. 2008;68:8127.

Ozaki, et al. Studies on 4(1H)-Quinazolinones. IV. Convenient Synthesis of 12-Methyl-6H-isoquino [2,1-a] quinazolin-6-one and 6-Methyl-13H-quinazolino [3,4-a] quinazolin-13-one. Chem. Pharm. Bull. Jun. 25, 1984;32 (6):2160-4.

Ozol, et al. Autoxidative transformations of 2-substituted 3-alkyl-4-hydroxy-1-oxo-1, 2-dihydroisoquinolines. Chemistry of Heterocyclic Compounds. Jun. 1978;14(6):644-8.

Patel, et al. Immunopathological aspects of age-related macular degeneration. Seminars in Immunopathology. 2008;30(2):97-110.

Stanoeva, et al. Homophthalic anhydrides and their application to the synthesis of heterocyclic compounds (review). Chemistry of Heterocyclic Compounds. Dec. 1984;20(12);1305-15.

Ames et al., "Heterocyclic Synthesis from o-Halogen-acids. Part II. Thienopyridinones and Thienopyranones from 3-bromothiophene -2- and 4-Bromothiophene-3-Carboxylic Acids", Journal of the Chemical Society, Perkin Transactions 1, Jan., 14:1390-1395 (1975).

Basotest®, "Test Kit for the Quantitative Determination of the Degranulation of Basophilic Granulocytes in Heparinized Human Whole Blood", [www.biocarta.com/TDS/10-0500.pdf], Retreived from the Internet Nov. 29, 2011.

Extended European Search Report from corresponding European Application No. 09700784.3 dated Oct. 28, 2011.

International Preliminary Report on Patentability from International Application No. PCT/US2009/000042 issued Jul. 6, 2010.

Kost et al., "Recyclization of 3-Alkyl- and 1,3-Dialkylisoquinolinium Salts to Naphthylamines", Chemistry of Heterocyclic Compounds, Jan., 16(9):965-970 (1981).

Kumar et al., "Keten Dithioacetals. Part II. Reaction of 3-Cyano-4-Methylthio-2(1H)-pyridones with Hydazine and Guanidine: Synthesis of Novel Substituted and Fused Pyrazolo[4,3-c]pyridone and Pyrido[4,3-d]pyrimidine Derivatives", Journal of the Chemical Society, Perkin Transactions 1, Chemical Society, Letchworth, Jan., 8:857-862 (1978).

Vasilevsky et al., "Study of the Heterocyclization of vic-Substituted Hydrazides of Acetylenylpyrazolecarboxylic Acids into N-Amino Pyrazolopyridinones", Journal of Heterocyclic Chemistry, Nov., 39(6):1229-1233 (2002).

Vasilevsky et al., "Unexpected results in the heterocyclization of 5-acetylenylpyrazole-4-carboxylic acid hydrazides under the influence of CuCl: formatin of a diazepinone and dehydrodimerization into the corresponding bis(pyrazolo [4,3-d] [1,2] diazepinone)", Tetrahedron Letters, Jan., 46(26): 4457- 4459 (2005).

Abe et al., "T cell receptor-mediated recognition of self-ligand induces signaling in immature thymocytes before negative selection", J. Exp. Med., Aug. 1992, vol. 176, pp. 459-468.

Ames et al., "Heterocyclic Synthesis from o-Halogen-acids. Part II. Thienopyridinones and Thienopyranones from 3-bromothiophene

(56) References Cited

OTHER PUBLICATIONS

-2- and 4-Bromothiophene-3-Carboxylic Acids", Journal of the Chemical Society, Perkin Transactions 1, Jan., 14: 1390-1395 (1975).
Anderson et al., "Paradoxical inhibition of T-cell function in response to CTLA-4 blockade; heterogeneity within the human T-cell population", Nature, 2000, vol. 6, No. 2, pp. 211-214.
Arcaro et al., "Wortmannin is a potent phosphatidylinositol 3-kinase inhibitor: the role of phosphatidylinositol 3,4,5-triphosphate in neutrophil responses", Biochem. J., Dec. 1, 1993, vol. 296, Pt. 2, pp. 297-301.
Augustine et al., "Interleukin 2- and polyomavirus middle T antigen-induced modification of phosphatidylinositol 3-kinase activity in activated T lymphocytes", Molecular and Cellular Biology, 1991, vol. 11, No. 9, pp. 4431-4440.
Baggiolini et al., "Inhibition of the phagocytosis-induced respiratory burst by the fungal metabolite wortmannin and some analogues", Experimental Cell Research, 1987, vol. 169, pp. 408-418.
Basotest®, "Test Kit for the Quantitative Determination of the Degranulation of Basophilic Granulocytes in Heparinized Human Whole Blood", Retreived from the Internet Nov. 29, 2011.
Blunden et al., "Mycotoxins in food", Medical Laboratory Sciences, 1991, vol. 48, pp. 271-282.
Bochner et al. "Immunological aspects of allergic asthma". Annual review of Immunology 1994—Annual Reviews, pp. 295-335.
Closse et al., "2,3-dihydrobenzofuran-2-ones: a new class of highly potent antiinflammatory agents", J. Med. Chem., 1981, vol. 24, pp. 1465-1471.
Cox et al., "Human colorectal cancer cells efficiently conjugate the cyclopentenone prostaglandin, prostaglandin J2 to glutathione", Biochem. Biophys. Acta., 2002, vol. 1584, pp. 37-45.
Davies et al., "The human T3y chain is phosphorylated at Serine 126 in response to T lymphocyte activation", The Journal of Biological Chemistry, 1987, vol. 262, No. 23, pp. 10918-10921.
Extended European Search Report from Eureopean Application No. 09700784.3 dated Oct. 28, 2011.
Graber et al., "The protein tyrosine kinase inhibitor herbimycin A, but not Genistein, specifically inhibits signal transduciton by the T cell antigen receptor", International Immunology, 1992, vol. 4, No. 1, pp. 1201-1210.
Gunther et al., "Acute pathological effects on rats of orally administered wortmannin-containing preparations and purified wortmannin from *Fusarium oxysporum*", Fd. Chem. Toxic., 1989, vol. 27, No. 3, pp. 173-179.
Gunther et al., "Immunosuppressive effects of dietary wortmaninn on rats and mice", Immunopharmacology and Immunotoxicology, 1989, vol. 11, No. 4, pp. 559-570.
Harada et al., "Novel role of phosphatidylinositol 3-kinase in CD28-mediated costimulation", J. Biol. Chem., 2001, vol. 276, No. 12, pp. 9003-9008.
Harding et al., "CD28-mediated signalling co-stimulates murine T cells and prevents induction of anergy in T-cell clones", Nature, Apr. 16, 1992, vol. 356, pp. 607-609.
Harding et al., "CD28-mediated signalling co-stimulates murine T cells and prevents induction of energy in T-cell clones", Nature, 1992, pp. 607-609.
International Search Report dated Aug. 22, 2011for PCT Application No. PCT/US2011/37412.
International Search Report dated Aug. 21, 1995 for PCT Application No. US1995/05213.
International Search Report dated Oct. 26, 2011, for International Application No. PCT/US2009/00038.
International Search Report dated Oct. 26, 2011, for International Application No. PCT/US09/00038.
Johnson et al., "Accessory cell-derived signals required for T cell activation", Immunologic Research, 1993, pp. 48-64.
June et al., "Evidence for the involvement of three distinct signals in the induction of IL-2 gene expression in human T lymphocytes", J. Immunol., Jul. 1, 1989, vol. 143, No. 1, pp. 153-161.

June et al., "Inhibition of tyrosine phosphorylation prevents T-cell receptor mediated signal transduction", Proc. Natl. Acad. Sci. USA, 1990, vol. 87, pp. 7722-7726.
June et al., "Role of CD28 receptor in T-cell activation", Immunology Today, 1990, vol. 11, No. 6, pp. 211-216.
June, "Signaling transduction in T cells", Current Opinion in Immunology, 1991, vol. 3, pp. 287-293.
Kost et al., "Recyclization of 3-Alkyl- and 1,3-Dialkylisoquinolinium Salts to Naphthylamines", Chemistry of Heterocyclic Compounds, Jan., 16(9): 965-970 (1981).
Kumar et al., "Keten Dithioacetals. Part 11. Reaction of 3-Cyano-4-Methylthio-2(1H)-pyridones with Hydazine and Guanidine: Synthesis of Novel Substituted and Fused Pyrazolo[4,3-c]pyridone and Pyrido[4,3-d]pyrimidine derivatives", Journal of the Chemical Society, Perkin Transactions 1, Chemical Society, Letchworth, Jan., 8: 857-862 (1978).
Ledbetter et al., "CD28 ligation in T-cell activation: evidence for two signal transduction pathways", Blood, Apr. 1, 1990, vol. 75, No. 1, pp. 1531-1539.
Ledbetter et al., "Crosslinking of surface antigens cause mobilization of intracellular ionized calcium in T lymphocytes", Proc. Natl. Acad. Sci. USA, Mar. 1987, vol. 84, pp. 1384-1388.
Lee et al., "The CD28 signal transduction pathway in T cell activation", Advances in Cell Regulation of Cell Growth, 1991, vol. 2, pp. 141-160, New York: Raven Press, Ltd.
Ley et al., "The T cell receptor/CD3 complex and CD2 stimulate the tyrosine phosphorylation of indistinguishable patterns of polypeptides in the human T leukemic cell line Jurkat", Eur. J. Immunol., 1991, vol. 21, pp. 2203-2209.
Liu et al., "Costimulation of T-cell growth", Current Biology, 1992, pp. 265-270.
Lu et al., "CD28-induced T cell activation: evidence for the protein-tyrosine kinase signal transduction pathway", J. Immunol., Jul. 1, 1992, vol. 149, No. 1, pp. 24-29.
Merida et al., "IL-2 binding activates a tyrosine-phosphorylated phosphatidylinositol-3-kinase", The Journal of Immunology, 1991, vol. 147, pp. 2202-207.
Mosmann et al., "The expanding universe of T-cell subsets: Th1, Th2 and more", Immunology Today, 1996, pp. 138-146.
Nunes et al., "Signalling Through CD28 T-Cell Activation Pathway Involves an Inositol Phospholipid-Specific Phospholipase C Activity". Biochem. J., 1993, vol. 293, pp. 835-842.
O'Shea et al., "Activaiton of human peripheral blood T lymphocytes by pharmacological induction of protein-tyrosine phosphorylation", Proc. Natl. Acad. Sci. USA, Nov. 1992, vol. 89, pp. 10306-10310.
Okada et al., "Essential role of phosphatidylinositol 3-kinase in insulin-induced glucose transport and antilipolysis in rat adipocytes", J. Biol. Chem., Feb. 4, 1994, vol. 269, No. 5, pp. 3568-3573.
Okada et al., "Blockage of chemotactic peptide-induced stimulation of neutrophils by wortmannin as a result of selective inhibition of phosphatidylinositol 3-kinase", J. Biol. Chem., Feb. 4, 1994, vol. 269, No. 5, pp. 3568-3573.
Prasad et al., "Phosphatidylinositol (PI) 3-kinase and PI 4-kinase binding to the CD4-p56lck complex: the p56lck SH3 domain binds to PI 3-kinase but not PI 4-kinase", Molecular and Cellular Biology, Dec. 1993, vol. 13, No. 12, pp. 7708-7717.
Prasad et al., "Src-homology 3 domain of protein kinase p59fyn mediates binding phosphatidylinositol 3-kinase in T cells", Proc. Natl. Acad. Sci. USA, Aug. 1993, vol. 90, pp. 7366-7370.
Prasad et al., "T-cell antigen CD28 interacts with the lipid kinase phosphatidylinositol 2-kinase by a cytoplasmic Tyr(P)-Met-Xaa-Met motif", Proc. Natl. Acad. Sci. USA, 1994, vol. 91, pp. 2834-2838.
Pérez-Blas et al., "Impaired T cell signal transduction through CD28 in a patient with idiopathic thrombocytopenia", Clin. Exp. Immunol., 1991, vol. 85, pp. 424-428.
Reif et al., "Divergent regulation of phosphatidylinositol 3-kinase P85a and P85b isoforms upon T cell activation", The Journal of Biological Chemistry, 1993, vol. 268, pp. No. 15, pp. 10780-10788.
Rott et al., "Recent development in the use of biologics in psoriasis and autoimmune disorders. The role of autoantibodies", BMJ, Mar. 26, 2005, vol. 330, No. 7493, pp. 716-720.

(56) References Cited

OTHER PUBLICATIONS

Schwartz et al., "Quercetin inhibition of the induction and function of cytotoxic T lymphocytes", Immunopharmacology, 1982, vol. 4, pp. 125-138.
Schwartz, "A cell culture model for T lymphocyte clonal anergy", Science, Jun. 15, 1990, vol. 248, pp. 1349-1356.
Shibasaki et al., "Different properties of monomer and heterodimer forms of phosphatidylinositol 3-kinase", Biochem. J., 1993, vol. 289, pp. 227-231.
Sykes et al., "Treatment of severe autoimmune disease by stem-cell transplantation", Nature, Jun. 2, 2005, vol. 35, No. 7042, pp. 620-627.
Thompson et al., "Identification of distinct populations of PI-3 kinase activity following T-cell activation", Oncogene, 1992, vol. 7, pp. 719-725.
Torimoto et al., "CD45 molecule and T cell activation", 1990, vol. 27, pp. 63-71.
Truitt et al., "Stimulation of CD28 triggers an association between CD 28 and phosphatidylinositol 3-kinase in Jurkat T cells", J. Exp. Med., Mar. 1994, vol. 179, pp. 1071-1076.
Vandenberghe et al., "Antibody and B7/BB1-mediated ligation of the CD28 receptor induces tyrosine phosphorylation in human T cells", J. Exp. Med., Apr. 1992, vol. 175, pp. 951-960.
Vasilevsky et al., "Study of the Heterocyclization of vic-Substituted Hydrazides of Acetylenylpyrazolecarboxylic Acids into N-Amino Pyrazolopyridinones", Journal of Heterocyclic Chemistry, Nov., 39(6): 1229-1233 (2002).
Vasilevsky et al., "Unexpected results in the heterocyclization of 5-acetylenylpyrazole-4-carboxylic acid hydrazides under the influence of CuCl: formatin of a diazepinone and dehydrodimerization into the corresponding bis(pyrazolo [4,3-d] [1,2] diazepinone)", Tetrahedron Letters, Jan., 46(26): 4457-4459 (2005).
Vitali et al., "Immunotherapy in rheumatoid arthritis: a review", Int. J. Artif. Organs, Dec. 1993, vol. 16, Suppl. 5, pp. 196-200.
Vlahos et al., "A specific inhibitor of phosphatidylinositol 3-kinase, 2-(4-morpholinyl)-8-phenyl-4H-1-benzopyran-4-one (LY294002)", The Journal of Biological Chemistry, 1994, vol. 269, No. 7, pp. 5241-5248.
Ward et al., "Ligation of CD28 receptor by B7 induces formation of D-3 phosphoinositides in T lymphocytes independently of T cell receptor/CD3 activation", Eur. J. Immunol., 1993, vol. 23, pp. 2572-2577.
Ward et al., "Inhibition of CD28-mediated T cell costimulation by the phosphoinisitide 3-kinase inhibitor wortmannin", Eur. J. Immunol., 1995, vol. 25, pp. 526-532.
Ward et al., "Regulation of D-3 phosphoinositides during T cell activation via the T cell antigen receptor/CD3 complex and CD2 antigens", Eur. J. Immunol., 1992, vol. 22, pp. 45-49.
Ward et al., "Regulation of phosphoinositide kinases in T cells", J. Biol. Chem., Nov. 25, 1992, vol. 267, No. 33, pp. 23862-23869.
Wiesinger et al., "Antiinflammatory activity of the new mold metabolite 11-desacetoxy-wortmannin and some of its derivatives", Experientia, 1974, vol. 30, pp. 135-136.
Woscholski et al., "A comparison of demthoxyviridin and wortmannin as inhibitors of phosphatidylinositol 3-kinase", FEBS letters, 1994, vol. 342, pp. 109-114.
Wu et al., "Decreased immunological responses by wortmannin-containing rice culture of Fusarium oxysporum and by purified wortmannin in avian species", Immunopharmacology and Immunotoxicology, 1992, vol. 14, No. 4, pp. 913-923.
Wu et al., "Wortmannin (a mycotoxin) inhibited immune responses in chickens", Poultry Science, 1992, vol. 71, Suppl. 1, pp. 13.
Yaguchi et al., "Antitumor activity of ZSTK474, a new phosphatidylinositol 3-kinase inhibitor", J. Natl. Cancer Inst., 2006, vol. 98, No. 8, pp. 545-556.
Yang et al., "A novel activation pathway for mature thymocytes", J Exp. Med., Oct. 1988, vol. 168, pp. 1457-1486.
Yano et al., "Inhibition of histamine secretion by wortmannin through the blockade of phosphatidylinositol 3-kinase in RBL-2H3 cells", J. Biol. Chem., Dec. 5, 1993, vol. 268, No. 34, pp. 25846-25856.
Yoshida et al., "Quercetin arrests human leukemic T-cells in late G1 phase of the cell cycle", 1992, vol. 52, pp. 6676-6681.
European Seach Report dated Oct. 28, 2011, for EP Application No. 09700784.3.
J.C.S. Perkin!, 1978, 857-862.
Takeuchi et al. "Synergistic Augmentation of Rapamycin-Induced Autophagy in Malignant Glioma Cells by Phosphatidylinositol 3-Kinase/Protein Kinase B Inhibitors". Cancer Res. 65(8):3336-46. Apr. 15, 2005.
Beeram et al. Akt-Induced Endocrine Therapy Resistance is Reversed by Inhibition of mTOR Signaling. Ann Oncol. Aug. 2007. 18(8):1323-8.
Feldman et al. Active-Site Inhibitors of mTOR Target Rapamycin-Resistant Outputs of mTORC1 and mTORC2. PLoS Biol. Feb. 10, 2009. 7(2):371-383.
U.S. Appl. No. 13/016,957, filed Jan. 28, 2011.
Abdel-Mohsen. Synthesis, Reactions and Antimicrobial Activity of 2-Amino-4-(8-quinolinol-5-y1)-1-(p-toly1)-pyrrole-3-carbonitrile. Bull. Korean Chem. Soc. 2005;26(5):719-728.
Kim et al. "Activation and Function of the mTORC1 Pathway in Mast Cells". J Immunol. Apr. 1, 2008; 180(7):4586-95.
International Preliminary Report on Patentability and Written Opinion for PCT/US2009/060985 dated Apr. 19, 2011.
International Preliminary Report on Patentability and Written Opinion for PCT/US2009/049969 dated Jan. 1, 2011.
International Preliminary Report on Patentability and Written Opinion for PCT/US2005/042524 dated May 22, 2007.
International Preliminary Report on Patentability and Written Opinion for PCT/US2007/008355 dated Nov. 4, 2008.
International Preliminary Report on Patentability and Written Opinion for PCT/US2007/008395 dated Oct. 8, 2008.
International Search Report and Written Opinion for PCT/US2009/049969 dated Mar. 15, 2010.
International Search Report and Written Opinion for PCT/US2009/005380 dated Nov. 20, 2009.
International Search Report for PCT/US2010/02020 dated Nov. 2, 2010.
International Search Report for PCT/US2009/060985 dated Jun. 28, 2010.
European Search Report for EP 07873406.8 dated Mar. 1, 2010.
European Search Report and Search Opinion for EP 09700424.6 dated Oct. 26, 2011.
European Examination Report for EP 07873406.8 dated Sep. 14, 2011.
Kreutzberger et al. 5-Substituierte 4-Aminopyrimidine durch Aminomethinylierung von Acetonitrilen. Liebigs Ann. Chem. 1977: pp. 537-544.
Supplementary European Examination Report EP 07754845.1 dated Sep. 20, 2011.
Gillespie et al. "Antagonists of the Human Adenosine A2A Receptor. Part 3. Design and Synthesis of Pyrazolo [3,4d] Pyrimidines, Pyrrolo [2, 3-d] Pyrimidines, and 6-arylpurines". Bioorganic and Medicinal Chemistry Letters. vol. 18, No. 9. Mar. 30, 2008. pp. 2924-2929.
Ballell et al. "New Thiopyrazolo[3,4-d] pryimidine derivatives as anti-mycobacterial agents". Bioorganic and Medicinal Chemistry Letters. vol. 17. Dec. 22, 2006. pp. 1736-1740.
Extended European Search Report for EP 09816603 dated Mar. 19, 2012.
International Search Report and Written Opinion for PCT/US2012/20831 dated May 2, 2012.
Berndt et al., "The P110 Structure: Mechanisms for selectivity and potency of new P1(3)K Inhibitors", Nat Chem Biol. Feb. 2010;6(2):117-24.
International Search Report & Written Opinion for PCT/US2011/60212 dated Jun. 1, 2012.
International Search Report & Written Opinion issued after Submission of Request for Additional Search for PCT/US2011/60212 dated Jul. 6, 2012.

(56) References Cited

OTHER PUBLICATIONS

Bansal, N., et al., "The Molecular Biology of Endometrial Cancers and the Implications for Pathogenesis, Classification, and Targeted Therapies," Cancer Control, 16(1):8-13 (2009).
Billottet, C., et al., "A Selective Inhibitor of the p110d Isoform of PI 3-Kinase Inhibits AML Cell Proliferation and Survival and Increases the Cytotoxic Effects of VP16," Oncogene, 25:6648-6659 (2006).
Billottet, C., et al., "Inhibition of Class 1 Phosphoinositide 3-Kinase Activity Impairs Proliferation and Triggers Apoptosis in Acute Promyelocytic Leukemia without Affecting Atra-Induced Differentiation," Cancer Res. 69(3):1027-36 (2009).
Chapuis, N., et al., "Dual Inhibition of P13K and mTORC1/2 Signaling by NVP-BEZ235 as a New Therapeutic Strategy for Acute Myeloid Leukemia," Clin. Cancer Res., 16(22):5424-35 (2010).
Chen, J.S., et al., "Characterization of Structurally Distinct, Isoform-Selective Phosphoinositide 3'-Kinase Inhibitors in Combination with Radiation in the Treatment of Glioblastoma," Mol. Cancer Ther., 7(4):841-50 (2008).
Courtney, K.D., et al., "The P13K Pathway As Drug Target in Human Cancer," J. of Clinical Oncology, 28 (6):1075-1083 (2010).
Brzezianska, E., et al., "A Minireview: The Role of MAPK/ERK and P13K/Akt Pathways in Thyroid Follicular Cell-Derived Neoplasm," Frontiers in Bioscience, 16:422-439 (2011).
Flinn, I.W., et al., "Preliminary Evidence of Clinical Activity in a Phase I Study of CAL-101, a Selective Inhibitor of the p1108 Isoform of Phosphatidylinositol 3-Kinase (P13K), in Patients with Select Hematologic Malignancies," J. Clin. Oncol. 27:156s (Suppl: Abstr 3543) (2009).
Vara, J.A.F., et al., "P13K/Akt Signalling Pathway and Cancer," Cancer Treat. Rev. 30(2):193-204 (2004).
Furukawa, T., "Molecular Targeting Therapy for Pancreatic Cancer: Current Knowledge and Perspectives from Bench to Bedside," J. Gastroenterol., 43:905-911 (2008).
Haluska, F., et al., "The RTS/RAS/BRAF/P13K Pathways in Melanoma: Biology, Small Molecule Inhibitors, and Potential Applications," Semin. Oncol., 34(6):546-54 (2007).
Herman, S.E.M., et al., "Phosphatidylinositol 3-Kinase-d Inhibitor Cal-101 Shows Promising Preclinical Activity in Chronic Lymphocytic Leukemia by Antagonizing Intrinsic and Extrinsic Cellular Survival Signals," Blood, 116 (12):2078-88 (2010).
Herman, S.E.M., et al., "The Role of Phosphatidylinositol 3-Kinase-d in the Immunomodulatory Effects of Lenalidomide in Chronic Lymphocytic Leukemia," Blood, 117(16):4323-7 (2011).
Herrera, V.A., et al., "The Dual P13K/mTOR Inhibitor BEZ235 Is Effective in Lung Cancer Cell Lines," Anticancer Research, 31:849-854 (2011).
Ikeda, H., et al., "P13K/p110d is a Novel Therapeutic Target in Multiple Myeloma," Blood, 116(9):1460-8 (2010).
Khwaja, A., "P13K as a Target for Therapy in Haematological Malignancies," Curr Top Microbiol immunol., 347:169-88 (2010).
Kong, D. and Yamori, T., "Advances in Development of Phosphatidylinositol 3-Kinase Inhibitors," Curr. Med. Chem., 16:2839-2854 (2009).
Markman, B., et al., "Status of P13K Inhibition and Biomarker Development in Cancer Therapeutics," Ann. Oncol., 21 (4):683-91 (2010).
Mazzoletti, M. and Broggini, M., "P13K/AKT/mTOR Inhibitors in Ovarian Cancer," Curr. Med. Chem., 17:4433-4447 (2010).
Meadows, S.A., et al., "Cal-101, a Potent Selective Inhibitor of the p110d Isoform of Phosphatidylinositol 3-Kinase, Attenuates Pathway Signaling, Induces Apoptosis, and Oversomces Signals From the Microenvironment in Cellular Models of Hodgkin Lymphoma," Blood (ASH Annual Meeting Abstracts), 116:Abstract 3926 (2010).
Porta, C. and Figlin, R.A., "Phsophatidylinositol-3-Kinase/Akt Signaling Pathway and Kidney Cancer, and the Therapeutic Potential of Phosphatidylinositol-3-Kinase/Akt Inhibitors," J. Urol., 182(6):2569-77 (2009).
Saif, M.W. and Chu, E., "Biology of Colorectal Cancer," Cancer J., 16(3):196-201 (2010).

Salmena, L., et al. "Tenets of PTEN Tumor Suppression," Cell, 133:403-414(2008).
Sarker, D., et al., "Targeting the P13K/AKT Pathway for the Treatment of Prostate Cancer," Clin. Cancer Res., 15 (15):4799-805 (2009).
Shapiro, G., et al., "Phase I Dose-Escalation Study of XL147, A P13K Inhibitor Administered Orally to Patients with Solid Tumors," J. Clin. Oncol., 27:146x (Suppl Abstr 3500) (2009).
Torbett, N. E., et al., "A Chemical Screen in Diverse Breast Cancer Cell Lines Reveals Genetic Enhancers and Suppressors of Sensitvity to PI3K Isoform-Selective Inhibition," Biochem. J., 415:97-100 (2008).
Vogt, P.K., et al., "Phosphoinositide 3-Kinase: From Viral Oncoprotein to Drug Target," Virology, 344:131-138 (2006).
Vogt, P.K., et al., "Phosphatidylinositol 3-Kinase: The Oncoprotein," Curr. Top. Microbiol. Immunol., 347:79-104 (2010).
Wagner, A.J., et al., "A First-in-Human Phase I Study to Evaluate the Pan-P13K Inhibitor GDC-0941 Administered QD or BID in Patients with Advanced Solid Tumors," J. Clin. Oncol., 27:146s (Suppl, Abstr 3501) (2009).
Ward, S., et al., "Therapeutic Potential of Phosphoinositide 3-Kinase Inhibitors," Chem. & Biol., 10:207-213 (2003).
Zhao, L. And Vogt, P.K., "Class I P13K in Oncogenic Cellular Transformation," Oncogene, 27:5486-5496 (2008).
Jimeno, A., et al., "Phase I Trial of PX-866, A Novel Phosphoinositide-3-Kinase (P1-3K) Inhibitor," J. Clin. Oncol., 27:15s (Suppl Abstr 3542) (2009).
International Preliminary Report on Patentability for PCT/US2009/000038 dated Jul. 6, 2010.
European Search Report for EP 07 754 845.1, dated Sep. 20, 2011.
International Preliminary Report on Patentability for PCT/US2010/002020 dated Jan. 26, 2012.
International Preliminary Report on Patentability for PCT/US2009/005380 dated Apr. 7, 2011.
Abrahamian et al. "Immunological and Clinical Profile of Adult Patients with Selective Immunoglobulin Subclass Deficiency: Response to Intravenous Immunoglobulin Therapy". Clinical & Experimental Immunology. The Journal of Translational Immunology vol. 159, pp. 344-350 (2009).
Bartholomeusz et al. "Targeting the P13K Signaling Pathway in Cancer Therapy". Expert Opin. Ther. Targets (2012). pp. 121-130.
International Search Report and Written Opinion, International Application No. PCT/US10/33939, date of mailing Nov. 5, 2010.
Supplementary European Search Report, International Application No. PCT/US2010/002020, date of mailing Nov. 7, 2012.
Basotest(R), "Test Kit for the Quantitative Determination of the Degranulation of Basophilic Granulocytes in Heparnized Human Whole Blood" [www.biocarta.com/TDS/10-0500.pdf], Retrieved from the Internet on Nov. 29, 2011.
Mattes, W.13., et al., "DNA Sequence Selectively of Guanine-N7 Alkylation by Nitrogen Mustards," Nucleic Acids Research, 14(7):2971 (1986).
Cheson, B.D. And Rummel, M.J., "Bendannustine: Rebirth of an Old Drug," Journal of Clinical Oncology, 27(9):1492, Mar. 20, 2009.
Cho, W.-J., et al., "A Novel Synthesis of Benzo[c] phenanthridine Skeleton and Biological Evaluation of Isoquinoline Derivatives," Chem. Pharm. Bull., 47(6):900-902 (1999).
Abraham, T., "Thermally induced intramolecular cycloaddition reaction of N-pheny1-2-phenylethynlbenzamide potential cure reaction for thermosetting polymers," J. Polym. Sci. Polym. Chem. Ed. 20(7):1953-1957 (1982).
Ames et al., "Heterocyclic Syntheses from o-Halogeno-acids. Part II. Thienopyridinones and Thienopyranones from 3-Bromothiophen-2- and 4-Bromothiophen-3-carboxylic Acids," J.C.S. Perkin I 1390-1395 (1975).
Andrews et al., "Effects of the 11β-hydroxysteroid dehydrogenase inhibitor carbenoxolone on insulin sensitive in men with type 2 diabetes," J. Clin. Endocrinol. Metab. 88(1):285-291 (2003).
Arnold et al., Pyrrolo[2,3-d]pyrimidines containing an extended 5-substituent as potent and selective inhibitors of Ick I, Bioorg. Med. Chem. Lett. 10(19):2167-2170 (2000).
Banker et al., Modern Pharmaceutics, pp. 451, 596, $3^{rd}$ed., Marcel Dekker, New York (1996).

(56) References Cited

OTHER PUBLICATIONS

Barf et al., "Arylsulfonamidothiazoles as a new class of potential antidiabetic drugs. Discovery of potent and selective inhibitors of the 11β-hydroxysteroid dehydrogenase Type 1," *J. Med. Chem.* 45(18):3813-3815 (2002).
Barnes et al., "Efficacy and Safety of Inhaled Corticosteroids in Asthma—Report of a Workshop Held in Eze, France Oct. 1992," *Am. Rev. Respir. Dis.* 148:S1-S26 (1993).
Bell et al., "Glucokinase mutations insulin secretion, and diabetes mellitus", *Annu. Rev. Physiol.* 58:171-186 (1996).
Bhat et al., "Pyrazolopyrimidine nucleosides. 12. Synthesis and biological activity of certain pyrazolo[3,4-d]pyrimidine nucleosides related to adenosine," *J. Med. Chem.* 24(10):1165-1172 (1981).
Bhatt et al., "Dual inhibition of PI3K and mTOR inhibits autocrine and paracrine proliferative loops in PI3K/Akt/mTOR-addicted lymphomas," *Blood* 115(22):4455-4463 (2010).
Bishop et al., "Generation of monospecific nanomolar tyrosine kinase inhibitors via a chemical genetic approach," *J. Am. Chem. Soc.* 121(4):627-631 (1999).
Blunden et al., "Mycotoxins in food," *Med. Lab. Sci.* 48(4):271-282 (1991).
Bohren et al., "Expression, crystallization and preliminary crystallographic analysis of human carbonyl reductase," *J. Mol. Biol.* 224:659-664 (1994).
Bone et al., "Phosphoinositide 3-kinase signalling regulates early development and developmental haemopoiesis," *J. Cell. Sci.* 120(Pt 10):1752-1762 (2007).
Buitenhuis et al., "The role of the PI3k-PKB signaling module in regulation of hematopoiesis," *Cell Cycle* 8(4):560-566 (2009).
Burger et al., "Phosphoinositide 3'-kinase delta: turning off Bcr signaling in Chronic Lymphocytic Leukemia," *Oncotarget* 2(10):737-738 (2011).
Burger et al., "High-level expression of the T-cell chemokines CCL3 and CCL4 by chronic lymphocytic leukemia B cells in nurselike cell cocultures and after BCR stimulation," *Blood* 113(13):3050-3058 (2009).
Burger, "Inhibiting B-Cell Receptor Signaling Pathways in Chronic Lymphocytic Leukemia," *Curr. Mematol. Malig. Rep.* 7:26-33 (2012).
Byrd et al., "Translating PI3K-Delta Inhibitors to the Clinic in Chronic Lymphocytic Leukemia: The Story of CAL-101 (GS1101)," *ASCO Program Proceedings*, pp. 691-694 (2012).
Camps et al., "Blockade of PI3Kγ suppresses joint inflammation and damage in mouse models of rheumatoid arthritis," *Nat. Med.* 11(9):936-943 (2005).
Chang et al., "The Bruton tyrosine kinase inhibitor PCI-32765 ameliorates autoimmune arthritis by inhibition of multiple effector cells," *Arthritis Research & Therapy* 13:R115 (2011).
Chawla et. al., "Challenges in Polymorphism of Pharmaceuticals," *Current Research & Information on Pharmaceutical Science* 5(1):9-12.
Chiarini et al., "Activity of the Novel Dual Phosphatidylinositol 3-Kinase/Mammalian Target of Rapamycin Inhibitor NVP-BEZ235 against T-Cell Acute Lymphoblastic Leukemia," *Cancer Res.* 70(20):8097-8107 (2010).
Chiarini et al., "Dual Inhibition of Class IA Phosphatidylinositol 3-Kinase and Mammalian Target of Rapamycin as a New Therapeutic Option for T-Cell Acute Lymphoblastic Leukemia," *Cancer Res.* 69(8): 3520-3528 (2009).
Cushing et al., "PI3Kδ and PI3Kγ as Targets for Autoimmune and Inflammatory Diseases," *J. Med. Chem.* 55:8559-8581 (2012).
Dai et al., "Distinct Roles of Phosphoinositide-3 Kinase and Phospholipase Cγ2 in B-Cell Receptor-Mediated Signal Transduction," *Mol. Cell. Biol.* 26(1):88-99 (2006).
Davids et al., "Decreased mitochondrial apoptotic priming underlies stroma-mediated treatment resistance in chronic lymphocytic leukemia," *Blood* 120(17):3501-3509 (2012).
Davis et al., "Chronic active B-cell-receptor signaling in diffuse large B-cell lymphoma," *Nature* 463:88-92 (2010).
De Weers et al., "The Bruton's tyrosine kinase gene is expressed throughout B cell differentiation, from early precursor B cell stages preceding immunoglobulin gene rearrangement up to mature B cell stages," *Eur. J. Immunol.* 23:3109-3114 (1993).
Diederich et al., "In search for specific inhibitors of human 11β-hydroxysteroid-dehydrogenases (11βHSDs): chenodeoxycholic acid selectively inhibits 11β-HSD-I," *Eur. J. Endocrinol.* 142(2):200-207 (2000).
Ding et al., "A combinatorial scaffold approach toward kinase-directed heterocycle libraries," *J. Am. Chem. Soc.* 124(8):1594-1596 (2002).
Ding et al., "A concise and traceless linker strategy toward combinatorial libraries of 2,6,9-substituted purines," *J. Org. Chem.* 66(24):8273-8276 (2001).
Ding et al., "Resin-capture and release strategy toward combinatorial libraries of 2,6,9-substituted purines," *J. Comb. Chem.* 4(2):183-186 (2002).
European Seach Report for EP Application No. 05857011.0 dated Feb. 4, 2011.
Examination Report for GB Application No. GB 0819947.3 dated Oct. 27, 2010.
Fajans et al., "Maturity onset diabetes of the young (MODY)," *Diabet. Med.* 13(9 Suppl 6):S90-S95 (1996).
Feinstein et al., "Regulation of the action of hydrocotisone in airway epithelial cells by 11b-hydroxysteroid dehydrogenase," *Am. J. Respir. Cell. Mol. Biol.* 21(3):403-408 (1999).
Fingl et al., "Chapter 1—General Principles," The Pharmacological Basis of Therapeutics, 5th edition, Goodman and Gilman editors, MacMillan Publishings Co., Inc., New York, pp. 1-46 (1975).
Forrest et al., "Carbonyl Reductase," *Chem. Biol. Interact.* 129(1-2): 21-40 (2000).
Forrest et al., "Induction of a human carbonyl reductase gene located on chromosome 21," *Biochem. Biophys. Acta.* 1048(2-3):149-155 (1990).
Franzen, "The Suzuki, the Heck, and the Stille reaction—three versatile methods for the introduction of new C-C bonds on solid support," *Can. J. Chem.* 78:957-962 (2000).
Funder et al., "Mineralocorticoid action: target tissue specificity is enzyme, not receptor, mediated," *Science* 242:583-585 (1998).
Garber et al., "Diversity of gene expression in adenocarcinoma of the lung," *Proc. Natl. Acad. Sci. U.S.A.* 98(24):13784-13789 (2001).
Gonzalez et al., "Protection against daunorubicin cytotoxicity by expression of a cloned human carbonyl reductase cDNA in K562 leukemia cells," *Cancer Res.* 55(20):4646-4650 (1995).
Gunther et al., "Immunosuppressive effects of dietary wortmannin on rats and mice," *Immunopharmacol. Immunotoxicol.* 11(4):559-570 (1989).
Haase et al., "Detection of viral nucleic acids by in situ hybridization," *Methods in Virology* 7:189-226 (1984).
Hanefeld et al., "One-pot synthesis of tetrasubstituted pyrazoles proof of regiochemistry," *J. Chem. Soc. Perkin 1* 1545-1552 (1996).
Hasselblom et al., "High immunohistochemical expression of p-AKT predicts inferior survival in patients with diffuse large B-cell lymphoma treated with immunochemotherapy," *Brit. J. Haematol.* 149:560-568 (2010).
Haylock-Jacobs et al., "PI3Kδ drives the pathogenesis of experimental autoimmune encephalomyelitis by inhibiting effector T cell apoptosis and promoting Th17 differentiation," *J. Autoimmun.* 36:278-287 (2011).
Herishanu et al., "The lymph node microenvironment promotes B-cell receptor signaling, Nf-κB activation, and tumor proliferation in chronic lymphocytic leukemia," *Blood* 117(2):563-574 (2011).
Hickey et al., "BCR-ABL Regulates Phosphatidylinositol 3-Kinase-p110γ Transcription and Activation and Is Required for Proliferation and Drug Resistance," *J. Biol. Chem.* 281(5):2441-2450 (2006).
Hirsch et al., "CALming Down T Cell Acute Leukemia," *Cancer Cell* 21:449-450 (2012).
Hirsch et al., "Central Role for G Protein-Coupled Phosphoinositide 3-Kinase γ in Inflammation," *Science* 287:1049-1053 (2000).
Hoellenriegel and Burger, "Phosphoinositide 3'-kinase delta: turning off BCR signaling in Chronic Lymphocytic Leukemia," *Oncotarget* 2(10):737-738 (2011).

(56) References Cited

OTHER PUBLICATIONS

Hoellenriegel et al., "The phosphoinositide 3'-kinase delta inhibitor, CAL-101, inhibits B-cell receptor signaling and chemokine networks in chronic lymphocytic leukemia," *Blood* 118(13):3603-3612 (2011).

Hoellenriegel, J. et al., "Phosphoinositide 3'-kinase (PI3K) Delta Inhibition with Cal-101 Blocks B-cell Receptor (BCR) Signaling and the Prosurvival Actions of Nurse-Like Cells (NLC) in Chronic Lymphocytic Leukemia (CLL)," (ASH Annual Meeting 2010).

Honigberg et al., "The Bruton tyrosine kinase inhibitor PCI-32765 blocks B-Cell activation and is efficacious in models of autoimmune disease and B-cell malignancy," *PNAS* 107(29):13075-13080 (2010).

International Search Report and Written Opinion for PCT/US2012/047190 dated Oct. 2, 2012.

International Search Report for PCT/US2007/008395 (4 pages) dated Aug. 27, 2008.

International Search Report for PCT/US2005/042524 (7 pages) dated Oct. 2, 2006.

International Search Report for PCT/US2007/008355 dated Sep. 25, 2008.

Ishiyama et al., "A stoichiometric aromatic C-H borylation catalyzed by iridium(I)/2,2'-bipyridine complexes at room temperature," *Angew. Chem. Int. Ed. Engl.* 41(16):3056-3058 (2002).

Ishiyama et al., "Mild iridium-catalyzed borylation of arenes. High turnover numbers, room temperature reactions, and isolation of a potential intermediate," *J. Am. Chem. Soc.* 124(3):390-391 (2002).

Kallberg et al., "Short-chain dehydrogenase/reductase (SDR) relationships: a large family with eight clusters common to human, animal, and plant genomes," *Protein Sci.* 11(3):636-641 (2002).

Kallberg et al., "Short-Chain Dehydrogenases/Reductases (SDRs)—Coenzyme-Based Functional Assignments in Completed Genomes," *Eur. J. Biochem.* 269(18):4409-4417 (2002).

Kang et al., "Oncogenic transfon lation induced by the p110$\beta$, -$\gamma$, and -$\delta$isoforms of class I phosphoinositide 3-kinase," *PNAS* 103(5):1289-1294 (2006).

Karpeiskii et al., "Pyridoxal-5'-Derivatives of Nucleobases," *Bioorganicheskaya Khimiya.* 11(8):1097-1104 (1985).

Knight et al., "A Pharmacological Map of the PI3-K Family Defines a Role for p110$\alpha$ in Insulin Signaling," *Cell* 125(4):733-747 (2006).

Kraybill et al., "Inhibitor scaffolds as new allele specific kinase substrates," *J. Am. Chem. Soc.* 124(41):12118-12128 (2002).

Kurtova et al., "Diverse marrow stromal cells protect CLL cells from spontaneous and drug-induced apoptosis: development of a reliable and reproducible system to assess stromal cell adhesion-mediated drug resistance," *Blood* 114(20): 4441-4450 (2009).

Kwok et al., "The anti-inflammatory natural product parthenolide from the medicinal herb Feverfew directly binds to and inhibits I$\kappa$B kinase," *Chem. Biol.* 8(8):759-766 (2001).

Lannutti et al., "CAL-101 a p110$\delta$ selective phosphatidylinositol-3-kinase inhibitor for the treatment of B-cell malignancies, inhibits PI3K signaling and cellular viability," *Blood* 117(2):591-594 (2011).

Li et al., "Roles of PLC-$\beta$2 and -$\beta$ and PI3K$\gamma$ in Chemoattractant-Mediated Signal Transduction," *Science* 287:1046-1049 (2000).

Martelli et al., "The emerging role of the phosphatidylinositol 3-kinase/Akt/mammalian target of rapamycin signaling network in normal myelopoiesis and leukemogenesis," *Biochim. Biophys. Acta.* 803:991-1002 (2010).

Martinez et al., "The Molecular Signature of Mantle Cell Lymphoma Reveals Multiple Signals Favoring Cell Survival," *Cancer Res.* 63:8226-8232 (2003).

Martin-Sanchez et al., "PI3K Inhibition As a Potential Therapeutic Strategy Peripheral T-Cell Lymphomas," *Blood (ASH Annual Meeting Abstracts)* 118: in Abstract 3493.

Maxwell et al., "Attenuation of phosphoinositide 3-kinase 6 signaling restrains autoimmune disease," *J. Autoimmun* 38:381-391 (2012).

Mayer et al., "Small molecule inhibitor of mitotic spindle bipolarity identified in a pheontype-cased screen", *Science* 286(5441):971-974 (1999).

Miyaura et al., "Palladium-catalyzed cross-coupling reactions of organoboron compounds," *Chem. Rev.* 95(7):2457-2483 (1995).

Moon et al., "A novel microtubule destabilizing entity from orthogonal synthesis of triazine library and zebrafish embryo screening," *J. Am. Chem. Soc.* 124(39):11608-11609 (2002).

Nakanishi et al., "Cloning and sequence analysis of a cDNA encoding tetrameric carbonyl reductase of pig lung," *Biochem. Biophys. Res. Commun* (3):1311-1316 (1993).

Newman et al., "Solid state analysis of the active pharmaceutical ingredient in drug products," *Drug Discov. Today* 8(19):898-905 (2003).

Nisitani et al., "Posttranscriptional regulation of Bruton's tyrosine kinase expression in antigen receptor-stimulated splenic B cells," *PNAS* 97(6):2737-2742 (2000).

Niswender et al., "Protein engineering of protein kinase a catalytic subunits results in the acquisition of novel inhibitor sensitivity," *J. Biol. Chem.* 277(32):28916-28922 (2002).

Nobel et al., "Purification of full-length recombinant human and rat type 1 11$\beta$-hydroxysteroid dehydrogenases with retained oxidoreductase activities," *Protein Expr. Purif.* 26(3):349-356 (2002).

Norman, "Selective PI3K-delta Inhibitors, A Review of the Patent Literature," *Expert Opinion on Therapeutic Patents* 21(11):1773-1790 (2011).

Oppermann et al., "Forms and functions of human SDR enzymes," *Chem. Biol. Interact.* 130-132(1-3):699-705 (2001).

Persson, "Glucocorticoids for asthma—early contributions," *Pulm. Pharmacol.* 2(3):163-166 (1989).

Petrie et al., "Novel biotinylated adenylate analogue derived from pyrazolo[3,4- d]pyrimidine for labeling DNA probes," *Bioconjug. Chem.* 2(6):441-446 (1991).

Pighi et al., "Phospho-proteomic analysis of mantle cell lymphoma cells suggests a pro-survival role of B-cell receptor signaling," *Cell Oncol. (Dordr)* 34(2):141-153 (2011).

Polak et al., "The PI3K/PKB signaling module as key regulator of hematopoiesis: implications for therapeutic strategies in leukemia," *Blood* 119(4):911-923 (2012).

Pudlo et al., "Synthesis, antiproliferative, and antiviral activity of certain 4-substituted and 4,5 disubstituted 7-[1,3-dihydroxy-2-propoxy)methyl]pyrrolo[2,3-d]pyrimidines," *J. Med. Chem.* 33(7):1984-1992 (1990).

Puri and Gold, "Selective inhibitors of phosphoinositide 3-kinase delta: modulators of B-cell function with potential for treating autoimmune inflammatory disease and B-cell malignancies," *Front. Immunol.* 3:256 (2012).

Quiroga et al., "B-cell antigen receptor signaling enhances chronic lymphocytic leukemia cell migration and survival: specific targeting with a novel spleen tyrosine kinase inhibitor, R406," *Blood* 114(5):1029-1037 (2009).

Report of the Expert Committee on the Diagnosis and Classification of Diabetes Mellitus, *Diabetes Care* 2( Suppl. 1):S5-S19 (1992).

Rizzatti et al., "Gene expression profiling of mantle cell lymphoma cells reveals aberrant expression of genes from the PI3K-AKT, WNT and TGF$\beta$ signaling pathways," *Brit. J. Haematol.* 130:516-526 (2005).

Robertson, "Eicosanoids and human disease", Harrison's Principles of Internal Medicine, Isselbacher K.J. et al. (eds.), vol. 1, pp. 431-435, McGraw-Hill, New York City (1994).

Roller et al., "Blockade of Phosphatidylinositol 3-Kinase (PI3K)$\delta$ or PI3K$\gamma$ Reduces IL-17 and Ameliorates Imiquimod-Induced Psoriasis-like Dermatitis, " *J. Immunol.* 189:4612-4620 (2012).

Romero et al., "Cloning and expression of the bovine 11b-hydroxysteroid dehydrogenase type-2," *J. Steroid Biochem. Mol. Biol.* 72(5):231-237 (2000).

Rommel et al., "PI3K$\delta$ and PI3K$\gamma$: partners in crime in inflammation in rheumatoid arthritis and beyond?" *Nat. Rev. Immunol.* 7:191-201 (2007).

Rudelius et al., "Constitutive activation of Akt contributes to the pathogenesis and survival of mantle cell lymphoma," *Blood* 108(5):1668-1676 (2006).

Sasaki et al., "Function of PI3K$\gamma$ in Thymocyte Development, T Cell Activation, and Neutrophil Migration," *Science* 287:1040-1046 (2000).

Sinclair et al., "Phosphatidylinositol-3 Kinase Delta (PI3K$\delta$) Inhibitor AMG 319 is a Potent, Selective and Orally Bioavailable Small

(56) References Cited

OTHER PUBLICATIONS

Molecule Inhibitor That Suppresses P13K-Mediated Signaling and Viability in Neoplastic B Cells," *Blood (ASH Annual Meeting Abstracts)* 118: Abstract 4964 (2011).

Singer et al., "Optimization of in situ hybridization using isotopic and non-isotopic detection methods," *Biotechniques* 4(3):230-250 (1986).

Smith et al., "Expression of Bruton's Agammaglobulinemia Tyrosine Kinase Gene, BTK, is Selectively Down-Regulated in T Lymphocytes and Plasma Cells," *J. Immunol.* 152:557-565 (1994).

Soldan et al., "Induction of daunorubicin carbonyl reducing enzymes by daunorubicin in sensitive and resistant pancreas carcinoma cells," *Biochem. Pharmacol.* 51(2):117-123(1996).

Soond et al., "PI3K p110δ regulates T-cell cytokine production during primary and secondary immune responses in mice and humans," *Blood* 115(11):2203-2213 (2010).

Srinivasan et al., "PI3 Kinase Signals BCR-Dependent Mature B Cell Survival," *Cell* 139:573-586 (2009).

Subramaniam et al., "Targeting Nonclassical Oncogenes for Therapy in T-ALL," *Cancer Cell* 21:459-472 (2012).

Sujobert et al., "Essential role for the p110δ isoform in phosphoinositide 3-kinase activation and cell proliferation in acute myeloid leukemia," *Blood* 106(3):1063-1066 (2005).

Supplementary European Search Report for EP Application No. 07754845.1 (4 pages) dated Feb. 24, 2010.

Tanaka et al., "An unbiased cell morphology-based screen for new, biologically active small molecules," *PLoS Biol.* 3(5):0764-0776 (2005).

Tyukavkina et al., Bioorganicheskaya Khimiya, Moskva, DROFA, pp. 83-85 (2004).

Uddin et al., "Role of phosphatidylinositol 3'-kinase/Akt pathway in diffuse large B-cell lymphoma survival," *Blood* 108(13):4178-4186 (2006).

Ugarkar et al., "Adenosine kinase inhibitors. 2. Synthesis, enzyme inhibition, and antiseizure activity of diaryltubercidin analogues," *J. Med. Chem.* 43(15):2894-2905 (2000).

Vippagunta et al., "Crystalline Solids," *Adv. Drug Deliv. Rev.* 48(1):3-26 (2001).

Wahlstrom et al., "Aberrant MAPK and PI3K Signaling Contribute to Chemotherapy Resistance in T Cell Acute Lymphoblastic Leukemia by Altering the Balance of Apoptosis Mediators," *Blood (Ash Annual Meeting Abstracts)* 118: Abstract 3490 (2011).

White et al., "11δ-Hydroxysteroid Dehyrdogenase and the Syndrome of Apparent Mineralocorticoid Excess," *Endocr. Rev.* 18(1):135-156 (1997).

Widler et al., "7-alkyl- and 7-Cycloalky1-5-aryl-pyrrolo[2,3-d]pyrimidines- potent inhibitors of the tyrosine kinase c-Src," *Bioorg. Med. Chem. Lett.* 11(6):849-852 (2001).

Wolff, Burger's Medicinal Chemistry, $5^{th}$ ed., Part 1, pp. 975-977, John Wiley & Sons (1995).

Barber et al., "PI3Kgamma inhibition blocks glomerulonephritis and extends lifespan in a mouse model of systemic lupus," *Nat. Med.* 11(9):933-935 (2005). (Epub Aug. 28, 2005).

\* cited by examiner

CERTAIN CHEMICAL ENTITIES, COMPOSITIONS AND METHODS

This application is a §371 national phase application of International Patent Application No. PCT/US2009/000042, filed on Jan. 5, 2009, which is a continuation-in-part of International Patent Application No. PCT/US2009/000038, filed on Jan. 5, 2009, and which claims the benefit of U.S. Provisional Application Ser. Nos. 61/009,971, filed on Jan. 4, 2008, 61/194,294, filed on Sep. 26, 2008, and 61/201,146, filed on Dec. 5, 2008, each of which is hereby incorporated by reference in its entirety.

BACKGROUND OF THE INVENTION

The activity of cells can be regulated by external signals that stimulate or inhibit intracellular events. The process by which stimulatory or inhibitory signals are transmitted into and within a cell to elicit an intracellular response is referred to as signal transduction. Over the past decades, cascades of signal transduction events have been elucidated and found to play a central role in a variety of biological responses. Defects in various components of signal transduction pathways have been found to account for a vast number of diseases, including numerous forms of cancer, inflammatory disorders, metabolic disorders, vascular and neuronal diseases (Gaestel et al. *Current Medicinal Chemistry* (2007) 14:2214-2234).

Kinases represent a class of important signaling molecules. Kinases can generally be classified into protein kinases and lipid kinases, and certain kinases exhibit dual specificities. Protein kinases are enzymes that phosphorylate other proteins and/or themselves (i.e., autophosphorylation). Protein kinases can be generally classified into three major groups based upon their substrate utilization: tyrosine kinases which predominantly phosphorylate substrates on tyrosine residues (e.g., erb2, PDGF receptor, EGF receptor, VEGF receptor, src, abl), serine/threonine kinases which predominantly phosphorylate substrates on serine and/or threonine residues (e.g., mTor C1, mTor C2, ATM, ATR, DNA-PK, Akt), and dual-specificity kinases which phosphorylate substrates on tyrosine, serine and/or threonine residues.

Lipid kinases are enzymes that catalyze the phosphorylation of lipids. These enzymes, and the resulting phosphorylated lipids and lipid-derived biologically active organic molecules, play a role in many different physiological processes, including cell proliferation, migration, adhesion, and differentiation. Certain lipid kinases are membrane associated and they catalyze the phosphorylation of lipids contained in or associated with cell membranes. Examples of such enzymes include phosphoinositide(s) kinases (such as PI3-kinases, PI4-Kinases), diacylglycerol kinases, and sphingosine kinases.

The phosphoinositide 3-kinases (PI3Ks) signaling pathway is one of the most highly mutated systems in human cancers. PI3K signaling is also a key factor in many other diseases in humans. PI3K signaling is involved in many disease states including allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

PI3Ks are members of a unique and conserved family of intracellular lipid kinases that phosphorylate the 3'-OH group on phosphatidylinositols or phosphoinositides. The PI3K family comprises 15 kinases with distinct substrate specificities, expression patterns, and modes of regulation (Katso et al., 2001). The class I PI3Ks (p110α, p110β, p110δ, and p110γ) are typically activated by tyrosine kinases or G-protein coupled receptors to generate PIP3, which engages downstream effectors such as those in the Akt/PDK1 pathway, mTOR, the Tec family kinases, and the Rho family GTPases. The class II and III PI3-Ks play a key role in intracellular trafficking through the synthesis of PI(3)P and P1(3,4)P2. The PIKKs are protein kinases that control cell growth (mTORC1) or monitor genomic integrity (ATM, ATR, DNA-PK, and hSmg-1).

The delta (δ) isoform of class I PI3K has been implicated, in particular, in a number of diseases and biological processes. PI3K δ is expressed primarily in hematopoietic cells including leukocytes such as T-cells, dendritic cells, neutrophils, mast cells, B-cells, and macrophages. PI3K δ is integrally involved in mammalian immune system functions such as T-cell function, B-cell activation, mast cell activation, dendritic cell function, and neutrophil activity. Due to its integral role in immune system function, PI3K δ is also involved in a number of diseases related to undesirable immune response such as allergic reactions, inflammatory diseases, inflammation mediated angiogenesis, rheumatoid arthritis, auto-immune diseases such as lupus, asthma, emphysema and other respiratory diseases. Other class I PI3K involved in immune system function includes PI3K γ, which plays a role in leukocyte signaling and has been implicated in inflammation, rheumatoid arthritis, and autoimmune diseases such as lupus.

Downstream mediators of the PI3K signal transduction pathway include Akt and mammalian target of rapamycin (mTOR). Akt possesses a plckstrin homology (PH) domain that binds PIP3, leading to Akt kinase activation. Akt phosphorylates many substrates and is a central downstream effector of PI3K for diverse cellular responses. One important function of Akt is to augment the activity of mTOR, through phosphorylation of TSC2 and other mechanisms. mTOR is a serine-threonine kinase related to the lipid kinases of the PI3K family. mTOR has been implicated in a wide range of biological processes including cell growth, cell proliferation, cell motility and survival. Disregulation of the mTOR pathway has been reported in various types of cancer. mTOR is a multifunctional kinase that integrates growth factor and nutrient signals to regulate protein translation, nutrient uptake, autophagy, and mitochondrial function.

As such, kinases, particularly PI3Ks are prime targets for drug development. There remains a need for PI3K inhibitors suitable for drug development. The present invention addresses this need and provides related advantages as well by providing new classes of kinase inhibitors.

SUMMARY OF THE INVENTION

In a first aspect of the invention, compounds are provided which are of Formula I, or their pharmaceutically acceptable salts thereof, wherein

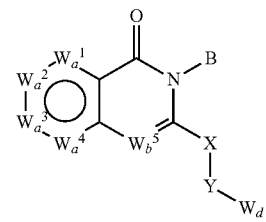

Formula 1

$W_a^1$ is $CR^3$ or N; $W_a^2$ is $CR^5$ or N; $W_a^3$ is $CR^6$ or N; $W_a^4$ is N or $CR^7$; $W_b^5$ is $CR^a$, $CHR^8$, or N, wherein no more than two adjacent ring atoms selected from $W_a^1$, $W_a^2$, $W_a^3$, $W_a^4$, and $W_b^5$ are heteroatoms. $W_d$ is heterocycloalkyl, aryl or heteroaryl. B is alkyl, amino, heteroalkyl, cycloalkyl, heterocycloalkyl, or a moiety of Formula II;

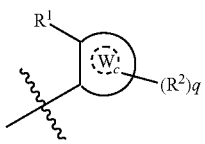

Formula II wherein $W_c$ is aryl, heteroaryl, heterocycloalkyl, or cycloalkyl, and q is an integer of 0, 1, 2, 3, or 4. X is absent or is —$(CH(R^9))_z$— and each instance of z is independently an integer of 1, 2, 3, or 4. Y is absent, —O—, —S—, —S(=O)—, —S(=O)$_2$—, —N($R^9$)—, —C(=O)—(CHR$^9$)$_z$—, —C(=O)—, —N($R^9$)—C(=O)—, or —N($R^9$)—C(=O)NH—, —N($R^9$)C($R^9$)$_2$—, or —C(=O)—(CHR$^9$)$_z$—; wherein when $W_b^5$ is N, no more than one of X or Y is absent. $R^1$ is hydrogen, alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, halo, cyano, hydroxy, nitro, phosphate, urea, or carbonate. $R^2$ is alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, halo, cyano, hydroxy, nitro, phosphate, urea, or carbonate. $R^3$ is hydrogen, alkyl, alkenyl, alkynyl, cycloalkyl, heterocycloalkyl, alkoxy, amido, amino, acyl, acyloxy, sulfonamido, halo, cyano, hydroxy or nitro. $R^5$, $R^6$, $R^7$, and $R^8$ are independently hydrogen, $C_1$-$C_4$alkyl, $C_2$-$C_5$alkenyl, $C_2$-$C_5$alkynyl, $C_3$-$C_5$cycloalkyl, heterocycloalkyl, $C_1$-$C_4$heteroalkyl, $C_1$-$C_4$amido, amino, acyl, $C_1$-$C_4$acyloxy, $C_1$-$C_4$sulfonamido, halo, cyano, hydroxy or nitro. Each instance of $R^9$ is independently hydrogen, $C_1$-$C_{10}$alkyl, $C_3$-$C_7$cycloalkyl, or $C_2$-$C_{10}$heteroalkyl.

In another aspect of the invention, compounds are provided which are of Formula IX or their pharmaceutically acceptable salts thereof, wherein

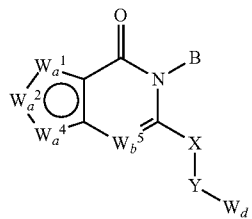

Formula IX $W_a^1$ and $W_a^2$ are independently $CR^5$, S, N, or $NR^4$, and $W_a^4$ is independently $CR^7$, S, N, or $NR^4$ wherein no more than two adjacent ring atoms are nitrogen or sulfur, and when $W_a^1$ is S, one of $W_a^2$ and $W_a^4$ is N or $NR^4$. $W_b^5$ is $CR^8$, N, or $NR^8$. B is alkyl, amino, heteroalkyl, cycloalkyl, heterocycloalkyl, or a moiety of Formula II:

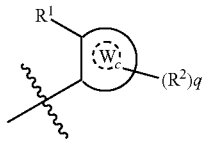

Formula II wherein $W_c$ is aryl, heteroaryl, heterocycloalkyl, or cycloalkyl, and q is an integer of 0, 1, 2, 3, or 4. $W_d$ is absent or is a heterocycloalkyl, aryl or heteroaryl moiety. X is absent or is —$(CH(R^9))_z$— and each instance of z independently is an integer of 1, 2, 3, or 4. Y is absent, —O—, —S—, —S(=O)—, —S(=O)2-, —N(R9)-, —C(=O)—(CHR9)z-, —C(=O)—, —N(R9)-C(=O)—, or —N(R9)-C(=O)NH—, —N(R9)C(R9)2-, or —C(=O)—(CHR9)z-. $R^1$ is hydrogen, alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, halo, cyano, hydroxy, nitro, phosphate, urea, or carbonate. $R^2$ is alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, halo, cyano, hydroxy, nitro, phosphate, urea, or carbonate. $R^3$ is hydrogen, alkyl, alkenyl, alkynyl, cycloalkyl, heterocycloalkyl, alkoxy, amido, amino, acyl, acyloxy, sulfonamido, halo, cyano, hydroxy or nitro. $R^4$ is hydrogen, acyl, $C_1$-$C_4$alkyl, $C_2$-$C_5$alkenyl, $C_2$-$C_5$alkynyl, $C_3$-$C_5$cycloalkyl, or $C_1$-$C_4$heteroalkyl; $R^5$, $R^7$, and $R^8$ are independently hydrogen, $C_1$-$C_4$alkyl, $C_2$-$C_5$alkenyl, $C_2$-$C_5$alkynyl, $C_3$-$C_5$cycloalkyl, $C_1$-$C_4$heteroalkyl, acyl, $C_1$-$C_4$amido, amino, $C_1$-$C_4$acyloxy, $C_1$-$C_4$sulfonamido, halo, cyano, hydroxy or nitro. Each instance of $R^9$ is independently hydrogen, $C_1$-$C_{10}$alkyl, $C_3$-$C_7$cycloalkyl, or $C_2$-$C_{10}$heteroalkyl.

In some embodiments, the compound of Formula I has a structure of Formula IV:

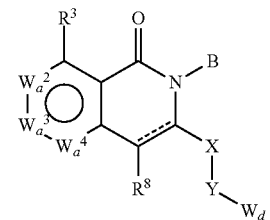

Formula IV

In some embodiments a compound of Formula IV is of Formula V or VI:

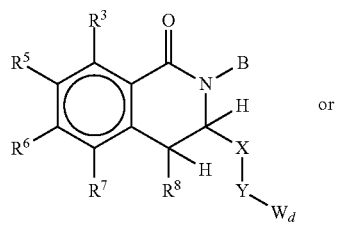

Formula V

In some embodiments, the compound of Formula VI has the structure of Formula VI-A:

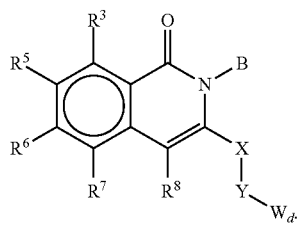

Formula VI

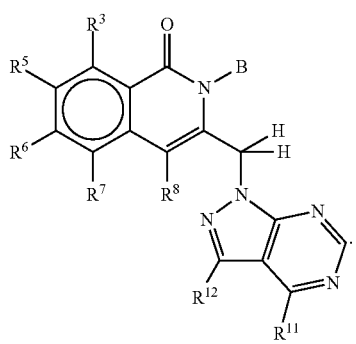

Formula VI-A

In some embodiments of the compound of Formula VI-A, $R^{11}$ is amino. In some embodiments of the compound of Formula VI-A, $R^{12}$ is alkyl, alkenyl, alkynyl, heteroaryl, aryl, heterocycloalkyl, cyano, amino, carboxylic acid, or amido. In some embodiments of the compound of Formula VI-A, $R^{12}$ is a monocyclic heteroaryl or a bicyclic heteroaryl.

In some embodiments of the compound of Formula VI, the compound has the structure of Formula VI-C:

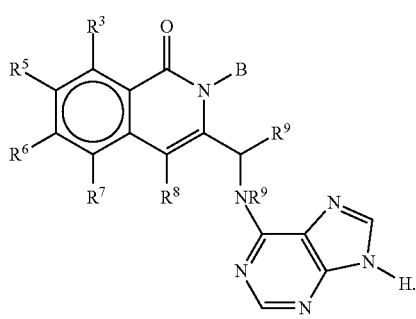

Formula VI-C

In some of the embodiments of Formula VI, the compound has a structure of Formula VI-D;

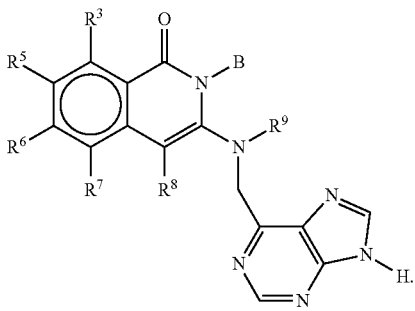

Formula VI-D

In another aspect of the invention a compound or its pharmaceutically acceptable salts having the structure of Formula VI is provided, wherein: B is alkyl, amino, heteroalkyl, or a moiety of Formula II; wherein $W_c$ is aryl, heteroaryl, heterocycloalkyl, or cycloalkyl, and q is an integer of 0, 1, 2, 3, or 4; X is absent or —(CH($R^9$))$_z$— and z is an integer of 1, 2, 3, or 4; Y is absent, —N($R^9$)—, or —N($R^9$)—CH($R^9$)—; $W_d$ is:

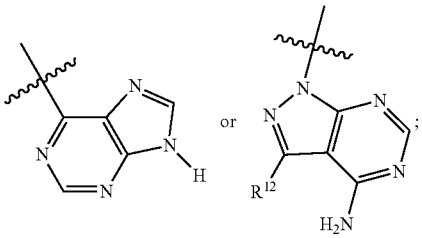

$R^1$ is hydrogen, alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, halo, cyano, hydroxy, nitro, phosphate, urea, or carbonate; $R^2$ is alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, halo, cyano, hydroxy, nitro, or phosphate;

$R^3$ is hydrogen, alkyl, alkenyl, alkynyl, cycloalkyl, heterocycloalkyl, alkoxy, amido, amino, acyl, acyloxy, alkoxycarbonyl, sulfonamido, halo, cyano, hydroxy, nitro, aryl or heteroaryl; each instance of $R^9$ is independently hydrogen, $C_1$-$C_{10}$alkyl, $C_3$-$C_7$cycloalkyl, heterocycloalkyl, or $C_2$-$C_{10}$heteroalkyl; and $R^{12}$ is H, alkyl, alkynyl, alkenyl, halo, aryl, heteroaryl, heterocycloalkyl, cycloalkyl, cyano, amino, carboxylic acid, alkoxycarbonyl or amido.

In some embodiments, the compound of Formula VI has the structure of Formula 6-A:

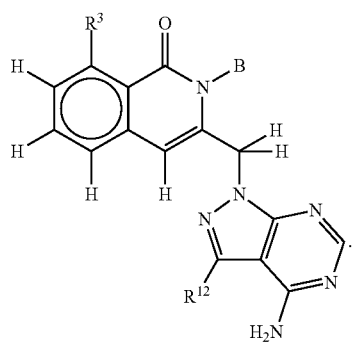

Formula 6-A

In some embodiments, the compound of Formula VI has the structure of Formula 6-C1:

Formula 6-C1

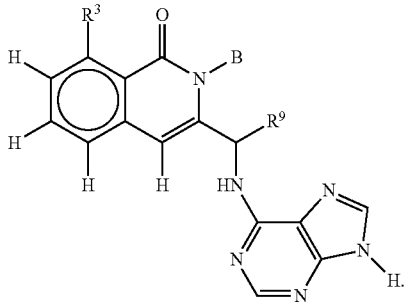

In some embodiments, the compound of Formula VI has the structure of Formula 6-C2:

Formula 6-C2

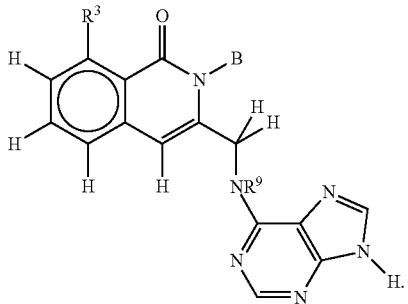

In some embodiments, the compound of Formula VI has the structure of Formula 6-D:

Formula 6-D

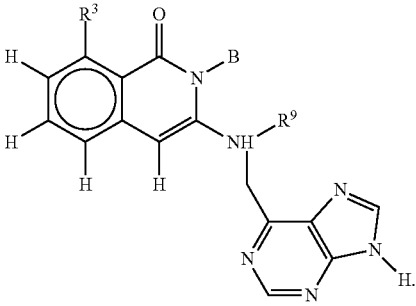

In some embodiments a compound of Formula I is of Formula VII:

Formula VII

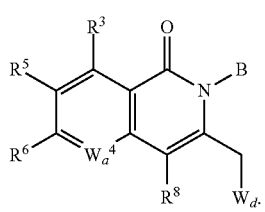

In some embodiments, the compound of Formula I has a structure of Formula VIII:

Formula VIII

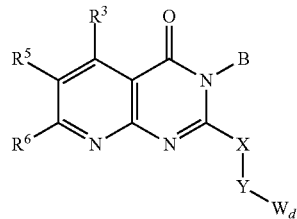

where X is absent and Y is —O—, —S—, —S(=O)—, —S(=O)$_2$—, —N(R$^9$)—, —C(=O)—(CHR$^9$)$_z$—, —C(=O)—, —N(R$^9$)(C=O)—, or —N(R$^9$)(C=O)NH—; or X is —(CH(R$^9$))$_z$—, and Y is absent; or X is —(CH(R$^9$))$_z$—, and Y is O—, —S—, —S(=O)—, —S(=O)$_2$—, —N(R$^9$)—, —C(=O)—(CHR$^9$)$_z$—, —C(=O)—, —N(R$^9$)—C(=O)—, or —N(R$^9$)—C(=O)NH—, —N(R$^9$)C(R$^9$)$_2$—, or —C(=O)—(CHR$^9$)$_z$. Each instance of z independently is an integer of 1, 2, 3, or 4. $W_d$ is bicyclic aryl or bicyclic heteroaryl.

In some embodiments of the compound of Formula IX, the compound has a structure which is a member of the group consisting of: (i) $W_a^1$ is NR$^4$, $W_a^2$ is CR$^5$, $W_a^4$ is CR$^7$, and $W_b^5$ is CR$^8$; (ii) $W_a^1$ is NR$^4$, $W_a^2$ is CR$^5$, $W_a^4$ is CR$^7$, and $W_b^5$ is CHR$^8$; (iii) $W_a^1$ is NR$^4$, $W_a^2$ is CR$^5$, $W_a^4$ is CR$^7$, and $W_b^5$ is N; (iv) $W_a^1$ is NR$^4$, $W_a^2$ is CR$^5$, $W_a^4$ is CR$^7$, and $W_b^5$ is NR$^8$; (v) $W_a^1$ is NR$^4$, $W_a^2$ is N, $W_a^4$ is CR$^7$, and $W_b^5$ is CR$^8$; (vi) $W_a^1$ is NR$^4$, $W_a^2$ is N, $W_a^4$ is CR$^7$, and $W_b^5$ is CHR$^8$; (vii) $W_a^1$ is NR$^4$, $W_a^2$ is N, $W_a^4$ is CR$^7$, and $W_b^5$ is N; (viii) $W_a^1$ is NR$^4$, $W_a^2$ is N, $W_a^4$ is CR$^7$, and $W_b^5$ is NR$^8$; (ix) $W_a^1$ is NR$^4$, $W_a^2$ is CR$^5$, $W_a^4$ is N, and $W_b^5$ is CR$^8$; (x) $W_a^1$ is NR$^4$, $W_a^2$ is CR$^5$, $W_a^4$ is N, and $W_b^5$ is CHR$^8$; (xi) $W_a^1$ is NR$^4$, $W_a^2$ is CR$^5$, $W_a^4$ is N, and $W_b^5$ is N; (xii) $W_a^1$ is NR$^4$, $W_a^2$ is CR$^5$, $W_a^4$ is N, and $W_b^5$ is NR$^8$; (xiii) $W_a^1$ is S, $W_a^2$ is CR$^5$, $W_a^4$ is N, and $W_b^5$ is CR$^8$; (xiv) $W_a^1$ is S, $W_a^2$ is CR$^5$, $W_a^4$ is N, and $W_b^5$ is CHR$^8$; (xv) $W_a^1$ is S, $W_a^2$ is CR$^5$, $W_a^4$ is N, and $W_b^5$ is N; (xvi) $W_a^1$ is S, $W_a^2$ is CR$^5$, $W_a^4$ is N, and $W_b^5$ is NR$^8$; (xvii) $W_a^1$ is N, $W_a^2$ is CR$^5$, $W_a^4$ is S, and $W_b^5$ is CR$^8$; (xviii) $W_a^1$ is N, $W_a^2$ is CR$^5$, $W_a^4$ is S, and $W_b^5$ is CHR$^8$; (xix) $W_a^1$ is N, $W_a^2$ is CR$^5$, $W_a^4$ is S, and $W_b^5$ is N; (xx) $W_a^1$ is N, $W_a^2$ is CR$^5$, $W_a^4$ is S, and $W_b^5$ is NR$^8$; (xxi) $W_a^1$ is CR$^5$, $W_a^2$ is N, $W_a^4$ is S, and $W_b^5$ is CR$^8$; (xxi) $W_a^1$ is CR$^5$, $W_a^2$ is N, $W_a^4$ is S, and $W_b^5$ is CHR$^8$; (xxii) $W_a^1$ is CR$^5$, $W_a^2$ is N, $W_a^4$ is S, and $W_b^5$ is N; (xxiii) $W_a^1$ is CR$^5$, $W_a^2$ is N, $W_a^4$ is S, and $W_b^5$ is NR$^8$; (xxiv) $W_a^1$ is S, $W_a^2$ is N, $W_a^4$ is CR$^7$, and $W_b^5$ is CR$^8$; (xxv) $W_a^1$ is S, $W_a^2$ is N, $W_a^4$ is CR$^7$, and $W_b^5$ is CHR$^8$; (xxvi) $W_a^1$ is S, $W_a^2$ is N, $W_a^4$ is CR$^7$, and $W_b^5$ is N; (xxvii) $W_a^1$ is S, $W_a^2$ is N, $W_a^4$ is CR$^7$, and $W_b^5$ is NR$^8$; (xxviii) $W_a^1$ is CR$^5$, $W_a^2$ is N, $W_a^4$ is NR$^4$, and $W_b^5$ is CR$^8$; (xxix) $W_a^1$ is CR$^5$, $W_a^2$ is N, $W_a^4$ is NR$^4$, and $W_b^5$ is CHR$^8$; (xxx) $W_a^1$ is CR$^5$, $W_a^2$ is N, $W_a^4$ is NR$^4$, and $W_b^5$ is N; (xxxi) $W_a^1$ is CR$^5$, $W_a^2$ is N, $W_a^4$ is NR$^4$, and $W_b^5$ is NR$^8$; (xxxii) $W_a^1$ is CR$^5$, $W_a^2$ is CR$^5$, $W_a^4$ is S, and $W_b^5$ is CHR$^8$; (xxxiii) $W_a^1$ is CR$^5$, $W_a^2$ is CR$^5$, $W_a^4$ is S, and $W_b^5$ is CR$^8$; (xxxiv) $W_a^1$ is CR$^5$, $W_a^2$ is CR$^5$, $W_a^4$ is S, and $W_b^5$ is N; and (xxxv) $W_a^1$ is CR$^5$, $W_a^2$ is CR$^5$, $W_a^4$ is S, and $W_b^5$ is NR$^8$.

In some embodiments of the invention, the compound of Formula IX is of Formula X:

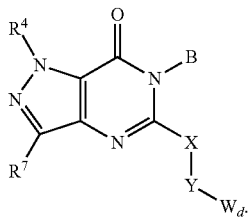

Formula X

In some embodiments of the invention, the compound of Formula IX is the compound wherein $R^4$ is $C_1$-$C_4$alkyl or $C_3$-$C_5$cycloalkyl. In some embodiments of the invention, the compound of Formula IX is the compound wherein $R^4$ is methyl or ethyl.

In some embodiments of the invention, the compound of Formula IX is the compound of Formula XI:

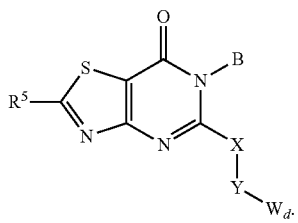

Formula XI

In some embodiments of the invention, the compound of Formula IX is the compound of Formula XII:

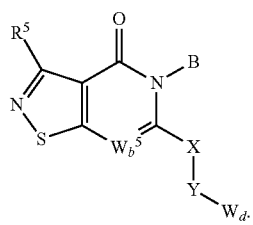

Formula XII

In some embodiments of the invention, the compound of Formula VIII is the compound of Formula XII or XIII

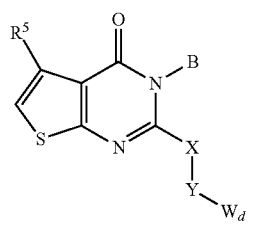

Formula XIII

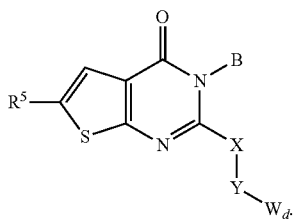

Formula XIV

In some embodiments of the invention, the compound of Formula I, IV, V, VI, VI-A, VI-C, VI-D, 6-A, 6-C1, 6-C2, 6-D, VII, VIII, IX, X, XI, XII, XIII, or XIV is the compound wherein B is a member of the group consisting of a moiety of Formula II, wherein $W_c$ is aryl including but not limited to substituted phenyl, heteroaryl including but not limited to monocyclic heteroaryl, heterocycloalkyl, or cycloalkyl, heterocycloalkyl, alkyl, including but not limited to a moiety having the formula —$(CH_2)_2$—$NR^aR^a$, wherein each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, or —$NR^aR^a$ are combined together to form a cyclic moiety.

In some embodiments of the invention, the compound of Formula I, IV, V, VI, VI-A, VI-C, VI-D, 6-A, 6-C1, 6-C2, 6-D, VII, VIII, IX, X, XI, XII, XIII, or XIV is the compound wherein $R^1$ is H, —F, —Cl, —CN, —$CH_3$, isopropyl, —$CF_3$, —$OCH_3$, nitro, or phosphate.

In some embodiments of the invention, the compound of Formula I, IV, V, VI, VI-A, VI-C, VI-D, 6-A, 6-C1, 6-C2, 6-D, VII, VIII, IX, X, XI, XII, XIII, or XIV is the compound wherein $R^2$ is a alkyl, halo, hydroxy, cyano, nitro, or phosphate and q is 1 or 2.

In some embodiments of the invention, the compound of Formula I, IV, V, VI, VI-A, VI-C, VI-D, 6-A, 6-C1, 6-C2, 6-D, VII, or VIII is the compound wherein $R^3$ is —H, halo including but not limited to —Cl or —F, alkyl including but not limited to —$CH_3$ or —$CH_2CH_3$, alkoxy, cycloalkyl, or —$CF_3$.

In some embodiments of the invention, the compound of Formula IX, or X, $R^4$ is selected from —H, methyl, ethyl, n-propyl, iso-propyl, cyclopropyl, cyclobutyl, and cyclopentyl.

In some embodiments of the invention, the compound of Formula I, IV, V, VI, VI-A, VI-C, VI-D, VII, VIII, IX, XI, XII, XIII or XIV is the compound wherein $R^5$ is H, —CN, —$NH_2$, $C_1$-$C_4$alkyl, $C_1$-$C_4$alkoxy, —$CF_3$, $NO_2$, —$CH_3$, —$CH_2CH_3$, —$OCH_3$, —$OCH_2CH_3$, or halo, which includes but is not limited to —Cl or —F.

In some embodiments of the invention, the compound of Formula I, IV, V, VI, VI-A, VI-C, VI-D, VII, or VIII is the compound wherein $R^6$ is H, —CN, —$NH_2$, $C_1$-$C_4$alkyl, $C_1$-$C_4$alkoxy, —$CF_3$, $NO_2$, —$CH_3$, or halo.

In some embodiments of the invention, the compound of Formula I, IV, V, VI, VI-A, VI-C, VI-D, VII, VIII, IX, or X is the compound wherein $R^7$ is H, —CN, —$NH_2$, $C_1$-$C_4$alkyl, $C_1$-$C_4$alkoxy, —$CF_3$, $NO_2$, —$CH_3$, —$CH_2CH_3$, —$OCH_3$, —$OCH_2CH_3$, or halo.

In some embodiments of the invention, the compound of Formula I, IV, V, VI, VI-A, VI-C, VI-D, VII, IX, or XII is the compound wherein $R^8$ is H, —CN, —$NH_2$, $C_1$-$C_4$alkyl, $C_1$-$C_4$alkoxy, —$CF_3$, $NO_2$, —$CH_3$, —$CH_2CH_3$, —$OCH_3$, —$OCH_2CH_3$, or halo.

In some of the embodiments of Formula I, IV, VI, or VII, $R^5$, $R^6$, $R^7$, and $R^8$ are hydrogen.

In some embodiments of the invention, the compound of Formula I, IV, V, VI, VI-A, VI-C, VI-D, VII, VIII, IX, X, XI, XII, XIII or XIV is the compound wherein X is —$CH_2$—, —$CH(CH_2CH_3)$— or —$CH(CH_3)$—, including but not limited wherein —$CH(CH_2CH_3)$— or —$CH(CH_3)$— is in a (S) or (R) stereochemical configuration. In some embodiments of the invention, the compound of Formula I, IV, V, VI, VII, VIII, IX, X, XI, XII, XIII or XIV is the compound wherein Y is absent, —O—, —$NH(R^9)$—, or —$S(=O)_2$—. In some embodiments of the invention, the compound of Formula I, IV, V, VI, VII, VIII, IX, X, XI, XII, XIII or XIV is the compound wherein $R^9$ is methyl or hydrogen. In some embodiments of the invention, the compound of Formula I, IV, V, VI, VII, VIII, IX, X, XI, XII, XIII or XIV is the compound wherein X—Y is —CH₂N(CH₃), —CH₂—N (CH₂CH₃), —CH(CH₃)NH—, —CH(CH₂CH₃)—NH—, —N(H)CH₂—, —N(CH₂CH₃)CH₂— or —N(CH₃)CH₂—, including but not limited to —CH(CH₃)NH— or —CH (CH₂CH₃)—NH having a (S) or (R) stereochemical configuration.

In some embodiments of the invention, the compound of Formula I, IV, V, VI, VII, VIII, IX, X, XI, XII, XIII or XIV is the compound wherein $W_d$ is pyrazolopyrimidine including but not limited to 4-amino-1H-pyrazolo[3,4-d]pyrimidin-1-yl or 7-amino-2-methyl-2H-pyrazolo[4,3-d]pyrimidin-3-yl, purine including but not limited to 6-amino-9H-purin-9-yl or 6-methylenyl-9H-purin-6-yl. In some embodiments of the invention, the compound of Formula I, IV, V, VI, VII, VIII, IX, X, XI, XII, XIII or XIV is the compound wherein the pyrazolopyrimidine is of Formula III:

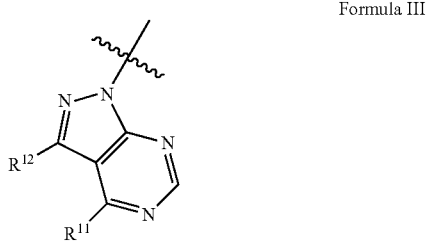

Formula III wherein $R^{11}$ is H, alkyl, halo, amino, amido, hydroxy, or alkoxy, and $R^{12}$ is H, alkyl, alkynyl, alkenyl, halo, aryl, heteroaryl including but not limited to monocyclic or bicyclic heteroaryl, heterocycloalkyl, cycloalkyl, cyano, amino, carboxylic acid, alkoxycarbonyl, or amido.

In another aspect of the invention, a method of inhibiting a phosphatidyl inositol-3 kinase (PI3 kinase), is provided comprising: contacting the PI3 kinase with an effective amount of one or more compounds disclosed herein. For instance, the step of contacting involves the use of one or more compounds of Formula I, IV, V, VI, VII, VIII, IX, X, XI, XII, XIII, and/or XIV. In some embodiments, the step of contacting comprises contacting a cell that contains said PI3 kinase. In some embodiments of the method, the inhibition takes place in a subject suffering from a disorder involving malfunctioning of one or more types of PI3 kinase. Some exemplary diseases involving malfunctioning of PI3 kinases are selected from the group consisting of autoimmune diseases, rheumatoid arthritis, respiratory disease, and various types of cancers. Where desired, the compound used in the method has the structure of Formula 6-A, wherein $R^{11}$ is amino and $R^{12}$ is substituted phenyl.

In some embodiments of the method, the inhibition takes place in a subject suffering from rheumatoid arthritis or a respiratory disease, and wherein the compound has the structure of Formula 6-A, and wherein $R^{11}$ is amino and $R^{12}$ is bicyclic heteroaryl.

In some embodiments, the method comprises administering a second therapeutic agent to the subject.

In yet another aspect, the present invention provides a method of treating a disease manifesting an undesired immune response. The method comprises the step of administering to a subject in need thereof, one or more compounds disclosed herein including compounds of Formula I, IV, V, VI, VII, VIII, IX, X, XI, XII, XIII, and/or XIV, in an amount that is effective in ameliorating said undesired immune response. In some embodiments, the one or more compounds inhibit T-cell independent B-cell activation as evidenced by a reduction in production of anti-TNP IgG3 by at least about five folds when administered in an amount less than about 30 mg/kg BID dose to a test animal.

In some embodiments, the disease treated is associated with swelling or pain of a joint of a subject. The method can be effective in ameliorating one or more rheumatoid arthritis symptoms as evidenced by reduction in mean joint diameter by at least about 10% after 17 days and/or reduction in ankle diameter by at least 5-10% or more after several days to weeks of treatment, including for example reduction in ankle diameter by at least 5% after 7 days of treatment. In another embodiment, the undesired immune response is evidenced by enhanced production of anti-type II collagen antibodies, and the use of one or more subject compounds reduces the serum anti-type II collagen level at an ED50 of less than about 10 mg/kg.

In another aspect of the invention, a composition is provided which comprises a pharmaceutically acceptable excipient and one or more compounds of Formula I, IV, V, VI, VII, VIII, IX, X, XI, XII, XIII and/or XIV. In some of the embodiments of the invention, the composition is a liquid, solid, semi-solid, gel, or an aerosol form.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
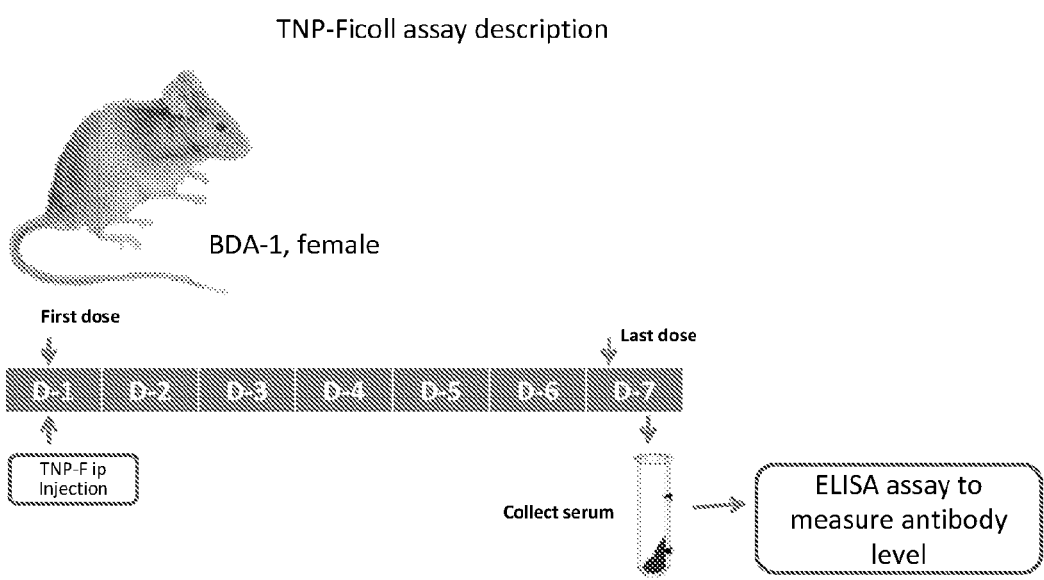
FIG. 1 depicts an exemplary protocol for measuring T-cell independent production of TNP specific antibodies in vivo.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the appended claims define the scope of the invention and that methods and structures within the scope of these claims and their equivalents be covered thereby.

Unless defined otherwise, all technical and scientific terms used herein have the same meaning as is commonly understood by one of skill in the art to which this invention belongs. All patents and publications referred to herein are incorporated by reference.

As used in the specification and claims, the singular form "a", "an" and "the" includes plural references unless the context clearly dictates otherwise.

As used herein, "agent" or "biologically active agent" refers to a biological, pharmaceutical, or chemical compound or other moiety. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g. bind to) the target, compounds that initiate or enhance a biological activity of the target polypeptide by interacting with other members of the signal transduction pathway of which the target polypeptide is a member are also specifically included within this definition.

The terms "antagonist" and "inhibitor" are used interchangeably, and they refer to a compound having the ability to inhibit a biological function of a target protein, whether by inhibiting the activity or expression of the target protein. Accordingly, the terms "antagonist" and "inhibitors" are defined in the context of the biological role of the target protein. While preferred antagonists herein specifically interact with (e.g. bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor, or an undesired immune response as manifested in autoimmune disease.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation" refers to a phenomenon by which the cell number has changed as a result of division. This term also encompasses cell growth by which the cell morphology has changed (e.g., increased in size) consistent with a proliferative signal.

The term "co-administration," "administered in combination with," and their grammatical equivalents, as used herein, encompasses administration of two or more agents to an animal so that both agents and/or their metabolites are present in the animal at the same time. Co-administration includes simultaneous administration in separate compositions, administration at different times in separate compositions, or administration in a composition in which both agents are present.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the invention is contemplated. Supplementary active ingredients can also be incorporated into the compositions.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

The term "selective inhibition" or "selectively inhibit" as applied to a biologically active agent refers to the agent's ability to selectively reduce the target signaling activity as compared to off-target signaling activity, via direct or interact interaction with the target.

The term "B-ALL" as used herein refers to B-cell Acute Lymphoblastic Leukemia.

"Subject" refers to an animal, such as a mammal, for example a human. The methods described herein can be useful in both human therapeutics and veterinary applications. In some embodiments, the patient is a mammal, and in some embodiments, the patient is human.

"Radiation therapy" means exposing a patient, using routine methods and compositions known to the practitioner, to radiation emitters such as alpha-particle emitting radionuclides (e.g., actinium and thorium radionuclides), low linear energy transfer (LET) radiation emitters (i.e. beta emitters), conversion electron emitters (e.g. strontium-89 and samarium-153-EDTMP, or high-energy radiation, including without limitation x-rays, gamma rays, and neutrons.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversibte Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

The term "in vivo" refers to an event that takes place in a subject's body.

The term "in vitro" refers to an event that takes places outside of a subject's body. For example, an in vitro assay encompasses any assay run outside of a subject assay. In vitro assays encompass cell-based assays in which cells alive or dead are employed. In vitro assays also encompass a cell-free assay in which no intact cells are employed.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are encompassed within the scope of the present invention.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments, for example, an embodiment of any composition of matter, composition, method, or process, or the like, that "consist of" or "consist essentially of" the described features.

The following abbreviations and terms have the indicated meanings throughout PI3-K=Phosphoinositide 3-kinase; PI=phosphatidylinositol; PDK=Phosphoinositide Dependent Kinase; DNA-PK=Deoxyribose Nucleic Acid Dependent Protein Kinase; PTEN=Phosphatase and Tensin homolog deleted on chromosome Ten; PIKK=Phosphoinositide Kinase Like Kinase; AIDS=Acquired Immuno Deficiency Syndrome; HIV=Human Immunodeficiency Virus; MeI=Methyl Iodide; POCl$_3$=Phosphorous Oxychloride; KCNS=Potassium IsoThiocyanate; TLC=Thin Layer Chromatography; MeOH=Methanol; and CHCl$_3$=Chloroform.

Abbreviations used herein have their conventional meaning within the chemical and biological arts.

"Alkyl" refers to a straight or branched hydrocarbon chain radical consisting solely of carbon and hydrogen atoms, containing no unsaturation, having from one to ten carbon atoms (e.g., $C_1$-$C_{10}$ alkyl). Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated. In some embodiments, it is a $C_1$-$C_4$ alkyl group. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, septyl, octyl, nonyl, decyl, and the like. The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group is optionally substituted by one or more of substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$ where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkylaryl" refers to an -(alkyl)aryl radical where aryl and alkyl are as disclosed herein and which are optionally substituted by one or more of the substituents described as suitable substituents for aryl and alkyl respectively.

"Alkylhetaryl" refers to an -(alkyl)hetaryl radical where hetaryl and alkyl are as disclosed herein and which are optionally substituted by one or more of the substituents described as suitable substituents for aryl and alkyl respectively.

"Alkylheterocycloalkyl" refers to an -(alkyl) heterocycyl radical where alkyl and heterocycloalkyl are as disclosed herein and which are optionally substituted by one or more of the substituents described as suitable substituents for heterocycloalkyl and alkyl respectively.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

"Alkenyl" refers to a straight or branched hydrocarbon chain radical group consisting solely of carbon and hydrogen atoms, containing at least one double bond, and having from two to ten carbon atoms (i.e. $C_2$-$C_{10}$ alkenyl). Whenever it appears herein, a numerical range such as "2 to 10" refers to each integer in the given range; e.g., "2 to 10 carbon atoms" means that the alkenyl group may consist of 2 carbon atoms, 3 carbon atoms, etc., up to and including 10 carbon atoms. In certain embodiments, an alkenyl comprises two to eight carbon atoms. In other embodiments, an alkenyl comprises two to five carbon atoms (e.g., $C_2$-$C_5$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$_a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkenyl-cycloalkyl" refers to refers to an -(alkenyl)cycloalkyl radical where alkenyl and cyclo alkyl are as disclosed herein and which are optionally substituted by one or more of the substituents described as suitable substituents for alkenyl and cycloalkyl respectively.

"Alkynyl" refers to a straight or branched hydrocarbon chain radical group consisting solely of carbon and hydrogen atoms, containing at least one triple bond, having from two to ten carbon atoms (i.e. $C_2$-$C_{10}$ alkynyl). Whenever it appears herein, a numerical range such as "2 to 10" refers to each integer in the given range; e.g., "2 to 10 carbon atoms" means that the alkynyl group may consist of 2 carbon atoms, 3 carbon atoms, etc., up to and including 10 carbon atoms. In certain embodiments, an alkynyl comprises two to eight carbon atoms. In other embodiments, an alkynyl has two to five carbon atoms (e.g., $C_2$-$C_5$ alkynyl). The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkynyl-cycloalkyl" refers to refers to an -(alkynyl)cycloalkyl radical where alkynyl and cycloalkyl are as disclosed herein and which are optionally substituted by one or more of the substituents described as suitable substituents for alkynyl and cycloalkyl respectively.

"Carboxaldehyde" refers to a —(C═O)H radical.

"Carboxyl" refers to a —(C═O)OH radical.

"Cyano" refers to a —CN radical.

"Cycloalkyl" refers to a monocyclic or polycyclic radical that contains only carbon and hydrogen, and may be saturated, or partially unsaturated. Cycloalkyl groups include groups having from 3 to 10 ring atoms (i.e. $C_2$-$C_{10}$ cycloalkyl). Whenever it appears herein, a numerical range such as "3 to 10" refers to each integer in the given range; e.g., "3 to 10 carbon atoms" means that the cycloalkyl group may consist of 3 carbon atoms, etc., up to and including 10 carbon atoms. In some embodiments, it is a $C_3$-$C_3$ cycloalkyl radical. In some embodiments, it is a $C_3$-$C_5$ cycloalkyl radical. Illustrative examples of cycloalkyl groups include, but are not limited to the following moieties: cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkyl-alkenyl" refers to a -(cycloalkyl)alkenyl radical where cycloalkyl and heterocycloalkyl are as disclosed herein and which are optionally substituted by one or more of the substituents described as suitable substituents for heterocycloalkyl and cycloalkyl respectively.

"Cycloalkyl-heterocycloalkyl" refers to a -(cycloalkyl)heterocycyl radical where cycloalkyl and heterocycloalkyl are as disclosed herein and which are optionally substituted by one or more of the substituents described as suitable substituents for heterocycloalkyl and cycloalkyl respectively.

"Cycloalkyl-heteroaryl" refers to a -(cycloalkyl) heteroaryl radical where cycloalkyl and heterocycloalkyl are as disclosed herein and which are optionally substituted by one or more of the substituents described as suitable substituents for heterocycloalkyl and cycloalkyl respectively.

The term "alkoxy" refers to the group —O-alkyl, including from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. "Lower alkoxy" refers to alkoxy groups containing one to six carbons. In some embodiments, $C_1$-$C_4$ alkyl, is an alkyl group which encompasses both straight and branched chain alkyls of from 1 to 4 carbon atoms.

The term "substituted alkoxy" refers to alkoxy wherein the alkyl constituent is substituted (i.e., —O-(substituted alkyl)). Unless stated otherwise specifically in the specification, the alkyl moiety of an alkoxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "alkoxycarbonyl" refers to a group of the formula (alkoxy)(C═O)— attached through the carbonyl carbon wherein the alkoxy group has the indicated number of carbon atoms. Thus a $C_1$-$C_6$ alkoxycarbonyl group is an alkoxy group having from 1 to 6 carbon atoms attached through its oxygen to a carbonyl linker. "Lower alkoxycarbonyl" refers to an alkoxycarbonyl group wherein the alkoxy group is a lower alkoxy group. In some embodiments, $C_1$-$C_4$ alkoxy, is an alkoxy group which encompasses both straight and branched chain alkoxy groups of from 1 to 4 carbon atoms.

The term "substituted alkoxycarbonyl" refers to the group (substituted alkyl)-O—C(O)— wherein the group is attached to the parent structure through the carbonyl functionality. Unless stated otherwise specifically in the specification, the alkyl moiety of an alkoxycarbonyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyl" refers to the groups (alkyl)-C(O)—, (aryl)-C(O)—, (heteroaryl)-C(O)—, (heteroalkyl)-C(O)—, and (heterocycloalkyl)-C(O)—, wherein the group is attached to the parent structure through the carbonyl functionality. In some embodiments, it is a $C_1$-$C_{10}$ acyl radical which refers to the total number of chain or ring atoms of the alkyl, aryl, heteroaryl or heterocycloalkyl portion of the acyloxy group plus the carbonyl carbon of acyl, i.e three other ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyloxy" refers to a R(C=O)O— radical wherein "R" is alkyl, aryl, heteroaryl, heteroalkyl, or heterocycloalkyl, which are as described herein. In some embodiments, it is a $C_1$-$C_4$ acyloxy radical which refers to the total number of chain or ring atoms of the alkyl, aryl, heteroaryl or heterocycloalkyl portion of the acyloxy group plus the carbonyl carbon of acyl, i.e three other ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2-S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Amino" or "amine" refers to a —N(R$^8$)$_2$ radical group, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —N(R$^a$)$_2$ group has two Ra other than hydrogen they can be combined with the nitrogen atom to form a 4-, 5-, 6-, or 7-membered ring. For example, —N(R$^a$)$_2$ is meant to include, but not be limited to, 1-pyrrolidinyl and 4-morpholinyl. Unless stated otherwise specifically in the specification, an amino group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl and each of these moieties may be optionally substituted as defined herein.

The term "substituted amino" also refers to N-oxides of the groups —NHR$^d$, and NR$^d$R$^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

"Amide" or "amido" refers to a chemical moiety with formula —C(O)N(R)$_2$ or —NHC(O)R, where R is selected from the group consisting of hydrogen, alkyl, cycloalkyl, aryl, heteroaryl (bonded through a ring carbon) and heteroalicyclic (bonded through a ring carbon), each of which moiety may itself be optionally substituted. In some embodiments it is a $C_1$-$C_4$ amido or amide radical, which includes the amide carbonyl in the total number of carbons in the radical. The $R_2$ of —N(R)$_2$ of the amide may optionally be taken together with the nitrogen to which it is attached to form a 4-, 5-, 6-, or 7-membered ring. Unless stated otherwise specifically in the specification, an amido group is optionally substituted independently by one or more of the substituents as described herein for alkyl, cycloalkyl, aryl, heteroaryl, or heterocycloalkyl. An amide may be an amino acid or a peptide molecule attached to a compound of Formula (I), thereby forming a prodrug. Any amine, hydroxy, or carboxyl side chain on the compounds described herein can be amidified. The procedures and specific groups to make such amides are known to those of skill in the art and can readily be found in reference sources such as Greene and Wuts, Protective Groups in Organic Synthesis, 3.sup.rd Ed., John Wiley & Sons, New York, N.Y., 1999, which is incorporated herein by reference in its entirety.

"Aromatic" or "aryl" refers to an aromatic radical with six to ten ring atoms (e.g., $C_6$-$C_{10}$ aromatic or $C_6$-$C_{10}$ aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Aralkyl" or "arylalkyl" refers to an (aryl)alkyl-radical where aryl and alkyl are as disclosed herein and which are optionally substituted by one or more of the substituents described as suitable substituents for aryl and alkyl respectively.

"Ester" refers to a chemical radical of formula —COOR, where R is selected from the group consisting of alkyl, cycloalkyl, aryl, heteroaryl (bonded through a ring carbon) and heteroalicyclic (bonded through a ring carbon). Any amine, hydroxy, or carboxyl side chain on the compounds described herein can be esterified. The procedures and specific groups to make such esters are known to those of skill in the art and can readily be found in reference sources such as Greene and Wuts, Protective Groups in Organic Synthesis, 3.sup.rd Ed., John Wiley & Sons, New York, N.Y., 1999, which is incorporated herein by reference in its entirety. Unless stated otherwise specifically in the specification, an ester group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl" "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given, e.g. $C_1$-$C_4$ heteroalkyl which refers to the chain length in total, which in this example is 4 atoms long. For example, a —CH$_2$OCH$_2$CH$_3$ radical is referred to as a "C$_4$" heteroalkyl, which includes the heteroatom center in the atom chain length description. Connection to the rest of the molecule may be through either a heteroatom or a carbon in the heteroalkyl chain. A heteroalkyl group may be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heteroalkylaryl" refers "to an -(heteroalkyl)aryl radical where heteroalkyl and aryl are as disclosed herein and which are optionally substituted by one or more of the substituents described as suitable substituents for heteroalkyl and aryl respectively.

"Heteroalkylheteroaryl" refers "to an -(heteroalkyl)heteroaryl radical where heteroalkyl and heteroaryl are as disclosed herein and which are optionally substituted by one or more of the substituents described as suitable substituents for heteroalkyl and heteroaryl respectively "Heteroalkylheterocycloalkyl" refers "to an -(heteroalkyl)heterocycloalkyl radical where heteroalkyl and heteroaryl are as disclosed herein and which are optionally substituted by one or more of the substituents described as suitable substituents for heteroalkyl and heterocycloalkyl respectively "Heteroalkylcycloalkyl" refers "to an -(heteroalkyl)cycloalkyl radical where heteroalkyl and cycloalkyl are as disclosed herein and which are optionally substituted by one or more of the substituents described as suitable substituents for heteroalkyl and cycloalkyl respectively.

"Heteroaryl" or, alternatively, "heteroaromatic" refers to a 5- to 18-membered aromatic radical (e.g., $C_5$-$C_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range; e.g., "5 to 18 ring atoms" means that the heteroaryl group may consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. An N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, a heteraryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

Substituted heteroaryl also includes ring systems substituted with one or more oxide (—O—) substituents, such as pyridinyl N-oxides.

"Heteroarylalkyl" refers to a moiety having an aryl moiety, as described herein, connected to an alkylene moiety, as described herein, wherein the connection to the remainder of the molecule is through the alkylene group.

"Heterocycloalkyl" refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18" refers to each integer in the given range; e.g., "3 to 18 ring atoms" means that the heterocycloalkyl group may consist of 3 ring atoms, 4 ring atoms, etc., up to and including 18 ring atoms. In some embodiments, it is a C$_5$-C$_{10}$ heterocycloalkyl. In some embodiments, it is a C$_4$-C$_{10}$ heterocycloalkyl. In some embodiments, it is a C$_3$-C$_{10}$ heterocycloalkyl. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, a heterocycloalkyl moiety is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heteroaryl or heteroarylalkyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(.±.)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Moiety" refers to a specific segment or functional group of a molecule. Chemical moieties are often recognized chemical entities embedded in or appended to a molecule.

"Nitro" refers to the —NO$_2$ radical.

"Oxa" refers to the —O— radical.

"Oxo" refers to the =O radical.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

The compounds of the present invention may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

A "leaving group or atom" is any group or atom that will, under the reaction conditions, cleave from the starting material, thus promoting reaction at a specified site. Suitable examples of such groups unless otherwise specified are halogen atoms, mesyloxy, p-nitrobenzensulphonyloxy and tosyloxy groups.

"Protecting group" has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in T. H. Greene and P. G. M. Wuts, Protective Groups in Organic Synthesis, Third Edition, John Wiley & Sons, New York (1999). For example, a hydroxy protected form is where at least one of the hydroxy groups present in a compound is protected with a hydroxy protecting group. Likewise, amines and other reactive groups may similarly be protected.

"Solvate" refers to a compound (e.g., a compound selected from Formula I or a pharmaceutically acceptable salt thereof) in physical association with one or more molecules of a pharmaceutically acceptable solvent. It will be understood that "a compound of Formula I" encompass the compound of Formula I and solvates of the compound, as well as mixtures thereof.

"Substituted" means that the referenced group may be substituted with one or more additional group(s) individually and independently selected from acyl, alkyl, alkylaryl, cycloalkyl, aralkyl, aryl, carbohydrate, carbonate, heteroaryl, heterocycloalkyl, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfoxyl, sulfonate, urea, and amino, including mono- and di-substituted amino groups, and the protected derivatives thereof. Di-substituted amino groups encompass those which form a ring together with the nitrogen of the amino group, such as for instance, morpholino. The substituents themselves may be substituted, for example, a cycloalkyl substituent may have a halide substituted at one or more ring carbons, and the like. The protecting groups that may form the protective derivatives of the above substituents are known to those of skill in the art and may be found in references such as Greene and Wuts, above.

"Sulfanyl" refers to the groups: —S-(optionally substituted alkyl), —S-(optionally substituted aryl), —S-(optionally substituted heteroaryl), and —S-(optionally substituted heterocycloalkyl).

"Sulfinyl" refers to the groups: —S(O)—H, —S(O)-(optionally substituted alkyl), —S(O)-(optionally substituted amino), —S(O)-(optionally substituted aryl), —S(O)-(optionally substituted heteroaryl), and —S(O)-(optionally substituted heterocycloalkyl).

"Sulfonyl" refers to the groups: —S(O$_2$)—H, —S(O$_2$)-(optionally substituted alkyl), —S(O$_2$)-(optionally substituted amino), —S(O$_2$)-(optionally substituted aryl), —S(O$_2$)-(optionally substituted heteroaryl), and —S(O$_2$)-(optionally substituted heterocycloalkyl).

"Sulfonamidyl" or "sulfonamido" refers to a —S(=O)$_2$—NRR radical, where each R is selected independently from the group consisting of hydrogen, alkyl, cycloalkyl, aryl, heteroaryl (bonded through a ring carbon) and heteroalicyclic (bonded through a ring carbon). The R groups in —NRR of the —S(=O)$_2$—NRR radical may be taken together with the nitrogen to which it is attached to form a 4-, 5-, 6-, or 7-membered ring. In some embodiments, it is a C$_1$-C$_{10}$ sulfonamido, wherein each R in sulfonamido contains 1 carbon, 2 carbons, 3 carbons, or 4 carbons total. A sulfonamido group is optionally substituted by one or more of the substituents described for alkyl, cycloalkyl, aryl, heteroaryl respectively "Sulfoxyl" refers to a —S(=O)$_2$OH radical.

"Sulfonate" refers to a —S(=O)$_2$—OR radical, where R is selected from the group consisting of alkyl, cycloalkyl, aryl, heteroaryl (bonded through a ring carbon) and heteroalicyclic (bonded through a ring carbon). A sulfonate group is optionally substituted on R by one or more of the substituents described for alkyl, cycloalkyl, aryl, heteroaryl respectively.

Where substituent groups are specified by their conventional chemical formulae, written from left to right, they equally encompass the chemically identical substituents that would result from writing the structure from right to left, e.g., —CH$_2$O— is equivalent to —OCH$_2$—.

Compounds of the present invention also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form," "polymorph," and "novel form" may be used interchangeably herein, and are meant to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

Chemical entities include, but are not limited to, compounds of Formula I, IV, V. VI, VII, VIII, IX, X, XI, XII, XIII, and XIV and all pharmaceutically acceptable forms thereof. Pharmaceutically acceptable forms of the compounds recited herein include pharmaceutically acceptable salts, chelates, non-covalent complexes, prodrugs, and mixtures thereof. In certain embodiments, the compounds described herein are in the form of pharmaceutically acceptable salts. Hence, the terms "chemical entity" and "chemical entities" also encompass pharmaceutically acceptable salts, chelates, non-covalent complexes, prodrugs, and mixtures.

In addition, if the compound of Formula I, IV, V. VI, VII, VIII, IX, X, XI, XII, XIII, or XIV is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

In one aspect, the present invention provides a compound of Formula I or a pharmaceutically acceptable salt thereof:

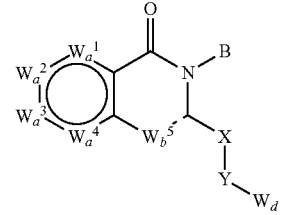

Formula I wherein $W_a^1$ is $CR^3$ or N; $W_a^2$ is $CR^5$ or N; $W_a^3$ is $CR^6$ or N; $W_a^4$ is N or $CR^7$; $W_b^5$ is $CR^8$, $CHR^8$, or N, wherein no more than two adjacent ring atoms selected from $W_a^1$, $W_a^2$, $W_a^3$, $W_a^4$, and $W_b^5$ are heteroatoms;

$W_d$ is heterocycloalkyl, aryl or heteroaryl;

B is alkyl, amino, heteroalkyl, cycloalkyl, heterocycloalkyl, or a moiety of Formula II;

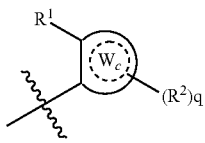

Formula II wherein $W_c$ is aryl, heteroaryl, heterocycloalkyl, or cycloalkyl, and q is an integer of 0, 1, 2, 3, or 4;

X is absent or is —(CH($R^9$))z and each instance of z independently is an integer of 1, 2, 3, or 4;

Y is absent, —O—, —S—, —S(=O)—, —S(=O)$_2$—, —N($R^9$)—, —C(=O)—(CHR$^9$)$_z$—, —C(=O)—, —N($R^9$)—C(=O)—, or —N($R^9$)—C(=O)NH—, —N($R^9$)C($R^9$)$_2$—, or —C(=O)—(CHR$^9$)$_z$—;

$R^1$ is hydrogen, alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, halo, cyano, hydroxy, nitro, phosphate, urea, or carbonate;

$R^2$ is alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, halo, cyano, hydroxy, nitro, phosphate, urea, or carbonate;

$R^3$ is hydrogen, alkyl, alkenyl, alkynyl, cycloalkyl, heterocycloalkyl, alkoxy, amido, amino, acyl, acyloxy, alkoxycarbonyl, sulfonamido, halo, cyano, hydroxy, nitro, aryl, or heteroaryl;

$R^5$, $R^6$, $R^7$, and $R^8$ are independently hydrogen, alkyl, alkenyl, alkynyl, cycloalkyl, heteroalkyl, alkoxy, amido, amino, acyl, acyloxy, sulfonamido, halo, cyano, hydroxy or nitro; and each instance of $R^9$ is independently hydrogen, $C_1$-$C_{10}$alkyl, $C_3$-$C_7$cycloalkyl, heterocycloalkyl, or $C_2$-$C_{10}$heteroalkyl.

In some embodiments, $W_a^1$ is $CR^3$. In some embodiments, $W_a^1$ is N. In some embodiments, $W_a^2$ is $CR^5$. In some embodiments, $W_a^2$ is N. In some embodiments, $W_a^3$ is $CR^6$. In some embodiments, $W_a^3$ is N. In some embodiments, $W_a^4$ is $CR^7$. In some embodiments, $W_a^4$ is N. In some embodiments, $W_b^5$ is $CR^8$. In some embodiments, $W_b^5$ is $CHR^8$. In some embodiments, $W_b^5$ is N. In some embodiments, $W_a^2$ is $CR^5$, $W_a^3$ is $CR^6$ and $W_a^4$ is $CR^7$. In some embodiments, $W_a^2$ is N, $W_a^3$ is $CR^6$, and $W_a^4$ is $CR^7$. In some embodiments, $W_a^2$ is $CR^5$, $W_a^3$ is N, and $W_a^4$ is $CR^7$. In some embodiments, $W_a^2$ is $CR^5$, $W_a^3$ is $CR^6$, and $W_a^4$ is N. In some embodiments, $W_a^2$ and $W_a^3$ are N and $W_a^4$ is $CR^7$. In some embodiments, $W_a^2$ is $CR^5$, and $W_a^3$ and $W_a^4$ are N. In some embodiments, $W_b^5$ is $CR^8$. In some embodiments, $W_b^5$ is $CHR^8$. In some embodiments, $W_b^5$ is N. In some embodiments, $W_a^2$ is $CR^5$, $W_a^3$ is $CR^6$, $W_a^4$ is $CR^7$, and $W_b^5$ is $CR^8$. In some embodiments, $W_a^2$ is $CR^5$, $W_a^3$ is $CR^6$, $W_a^4$ is $CR^7$, and $W_b^5$ is $CHR^8$. In some embodiments, $W_a^2$ is $CR^5$, $W_a^3$ is $CR^6$, $W_a^4$ is $CR^7$, and $W_b^5$ is N. In some embodiments, $W_a^2$ is N, $W_a^3$ is $CR^6$, $W_a^4$ is $CR^7$, and $W_b^5$ is $CR^8$. In some embodiments, $W_a^2$ is N, $W_a^3$ is $CR^6$, $W_a^4$ is $CR^7$, and $W_b^5$ is $CHR^8$. In some embodiments, $W_a^2$ is N, $W_a^3$ is $CR^6$, $W_a^4$ is $CR^7$, and $W_b^5$ is N. In some embodiments, $W_a^2$ is $CR^5$, $W_a^3$ is N, $W_a^4$ is $CR^7$, and $W_b^5$ is $CR^8$. In some embodiments, $W_a^2$ is $CR^5$, $W_a^3$ is N, $W_a^4$ is $CR^7$, and $W_b^5$ is $CHR^8$. In some embodiments, $W_a^2$ is $CR^5$, $W_a^3$ is N, $W_a^4$ is $CR^7$, and $W_b^5$ is N. In some embodiments,
$W_a^2$ is $CR^5$, $W_a^3$ is $CR^6$, $W_a^4$ is N, and $W_b^5$ is $CR^8$. In some embodiments, $W_a^2$ is $CR^5$, $W_a^3$ is $CR^6$, $W_a^4$ is N, and $W_b^5$ is $CHR^8$. In some embodiments, $W_a^2$ is $CR^5$, $W_a^3$ is $CR^6$, $W_a^4$ is N, and $W_b^5$ is N. In some embodiments, $W_a^2$ and $W_a^3$ are N, $W_a^4$ is $CR^7$, and $W_b^5$ is $CR^8$. In some embodiments, $W_a^2$ and $W_a^3$ are N, $W_a^4$ is $CR^7$, and $W_b^5$ is $CHR^8$. In some embodiments, $W_a^2$ and $W_a^3$ are N, $W_a^4$ is $CR^7$, and $W_b^5$ is N. In some embodiments, $W_a^2$ is $CR^5$, $W_a^3$ and $W_a^4$ are N, and $W_b^5$ is $CR^8$. In some embodiments, $W_a^2$ is $CR^5$, $W_a^3$ and $W_a^4$ are N, and $W_b^5$ is $CHR^8$. In some embodiments, $W_a^2$ is $CR^5$, $W_a^3$ and $W_a^4$ are N, and $W_b^5$ is N.

In some embodiments, B is unsubstituted or substituted alkyl, including but not limited to $(CH_2)_2$—$NR^aR^a$, wherein each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, or $NR^aR^a$ are combined together to form a cyclic moiety, which includes but is not limited to piperidinyl, piperazinyl, and morpholinyl. In some embodiments, B is unsubstituted or substituted amino. In some embodiments, B is unsubstituted or substituted heteroalkyl.

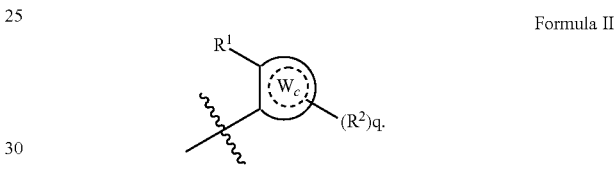

Formula II

In some embodiments, B is a moiety of Formula II and wherein $W_c$ is a member selected from the group consisting of unsubstituted or substituted aryl, substituted phenyl, unsubstituted or substituted heteroaryl including but not limited to pyridin-2-yl, pyridin-3-yl, pyridin-4-yl, pyrimidin-4-yl, pyrimidin-2-yl, pyrimidin-5-yl, or pyrazin-2-yl, unsubstituted or substituted monocyclic heteroaryl, unsubstituted or substituted bicyclic heteroaryl, a heteroaryl comprising two heteroatoms as ring atoms, unsubstituted or substituted heteroaryl comprising a nitrogen ring atom, heteroaryl comprising two nitrogen ring atoms, heteroaryl comprising a nitrogen and a sulfur as ring atoms, unsubstituted or substituted heterocycloalkyl including but not limited to morpholinyl, tetrahydropyranyl, piperazinyl, and piperidinyl, unsubstituted or substituted cycloalkyl including but not limited to cyclopentyl and cyclohexyl.

In some embodiments, B is one of the following moieties:

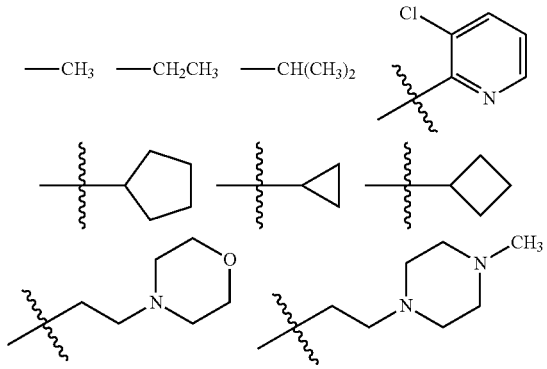

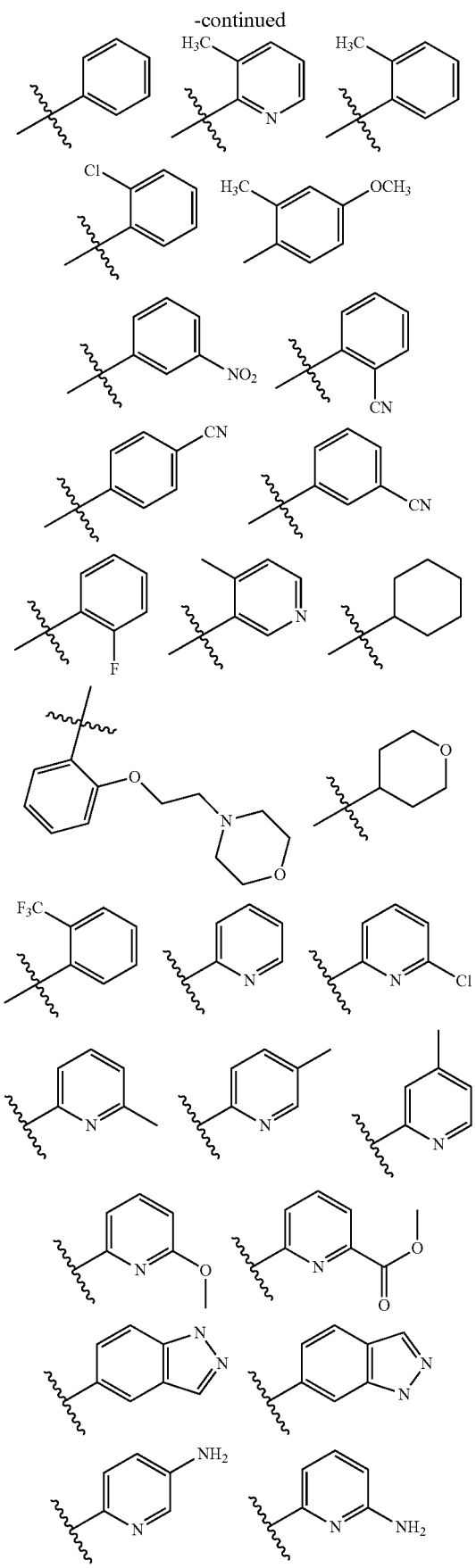
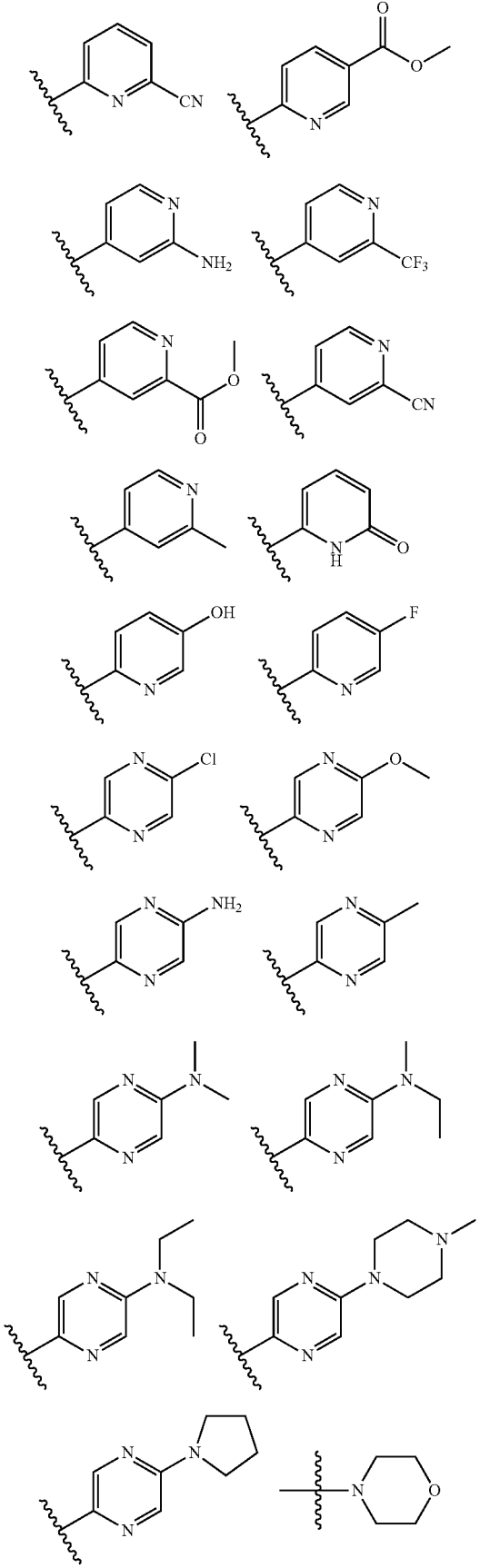

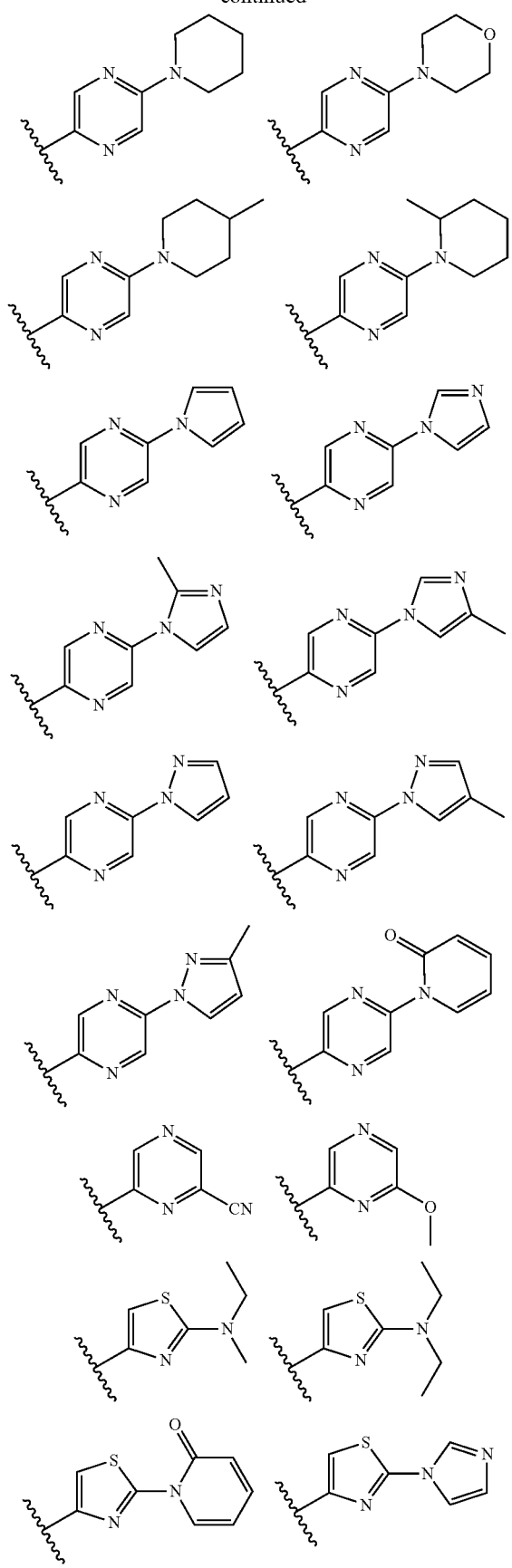
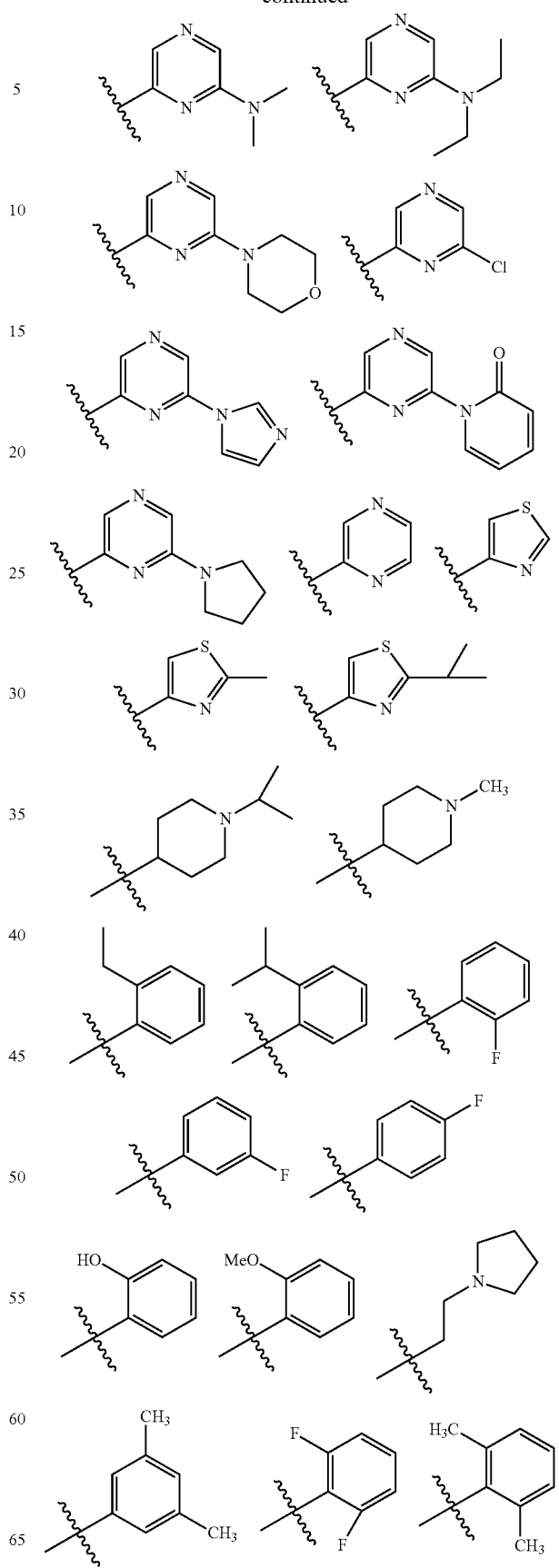

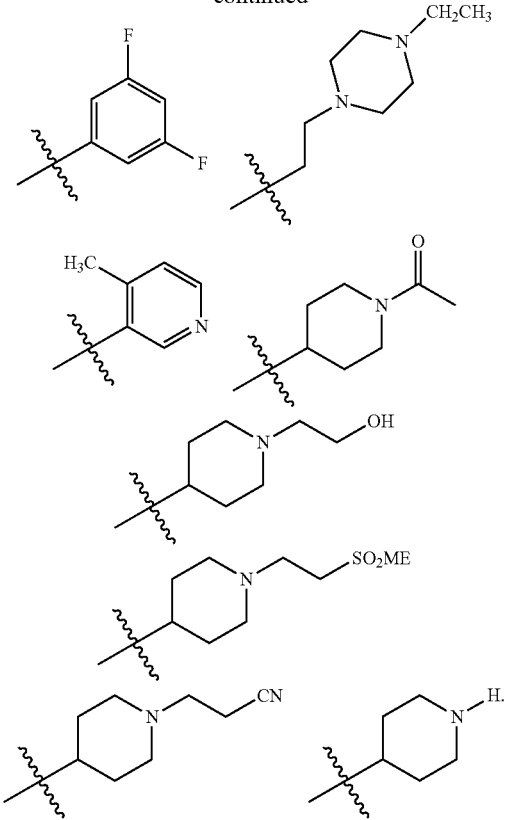

In some embodiments, B is substituted by one or more of alkyl, heteroalkyl, alkenyl, alkynyl, cycloalkyl, heterocycloalkyl, aryl, heteroaryl alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, or sulfonamido, may itself be substituted.

In some embodiments, $R^1$ is a member selected from the group consisting of hydrogen, unsubstituted or substituted alkyl, unsubstituted or substituted heteroalkyl, unsubstituted or substituted alkenyl, unsubstituted or substituted alkynyl, unsubstituted or substituted cycloalkyl, or unsubstituted or substituted heterocycloalkyl. In some embodiments, $R^1$ is unsubstituted or substituted aryl, unsubstituted or substituted arylalkyl, unsubstituted or substituted heteroaryl, or unsubstituted or substituted heteroarylalkyl. In some embodiments, $R^1$ is unsubstituted or substituted alkoxy, unsubstituted or substituted amido, unsubstituted or substituted amino. In some embodiments, $R^1$ is unsubstituted or substituted acyl, unsubstituted or substituted acyloxy, unsubstituted or substituted alkoxycarbonyl, or unsubstituted or substituted sulfonamido. In some embodiments, $R^1$ is halo which includes —Cl, —F, —I, and —Br. In some embodiments, $R^1$ is selected from the group consisting of cyano, hydroxy, nitro, unsubstituted or substituted phosphate, unsubstituted or substituted urea, and carbonate.

In some embodiments, when $R^1$ is alkyl, $R^1$ is methyl, ethyl, propyl, isopropyl, n-butyl, tert-butyl, sec-butyl, pentyl, hexyl or heptyl.

In some embodiments, when $R^1$ is alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, or hydroxy, $R^1$ is substituted by phosphate, or unsubstituted urea, or substituted urea, or carbonic acid, or carbonate.

In some embodiments, when $R^1$ is alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, or sulfonamido, $R^1$ is substituted by one or more of alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, or sulfonamido may itself be substituted.

In some embodiments, $R^2$ is a member selected from the group consisting of unsubstituted or substituted alkyl, unsubstituted or substituted heteroalkyl, unsubstituted or substituted alkenyl, unsubstituted or substituted alkynyl, unsubstituted or substituted cycloalkyl, and unsubstituted or substituted heterocycloalkyl. In some embodiments, $R^2$ is unsubstituted or substituted aryl, unsubstituted or substituted arylalkyl, unsubstituted or substituted heteroaryl, or unsubstituted or substituted heteroarylalkyl. In some embodiments, $R^2$ is unsubstituted or substituted alkoxy, unsubstituted or substituted amido, unsubstituted or substituted amino. In some embodiments, $R^2$ is unsubstituted or substituted acyl, unsubstituted or substituted acyloxy, unsubstituted or substituted alkoxycarbonyl, or unsubstituted or substituted sulfonamido. In some embodiments, $R^2$ is halo, which is —I, —F, —Cl, or —Br. In some embodiments, $R^2$ is selected from the group consisting of cyano, hydroxy, nitro, a carbonic acid, and a carbonate. In some embodiments, $R^2$ is unsubstituted or substituted phosphate. In some embodiments, $R^2$ is unsubstituted or substituted urea. In some embodiments, when $R^2$ is alkyl, $R^2$ is methyl, ethyl, propyl, isopropyl, n-butyl, tert-butyl, sec-butyl, pentyl, hexyl or heptyl.

In some embodiments, when $R^2$ is alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, or hydroxy, it is substituted by phosphate, substituted by urea, or substituted by carbonate.

In some embodiments, when $R^2$ is alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, or sulfonamido, it is substituted by one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, alkoxycarbonyl, or sulfonamido may itself be substituted.

In some embodiments, q is an integer of 0. In some embodiments, q is an integer of 1. In some embodiments, q is an integer of 2. In some embodiments, q is an integer of 3. In some embodiments, q is an integer of 4.

In some embodiments, $R^3$ is a member selected from the group consisting of hydrogen, unsubstituted or substituted alkyl, unsubstituted or substituted alkenyl, and unsubstituted or substituted alkynyl. In some embodiments, $R^3$ is unsubstituted or substituted aryl, unsubstituted or substituted heteroaryl, unsubstituted or substituted cycloalkyl, or unsubstituted or substituted heterocycloalkyl. In some embodiments, $R^3$ is unsubstituted or substituted alkoxy, unsubstituted or substituted amido, unsubstituted or substituted amino. In some embodiments, $R^3$ is unsubstituted or substituted acyl, unsubstituted or substituted acyloxy, unsubstituted or substituted alkoxycarbonyl, or unsubstituted or substituted sulfonamido. In some embodiments, $R^3$ is halo, which is —I, —F, —Cl, or —Br.

In some embodiments, $R^3$ is selected from the group consisting of cyano, hydroxy, and nitro. In some embodiments, when $R^3$ is alkyl, $R^3$ is methyl, ethyl, propyl, isopropyl, n-butyl, tert-butyl, sec-butyl, pentyl, hexyl or heptyl. In some embodiments, $R^3$ is —$CF_3$.

In some embodiments, when $R^3$ is alkyl, alkenyl, alkynyl, aryl, heteroaryl, cycloalkyl, heterocycloalkyl, alkoxy, amido, amino, acyl, acyloxy, alkoxycarbonyl, or sulfonamido, it is substituted with one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, alkoxycarbonyl, or sulfonamido may itself be substituted.

In some embodiments, $R^5$ is hydrogen, unsubstituted or substituted alkyl (including but not limited to unsubstituted or substituted $C_1$-$C_4$alkyl). In some embodiments, $R^5$ is unsubstituted or substituted alkenyl including but not limited to unsubstituted or substituted $C_2$-$C_5$alkenyl. In some embodiments, $R^5$ is unsubstituted or substituted alkynyl including but not limited to unsubstituted or substituted $C_2$-$C_5$alkynyl. In some embodiments, $R^5$ is unsubstituted or substituted cycloalkyl including but not limited to unsubstituted or substituted $C_3$-$C_5$cycloalkyl. In some embodiments, $R^5$ is unsubstituted or substituted heterocycloalkyl. In some embodiments, $R^5$ is unsubstituted or substituted heteroalkyl including but not limited to unsubstituted or substituted $C_1$-$C_4$heteroalkyl. In some embodiments, $R^5$ is unsubstituted or substituted alkoxy including but not limited to unsubstituted or substituted $C_1$-$C_4$alkoxy. In some embodiments, $R^5$ is unsubstituted or substituted amido including but not limited to unsubstituted or substituted $C_1$-$C_4$amido. In some embodiments, $R^5$ is unsubstituted or substituted amino. In some embodiments, $R^5$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted sulfonamido, or unsubstituted or substituted $C_1$-$C_4$sulfonamido. In some embodiments, $R^5$ is halo, which is —I, —F, —Cl, or —Br. In some embodiments, $R^5$ is selected from the group consisting of cyano, hydroxy, and nitro. In some other embodiments, $R^5$ is —$CH_3$, —$CH_2CH_3$, n-propyl, isopropyl, —$OCH_3$, —$OCH_2CH_3$, or —$CF_3$.

In some embodiments, when $R^5$ is alkyl, alkenyl, alkynyl, cycloalkyl, heteroalkyl, acyl, alkoxy, amido, amino, acyloxy, alkoxycarbonyl, or sulfonamido, $R^5$ is optionally substituted with one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, alkoxycarbonyl, or sulfonamido may itself be substituted.

In some embodiments, $R^6$ is hydrogen, unsubstituted or substituted alkyl (including but not limited to unsubstituted or substituted $C_1$-$C_4$alkyl). In some embodiments, $R^6$ is unsubstituted or substituted alkenyl including but not limited to unsubstituted or substituted $C_2$-$C_5$alkenyl. In some embodiments, $R^6$ is unsubstituted or substituted alkynyl including but not limited to unsubstituted or substituted $C_2$-$C_5$alkynyl. In some embodiments, $R^6$ is unsubstituted or substituted cycloalkyl including but not limited to unsubstituted or substituted $C_3$-$C_5$cycloalkyl. In some embodiments, $R^6$ is unsubstituted or substituted heterocycloalkyl. In some embodiments, $R^6$ is unsubstituted or substituted heteroalkyl including but not limited to unsubstituted or substituted $C_1$-$C_4$heteroalkyl. In some embodiments, $R^6$ is unsubstituted or substituted alkoxy including but not limited to unsubstituted or substituted $C_1$-$C_4$alkoxy. In some embodiments, $R^6$ is unsubstituted or substituted amido including but not limited to unsubstituted or substituted $C_1$-$C_4$amido. In some embodiments, $R^6$ is unsubstituted or substituted amino. In some embodiments, $R^6$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted sulfonamido, or unsubstituted or substituted $C_1$-$C_4$sulfonamido. In some embodiments, $R^6$ is halo, which is —I, —F, —Cl, or —Br. In some embodiments, $R^6$ is selected from the group consisting of cyano, hydroxy, and nitro. In some other embodiments, $R^6$ is —$CH_3$, —$CH_2CH_3$, n-propyl, isopropyl, —$OCH_3$, —$OCH_2CH_3$, or —$CF_3$.

In some embodiments, when $R^6$ is alkyl, alkenyl, alkynyl, cycloalkyl, heteroalkyl, acyl, alkoxy, amido, amino, acyloxy, alkoxycarbonyl, or sulfonamido, $R^6$ is optionally substituted with one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, alkoxycarbonyl, or sulfonamido may itself be substituted.

In some embodiments, $R^7$ is hydrogen, unsubstituted or substituted alkyl (including but not limited to unsubstituted or substituted $C_1$-$C_4$alkyl). In some embodiments, $R^7$ is unsubstituted or substituted alkenyl including but not limited to unsubstituted or substituted $C_2$-$C_5$alkenyl. In some embodiments, $R^7$ is unsubstituted or substituted alkynyl including but not limited to unsubstituted or substituted $C_2$-$C_5$ alkynyl. In some embodiments, $R^7$ is unsubstituted or substituted cycloalkyl including but not limited to unsubstituted or substituted $C_3$-$C_5$cycloalkyl. In some embodiments, $R^7$ is unsubstituted or substituted heterocycloalkyl. In some embodiments, $R^7$ is unsubstituted or substituted heteroalkyl including but not limited to unsubstituted or substituted $C_1$-$C_4$heteroalkyl. In some embodiments, $R^7$ is unsubstituted or substituted alkoxy including but not limited to unsubstituted or substituted $C_1$-$C_4$alkoxy. In some embodiments, $R^7$ is unsubstituted or substituted amido including but not limited to unsubstituted or substituted $C_1$-$C_4$amido. In some embodiments, $R^7$ is unsubstituted or substituted amino. In some embodiments, $R^7$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted sulfonamido, or unsubstituted or substituted $C_1$-$C_4$sulfonamido. In some embodiments, $R^7$ is halo, which is —I, —F, —Cl, or —Br. In some embodiments, $R^7$ is selected from the group consisting of cyano, hydroxy, and nitro. In some other embodiments, $R^7$ is —$CH_3$, —$CH_2CH_3$, n-propyl, isopropyl, —$OCH_3$, —$OCH_2CH_3$, or —$CF_3$.

In some embodiments, when $R^7$ is alkyl, alkenyl, alkynyl, cycloalkyl, heteroalkyl, acyl, alkoxy, amido, amino, acyloxy, alkoxycarbonyl, or sulfonamido, $R^7$ is optionally substituted with one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, alkoxycarbonyl, or sulfonamido may itself be substituted.

In some embodiments, $R^8$ is hydrogen, unsubstituted or substituted alkyl (including but not limited to unsubstituted or substituted $C_1$-$C_4$alkyl). In some embodiments, $R^8$ is unsubstituted or substituted alkenyl including but not limited to unsubstituted or substituted $C_2$-$C_5$alkenyl. In some embodiments, $R^8$ is unsubstituted or substituted alkynyl including but not limited to unsubstituted or substituted $C_2$-$C_5$alkynyl. In some embodiments, $R^8$ is unsubstituted or substituted cycloalkyl including but not limited to unsubstituted or substituted $C_3$-$C_5$cycloalkyl. In some embodiments, $R^8$ is unsubstituted or substituted heterocycloalkyl. In some embodiments, $R^8$ is unsubstituted or substituted heteroalkyl including but not limited to unsubstituted or substituted $C_1$-$C_4$heteroalkyl. In some embodiments, $R^8$ is unsubstituted or substituted alkoxy including but not limited to unsubstituted or substituted $C_1$-$C_4$alkoxy. In some embodiments, $R^8$ is unsubstituted or substituted amido including but not limited to unsubstituted or substituted $C_1$-$C_4$amido. In some embodiments, $R^8$ is unsubstituted or substituted amino. In some embodiments, $R^8$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted sulfonamido, or unsubstituted or substituted $C_1$-$C_4$sulfonamido. In some embodiments, $R^8$ is halo, which is —I, —F, —Cl, or —Br. In some embodiments, $R^8$ is selected from the group consisting of cyano, hydroxy, and nitro. In some other embodiments, $R^8$ is —$CH_3$, —$CH_2CH_3$, n-propyl, isopropyl, —$OCH_3$, —$OCH_2CH_3$, or —$CF_3$.

In some embodiments, when $R^8$ is alkyl, alkenyl, alkynyl, cycloalkyl, heteroalkyl, acyl, alkoxy, amido, amino, acyloxy, alkoxycarbonyl, or sulfonamido, $R^8$ is optionally substituted with one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, alkoxycarbonyl, or sulfonamido may itself be substituted.

In some embodiments, $R^5$, $R^6$, $R^7$, and $R^8$ are H.

In some embodiments, X is absent. In some embodiments, X is —$(CH(R^9))_z$, and z is an integer of 1, 2, 3 or 4.

In some embodiments, $R^9$ is unsubstituted or substituted alkyl including but not limited to unsubstituted or substituted $C_1$-$C_{10}$alkyl. In some embodiments, $R^9$ is unsubstituted or substituted cycloalkyl including but not limited to unsubstituted or substituted $C_3$-$C_2$cycloalkyl. In some embodiments, $R^9$ is methyl or hydrogen. In some embodiments, $R^9$ is unsubstituted or substituted heterocycloalkyl including but not limited to unsubstituted or substituted $C_2$-$C_{10}$heteroalkyl. In some embodiments, $R^9$ is unsubstituted or substituted heteroalkyl including but not limited to unsubstituted or substituted $C_2$-$C_{10}$heteroalkyl.

When $R^9$ is any of the above, in some embodiments, X is —$CH_2$—, —$CH_2CH_2$—, —$CH_2CH_2CH_2$—, —$CH(CH_3)$—, or —$CH(CH_2CH_3)$—. In some embodiments, when X is —$CH(CH_3)$—, —$CH(CH_3)$— is in an (S)- or (R)-stereochemical configuration.

In some embodiments of the compound of Formula I, Y is absent. In some embodiments, Y is —O—, —S—, —S(=O)—, —S(=O)$_2$—, —C(=O)—, —N($R^9$) (C=O)—, —N($R^9$)(C=O)NH—, —N($R^9$)C($R^9$)$_2$— (such as —N($R^9$)$CH_2$—, specifically —N($CH_3$)$CH_2$—, N(CH ($CH_3$)$_2$)$CH_2$— or N($CH_2CH_3$)$CH_2$—), —N($R^9$)—, —N($CH_3$)—, —N($CH_2CH_3$)—, or —N(CH($CH_3$)$_2$)—. In some embodiments, Y is —C(=O)—(CHR$^9$)$_z$— and z is an integer of 1, 2, 3, or 4.

In some embodiments, X—Y is —$CH_2$—, —$CH_2$—N ($CH_3$), —$CH(CH_3)$—NH—, (S)—$CH(CH_3)$—NH—, or (R)—$CH(CH_3)$—NH—. In some embodiments, X—Y is —N($CH_3$)$CH_2$—, N($CH_2CH_3$)$CH_2$—, —N(CH($CH_3$)$_2$) $CH_2$—, or —NH$CH_2$—.

In some embodiments, $W_d$ is a member selected from the group consisting of unsubstituted or substituted heterocycloalkyl, unsubstituted or substituted aryl, and unsubstituted or substituted heteroaryl. In some embodiments, $W_d$ is unsubstituted or substituted monocyclic heteroaryl, or unsubstituted or substituted bicyclic heteroaryl. In some embodiments, $W_d$ is a bicyclic heteroaryl having at least one heteroatom, e.g., a bicyclic heteroaryl having at least one nitrogen ring atom. In some embodiments, $W_d$ is a bicyclic heteroaryl having at least two heteroatoms, e.g., a bicyclic heteroaryl having at least two nitrogen ring atoms. In some embodiments, $W_d$ is a bicyclic heteroaryl having two heteroatoms in the ring which is connected to XY. In some embodiments, $W_d$ is a bicyclic heteroaryl having two nitrogen ring atoms in the ring to which XY is connected. In some embodiments, $W_d$ is a bicyclic heteroaryl having four heteroatoms, e.g., a bicyclic heteroaryl having four nitrogen ring atoms. In some embodiments, $W_d$ is unsubstituted or substituted 4-amino-1H-pyrazolo[3,4-d]pyrimidin-1-yl, unsubstituted or substituted 7-amino-2-methyl-2H-pyrazolo[4,3-d]pyrimidin-3-yl. unsubstituted or substituted 6-methylenyl-9H-purin-6-yl, or unsubstituted or substituted 6-amino-9H-purin-9-yl.

In some embodiments $W_d$ is one of the following:

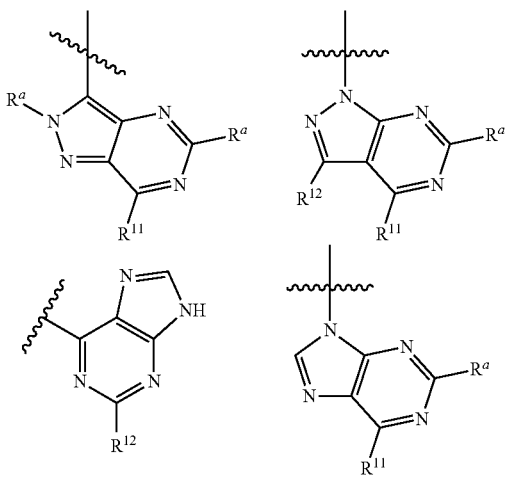

wherein $R^a$ is hydrogen, halo, phosphate, urea, carbonate, alkyl, alkenyl, alkynyl, cycloalkyl, heteroalkyl, or heterocycloalkyl;

$R^{11}$ is H, alkyl, halo, amino, amido, hydroxy, or alkoxy, and $R^{12}$ is H, alkyl, cyano, alkynyl, alkenyl, halo, aryl, heteroaryl, heterocycloalkyl, cycloalkyl, amino, carboxylic acid, alkoxycarbonyl, or amido.

In some embodiments, Wd is:

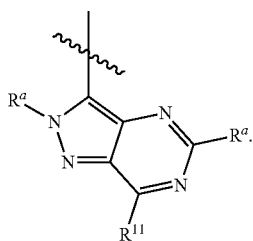

In some embodiments, $W_d$ is:

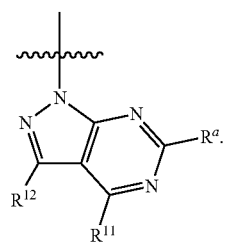

In some embodiments, $W_d$ is:

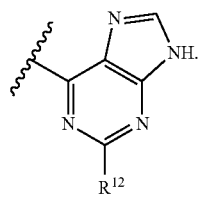

In some embodiments, $W_d$ is:

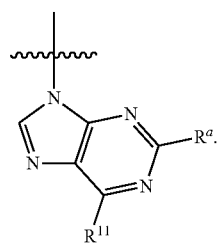

In some embodiments of $W_d$, $R^a$ is a member selected from the group consisting of hydrogen, halo, phosphate, urea, a carbonate, unsubstituted or substituted alkyl, unsubstituted or substituted alkenyl, unsubstituted or substituted alkynyl, unsubstituted or substituted cycloalkyl, unsubstituted or substituted heteroalkyl, and unsubstituted or substituted heterocycloalkyl.

In some embodiments of $W_d$, when $R^a$ is alkyl, alkynyl, cycloalkyl, heteroalkyl, or heterocycloalkyl, it is substituted by phosphate, urea, or carbonate.

In some embodiments, $R^{11}$ is a member of the group consisting of hydrogen, unsubstituted or substituted alkyl, and halo, which includes —I, —F, —Cl, or —Br. In some embodiments, $R^{11}$ is unsubstituted or substituted amino, unsubstituted or substituted amido, hydroxy, or unsubstituted or substituted alkoxy. In some embodiments, $R^{11}$ is phosphate, unsubstituted or substituted urea, or carbonate.

In some embodiments, when $R^{11}$ is alkyl, amino, amido, hydroxy, or alkoxy, it is substituted by phosphate, urea, or carbonate.

In some embodiments, —X—Y—$W_d$ is one of the following moieties:

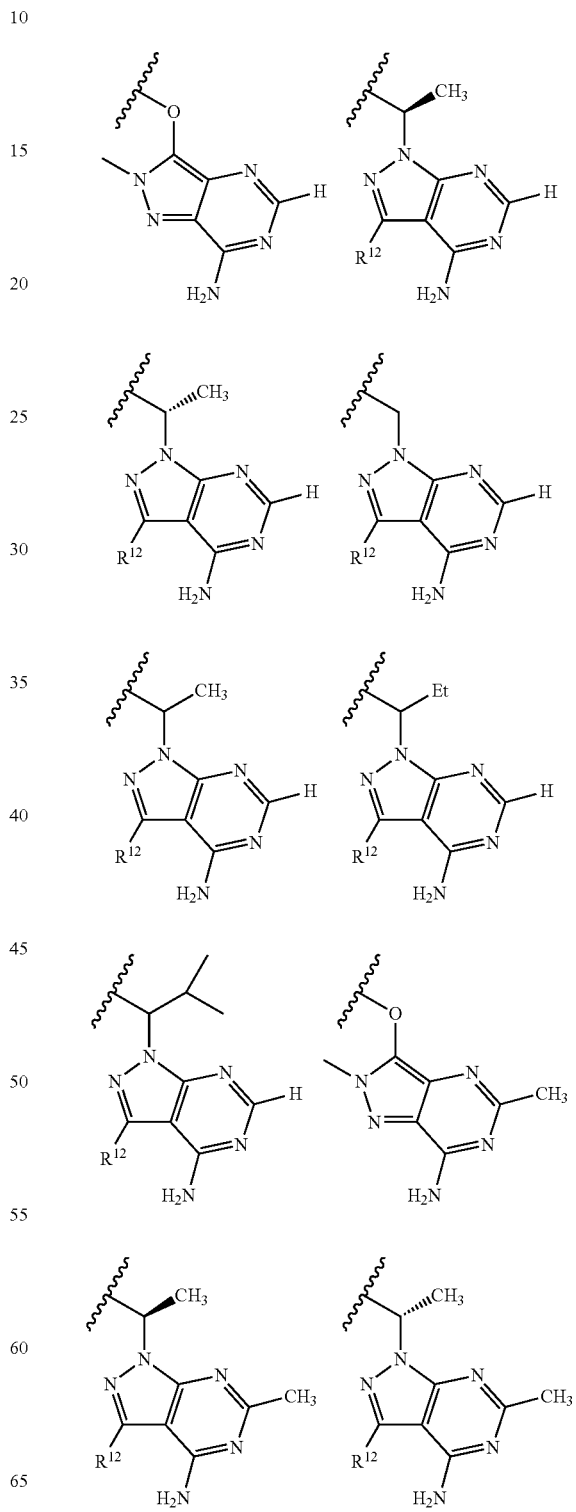

-continued
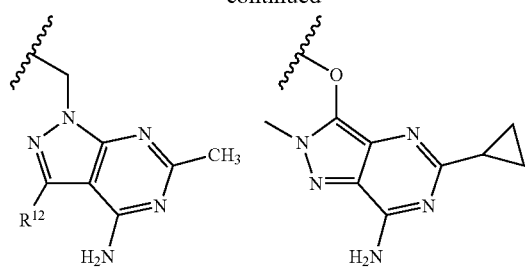
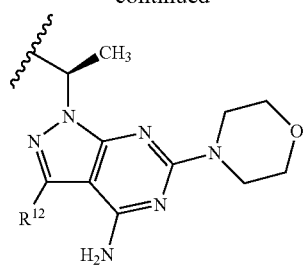
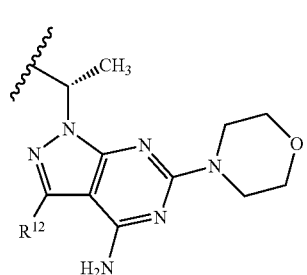
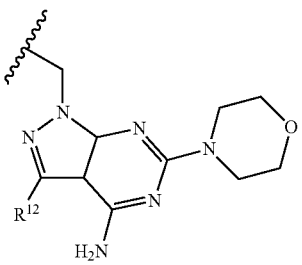
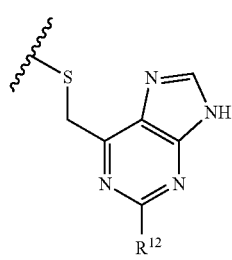
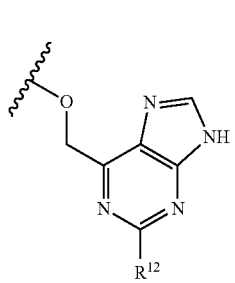
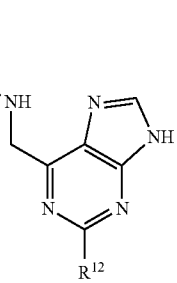
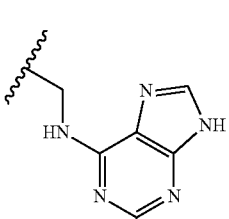
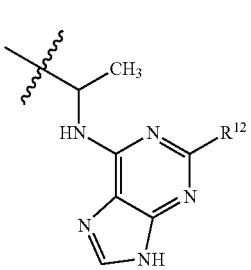
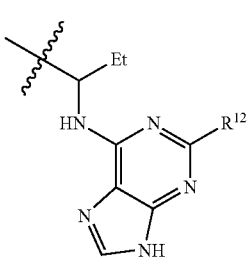
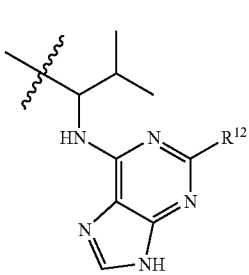

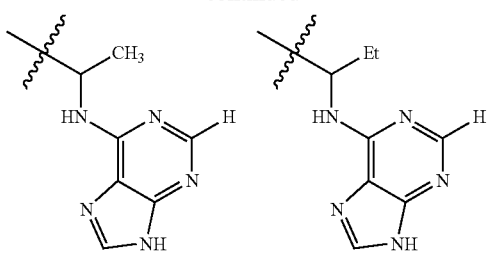
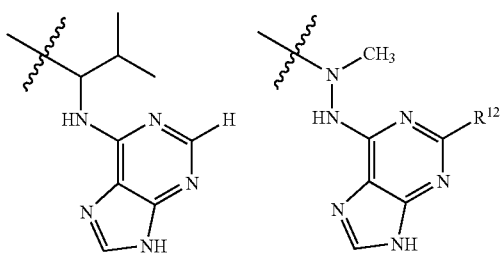
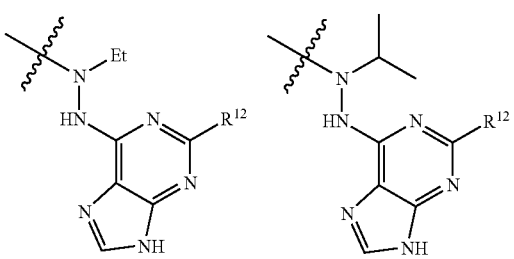
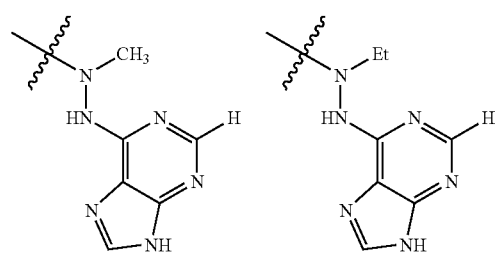
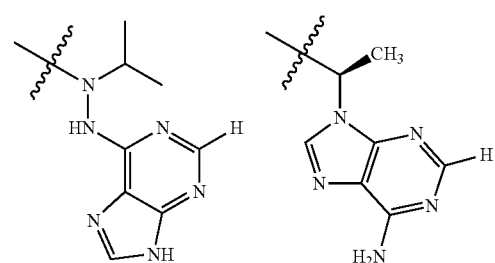
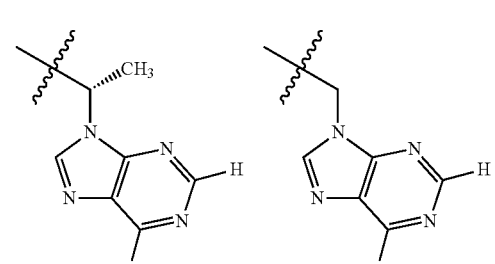
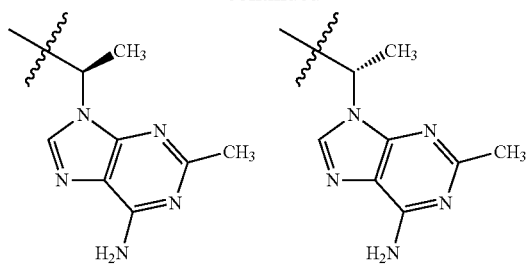
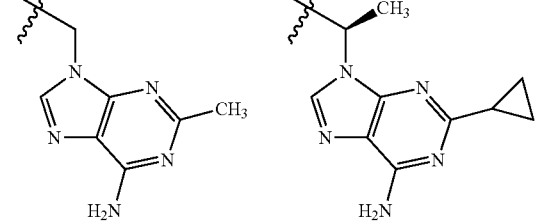
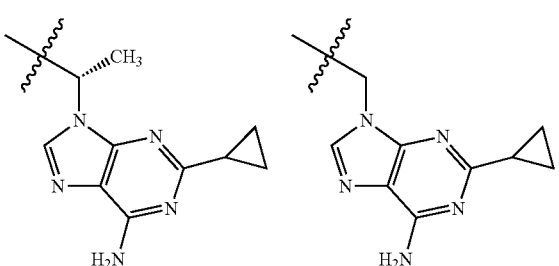
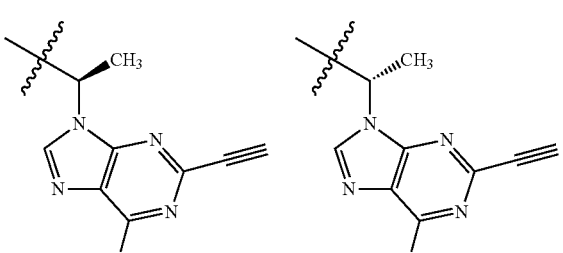
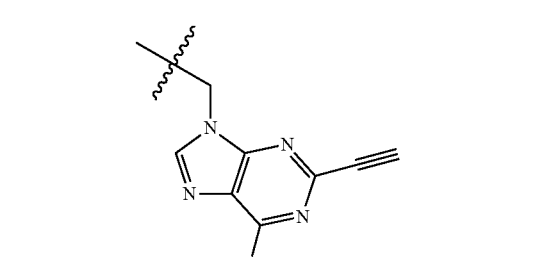
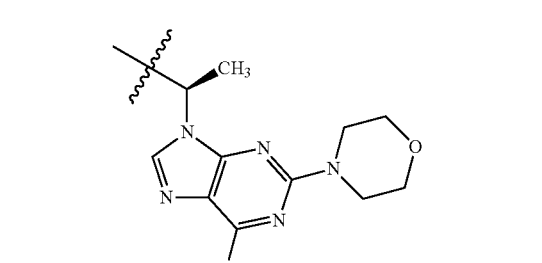

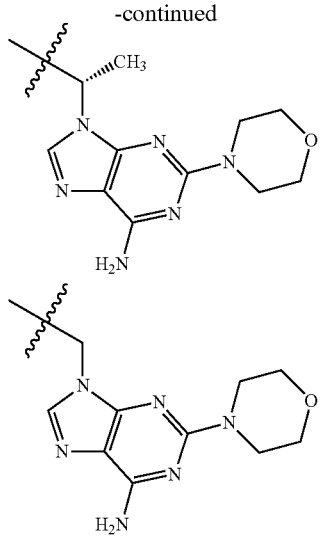

In some embodiments, $R^{12}$ is a member of the group consisting of hydrogen, cyano, halo, unsubstituted or substituted alkyl, and unsubstituted or substituted alkynyl unsubstituted or substituted alkenyl. In some embodiments, $R^{12}$ is unsubstituted or substituted aryl. In some embodiments, $R^{12}$ is unsubstituted or substituted heteroaryl, which includes but is not limited to heteroaryl having a 5 membered ring, heteroaryl having a six membered ring, heteroaryl with at least one nitrogen ring atom, heteroaryl with two nitrogen ring atoms, monocylic heteroaryl, and bicyclic heteroaryl. In some embodiments, $R^{12}$ is unsubstituted or substituted heterocycloalkyl, which includes but is not limited to heterocycloalkyl with one nitrogen ring atom, heterocycloalkyl with one oxygen ring atom, $R^{12}$ is heterocycloalkyl with one sulfur ring atom, 5 membered heterocycloalkyl, 6 membered heterocycloalkyl, saturated heterocycloalkyl, unsaturated heterocycloalkyl, heterocycloalkyl having an unsaturated moiety connected to the heterocycloalkyl ring, heterocycloalkyl substituted by oxo, and heterocycloalkyl substituted by two oxo. In some embodiments, $R^{12}$ is unsubstituted or substituted cycloalkyl, including but not limited to cyclopropyl, cyclobutyl, cyclopentyl, cyclohexyl, cycloalkyl substituted by one oxo, cycloalkyl having an unsaturated moiety connected to the cycloalkyl ring. In some embodiments, $R^{12}$ is unsubstituted or substituted amido, carboxylic acid, unsubstituted or substituted acyloxy, or unsubstituted or substituted alkoxycarbonyl.

In some embodiments, when $R^{12}$ is alkyl, alkynyl, alkenyl, aryl, heteroaryl, heterocycloalkyl, or cycloalkyl, it is substituted with phosphate. In some embodiments, when $R^{12}$ is alkyl, alkynyl, alkenyl, aryl, heteroaryl, heterocycloalkyl, or cycloalkyl, it is substituted with urea. In some embodiments, when $R^{12}$ is alkyl, alkynyl, alkenyl, aryl, heteroaryl, heterocycloalkyl, or cycloalkyl, it is substituted with carbonate.

In some embodiments, when $R^{12}$ is alkyl, alkynyl, alkenyl, aryl, heteroaryl, heterocycloalkyl, cycloalkyl, alkoxycarbonyl, amido, or acyloxy, it is substituted with one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, alkoxycarbonyl, or sulfonamido may itself be substituted.

In some embodiments, $R^{12}$ of $W_d$ is one of the following moieties:

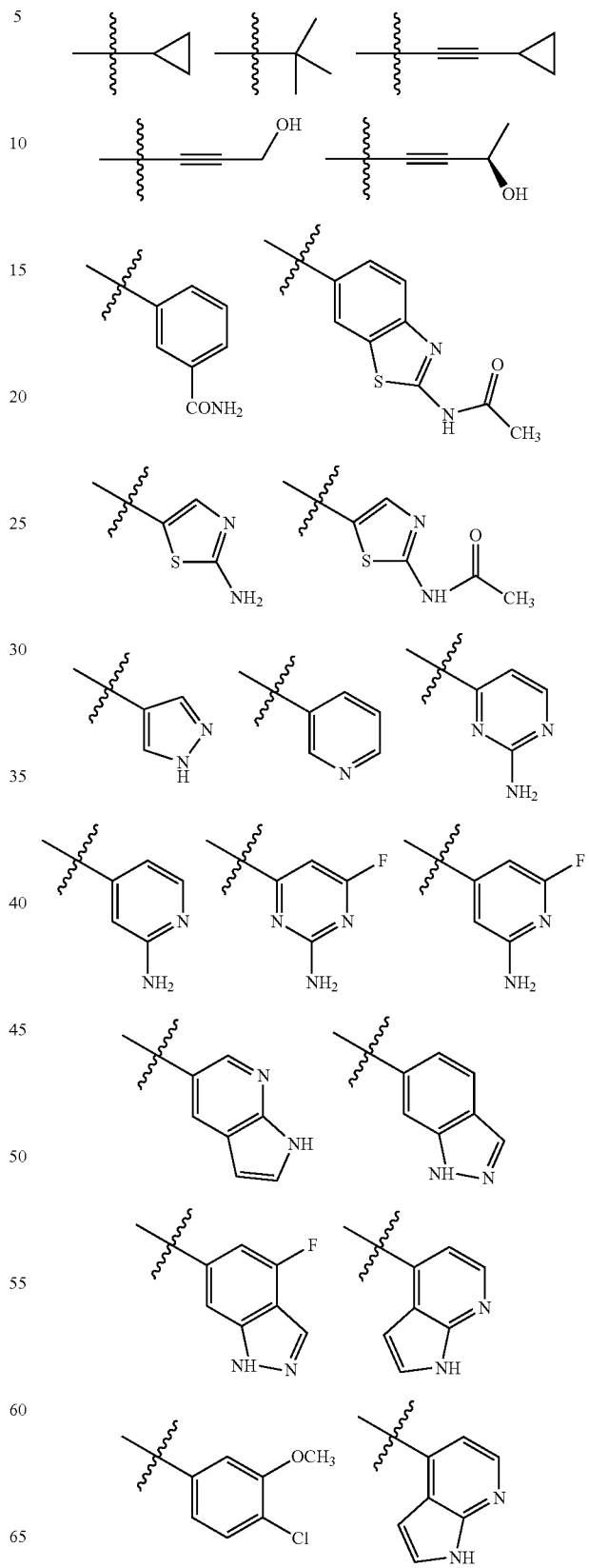

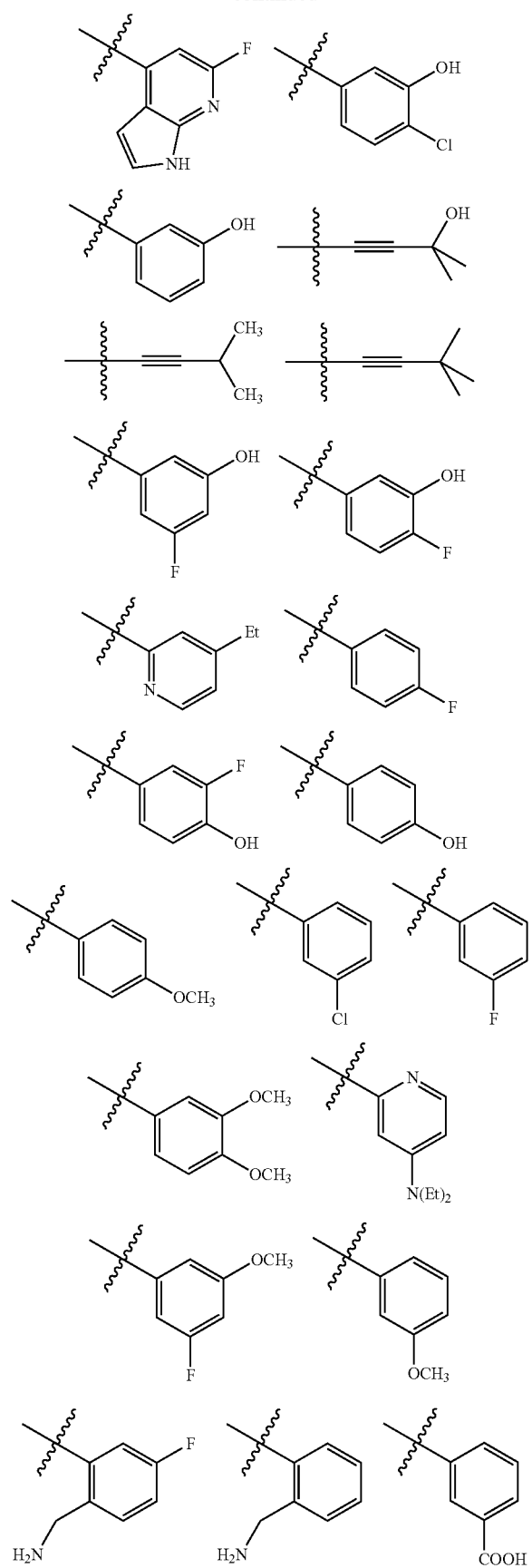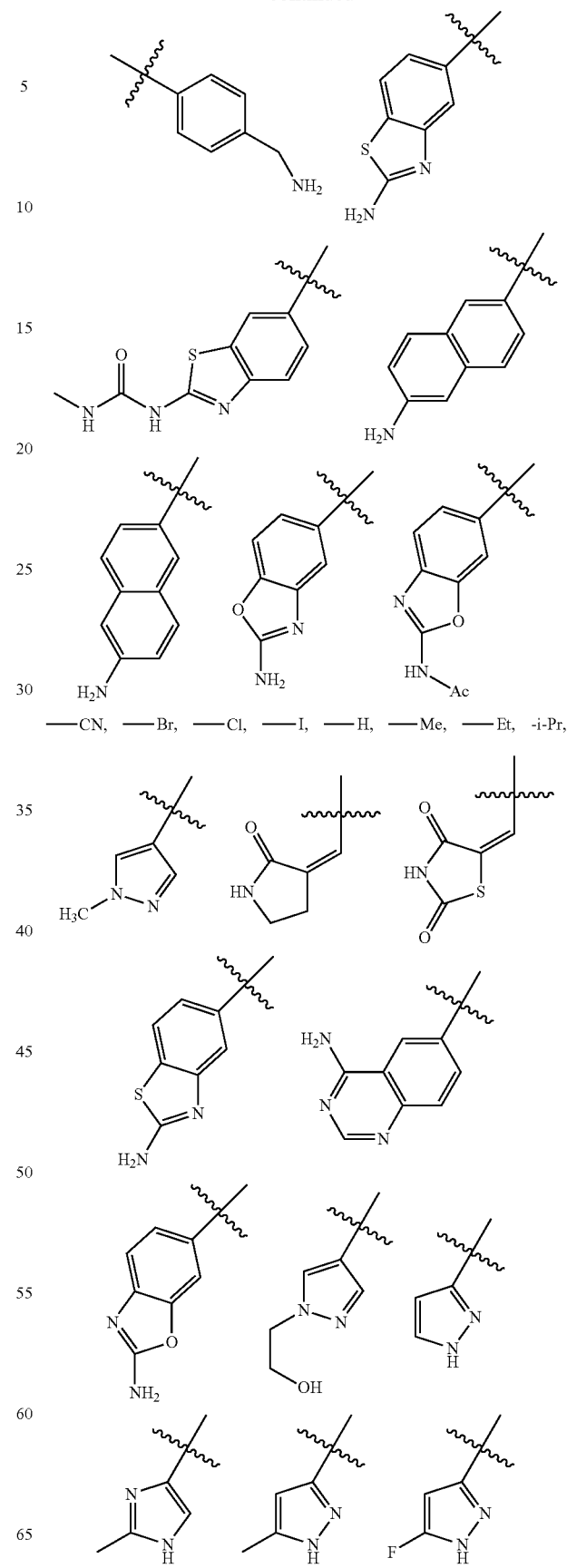

-continued

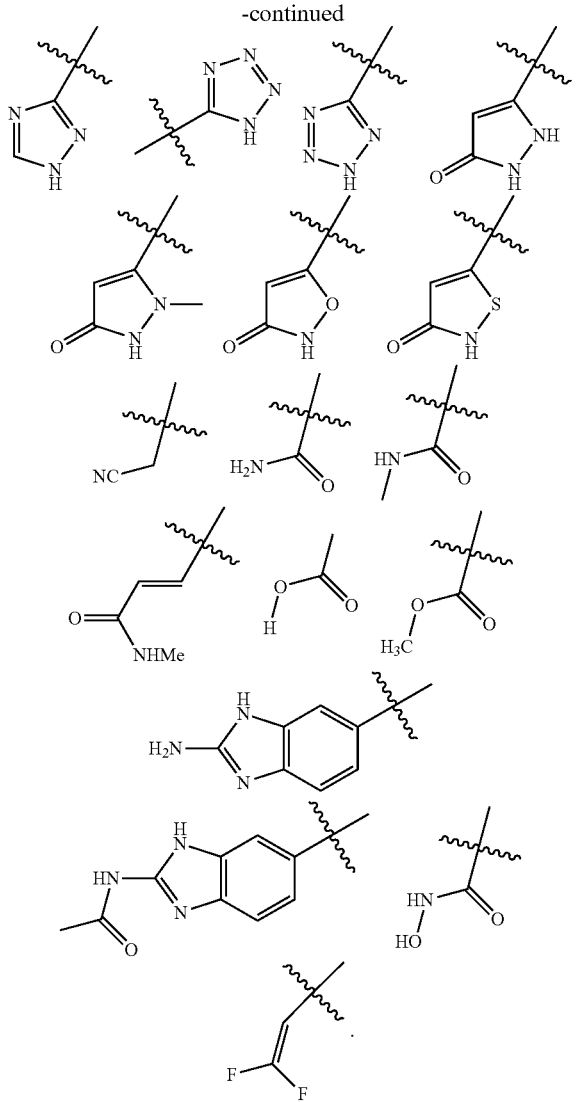

In some embodiments, $W_d$ is a pyrazolopyrimidine of Formula III:

Formula III

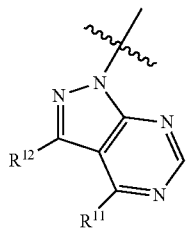

wherein $R^{11}$ is H, alkyl, halo, amino, amido, hydroxy, or alkoxy, and $R^{12}$ is H, alkyl, alkynyl, alkenyl, halo, aryl, heteroaryl, heterocycloalkyl, or cycloalkyl. In some embodiments, $R^{11}$ is amino and $R^{12}$ is H, alkyl, alkynyl, alkenyl, halo, aryl, heteroaryl, heterocycloalkyl, or cycloalkyl. In some embodiments, is amino and $R^{12}$ is alkyl, halo, aryl, heteroaryl, heterocycloalkyl, or cycloalkyl. In some embodiments, $R^{11}$ is amino and $R^{12}$ is monocyclic heteroaryl. In some embodiments, $R^{11}$ is amino and $R^{12}$ is bicyclic heteroaryl. In some embodiments, $R^{11}$ is amino and $R^{12}$ is cyano, amino, carboxylic acid, acyloxy, alkoxycarbonyl, or amido.

In some embodiments, the compound of Formula I is a compound which has a structure selected from the group consisting of Formula 1-A, 1-B, 2-A, 2-B. IV, V, V-A, VI, VI-A, VI-B, VI-C, 6-C1, 6-C2, V-1-D, and 6-D:

Formula 1-A

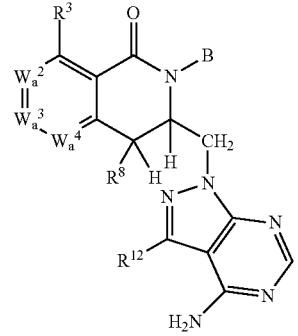

Formula 1-B

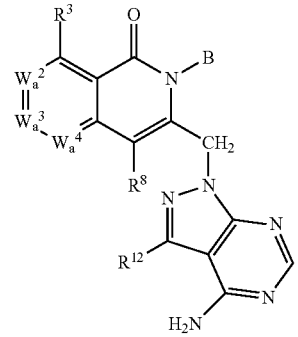

Formula 2-A

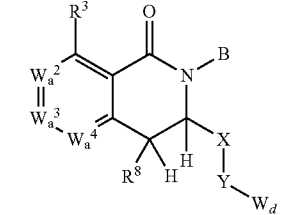

Formula 2-B

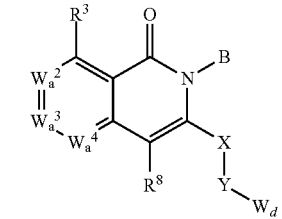

Formula IV

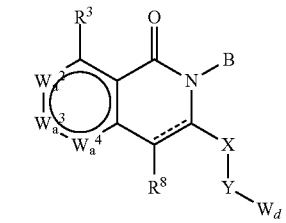

Formula V
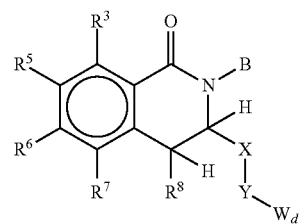
Formula V-A
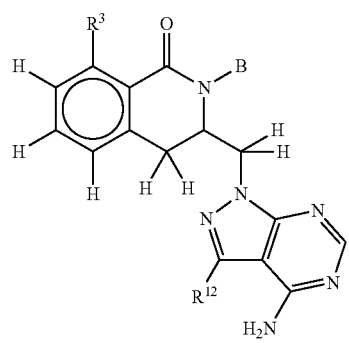
Formula VI
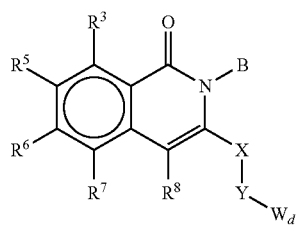
Formula VI-A
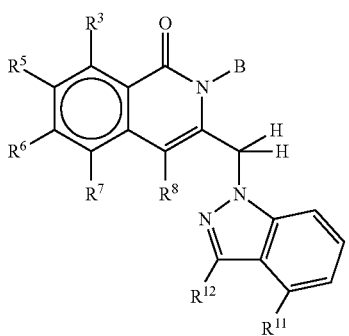
Formula 6-A
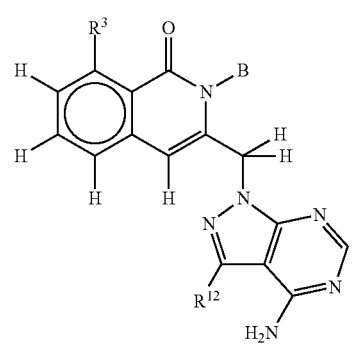
Formula VI-B
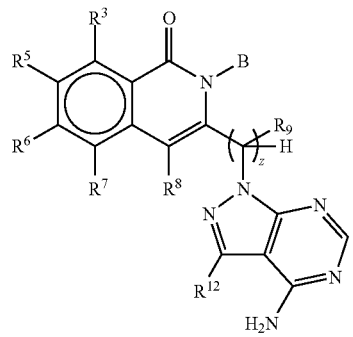
Formula VI-C
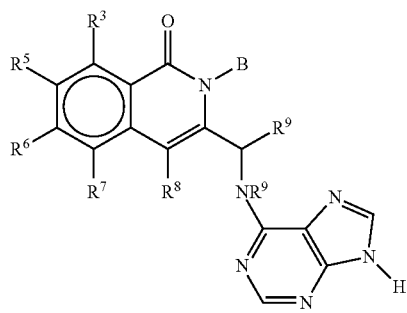
Formula 6-C1
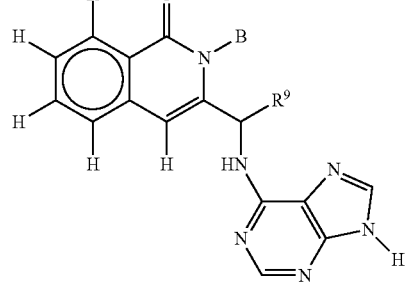
Formula 6-C2
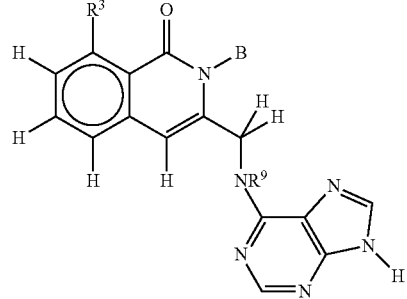
Formula VI-D
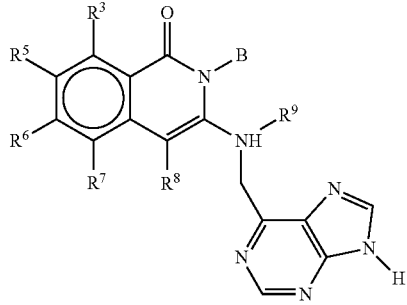

Formula 6-D

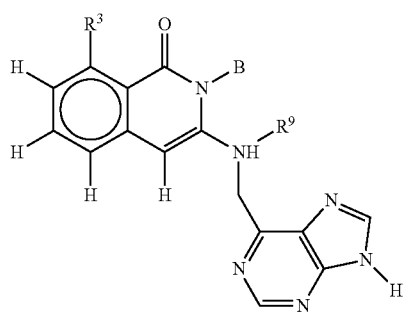

In another embodiment, the compound of Formula I is a compound which has a structure selected from the group consisting of Formula VII, 7-A, VIII, VIII-A, and 8-A:

Formula VII

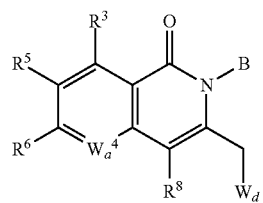

Formula 7-A

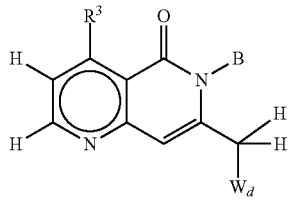

Formula VIII

Formula VIII-A

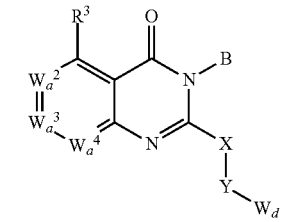

Formula 8-A

Any of the disclosed elements and their substituents for the compounds of Formula I can be used in any combination.

In one aspect, for compounds of Formula I, IV, V, VI, VII, or VIII, $R_3$ is H, $CH_3$, $CF_3$, Cl, F, aryl, or heteroaryl; B is alkyl or a moiety of Formula II;

Formula II

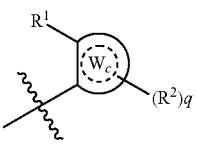

wherein $W_c$ is aryl, heteroaryl, heterocycloalkyl, or cycloalkyl; $R^1$ is H, —F, —Cl, —CN, —$CH_3$, isopropyl, —$CF_3$, —$OCH_3$, nitro, or phosphate; $R^2$ is halo, hydroxy, cyano, nitro, or phosphate; q is an integer of 0, 1, 2, 3, or 4; $R^5$, $R^6$, $R^7$, and $R^8$ are H; X is absent or $(CH_2)_z$; z is 1; Y is absent, —$N(R^9)$—, or —$N(R^9)CH(R^9)$—; $R^9$ is hydrogen, $C_1$-$C_{10}$alkyl, $C_3$-$C_7$cycloalkyl, or $C_2$-$C_{10}$heteroalkyl; and $W_d$ is pyrazolopyrimidine or purine.

In another aspect, for compounds of Formula I, IV, V, VI, VII, or VIII, $R_3$ is H, $CH_3$, $CF_3$, Cl, or F; B is alkyl or a moiety of Formula II which is aryl, heteroaryl, heterocycloalkyl, or cycloalkyl; $R^1$ is H, —F, —Cl, —CN, —$CH_3$, isopropyl, —$CF_3$, —$OCH_3$, nitro, or phosphate; $R^2$ is halo, hydroxy, cyano, nitro, or phosphate; q is 0, 1 or 2; $R^5$, $R^6$, $R^7$, and $R^8$ are H; X is absent or $(CH_2)_z$; z is 1; Y is absent, —$N(R^9)$—, or —$N(R^9)CH(R^9)$—; $R^9$ is hydrogen, methyl, or ethyl; $W_d$ is:

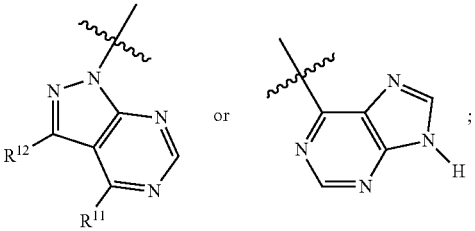

$R^{11}$ is amino; and $R^{12}$ is H, alkyl, alkynyl, alkenyl, halo, aryl, heteroaryl, heterocycloalkyl, cycloalkyl, cyano, amino, carboxylic acid, alkoxycarbonyl, or amido.

In another aspect, for compounds of Formula I, IV, V, VI, VII, or VIII, $R_3$ is H, $CH_3$, $CF_3$, Cl, or F; B is alkyl or a moiety of Formula II which is aryl, heteroaryl, heterocycloalkyl, or cycloalkyl; $R^1$ is H, —F, —Cl, —CN, —$CH_3$, isopropyl, —$CF_3$, —$OCH_3$, nitro, or phosphate; $R^2$ is halo, hydroxy, cyano, nitro or phosphate; q is 0, 1 or 2; $R^5$, $R^6$, $R^7$, and $R^8$ are H; X is $(CH_2)_z$; z is 1; Y is absent and $W_d$ is:

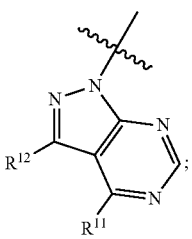

$R^{11}$ is amino; and $R^{12}$ is H, alkyl, alkynyl, alkenyl, halo, aryl, heteroaryl, heterocycloalkyl, cycloalkyl, cyano, amino, carboxylic acid, alkoxycarbonyl, or amido.

In another aspect, for compounds of Formula I, IV, V, VI, VII, or VIII, $R_3$ is H, $CH_3$, $CF_3$, Cl, or F; B is alkyl or a moiety of Formula II, which is aryl, heteroaryl, heterocycloalkyl, or cycloalkyl; $R^1$ is H, —F, —Cl, —CN, —$CH_3$, isopropyl, —$CF_3$, —$OCH_3$, nitro, or phosphate; $R^2$ is halo, hydroxy, cyano, nitro, or phosphate; q is 0, 1 or 2; $R^5$, $R^6$, $R^7$, and $R^8$ are H; X is $(CH_2)_z$; z is 1; Y is —N($R^9$)—; $R^9$ is hydrogen, methyl, or ethyl; and $W_d$ is

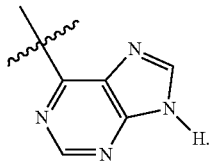

In another aspect, for compounds of Formula I, IV, V, VI, VII, or VIII, $R_3$ is H, $CH_3$, $CF_3$, Cl, or F; B is alkyl or a moiety of Formula II, which is aryl, heteroaryl, heterocycloalkyl, or cycloalkyl; $R^1$ is H, —F, —Cl, —CN, —$CH_3$, isopropyl, —$CF_3$, —$OCH_3$, nitro, or phosphate; $R^2$ is halo, hydroxy, cyano, nitro, or phosphate; q is 0, 1 or 2; $R^5$, $R^6$, $R^7$, and $R^8$ are H; X is absent; Y is —N($R^9$)CH($R^9$)—; $R^9$ is hydrogen, methyl, or ethyl; and $W_d$ is

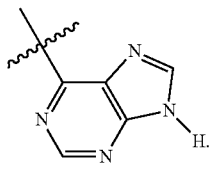

The invention also provides a compound of Formula IX or its pharmaceutically acceptable salt,

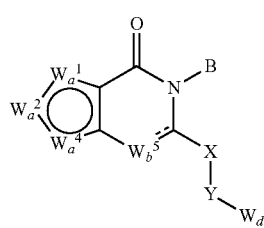

Formula IX wherein $W_a^1$ and $W_a^2$ are independently $CR^5$, S, N, or $NR^4$, and $W_a^4$ is independently $CR^7$, S, N, or $NR^4$ wherein no more than two adjacent ring atoms are nitrogen or sulfur, and when $W_a^1$ is S, one of $W_a^2$ and $W_a^4$ is N or $NR^4$;

$W_b^5$ is $CR^8$, N, or $NR^8$;

B is alkyl, amino, heteroalkyl, cycloalkyl, heterocycloalkyl, or a moiety of Formula II;

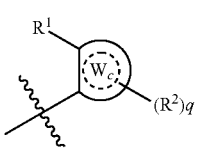

Formula II wherein $W_c$ is aryl, heteroaryl, heterocycloalkyl, or cycloalkyl, and q is an integer of 0, 1, 2, 3, or 4;

$W_d$ is absent or is a heterocycloalkyl, aryl or heteroaryl moiety;

X is absent or is —(CH($R^9$))$_z$— and each instance of z independently is an integer of 1, 2, 3, or 4;

Y is absent, —O—, —S—, —S(=O)—, —S(=O)$_2$—, —N($R^9$)—, —C(=O)—(CHR$^9$)$_z$—, —C(=O)—, —N($R^9$)—C(=O)—, or —N($R^9$)—C(=O)NH—, —N($R^9$)C($R^9$)$_2$—, or —C(=O)—(CHR$^9$)$_z$—;

$R^1$ is hydrogen, alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, halo, cyano, hydroxy, nitro, phosphate, urea, or carbonate;

$R^2$ is alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, halo, cyano, hydroxy, nitro, phosphate, urea, or carbonate;

$R^4$ is hydrogen, acyl, alkyl, alkenyl, alkynyl, cycloalkyl, heterocycloalkyl, or $C_1$-$C_4$heteroalkyl;

$R^5$, $R^7$, and $R^8$ are independently hydrogen, alkyl, alkenyl, alkynyl, cycloalkyl, heteroalkyl, alkoxy, amido, amino, acyl, acyloxy, alkoxycarbonyl, sulfonamido, halo, cyano, hydroxy or nitro;

each instance of $R^9$ is independently hydrogen, $C_1$-$C_{10}$alkyl, $C_3$-$C_7$cycloalkyl, heterocycloalkyl, or $C_2$-$C_{10}$heteroalkyl.

Substituents described for Formula I are equally applicable to compounds of Formula IX, except for $W_a^1$, $W_a^2$, $W_a^4$, and $W_b^5$ which are defined as follows:

In some embodiments, $W_a^1$ is $CR^5$, S, N, or $NR^4$.
In some embodiments, $W_a^2$ is $CR^5$, S, N, or $NR^4$.
In some embodiments, $W_a^4$ is $CR^7$, S, N, or $NR^4$.
In some embodiments, $W_b^5$ is $CR^8$, N, or $NR^8$.
In some embodiments, the compound of Formula IX has a structure which is a member of the group consisting of: (i) $W_a^1$ is $NR^4$, $W_a^2$ is $CR^5$, $W_a^4$ is $CR^7$, and $W_b^5$ is $CR^8$; (ii) $W_a^1$ is $NR^4$, $W_a^2$ is $CR^5$, $W_a^4$ is $CR^7$, and $W_b^5$ is $CHR^8$; (iii) $W_a^1$ is $NR^4$, $W_a^2$ is $CR^5$, $W_a^4$ is $CR^7$, and $W_b^5$ is N; (iv) $W_a^1$ is $NR^4$, $W_a^2$ is $CR^5$, $W_a^4$ is $CR^7$, and $W_b^5$ is $NR^8$; (v) $W_a^1$ is $NR^4$, $W_a^2$ is N, $W_a^4$ is $CR^7$, and $W_b^5$ is $CR^8$; (vi) $W_a^1$ is $NR^4$, $W_a^2$ is N, $W_a^4$ is $CR^7$, and $W_b^5$ is $CHR^8$; (vii) $W_a^1$ is $NR^4$, $W_a^2$ is N, $W_a^4$ is $CR^7$, and $W_b^5$ is N; (viii) $W_a^1$ is $NR^4$, $W_a^2$ is N, $W_a^4$ is $CR^7$, and $W_b^5$ is $NR^8$; (ix) $W_a^1$ is $NR^4$, $W_a^2$ is $CR^5$, $W_a^4$ is N, and $W_b^5$ is $CR^8$; (x) $W_a^1$ is $NR^4$, $W_a^2$ is $CR^5$, $W_a^4$ is N, and $W_b^5$ is $CHR^8$; (xi) $W_a^1$ is $NR^4$, $W_a^2$ is $CR^5$, $W_a^4$ is N, and $W_b^5$ is N; (xii) $W_a^1$ is $NR^4$, $W_a^2$ is $CR^5$, $W_a^4$ is N, and $W_b^5$ is $NR^8$; (xiii) $W_a^1$ is S, $W_a^7$ is $CR^5$, $W_a^4$ is N, and $W_b^5$ is $CR^8$; (xiv) $W_a^1$ is S, $W_a^2$ is $CR^5$, $W_a^4$ is N, and $W_b^5$ is $CHR^8$; (xv) $W_a^1$ is S, $W_a^2$ is $CR^5$, $W_a^4$ is N, and $W_b^5$ is N; (xvi) $W_a^1$ is S, $W_a^2$ is $CR^5$, $W_a^4$ is N, and $W_b^5$ is $NR^8$; (xvii) $W_a^1$ is N, $W_a^2$ is $CR^5$, $W_a^4$ is S, and $W_b^5$ is $CR^8$; (xviii) $W_a^1$ is N, $W_a^2$ is $CR^5$, $W_a^4$ is S, and $W_b^5$ is $CHR^8$; (xix) $W_a^1$ is N, $W_a^2$ is $CR^5$, $W_a^4$ is S, and $W_b^5$ is N; (xx) $W_a^1$ is N, $W_a^2$ is $CR^5$, $W_a^4$ is S, and $W_b^5$ is $NR^8$; (xxi) $W_a^1$ is $CR^5$, $W_a^2$ is N, $W_a^4$ is S, and $W_b^5$ is $CR^8$; (xxi) $W_a^1$ is $CR^5$, $W_a^2$ is N, $W_a^4$ is S, and $W_b^5$ is $CHR^8$; (xxii) $W_a^1$ is $CR^5$, $W_a^2$ is N, $W_a^4$ is S, and $W_b^5$ is N; (xxiii) $W_a^1$ is $CR^5$, $W_a^2$ is N, $W_a^4$ is S, and $W_b^5$ is $NR^8$; (xxiv) $W_a^1$ is S, $W_a^2$ is N, $W_a^4$ is $CR^7$, and $W_b^5$ is $CR^8$; (xxv) $W_a^1$ is S, $W_a^2$ is N, $W_a^4$ is $CR^7$, and $W_b^5$ is $CHR^8$; (xxvi) $W_a^1$ is S, $W_a^2$ is N, $W_a^4$ is $CR^7$, and $W_b^5$ is N; (xxvii) $W_a^1$ is S, $W_a^2$ is N, $W_a^4$ is $CR^7$, and $W_b^5$ is $NR^8$; (xxviii) $W_a^1$ is $CR^5$, $W_a^7$ is N, $W_a^4$ is $NR^4$, and $W_b^5$ is $CR^8$; (xxix) $W_a^1$ is $CR^5$, $W_a^7$ is N, $W_a^4$ is $NR^4$, and $W_b^5$ is $CHR^8$; (xxx) $W_a^1$ is $CR^5$, $W_a^2$ is N, $W_a^4$ is $NR^4$, and $W_b{}^5$ is N; (xxxi) $W_a{}^1$ is $CR^5$, $W_a{}^2$ is N, $W_a{}^4$ is $NR^4$, and $W_b{}^5$ is $NR^8$; (xxxii) $W_a{}^1$ is $CR^5$, $W_a{}^7$ is $CR^5$, $W_a{}^4$ is S, and $W_b{}^5$ is $CHR^8$; (xxxiii) $W_a{}^1$ is $CR^5$, $W_a{}^7$ is $CR^5$, $W_a{}^4$ is S, and $W_b{}^5$ is $CR^8$; (xxxiv) $W_a{}^1$ is $CR^5$, $W_a{}^2$ is $CR^5$, $W_a{}^4$ is S, and $W_b{}^5$ is N; and (xxxv) $W_a{}^1$ is $CR^5$, $W_a{}^2$ is $CR^5$, $W_a{}^4$ is S, and $W_b{}^5$ is $NR^8$.

In some embodiments, $R^4$ is a member of the group consisting of hydrogen, unsubstituted or substituted acyl, unsubstituted or substituted alkyl which includes but is not limited to unsubstituted or substituted $C_1$-$C_4$alkyl, unsubstituted or substituted alkenyl which includes but is not limited to $C_2$-$C_5$alkenyl, unsubstituted or substituted alkynyl which includes but is not limited to $C_2$-$C_5$alkynyl, unsubstituted or substituted cycloalkyl which includes but is not limited to $C_3$-$C_5$cycloalkyl, unsubstituted or substituted heterocycloalkyl, and unsubstituted or substituted heteroalkyl which includes but is not limited to unsubstituted or substituted $C_1$-$C_4$heteroalkyl.

In some embodiments, when $R^4$ is acyl, alkyl, alkenyl, alkynyl, cycloalkyl, heterocycloalkyl, or heteroalkyl, it is substituted with one or more of alkyl, heteroalkyl, alkenyl, alkynyl, cycloalkyl, heterocycloalkyl, aryl, heteroaryl, alkoxy, amido, amino, acyl, acyloxy, sulfonamido, halo, cyano, hydroxy or nitro, each of which alkyl, heteroalkyl, alkenyl, alkynyl, cycloalkyl, heterocycloalkyl, aryl, heteroaryl, alkoxy, amido, amino, acyl, acyloxy, or sulfonamido may itself be substituted.

In some embodiments, the compound of Formula IX is a compound which has a structure selected from the group consisting of Formula X, XI, XII, XIII, and XIV:

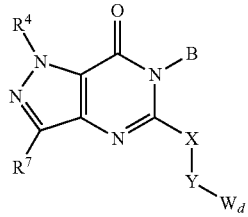

Formula X

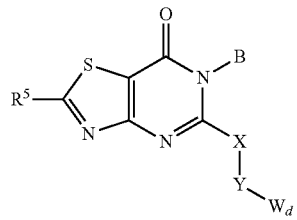

Formula XI

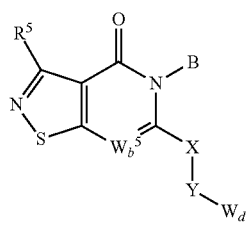

Formula XII

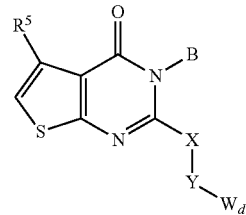

Formula XIII

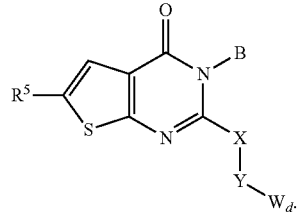

Formula XIV

Any of the disclosed elements and their substituents for the compounds of Formula IX can be used in any combination.

In one aspect, for compounds of Formula IX, X, XI, XII, XIII or XIV, B is alkyl or a moiety of Formula II;

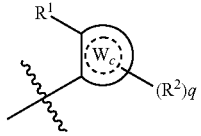

Formula II wherein $W_c$ is aryl, heteroaryl, heterocycloalkyl, or cycloalkyl; $R^1$ is H, —F, —Cl, —CN, —CH$_3$, isopropyl, —CF$_3$, —OCH$_3$, nitro, or phosphate; $R^2$ is halo, hydroxy, cyano, nitro, or phosphate; q is an integer of 0, 1, 2, 3, or 4; $R^4$, $R^5$, $R^7$, and $R^8$ are H or methyl; X is absent or (CH$_2$)$_z$; z is 1; Y is absent —N($R^9$)—, or —N($R^9$)CH($R^9$)—; $R^9$ is hydrogen, $C_1$-$C_{10}$alkyl, $C_3$-$C_7$cycloalkyl, or $C_2$-$C_{10}$heteroalkyl; and $W_d$ is pyrazolopyrimidine or purine.

In another aspect, for compounds of Formula IX, X, XI, XII, XIII or XIV, B is alkyl or a moiety of Formula II wherein $W_c$ is aryl, heteroaryl, heterocycloalkyl, or cycloalkyl; $R^1$ is H, —F, —CN, —CH$_3$, isopropyl, —CF$_3$, —OCH$_3$, nitro, or phosphate; $R^2$ is halo, hydroxy, cyano, nitro, or phosphate; q is an integer of 0, 1, 2, 3, or 4; $R^4$, $R^5$, and $R^7$ are H or methyl; $R^8$ is H; X is absent or (CH$_2$)$_z$; z is 1; Y is absent or —N($R^9$)—; $R^9$ is hydrogen, methyl, or ethyl; $W_d$ is:

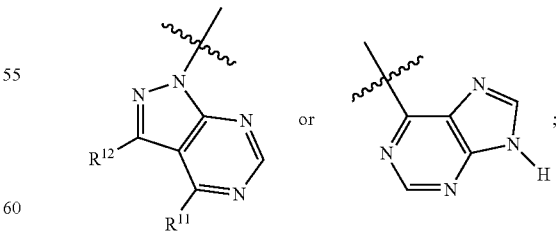

$R^{11}$ is amino; and $R^{12}$ is H, alkyl, alkynyl, alkenyl, halo, aryl, heteroaryl, heterocycloalkyl, cycloalkyl, cyano, amino, carboxylic acid, alkoxycarbonyl, or amido.

In another aspect, for compounds of Formula IX, X, XI, XII, XIII or XIV, B is a moiety of Formula II wherein $W_c$ is aryl, heteroaryl, heterocycloalkyl, or cycloalkyl; $R^1$ is H, —F, —Cl, —CN, —$CH_3$, isopropyl, —$CF_3$, —$OCH_3$, or nitro; $R^2$ is halo, hydroxy, cyano, or nitro; q is 0, 1 or 2; $R^4$, $R^5$, and $R^7$ are H or methyl; $R^8$ is H; X is $(CH_2)_z$; z is 1; Y is absent and $W_d$ is:

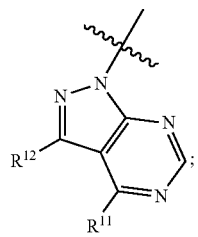

$R^{11}$ is amino; and $R^{12}$ is H, alkyl, alkynyl, alkenyl, halo, aryl, heteroaryl, heterocycloalkyl, or cycloalkyl.

In another aspect, for compounds of Formula IX, X, XI, XII, XIII or XIV, B is alkyl or a moiety of Formula II wherein $W_c$ is aryl, heteroaryl, heterocycloalkyl, or cycloalkyl, $R^1$ is H, —F, —Cl, —CN, —$CH_3$, isopropyl, —$CF_3$, —$OCH_3$, nitro, or phosphate; $R^2$ is halo, hydroxy, cyano, nitro, or phosphate; q is 0, 1 or 2; $R^4$, $R^5$, and $R^7$ are H or methyl; $R^8$ is H; X is $(CH_2)_z$; z is 1; Y is absent and $W_d$ is:

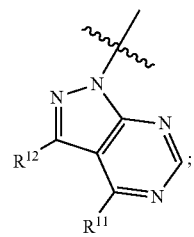

$R^{11}$ is amino; and $R^{12}$ is H, alkyl, alkynyl, alkenyl, halo, aryl, heteroaryl, heterocycloalkyl, cycloalkyl, cyano, amino, carboxylic acid, alkoxycarbonyl, or amido.

In another aspect, for compounds of Formula IX, X, XI, XII, XIII or XIV, B is alkyl or a moiety of Formula II wherein $W_c$ is aryl, heteroaryl, heterocycloalkyl, or cycloalkyl; $R^1$ is H, —F, —Cl, —CN, —$CH_3$, isopropyl, —$CF_3$, —$OCH_3$, nitro, or phosphate; $R^2$ is halo, hydroxy, cyano, nitro, or phosphate; q is 0, 1 or 2; $R^4$, $R^5$, and $R^7$ are H or methyl; $R^8$ is H; X is $(CH_2)_z$; z is 1; X is $(CH_2)_z$; z is 1; Y is —N($R^9$)—; $R^9$ is hydrogen, methyl, or ethyl; and $W_d$ is

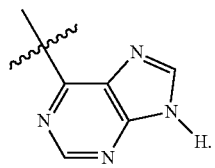

In another aspect, for compounds of Formula IX, X, XI, XII, XIII or XIV, B is alkyl or a moiety of Formula II wherein $W_c$ is aryl, heteroaryl, heterocycloalkyl, or cycloalkyl, $R^1$ is H, —F, —Cl, —CN, —$CH_3$, isopropyl, —$CF_3$, —$OCH_3$, nitro, or phosphate; $R^2$ is halo, hydroxy, cyano, nitro, or phosphate; q is 0, 1 or 2; $R^4$, $R^5$, and $R^7$ are H or methyl; $R^8$ is H; X is absent; Y is —N($R^9$)CH($R^9$)—; $R^9$ is hydrogen, methyl, or ethyl; $W_d$ is:

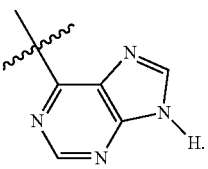

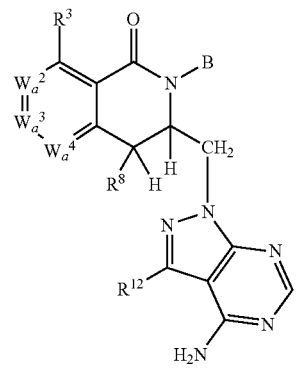

Formula 1-A

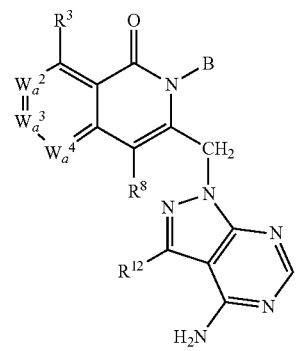

Formula 1-B

Illustrative embodiments of Formula 1-A and Formula 1-B are provided, wherein $R^3$ is selected from any of H, Cl, F, or methyl; any of $W_a^2$ is elected from CH, N, C—CN, or C—$OCH_3$; any of $W_a^3$ is selected from CH, N, C—$CF_3$, or C—$CH_3$; any of $W_a^4$ is selected from CH, N, or C—$CF_3$; any of $R^8$ $^{is}$ selected from H, Me, or Cl; any of B as described in Table 1; and any of $R^{12}$ as described in Table 2. The compounds of Formula 1-A and Formula 1-B can contain any substituents specified under $R^3$, $W_a^2$, $W_a^3$, $W_a^3$, $W_a^4$, $R^8$, B, and $R^{12}$. The specific embodiments described in no way limit the invention, but are descriptive of the compounds of the invention. Some additional exemplary compounds of Formulas 1-A and 1-B are illustrated in Table 5.

TABLE 1

Illustrative B of a compound having a structure of Formula I, IV, V, VI, VII, VII, IX, X, XI, XII, XIII, or XIV.

| Sub-class # | B |
|---|---|
| B-1 | cyclopentyl |

TABLE 1-continued

Illustrative B of a compound having a structure of Formula I, IV, V, VI, VII, VII, IX, X, XI, XII, XIII, or XIV.

| Sub-class # | B |
|---|---|
| B-2 | 4-isopropylpiperidin-1-yl (piperidine with N-isopropyl, attached at 4-position) |
| B-3 | —CH(CH₃)₂ |
| B-4 | 2-(trifluoromethyl)phenyl |
| B-5 | cyclopropylmethyl |
| B-6 | 2-chlorophenyl |
| B-7 | 2-methylphenyl |
| B-8 | 3-methylpyridin-2-yl |
| B-9 | 2-ethylphenyl |
| B-10 | 2-fluorophenyl |
| B-11 | 1-methylpiperidin-4-yl |
| B-12 | 2-isopropylphenyl |
| B-13 | 2-methoxyphenyl |
| B-14 | 3-fluorophenyl |
| B-15 | 2-hydroxyphenyl |
| B-16 | 2-cyanophenyl |
| B-17 | 3-cyanophenyl |
| B-18 | 4-cyanophenyl |
| B-19 | 2-morpholinoethyl |
| B-20 | phenyl |
| B-21 | 4-methoxy-2-methylphenyl |

TABLE 1-continued
Illustrative B of a compound having a structure of
Formula I, IV, V, VI, VII, VIII, IX, X, XI, XII, XIII, or XIV.
| Sub-class # | B |
|---|---|
| B-22 | 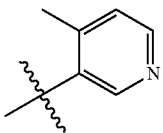 [SMILES: *c1cnccc1C] |
| B-23 | 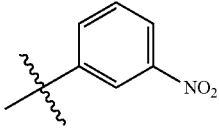 [SMILES: *c1cccc([N+](=O)[O-])c1] |
| B-24 | 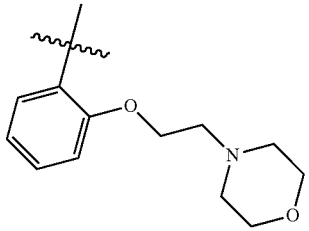 [SMILES: *c1ccccc1OCCN1CCOCC1] |
| B-25 | 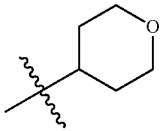 [SMILES: *C1CCOCC1] |
| B-26 | 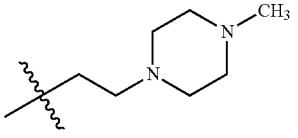 [SMILES: *CCN1CCN(C)CC1] |
| B-27 | 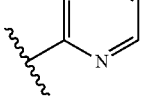 |
| B-28 | 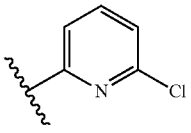 [SMILES: *c1cccc(Cl)n1] |
| B-29 | 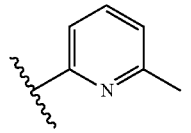 [SMILES: *c1cccc(C)n1] |
| B-30 | 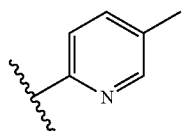 [SMILES: *c1ccc(C)cn1] |
| B-31 | 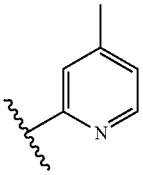 [SMILES: *c1cc(C)ccn1] |
| B-32 | 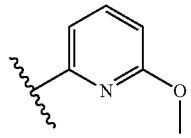 [SMILES: *c1cccc(OC)n1] |
| B-33 | 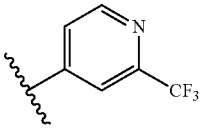 [SMILES: *c1ccnc(C(F)(F)F)c1] |
| B-34 | 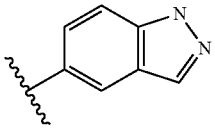 |
| B-35 | 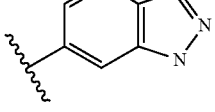 |
| B-36 | 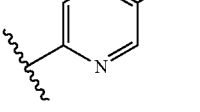 |
| B-37 | 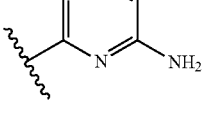 |
| B-38 | 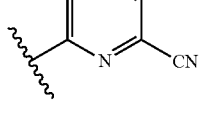 |
| B-39 | 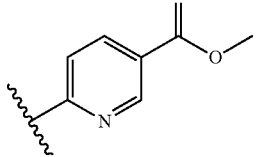 |

TABLE 1-continued

Illustrative B of a compound having a structure of Formula I, IV, V, VI, VII, VII, IX, X, XI, XII, XIII, or XIV.

| Sub-class # | B |
|---|---|
| B-40 | 5-chloropyrazin-2-yl |
| B-41 | methyl 6-pyridine-2-carboxylate (linked at 6) |
| B-42 | methyl 2-pyridinecarboxylate (linked at 4) |
| B-43 | 2-cyanopyridin-4-yl |
| B-44 | 2-methylpyridin-4-yl |
| B-45 | 6-oxo-1,6-dihydropyridin-2-yl |
| B-46 | 5-hydroxypyridin-2-yl |
| B-47 | 5-fluoropyridin-2-yl |
| B-48 | 2-aminopyridin-4-yl |
| B-49 | 5-methoxypyrazin-2-yl |
| B-50 | 5-aminopyrazin-2-yl |
| B-51 | 5-methylpyrazin-2-yl |
| B-52 | 5-(dimethylamino)pyrazin-2-yl |
| B-53 | 5-(N-ethyl-N-methylamino)pyrazin-2-yl |
| B-54 | 5-(diethylamino)pyrazin-2-yl |
| B-55 | 5-(4-methylpiperazin-1-yl)pyrazin-2-yl |
| B-56 | 5-(pyrrolidin-1-yl)pyrazin-2-yl |
| B-57 | 5-(piperidin-1-yl)pyrazin-2-yl |

TABLE 1-continued
Illustrative B of a compound having a structure of
Formula I, IV, V, VI, VII, VII, IX, X, XI, XII, XIII, or XIV.
| Sub-class # | B |
|---|---|
| B-58 | 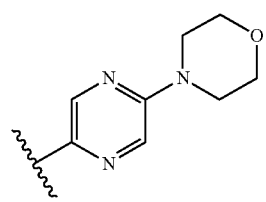 [SMILES: *c1cnc(N2CCOCC2)cn1] |
| B-59 | 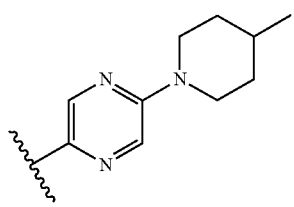 [SMILES: *c1cnc(N2CCC(C)CC2)cn1] |
| B-60 | 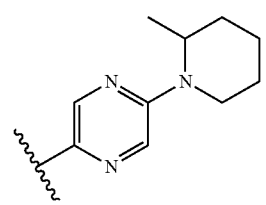 [SMILES: *c1cnc(N2CCCCC2C)cn1] |
| B-61 | 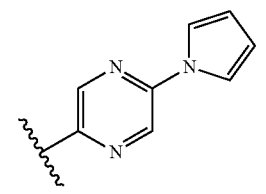 [SMILES: *c1cnc(-n2cccc2)cn1] |
| B-62 | 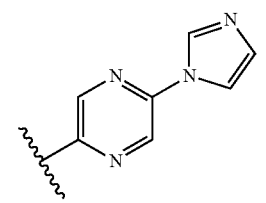 [SMILES: *c1cnc(-n2ccnc2)cn1] |
| B-63 | 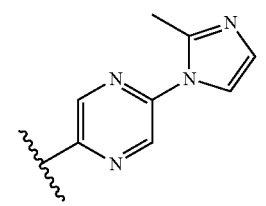 [SMILES: *c1cnc(-n2ccnc2C)cn1] |
| B-64 | 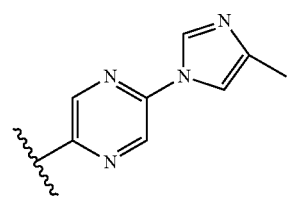 [SMILES: *c1cnc(-n2cnc(C)c2)cn1] |
TABLE 1-continued
Illustrative B of a compound having a structure of
Formula I, IV, V, VI, VII, VII, IX, X, XI, XII, XIII, or XIV.
| Sub-class # | B |
|---|---|
| B-65 | 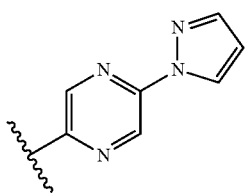 [SMILES: *c1cnc(-n2cccn2)cn1] |
| B-66 | 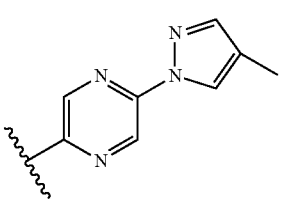 [SMILES: *c1cnc(-n2cc(C)cn2)cn1] |
| B-67 | 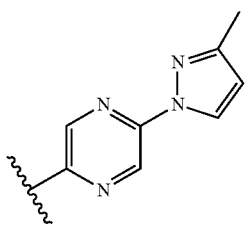 [SMILES: *c1cnc(-n2ccc(C)n2)cn1] |
| B-68 | 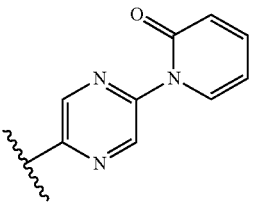 [SMILES: *c1cnc(-n2ccccc2=O)cn1] |
| B-69 | 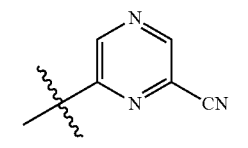 [SMILES: *c1cncc(C#N)n1] |
| B-70 | 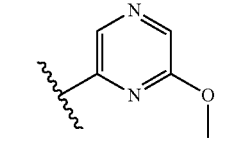 [SMILES: *c1cncc(OC)n1] |
| B-71 | 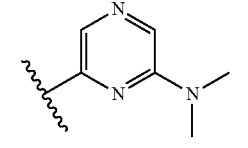 [SMILES: *c1cncc(N(C)C)n1] |
| B-72 | 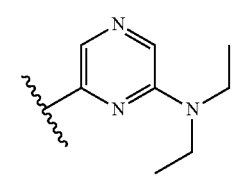 [SMILES: *c1cncc(N(CC)CC)n1] |

TABLE 1-continued

Illustrative B of a compound having a structure of
Formula I, IV, V, VI, VII, VII, IX, X, XI, XII, XIII, or XIV.

| Sub-class # | B |
|---|---|
| B-73 | (pyrazine substituted with morpholine) |
| B-74 | (pyrazine substituted with Cl) |
| B-75 | (pyrazine substituted with imidazole) |
| B-76 | (pyrazine substituted with pyridinone) |
| B-77 | (pyrazine substituted with pyrrolidine) |
| B-78 | (pyrazine) |
| B-79 | (thiazole) |
| B-80 | (2-methylthiazole) |
| B-81 | (2-isopropylthiazole) |
| B-82 | (thiazole substituted with N-methyl-N-methylamine) |
| B-83 | (thiazole substituted with N,N-diethylamine) |
| B-84 | (thiazole substituted with pyridinone) |
| B-85 | (thiazole substituted with imidazole) |
| B-86 | (cyclohexyl) |
| B-87 | —CH$_3$ |
| B-88 | —CH$_2$CH$_3$ |
| B-89 | (cyclobutyl) |
| B-90 | (4-methylpyridin-3-yl) |
| B-91 | (propyl-pyrrolidine) |
| B-92 | (3,5-dimethylphenyl) |

TABLE 1-continued

Illustrative B of a compound having a structure of
Formula I, IV, V, VI, VII, VII, IX, X, XI, XII, XIII, or XIV.

| Sub-class # | B |
|---|---|
| B-93 |  |
| B-94 | 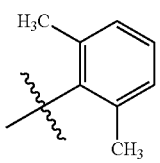 |
| B-95 | 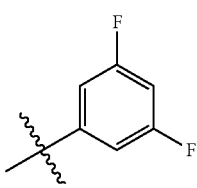 [SMILES: *c1cc(F)cc(F)c1] |
| B-96 | 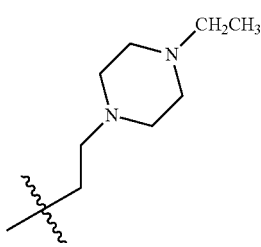 [SMILES: *CCN1CCN(CC)CC1] |
| B-97 | 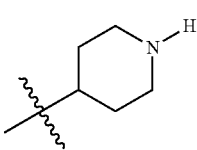 [SMILES: *C1CCNCC1] |
| B-98 | 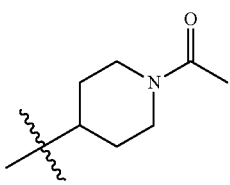 [SMILES: *C1CCN(C(C)=O)CC1] |
| B-99 | 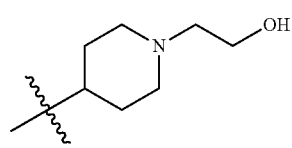 [SMILES: *C1CCN(CCO)CC1] |
| B-100 | 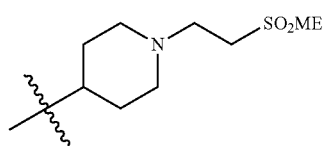 |

TABLE 1-continued

Illustrative B of a compound having a structure of
Formula I, IV, V, VI, VII, VII, IX, X, XI, XII, XIII, or XIV.

| Sub-class # | B |
|---|---|
| B-101 | 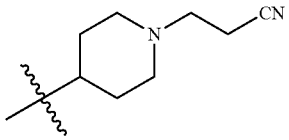 [SMILES: *C1CCN(CCC#N)CC1] |
| B-102 | 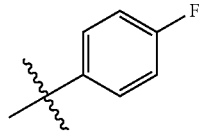 [SMILES: *c1ccc(F)cc1] |

TABLE 2

Illustrative $R^{12}$ of a compound having a structure of Formula I, IV, V, VI, VII, VIII, IX, X, XI, XII, XIII, or XIV.

| Sub-class # | $R^{12}$ |
|---|---|
| 12-1 | —CN |
| 12-2 | —Br |
| 12-3 | —Cl |
| 12-4 | —CH$_2$CH$_3$ |
| 12-5 | —CH$_3$ |
| 12-6 | —CH(CH$_3$)$_2$ |
| 12-7 | 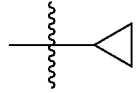 |
| 12-8 | 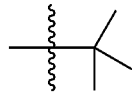 |
| 12-9 | 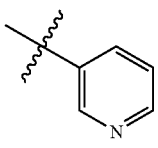 [SMILES: *c1cccnc1] |
| 12-10 | 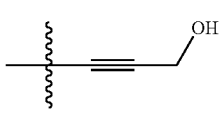 [SMILES: *C#CCO] |
| 12-11 | 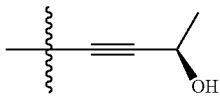 |
| 12-12 | 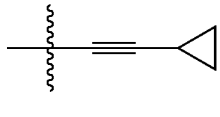 [SMILES: *C#CC1CC1] |
| 12-13 | 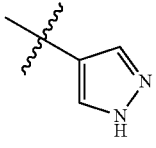 |

TABLE 2-continued

Illustrative R¹² of a compound having a structure of Formula I, IV, V, VI, VII, VIII, IX, X, XI, XII, XIII, or XIV.

| Sub-class # | R¹² |
| --- | --- |
| 12-14 | 3-carbamoylphenyl (CONH₂) |
| 12-15 | 2-(acetylamino)-1,3-thiazol-5-yl |
| 12-16 | 2-(acetylamino)-1,3-benzothiazol-6-yl |
| 12-17 | 2-amino-1,3-thiazol-5-yl |
| 12-18 | 2-aminopyridin-4-yl |
| 12-19 | 2-amino-6-fluoropyridin-4-yl |
| 12-20 | 2-aminopyrimidin-4-yl |
| 12-21 | 2-amino-6-fluoropyrimidin-4-yl |
| 12-22 | 1H-pyrrolo[2,3-b]pyridin-5-yl |
| 12-23 | 1H-indazol-6-yl |
| 12-24 | 4-fluoro-1H-indazol-6-yl |
| 12-25 | 1H-pyrrolo[2,3-b]pyridin-4-yl |
| 12-26 | 3-methoxyphenyl (OCH₃) |
| 12-27 | 6-fluoro-1H-pyrrolo[2,3-b]pyridin-4-yl |
| 12-28 | 3-hydroxy-3-methylbut-1-yn-1-yl (OH) |

TABLE 2-continued
Illustrative R¹² of a compound having a structure of Formula I, IV, V, VI, VII, VIII, IX, X, XI, XII, XIII, or XIV.
| Sub-class # | R¹² |
|---|---|
| 12-29 | 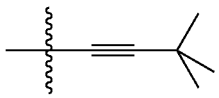 [SMILES: *C#CC(C)(C)C] |
| 12-30 | 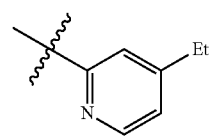 [SMILES: *c1cc(CC)ccn1] |
| 12-31 | 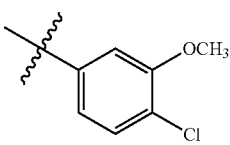 [SMILES: *c1ccc(Cl)c(OC)c1] |
| 12-32 | 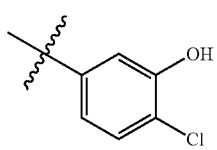 [SMILES: *c1ccc(Cl)c(O)c1] |
| 12-33 | 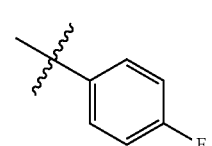 |
| 12-34 | 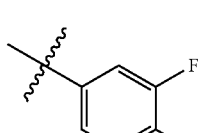 |
| 12-35 | —H |
| 12-36 | 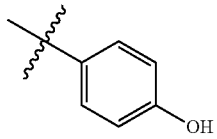 [SMILES: *c1ccc(O)cc1] |
| 12-37 | 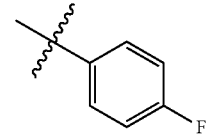 [SMILES: *c1ccc(F)cc1] |
| 12-38 | 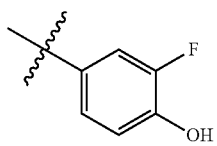 [SMILES: *c1ccc(O)c(F)c1] |
| 12-39 | 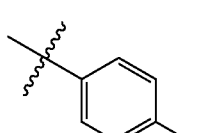 |
| 12-40 | 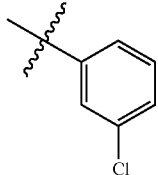 [SMILES: *c1cccc(Cl)c1] |
| 12-41 | 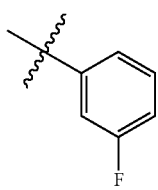 [SMILES: *c1cccc(F)c1] |
| 12-42 | 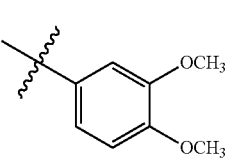 [SMILES: *c1ccc(OC)c(OC)c1] |
| 12-43 | 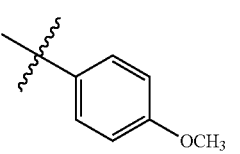 [SMILES: *c1ccc(OC)cc1] |
| 12-44 | 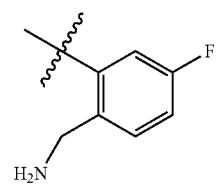 [SMILES: *c1cc(F)ccc1CN] |
| 12-45 | 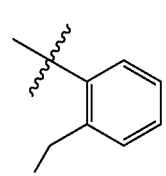 |
| 12-46 | 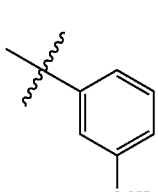 |
| 12-47 | 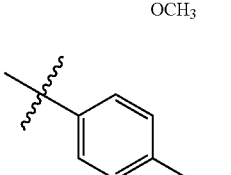 |

/ TABLE 2-continued
Illustrative R[12] of a compound having a structure of Formula I, IV, V, VI, VII, VIII, IX, X, XI, XII, XIII, or XIV.
| Sub-class # | R[12] |
|---|---|
| 12-48 | 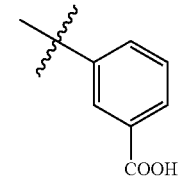 [SMILES: *c1cccc(C(=O)O)c1] |
| 12-49 | 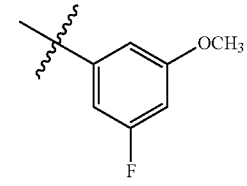 [SMILES: *c1cc(F)cc(OC)c1] |
| 12-50 | 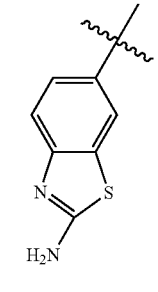 [SMILES: *c1ccc2nc(N)sc2c1] |
| 12-51 | 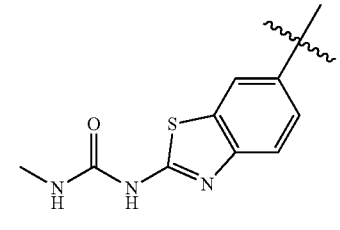 [SMILES: *c1ccc2nc(NC(=O)NC)sc2c1] |
| 12-52 | 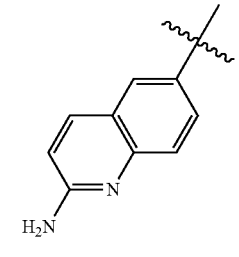 [SMILES: *c1ccc2nc(N)ccc2c1] |
| 12-53 | 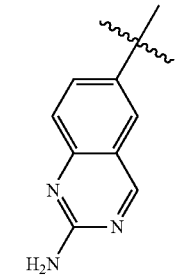 [SMILES: *c1ccc2nc(N)ncc2c1] |
| 12-54 |  |
| 12-55 |  |
| 12-56 |  |
| 12-57 |  |
| 12-58 |  |
| 12-59 |  |

TABLE 2-continued

Illustrative R[12] of a compound having a structure of Formula I, IV, V, VI, VII, VIII, IX, X, XI, XII, XIII, or XIV.

| Sub-class # | R[12] |
|---|---|
| 12-60 | [structure: cyclic lactam with exocyclic alkene] |
| 12-61 | —I |
| 12-62 | [structure: 3-hydroxyphenyl] |
| 12-63 | [structure: 3-hydroxy-5-fluorophenyl] |
| 12-64 | [structure: 3-hydroxy-4-fluorophenyl] |
| 12-65 | [structure: alkyne with isopropyl group] |
| 12-66 | [structure: 4-(diethylamino)pyridin-2-yl] |
| 12-67 | [structure: 2-aminobenzothiazol-6-yl] |
| 12-68 | [structure: 1H-pyrazol-3-yl] |
| 12-69 | [structure: 2-methyl-1H-imidazol-4-yl] |
| 12-70 | [structure: 5-methyl-1H-pyrazol-3-yl] |
| 12-71 | [structure: 5-fluoro-1H-pyrazol-3-yl] |
| 12-72 | [structure: 1H-1,2,4-triazol-3-yl] |
| 12-73 | [structure: 5-oxo-2,5-dihydro-1H-pyrazol-3-yl] |
| 12-74 | [structure: 1-methyl-5-oxo-2,5-dihydro-1H-pyrazol-3-yl] |
| 12-75 | [structure: 3-oxo-2,3-dihydroisoxazol-5-yl] |
| 12-76 | [structure: 3-oxo-2,3-dihydroisothiazol-5-yl] |

TABLE 2-continued

Illustrative R[12] of a compound having a structure of Formula I, IV, V, VI, VII, VIII, IX, X, XI, XII, XIII, or XIV.

| Sub-class # | R[12] |
|---|---|
| 12-77 | NC– |
| 12-78 | H$_2$N–C(=O)– |
| 12-79 | MeHN–C(=O)– |
| 12-80 | MeHN–C(=O)–CH=CH– |
| 12-81 | morpholinomethyl |
| 12-82 | H$_3$C–O–C(=O)– |
| 12-83 | HO–C(=O)–O– |
| 12-84 | HO–NH–C(=O)– |
| 12-85 | 2-amino-1H-benzimidazol-5-yl |
| 12-86 | 2-acetamido-1H-benzimidazol-5-yl |
| 12-87 | F$_2$C=C< |
| 12-88 | 1H-pyrazol-3-yl |
| 12-89 | 1-methyl-1H-pyrazol-5-yl |
| 12-90 | H$_2$N–C(=O)–CH$_2$CH$_2$– |
| 12-91 | 2-acetamido-benzoxazol-6-yl |
| 12-92 | morpholin-4-yl–C(=O)–CH=CH– |

TABLE 2-continued

Illustrative R$^{12}$ of a compound having a structure of Formula I, IV, V, VI, VII, VIII, IX, X, XI, XII, XIII, or XIV.

| Sub-class # | R$^{12}$ |
|---|---|
| 12-93 | (morpholine-N-carbonyl-alkyl group) |
| 12-94 | (acrylamide group, CH=CH-C(O)-NH$_2$) |
| 12-95 | (tetrazolyl group) |
| 12-96 | (tetrazolyl group isomer) |

Illustrative embodiments of Formula 2-A and Formula 2-B are provided, wherein R$^3$ is selected from any of H, Cl, F, or methyl; any of W$_a^2$ is elected from CH, N, C—CN, or C—OCH$_3$; any of W$_a^3$ is selected from CH, N, C—CF$_3$, or C—CH$_3$; any of W$_a^4$ is selected from CH, N, or C—CF$_3$; any of R$^8$ is selected from H, Me, or Cl; any of B as described in Table 1; any of R$^{12}$ as described in Table 2, and any of X—Y—W$_d$ as described in Table 3. The compounds of Formula 2-A and Formula 2-B can contain any substituents specified under R$^3$, W$_a^2$, W$_a^3$, W$_a^4$, R$^8$, B, R$^{12}$, and X—Y—W$_d$. The specific embodiments described in no way limit the invention, but are descriptive of the compounds of the invention. Some additional exemplary compounds of Formulas 2-A and 2-B are illustrated in Table 5.

TABLE 3

Exemplary X—Y—W$_d$ for a compound having a structure of Formula I, IV, V, VI, VII, VIII, IX, X, XI, XII, XIII, or XIV.

Formula 2-A

Formula 2-B

| Sub-class # | X—Y—W$_d$ |
|---|---|
| 1 | (O-linked 2-methyl-2H-pyrazolo[3,4-d]pyrimidin-4-amine) |
| 2 | (N-linked (S)-1-methylethyl pyrazolo[3,4-d]pyrimidin-4-amine with R$^{12}$) |
| 3 | (N-linked (R)-1-methylethyl pyrazolo[3,4-d]pyrimidin-4-amine with R$^{12}$) |
| 4 | (O-linked 2,5-dimethyl-2H-pyrazolo[3,4-d]pyrimidin-4-amine) |
| 5 | (N-linked (S)-1-methylethyl 6-methyl pyrazolo[3,4-d]pyrimidin-4-amine with R$^{12}$) |

TABLE 3-continued
| | |
|---|---|
| 6 | 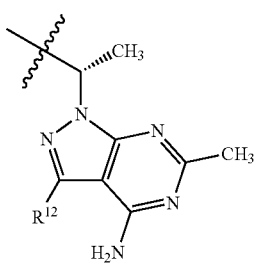 |
| 7 | 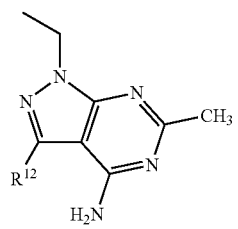 |
| 8 | 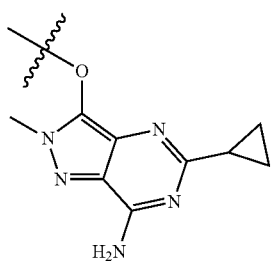 [SMILES: *Oc1c2nc(C3CC3)nc(N)c2nn1C] |
| 9 | 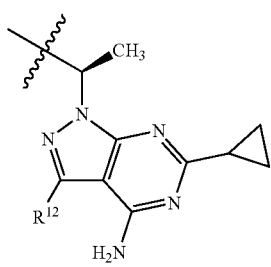 |
| 10 | 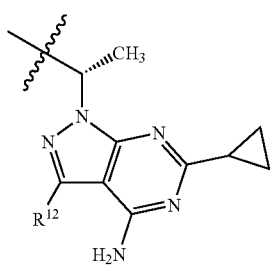 |
| 11 | 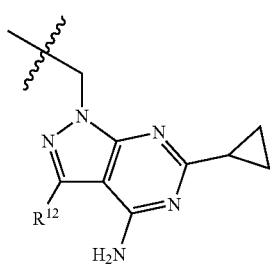 |
| 12 | 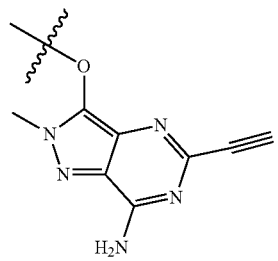 [SMILES: *Oc1c2nc(C#C)nc(N)c2nn1C] |
| 13 | 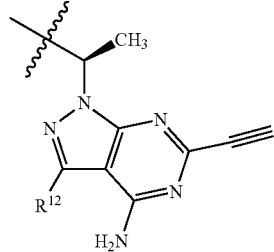 |
| 14 | 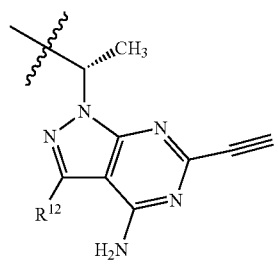 |
| 15 | 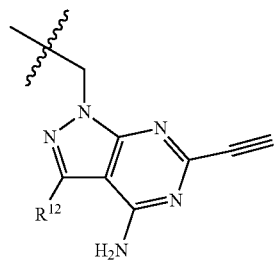 |
| 16 | 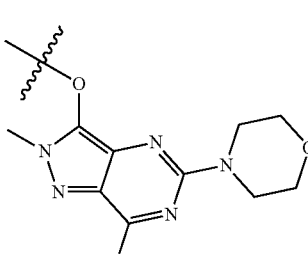 |
| 17 | 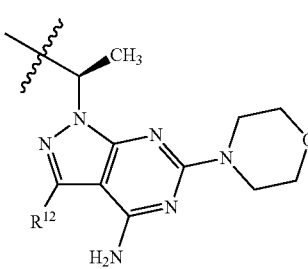 |

TABLE 3-continued
| | |
|---|---|
| 18 | 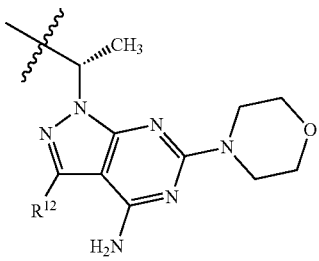 |
| 19 | 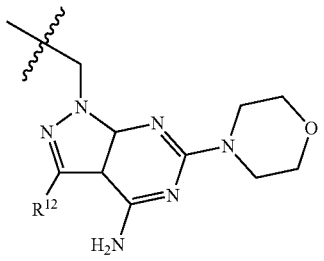 |
| 20 | 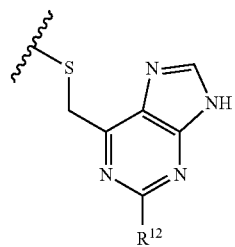 |
| 21 | 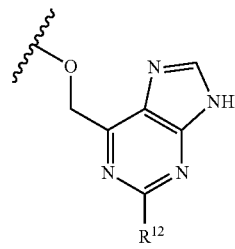 |
| 22 | 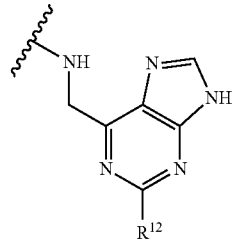 |
| 23 | 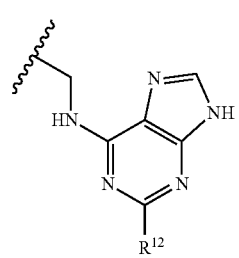 |
TABLE 3-continued
| | |
|---|---|
| 24 | 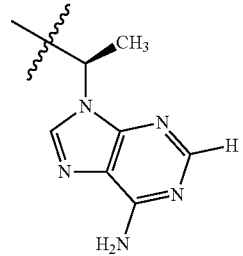 [SMILES: *[C@@H](C)n1cnc2c(N)ncnc21] |
| 25 | 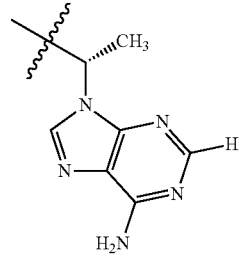 [SMILES: *[C@H](C)n1cnc2c(N)ncnc21] |
| 26 | 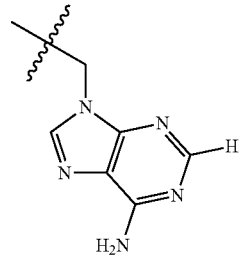 [SMILES: *Cn1cnc2c(N)ncnc21] |
| 27 | 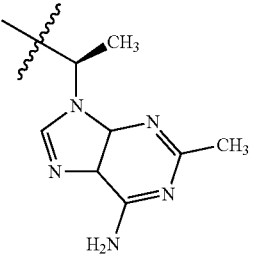 [SMILES: *[C@@H](C)N1C=NC2C(N)=NC(C)=NC21] |
| 28 | 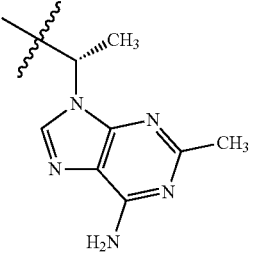 [SMILES: *[C@H](C)n1cnc2c(N)nc(C)nc21] |
| 29 | 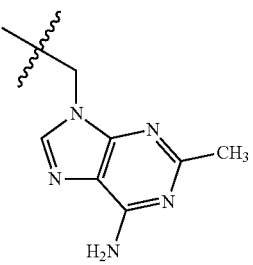 [SMILES: *Cn1cnc2c(N)nc(C)nc21] |

TABLE 3-continued
| | |
|---|---|
| 30 | 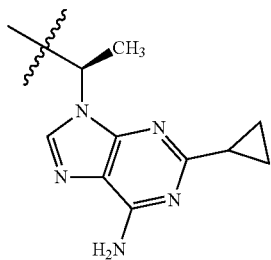 [SMILES: *[C@@H](C)n1cnc2c(N)nc(C3CC3)nc21] |
| 31 | 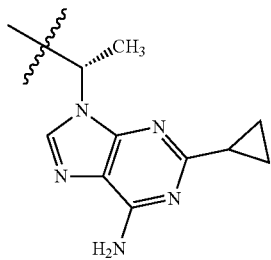 [SMILES: *[C@H](C)n1cnc2c(N)nc(C3CC3)nc21] |
| 32 | 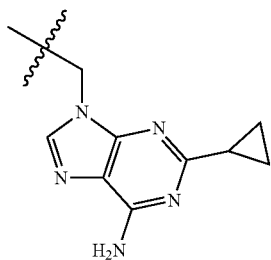 [SMILES: *Cn1cnc2c(N)nc(C3CC3)nc21] |
| 33 | 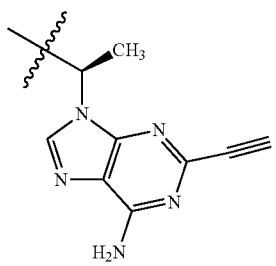 [SMILES: *[C@@H](C)n1cnc2c(N)nc(C#C)nc21] |
| 34 | 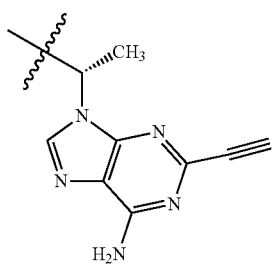 [SMILES: *[C@H](C)n1cnc2c(N)nc(C#C)nc21] |
| 35 | 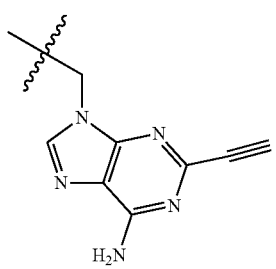 [SMILES: *Cn1cnc2c(N)nc(C#C)nc21] |
TABLE 3-continued
| | |
|---|---|
| 36 | 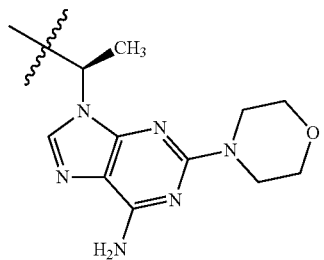 [SMILES: *[C@@H](C)n1cnc2c(N)nc(N3CCOCC3)nc21] |
| 37 | 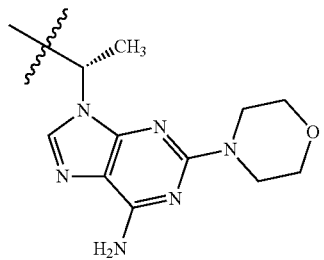 [SMILES: *[C@H](C)n1cnc2c(N)nc(N3CCOCC3)nc21] |
| 38 | 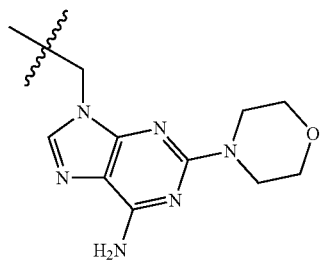 [SMILES: *Cn1cnc2c(N)nc(N3CCOCC3)nc21] |
| 39 | 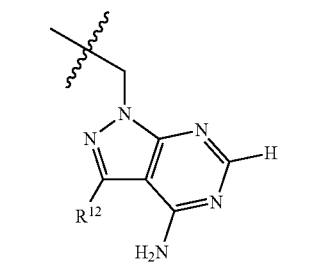 |
| 40 | 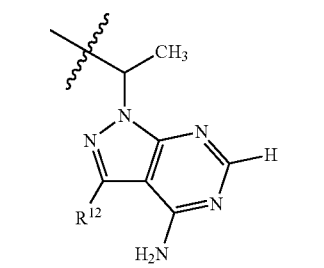 |
| 41 | 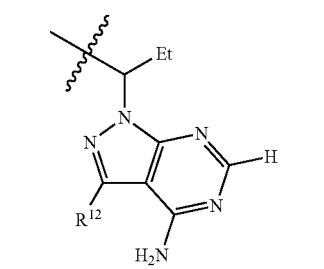 |

| | | | | |
|---|---|---|---|---|
| 42 | 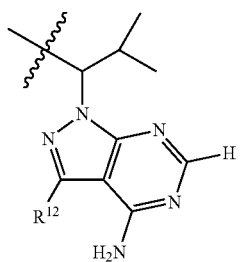 | | 48 | 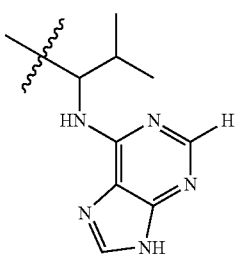 |
| 43 | 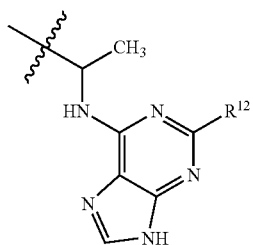 | | 49 | 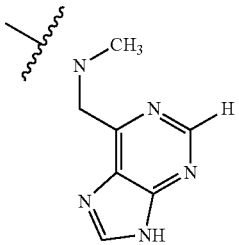 |
| 44 | 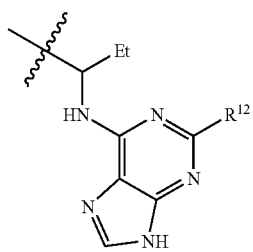 | | 50 | 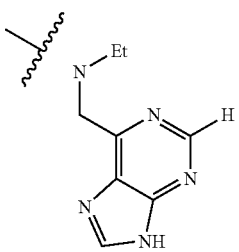 |
| 45 | 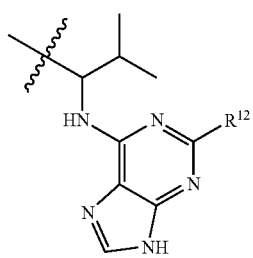 | | 51 | 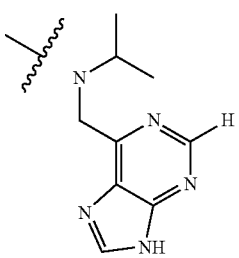 |
| 46 | 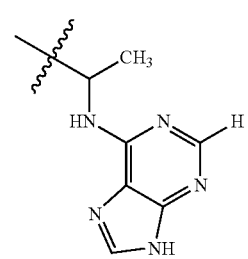 [SMILES: *C(C)Nc1ncnc2[nH]cnc12] | | 52 | 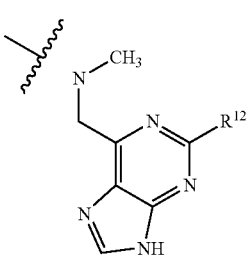 |
| 47 | 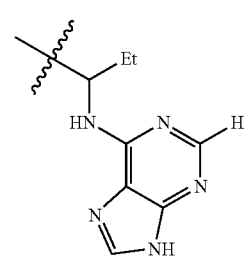 [SMILES: *C(CC)Nc1ncnc2[nH]cnc12] | | 53 | 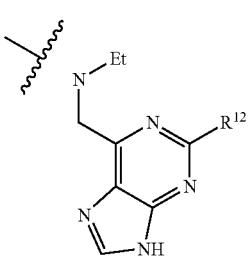 |

TABLE 3-continued

54
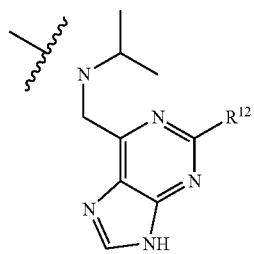

55
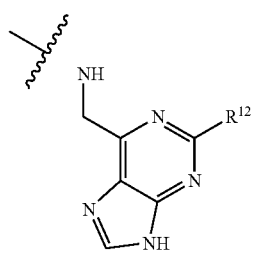

Illustrative embodiments of Formula 6-A are provided, wherein $R^3$ is selected from any of H, Cl, F, or methyl; any of B as described in Table 1; and any of $R^{12}$ as described in Table 2. The compounds of Formula 6-A can contain any substituents specified under $R^3$, B, and $R^{12}$. The specific embodiments described in no way limit the invention, but are descriptive of the compounds of the invention. Some additional exemplary compounds of Formulas 6-A are illustrated in Table 5.

Formula 6-A
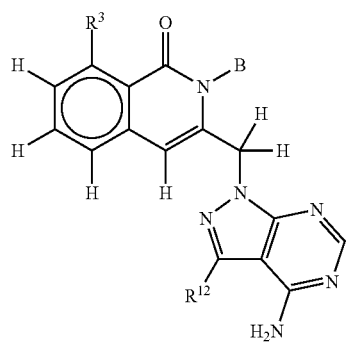

Illustrative embodiments of Formula 6-C1 are provided, wherein $R^3$ is selected from any of H, Cl, F, or methyl; any of B as described in Table 1; any of $R^9$, which is selected from —H, —$CH_3$, or —$CH_2CH_3$, and any of $R^{12}$ as described in Table 2. The compounds of Formula 6-C1 can contain any substituents specified under $R^3$, B, $R^9$, and $R^{12}$. The specific embodiments described in no way limit the invention, but are descriptive of the compounds of the invention. Some additional exemplary compounds of Formulas 6-C1 are illustrated in Table 5.

Formula 6-C1
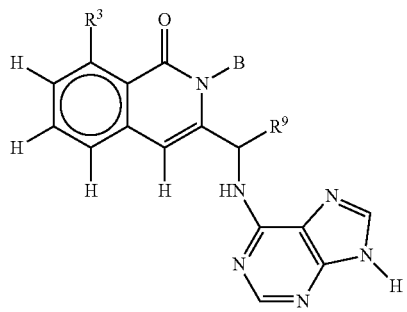

Illustrative embodiments of Formula 6-C2 are provided, wherein $R^3$ is selected from any of H, Cl, F, or methyl; any of B as described in Table 1; and any of $R^9$, which is selected from —H, —$CH_3$, or —$CH_2CH_3$. The compounds of Formula 6-C2 can contain any substituents specified under $R^3$, B, and $R^9$. The specific embodiments described in no way limit the invention, but are descriptive of the compounds of the invention. Some additional exemplary compounds of Formulas 6-C2 are illustrated in Table 5.

Formula 6-C2
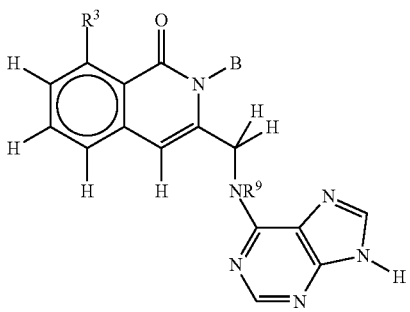

Illustrative embodiments of Formula 6-D are provided, wherein $R^3$ is selected from any of H, Cl, F, or methyl; any of B as described in Table 1; and any of $R^9$, which is selected from —H, —$CH_3$, or —$CH_2CH_3$. The compounds of Formula 6-D can contain any substituents specified under $R^3$, B, and $R^9$. The specific embodiments described in no way limit the invention, but are descriptive of the compounds of the invention. Some additional exemplary compounds of Formulas 6-D are illustrated in Table 5.

Formula 6-D
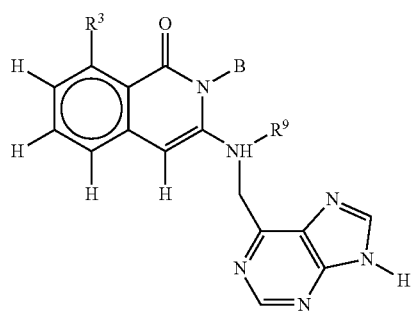

Illustrative embodiments of Formula VIII are provided, wherein $R^3$ is selected from any of H, Cl, F, or methyl; any of $W_a^2$ is elected from CH, N, C—CN, or C—OCH$_3$; any of $W_a^3$ is selected from CH, N, C—CF$_3$, or C—CH$_3$; any of $W_a^4$ is selected from CH, N, or C—CF$_3$; any of B as described in Table 1; any of $R^{12}$ as described in Table 2, and any of X—Y—W$_d$ as described in Table 3. The compounds of Formula VIII can contain any substituents specified under $R^3$, $W_a^2$, $W_a^3$, $W_a^4$, B, $R^{12}$, and X—Y—W$_d$. The specific embodiments described in no way limit the invention, but are descriptive of the compounds of the invention. Some additional exemplary compounds of Formula VIII are illustrated in Table 5.

Formula VIII
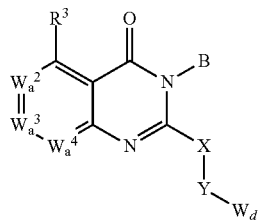

Also provided are compounds of substructure Formulae 9A-9BD under generic structure Formula IX, wherein $R^4$ is selected from —H, methyl, ethyl, n-propyl, iso-propyl, cyclopropyl, cyclobutyl, and cyclopentyl; any of $R^5$ is selected from H, Cl, F, methyl, or trifluoromethyl; any of $R^7$ is selected from H, Cl, F, methyl, trifluoromethyl; cyano, hydroxyl, ethyl, iso-propyl, and cyclopropyl; any of $R^8$ is selected from H, methyl or iso-propyl; any of B as described in Table 1; any of X—Y—W$_d$ as described in Table 3, and any of $R^{12}$ as described in Table 2. The compounds of Formulae 9A-9BD can contain any substituents specified under $R^4$, $R^5$, $R^7$, $R^8$B, X—Y—W$_d$, and $R^{12}$. The specific embodiments described in no way limit the invention, but are descriptive of the compounds of the invention. Some additional exemplary compounds of Formulae 9-A to 9-BD are illustrated in Table 5.

Formula 9-B
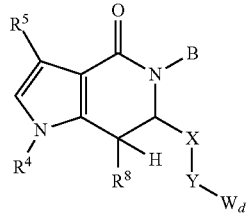

Formula 9-C
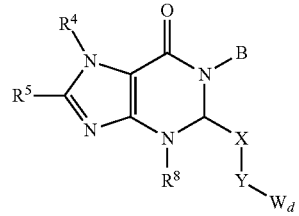

Formula 9-A
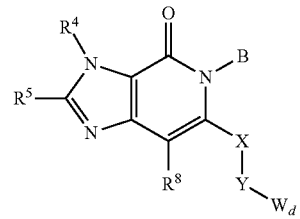

Formula 9-D
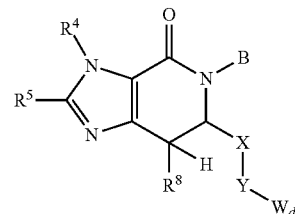

Formula 9-E

Formula 9-F
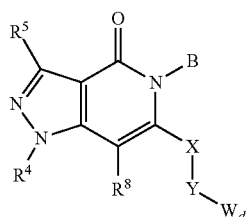

Formula 9-G
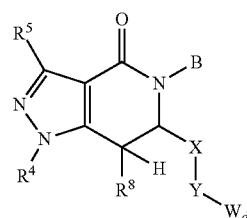

Formula 9-H

Formula 9-I

Formula 9-J

Formula 9-K

Formula 9-L

Formula 9-M

Formula 9-N

Formula 9-O

Formula 9-P

Formula 9-Q

Formula 9-R

Formula 9-S

Formula 9-T

Formula 9-U

Formula 9-V

Formula 9-W

Formula 9-X
Formula 9-Y
Formula 9-Z
Formula 9-AA
Formula 9-AB
Formula 9-AC
Formula 9-AD
Formula 9-AE
Formula 9-AF
Formula 9-AG
Formula 9-AH
Formula 9-AI
Formula 9-AJ
Formula 9-AK Formula 9-AL
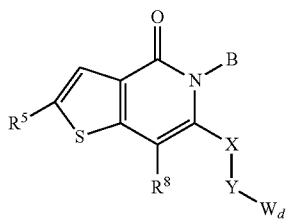
Formula 9-AM
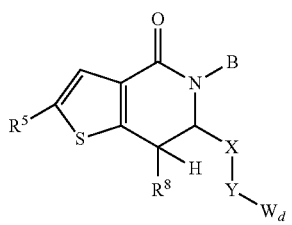
Formula 9-AN
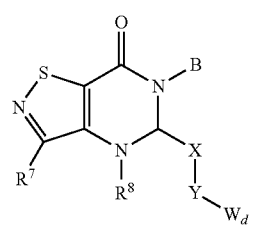
Formula 9-AO
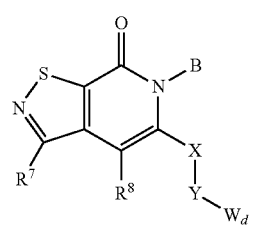
Formula 9-AP
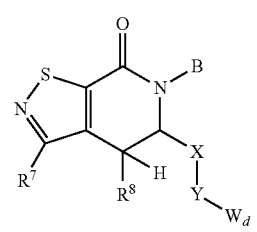
Formula 9-AQ
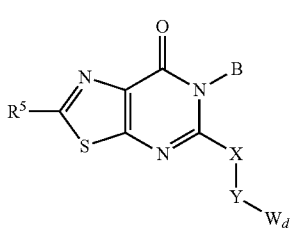
Formula 9-AR
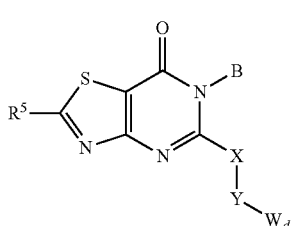
Formula 9-AS
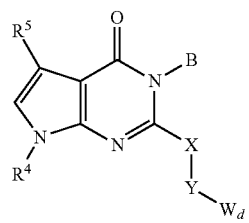
Formula 9-AT
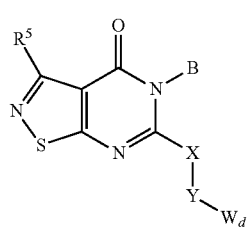
Formula 9-AU
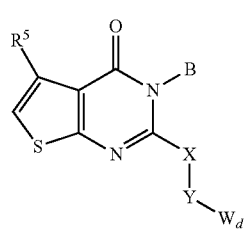
Formula 9-AV
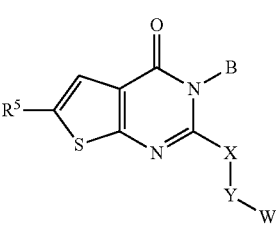
Formula 9-AW
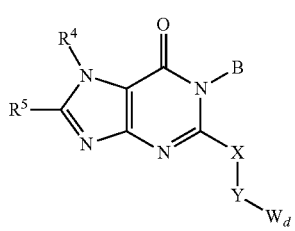
Formula 9-AX
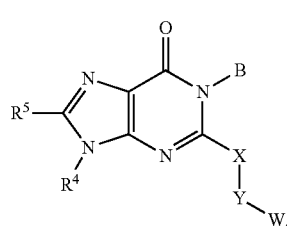
Formula 9-AY
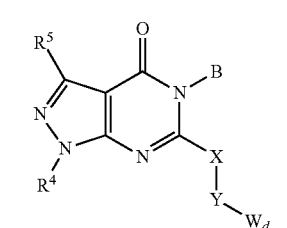

Formula 9-AZ
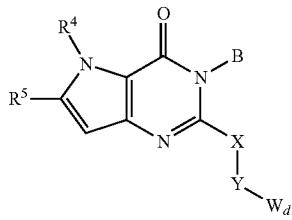
Formula 9-BA
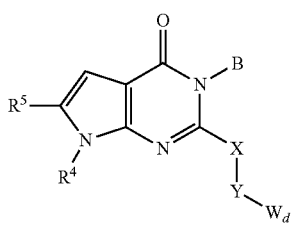
Formula 9-BB
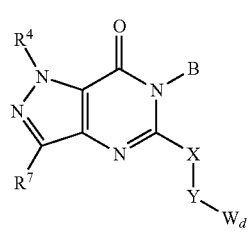
Formula 9-BC
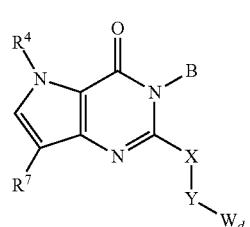
Formula 9-BD
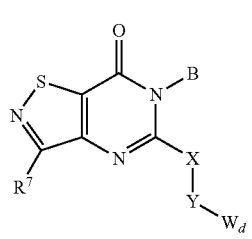
Other illustrative compounds include but are not limited to the following:
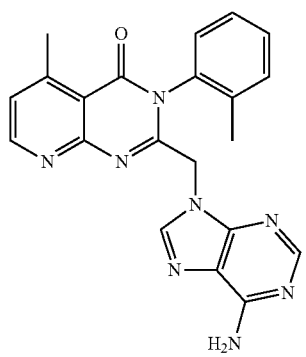
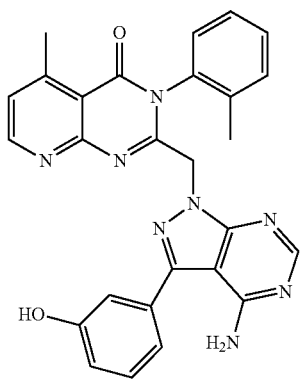
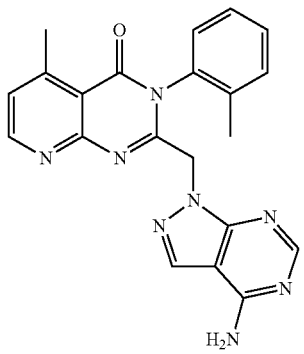
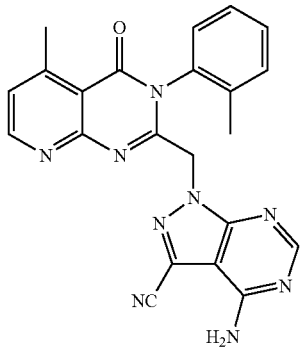
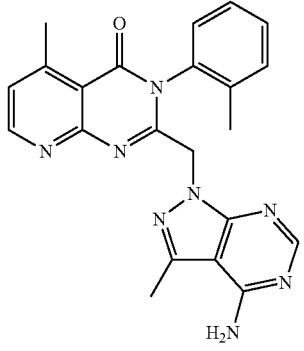

107
-continued
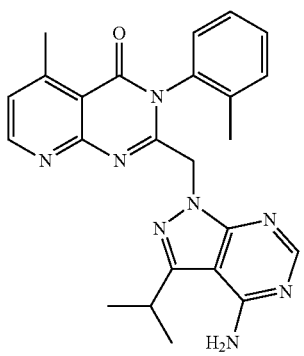
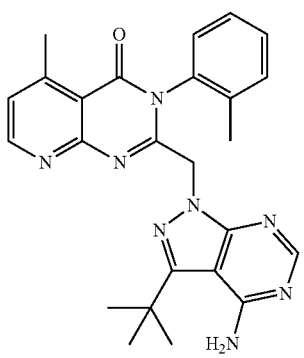
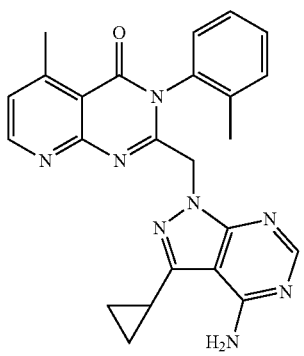
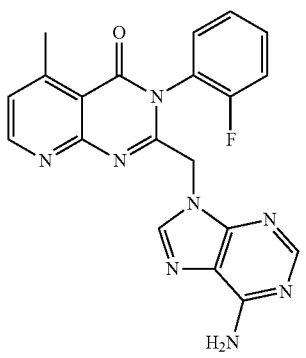
108
-continued
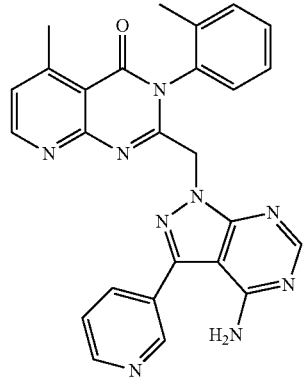
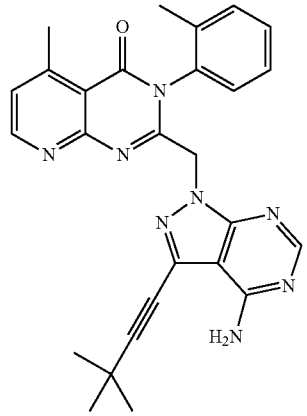
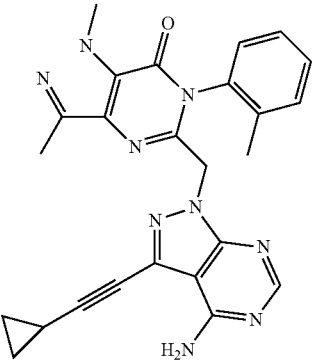
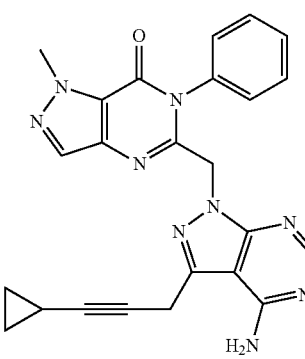

-continued
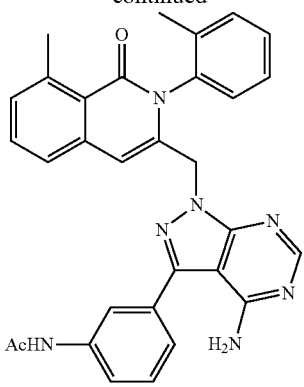
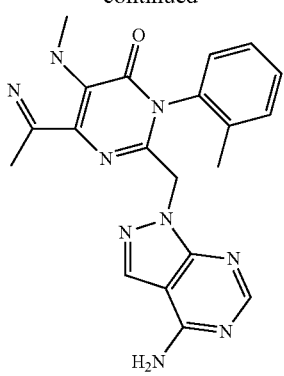
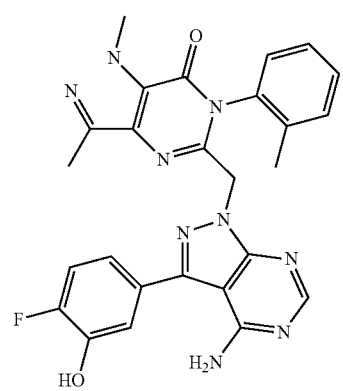
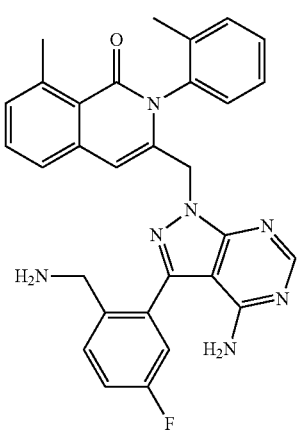
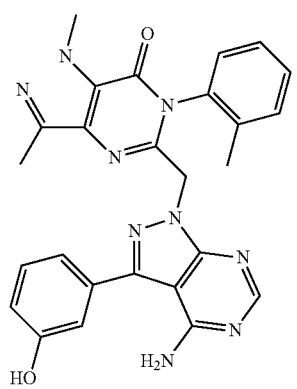
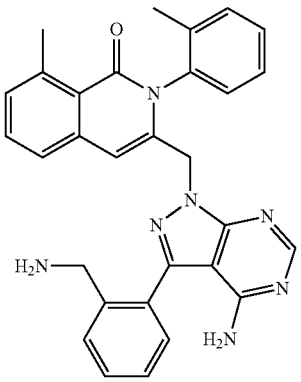
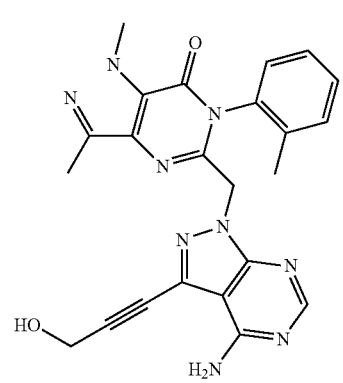
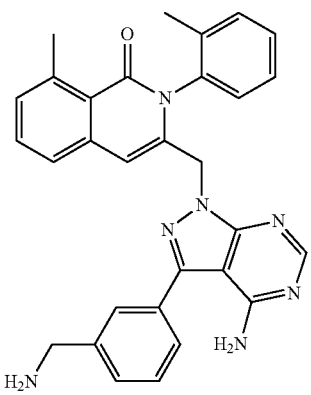

111
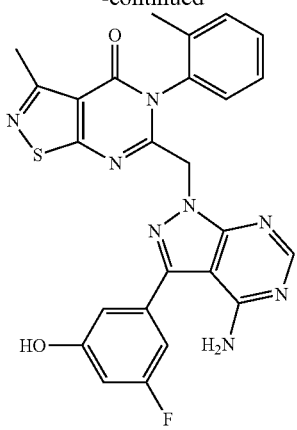
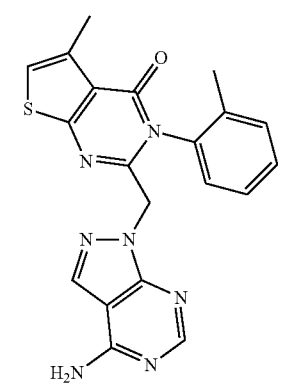
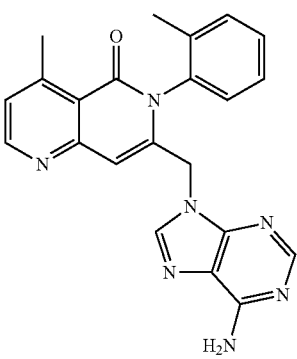
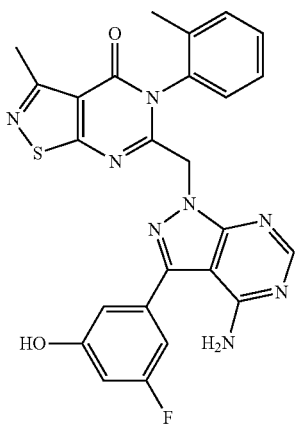
112
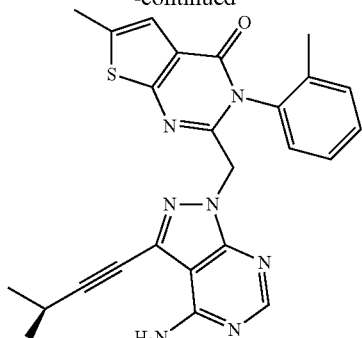
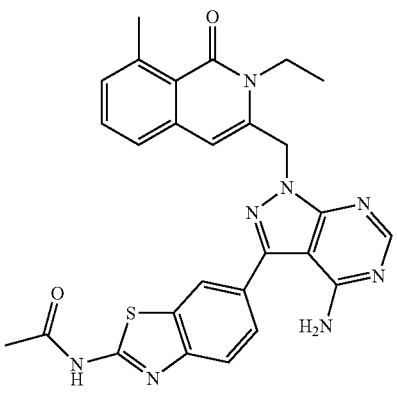
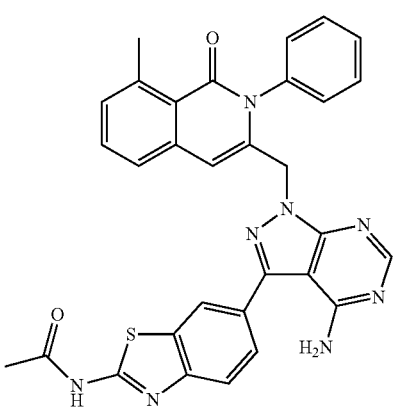
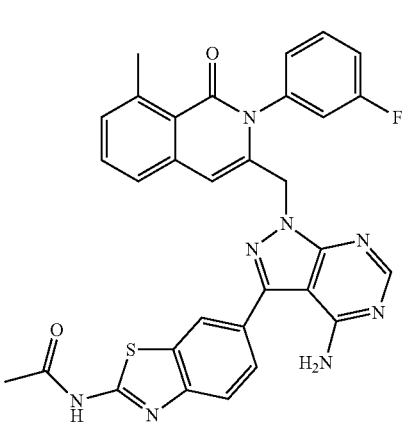

113
-continued
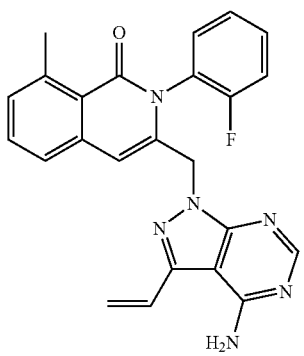
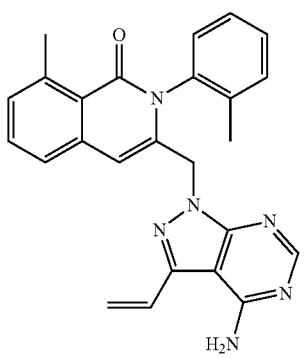
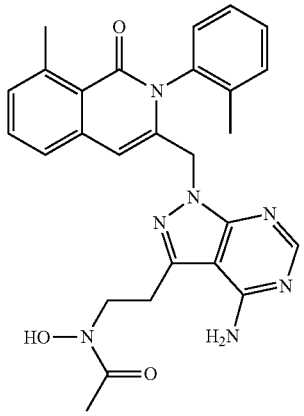
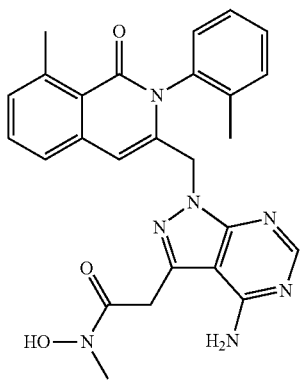
114
-continued
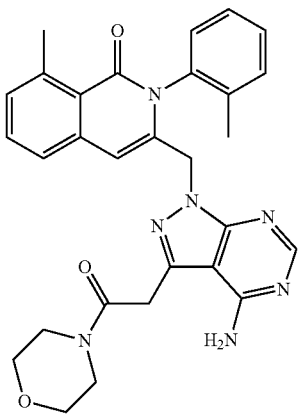
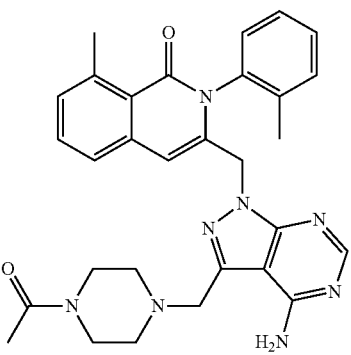
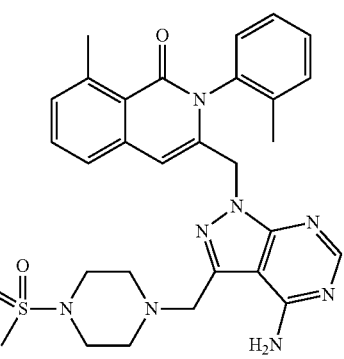
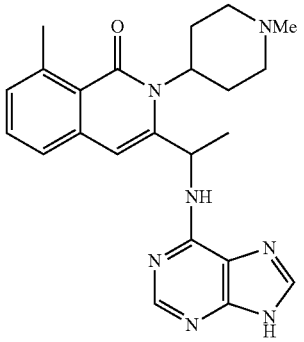

115
-continued
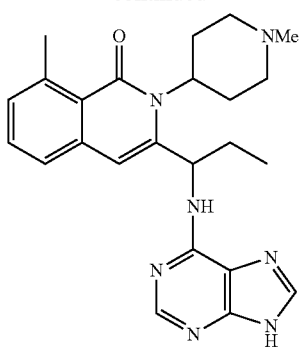
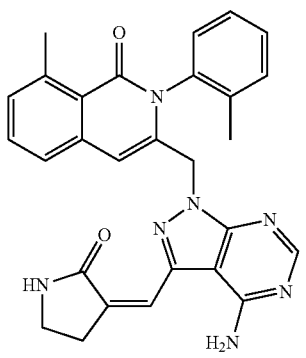
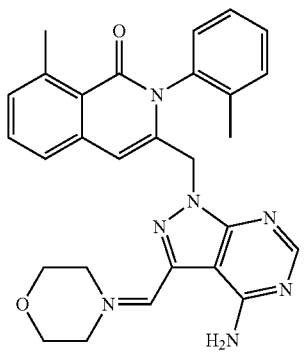
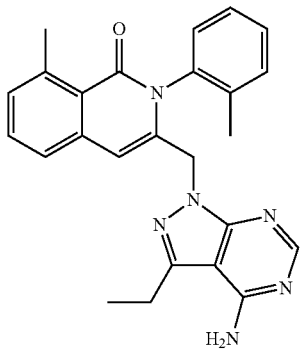
116
-continued
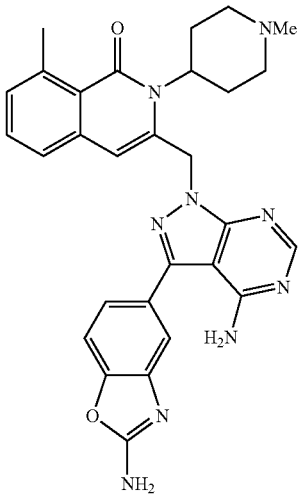
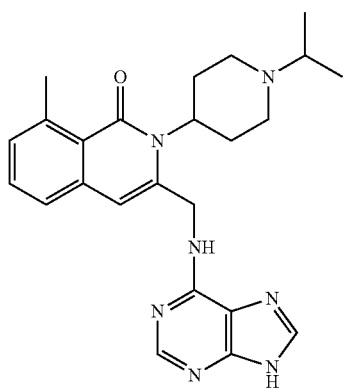
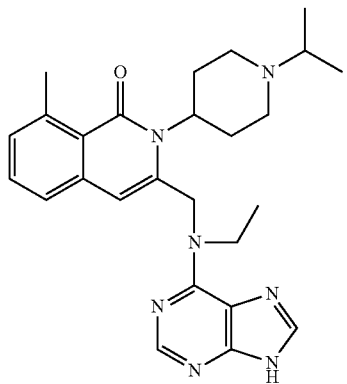
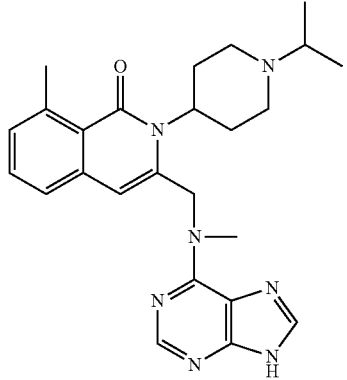

117
-continued
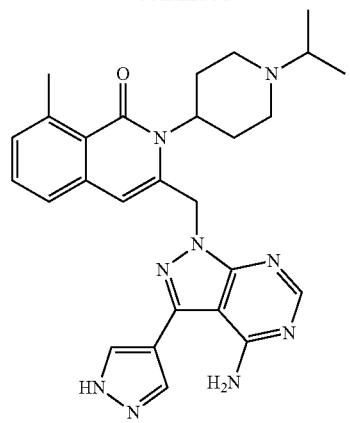
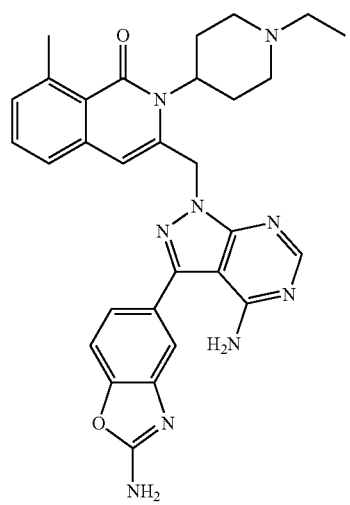
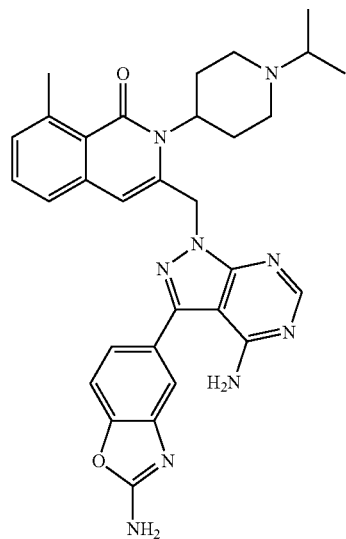
118
-continued
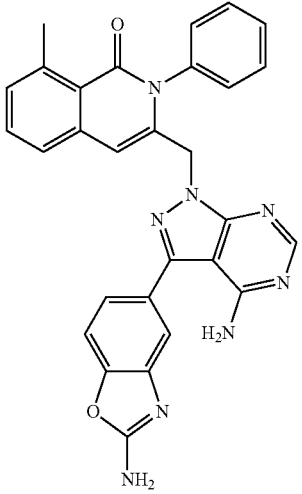
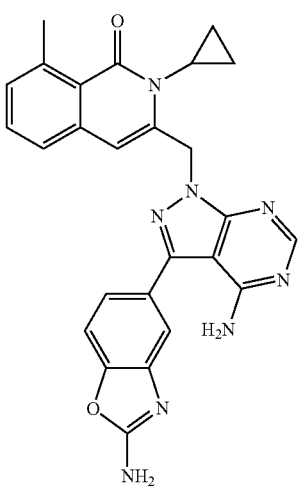
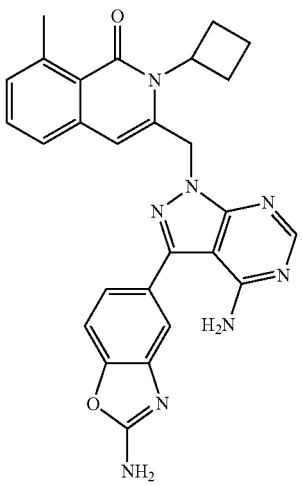

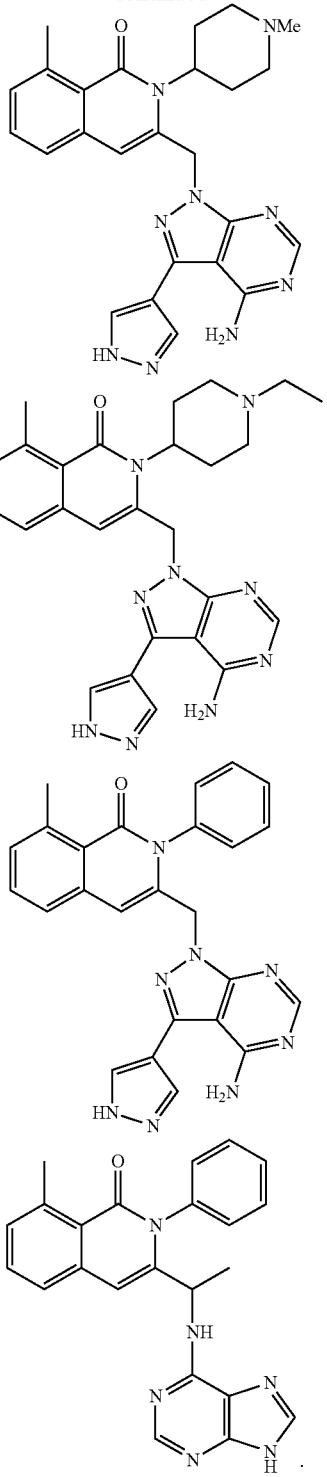

The chemical entities described herein can be synthesized according to one or more illustrative schemes herein and/or techniques well known in the art.

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

The terms "solvent," "organic solvent," or "inert solvent" each mean a solvent inert under the conditions of the reaction being described in conjunction therewith including, for example, benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine and the like. Unless specified to the contrary, the solvents used in the reactions described herein are inert organic solvents. Unless specified to the contrary, for each gram of the limiting reagent, one cc (or mL) of solvent constitutes a volume equivalent.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can also be used.

When desired, the (R)- and (S)-isomers of the compounds of the present invention, if present, may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts.

Many of the optionally substituted starting compounds and other reactants are commercially available, e.g., from Aldrich Chemical Company (Milwaukee, Wis.) or can be readily prepared by those skilled in the art using commonly employed synthetic methodology.

The compounds of the invention can generally be synthesized by an appropriate combination of generally well known synthetic methods. Techniques useful in synthesizing these chemical entities are both readily apparent and accessible to those of skill in the relevant art, based on the instant disclosure.

The compounds of the invention can be synthesized by an appropriate combination of known synthetic methods in the art. The discussion below is offered to illustrate certain of the diverse methods available for use in making the compounds of the invention and is not intended to limit the scope of reactions or reaction sequences that can be used in preparing the compounds of the present invention.

Reaction Scheme 1

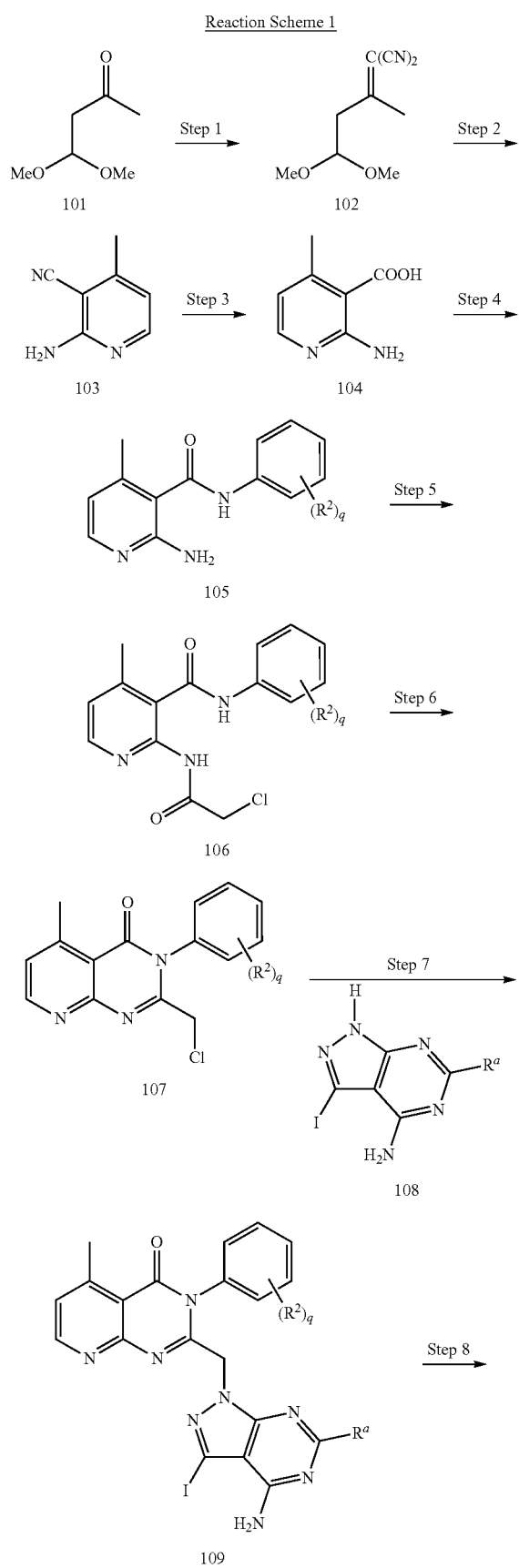

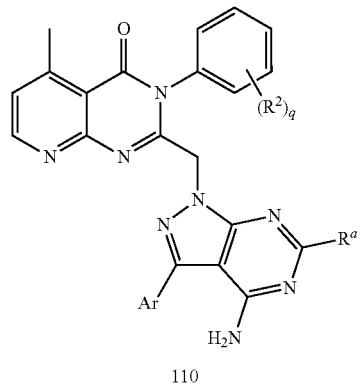

Referring to Scheme 1, Step 1, ketone 101 is converted to the corresponding alkene using, for example, malononitrile and piperidine in acetic acid. The product, a compound of Formula 102, is isolated. Referring to Scheme 1, Step 2, a compound of Formula 102 is cyclized to a pyridine using, for example, ammonia in methanol. The product, a compound of Formula 103, is isolated. Referring to Scheme 1, Step 3, a compound of Formula 103 is hydrolyzed to the corresponding carboxylic acid. The product, a compound of formula 104, is isolated. Referring to Scheme 1, Step 4, a compound of Formula 104 is converted to an amide using, for example, a standard amide coupling reagent, such as EDCI. The product, a compound of Formula 105, is isolated. Referring to Scheme 1, Step 5, a compound of Formula 105 is converted to the corresponding amide using, for example, chloroacetyl chloride. The product, a compound of Formula 106, is isolated. Referring to Scheme 1, Step 6, a compound of Formula 106 is converted to a compound of Formula 107, using, for example, acetic acid. The product, a compound of Formula 107, is isolated. Referring to Scheme 1, Step 7, a compound of Formula 107 undergoes a displacement at the chlorine when reacted with a nucleophile and a base, such as pyrazolopyrimidine 108 and potassium carbonate. The product, a compound of Formula 109, is isolated. Referring to Scheme 1, Step 8, a compound of Formula 109 is coupled with an aryl or heteroaryl boronic acid or boronic acid derivative such as, for example, a borolan, using, for example, palladium catalyzed coupling conditions. The product, a compound of Formula 110, is isolated.

Reaction Scheme 2

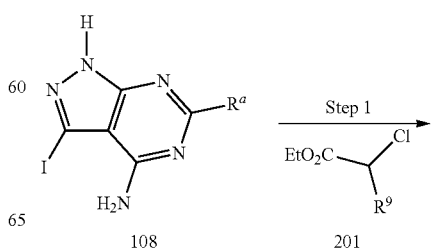

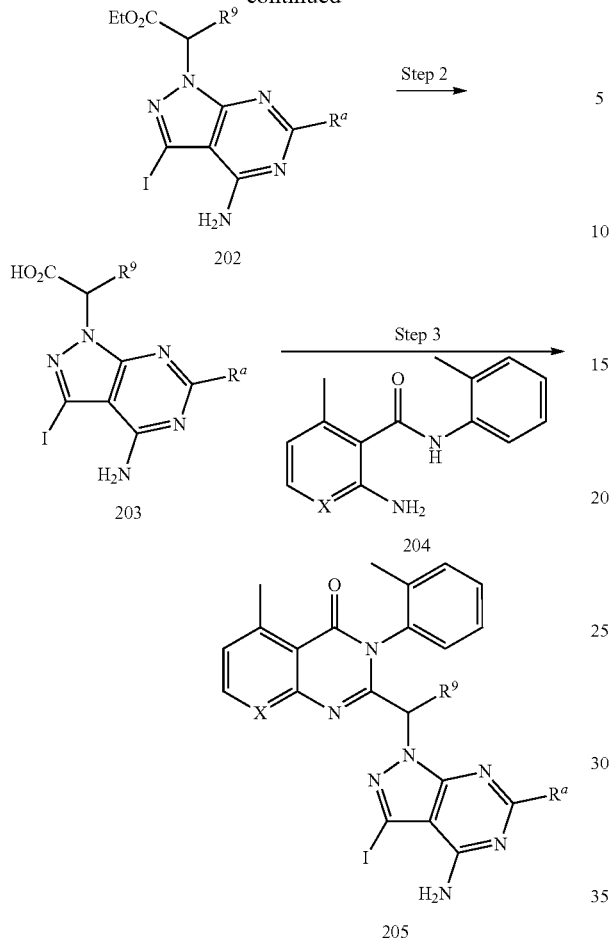

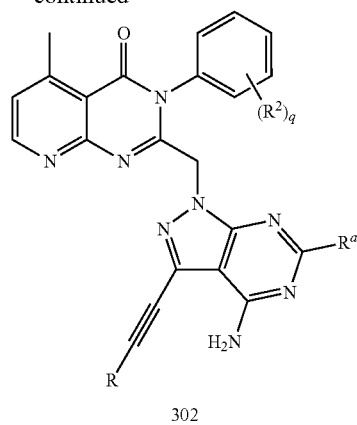

Referring to Scheme 2, Step 1, a compound of Formula 108 is converted to a compound of Formula 202, for example, via an alkylation of a compound of Formula 201. The product, a compound of Formula 202, is isolated. Referring to Scheme 2, Step 2, a compound of Formula 202 is converted to a compound of Formula 203, for example, via saponification. The product, a compound of Formula 203, is isolated. Referring to Scheme 2, Step 3, a compound of Formula 203 is cyclized to a quinazoline of Formula 205, for example, via sealed tube reaction with a compound of Formula 204 and a dehydrating agent, such as $PCl_5$. The product, a compound of Formula 205, is isolated.

Reaction Scheme 3

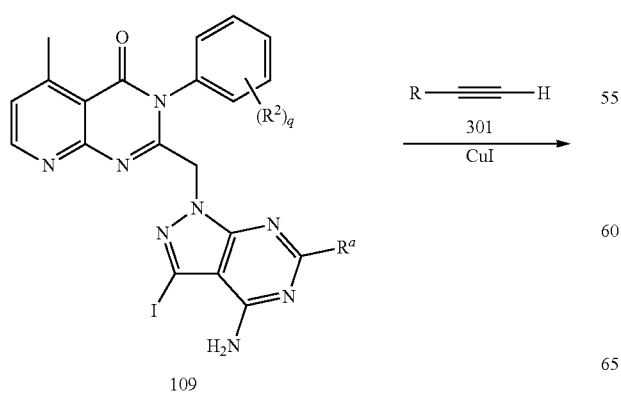

Referring to Scheme 3, a compound of Formula 109 is converted to a compound of Formula 302, for example, via a Sonagashira coupling with a compound of Formula 301. The product, a compound of Formula 302, is isolated.

Reaction Scheme 4

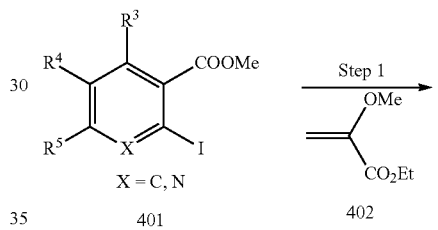

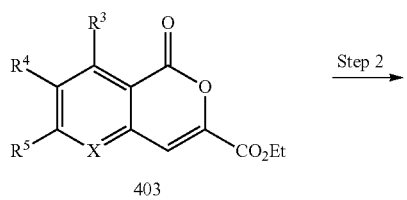

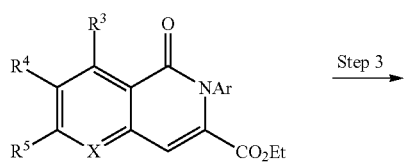

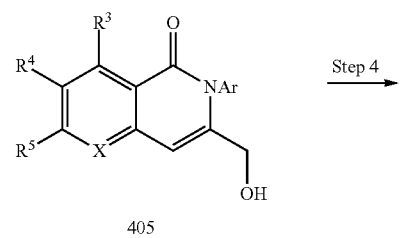

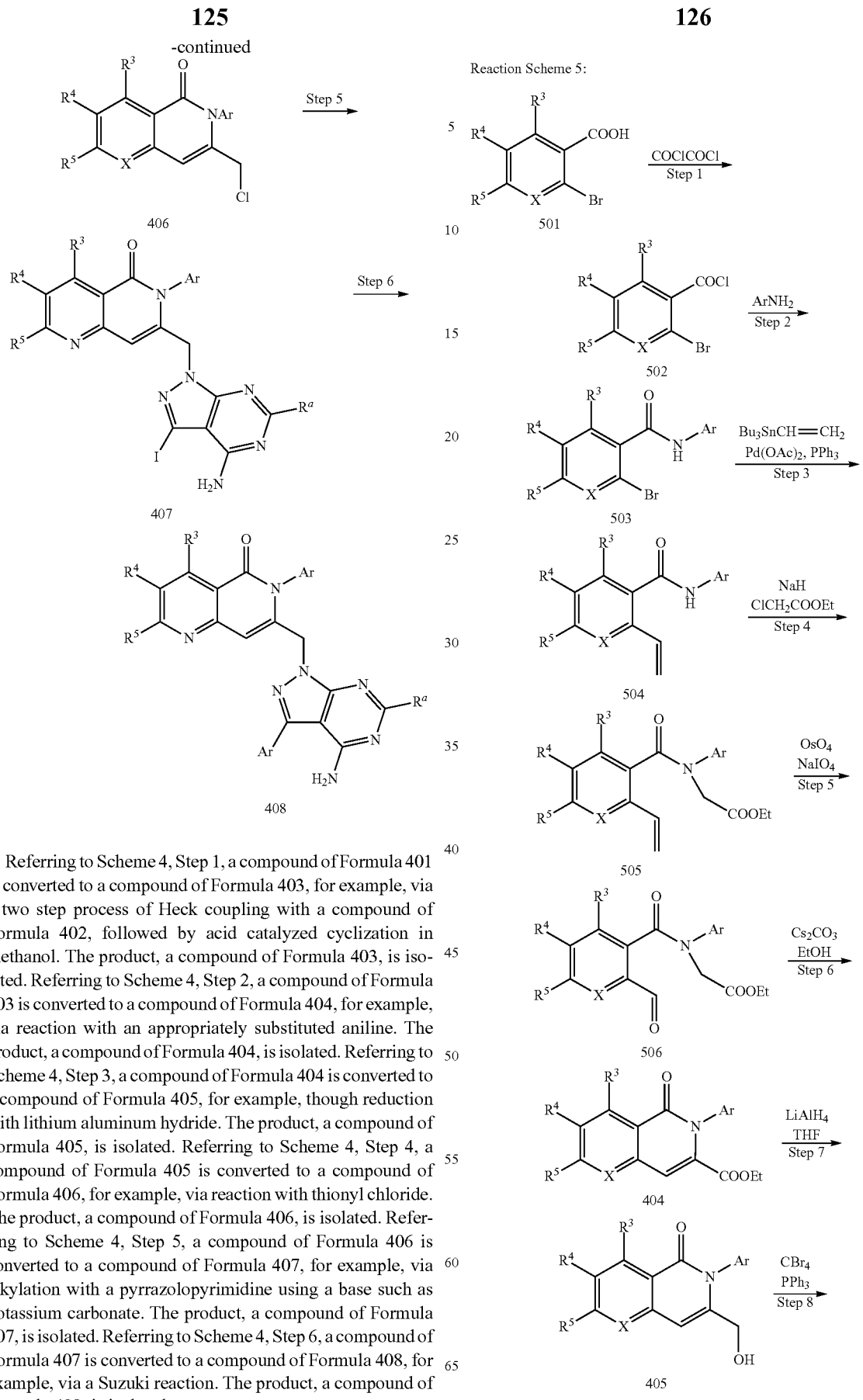

Referring to Scheme 4, Step 1, a compound of Formula 401 is converted to a compound of Formula 403, for example, via a two step process of Heck coupling with a compound of Formula 402, followed by acid catalyzed cyclization in methanol. The product, a compound of Formula 403, is isolated. Referring to Scheme 4, Step 2, a compound of Formula 403 is converted to a compound of Formula 404, for example, via reaction with an appropriately substituted aniline. The product, a compound of Formula 404, is isolated. Referring to Scheme 4, Step 3, a compound of Formula 404 is converted to a compound of Formula 405, for example, though reduction with lithium aluminum hydride. The product, a compound of Formula 405, is isolated. Referring to Scheme 4, Step 4, a compound of Formula 405 is converted to a compound of Formula 406, for example, via reaction with thionyl chloride. The product, a compound of Formula 406, is isolated. Referring to Scheme 4, Step 5, a compound of Formula 406 is converted to a compound of Formula 407, for example, via alkylation with a pyrrazolopyrimidine using a base such as potassium carbonate. The product, a compound of Formula 407, is isolated. Referring to Scheme 4, Step 6, a compound of Formula 407 is converted to a compound of Formula 408, for example, via a Suzuki reaction. The product, a compound of Formula 408, is isolated.

-continued

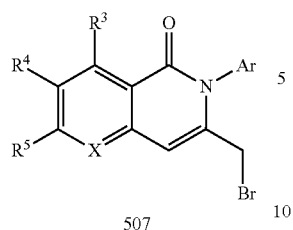
507

Referring to Scheme 5, Step 1, a compound of Formula 501 is converted to a compound of Formula 502, for example, with a reagent suitable for introduction of an acid chloride, for example, oxalyl chloride. The product, a compound of Formula 502, is optionally isolated. Referring to Scheme 5, Step 2, a compound of Formula 502 is converted to a compound of Formula 503 for example, reaction with, for example, an aryl amine. The product, a compound of Formula 503, is isolated. Referring to Scheme 5, Step 3, a compound of Formula 503 is converted to a compound of Formula 504, for example, via a Stille coupling using an appropriate vinyl-stannane. The product, a compound of Formula 504, is isolated. Referring to Scheme 5, Step 4, a compound of Formula 504 is converted to a tertiary amide, a compound of Formula 505, via reaction with chloroethyl acetate and sodium hydride base. The compound of Formula 505 is isolated. Referring to Scheme 5, Step 5, a compound of Formula 505 is oxidized to an aldehyde, using, for example, osmium tetraoxide and sodium periodinate. The product, a compound of Formula 506, is isolated. Referring to Scheme 5, Step 6, a compound of Formula 506 is converted to a compound of Formula 404, for example, though aldol reaction in ethanol with a base, such as cesium carbonate. The product, a compound of Formula 404, is isolated. Referring to Scheme 5, Step 7, a compound of Formula 404 is reduced to a primary alcohol via reduction with, for example, lithium aluminum hydride, to produce a compound of Formula 405, which is isolated. Referring to Scheme 5, Step 8, a compound of Formula 405 is converted to a compound of Formula 507 via reaction with carbon tetrabromide and triphenylphosphine. The compound of Formula 507 is optionally isolated. This compound can be a central intermediate in the synthesis of the compounds of the invention.

Reaction Scheme 6:

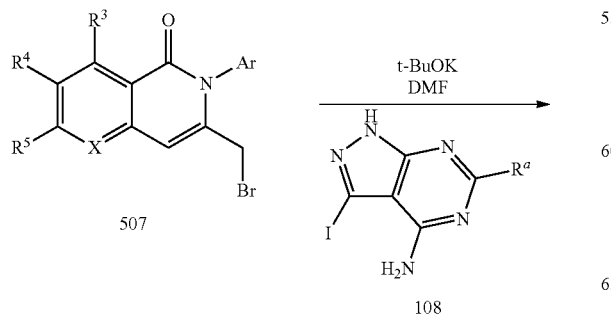

-continued

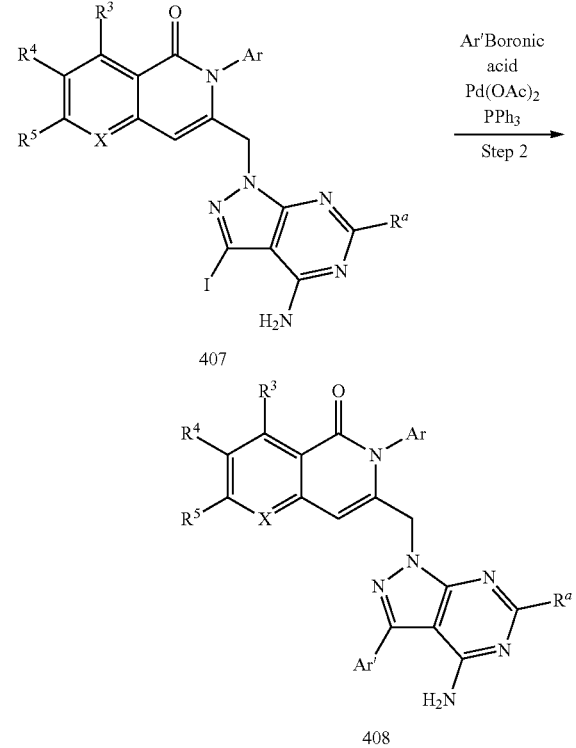

Referring to Scheme 6, Step 1, a compound of Formula 507, synthesized as described in Reaction Scheme 5 is converted to a compound of Formula 407 via coupling with a compound of Formula 108 in the presence of base, for example, potassium t-butoxide. The compound of Formula 407 is isolated. Referring to Scheme 6, Step 2, a compound of Formula 407 is converted to a compound of Formula 408 via coupling with, for example, an aryl boronic acid, in the presence of coupling catalysts and base, for example, palladium acetate, triphenylphosphine and sodium carbonate, for example. The compound of Formula 408 is isolated.

Reaction Scheme 7:

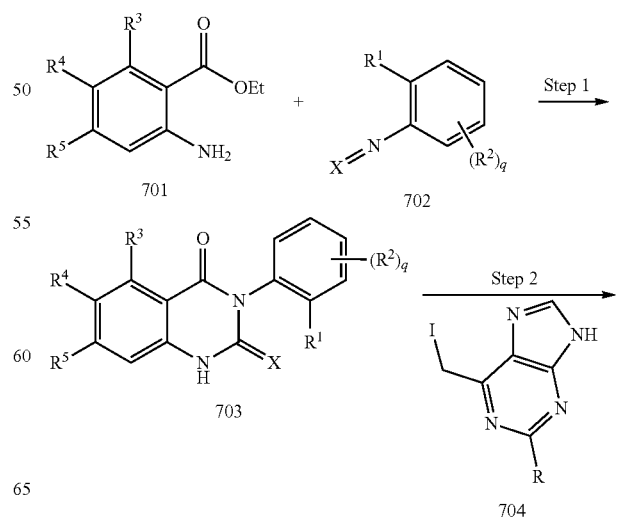

-continued

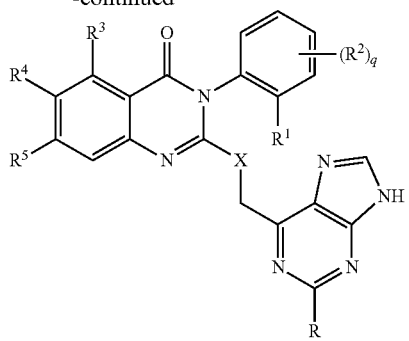

705

X = O, S, N

-continued

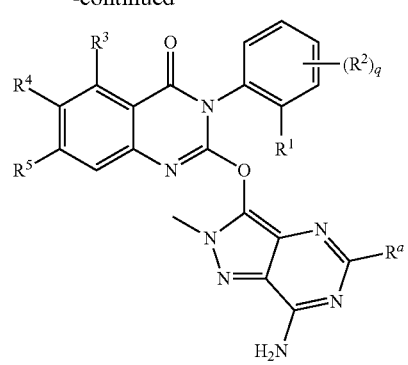

805

Referring to Scheme 7, Step 1, a compound of Formula 701 is reacted with a compound of Formula 702. The product, a compound of Formula 703, is isolated. Referring to Scheme 7, Step 2, a compound of Formula 703 is reacted with an optionally substituted purine such as a compound of Formula 704. The product, a compound of Formula 705, is isolated.

Referring to Scheme 8, Step 1, a compound of Formula 801 is treated with a reagent such as thionyl chloride to produce a compound of Formula 802, which, is isolated. Referring to Scheme 8, Step 2, a compound of Formula 802 and a compound of Formula 803 are combined in the presence of base. The product, a compound of Formula 804, is isolated. Referring to Scheme 8, Step 3, a compound of Formula 804 is converted to a compound of Formula 805, which is isolated.

Reaction Scheme 8:

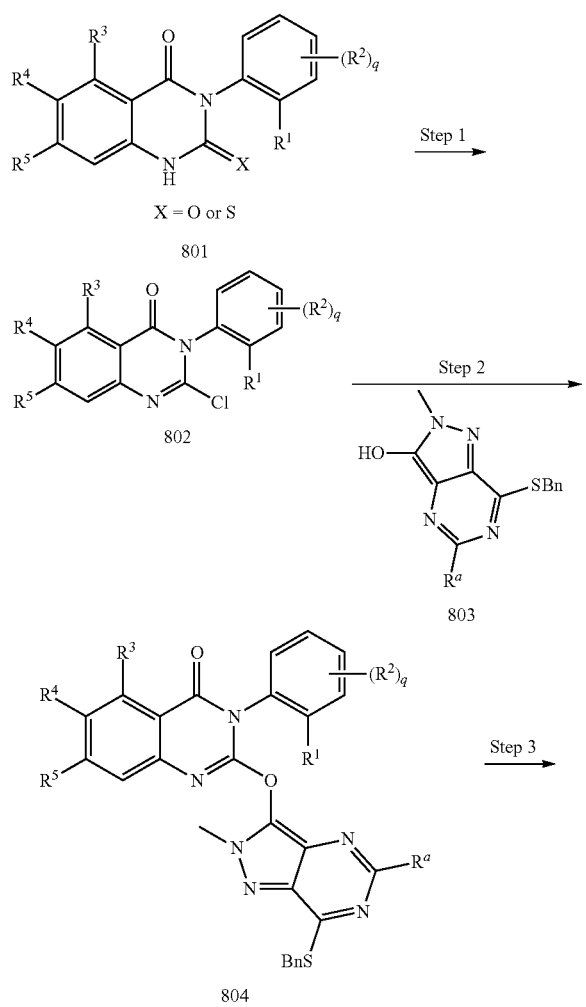

Reaction Scheme 9:

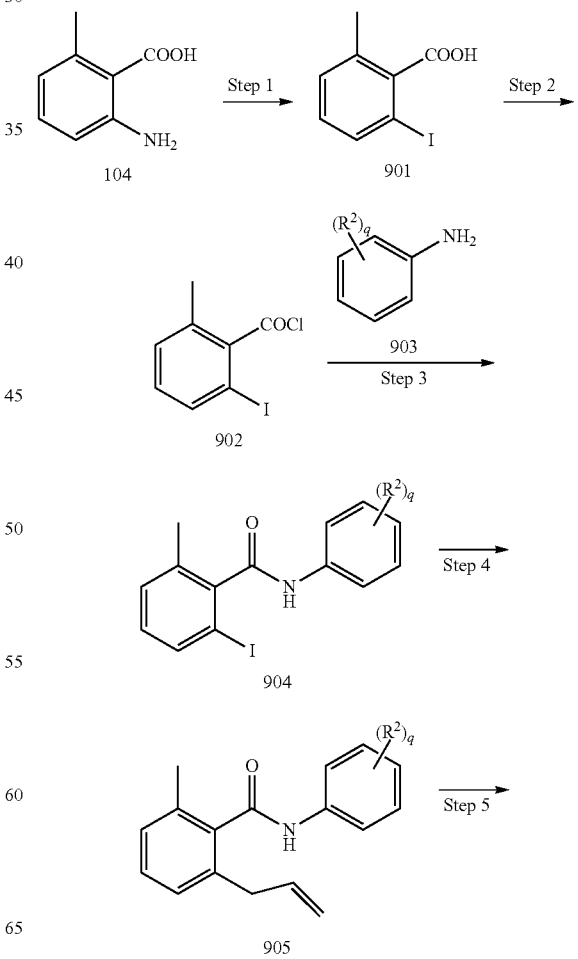

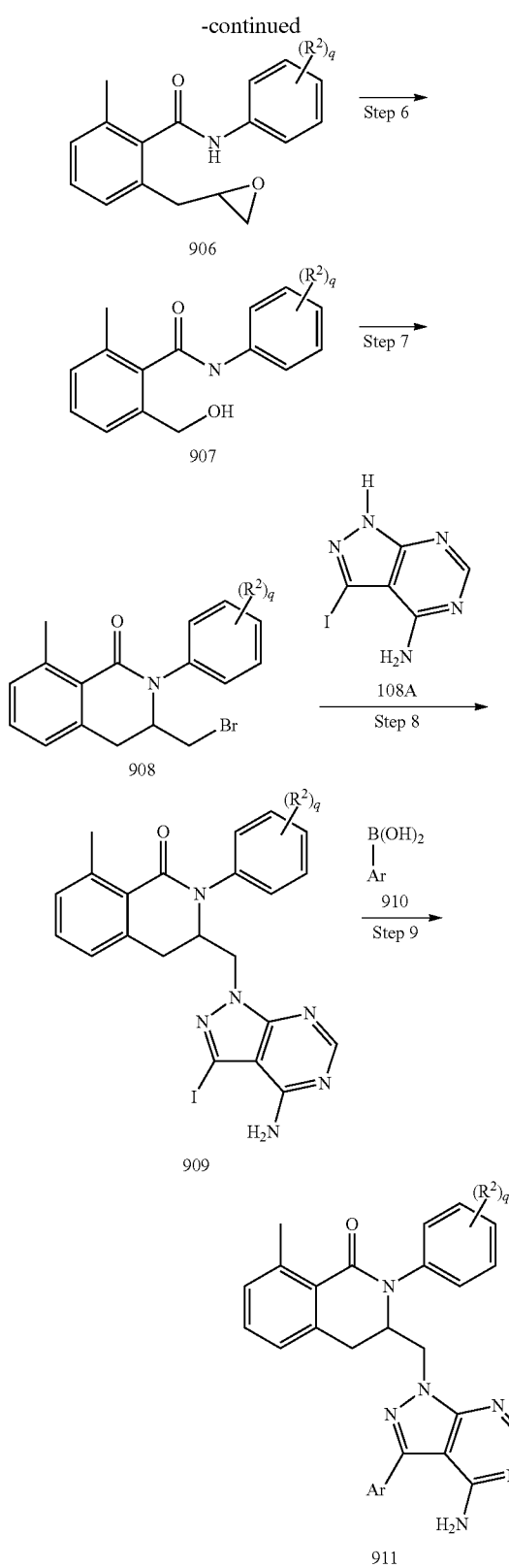

chloride by reaction with, for example, oxalyl chloride, to obtain a compound of Formula 902, which can be isolated. Referring to Scheme 9, Step 3, the acid chloride of Formula 902 is reacted with an optionally substituted amino-aryl or amino-hetaryl, compound 903, to yield a compound of Formula 904, which is isolated. Referring to Scheme 9, Step 4, the compound of Formula 904 is coupled, for example, with an allyl stannane, to produce a compound of Formula 905, which is isolated. Referring to Scheme 9, Step 5, the compound of Formula 905 is converted to its epoxide by treatment with, for example, meta-chloroperbenzoic acid, to yield a compound of Formula 906, which can be isolated. Referring to Scheme 9, Step 6, the compound of Formula 906 is cyclized by treatment, for example, sodium hydride in dimethyl formamide, to obtain a compound of Formula 907, which is isolated. Referring to Scheme 9, Step 7, the primary hydroxyl of the compound of Formula 907 is converted to the bromide by treatment, for example, with carbon tetrabromide and triphenylphosphine, to produce a compound of Formula 908, which is isolated. Referring to Scheme 9, Step 8, the compound of Formula 908 is coupled to a pyrazolopyrimidine of Formula 108A by treatment, for example, with potassium carbonate in dimethylformamide, to yield a compound of Formula 909, which is isolated. Referring to Scheme 9, Step 9, the dihydroisoquinolone of Formula 909 is coupled with an optionally substituted aryl or hetaryl boronic acid of Formula 910 to produce a compound of Formula 911, which is isolated.

Reaction Scheme 10:

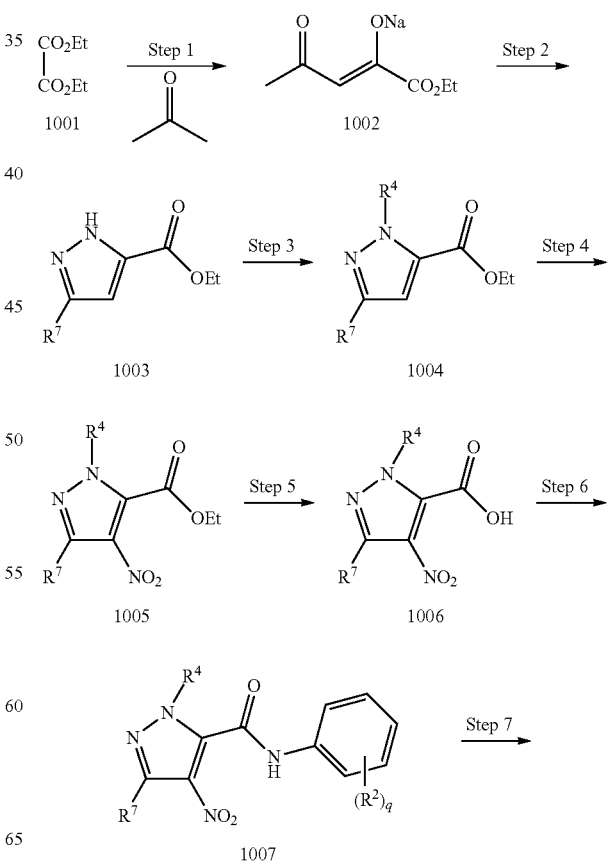

Referring to Scheme 9, Step 1, a compound of Formula 104 is reacted, for example, with sodium nitrite and potassium iodide under acidic conditions, to produce a compound of Formula 901, which can be isolated. Referring to Scheme 9, Step 2, the compound of Formula 901 is converted to its acid

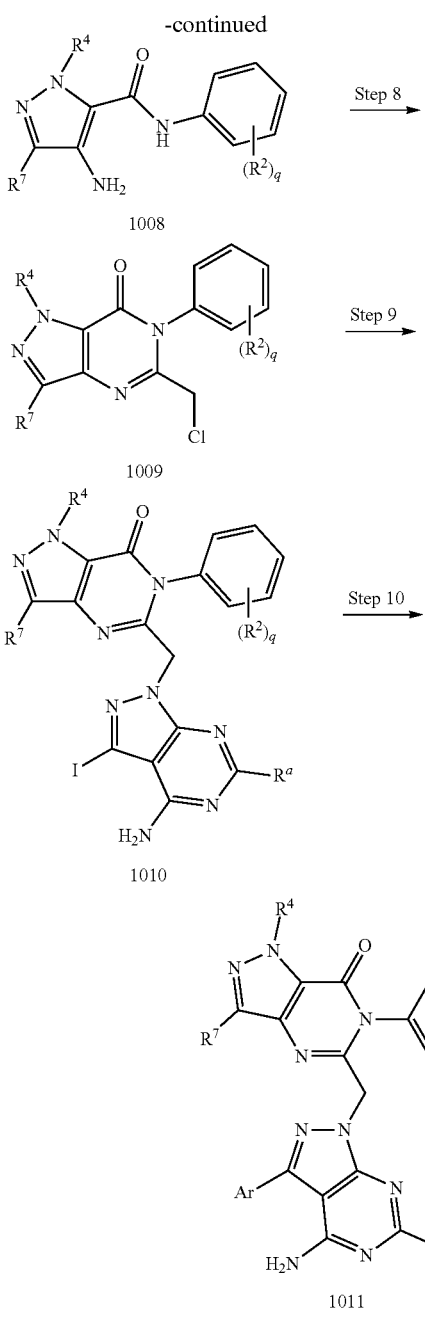

Formula 1006 is first converted to an acid chloride using thionyl chloride, then reacted with an appropriately substituted aniline to create the corresponding amide. The product, a compound of Formula 1007, is isolated. Referring to Scheme 10, Step 7, a compound of Formula 1007 is reduced to the corresponding amino-pyrazole using hydrogenation conditions with Pd/C as catalyst. The product, a compound of Formula 1008, is isolated. Referring to Scheme 10, Step 8, a compound of Formula 1008 is cyclized to the corresponding quinazolinone using conditions such as chloroacetyl chloride and acetic acid. The product, a compound of Formula 1009, is isolated. Referring to Scheme 10, Step 9, a compound of Formula 1009 is coupled with a pyrazolopyrmidine of Formula 108, for example using conditions such as potassium t-butoxide in DMF at room temperature. The product, a compound of Formula 1010, is isolated. Referring to Scheme 10, Step 9, a compound of Formula 1010 is coupled with an aryl boronic acid of Formula of 910, for example, using palladium acetate catalysis, in the presence of triphenyl phosphine and sodium carbonate in DMF to produce a compound of Formula 1011. The product, a compound of Formula 1011, is isolated.

Reaction Scheme 11:

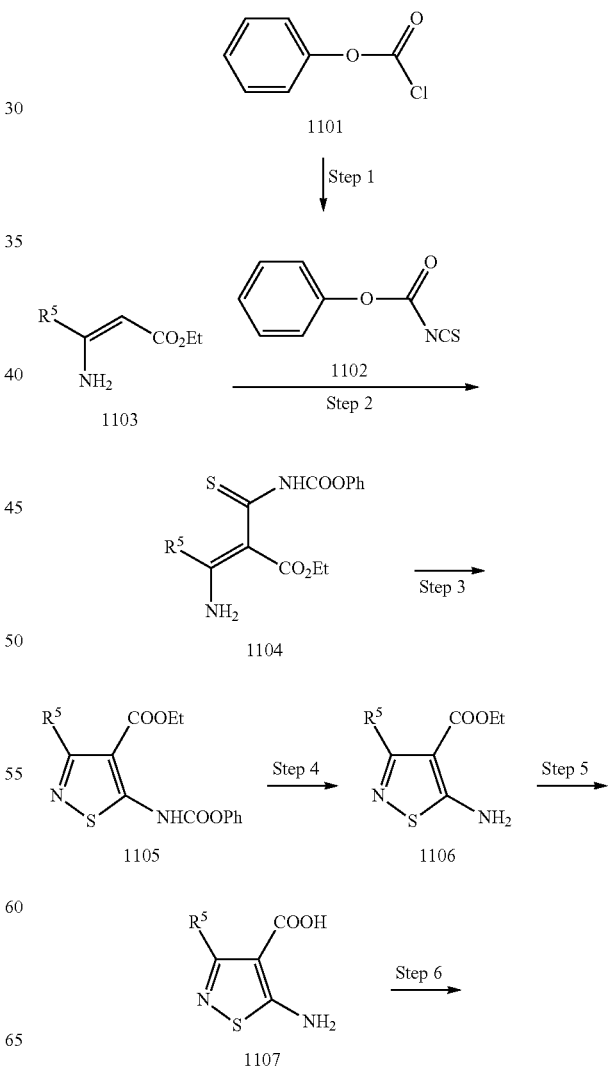

Referring to Scheme 10, Step 1, a compound of Formula 1001 is treated with a sodium acetate and acetone. The product, a compound of Formula 1002, is isolated. Referring to Scheme 10, Step 2, a compound of Formula 1002 is cyclized to the corresponding pyrazole, for example, with hydrazine in acetic acid and water. The product, a compound of Formula 1003, is isolated. Referring to Scheme 10, Step 3, a compound of Formula 1003 is, for example, alkylated using dimethyl sulfate. The product, a compound of Formula 1004, is isolated. Referring to Scheme 10, Step 4, a compound of Formula 1004 is nitrated using, for example, a solution of nitric acid and sulfuric acid. The product, a compound of Formula 1005, is isolated. Referring to Scheme 10, Step 5, a compound of Formula 1005 is saponified using a base, such as sodium hydroxide. The product, a compound of Formula 1006, is isolated. Referring to Scheme 10, Step 6, a compound of

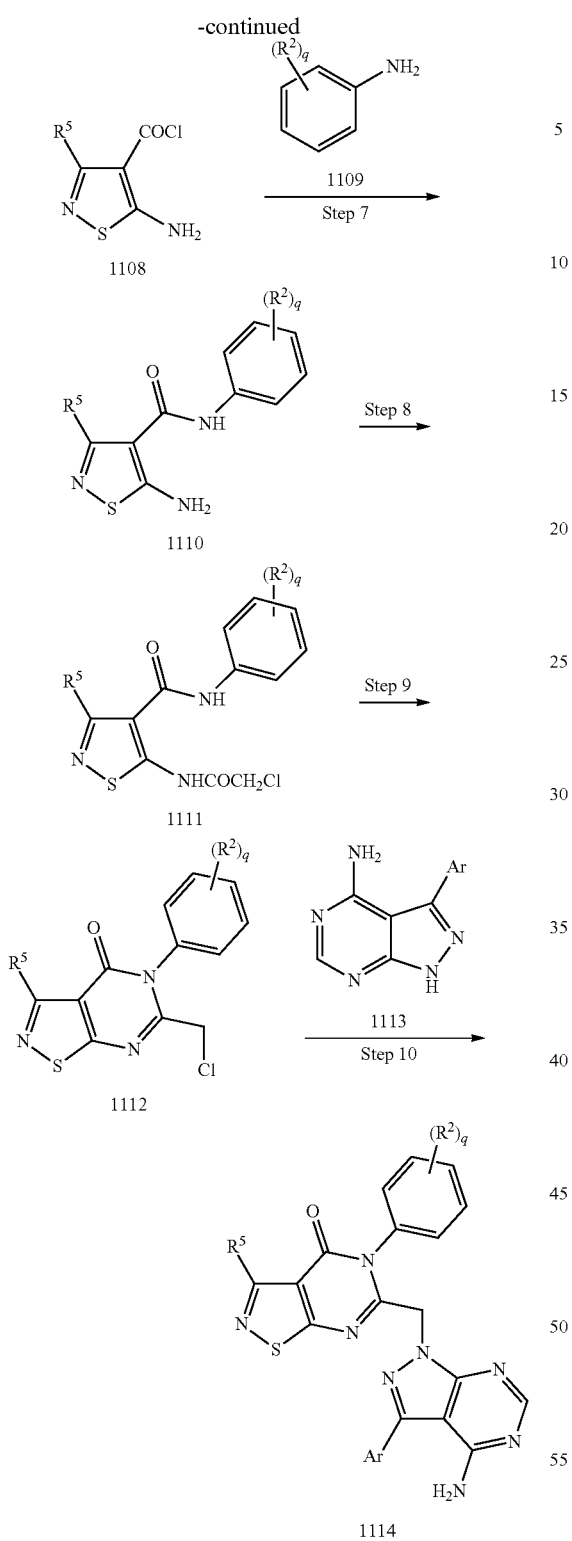

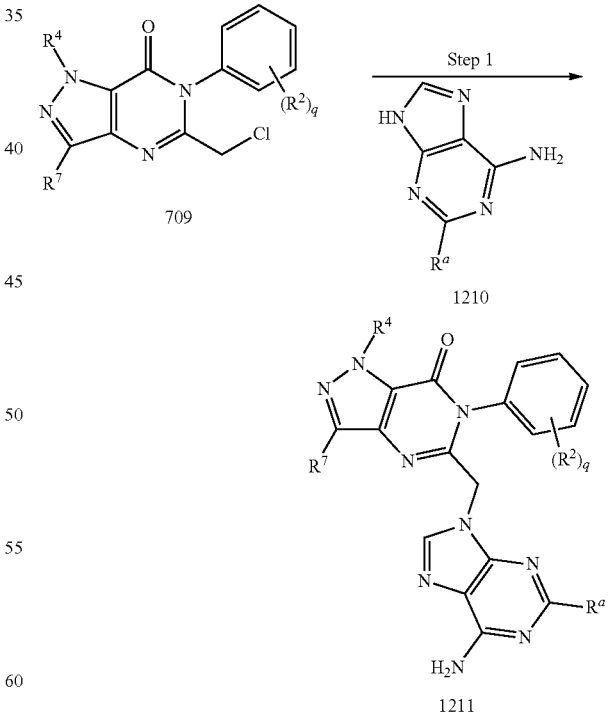

Reaction Scheme 12:

ethanol, to obtain a thiazole of Formula 1105, which is isolated. Referring to Scheme 11, Step 4, the compound of Formula 1105 is deprotected with, for example, potassium carbonate in aqueous dimethylformamide, to yield a compound of Formula 1106, which is isolated. Referring to Scheme 11, Step 5, the ester of the compound of Formula 1106 is saponified with, for example, sodium hydroxide in water, to produce the compound of Formula 1107, which is isolated. Referring to Scheme 11, Step 6, the free acid of the compound of Formula 1107 is converted to the acid chloride by treating it with, for example, thionyl chloride, to produce a compound of Formula 1108, which can be isolated. Referring to Scheme 11, Step 7, the acid chloride of the compound of Formula 1108 is reacted with an optionally substituted amino-aryl or amino-heteroaryl compound of Formula 1109, to obtain a compound of Formula 1110, which is isolated. Referring to Scheme 11, Step 8, the primary amine of the compound of Formula 1110 is reacted with a haloacyl chloride, for example, chloroacetyl chloride in pyridine and methylene chloride to produce a compound of Formula 1111, which is isolated. Referring to Scheme 11, Step 9, the compound of Formula 1111 is cyclized by, for example, heating in a sealed tube in the presence of phosphoryl chloride, to yield a compound of Formula 1112, which is isolated. Referring to Scheme 11, Step 10, the thiazolopyrimidone compound of Formula 1112 is reacted with an pyazolopyrimidine of Formula 1113 in the presence of a base, for example potassium t-butoxide in dimethylformamide to produce a compound of Formula 1114, which is isolated.

Referring to Scheme 11, Step 1, a compound of Formula 1101 is reacted with potassium thiocyanide in acetonitrile to produce a compound of Formula 1102, which can be isolated. Referring to Scheme 11, Step 2, the compound of Formula 1102 is reacted with a conjugated ester of Formula 1103, to produce a compound of Formula 1104, which is isolated. Referring to Scheme 11, Step 3, the compound of Formula 1104 is cyclized, for example, by treating it with bromine in Referring to Scheme 12, Step 1, a compound of Formula 709 is alkylated with an optionally substituted 10 purine of Formula 1210. The product, a compound of Formula 1211, is isolated.

Reaction Scheme 13:

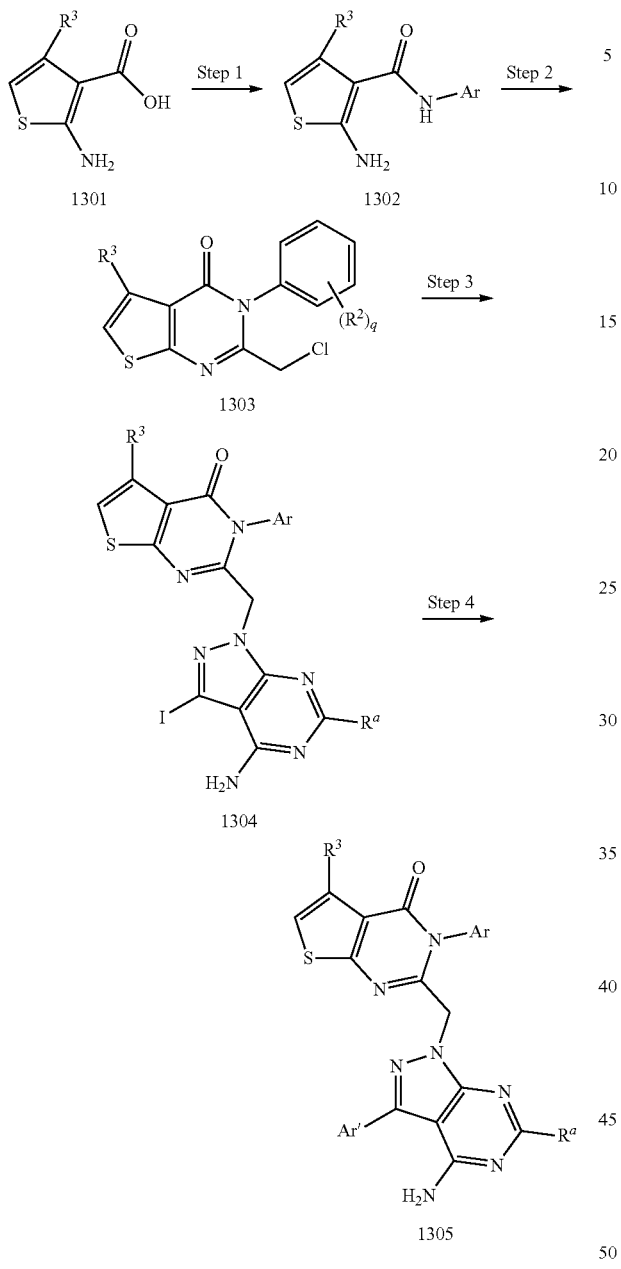

Reaction Scheme 14:

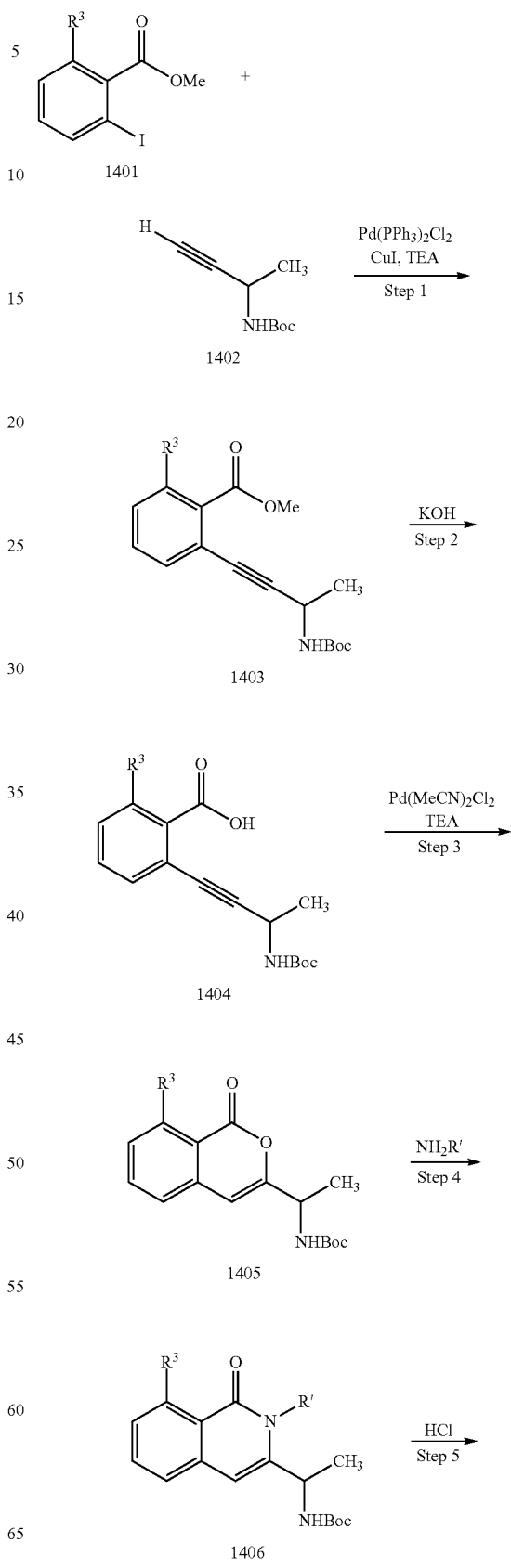

Referring to Scheme 13, Step 1, a compound of Formula 1301 is first converted to an acid chloride using thionyl chloride, then reacted with an appropriately substituted aniline. The product, a compound of Formula 1302, is isolated. Referring to Scheme 13, Step 2, a compound of Formula 1302 is cyclized to the corresponding thieno-pyrimidinone, for example, with chloroacetyl chloride in acetic acid. The product, a compound of Formula 1303, is isolated. Referring to Scheme 13, Step 3, a compound of Formula 1303 is, for example, alkylated using an appropriately substituted pyrazolo-pyrimidine. The product, a compound of Formula 1304, is isolated. Referring to Scheme 13, Step 4, a compound of Formula 1304 is, for example, arylated using an appropriately substituted boronic acid. The product, a compound of Formula 1305, is isolated.

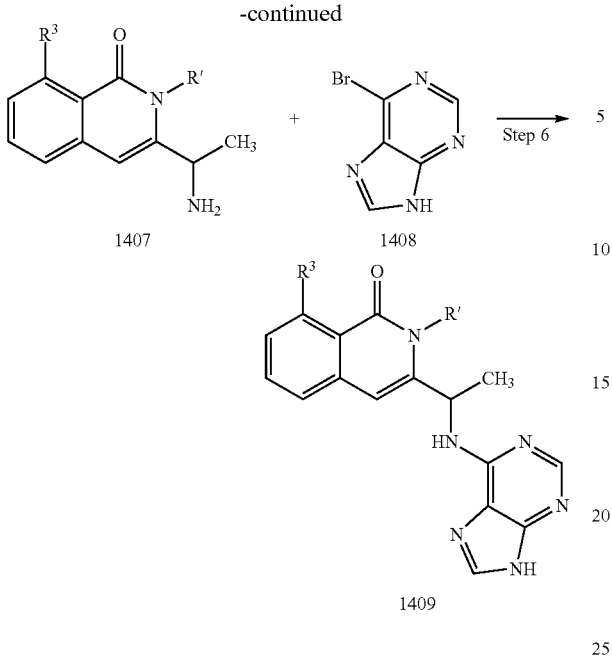

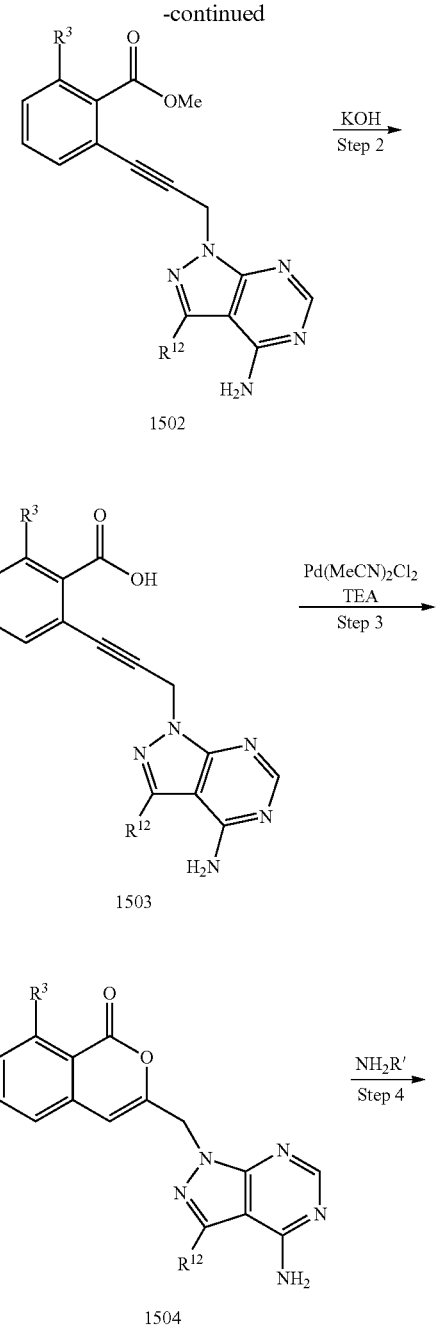

Referring to Reaction Scheme 14, Step 1, iodo ester 1401, is reacted with an alkyne 1402 in the presence of a palladium catalyst, copper iodide and triethylamine (TEA) to couple the alkyne to the aryl core of 1401 to produce a compound of Formula 1403. The compound of Formula 1403 is isolated. Referring to Reaction Scheme 14, Step 2, a compound of Formula 1403 is treated with potassium hydroxide base to obtain the carboxylic acid, a compound of Formula 1404, if the reaction product is acidified, or its salt. The compound of Formula 1404 is isolated. Referring to Reaction Scheme 14, Step 3, a compound of Formula 1404 is treated with bis (acetonitrile)dichloropalladium (II) and TEA to effect intramolecular ring closure to produce a compound of Formula 1405. The compound of Formula 1405 is isolated. Referring to Reaction Scheme 14, Step 4, a compound of Formula 1405 is reacted with a primary amine to produce a compound of Formula 1406. The compound of Formula 1406 is isolated. Referring to Reaction Scheme 14, Step 5, a compound of Formula 1406 is treated with hydrochloric acid, removing the protecting group on nitrogen, and to obtain a compound of Formula 1407. The compound of Formula 1407 can be isolated. Referring to Reaction Scheme 14, Step 6, a compound of Formula 1407 is reacted with a compound of Formula 1408, to produce a compound of Formula 1409. The compound of Formula 1409 is isolated.

Reaction Scheme 15:

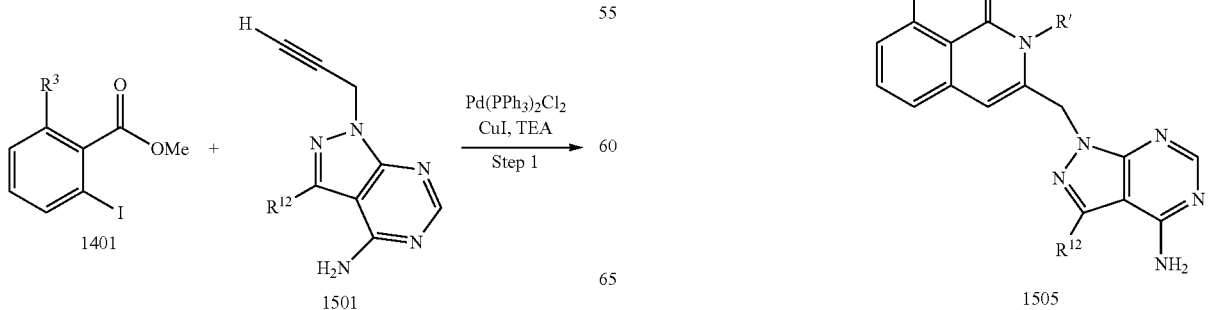

Referring to Reaction Scheme 15, Step 1, iodo ester 1401 is reacted with alkyne 1501 in the presence of palladium coupling catalyst, copper iodide, and TEA, to obtain a compound of Formula 1502. The compound of Formula 1502 is isolated. Referring to Reaction Scheme 15, Step 2, the compound of Formula 1502 is treated with potassium hydroxide base to obtain the carboxylate or free acid of a compound of Formula 1503. Referring to Reaction Scheme 15, Step 3, the compound of Formula 1503 is treated with bis(acetonitrile)dichloropalladium (II) and TEA to effect intramolecular ring closure to produce a compound of Formula 1504. The compound of Formula 1504 is isolated. Referring to Reaction Scheme 15, Step 4, the compound of Formula 1504 is treated with a primary amine to produce a compound of Formula 1505. The compound of Formula 1505 is isolated.

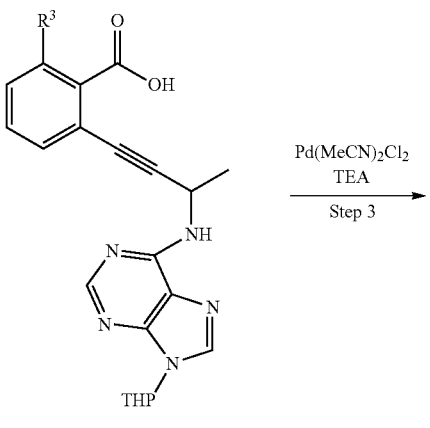

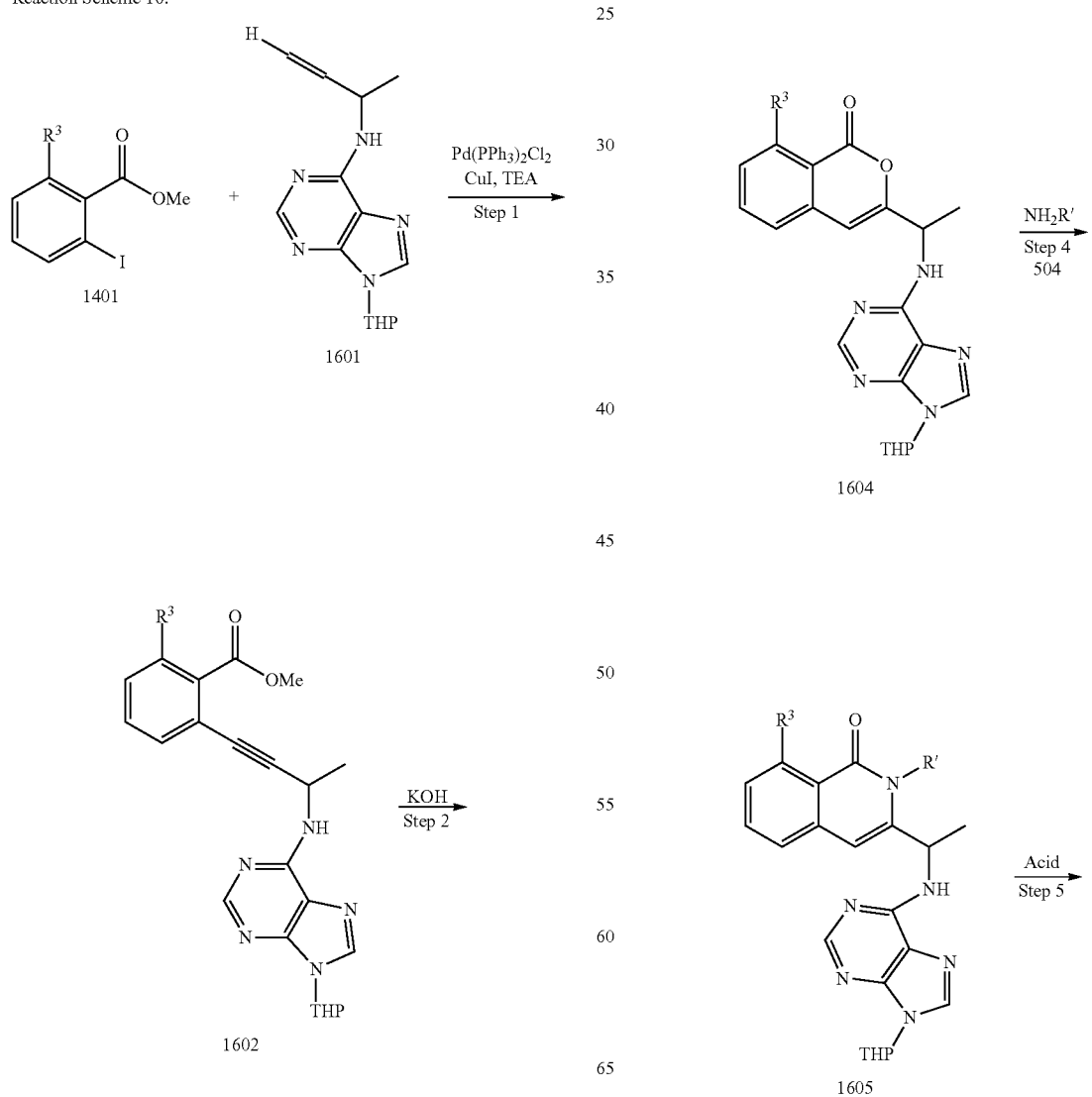

-continued

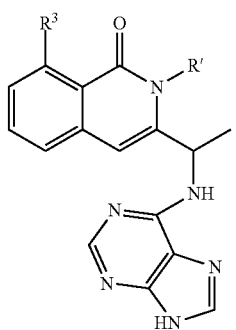

1606

Referring to Reaction Scheme 16, Step 1, iodo ester 1401 is reacted with alkyne 1601 in the presence of palladium coupling catalyst, copper iodide, and TEA, to obtain a compound of Formula 1602. The compound of Formula 1602 is isolated. Referring to Reaction Scheme 16, Step 2, the compound of Formula 1602 is treated with potassium hydroxide base to obtain the carboxylate or free acid of a compound of Formula 1603. Referring to Reaction Scheme 16, Step 3, the compound of Formula 1603 is treated with bis(acetonitrile) dichoropalladium (II) and TEA to effect intramolecular ring closure to produce a compound of Formula 1604. The compound of Formula 1604 is isolated. Referring to Reaction Scheme 16, Step 4, the compound of Formula 1604 is treated with a primary amine to produce a compound of Formula 1605. The compound of Formula 1605 is isolated. Referring to Reaction Scheme 16, Step 5, the compound of Formula 1605 is treated with acid to remove the THP protecting group to obtain a compound of Formula 1606. The compound of Formula 1606 is isolated.

Reaction Scheme 17:

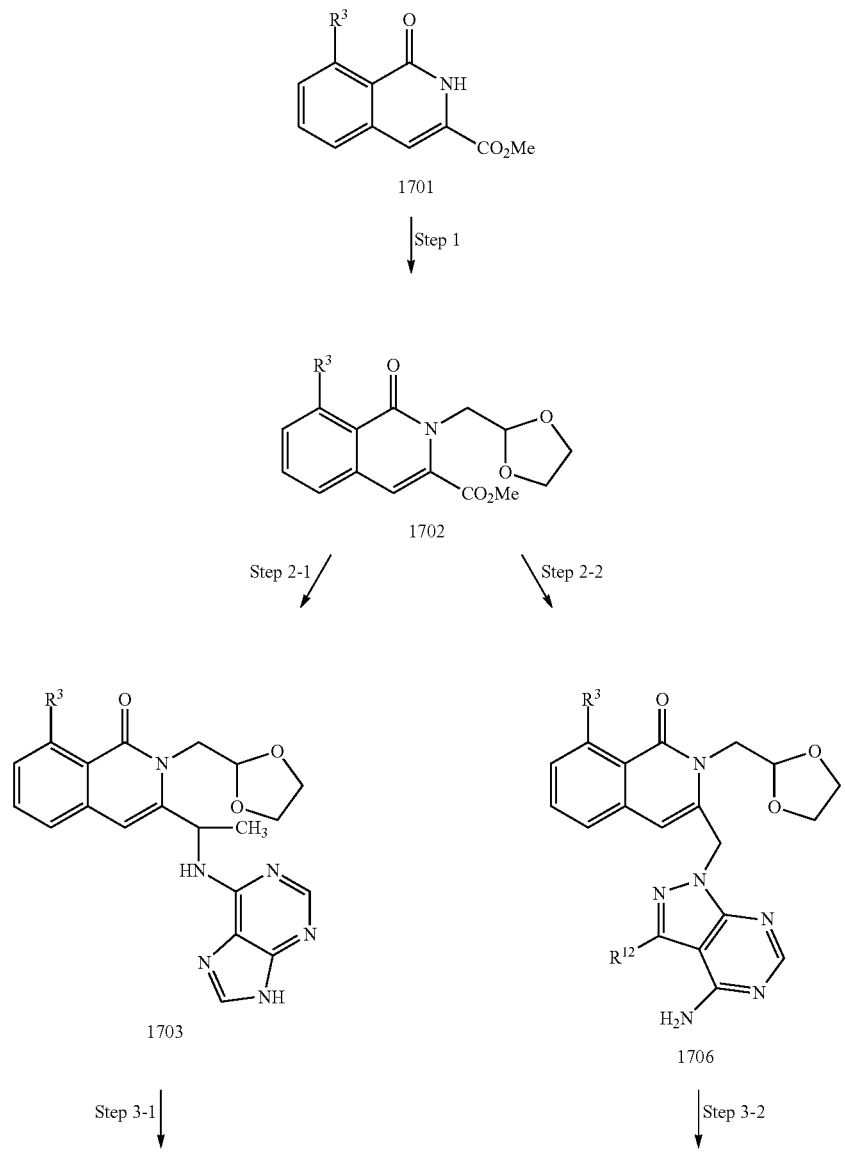

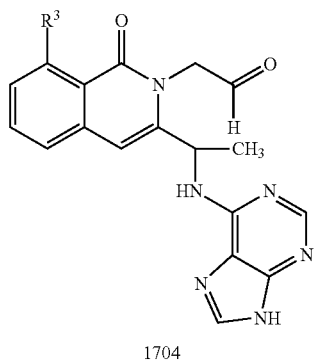

1704

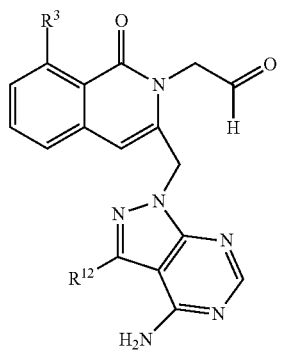

1707

Step 4-1 ↓

Step 4-2 ↓

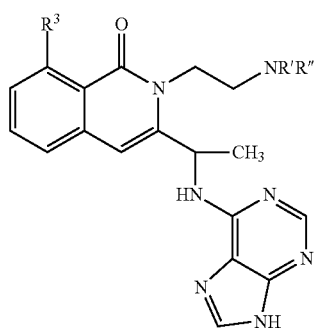

1705

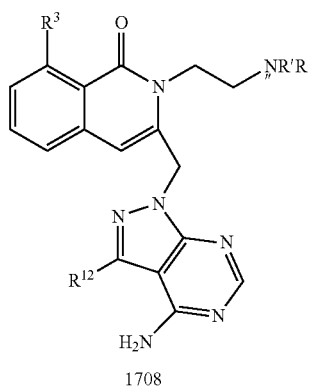

1708

Referring to Reaction Scheme 17, Step 1 the compound of Formula 1701 is synthesized by a variety of synthetic routes, including variations of Schemes 1 or 2 where, for example, a benzyl amine is used in the step of converting a compound of Formula 403 to a compound of Formula 404. The benzyl protecting group of the amine may be removed by standard deprotection chemistry to produce a compound of 1701. The compound of Formula 1701 is converted to a compound of Formula 1702 by alkylation of the amide nitrogen with a number of 2-carbon containing synthons which can be deprotected, oxidized and reprotected as the respective ketal, the compound of Formula 1702, which can be isolated. Referring to Reaction Scheme 17, Step 2-1, the compound of Formula 1702 is transformed by, for example, reductive amination of the ester moiety to introduce the purinyl moiety of a compound of Formula 1703, or alternatively, is alkylated to so introduce a purinyl moiety and obtain a compound of Formula 1703. Referring to Reaction Scheme 17, Step 3-1, the compound of Formula 1703 is treated with acid to remove the ketal protecting group to produce a compound of Formula 1704. The compound of Formula 1704 is isolated. Referring to Reaction Scheme 17, Step 4-1, the compound of Formula 1704 is reductively aminated with an amine to produce a compound of Formula 1705. The compound of Formula 1705 is isolated. Referring to Reaction Scheme 17, Step 2-2, the compound of Formula 1702 is transformed by, steps 7 and 8 of Scheme 5 and step 1 of Scheme 6 to introduce the pyrazolopyrimidine moiety of a compound of Formula 1706. The compound of Formula 1706 is isolated. Referring to Reaction Scheme 17, Step 3-2, the compound of Formula 1706 is treated with acid to remove the ketal protecting group to produce a compound of Formula 1707. The compound of Formula 1707 can be isolated. Referring to Reaction Scheme 17, Step 4-2, the compound of Formula 1707 is reductively aminated with an amine to produce a compound of Formula 1708. The compound of Formula 1708 is isolated.

Reaction Scheme 18:

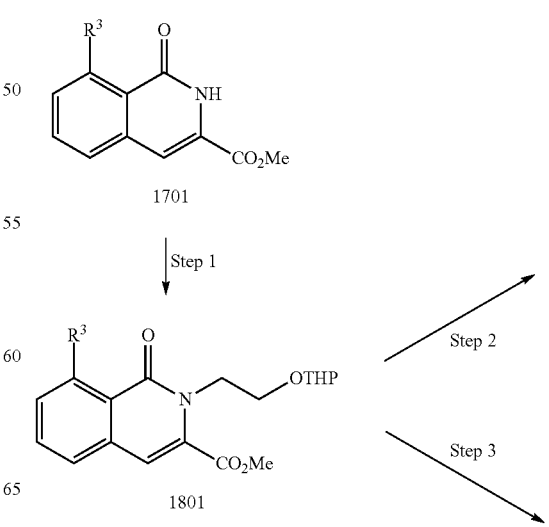

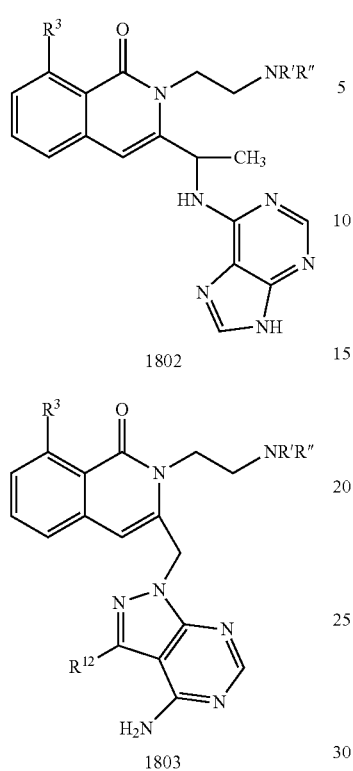

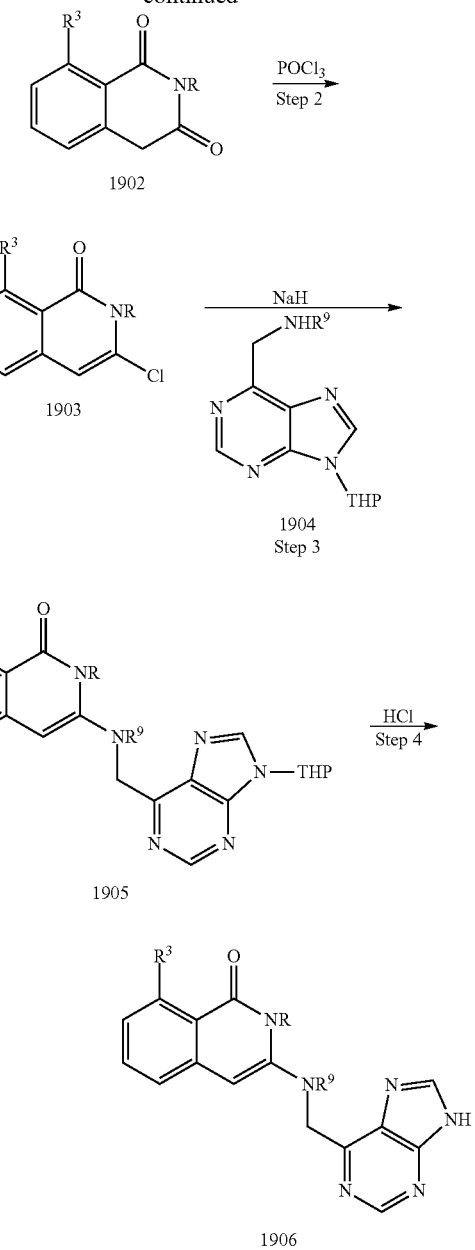

Referring to Reaction Scheme 18, Step 1, the compound of Formula 1701 is synthesized as described in Scheme 17 or any other generally known chemistry. The compound of Formula 1701 is transformed by alkylation of the amide nitrogen with a number of 2-carbon containing synthons which can be deprotected, and converted to the alkoxy protected species as shown in the compound of Formula 1801, which can be isolated. Referring to Reaction Scheme 18, Step 2, the compound of Formula 1801 is converted via chemistry described in Step 2-1 of Scheme 17 to introduce a purinyl moiety, and that resultant compound is transformed by deprotection, activation and amination with an amine to produce a compound of Formula 1802, which is isolated.

Referring to Reaction Scheme 18, Step 3, the compound of Formula 1801 is converted via chemistry described in Step 2-2 of Scheme 17 to introduce a pyrazolopyrimidine moiety, and that resultant compound is transformed by deprotection, activation and amination with an amine to produce a compound of Formula 1803, which is isolated.

Reaction Scheme 19:

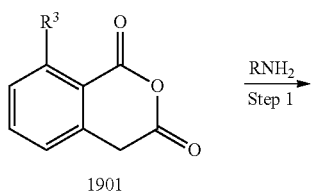

Referring to Reaction Scheme 19, Step 1, the compound of Formula 1901 is treated with an amine to produce a compound of Formula 1902. The compound of Formula 1902 is isolated. Referring to Reaction Scheme 19, Step 2, the compound of Formula 1902 is treated with phosphorus oxychloride to generate a compound of Formula 1903. The compound of Formula 1903 is isolated. Referring to Reaction Scheme 19, Step 3, the compound of Formula 1903 is reacted with an amino purine of Formula 1904 to obtain a compound of Formula 1905. The compound of Formula 1905 is isolated. Referring to Reaction Scheme 19, Step 4, the compound of Formula 1905 is treated with hydrochloric acid to remove the protecting group at nitrogen on the purine moiety to produce a compound of Formula 1906. The compound of 1906 is isolated.

Reaction Scheme 20:

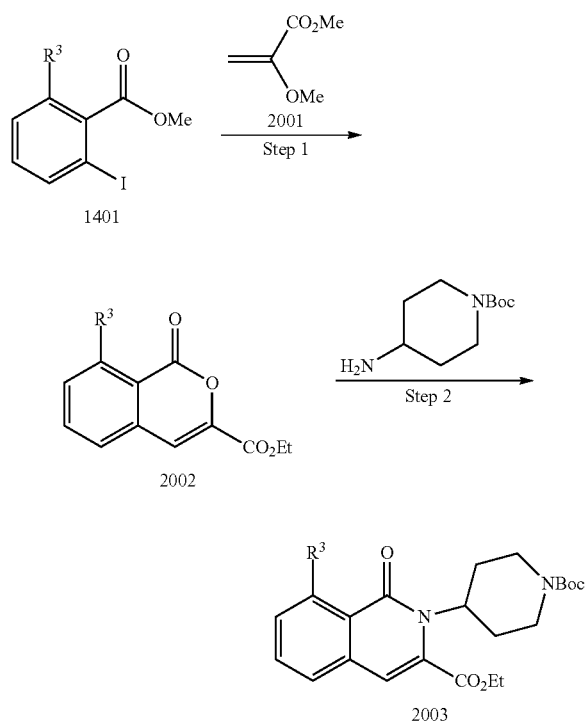

Referring to Reaction Scheme 20, Step 1, the compound of Formula 1401 is treated with vinylogous ester 2001 using, for example a Heck reaction with subsequent cyclization, to produce a compound of Formula 2002. The compound of Formula 2002 is isolated. Referring to Reaction Scheme 20, Step 2, the compound of Formula 2002 is reacted with 4-amino N-Boc piperidine to produce a compound of Formula 2002. The compound of Formula 2003 is isolated. The compound of Formula 2003 can be used as an intermediate in the synthesis of the compounds of the invention.

Reaction Scheme 21:

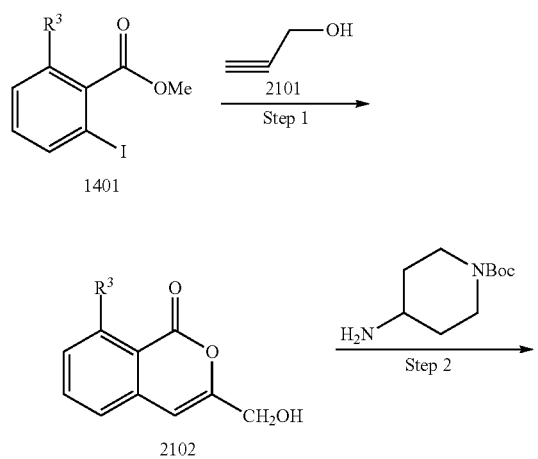

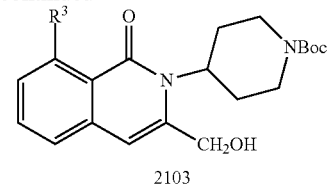

Referring to Reaction Scheme 21, Step 1, the compound of Formula 1401 is treated with an alkynyl alcohol, for example, of Formula 2101, the presence of copper iodide and palladium on carbon catalyst, to produce a compound of Formula 2102. The compound of Formula 2102 is optionally isolated and optionally purified. Referring to Reaction Scheme 21, Step 1, the compound of Formula 2102 is reacted with 4-amino N-Boc piperidine to produce a compound of Formula 2103. The compound of Formula 2103 is isolated. The compound of Formula 2103 can be used as an intermediate in the synthesis of the compounds of the invention.

Any of the compounds of Formula I, IV, V, VI, VII, VIII, IX, X, XI, XII, XIII, or XIV can be synthesized using the reaction schemes as disclosed herein or variants of these processes as well known in the art.

The chemical entities can be synthesized by an appropriate combination of generally well known synthetic methods.

In some embodiments, one or more subject compounds bind specifically to a PI3 kinase or a protein kinase selected from the group consisting of mTor, DNA-dependent protein kinase DNA-dependent protein kinase (Pubmed protein accession number (PPAN) AAA79184), Abl tyrosine kinase (CAA52387), Bcr-Abl, hemopoietic cell kinase (PPAN CAI19695), Src (PPAN CAA24495), vascular endothelial growth factor receptor 2 (PPAN ABB82619), vascular endothelial growth factor receptor-2 (PPAN ABB82619), epidermal growth factor receptor (PPAN AG43241), EPH receptor B4 (PPAN EAL23820), stem cell factor receptor (PPAN AAF22141), Tyrosine-protein kinase receptor TIE-2 (PPAN Q02858), fms-related tyrosine kinase 3 (PPAN NP_004110), platelet-derived growth factor receptor alpha (PPAN NP_990080), RET (PPAN CAA73131), and any other protein kinases listed in the appended tables and figures, as well as any functional mutants thereof. In some embodiments, the IC50 of a subject compound for p110α, p110β, p110γ, or p110δ is less than about 1 uM, less than about 100 nM, less than about 50 nM, less than about 10 nM, less than 1 nM or even less than about 0.5 nM. In some embodiments, the IC50 of a subject compound for mTor is less than about 1 uM, less than about 100 nM, less than about 50 nM, less than about 10 nM, less than 1 nM or even less than about 0.5 nM. In some other embodiments, one or more subject compounds exhibit dual binding specificity and are capable of inhibiting a PI3 kinase (e.g., a class I PI3 kinase) as well as a protein kinase (e.g., mTor) with an IC50 value less than about 1 uM, less than about 100 nM, less than about 50 nM, less than about 10 nM, less than 1 nM or even less than about 0.5 nM. One or more subject compounds are capable of inhibiting tyrosine kinases including, for example, DNA-dependent protein kinase DNA-dependent protein kinase (Pubmed protein accession number (PPAN) AAA79184), Abl tyrosine kinase (CAA52387), Bcr-Abl, hemopoietic cell kinase (PPAN CAI19695), Src (PPAN CAA24495), vascular endothelial growth factor receptor 2 (PPAN ABB82619), vascular endothelial growth factor receptor-2 (PPAN ABB82619), epidermal growth factor receptor (PPAN AG43241), EPH receptor B4 (PPAN EAL23820), stem cell factor receptor (PPAN AAF22141), Tyrosine-protein kinase receptor TIE-2 (PPAN Q02858), fms-related tyrosine kinase 3 (PPAN NP_004110), platelet-derived growth factor receptor alpha (PPAN NP_990080), RET (PPAN CAA73131), and functional mutants thereof. In some embodiments, the tyrosine kinase is Abl, Bcr-Abl, EGFR, or Flt-3, and any other kinases listed in the Tables herein.

In some embodiments, the compounds of the present invention exhibits one or more functional characteristics disclosed herein. For example, one or more subject compounds bind specifically to a PI3 kinase. In some embodiments, the IC50 of a subject compound for p110α, p110β, p110γ, or p110δ is less than about 1 uM, less than about 100 nM, less than about 50 nM, less than about 10 nM, less than about 1 nM, less than about 0.5 nM, less than about 100 pM, or less than about 50 pM.

In some embodiments, one or more of the subject compound may selectively inhibit one or more members of type I or class I phosphatidylinositol 3-kinases (PI3-kinase) with an IC50 value of about 100 nM, 50 nM, 10 nM, 5 nM, 100 pM, 10 pM or 1 pM, or less as measured in an in vitro kinase assay.

In some embodiments, one or more of the subject compound may selectively inhibit one or two members of type I or class I phosphatidylinositol 3-kinases (PI3-kinase) consisting of PI3-kinase α, PI3-kinase β, PI3-kinase γ, and PI3-kinase δ. In some aspects, some of the subject compounds selectively inhibit PI3-kinase δ as compared to all other type I PI3-kinases. In other aspects, some of the subject compounds selectively inhibit PI3-kinase δ and PI3-kinase γ as compared to the rest of the type I PI3-kinases. In yet other aspects, some of the subject compounds selectively inhibit PI3-kinase α and PI3-kinase β as compared to the rest of the type I PI3-kinases. In still yet some other aspects, some of the subject compounds selectively inhibit PI3-kinase δ and PI3-kinase α as compared to the rest of the type I PI3-kinases. In still yet some other aspects, some of the subject compounds selectively inhibit PI3-kinase δ and PI3-kinase β as compared to the rest of the type I PI3-kinases, or selectively inhibit PI3-kinase δ and PI3-kinase α as compared to the rest of the type I PI3-kinases, or selectively inhibit PI3-kinase α and PI3-kinase γ as compared to the rest of the type I PI3-kinases, or selectively inhibit PI3-kinase γ and PI3-kinase β as compared to the rest of the type I PI3-kinases.

In yet another aspect, an inhibitor that selectively inhibits one or more members of type I PI3-kinases, or an inhibitor that selectively inhibits one or more type I PI3-kinase mediated signaling pathways, alternatively can be understood to refer to a compound that exhibits a 50% inhibitory concentration (IC50) with respect to a given type I PI3-kinase, that is at least at least 10-fold, at least 20-fold, at least 50-fold, at least 100-fold, at least 1000-fold, at least 10,100-fold, or lower, than the inhibitor's IC50 with respect to the rest of the other type I PI3-kinases.

Pharmaceutical Compositions

The invention provides pharmaceutical compositions comprising one or more compounds of the present invention.

In some embodiments, the invention provides pharmaceutical compositions for treating diseases or conditions related to an undesirable, over-active, harmful or deleterious immune response in a mammal. Such undesirable immune response can be associated with or result in, e.g., asthma, emphysema, bronchitis, psoriasis, allergy, anaphylaxis, auto-immune diseases, rhuematoid arthritis, graft versus host disease, and lupus erythematosus. The pharmaceutical compositions of the present invention can be used to treat other respiratory diseases including but not limited to diseases affecting the lobes of lung, pleural cavity, bronchial tubes, trachea, upper respiratory tract, or the nerves and muscle for breathing.

In some embodiments, the invention provides pharmaceutical compositions for the treatment of disorders such as hyperproliferative disorder including but not limited to cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal; kidney, liver, ovarian, prostate, colorectal, esophageal, testicular, gynecological, thyroid, CNS, PNS, AIDS related AIDS-Related (e.g. Lymphoma and Kaposi's Sarcoma) or Viral-Induced cancer. In some embodiments, said pharmaceutical composition is for the treatment of a non-cancerous hyperproliferative disorder such as benign hyperplasia of the skin (e.g., psoriasis), restenosis, or prostate (e.g., benign prostatic hypertrophy (BPH)).

The invention also provides compositions for the treatment of liver diseases (including diabetes), pancreatitis or kidney disease (including proliferative glomerulonephritis and diabetes-induced renal disease) or pain in a mammal.

The invention further provides a composition for the prevention of blastocyte implantation in a mammal.

The invention also relates to a composition for treating a disease related to vasculogenesis or angiogenesis in a mammal which can manifest as tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The subject pharmaceutical compositions are typically formulated to provide a therapeutically effective amount of a compound of the present invention as the active ingredient, or a pharmaceutically acceptable salt, ester, prodrug, solvate, hydrate or derivative thereof. Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the subject compounds and other agent(s) may be mixed into a preparation or both components may be formulated into separate preparations to use them in combination separately or at the same time.

In some embodiments, the concentration of one or more of the compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more of the compounds of the present invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more of the compounds of the present invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v. v/v.

In some embodiments, the concentration of one or more of the compounds of the present invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more of the compounds of the present invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more of the compounds of the present invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more of the compounds of the present invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound is administered, the subject to be treated, the body weight of the subject to be treated, and the preference and experience of the attending physician.

Described below are non-limiting exemplary pharmaceutical compositions and methods for preparing the same.

Pharmaceutical Compositions for Oral Administration

In some embodiments, the invention provides a pharmaceutical composition for oral administration containing a compound of the present invention, and a pharmaceutical excipient suitable for oral administration.

In some embodiments, the invention provides a solid pharmaceutical composition for oral administration containing: (i) an effective amount of a compound of the present invention; optionally (ii) an effective amount of a second agent; and (iii) a pharmaceutical excipient suitable for oral administration. In some embodiments, the composition further contains: (iv) an effective amount of a third agent.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions.

Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, microcrystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof;

lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methylpyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, antifoaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Compositions for Injection.

In some embodiments, the invention provides a pharmaceutical composition for injection containing a compound of the present invention and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical (e.g., Transdermal) Delivery.

In some embodiments, the invention provides a pharmaceutical composition for transdermal delivery containing a compound of the present invention and a pharmaceutical excipient suitable for transdermal delivery.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of a compound of the present invention in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical Compositions for Inhalation.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other Pharmaceutical Compositions.

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., See, e.g., Anderson, Philip O.; Knoben, James E.; Troutman, William G, eds., Handbook of Clinical Drug Data, Tenth Edition, McGraw-Hill, 2002; Pratt and Taylor, eds., *Principles of Drug Action*, Third Edition, Churchill Livingston, New York, 1990; Katzung, ed., *Basic and Clinical Pharmacology*, Ninth Edition, McGraw Hill, 20037ybg; Goodman and Gilman, eds., *The Pharmacological Basis of Therapeutics*, Tenth Edition, McGraw Hill, 2001; *Remingtons Pharmaceutical Sciences*, 20th Ed., Lippincott Williams & Wilkins., 2000; Martindale, *The Extra Pharmacopoeia*, Thirty-Second Edition (The Pharmaceutical Press, London, 1999); all of which are incorporated by reference herein in their entirety.

Administration of the compounds or pharmaceutical composition of the present invention can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent or through inhalation. Compounds can also abe administered intraadiposally or intrathecally.

The amount of the compound administered will be dependent on the mammal being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

In some embodiments, a compound of the invention is administered in a single dose. Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the agents of the invention may continue as long as necessary. In some embodiments, an agent of the invention is administered for more than 1, 2, 3, 4, 5, 6, 7, 14, or 28 days. In some embodiments, an agent of the invention is administered for less than 28, 14, 7, 6, 5, 4, 3, 2, or 1 day. In some embodiments, an agent of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (ether-ester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds.

Compounds of the invention may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. Compounds of the invention may additionally be administered intravascularly from a balloon used during angioplasty. Extravascular administration of the compounds via the pericard or via advential application of formulations of the invention may also be performed to decrease restenosis.

A variety of stent devices which may be used as described are disclosed, for example, in the following references, all of which are hereby incorporated by reference: U.S. Pat. No. 5,451,233; U.S. Pat. No. 5,040,548; U.S. Pat. No. 5,061,273; U.S. Pat. No. 5,496,346; U.S. Pat. No. 5,292,331; U.S. Pat. No. 5,674,278; U.S. Pat. No. 3,657,744; U.S. Pat. No. 4,739,762; U.S. Pat. No. 5,195,984; U.S. Pat. No. 5,292,331; U.S. Pat. No. 5,674,278; U.S. Pat. No. 5,879,382; U.S. Pat. No. 6,344,053.

The compounds of the invention may be administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

When a compound of the invention, is administered in a composition that comprises one or more agents, and the agent has a shorter half-life than the compound of the invention unit dose forms of the agent and the compound of the invention may be adjusted accordingly.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compound in sterile aqueous solutions, for example, aqueous propylene glycol or dextrose solutions. Such dosage forms can be suitably buffered, if desired.

The activity of the compounds of the present invention may be determined by the following procedure, as well as the procedure described in the examples below. The activity of the kinase is assessed by measuring the incorporation of $\gamma$-$^{33}$P-phosphate from $\gamma$-$^{33}$P-ATP onto N-terminal His tagged substrate, which is expressed in E. coli and is purified by conventional methods, in the presence of the kinase. The assay is carried out in 96-well polypropylene plate. The incubation mixture (100, μL) comprises of 25 mM Hepes, pH 7.4, 10 mM MgCl$_2$, 5 mM β-glycerolphosphate, 100 μM Na-orthovanadate, 5 mM DTT, 5 nM kinase, and 1 μM substrate. Inhibitors are suspended in DMSO, and all reactions, including controls are performed at a final concentration of 1% DMSO. Reactions are initiated by the addition of 10 μM ATP (with 0.5 μCi $\gamma$-$^{33}$P-ATP/well) and incubated at ambient temperature for 45 minutes. Equal volume of 25% TCA is added to stop the reaction and precipitate the proteins. Precipitated proteins are trapped onto glass fiber B filterplates, and excess labeled ATP washed off using a Tomtec MACH III harvestor. Plates are allowed to air-dry prior to adding 30 μL/well of Packard Microscint 20, and plates are counted using a Packard TopCount.

The invention also provides kits. The kits include a compound or compounds of the present invention as described herein, in suitable packaging, and written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another agent. In some embodiments, the compound of the present invention and the agent are provided as separate compositions in separate containers within the kit. In some embodiments, the compound of the present invention and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

Methods

The invention also provides methods of using the compounds or pharmaceutical compositions of the present invention to treat disease conditions, including but not limited to diseases associated with malfunctioning of one or more types of PI3 kinase. A detailed description of conditions and disorders mediated by p110δ kinase activity is set forth in Sadu et al., WO 01/81346, which is incorporated herein by reference in its entirety for all purposes.

The treatment methods provided herein comprise administering to the subject a therapeutically effective amount of a compound of the invention. In one embodiment, the present invention provides a method of treating an inflammation disorder, including autoimmune diseases in a mammal. The method comprises administering to said mammal a therapeutically effective amount of a compound of the present invention, or a pharmaceutically acceptable salt, ester, prodrug, solvate, hydrate or derivative thereof. Examples of autoimmune diseases includes but is not limited to acute disseminated encephalomyelitis (ADEM), Addison's disease, antiphospholipid antibody syndrome (APS), aplastic anemia, autoimmune hepatitis, coeliac disease, Crohn's disease, Diabetes mellitus (type 1), Goodpasture's syndrome, Graves' disease, Guillain-Barré syndrome (GBS), Hashimoto's disease, lupus erythematosus, multiple sclerosis, myasthenia gravis, opsoclonus myoclonus syndrome (OMS), optic neuritis, Ord's thyroiditis, oemphigus, polyarthritis, primary biliary cirrhosis, psoriasis, rheumatoid arthritis, Reiter's syndrome, Takayasu's arteritis, temporal arteritis (also known as "giant cell arteritis"), warm autoimmune hemolytic anemia, Wegener's granulomatosis, alopecia universalis, Chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, and vulvodynia. Other disorders include bone-resorption disorders and thromobsis.

In some embodiments, the method of treating inflammatory or autoimmune diseases comprises administering to a subject (e.g. a mammal) a therapeutically effective amount of one or more compounds of the present invention that selectively inhibit PI3K-δ and/or PI3K-γ as compared to all other type I PI3 kinases. Such selective inhibition of PI3K-δ and/or PI3K-γ may be advantageous for treating any of the diseases or conditions described herein. For example, selective inhibition of PI3K-δ may inhibit inflammatory responses associated with inflammatory diseases, autoimmune disease, or diseases related to an undesirable immune response including but not limited to asthma, emphysema, allergy, dermatitis, rhuematoid arthritis, psoriasis, lupus erythematosus, or graft versus host disease. Selective inhibition of PI3K-δ may further provide for a reduction in the inflammatory or undesirable immune response without a concomittant reduction in the ability to reduce a bacterial, viral, and/or fungal infection. Selective inhibition of both PI3K-δ and PI3K-γ may be advantageous for inhibiting the inflammatory response in the subject to a greater degree than that would be provided for by inhibitors that selectively inhibit PI3K-δ or PI3K-γ alone. In one aspect, one or more of the subject methods are effective in reducing antigen specific antibody production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more. In another aspect, one or more of the subject methods are effective in reducing antigen specific IgG3 and/or IgGM production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more.

In one aspect, one of more of the subject methods are effective in ameliorating symptoms associated with rheumatoid arthritis including but not limited to a reduction in the swelling of joints, a reduction in serum anti-collagen levels, and/or a reduction in joint pathology such as bone resorption, cartilage damage, pannus, and/or inflammation. In another aspect, the subject methods are effective in reducing ankle inflammation by at least about 2%, 5%, 10%, 15%, 20%, 25%, 30%, 50%, 60%, or about 75% to 90%. In another aspect, the subject methods are effective in reducing knee inflammation by at least about 2%, 5%, 10%, 15%, 20%, 25%, 30%, 50%, 60%, or about 75% to 90% or more. In still another aspect, the subject methods are effective in reducing serum anti-type II collagen levels by at least about 10%, 12%, 15%, 20%, 24%, 25%, 30%, 35%, 50%, 60%, 75%, 80%, 86%, 87%, or about 90% or more. In another aspect, the subject methods are effective in reducing ankle histopathology scores by about 5%, 10%, 15%, 20%, 25%, 30%, 40%, 50%, 60%, 75%, 80%, 90% or more. In still another aspect, the subject methods are effective in reducing knee histopathology scores by about 5%, 10%, 15%, 20%, 25%, 30%, 40%, 50%, 60%, 75%, 80%, 90% or more.

In other embodiments, the present invention provides methods of using the compounds or pharmaceutical compositions to treat respiratory diseases including but not limited to diseases affecting the lobes of lung, pleural cavity, bronchial tubes, trachea, upper respiratory tract, or the nerves and muscle for breathing. For example, methods are provided to treat obstructive pulmonary disease. Chronic obstructive pulmonary disease (COPD) is an umbrella term for a group of respiratory tract diseases that are characterized by airflow obstruction or limitation. Conditions included in this umbrella term are: chronic bronchitis, emphysema, and bronchiectasis.

In another embodiment, the compounds described herein are used for the treatment of asthma. Also, the compounds or pharmaceutical compositions described herein may be used for the treatment of endotoxemia and sepsis. In one embodiment, the compounds or pharmaceutical compositions described herein are used to for the treatment of rheumatoid arthritis (RA). In yet another embodiment, the compounds or pharmaceutical compositions described herein is used for the treatment of contact or atopic dermatitis. Contact dermatitis includes irritant dermatitis, phototoxic dermatitis, allergic dermatitis, photoallergic dermatitis, contact urticaria, systemic contact-type dermatitis and the like. Irritant dermatitis can occur when too much of a substance is used on the skin of when the skin is sensitive to certain substance. Atopic dermatitis, sometimes called eczema, is a kind of dermatitis, an atopic skin disease.

The invention also relates to a method of treating a hyperproliferative disorder in a mammal that comprises administering to said mammal a therapeutically effective amount of a compound of the present invention, or a pharmaceutically acceptable salt, ester, prodrug, solvate, hydrate or derivative thereof. In some embodiments, said method relates to the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g. Lymphoma and Kaposi's Sarcoma) or viral-induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

The invention also relates to a method of treating diseases related to vasculogenesis or angiogenesis in a mammal that comprises administering to said mammal a therapeutically effective amount of a compound of the present invention, or a pharmaceutically acceptable salt, ester, prodrug, solvate, hydrate or derivative thereof. In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Patients that can be treated with compounds of the present invention, or pharmaceutically acceptable salt, ester, prodrug, solvate, hydrate or derivative of said compounds, according to the methods of this invention include, for example, patients that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor; oral cavity and oropharyngeal cancer such as, hypopharyngeal cancer, laryngeal cancer, nasopharyngeal cancer, and oropharyngeal cancer; stomach cancer such as lymphomas, gastric stomal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer.

The invention also relates to a method of treating diabetes in a mammal that comprises administering to said mammal a therapeutically effective amount of a compound of the present invention, or a pharmaceutically acceptable salt, ester, prodrug, solvate, hydrate or derivative thereof.

In addition, the compounds described herein may be used to treat acne.

In addition, the compounds described herein may be used for the treatment of arteriosclerosis, including atherosclerosis. Arteriosclerosis is a general term describing any hardening of medium or large arteries. Atherosclerosis is a hardening of an artery specifically due to an atheromatous plaque.

Further the compounds described herein may be used for the treatment of glomerulonephritis. Glomerulonephritis is a primary or secondary autoimmune renal disease characterized by inflammation of the glomeruli. It may be asymptomatic, or present with hematuria and/or proteinuria. There are many recognized types, divided in acute, subacute or chronic glomerulonephritis. Causes are infectious (bacterial, viral or parasitic pathogens), autoimmune or paraneoplastic.

Additionally, the compounds described herein may be used for the treatment of bursitis, lupus, acute disseminated encephalomyelitis (ADEM), addison's disease, antiphospholipid antibody syndrome (APS), aplastic anemia, autoimmune hepatitis, coeliac disease, crohn's disease, diabetes mellitus (type 1), goodpasture's syndrome, graves' disease, guillain-barré syndrome (GBS), hashimoto's disease, inflammatory bowel disease, lupus erythematosus, myasthenia gravis, opsoclonus myoclonus syndrome (OMS), optic neuritis, ord's thyroiditis, ostheoarthritis, uveoretinitis, pemphigus, polyarthritis, primary biliary cirrhosis, reiter's syndrome, takayasu's arteritis, temporal arteritis, warm autoimmune hemolytic anemia, wegener's granulomatosis, alopecia universal is, chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, dermatomyositis, endocarditis, endometritis, enteritis, enterocolitis, epicondylitis, epididymitis, fasciitis, fibrositis, gastritis, gastroenteritis, gingivitis, hepatitis, hidradenitis, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis, vaginitis, vasculitis, or vulvitis.

The invention also relates to a method of treating a cardiovascular disease in a mammal that comprises administering to said mammal a therapeutically effective amount of a compound of the present invention, or a pharmaceutically acceptable salt, ester, prodrug, solvate, hydrate or derivative thereof. Examples of cardiovascular conditions include, but are not limited to, atherosclerosis, restenosis, vascular occlusion and carotid obstructive disease.

In another aspect, the present invention provides methods of disrupting the function of a leukocyte or disrupting a function of an osteoclast. The method includes contacting the leukocyte or the osteoclast with a function disrupting amount of a compound of the invention.

In another aspect of the present invention, methods are provided for treating ophthalmic disease by administering one or more of the subject compounds or pharmaceutical compositions to the eye of a subject.

Methods are further provided for administering the compounds of the present invention via eye drop, intraocular injection, intravitreal injection, topically, or through the use of a drug eluting device, microcapsule, implant, or microfluidic device. In some cases, the compounds of the present invention are administered with a carrier or excipient that increases the intraocular penetrance of the compound such as an oil and water emulsion with colloid particles having an oily core surrounded by an interfacial film.

In some cases, the colloid particles include at least one cationic agent and at least one non-ionic surfactant such as a poloxamer, tyloxapol, a polysorbate, a polyoxyethylene castor oil derivative, a sorbitan ester, or a polyoxyl stearate. In some cases, the cationic agent is an alkylamine, a tertiary alkyl amine, a quarternary ammonium compound, a cationic lipid, an amino alcohol, a biguanidine salt, a cationic compound or a mixture thereof. In some cases the cationic agent is a biguanidine salt such as chlorhexidine, polyaminopropyl biguanidine, phenformin, alkylbiguanidine, or a mixture thereof. In some cases, the quaternary ammonium compound is a benzalkonium halide, lauralkonium halide, cetrimide, hexadecyltrimethylammonium halide, tetradecyltrimethylammonium halide, dodecyltrimethylammonium halide, cetrimonium halide, benzethonium halide, behenalkonium halide, cetalkonium halide, cetethyldimonium halide, cetylpyridinium halide, benzododecinium halide, chlorallyl methenamine halide, myristylalkonium halide, stearalkonium halide or a mixture of two or more thereof. In some cases, cationic agent is a benzalkonium chloride, lauralkonium chloride, benzododecinium bromide, benzethenium chloride, hexadecyltrimethylammonium bromide, tetradecyltrimethylammonium bromide, dodecyltrimethylammonium bromide or a mixture of two or more thereof. In some cases, the oil phase is mineral oil and light mineral oil, medium chain triglycerides (MCT), coconut oil; hydrogenated oils comprising hydrogenated cottonseed oil, hydrogenated palm oil, hydrogenate castor oil or hydrogenated soybean oil; polyoxyethylene hydrogenated castor oil derivatives comprising poluoxyl-40 hydrogenated castor oil, polyoxyl-60 hydrogenated castor oil or polyoxyl-100 hydrogenated castor oil.

The invention further provides methods of modulating kinase activity by contacting a kinase with an amount of a compound of the invention sufficient to modulate the activity of the kinase. Modulate can be inhibiting or activating kinase activity. In some embodiments, the invention provides methods of inhibiting kinase activity by contacting a kinase with an amount of a compound of the invention sufficient to inhibit the activity of the kinase. In some embodiments, the invention provides methods of inhibiting kinase activity in a solution by contacting said solution with an amount of a compound of the invention sufficient to inhibit the activity of the kinase in said solution. In some embodiments, the invention provides methods of inhibiting kinase activity in a cell by contacting said cell with an amount of a compound of the invention sufficient to inhibit the activity of the kinase in said cell. In some embodiments, the invention provides methods of inhibiting kinase activity in a tissue by contacting said tissue with an amount of a compound of the invention sufficient to inhibit the activity of the kinase in said tissue. In some embodiments, the invention provides methods of inhibiting kinase activity in an organism by contacting said organism with an amount of a compound of the invention sufficient to inhibit the activity of the kinase in said organism. In some embodiments, the invention provides methods of inhibiting kinase activity in an animal by contacting said animal with an amount of a compound of the invention sufficient to inhibit the activity of the kinase in said animal. In some embodiments, the invention provides methods of inhibiting kinase activity in a mammal by contacting said mammal with an amount of a compound of the invention sufficient to inhibit the activity of the kinase in said mammal. In some embodiments, the invention provides methods of inhibiting kinase activity in a human by contacting said human with an amount of a compound of the invention sufficient to inhibit the activity of the kinase in said human. In some embodiments, the % of kinase activity after contacting a kinase with a compound of the invention is less than 1, 5, 10, 20, 30, 40, 50, 60, 70, 80 90, 95, or 99% of the kinase activity in the absence of said contacting step.

In some embodiments, the kinase is a lipid kinase or a protein kinase. In some embodiments, the kinase is selected from the group consisting of PI3 kinase including different isoforms such as PI3 kinase α, PI3 kinase β, PI3 kinase γ, PI3 kinase δ; DNA-PK; mTor; Abl, VEGFR, Ephrin receptor B4 (EphB4); TEK receptor tyrosine kinase (TIE2); FMS-related tyrosine kinase 3 (FLT-3); Platelet derived growth factor receptor (PDGFR); RET; ATM; ATR; hSmg-1; Hck; Src; Epidermal growth factor receptor (EGFR); KIT; Inulsin Receptor (IR) and IGFR.

The invention further provides methods of modulating PI3 kinase activity by contacting a PI3 kinase with an amount of a compound of the invention sufficient to modulate the activity of the PI3 kinase. Modulate can be inhibiting or activating PI3 kinase activity. In some embodiments, the invention provides methods of inhibiting PI3 kinase activity by contacting a PI3 kinase with an amount of a compound of the invention sufficient to inhibit the activity of the PI3 kinase. In some embodiments, the invention provides methods of inhibiting PI3 kinase activity. Such inhibition can take place in solution, in a cell expressing one or more PI3 kinases, in a tissue comprising a cell expressing one or more PI3 kinases, or in an organism expressing one or more PI3 kinases. In some embodiments, the invention provides methods of inhibiting PI3 kinase activity in an animal (including mammal such as humans) by contacting said animal with an amount of a compound of the invention sufficient to inhibit the activity of the PI3 kinase in said animal.

Combination Treatment

The present invention also provides methods for combination therapies in which an agent known to modulate other pathways, or other components of the same pathway, or even overlapping sets of target enzymes are used in combination with a compound of the present invention, or a pharmaceutically acceptable salt, ester, prodrug, solvate, hydrate or derivative thereof. In one aspect, such therapy includes but is not limited to the combination of the subject compound with chemotherapeutic agents, therapeutic antibodies, and radiation treatment, to provide a synergistic or additive therapeutic effect.

In one aspect, the compounds or pharmaceutical compositions of the present invention may present synergistic or additive efficacy when administered in combination with agents that inhibit IgE production or activity. Such combination can reduce the undesired effect of high level of IgE associated with the use of one or more PI3Kδ inhibitors, if such effect occurs. This may be particularly useful in treatment of autoimmune and inflammatory disorders (AIID) such as rheumatoid arthritis. Additionally, the administration of MKS or PI3Kδ/γ inhibitors of the present invention in combination with inhibitors of mTOR may also exhibit synergy through enhanced inhibition of the PI3K pathway.

In a separate but related aspect, the present invention provides a combination treatment of a disease associated with PI3Kδ comprising administering to a PI3Kδ inhibitor and an agent that inhibits IgE production or activity. Other exemplary PI3Kδ inhibitors are applicable for this combination and they are described, e.g., U.S. Pat. No. 6,800,620. Such combination treatment is particularly useful for treating autoimmune and inflammatory diseases (AIID) including but not limited to rheumatoid arthritis.

Agents that inhibit IgE production are known in the art and they include but are not limited to one or more of TEI-9874, 2-(4-(6-cyclohexyloxy-2-naphtyloxy)phenylacetamide)benzoic acid, rapamycin, rapamycin analogs (i.e. rapalogs), TORC1 inhibitors, TORC2 inhibitors, and any other compounds that inhibit mTORC1 and mTORC2. Agents that inhibit IgE activity include, for example, anti-IgE antibodies such as for example Omalizumab and TNX-901.

For treatment of autoimmune diseases, the subject compounds or pharmaceutical compositions can be used in combination with commonly prescribed drugs including but not limited to Enbrel®, Remicade®, Humira®, Avonex®, and Rebif®. For treatment of respiratory diseases, the subject compounds or pharmaceutical compositions can be administered in combination with commonly prescribed drugs including but not limited to Xolair®, Advair®, Singulair®, and Spiriva®.

The compounds of the invention may be formulated or administered in conjunction with other agents that act to relieve the symptoms of inflammatory conditions such as encephalomyelitis, asthma, and the other diseases described herein. These agents include non-steroidal anti-inflammatory drugs (NSAIDs), e.g. acetylsalicylic acid; ibuprofen; naproxen; indomethacin; nabumetone; tolmetin; etc. Corticosteroids are used to reduce inflammation and suppress activity of the immune system. The most commonly prescribed drug of this type is Prednisone. Chloroquine (Aralen®) or hydroxychloroquine (Plaquenil®) may also be very useful in some individuals with lupus. They are most often prescribed for skin and joint symptoms of lupus. Azathioprine (Imuran®) and cyclophosphamide (Cytoxan®) suppress inflammation and tend to suppress the immune system. Other agents, e.g. methotrexate and cyclosporin are used to control the symptoms of lupus. Anticoagulants are employed to prevent blood from clotting rapidly. They range from aspirin at very low dose which prevents platelets from sticking, to heparin/coumadin.

In another one aspect, this invention also relates to a pharmaceutical composition for inhibiting abnormal cell growth in a mammal which comprises an amount of a compound of the present invention, or a pharmaceutically acceptable salt, ester, prodrug, solvate, hydrate or derivative thereof, in combination with an amount of an anti-cancer agent (e.g. a chemotherapeutic agent). Many chemotherapeutics are presently known in the art and can be used in combination with the compounds of the invention.

In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec® (Imatinib Mesylate), Velcade® (bortezomib), Casodex® (bicalutamide), Iressa® (gefitinib), and Adriamycin® as well as a host of chemotherapeutic agents. Non-limiting examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.R™; razoxane; sizofiran; spirogermanium; tenuazonic acid; triaziquone; 2,2',2"-trichlorotriethyla-mine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen (Nolvadex™), raloxifene, aromatase inhibiting 4(5)-imidazoles, 4-hydroxytamoxifen, trioxifene, keoxifene, LY 117018, onapristone, and toremifene (Fareston®); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; Xeloda®; ibandronate; camptothecin-11 (CPT-11); topoisomerase inhibitor RFS 2000; difluoromethylornithine (DMFO). Where desired, the compounds or pharmaceutical composition of the present invention can be used in combination with commonly prescribed anti-cancer drugs such as Herceptin®, Avastin®, Erbitux®, Rituxan®, Taxol®, Arimidex®, Taxotere®, and Velcade®.

This invention further relates to a method for using the compounds or pharmaceutical composition in combination with radiation therapy in inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of the present invention or pharmaceutically acceptable salt, ester, prodrug, solvate, hydrate or derivative thereof, which amount is effective is sensitizing abnormal cells to treatment with radiation. The amount of the compound, salt, or solvate in this method can be determined according to the means for ascertaining effective amounts of such compounds described herein.

The compounds or pharmaceutical compositions of the present invention can be used in combination with an amount of one or more substances selected from anti-angiogenesis agents, signal transduction inhibitors, and antiproliferative agents.

Anti-angiogenesis agents, such as MMP-2 (matrix-metalloprotienase 2) inhibitors, MMP-9 (matrix-metalloprotienase 9) inhibitors, and COX-11 (cyclooxygenase 11) inhibitors, can be used in conjunction with a compound of the present invention and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in the present invention are AG-3340, RO 32-3555, and RS 13-0830.

The invention also relates to a method of and to a pharmaceutical composition of treating a cardiovascular disease in a mammal which comprises an amount of a compound of the present invention, or a pharmaceutically acceptable salt, ester, prodrug, solvate, hydrate or derivative thereof, or an isotopically-labeled derivative thereof, and an amount of one or more therapeutic agents use for the treatment of cardiovascular diseases.

Examples for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, anti-proliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings comprised by the invention. Moreover, a coating can be used to effect therapeutic delivery focally within the vessel wall. By incorporation of the active agent in a swellable polymer, the active agent will be released upon swelling of the polymer.

The compounds describe herein may be formulated or administered in conjunction with liquid or solid tissue barriers also known as lubricants. Examples of tissue barriers include, but are not limited to, polysaccharides, polyglycans, seprafilm, interceed and hyaluronic acid.

Medicaments which may be administered in conjunction with the compounds described herein include any suitable drugs usefully delivered by inhalation for example, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines or pentamidine; antihistamines, e.g. methapyrilene; anti-inflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino] methyl]benzenemethanol; diuretics, e.g. amiloride; anticholinergics e.g. ipratropium, atropine or oxitropium;

hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-Lactam antibiotics, an agent comprising an aminoglycoside, protein synthesis inhibitors, drugs used in the chemotherapy of tuberculosis, *mycobacterium avium* complex disease, and leprosy, antifungal agents, antiviral agents including nonretroviral agents and antiretroviral agents.

Examples of therapeutic antibodies that can be combined with a subject compound include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

Further therapeutic agents that can be combined with a subject compound may be found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein can be used in combination with the agents disclosed herein or other suitable agents, depending on the condition being treated. Hence, in some embodiments the compounds of the invention will be co-administer with other agents as described above. When used in combination therapy, the compounds described herein may be administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the present invention and any of the agents described above can be simultaneously administered, wherein both the agents are present in separate formulations. In another alternative, a compound of the present invention can be administered just followed by and any of the agents described above, or vice versa. In the separate administration protocol, a compound of the present invention and any of the agents described above may be administered a few minutes apart, or a few hours apart, or a few days apart.

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXAMPLES

Example 1

Synthesis of 2-((4-amino-3-(3-hydroxyphenyl)-1H-pyrazolo[3,4-d]pyrimidin-1-yl)methyl)-5-methyl-3-o-tolylpyrido[2,3-d]pyrimidin-4(3H)-one (Compound 1406)

Scheme 14. Synthesis of 2-((4-amino-3-(3-hydroxyphenyl)-1H-pyrazolo[3,4-d]pyrimidin-1-yl)methyl)-5-methyl-3-o-tolylpyrido[2,3-d]pyrimidin-4(3H)-one (Compound 1406) is described.

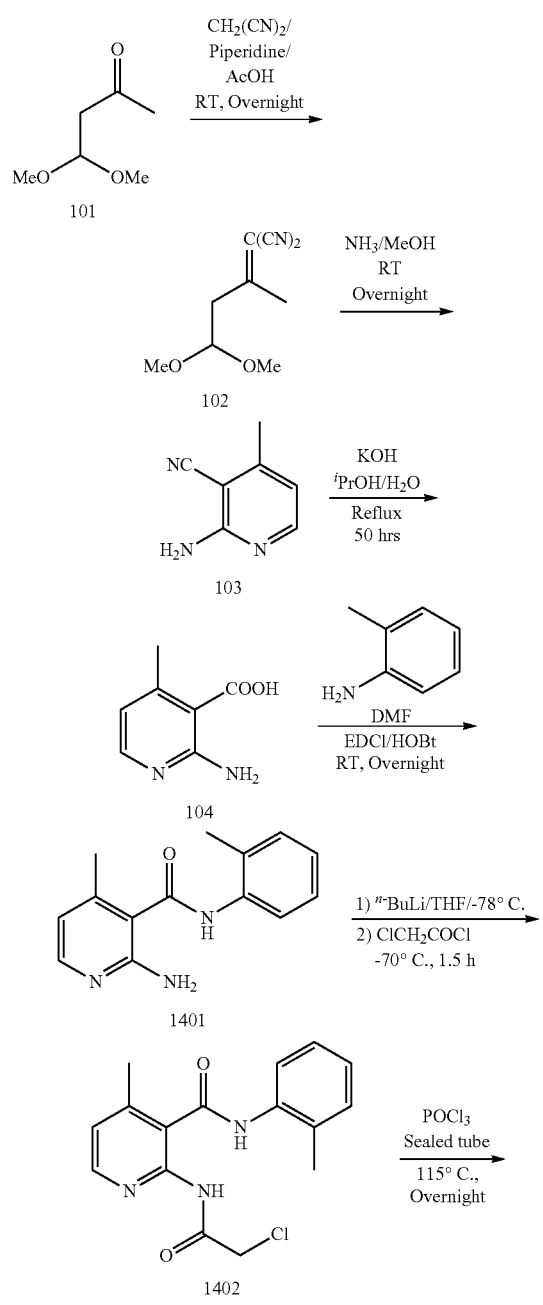

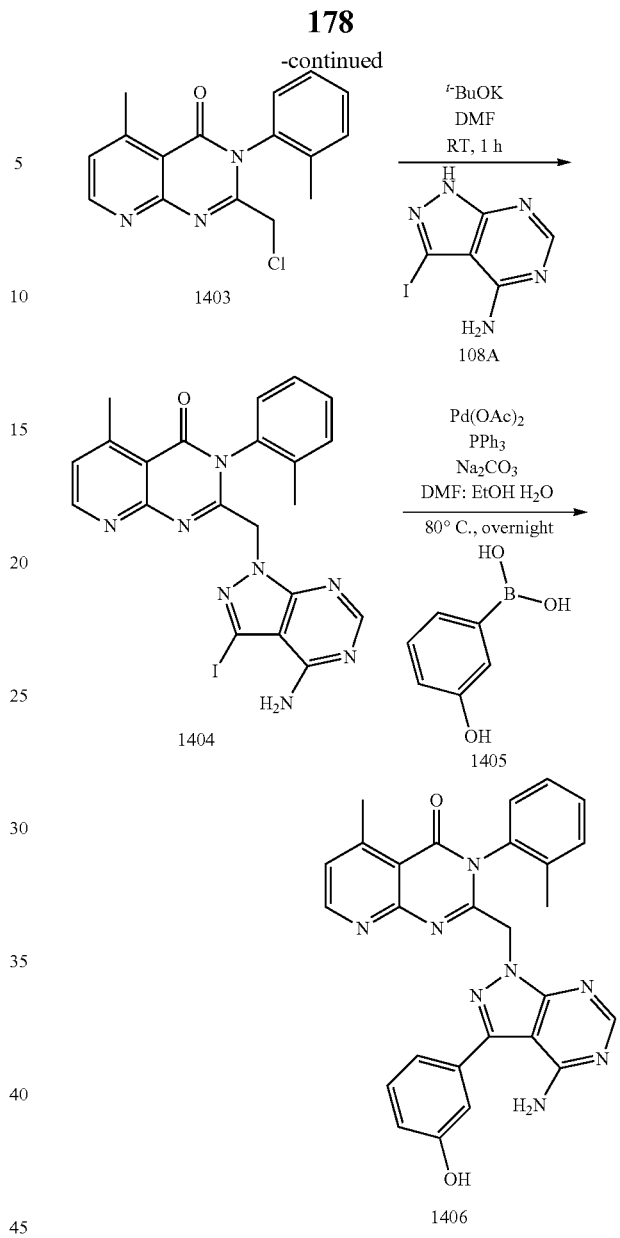

To a stirred solution of 4,4-dimethoxy-2-butanone (101) (61 g, 85%, 0.393 mol), acetic acid (2.2 mL, 0.038 mmol) and piperidine (3.8 mL, 0.038 mol) in toluene (150 mL), malononitrile (25 g, 0.394 mmol) was added in portions over 20 min. The reaction mixture was stirred overnight at room temperature. The resulting dark red solution was washed with $H_2O$ (50 mL), dried over $MgSO_4$ and concentrated in vacuo to afford the desired product 2-(4,4-dimethoxybutan-2-ylidene)malononitrile (102) (70 g, 99%), which was used directly in the next step.

Ammonia gas was bubbled through a solution of 102 (32 g, 0.178 mmol) in MeOH (500 mL) for 3 h, the resulting deep-red solution was stirred overnight at room temperature. The mixture was concentrated and the residue was partitioned between HCl solution (2 N, 600 mL) and EtOAc (600 mL). The aqueous layer was separated and basified with ice-cold concentrated $NaHCO_3$ (600 mL) solution. The solid was precipitated out of the solution and collected by filtration to afford the desired product 2-amino-4-methylnicotinonitrile (103) (3.0 g, 33%).

Compound 103 (5.32 g, 40 mmol) was suspended in a solution of potassium hydroxide (26.88 g, 480 mmol) in water (26.85 mL) and iso-propanol (9.6 mL). The reaction mixture was heated to reflux for 50 h, then cooled to room temperature and diluted with ice-water (100 mL) and neutralized with concentrated HCl solution until PH=6-7. The mixture was concentrated in vacuo and the resulting residue was purified by flash chromatography eluting with ethanol to afford the desired product 2-amino-4-methylnicotinic acid (104) (3.284 g, 54.7%).

To a stirred solution of 104 (3.2 g, 21.2 mmol) in DMF (40 mL) and DCM (80 mL) was added EDCI (8.12 g, 42.4 mmol), HOBt (2.86 g, 21.4 mmol) and o-Toluidine (4.53 mL, 42.4 mmol). The reaction mixture was stirred overnight at room temperature and then poured into water (120 mL). The aqueous phase was extracted with DCM (60 mL×2). The combined organic phases were washed with brine, dried over MgSO$_4$, filtered and concentrated. The solid was precipitated out of the solution. The solid was collected by filtration and dried to afford the desired product 2-amino-4-methyl-N-o-tolylnicotinamide (1401) (3.6 g, 70.4%).

A suspension of 1401 (1.2 g, 4.96 mmol) in dry THF (60 mL) was added butyllithium (2.5M, 2.38 mL, 5.96 mmol) dropwise under Argon at −40° C. and stirred at this temperature for 1 h. Then the reaction mixture was cooled to −78° C. and chloroacetyl chloride (0.432 mL, 5.4 mmol) was added. After stirring for 2 h at −78° C., the reaction mixture was poured into ice-water (100 mL). After most of THF was removed in vacuo, the solid was precipitated out of the solution. The solid was collected by filtration and washed with ether to afford the desired product 2-(2-chloroacetamido)-4-methyl-N-o-tolylnicotinamide (1402) (890 mg, 56.4%).

A mixture of 1402 (320 mg, 1 mmol) and phosphorus oxychloride (20 mL, 214 mmol) was heated at 115° C. overnight in a sealed-tube. The reaction mixture was cooled to room temperature and concentrated in vacuo. The residue was poured into ice-water and neutralized with saturated NaHCO$_3$ solution until PH 8-9, the resulting precipitate solid was collected by filtration and washed with ether to afford the desired product 2-(chloromethyl)-5-methyl-3-o-tolylpyrido[2,3-d]pyrimidin-4(3H)-one (1403) (200 mg, 66.8%).

To a solution of 3-iodo-4-amine-1H-pyrazolo[3,4-d]pyrimidin (108A) (261 mg, 1.2 mmol) in dry DMF (9 mL) under nitrogen, potassium tert-butoxide (123 mg, 1.1 mmol) was added at 0° C. The resulting mixture was stirred at this temperature for 45 min. A solution of 1403 (300 mg, 1 mmol) in dry DMF (5 mL) was added. The reaction mixture was stirred for 1 h at 0° C. and then an additional 1 h at room temperature. The mixture was concentrated in vacuo and the resulting residue was purified by flash chromatography to afford the desired product 2-((4-amino-3-iodo-1H-pyrazolo[3,4-d]pyrimidin-1-yl)methyl)-5-methyl-3-o-tolylpyrido[2,3-d]pyrimidin-4(3H)-one (1404) (450 mg, 83.3%).

To a solution of 1404 (36 mg, 0.069 mmol) and 3-hydroxyphenylboronic acid (1405) (12 mg, 0.083 mmol) in DMF (2 mL), EtOH (1 mL) and water (1 mL) was added Pd(PPh$_3$)$_4$ (7 mg, 0.006 mmol) and Na$_2$CO$_3$ solution (1M, 0.5 mL, 0.5 mmol) under Argon. The resulting mixture was degassed and back-filled with argon three times and then heated overnight at 80° C. The reaction mixture was allowed to cool to room temperature, concentrated. The residue was diluted with water (20 mL), neutralized with HCl solution (1M) until pH 6-7 and extracted with DCM (10 mL×3). The combined organic layers were washed with brine, dried over Na$_2$SO$_4$ and concentrated. The residue was purified by flash chromatography to afford the desired product 2-((4-amino-3-(3-hydroxyphenyl)-1H-pyrazolo[3,4-d]pyrimidin-1-yl)methyl)-5-methyl-3-o-tolylpyrido[2,3-d]pyrimidin-4(3H)-one (1406) (8 mg, 23.7%).

Example 2

Synthesis of 5-((4-amino-3-(3-fluoro-4-hydroxyphenyl)-1H-pyrazolo[3,4-d]pyrimidin-1-yl)methyl)-1,3-dimethyl-6-o-tolyl-1H-pyrazolo[4,3-d]pyrimidin-7 (6H)-one (Compound 1511)

Scheme 15. Synthesis of 5-((4-amino-3-(3-fluoro-4-hydroxyphenyl)-1H-pyrazolo[3,4-d]pyrimidin-1-yl)methyl)-1,3-dimethyl-6-o-tolyl-1H-pyrazolo[4,3-d]pyrimidin-7(6H)-one (Compound 1512) is described.

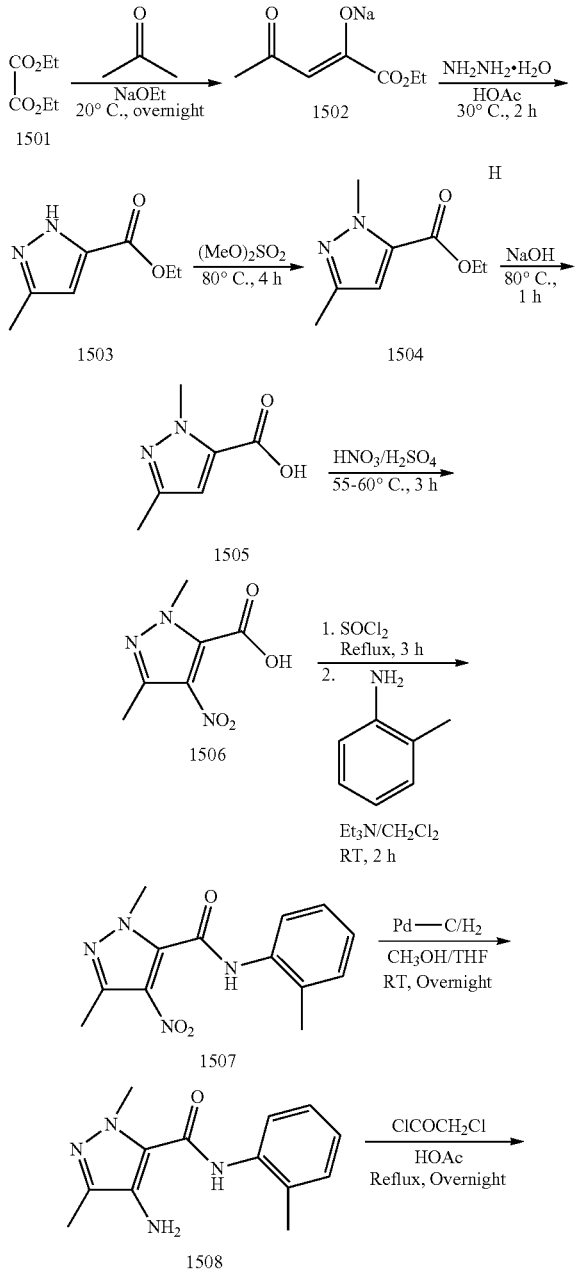

-continued

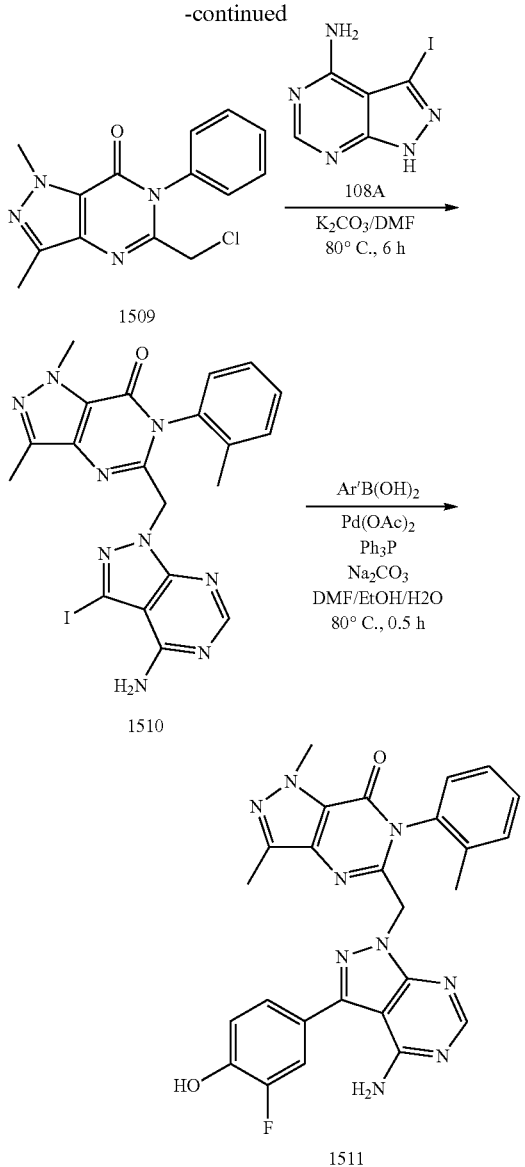

Sodium (5.2 g, 0.226 mol) was dissolved in anhydrous ethanol (120 mL). A mixture of diethyl oxalate (1501) (31.8 mL, 0.235 mol) and acetone (16.0 mL, 0.218 mol) was added to the above solution keeping the temperature under 10° C. The reaction mixture was stirred overnight at RT. The resulting precipitate was collected by filtration, washed with petroether and dried to afford the desired product 1502 as a yellow solid. (30.4 g, 77.5%).

Hydrazine hydrate (9.7 mL, 85%, 0.200 mol) was added dropwise to acetic acid (34 mL). To this solution, compound 1502 (30.4 g, 0.169 mol) was added in portions at 25° C. The resulting mixture was stirred for 2 h at room temperature, then basified with saturated NaHCO$_3$ solution until pH 8 and extracted with DCM (200 mL×3). The combined organic phases were washed with brine, dried and concentrated to afford the desired product, compound 1503, as a yellow solid (22 g, 84.6%).

Dimethyl sulfate (3.2 mL, 33.8 mmol) was added dropwise to a solution of compound 1503 (4.2 g, 29.9 mmol) in toluene (20 mL). The reaction mixture was stirred for 4 h at 80° C., then allowed to cool to room temperature and concentrated. A 40% NaOH solution (15 mL) was added to the residue. The resulting mixture was stirred for 1 h at 80° C., then cooled to room temperature and diluted with H$_2$O (30 mL), acidified with concentrated HCl solution until pH 3-4. The precipitated solid was collected by filtration, washed with cold water and dried to afford the desired product, compound 1505, as an off-white solid. (3.54 g, 84.4%).

To a stirred mixture of concentrated H$_2$SO$_4$ (3.6 mL) and fuming HNO$_3$ (3.1 mL, 73.9 mmol), the acid 1505 (2.813 g, 20 mmol) was added at 70-80° C. The reaction mixture was stirred for 6 h at 70° C., and cooled to room temperature and then poured into ice-water. The precipitated solid was collected by filtration, washed with water and dried to afford the desired product, compound 1506, as a yellow solid (0.795 g, 21.5%).

A mixture of compound 1506 (1.508 g, 8.15 mmol) and SOCl$_2$ (6 mL) was refluxed for 3 h, then concentrated to remove SOCl$_2$. The residue was dissolved in CH$_2$Cl$_2$ (8 mL). To this solution, Et$_3$N (1.13 mL) and o-toluidine (1.12 g, 12.23 mmol) was added at 0° C. The resulting mixture was stirred for 2 h at 10° C., concentrated and diluted with water. The solid was collected by filtration, washed with water and petroether, dried to afford the desired product, compound 1507, as a yellow solid (1.74 g, 77.6%).

To a stirred mixture of compound 1507 (1.73 g, 6.31 mmol) in MeOH (100 mL) and THF (10 mL), 5% Pd/C (0.2 g) was added. The mixture was degassed and back-filled with hydrogen three times. The reaction mixture was stirred overnight at room temperature and then filtrated. The filtrate was concentrated in vacuo. The solid was dried to afford the desired product, compound 1508, as a pale solid (1.47 g, 95.4%).

Chloroacetyl chloride (1.44 mL, 1.99 mmol) was added to a solution of compound 1508 (1.46 g, 5.98 mmol) in acetic acid (20 mL) and the reaction mixture was heated to reflux for 4 h. The reaction mixture was cooled to room temperature and concentrated in vacuo. The residue was diluted in DCM (100 mL), washed with saturated NaHCO$_3$ solution and brine, dried and concentrated. The residue was purified by flash chromatography eluting with petroether in ethyl acetate (10/1) to afford the desired product, compound 1509, as a off-white solid (0.48 g, 26.7%).

A solution of 3-iodo-1H-pyrazolo[3,4-d]pyrimidin-4-amine (108A) (311 mg, 1.19 mmol) and K$_2$CO$_3$ (330 mg, 2.39 mmol) in DMF (10 mL) was stirred at room temperature for 15 min., a solution of compound (1509) (180 mg, 1.15 mmol, 1 eq.) in DMF (5 mL) was added dropwise at room temperature. The resulting mixture was stirred 2 h at 80° C. The reaction mixture was concentrated in vacuo to remove the organic solvent. The resulting residue was purified by a silica gel column chromatography to afford the desired product, compound 1509, (142 mg, 44.9% yield) as a pale yellow solid.

Compound 1510 (40 mg, 0.076 mmol), Na$_2$CO$_3$ (40 mg, 0.38 mmol), Pd(PPh$_3$)$_4$ (17.6 mg, 0.015 mmol), and 3-fluoro-4-hydroxyphenylboronic acid (15.8 mg, 0.101 mmol) were dissolved in a solution of DMF, ethanol and water (4 mL/2 mL/2 mL). The resulting mixture was degassed and back-filled with argon three times and then heated to 80° C. for 4 h with stirring. The reaction mixture was cooled to room temperature, neutralized with 1N HCl solution until pH 7, concentrated in vacuo and extracted with ethyl acetate. The combined organic phases were dried over Na$_2$SO$_4$, filtered and concentrated. The residue was purified by flash column chromatography eluting with DCM/MeOH=50/1 to afford the desired product 1511(32 mg, 82%).
Example 3
Synthesis of 3-((4-amino-3-(3-hydroxyphenyl)-1H-pyrazolo[3,4-d]pyrimidin-1-yl)methyl)-8-methyl-2-o-tolylisoquinolin-1(2H)-one (Compound 1610) (method A)
Scheme 16.: Synthesis of 3-((4-amino-3-(3-hydroxyphenyl)-1H-pyrazolo[3,4-d]pyrimidin-1-yl)methyl)-8-methyl-2-o-tolylsoquinolin-1(2H)-one (Compound 1610) via method A is described.
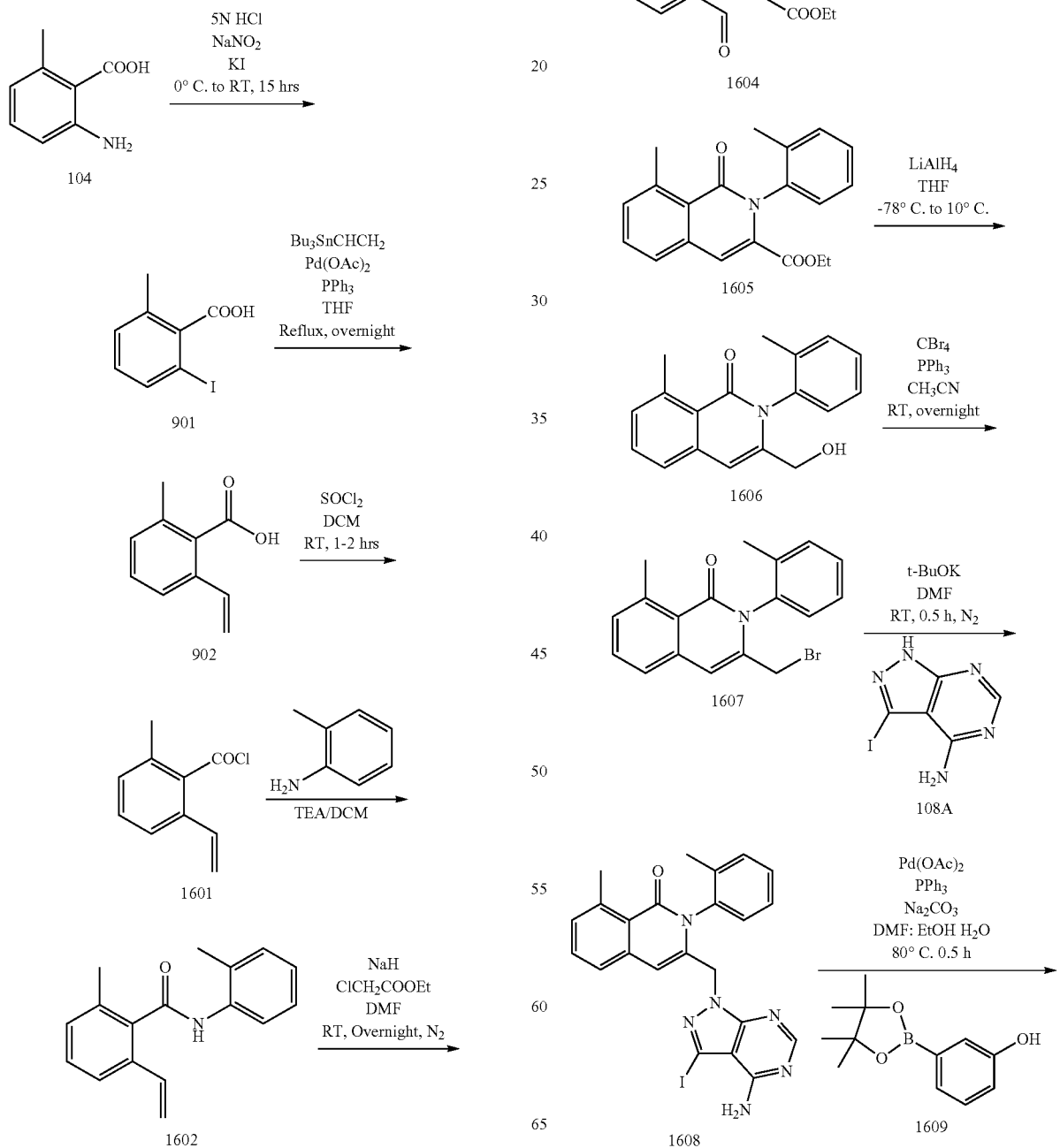

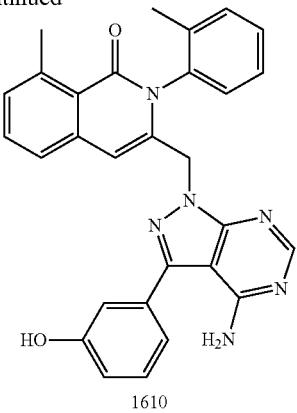

1610

A solution of 2-amino-6-methylbenzoic acid (104) (106.5 g, 705 mmol) in $H_2O$ (200 mL) was cooled to 0-5° C., con. HCl (250 mL) was added slowly. The solution was stirred for 15 min at 0-5° C. A solution of sodium nitrite (58.4 g, 6.85 mol) in $H_2O$ (120 mL) was added dropwise at 0-5° C., and the resulting mixture was stirred for 30 min. Then above solution was added to a solution of KI (351 g, 2.11 mol) in $H_2O$ (200 mL), and the resulting mixture was stirred at RT for 16 h. The solution was poured into ice water (2000 mL) and extracted with ethyl acetate (3×1000 mL). The combined organic layer was washed with aqueous NaOH (15%, 3×200 mL). The aqueous layer was acidified to PH=1, and extracted with ethyl acetate (3×1000 mL). The combined organic layer was dried over $Na_2SO_4$ and filtered. The filtrate was concentrated in vacuo to afford the desired product, 2-iodo-6-methylbenzoic acid (901) (145 g, 79% yield) as a yellow solid To a stirred mixture of 2-iodo-6-methylbenzoic acid (901) (105 g, 400 mmol), $Pd(OAc)_2$ (27 g, 120 mmol) and $PPh_3$ (63 g 240 mol) in THF (1000 mL) at RT, tributyl(vinyl)tin (152 g, 480 mmol) was added. The resulting mixture was heated to reflux overnight. The mixture was allowed to cool to RT, filtered through silica gel (10 g), and then concentrated in vacuo. The residue was poured into ice water (1000 mL) and extracted with ethyl acetate (3×1000 mL). The combined organic layer was washed with aqueous NaOH (15%, 5×200 mL). The combined aqueous layer was acidified to PH=1, extracted with ethyl acetate (3×1000 mL). The combined organic layer was dried over $Na_2SO_4$ and filtered. The filtrate was concentrated in vacuo to afford the desired product, 2-methyl-6-vinylbenzoic acid (902) (61 g, 95% yield) as a yellow solid.

A mixture of 2-methyl-6-vinylbenzoic acid (902) (56 g, 350 mmol) and thionyl chloride (208 g, 1750 mmol) in toluene (400 mL) was stirred at reflux for 2 h. The mixture was concentrated in vacuo to afford the desired product, 2-methyl-6-vinylbenzoyl chloride (1601) (63 g, 95% yield) as a yellow oil. The product obtained was used directly in the next step without purification.

A mixture of o-toluidine (45 g, 420 mmol) and Triethylamine (71 g, 70 mmol) in $CH_2Cl_2$ (300 mL) was stirred for 10 min at RT. To this mixture, 2-methyl-6-vinylbenzoyl chloride (1601) (63 g, 35 mmol) was added, and the resulting mixture was stirred at RT for 30 min. The solution was poured into water (300 mL) and extracted with $CH_2Cl_2$ (3×200 mL), dried over $Na_2SO_4$ and filtered. The filtrate was concentrated in vacuo to afford the crude product. The crude product was suspended in IPE (isopropyl ether) (300 mL), stirred at reflux for 30 min, and then cooled to 0-5° C. The precipitate was collected by filtration and further dried in vacuo to afford the desired product, 2-methyl-N-o-tolyl-6-vinylbenzamide (1602) (81 g, 80% yield) as a yellow solid.

To a solution of 2-methyl-N-o-tolyl-6-vinylbenzamide (1602) (80 g, 320 mmol) in DMF (250 mL) at RT, NaH (60% in mineral oil, 25.6 g, 640 mmol) was slowly added and the resulting mixture was stirred at RT for 30 min. To this mixture, ethyl chloroacetate (78 g, 640 mmol) was added and the resulting mixture was stirred at RT for 2 h. The solution was poured into water (500 mL) and extracted with ethyl acetate (3×200 mL), dried over $Na_2SO_4$ and filtered. The filtrate was concentrated in vacuo. The crude product was suspended in MeOH (160 mL), stirred at reflux for 10 min, and then cooled to 0-5° C. The precipitate was collected by filtration and further dried in vacuo to afford the desired product, ethyl 2-(2-methyl-N-o-tolyl-6-vinylbenzamido)acetate (1603) (67 g, 62% yield) as a white solid.

To a stirred mixture of ethyl 2-(2-methyl-N-o-tolyl-6-vinylbenzamido)acetate (1603) (67 g, 200 mmol) in 1, 4-dioxane (300 mL) and $H_2O$ (100 mL) at RT, Osmium tetroxide (20 mg) was added was and stirred at RT for 30 min. To this mixture, sodium periodate (86 g, 400 mmol) was added and the resulting mixture was stirred at RT for 16 h. The reaction mixture was filtered through silica gel (10 g), the filtrate was extracted with ethyl acetate (3×200 mL). The combined organic layers were washed with brine (100 mL), dried over $Na_2SO_4$ and filtered. The filtrate was concentrated in vacuo and the residue was further dried in vacuo to afford the desired product, ethyl 2-(2-formyl-6-methyl-N-o-tolylbenzamido) acetate (1604) (38 g, 57% yield) as a yellow solid.

To a stirred solution of ethyl 2-(2-formyl-6-methyl-N-o-tolylbenzamido)acetate (1604) (38 g, 112 mmol) in EtOH (200 mL) and ethyl acetate (100 mL) at RT, cesium carbonate (22 g, 112 mmol) was added. The resulting mixture was degassed and back-filled with argon three times and then stirred at 50° C. for 5 h. The mixture was allowed to cool to RT, filtered through silica gel (10 g), and the filtrate was concentrated in vacuo. The residue was poured into $H_2O$ (200 mL), extracted with ethyl acetate (3×200 mL). The combined organic layer was washed with brine (50 mL), dried over $Na_2SO_4$ and filtered. The filtrate was concentrated in vacuo. The crude product was suspended in IPE (120 mL), heated to reflux for 10 min, and then cooled to 0-5° C. The precipitate was collected by filtration and further dried in vacuo to afford the desired product, ethyl 8-methyl-1-oxo-2-o-tolyl-1,2-dihydroisoquinoline-3-carboxylate (1605) (28 g, 77% yield) as a white solid.

To a stirred solution of lithium aluminum hydride (8.28 g, 218 mol) in anhydrous THF (500 mL) at −78° C. under a nitrogen atmosphere, ethyl 8-methyl-1-oxo-2-o-tolyl-1,2-dihydroisoquinoline-3-carboxylate (1605) (28 g, 87 mmol) was slowly added over a 10 min period of time. The resulting mixture was allowed to warm to −30° C., stirred for 30 min and TLC showed the completion of the reaction. Then the mixture was cooled to −78° C., and water (50 mL) was slowly added. The mixture was allowed to warm to RT, filtered through silica gel (10 g), and the filtrate was concentrated in vacuo. The crude product was poured into $H_2O$ (200 mL) and extracted with ethyl acetate (3×200 mL). The combined organic layer was washed with brine (50 mL), dried over $Na_2SO_4$ and filtered. The filtrate was concentrated in vacuo. The crude product was suspended in ethyl acetate (30 mL) and stirred for 10 min. The solid was collected by filtration and further dried in vacuo to afford the desired product, 3-(hydroxymethyl)-8-methyl-2-o-tolylisoquinolin-1(2H)-one (1606) (22 g, 92% yield) as a white solid.

PBr₃ (25.6 g, 95 mmol) was slowly added to a stirred solution of DMF (11.5 g, 158 mol) in acetonitrile (200 mL) at 0° C., and the resulting mixture was stirred at 0° C. for 30 min. 3-(Hydroxymethyl)-8-methyl-2-o-tolylisoquinolin-1-(2H)-one (1606) (22 g, 78.8 mmol) was slowly added. Then the reaction mixture was allowed to warm to RT and stirred for 30 min. Saturated aqueous NaHCO₃ solution (50 mL) was slowly added and extracted with ethyl acetate (3×200 mL). The combined organic layer was washed with brine, dried over Na₂SO₄ and filtered. The filtrate was concentrated in vacuo. The crude product was suspended in IPE (50 mL) and then stirred for 10 min. The precipitate was collected by filtration and further dried in vacuo to afford the desired product, 3-(bromomethyl)-8-methyl-2-o-tolylisoquinolin-1 (2H)-one (1607) (21 g, 80% yield) as a white solid.

3-Iodo-1H-pyrazolo[3,4-d]pyrimidin-4-amine (108A) (10.8 g, 41.4 mmol) and potassium tert-butoxide (4.4 g, 40 mmol) were dissolved in anhydrous DMF (150 mL) and stirred at RT for 30 min. 3-(Bromomethyl)-8-methyl-2-o-tolylisoquinolin-1(2H)-one (1607) (13.7 g, 40 mmol) was added. The resulting mixture was stirred at RT for 30 min, poured into ice water (300 mL) and then extracted with ethyl acetate (3×200 mL). The combined organic layer was washed with brine (50 mL), dried over Na₂SO₄ and filtered. The filtrate was concentrated to about 100 ml in vacuo, the precipitate was collected by filtration to afford the first batch of desired product, 3-((4-amino-3-iodo-1H-pyrazolo[3,4-d]pyrimidin-1-yl)methyl)-8-methyl-2-o-tolylisoquinolin-1(2H)-one (1608) (12 g, 60% yield) as a white solid. The filtrate was concentrated in vacuo and the residue was purified by flash column chromatography on silica gel (2-20% MeOH/DCM) to afford the second batch of desired product, 3-((4-amino-3-iodo-1H-pyrazolo[3,4-d]pyrimidin-1-yl)methyl)-8-methyl-2-o-tolylisoquinolin-1(2H)-one (1608) (6 g, 30% yield) as a white solid.

3-((4-amino-3-iodo-1H-pyrazolo[3,4-d]pyrimidin-1-yl)methyl)-8-methyl-2-o-tolylisoquinolin-1(2H)-one (1608) (13 g, 24.9 mmol) and 3-(4,4,5,5-tetramethyl-1,3,2-dioxaborolan-2-yl)phenol (1609) (6.6 g, 30 mmol) were dissolved in DMF-EtOH—H₂O (120 mL, 40 mL, 40 mL). Pd(OAc)₂ (1.684 g, 7.5 mmol), PPh₃ (3.935 g 15 mmol) and Na₂CO₃ (13.25 g 125 mmol) were added sequentially. The resulting mixture was degassed and back-filled with argon three times and then stirred at 100° C. for 1 h. The mixture was allowed to cool to RT, filtered through silica gel (10 g) and concentrated in vacuo. The residue was purified by flash column chromatography on silica gel (2-20% MeOH/DCM) to afford the product (1610) (9 g, 76% yield) as a slight yellow solid. Then above product was suspended in EtOH (100 mL) and heated to reflux for 30 min. The mixture was allowed to cool to RT, and the solid was collected by filtration. The solid was then suspended in EA (100 mL) and stirred overnight. The precipitate was collected by filtration and further dried in vacuo to afford the desired product, 3-((4-amino-3-(3-hydroxyphenyl)-1H-pyrazolo[3,4-d]pyrimidin-1-yl)methyl)-8-methyl-2-o-tolylisoquinolin-1(2H)-one (1610) (8.4 g, 69% yield) as a white solid.

Example 4

Synthesis of 3-((4-amino-3-(3-hydroxyphenyl)-1H-pyrazolo[3,4-d]pyrimidin-1-yl)methyl)-8-methyl-2-o-tolylisoquinolin-1(2H)-one (Compound 1610) (method B)

Scheme 17. Synthesis of 3-((4-amino-3-(3-hydroxyphenyl)-1H-pyrazolo[3,4-d]pyrimidin-1-yl)methyl)-8-methyl-2-o-tolylisoquinolin-1(2H)-one (Compound 1610) via method B is described.

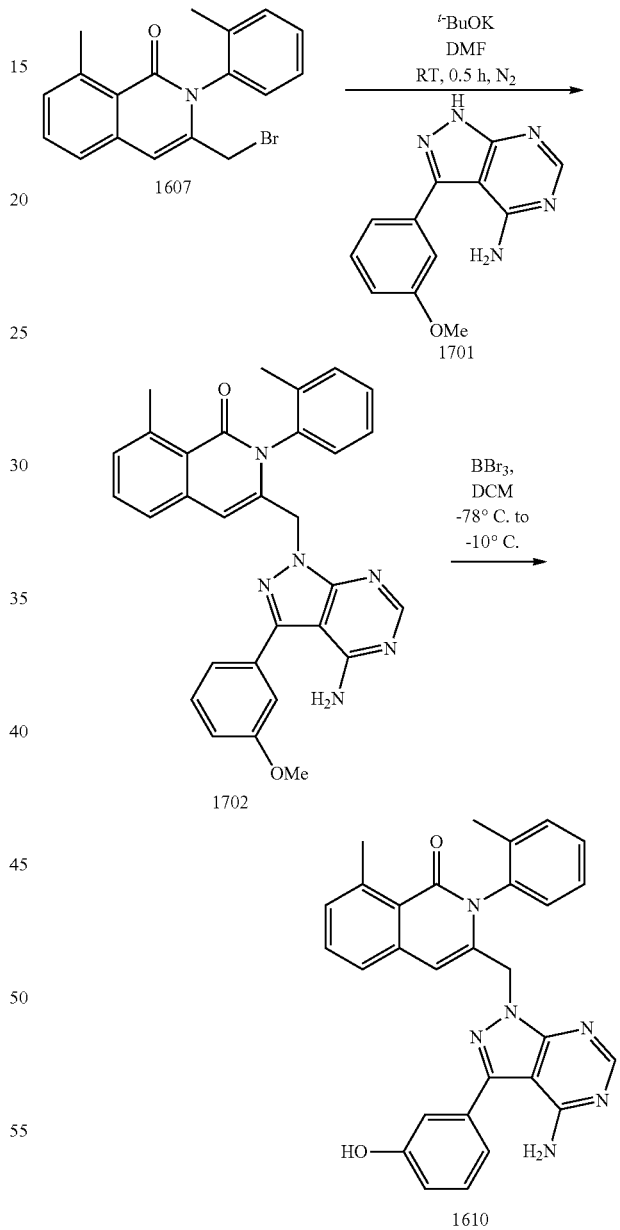

3-(3-Methoxyphenyl)-1H-pyrazolo[3,4-d]pyrimidin-4-amine (1701) (964 mg, 4 mmol) and potassium tert-butoxide (0.44 g, 4 mmol) were dissolved in anhydrous DMF (150 mL) and stirred at RT for 30 min. 3-(Bromomethyl)-8-methyl-2-o-tolylisoquinolin-1(2H)-one (1607) (1.37 g, 4.0 mmol) was added. The resulting mixture was stirred at RT for 30 min, poured into ice water (30 mL) and then extracted with ethyl acetate (3×50 mL). The combined organic layer was washed with brine (25 mL), dried over $Na_2SO_4$ and filtered. The filtrate was concentrated in vacuo and the residue was purified by flash column chromatography on silica gel (2-20% MeOH/DCM) to afford the desired product, 3-((4-amino-3-(3-methoxyphenyl)-1H-pyrazolo[3,4-d]pyrimidin-1-yl)methyl)-8-methyl-2-o-tolylisoquinolin-1(2H)-one (1702) (1.4 g, 70% yield) as a white solid.

To a solution of 3-((4-amino-3-(3-methoxyphenyl)-1H-pyrazolo[3,4-d]pyrimidin-1-yl)methyl)-8-methyl-2-o-tolyl-isoquinolin-1(2H)-one (1702) (100 mg, 0.2 mmol) in $CH_2Cl_2$ (20 mL) at −78° C. under a nitrogen atmosphere, $BBr_3$ (1 mL) was added and the resulting mixture was stirred at −78° C. for 3 h. The mixture was allowed to warm to RT, poured into ice-water (200 mL) and extracted with ethyl acetate (3×50 mL). The combined organic layer was washed with brine (20 mL), dried over $Na_2SO_4$ and filtered. The filtrate was concentrated in vacuo and the residue was purified by flash column chromatography on silica gel (10-50% MeOH/$CH_2Cl_2$) to afford the desired product, 3-((4-amino-3-(3-hydroxyphenyl)-1H-pyrazolo[3,4-d]pyrimidin-1-yl)methyl)-8-methyl-2-o-tolylisoquinolin-1(2H)-one (1610) (87 mg, 91% yield) as a white solid.

Example 5

Synthesis of (R)-3-((4-amino-3-(3-hydroxybut-1-ynyl)-1H-pyrazolo[3,4-d]pyrimidin-1-yl)methyl)-8-methyl-2-o-tolylisoquinolin-1(2H)-one (Compound 1802)

Scheme 18. Synthesis of (R)-3-((4-amino-3-(3-hydroxybut-1-ynyl)-1H-pyrazolo[3,4-d]pyrimidin-1-yl)methyl)-8-methyl-2-o-tolylisoquinolin-1(2H)-one (Compound 1802) is described.

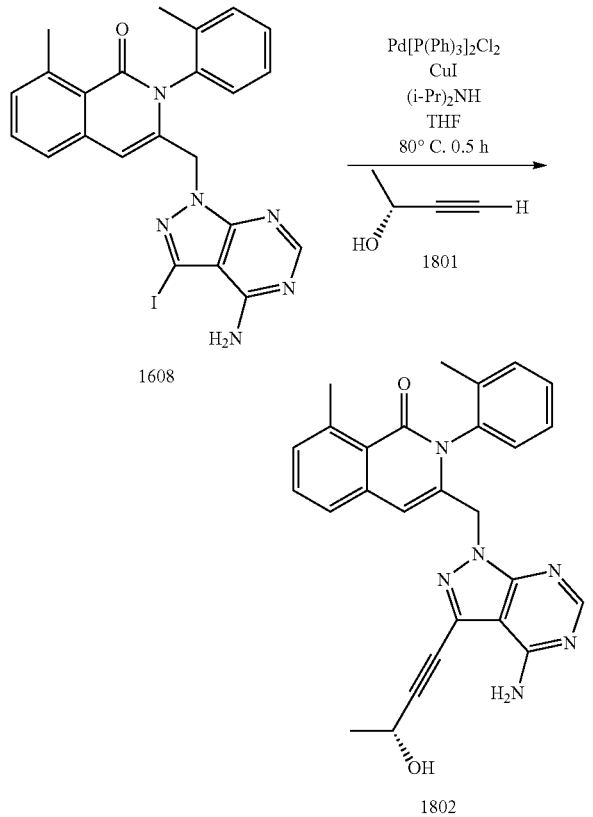

3-((4-amino-3-iodo-1H-pyrazolo[3,4-d]pyrimidin-1-yl)methyl)-8-methyl-2-o-tolylisoquinolin-1(2H)-one (1608) (522 mg, 1 mmol) and (R)-but-3-yn-2-ol (84 mg, 1.2 mmol) were dissolved in anhydrous THF (40 mL). The mixture was degassed and back-filled with nitrogen three times. $Pd(PPh_3)_2Cl_2$ (12 mg, 0.1 mmol), CuI (47 mg 0.25 mmol) and $(i-Pr)_2NH$ (505 mg, 5 mmol) were added sequentially. The resulting mixture was degassed and back-filled with argon three times and then stirred at reflux for 4 h. The mixture was allowed to cool to RT, filtered through silica gel (10 g) and concentrated in vacuo. The residue was purified by flash column chromatography on silica gel (2-20% MeOH/DCM) to afford the product, 3 (R)-3-((4-amino-3-(3-hydroxybut-1-ynyl)-1H-pyrazolo[3,4-d]pyrimidin-1-yl)methyl)-8-methyl-2-o-tolyl-isoquinolin-1(2H)-one (1802) (324 mg, 70% yield) as a slightly yellow solid.

Example 6

Synthesis of 3-((6-amino-9H-purin-9-yl)methyl)-8-methyl-2-o-tolylisoquinolin-1(2H)-one (Compound 1902)

Scheme 19. Synthesis of 3-((6-amino-9H-purin-9-yl)methyl)-8-methyl-2-o-tolylsoquinolin-1(2H)-one (Compound 1902) is described.

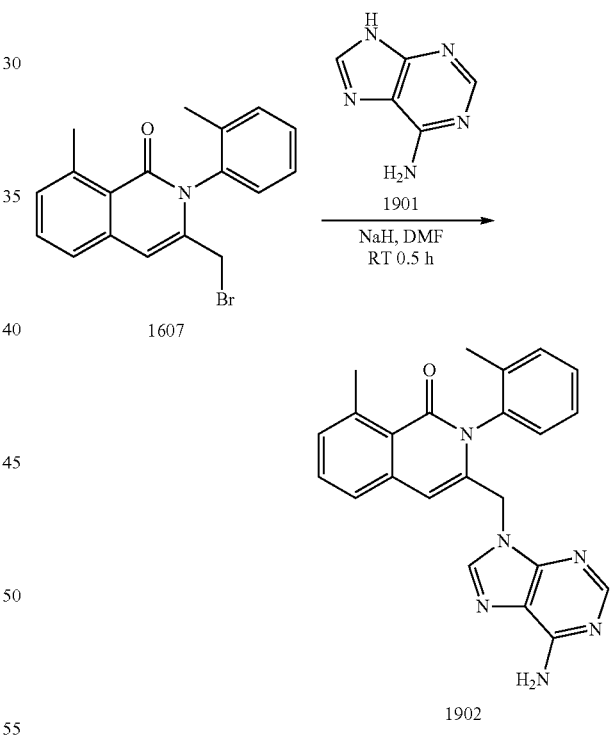

9H-Purin-6-amine (1901) (540 mg, 4.0 mmol) was dissolved in anhydrous DMF (20 mL). NaH (60% in mineral oil, 160 mg, 4.0 mmol) was added and the resulting mixture was stirred at RT for 30 min. 3-(Bromomethyl)-8-methyl-2-o-tolylisoquinolin-1(2H)-one (1607) (1.37 g, 4.0 mmol) was added. The reaction mixture was stirred at RT for 30 min, poured into ice-water (30 mL) and then extracted with ethyl acetate (3×50 mL). The combined organic layer was washed with brine (25 mL), dried over $Na_2SO_4$ and filtered. The filtrate was concentrated in vacuo and the residue was purified by flash column chromatography on silica gel (2-20%

MeOH/DCM) to afford the desired product, 3-((6-amino-9H-purin-9-yl)methyl)-8-methyl-2-o-tolylisoquinolin-1(2H)-one (1902) (1.1 g, 70% yield) as a white solid.

Example 7

Synthesis of 3-((4-amino-3-(3-hydroxyphenyl)-1H-pyrazolo[3,4-d]pyrimidin-1-yl)methyl)-2-isopropyl-8-methylisoquinolin-1(2H)-one (Compound 2009)

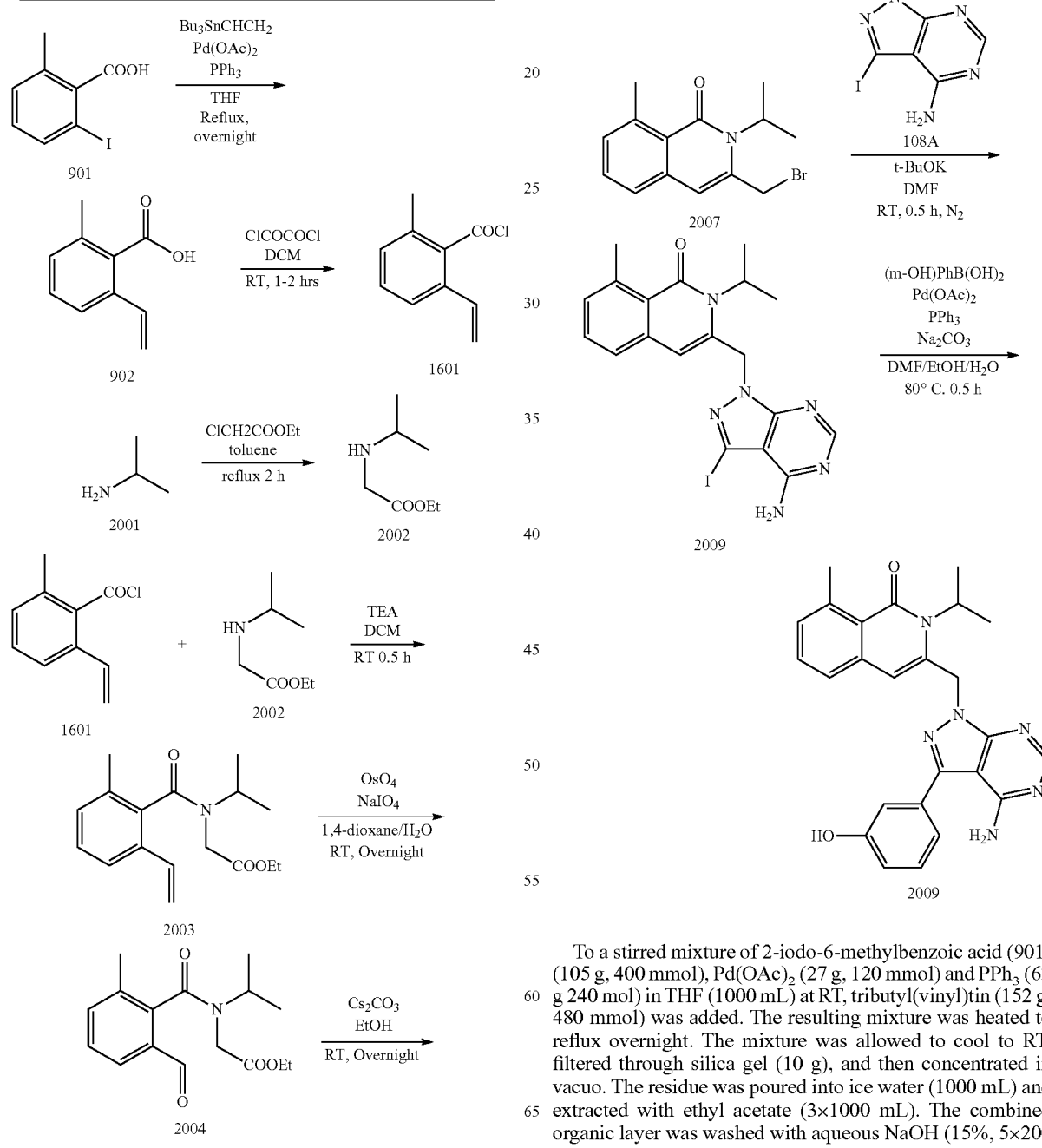

Scheme 20. Synthesis of 3-((4-amino-3-(3-hydroxyphenyl)-1H-pyrazolo[3,4-d]pyrimidin-1-yl)methyl)-2-isopropyl-8-methylisoquinolin-1(2H)-one (Compound 2009) is described.

To a stirred mixture of 2-iodo-6-methylbenzoic acid (901) (105 g, 400 mmol), Pd(OAc)$_2$ (27 g, 120 mmol) and PPh$_3$ (63 g 240 mol) in THF (1000 mL) at RT, tributyl(vinyl)tin (152 g, 480 mmol) was added. The resulting mixture was heated to reflux overnight. The mixture was allowed to cool to RT, filtered through silica gel (10 g), and then concentrated in vacuo. The residue was poured into ice water (1000 mL) and extracted with ethyl acetate (3×1000 mL). The combined organic layer was washed with aqueous NaOH (15%, 5×200 mL). The combined aqueous layer was acidified to PH=1, extracted with ethyl acetate (3×1000 mL). The combined organic layer was dried over Na$_2$SO$_4$ and filtered. The filtrate was concentrated in vacuo to afford the desired product, 2-methyl-6-vinylbenzoic acid (902) (61 g, 95% yield) as a yellow solid.

A mixture of 2-methyl-6-vinylbenzoic acid (902) (56 g, 350 mmol) and thionyl chloride (208 g, 1750 mmol) in toluene (400 mL) was stirred at reflux for 2 h. The mixture was concentrated in vacuo to afford the desired product, 2-methyl-6-vinylbenzoyl chloride (1601) (63 g, 95% yield) as a yellow oil. The product obtained was used directly in the next step without purification.

Propan-2-amine (2001) (59 g, 1.0 mol) and ethyl chloroacetate (122 g, 1.0 mol) were dissolved in toluene (200 mL) and the mixture was stirred at reflux for 2 h. The reaction mixture was allowed to cool to RT, poured into ice-water (500 mL) and extracted with ethyl acetate (3×250 mL). The combined organic layer was washed with brine (50 mL), dried over Na$_2$SO$_4$ and filtered. The filtrate was concentrated in vacuo and the residue was purified by flash column chromatography on silica gel (10-50% EA/PE) to afford the product, ethyl 2-(isopropylamino)acetate (2002) (70 g, 51% yield) as an oil.

Ethyl 2-(isopropylamino)acetate (2002) (14.5 g, 100 mmol) and triethylamine (200 g, 200 mmol) were dissolved in CH$_2$Cl$_2$ (300 mL) and the mixture was stirred for 10 min at RT. 2-Methyl-6-vinylbenzoyl chloride (1601) (18 g, 100 mmol) was added, and the resulting mixture was stirred at RT for 30 min. The reaction mixture was poured into water (300 mL) and extracted with CH$_2$Cl$_2$ (3×200 mL). The combined organic layer was washed with brine (50 mL), dried over Na$_2$SO$_4$ and filtered. The filtrate was concentrated in vacuo to afford the crude product. The crude product was suspended in IPE (isopropyl ether) (300 mL), stirred at reflux for 30 min, and then cooled to 0-5° C. The precipitate was collected by filtration and further dried in vacuo to afford the desired product, ethyl 2-(N-isopropyl-2-methyl-6-vinylbenzamido)acetate (2003) (14.5 g, 50% yield) as a yellow solid.

To a stirred solution of ethyl 2-(N-isopropyl-2-methyl-6-vinylbenzamido)acetate (2003) (14.0 g, 48.0 mmol) in 1,4-dioxane (100 mL) and H$_2$O (30 mL), Osmium tetroxide (20 mg) was added and the resulting mixture was stirred at RT for 30 min. To this mixture, sodium periodate (22 g, 100 mmol) was added and then stirred at RT for 16 h. The reaction mixture was filtered through silica gel (10 g), the filtrate was extracted with ethyl acetate (3×200 mL). The combined organic layer was washed with brine (50 mL), dried over Na$_2$SO$_4$ and filtered. The filtrate was concentrated in vacuo and the residue was further dried in vacuo to afford the desired product, ethyl 2-(2-formyl-N-isopropyl-6-methylbenzamido)acetate (2004) (8.33 g, 57% yield) as a yellow solid.

To a stirred solution of ethyl 2-(2-formyl-N-isopropyl-6-methylbenzamido)acetate (2004) (8.3 g, 28.0 mmol) in EtOH (100 mL) and ethyl acetate (50 mL) at RT, cesium carbonate (5.9 g, 30 mmol) was added. The resulting mixture was degassed and back-filled with argon three times and then stirred at 50° C. for 5 h. The mixture was allowed to cool to RT, filtered through silica gel (10 g), and the filtrate was concentrated in vacuo. The residue was poured into H$_2$O (200 mL), extracted with ethyl acetate (3×200 mL). The combined organic layer was washed with brine (50 mL), dried over Na$_2$SO$_4$ and filtered. The filtrate was concentrated in vacuo. The crude product was suspended in IPE (120 mL), stirred at reflux for 10 min, and then cooled to 0-5° C. The precipitate was collected by filtration and further dried in vacuo to afford the desired product, ethyl 2-isopropyl-8-methyl-1-oxo-1,2-dihydroisoquinoline-3-carboxylate (2005) (5.35 g, 70% yield) as a white solid.

To a stirred solution of lithium aluminum hydride (2.88 g, 76 mol) in anhydrous THF (200 mL) at −78° C. under a nitrogen atmosphere, ethyl 2-isopropyl-8-methyl-1-oxo-1,2-dihydroisoquinoline-3-carboxylate (2005) (5.2 g, 19 mmol) was slowly added over a 10 min period of time. The resulting mixture was allowed to warm to −30° C., stirred for 30 min and TLC showed the completion of the reaction. Then the mixture was cooled to −78° C., and water (50 mL) was slowly added. The mixture was allowed to warm to RT, filtered through silica gel (10 g), and the filtrate was concentrated in vacuo. The crude product was poured into H$_2$O (200 mL) and extracted with ethyl acetate (3×200 mL). The combined organic layer was washed with brine (50 mL), dried over Na$_2$SO$_4$ and filtered. The filtrate was concentrated in vacuo. The crude product was suspended in ethyl acetate (30 mL) and stirred for 10 min. The solid was collected by filtration and further dried in vacuo to afford the desired product, 3-(hydroxymethyl)-2-isopropyl-8-methylisoquinolin-1(2H)-one (2006) (3.51 g, 80% yield) as a white solid.

To a solution of 3-(hydroxymethyl)-2-isopropyl-8-methyl-isoquinolin-1(2H)-one (2006) (1.61 g, 7.0 mmol) in CH$_2$Cl$_2$, PPh$_3$ (3.67 g, 14.0 mmol) was added and the mixture was stirred at RT for 30 min. The mixture was cooled to 0° C., and CBr$_4$ (4.64 g, 14.0 mmol) was added in portions. The resulting mixture was stirred from 0° C. to RT for 30 min, and then concentrated in vacuo. The crude product was purified by flash column chromatography on silica gel (30-50% EA/PE) to afford the desired product, 3-(bromomethyl)-2-isopropyl-8-methylisoquinolin-1(2H)-one (2007) (1.65 g, 80% yield) as a white solid.

A mixture of 3-iodo-1H-pyrazolo[3,4-d]pyrimidin-4-amine (108A) (1.3 g, 5 mmol) and potassium tert-butoxide (0.55 g, 5 mmol) in anhydrous DMF (20 mL) was stirred at RT for 30 min and then 3-(bromomethyl)-2-isopropyl-8-methyl-isoquinolin-1(2H)-one (2007) (1.47 g, 5 mmol) was added. The resulting mixture was stirred at RT for 30 min, poured into ice-water (30 mL) and then extracted with ethyl acetate (3×50 mL). The combined organic layer was washed with brine (25 mL), dried over Na$_2$SO$_4$ and filtered. The filtrate was concentrated in vacuo, and the residue was purified by flash column chromatography on silica gel (2-20% MeOH/DCM) to afford the desired product, 3-((4-amino-3-iodo-1H-pyrazolo[3,4-d]pyrimidin-1-yl)methyl)-2-isopropyl-8-methylisoquinolin-1(2H)-one (2008) (1.66 g, 70% yield) as a white solid.

To a stirred mixture of 3-((4-Amino-3-iodo-1H-pyrazolo[3,4-d]pyrimidin-1-yl)methyl)-2-isopropyl-8-methylisoquinolin-1(2H)-one (2008) (95 mg, 0.2 mmol) and 3-(4,4,5,5-tetramethyl-1,3,2-dioxaborolan-2-yl)phenol (66 mg, 0.3 mmol) in DMF-EtOH—H$_2$O (3:1:1, 20 mL), Pd(OAc)$_2$ (16 mg, 0.075 mmol), PPh$_3$ (39.3 mg 0.15 mmol) and Na$_2$CO$_3$ (132 mg, 1.25 mmol) were added sequentially. The resulting mixture was degassed and back-filled with argon three times and then stirred at 100° C. for 1 h. The mixture was allowed to cool to RT, filtered through silica gel (10 g) and concentrated in vacuo. The residue was purified by flash column chromatography on silica gel (2-20% MeOH/DCM) to afford the product, 3-((4-amino-3-(3-hydroxyphenyl)-1H-pyrazolo[3,4-d]pyrimidin-1-yl)methyl)-2-isopropyl-8-methylisoquinolin-1(2H)-one (2009) (53 mg, 61% yield) as a slightly yellow solid.

Example 8
Synthesis of 7-((4-amino-3-(3-hydroxyphenyl)-1H-pyrazolo[3,4-d]pyrimidin-1-yl)methyl)-4-methyl-6-o-tolyl-1,6-naphthyridin-5(6H)-one (Compound 2115)
Scheme 21. Synthesis of 7-((4-amino-3-(3-hydroxyphenyl)-1H-pyrazolo[3,4-d]pyrimidin-1-yl)methyl)-4-methyl-6-o-tolyl-1,6-naphthyridin-5-(6H)-one (Compound 2115) is described.
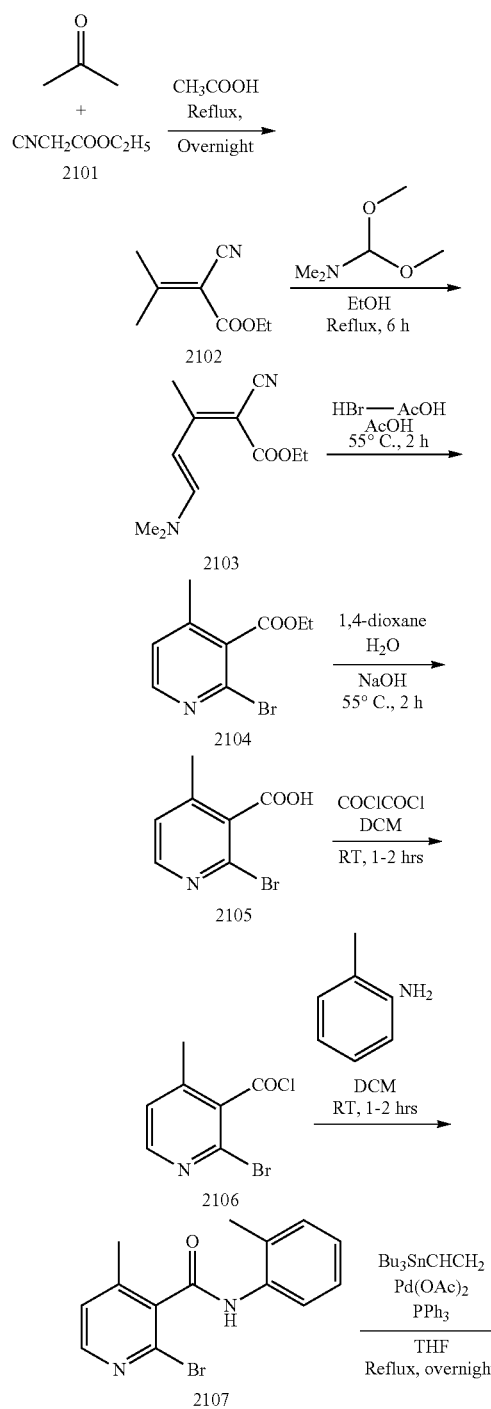
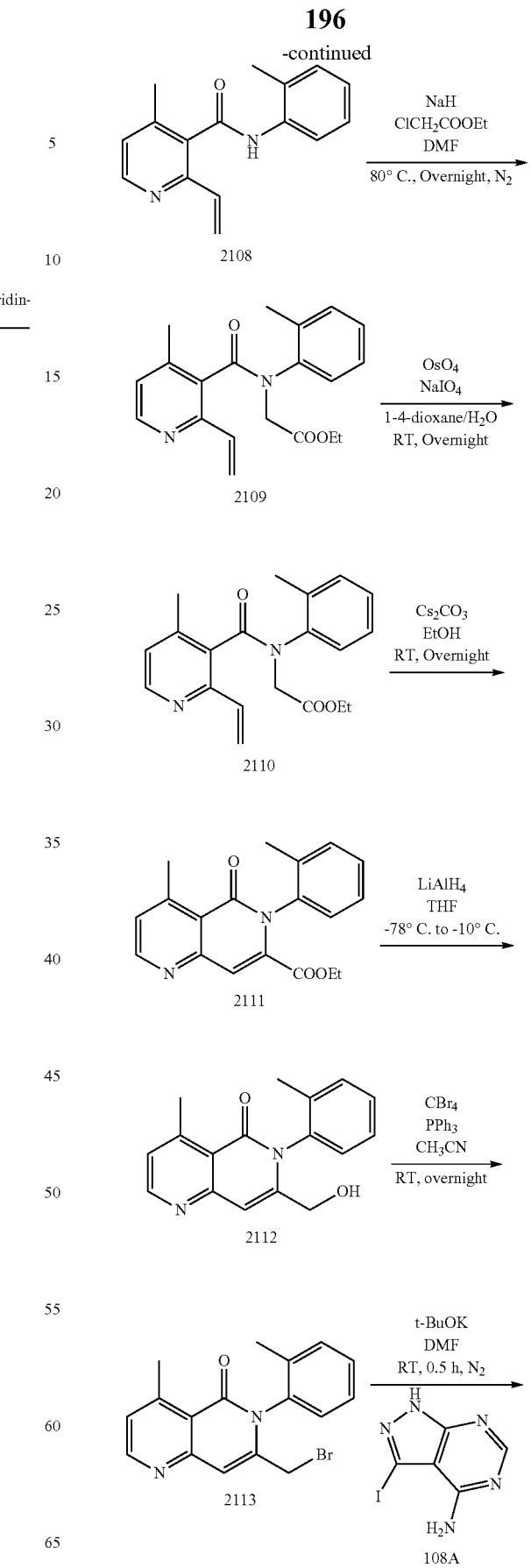

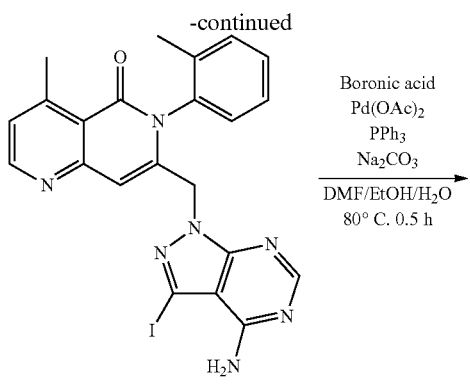

2114

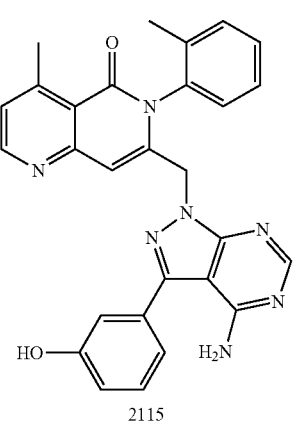 [SMILES: Cc1ccccc1-n1c(Cn2nc(-c3cccc(O)c3)c3c(N)ncnc32)cc2nccc(C)c2c1=O]

2115

To a mixture of ethyl 2-cyanoacetate (2101) (45.2 g, 400 mmol) and acetone (46.4 g, 800 mmol) in glacial acetic acid (50 mL), piperidine (2 mL, 20 mmol) was added and the resulting mixture stirred at reflux for 24 h. The reaction mixture was allowed to cool to RT, and then concentrated in vacuo. The residue was diluted with water (200 mL) and extracted with ethyl acetate (3×200 mL). The combined organic layer was washed with brine (50 mL), dried over $Na_2SO_4$ and filtered. The filtrate was concentrated in vacuo and the residue was purified by flash column chromatography on silica gel (0-2% EA/PE) to afford the desired product, ethyl 2-cyano-3-methylbut-2-enoate (2102) (49.6 g, 81% yield) as a white solid.

To a solution of ethyl 2-cyano-3-methylbut-2-enoate (2102) (43.6 g, 285 mol) in absolute EtOH (300 mL), N,N-dimethylformamide dimethyl acetal (37.3 g, 313 mmol) was added dropwise and the resulting mixture was stirred at reflux 6 h. The mixture was allowed to cool to RT, concentrated in vacuo to afford the crude desired product, ethyl 2-cyano-5-(dimethylamino)-3-methylpenta-2,4-dienoate (2103) (39.8 g, 67% yield) as a yellow solid.

Ethyl 2-cyano-5-(dimethylamino)-3-methylpenta-2,4-dienoate (2103) (30.8 g, 148 mmol) was dissolved in AcOH (120 mL) and the mixture was stirred at 40° C. A solution of 45% HBr-AcOH (120 mL) was added dropwise, and then the mixture was stirred at 55° C. for 2 h. The mixture was allowed to cool to RT, poured onto ice, neutralized with solid $Na_2CO_3$, and extracted with ethyl acetate (3×150 mL). The combined organic layer was washed with brine (50 mL), dried over $Na_2SO_4$ and filtered. The filtrate was concentrated in vacuo and the residue was purified by flash column chromatography on silica gel (5-20% EA/PE) to afford the desired product, ethyl 2-bromo-4-methylnicotinate (2104) (17.6 g, 49% yield) as a yellow oil.

To a solution of ethyl 2-bromo-4-methylnicotinate (2104) (12.8 g, 52 mmol) in 1,4-dioxane (15 mL), a solution of NaOH (8.0 g, 200 mmol) in $H_2O$ (15 mL) was added and the resulting mixture was stirred at reflux for 12 h. The mixture was allowed to cool to RT, diluted with $H_2O$, washed with ethyl acetate (3×30 mL). The aqueous layer was acidified with concentrated hydrochloric acid to pH=1, and extracted with ethyl acetate (3×50 mL). The combined organic layer was washed with brine (25 mL), dried over $Na_2SO_4$ and filtered. The filtrate was concentrated in vacuo to afford the desired product, 2-bromo-4-methylnicotinic acid (2105) (9.7 g, 85% yield) as a white solid.

To a solution of 2-bromo-4-methylnicotinic acid (2105) (13 g, 60 mmol) and DMF (3 drops) in $CH_2Cl_2$ (150 mL), oxalyl chloride (11.4 g, 90 mmol) was added dropwise and the resulting mixture was stirred at RT for 2 h. The reaction mixture was concentrated in vacuo to afford the desired product, 2-bromo-4-methylnicotinoyl chloride (2106) (13.4 g, 95% yield) as a yellow oil. The product obtained was used directly in the next step without further purification.

o-Toluidine (7.7 g, 72 mmol) and triethylamine (9.1 g, 90 mmol) were dissolved in $CH_2Cl_2$ (100 mL) and stirred for 10 min at RT. 2-Bromo-4-methylnicotinoyl chloride (2106) (13.4 g, 57 mmol) was added, and the resulting mixture was stirred at RT for 1 h. The mixture was poured into water (200 mL) and extracted with $CH_2Cl_2$ (3×50 mL). The combined organic layer was washed with brine (20 mL), dried over $Na_2SO_4$ and filtered. The filtrate was concentrated in vacuo to afford the crude product. The crude product was suspended in IPE (isopropyl ether) (50 mL). The mixture was stirred at reflux for 30 min and then was cooled to 0-5° C. The precipitate was collected by filtration and further dried in vacuo to afford the desired product, 2-bromo-4-methyl-N-o-tolylnicotinamide (2107) (13 g, 75% yield) as a yellow solid.

To a solution of 2-bromo-4-methyl-N-o-tolylnicotinamide (2107) (13 g, 43 mmol) and tributyl(vinyl)tin (16.4 g, 52 mmol) in THF (200 mL) under a nitrogen atmosphere, $Pd(OAc)_2$ (2.9 g, 13 mmol) and $PPh_3$ (6.8 g, 26 mol) were added. The resulting mixture was stirred at reflux for 16 h. The mixture was then allowed to cool to RT, filtered through silica gel (10 g), and concentrated in vacuo. The residue was poured into water (200 mL), extracted with ethyl acetate (3×50 mL). The combined organic layer was washed with brine (30 mL), dried over $Na_2SO_4$ and filtered. The filtrate was concentrated in vacuo and the residue was purified by flash column chromatography on silica gel (20-50% EA/PE) to afford the desired product, 4-methyl-N-o-tolyl-2-vinylnicotinamide (2108) (8.7 g, 80% yield) as a yellow solid.

To a stirred solution of 4-methyl-N-o-tolyl-2-vinylnicotinamide (2108 (8.1 g, 32 mmol) in DMF (50 mL) at RT, NaH (60% in mineral oil, 2.6 g, 65 mmol) was added slowly and the resulting mixture was stirred at RT for 30 min. Ethyl chloroacetate (78 g, 640 mmol) was added dropwise to this mixture at RT, and stirred for 2 h. The solution was poured into water (300 mL) and extracted with ethyl acetate (3×80 mL). The combined organic layer was washed with brine (25 mL), dried over $Na_2SO_4$ and filtered. The filtrate was concentrated in vacuo. The crude product was suspended in MeOH (60 mL) and stirred at reflux for 10 min. The mixture was then cooled to 0-5° C. The precipitate was collected by filtration and further dried in vacuo to afford the desired product, ethyl 2-(4-methyl-N-o-tolyl-2-vinylnicotinamido) acetate (2109) (6.3 g, 58% yield) as a white solid.

To a solution of ethyl 2-(4-methyl-N-o-tolyl-2-vinylnicotinamido) acetate (2109) (6.1 g, 18 mmol) in 1,4-dioxane (90 mL) and $H_2O$ (30 mL) at RT, Osmium tetroxide (5 mg) was added and the resulting mixture was stirred for 30 min.

Sodium periodate (7.7 g, 36 mmol) was added and the mixture was stirred at RT for 16 h. The mixture was filtered through silica gel (5 g), and the filtrate was extracted with ethyl acetate (3×50 mL). The combined organic layer was washed with brine (25 mL), dried over $Na_2SO_4$ and filtered. The filtrate was concentrated in vacuo and the residue was further dried under reduced pressure to afford the desired product, ethyl 2-(2-formyl-4-methyl-N-o-tolylnicotinamido)acetate (2110) (4.4 g, 72% yield) as a yellow solid.

To a stirred solution of ethyl 2-(2-formyl-4-methyl-N-o-tolylnicotinamido)acetate (2110) (4.4 g, 13 mmol) in EtOH (30 mL) and ethyl acetate (10 mL) at RT, cesium carbonate (4.3 g, 13 mmol) was added. The resulting mixture was degassed and back-filled with argon three times and then stirred at 50° C. for 5 h. The mixture was allowed to cool to RT, filtered through silica gel (5 g), and the filtrate was concentrated in vacuo. The residue was poured into $H_2O$ (200 mL), extracted with ethyl acetate (3×50 mL). The combined organic layer was dried over $Na_2SO_4$ and filtered. The filtrate was concentrated in vacuo. The crude product was suspended in IPE (30 mL), stirred at reflux for 10 min, and then cooled to 0-5° C. The precipitate was collected by filtration and further dried in vacuo to afford the desired product, ethyl 4-methyl-5-oxo-6-o-tolyl-5,6-dihydro-1,6-naphthyridine-7-carboxylate (2111) (3.0 g, 72% yield) as a white solid.

To a stirred solution of lithium aluminum hydride (0.86 g, 23 mol) in anhydrous THF (100 mL) at −78° C. under a nitrogen atmosphere, a solution of ethyl 4-methyl-5-oxo-6-o-tolyl-5,6-dihydro-1,6-naphthyridine-7-carboxylate (2111) (2.9 g, 9.0 mmol) in anhydrous THF (20 mL) was added dropwise. The resulting mixture was allowed to warm to −10° C., stirred for 30 min and TLC showed the completion of the reaction. Then the mixture was cooled to −78° C., and water (50 mL) was slowly added. The mixture was allowed to warm to RT, filtered through silica gel (5 g), and the filtrate was concentrated in vacuo. The crude product was poured into $H_2O$ (100 mL) and extracted with ethyl acetate (3×50 mL). The combined organic layer was washed with brine (25 mL), dried over $Na_2SO_4$ and filtered. The filtrate was concentrated in vacuo. The crude product was suspended in ethyl acetate (10 mL) and stirred for 10 min. The solid was collected by filtration and further dried in vacuo to afford the desired product, 7-(hydroxymethyl)-4-methyl-6-o-tolyl-1,6-naphthyridin-5(6H)-one (2112) (2.1 g, 83% yield) as a white solid.

To a solution of 7-(hydroxymethyl)-4-methyl-6-o-tolyl-1,6-naphthyridin-5(6H)-one (2112) (1.96 g, 7.0 mmol) in $CH_2Cl_2$, $PPh_3$ (3.67 g, 14.0 mmol) was added and stirred at RT for 30 min. $CBr_4$ (4.64 g, 14.0 mmol) was added to the mixture in portions at 0° C. The resulting mixture was allowed to warm to RT, stirred for 30 min, and concentrated in vacuo. The residue was purified by flash column chromatography on silica gel (30-50% EA/PE) to afford the desired product, 7-(bromomethyl)-4-methyl-6-o-tolyl-1,6-naphthyridin-5(6H)-one (2113) (1.92 g, 80% yield) as a white solid.

A mixture of 3-iodo-1H-pyrazolo[3,4-d]pyrimidin-4-amine (108A) (1.08 g, 4.14 mmol) and potassium tert-butoxide (0.44 g, 4.0 mmol) in anhydrous DMF (50 mL) was stirred at RT for 30 min and then 7-(bromomethyl)-4-methyl-6-o-tolyl-1,6-naphthyridin-5(6H)-one (2113) (1.37 g, 4.0 mmol) was added. The resulting mixture was stirred at RT for 30 min, poured into ice water (300 mL) and then extracted with ethyl acetate (3×100 mL). The combined organic layer was washed with brine (30 mL), dried over $Na_2SO_4$ and filtered. The filtrate was concentrated in vacuo and the residue was purified by flash column chromatography on silica gel (0-2% MeOH/DCM) to afford the desired product, 7-((4-amino-3-iodo-1H-pyrazolo[3,4-d]pyrimidin-1-yl)methyl)-4-methyl-6-o-tolyl-1,6-naphthyridin-5(6H)-one (2114) (1.07 g, 50% yield) as a white solid.

To a stirred mixture of 7-((4-amino-3-iodo-1H-pyrazolo[3,4-d]pyrimidin-1-yl)methyl)-4-methyl-6-o-tolyl-1,6-naphthyridin-5(6H)-one (2114) (1.05 g, 2.0 mmol) and 3-hydroxyphenylboronic acid (0.33 g, 2.4 mmol) in DMF-EtOH—$H_2O$ (3:1:1, 50 mL), $Pd(OAc)_2$ (0.14 g, 0.60 mmol), $PPh_3$ (0.31 g, 1.2 mmol) and $Na_2CO_3$ (1.06 g, 10.0 mmol) were added sequentially. The resulting mixture was degassed and back-filled with argon three times and then stirred at 80° C. for 1 h. The mixture was allowed to cool to RT, filtered through silica gel (5 g) and concentrated in vacuo. The residue was purified by flash column chromatography on silica gel (2-5% MeOH/DCM) to afford the desired product, 7-((4-amino-3-(3-hydroxyphenyl)-1H-pyrazolo[3,4-d]pyrimidin-1-yl)methyl)-4-methyl-6-o-tolyl-1,6-naphthyridin-5(6H)-one (2115) (0.68 g, 69% yield) as a slight yellow solid. Then the product was dissolved in EtOH (5 mL), and stirred at reflux for 30 min. The solution was allowed to cool to RT and the solid was collected by filtration. The solid was then suspended in ethyl acetate (5 mL), and stirred at RT for 16 h. The precipitate was collected by filtration and further dried in vacuo to afford the desired product, 7-((4-amino-3-(3-hydroxyphenyl)-1H-pyrazolo[3,4-d]pyrimidin-1-yl)methyl)-4-methyl-6-o-tolyl-1,6-naphthyridin-5(6H)-one (2115) (0.59 g, 60% yield) as a white solid.

Example 9

3-((4-amino-3-(3-fluoro-5-hydroxyphenyl)-1H-pyrazolo[3,4-d]pyrimidin-1-yl)methyl)-8-methyl-2-o-tolyl-3,4-dihydroisoquinolin-1(2H)-one (Compound 2208)

Scheme 22. 3-((4-amino-3-(3-fluoro-5-hydroxyphenyl)-1H-pyrazolo[3,4-d]pyrimidin-1-yl)methyl)-8-methyl-2-o-tolyl-3,4-dihydroisoquinolin-1(2H)-one (Compound 2208) is described.

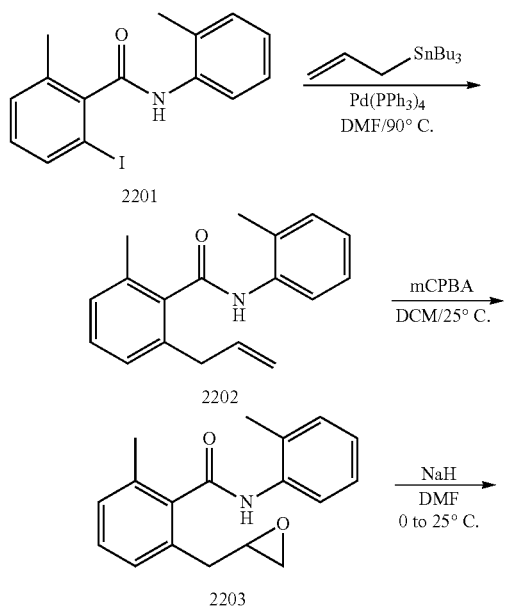

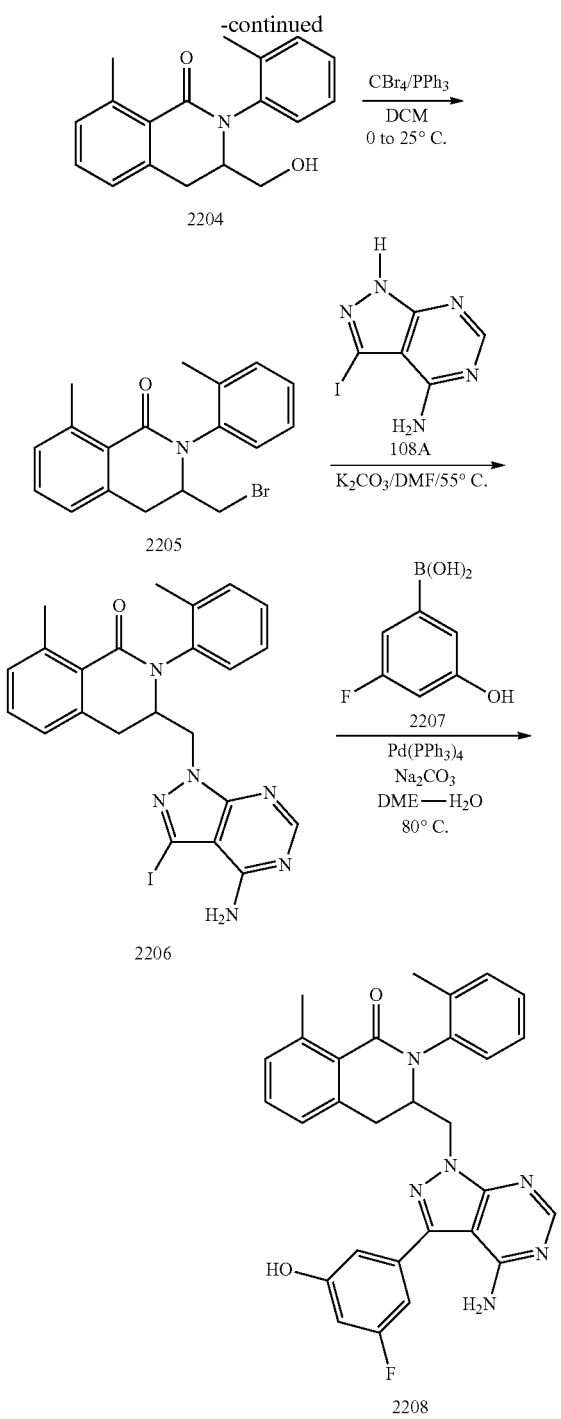

silica gel eluting with EtOAc and Hexanes to afford the desired product, 2-allyl-6-methyl-N-o-tolylbenzamide (2202) (1.1 g, 95% yield).

2-Allyl-6-methyl-N-o-tolylbenzamide (2202) (800 mg, 3.01 mmol) was dissolved in anhydrous dichloromethane (20 mL). mCPBA (70%, 1.11 g, 4.52 mmol) was added and the resulting mixture was stirred at RT for 24 h. $Na_2SO_3$ (1.0 g) was added and stirred for 1 h. The mixture was partitioned between EtOAc and water. The organic layer was washed with brine, dried over $Na_2SO_4$ and filtered. The filtrate was concentrated in vacuo, and the residue was purified by column chromatography on silica gel eluting with EtOAc and Hexanes to afford the desired product, 2-methyl-6-(oxiran-2-ylmethyl)-N-o-tolylbenzamide (2203) (660 mg, 83% yield).

2-Methyl-6-(oxiran-2-ylmethyl)-N-o-tolylbenzamide (2203) (860 mg, 3.06 mmol) was dissolved in anhydrous DMF (15 mL) and cooled to 0° C. under an argon atmosphere. NaH (60% in mineral oil, 245 mg, 6.12 mmol) was added in portions and the resulting mixture was stirred at 0° C. for 3 h. $H_2O$ (30 mL) was slowly added and the mixture was extracted with EtOAc (3×25 mL). The combined organic layers were washed with brine, dried over $Na_2SO_4$ and filtered. The filtrate was concentrated in vacuo, and the residue was purified by column chromatography on silica gel eluting with EtOAc and Hexanes to afford the desired product, 3-(hydroxymethyl)-8-methyl-2-o-tolyl-3,4-dihydroisoquinolin-1(2H)-one (2204) (435 mg, 51% yield).

3-(Hydroxymethyl)-8-methyl-2-o-tolyl-3,4-dihydroisoquinolin-1(2H)-one (2204) (430 mg, 1.53 mmol) was dissolved in anhydrous dichloromethane (25 mL) and cooled to 0° C. under an argon atmosphere. $PPh_3$ (600 mg, 2.29 mmol) and $CBr_4$ (761 mg, 2.29 mmol) were added sequentially and the resulting mixture was stirred from 0° C. to RT for 16 h. The reaction mixture was partitioned between EtOAc and water. The organic layer was washed with brine, dried over $Na_2SO_4$ and filtered. The filtrate was concentrated in vacuo, and the residue was purified by column chromatography on silica gel eluting with EtOAc and Hexanes to afford the desired product, 3-(bromomethyl)-8-methyl-2-o-tolyl-3,4-dihydroisoquinolin-1(2H)-one(2205) (480 mg, 91% yield).

3-(Bromomethyl)-8-methyl-2-o-tolyl-3,4-dihydroisoquinolin-1(2H)-one (2205) (387 mg, 1.12 mmol) and 3-iodo-1H-pyrazolo[3,4-d]pyrimidin-4-amine (108A) (440 mg, 1.69 mmol) were dissolved in anhydrous DMF (20 mL). $K_2CO_3$ (309 mg, 2.24 mmol) was added and the resulting mixture was stirred at 50° C. for 3 h. The reaction mixture was partitioned between EtOAc and water. The organic layer was washed with brine, dried over $Na_2SO_4$ and filtered. The filtrate was concentrated in vacuo, and the residue was purified by column chromatography on silica gel eluting with methanol and dichloromethane to afford the desired product, 3-((4-amino-3-iodo-1H-pyrazolo[3,4-d]pyrimidin-1-yl)methyl)-8-methyl-2-o-tolyl-3,4-dihydroisoquinolin-1(2H)-one (2206) (100 mg, 17% yield).

3-((4-Amino-3-iodo-1H-pyrazolo[3,4-d]pyrimidin-1-yl)methyl)-8-methyl-2-o-tolyl-3,4-dihydroisoquinolin-1(2H)-one (2206) (100 mg, 0.11 mmol) and 3-fluoro-5-hydroxyphenylbbronic acid (2207) (36 mg, 0.23 mmol) were dissolved in DME (4 mL). The solution was degassed and back-filled with argon (three times). $Pd(PPh_3)_4$ (6.4 mg, 5.5 µmol) and aqueous $Na_2CO_3$ solution (1.0 M, 0.44 mL, 0.44 mmol) were added sequentially. The reaction mixture was degassed and back-filled with argon (three times), and then stirred at 80° C. for 24 h. The mixture was allowed to cool to RT, partitioned between ethyl acetate and brine. The organic layer was dried over $Na_2SO_4$, filtered and concentrated in vacuo. The residue was purified by column chromatography on silica gel eluting 2-Iodo-6-methyl-N-o-tolylbenzamide (2201) (1.5 g, 4.27 mmol), which has been prepared from the reaction of compound 902 and 2-methyl aniline, and allyltributyl tin (2.10 g, 1.5 mmol) were dissolved in anhydrous DMF (12 mL). The solution was degassed and back-filled with argon (three times). $Pd(PPh_3)_4$ (148 mg, 0.13 mmol) was added. The reaction mixture was degassed and back-filled with argon (three times), and then stirred at 90° C. for 16 h. The mixture was allowed to cool to RT, partitioned between ethyl acetate and $H_2O$. The organic layer was washed with brine, dried over $Na_2SO_4$ and filtered. The filtrate was concentrated in vacuo and the residue was purified by column chromatography on with methanol and dichloromethane to afford the desired product, 3-((4-amino-3-(3-fluoro-5-hydroxyphenyl)-1H-pyrazolo[3,4-d]pyrimidin-1-yl)methyl)-8-methyl-2-o-tolyl-3,4-dihydroisoquinolin-1(2H)-one (2208) (12 mg, 22% yield).

Example 10

Synthesis of 6-((4-amino-3-(3-fluoro-5-hydroxyphenyl)-1H-pyrazolo[3,4-d]pyrimidin-1-yl)methyl)-3-methyl-5-o-tolylisothiazolo[5,4-d]pyrimidin-4(5H)-one (Compound 2313)

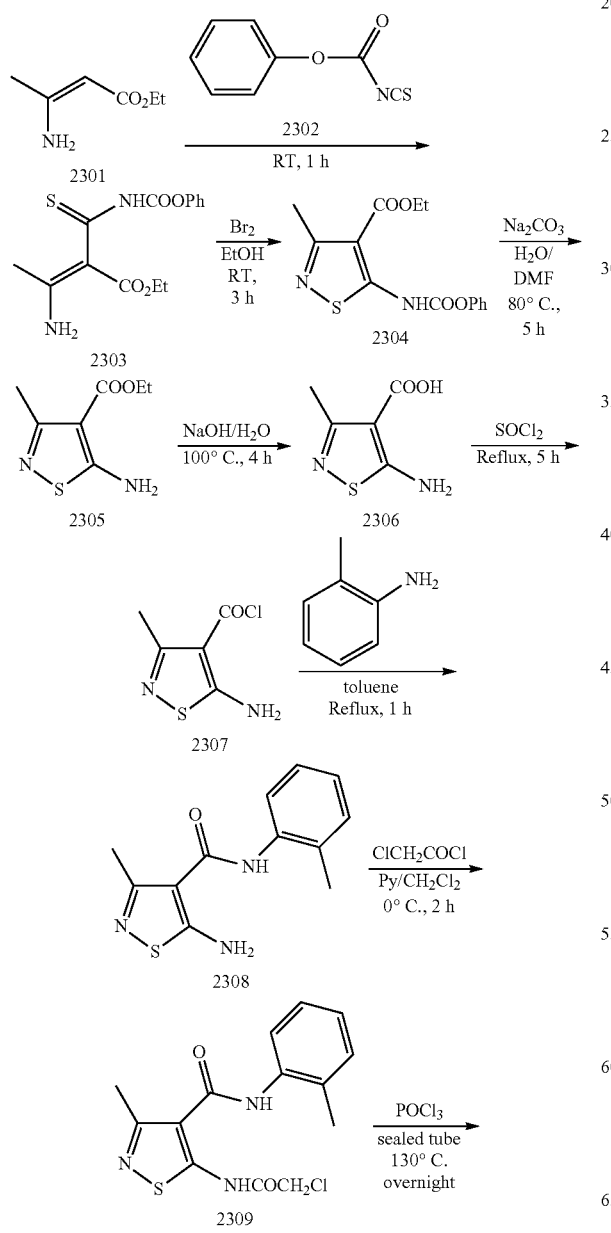

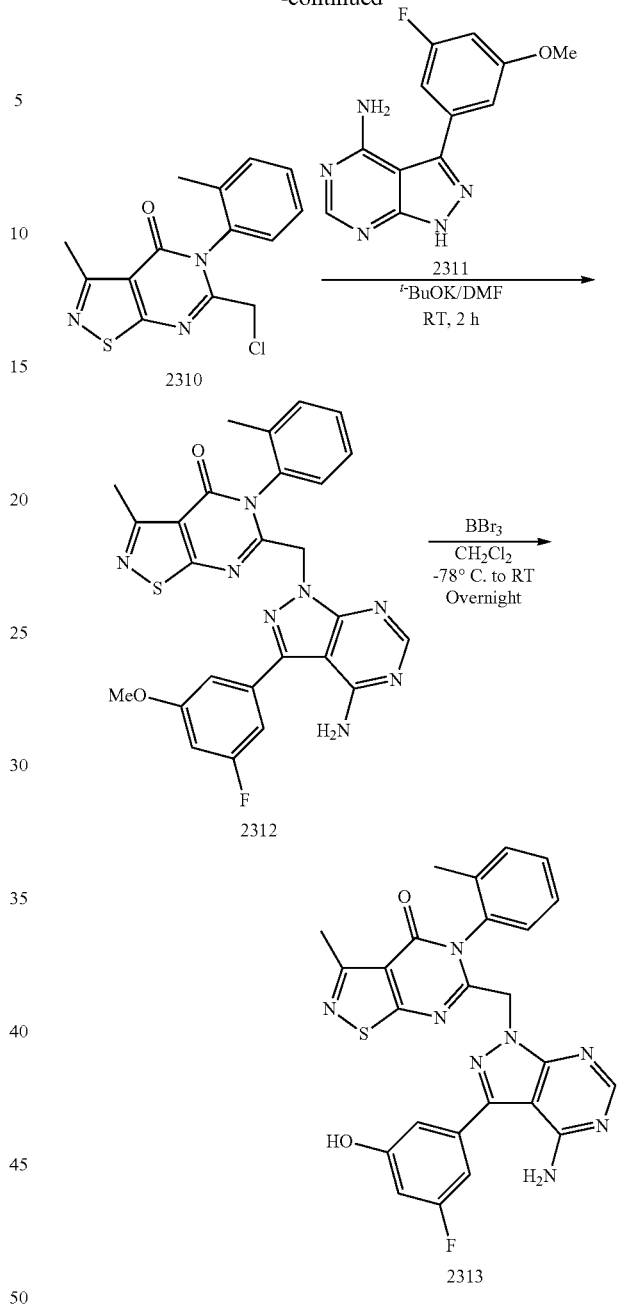

A solution of compound 2302 (24.9 g, 0.19 mol) in CH$_3$CN (50 mL) was added to a solution of compound 2301 (30 g, 0.19 mol) in at 0° C. The mixture was stirred for 1 hour at room temperature and poured into 500 mL of water. The reaction mixture was allowed to stand for 1 h. The solid was precipitated out of the solution, collected by filtration, washed with water and dried to afford the desired compound 2303 as a red-orange solid (50 g, 85.5%).

To a solution of compound 2303 (54 g, 0.175 mol) in ethyl acetate (200 mL), a solution of Br$_2$ (56 g, 0.35 mol) in ethyl acetate (50 mL) was added dropwise at room temperature. The resulting mixture was stirred for 3 h at room temperature. The solid was collected by filtration, washed with ethyl acetate to afford the desired product, compound 2304 (40 g, 74.6%).

A mixture of compound 2304 (40 g, 0.13 mol) and saturated Na$_2$CO$_3$ solution (10 mL) in DMF (100 mL) was heated for 5 h at 80° C. The reaction mixture was cooled to room temperature and 1 L of water was added. The solid was collected by filtration and dried to afford the desired product, compound 2305 (16 g, 66%).

A mixture of compound 2305 (16 g, 0.086 mol), NaOH (6.88 g, 0.172 mol) in water (50 mL) was heated for 4 h at reflux. The reaction mixture was cooled to room temperature and acidified with 1N HCl solution until PH=3-4. The solid was collected by filtration and dried to afford the desired product, compound 2306 (12 g, 88%). A mixture of compound 2306 (1 g, 0.0063 mol) in SOCl₂ (15 mL) was stirred for 5 h at reflux, the reaction mixture was cooled to room temperature and concentrated to remove excess SOCl₂. Anhydrous toluene (30 mL) was added to the residue and concentrated. This process was repeated twice to remove the residue of SOCl₂.

The crude compound 2307 was dissolved in dry toluene (5 mL). 2-Methyl-aniline (2 g, 0.0187 mol) was added to the above solution. The resulting mixture was heated for 1 h at reflux, cooled to room temperature and filtered. The filtrate was concentrated to dryness and partitioned between ethyl acetate and brine. The aqueous phase was extracted with ethyl acetate. The combined organic phases were washed with brine, dried with MgSO₄ and filtered. The residue was purified by flash chromatography eluting with petroether ethyl acetate from 50:1 to 5:1 to afford the desired product, compound 2308 (600 mg, 38.55%).

A solution of compound 2308 (600 mg, 2.43 mmol) and pyridine (0.78 mL) in DCM (30 mL) was stirred for 10 min at 0° C. Chloroacetyl chloride (423 mg, 3.74 mmol) was added. The reaction mixture was stirred for 2 h and quenched with water. The organic phase was separated and washed with water, brine, dried, filtered and concentrated to afford the desired product, compound 2309 (700 mg, 89%).

A mixture of compound 2309 (600 mg, 1.85 mmol) and POCl₃(10 mL) was heated overnight at 120-130° C. (oil bath) in a sealed tube. The reaction mixture was cooled to room temperature and concentrated. The residue was partitioned between ethyl acetate and water, and then basified with saturated Na₂CO₃ solution until PH 7-8. The organic layer was separated, washed with brine, dried over MgSO₄ and concentrated. The residue was purified by flash chromatography eluting with petroether in ethyl acetate (PE/EA=20/1) to afford the desired product, compound 2310 as a yellow powder (300 mg, 53.0%).

tert-BuOK (28.7 mg, 0.256 mmol) was added to a solution of compound 2311 (76 mg, 0.295 mmol) in dry DMF (3 mL) at RT. The reaction mixture was stirred for 30 min., and a solution of compound 2310 (60 mg, 0.196 mmol) in DMF (2 mL) was added dropwise. The resulting mixture was stirred for 2 h and concentrated. The residue was purified by flash chromatography eluting with (DCM/MeOH=50/1) to afford the desired product 2312 as off-white solid (65 mg, 62.7%).

To a solution of compound 2312 (40 mg, 0.076 mmol) in dry DCM (10 mL), BBr₃(190.4 mg, 0.76 mmol) was added dropwise at −78° C., then the reaction mixture was allowed to warm to room temperature and stirred for overnight. The reaction mixture was poured into ice-water, basified with saturated NaHCO₃ solution until PH 8-9 and extracted with DCM. The combined organic phases were dried over MgSO₄, filtered and concentrated. The residue was purified by flash chromatography eluting with DCM/MeOH=30/1 to afford the desired product, compound 2313 (15 mg, 38.5%).

Example 11

Synthesis of 2-((4-amino-3-(3-hydroxyphenyl)-1H-pyrazolo[3,4-d]pyrimidin-1-yl)methyl)-5-methyl-3-o-tolylthieno[2,3-d]pyrimidin-4(3H)-one (Compound 2407)

Scheme 24. Synthesis of 2-((4-amino-3-(3-hydroxyphenyl)-1H-pyrazolo[3,4-d]pyrimidin-1-yl)methyl)-5-methyl-3-o-tolylthieno[2,3-d]pyrimidin-4(3H)-one (Compound 2407) is described.

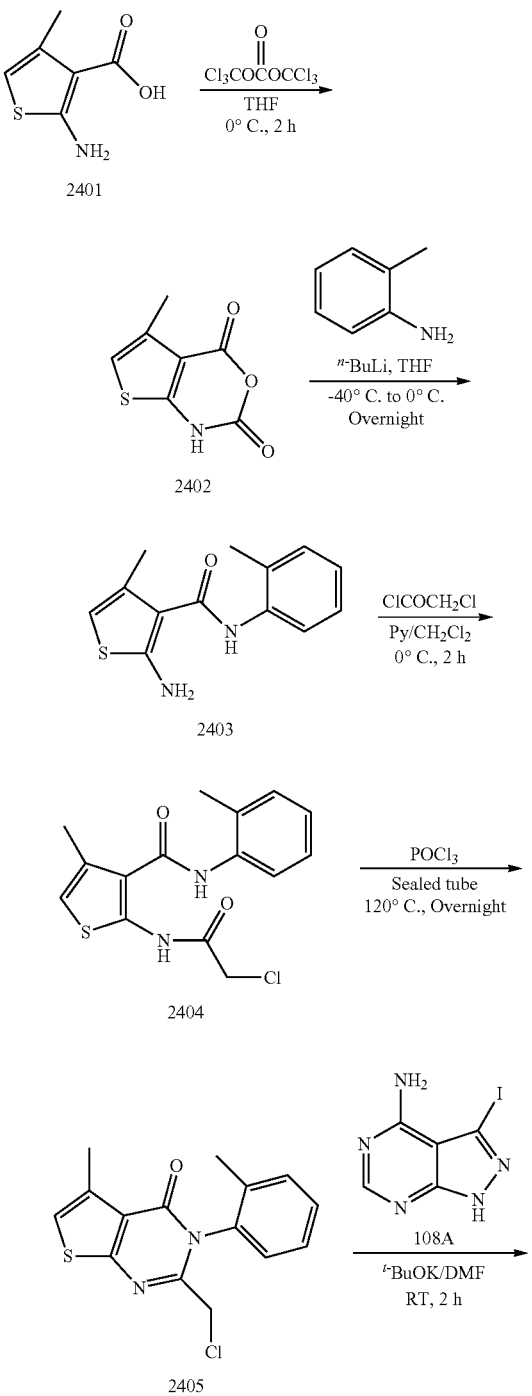

-continued

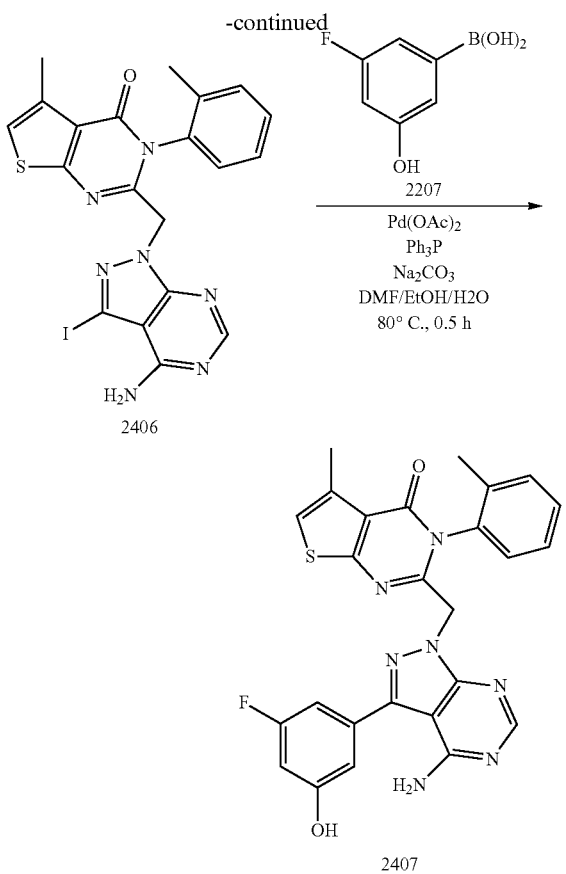

To a stirred solution of 2-amino-4-methylthiophene-3-carboxylic acid (2401) (2.4 g, 15.2 mmol) in THF (50 mL), a solution of triphosgene (9.0 g, 30 mmol, 2 eq.) in THF (10 mL) was added slowly dropwise at 0° C. in 20 min. The resulting mixture was stirred at 0° C. for 2 h. The reaction mixture was quenched with water (20 mL) at 0° C., and then concentrated in vacuo to remove the organic solvent. A brown solid was precipitated out of solution. The solid was collected by filtration, washed with water (5 mL×2) and dried in vacuo to afford the desired product 5-methyl-1H-thieno[2,3-d][1,3]oxazine-2,4-dione (2402) (2.5 g, 89.3% yield) as a brown solid.

To a stirred solution of o-toluidine, (1.4 g, 12.8 mmol, 1.2 eq) in dry THF (20 mL), n-BuLi (2.5 N, 7.7 mL, 19.3 mmol, 1.8 eq.) was added slowly dropwise at −40° C. under argon atmosphere in 30 min. The resulting mixture was stirred at −40° C. for another 30 min. A solution of 5-methyl-1H-thieno[2,3-d][1,3]oxazine-2,4-dione (2402) (1.95 g, 10.7 mmol, 1 eq) in dry THF (50 mL) was added slowly dropwise at −40° C. in 20 min. The reaction mixture was stirred at −40° C. for 1 h and then allowed to warm to room temperature for overnight. The reaction mixture was quenched with water (20 mL) at 0° C., and then neutralized with concentrated HCl solution until pH 8-9. The mixture was concentrated in vacuo to remove the organic solvent. The residue was extracted with ethyl acetate (25 mL×3). The combined organic phases were washed with brine (10 mL), dried over MgSO₄ and concentrated in vacuo. The resulting residue was purified by a silica gel column chromatography using 5% to 20% ethyl acetate in petroether as an eluent to afford the desired product 2-amino-4-methyl-N-o-tolylthiophene-3-carboxamide (2403) (0.74 g, 28.1% yield) as a yellow solid.

To a stirred solution of 2-amino-4-methyl-N-o-tolylthiophene-3-carboxamide (2403) (740 mg, 3 mmol) and pyridine (406.8 mg, 3.6 mmol, 1.2 eq) in dry DCM (20 mL), 2-chloroacetyl chloride (284.8 mg, 3.6 mmol, 1.2 eq.) was added slowly dropwise at 0° C. in 30 min. The resulting mixture was stirred at 0° C. for 2 h. The reaction mixture was quenched with water (20 mL) at 0° C. and extracted with DCM. The combined organic phases were washed with 1N of HCl solution (10 mL), brine (10 mL), dried over MgSO₄ and concentrated in vacuo to afford the desired product 2-(2-chloroacetamido)-4-methyl-N-o-tolylthiophene-3-carboxamide (2404) (950 mg, 98.1% yield) as a yellow solid.

A mixture of 2-(2-chloroacetamido)-4-methyl-N-o-tolylthiophene-3-carboxamide (2404) (1.07 g, 3.32 mmol) and POCl₃ (25 mL) was stirred overnight in a sealed tube at 120° C. The reaction mixture was concentrated in vacuo to remove excess POCl₃. The residue was partitioned between DCM (30 mL) and saturated NaHCO₃ solution (10 mL). The organic layer was separated and washed with sat. NaHCO₃ (10 mL), brine (10 mL), dried over MgSO₄ and concentrated in vacuo. The resulting residue was purified by a silica gel column chromatography to afford the desired product 2-(chloromethyl)-5-methyl-3-o-tolylthieno[2,3-d]pyrimidin-4(3H)-one (2405) (760 mg, 75.2% yield) as a yellow solid.

A solution of 3-iodo-1H-pyrazolo[3,4-d]pyrimidin-4-amine (108A) (314.3 mg, 1.2 mmol, 1.5 eq) and t-BuOK (155 mg, 1.38 mmol, 1.2 eq) in DMF (10 mL) was stirred at room temperature for 15 min., a solution of 2-(chloromethyl)-5-methyl-3-o-tolylthieno[2,3-d]pyrimidin-4(3H)-one (2405) (350 mg, 1.15 mmol, 1 eq.) in DMF (5 mL) was added dropwise at room temperature. The resulting mixture was stirred at room temperature for 2 h. The reaction mixture was concentrated in vacuo to remove the organic solvent. The resulting residue was purified by a silica gel column chromatography to afford the desired product 2-((4-amino-3-iodo-1H-pyrazolo[3,4-d]pyrimidin-1-yl)methyl)-5-methyl-3-o-tolylthieno[2,3-d]pyrimidin-4(3H)-one (2406) (250 mg, 41.1% yield) as a yellow solid.

2-((4-amino-3-iodo-1H-pyrazolo[3,4-d]pyrimidin-1-yl)methyl)-5-methyl-3-o-tolylthieno[2,3-d]pyrimidin-4(3H)-one (2406) (50 mg, 0.092 mmol), PPh₃ (14.5 mg, 0.056 mmol, 0.6 eq) and 3-fluoro-5-hydroxyphenylboronic acid (2207) (17.2 mg, 0.11 mmol, 1.2 eq) were dissolved in a solution of DMF, ethanol and water (5 mL/2 mL/2 mL). To this mixture Pd(OAc)₂ (4.14 mg, 0.018 mmol, 0.2 eq) and sodium carbonate (48.7 mg, 0.46 mmol, 5 eq) were added sequentially. The resulting mixture was degassed and backfilled with argon three times and then heated to 80° C. for 0.5 h with stirring. The reaction mixture was concentrated in vacuo to remove the organic solvent. The resulting residue was purified by a silica gel column chromatography to afford the desired product 2-((4-amino-3-(3-fluoro-5-hydroxyphenyl)-1H-pyrazolo[3,4-d]pyrimidin-1-yl)methyl)-5-methyl-3-o-tolylthieno[2,3-d]pyrimidin-4(3H)-one (2407) (22.8 mg, 48.2% yield) as a yellow solid.

Example 12

Synthesis of 8-methyl-3-((methyl(9H-purin-6-yl)amino)methyl)-2-o-tolylisoquinolin-1(2H)-one Scheme 25: The synthesis of 8-methyl-3-((methyl(9H-purin-6-yl)amino)methyl)-2-o-tolylisoquinolin-1(2H)-one (Compound 4004) is described.

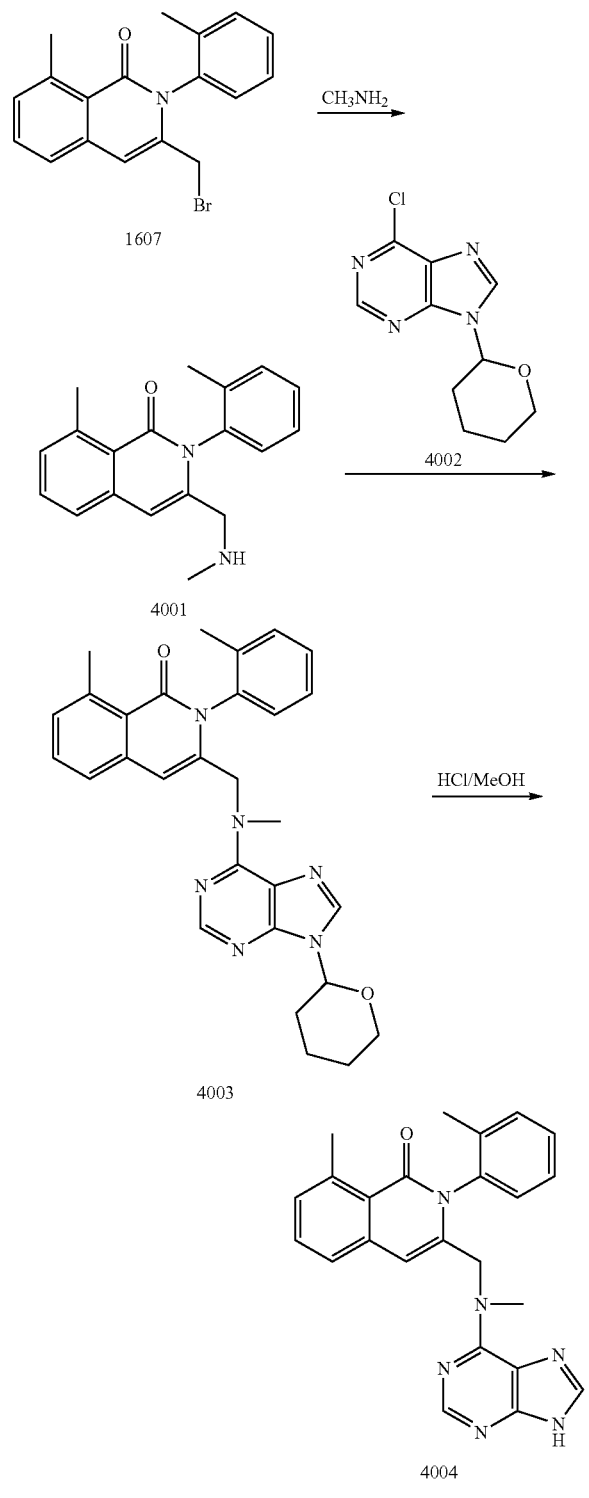

3-(Bromomethyl)-8-methyl-2-o-tolylisoquinolin-1(2H)-one (342 mg, 1.0 mmol) (1607) was dissolved in methylamine solution (100 mL) and stirred for 2 h. The mixture was poured into ice-water (200 mL) and extracted with ethyl acetate (3×50 mL). The combined organic layer was washed with brine (20 mL), dried over $Na_2SO_4$ and filtered. The filtrate was concentrated in vacuo to afford the desired product, 8-methyl-3-((methylamino)methyl)-2-o-tolylisoquinolin-1(2H)-one (4001) (250 mg, 86% yield) as a yellow solid. The product obtained was used directly in the next step without purification.

8-Methyl-3-((methylamino)methyl)-2-o-tolylisoquinolin-1(2H)-one (233 mg, 0.8 mmol) (4001) and 6-chloro-9-(tetrahydro-2H-pyran-2-yl)-9H-purine (4002) (238 mg, 1.0 mmol) were dissolved in EtOH (50 mL) and the resulting mixture was stirred at reflux for 2 h. The mixture was allowed to cool to RT, and concentrated in vacuo. The residue was purified by flash column chromatography on silica gel (2-20% MeOH/DCM) to afford the product, 8-Methyl-3-((methyl(9-(tetrahydro-2H-pyran-2-yl)-9H-purin-6-yl)amino)methyl)-2-o-tolylisoquinolin-1(2H)-one (4003) (200 mg, 51% yield) as a slight yellow solid.

8-Methyl-3-((methyl(9-(tetrahydro-2H-pyran-2-yl)-9H-purin-6-yl)amino)methyl)-2-o-tolylisoquinolin-1(2H)-one (4003) (180 mg 0.36 mmol) was dissolved in MeOH(HCl) (50 mL) and the mixture was stirred at RT for 2 h. Aqueous $NaHCO_3$ solution was added to the reaction mixture and the pH was adjusted to 9. The mixture was filtered and the filtrate was concentrated in vacuo to afford the desired product, 8-methyl-3-((methyl(9H-purin-6-yl)amino)methyl)-2-o-tolylisoquinolin-1(2H)-one (4004) (80 mg, 54% yield) as a yellow solid.

Example 13

Synthesis of 3-(1-(9H-purin-6-ylamino)ethyl)-8-methyl-2-o-tolylisoquinolin-1(2H)-one Scheme 26: The synthesis of 3-(1-(9H-purin-6-ylamino)ethyl)-8-methyl-2-o-tolylisoquinolin-1(2H)-one (Compound 4106) is described.

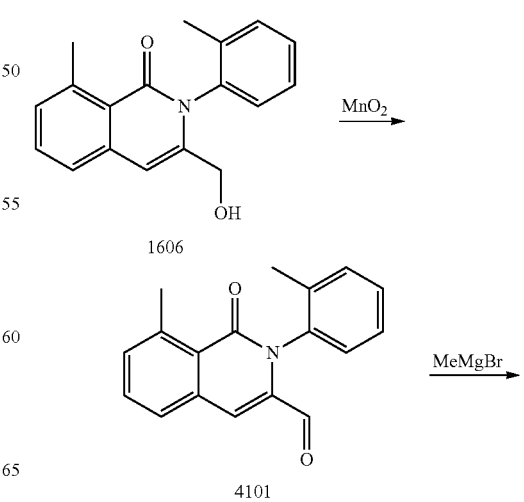

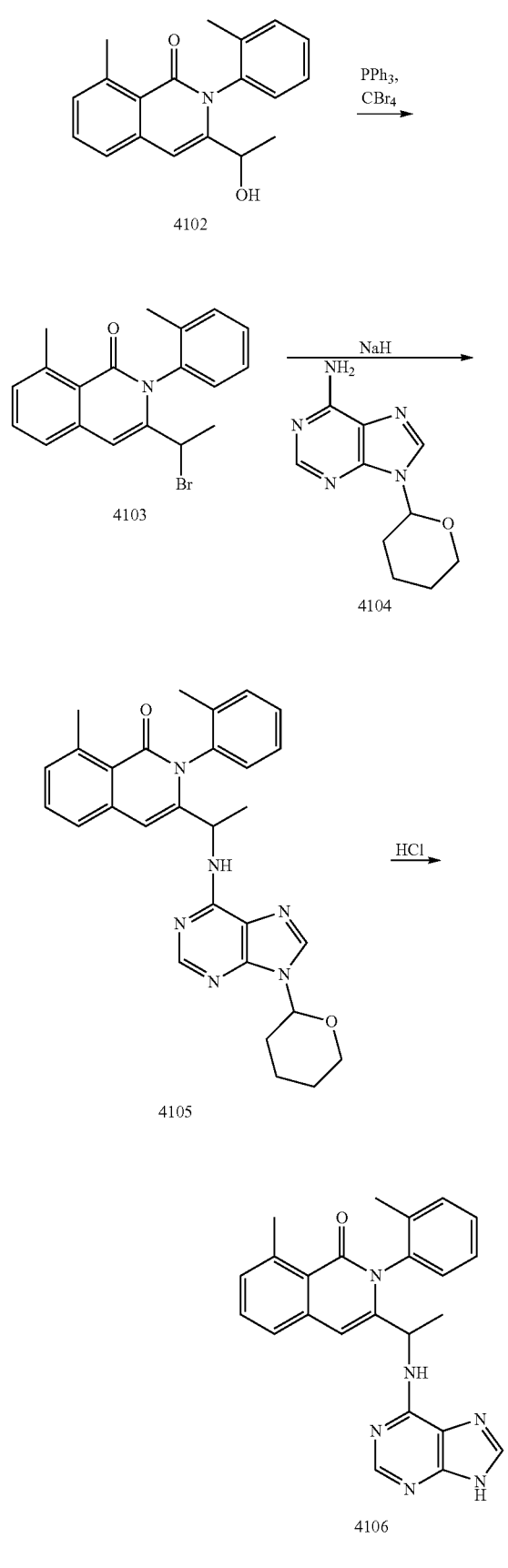

To a stirred solution of 3-(hydroxymethyl)-8-methyl-2-o-tolylisoquinolin-1(2H)-one 1606 (2.79 g, 10 mmol) in $CH_2Cl_2$ (200 mL), $MnO_2$ (5 g) was added and the resulting mixture was stirred at reflux for 3 h. The mixture was allowed to cool to RT, and concentrated in vacuo. The residue was purified by flash column chromatography on silica gel (10-50% EA/PE) to afford the product, 8-methyl-1-oxo-2-o-tolyl-1,2-dihydroisoquinoline-3-carbaldehyde 4101 (2.5 g, 90% yield) as a white solid.

8-Methyl-1-oxo-2-o-tolyl-1,2-dihydroisoquinoline-3-carbaldehyde 4161 (2.4 g, 8.6 mmol) was dissolved in anhydrous THF (280 mL) and cooled to −78° C. under a nitrogen atmosphere. Methyl MgBr (2 M, 5 mL, 10 mmol) was added slowly, and the resulting mixture was stirred at −78° C. for 2 h. $H_2O$ (5 mL) was added and then the solution was poured into ice-water (200 mL) and extracted with ethyl acetate (3×50 mL). The combined organic layer was washed with brine, dried over $Na_2SO_4$ and filtered. The filtrate was concentrated in vacuo, and the residue product was purified by flash column chromatography on silica gel (10-50% EA/PE) to afford the product, 3-(1-hydroxyethyl)-8-methyl-2-o-tolylisoquinolin-1(2H)-one 4102 (1.8 g, 71% yield) as a white solid.

To a solution of 3-(1-hydroxyethyl)-8-methyl-2-o-tolyl-isoquinolin-1(2H)-one 4102 (1.6 g, 5.5 mmol) in $CH_2Cl_2$, $PPh_3$ (2.88 g, 11.0 mmol) was added and the resulting mixture was stirred at RT for 30 min. Then $CBr_4$ (3.64 g, 11.0 mmol) was added in portions to the mixture at 0° C. The resulting mixture was allowed to warm to RT, stirred for 30 min, and concentrated in vacuo. The crude product was purified by flash column chromatography on silica gel (30-50% EA/PE) to afford the desired product, 3-(1-bromoethyl)-8-methyl-2-o-tolylisoquinolin-1(2H)-one 4103 (1.8 g, 91% yield) as a white solid.

To a stirred solution of 9-(tetrahydro-2H-pyran-2-yl)-9H-purin-6-amine 4103 (436 mg 2 mmol) in anhydrous DMF (10 mL), NaH (60% in mineral oil, 77 mg, 2 mmol) was added and the mixture was stirred for 30 min. 3-(1-Bromoethyl)-8-methyl-2-o-tolylisoquinolin-1(2H)-one 4104 (700 mg, 2 mmol) was added. The mixture was stirred for 2 h, poured into ice-water (200 mL) and extracted with ethyl acetate (3×50 mL). The combined organic layer was washed with brine (20 mL), dried over $Na_2SO_4$ and filtered. The filtrate was concentrated in vacuo and the residue was purified by flash column chromatography on silica gel (10-50% MeOH/DCM) to afford the product, 8-methyl-3-(1-(9-(tetrahydro-2H-pyran-2-yl)-9H-purin-6-ylamino)ethyl)-2-o-tolylisoquinolin-1(2H)-one 4105 (500 mg, 51% yield) as a white solid.

8-Methyl-3-(1-(9-(tetrahydro-2H-pyran-2-yl)-9H-purin-6-ylamino)ethyl)-2-o-tolylisoquinolin-1(2H)-one 4105 (180 mg, 0.36 mmol) was dissolved in MeOH(HCl) (50 mL) and stirred for 2 h. Aqueous $NaHCO_3$ solution was added to the reaction mixture and the pH value was adjusted to 9. The mixture was then filtered and the filtrate was concentrated in vacuo to afford the desired product, 3-(1-(9H-purin-6-ylamino)ethyl)-8-methyl-2-o-tolylisoquinolin-1(2H)-one 4106 (80 mg, 54% yield) as a yellow solid.

Example 14

Synthesis of 3-(4-amino-1-((8-methyl-1-oxo-2-o-tolyl-1,2-dihydroisoquinolin-3-yl)methyl)-1H-pyrazolo[3,4-d]pyrimidin-3-yl)-5-fluorophenyl dihydrogen phosphate Scheme 27. The synthesis of 3-(4-amino-1-((8-methyl-1-oxo-2-o-tolyl-1,2-dihydroisoquinolin-3-yl)methyl)-1H-pyrazolo[3,4-d]pyrimidin-3-yl)-5-fluorophenyl dihydrogen phosphate (Compound 4903) is described.

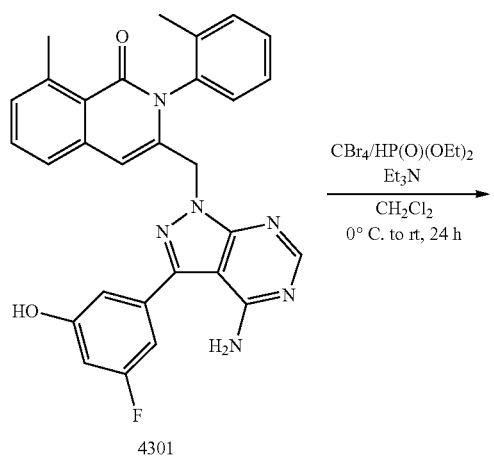

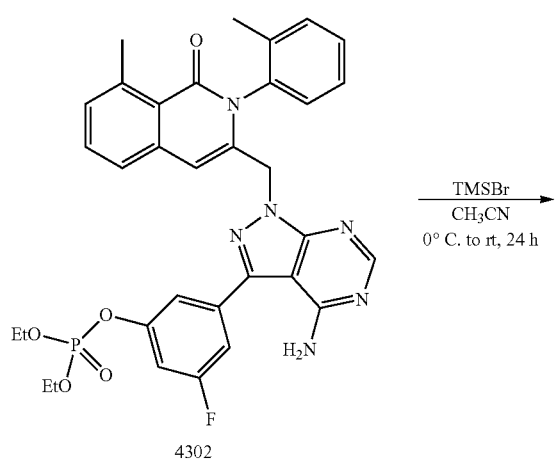

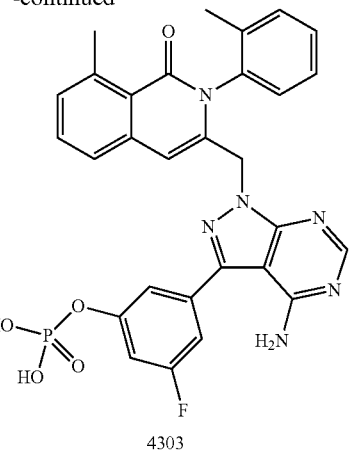

3-((4-Amino-3-(3-fluoro-5-hydroxyphenyl)-1H-pyrazolo[3,4-d]pyrimidin-1-yl)methyl)-8-methyl-2-o-tolylisoquinolin-1(2H)-one 4301 (250 mg, 0.5 mmol) was dissolved in anhydrous THF (15 mL) in a round bottom flask in dark (covered by aluminum foil) and cooled to 0° C. under an argon atmosphere. $CBr_4$ (498 mg, 1.5 mmol) was added followed by diethylphosphite (129 μL, 1.0 mmol) and triethylamine (417 μL, 1.5 mmol). The resulting mixture was stirred in dark from 0° C. to RT for 16 h. The mixture was then partitioned between ethyl acetate and brine. The organic layer was dried over $Na_2SO_4$, filtered and concentrated in vacuo. The residue was purified by column chromatography on silica gel eluting with methanol and dichloromethane to afford the desired product, 3-(4-amino-1-((8-methyl-1-oxo-2-o-tolyl-1,2-dihydroisoquinolin-3-yl)methyl)-1H-pyrazolo[3,4-d]pyrimidin-3-yl)-5-fluorophenyl diethyl phosphate 4302 (200 mg, 62% yield) as an off-white solid.

3-(4-Amino-1-((8-methyl-1-oxo-2-o-tolyl-1,2-dihydroisoquinolin-3-yl)methyl)-1H-pyrazolo[3,4-d]pyrimidin-3-yl)-5-fluorophenyl diethyl phosphate 4302 (170 mg, 0.26 mmol) was dissolved in anhydrous $CH_3CN$ (5 mL) and cooled to 0° C. under an argon atmosphere. TMSBr (0.34 mL, 2.64 mmol) was slowly added via a syringe and the resulting mixture was stirred from 0° C. to RT for 16 h. LC-MS showed small amount of starting material left, additional amount of TMSBr (0.1 mL) was added and stirred at RT for 5 h. LC-MS showed the complete conversion. The mixture was concentrated in vacuo, and the residue was dissolved in $Et_2O$ (10 mL) and $H_2O$ (0.5 mL) and stirred for 30 min. The mixture was concentrated in vacuo to affords the desired product, 3-(4-amino-1-((8-methyl-1-oxo-2-o-tolyl-1,2-dihydroisoquinolin-3-yl)methyl)-1H-pyrazolo[3,4-d]pyrimidin-3-yl)-5-fluorophenyl dihydrogen phosphate 4903 (140 mg, 91% yield).

Example 15

IC50 Values for Selected Compounds

TABLE 4

In Vitro $IC_{50}$ data for selected compounds.

| IC50(nM) | +(greater than 10 microMolar) Compound No. | ++(less than 10 microMolar) Compound No. | +++(less than 1 microMolar) Compound No. | ++++(less than 100 nM) Compound No. |
|---|---|---|---|---|
| PI3K δ | | 1, 5, 22, 27, 38, 39, 40, 41, 46, 92, 117, 118, 120, 129, 132, | 4, 14, 15, 17, 18, 21, 26, 29, 31, 32, 34, 35, 36, 42, 43, 44, | 2, 3, 6, 7, 8, 9, 10, 11, 12, 13, 16, 19, 20, 23, 24, 25, 28, |

TABLE 4-continued

In Vitro IC$_{50}$ data for selected compounds.

| IC50(nM) | +(greater than 10 microMolar) Compound No. | ++(less than 10 microMolar) Compound No. | +++(less than 1 microMolar Compound No. | ++++(less than 100 nM) Compound No. |
|---|---|---|---|---|
| | | 164, 165, 172, 188, 190, 197, 198, 205, 208, 210, 212, 214, 217, 218, 220, 222, 237, 263, 285, 294, 298 | 45, 47, 49, 57, 69, 71, 85, 87, 94, 106, 107, 140, 143, 175, 179, 183, 184, 191, 193, 196, 199, 200, 201, 202, 206, 207, 211, 213, 215, 219, 224, 225, 228, 229, 230, 232, 233, 239, 241, 243, 245, 253, 254, 255, 260, 262, 270, 293, 299 | 30, 33, 37, 48, 50, 51, 52, 53, 54, 55, 56, 58, 59, 60, 61, 62, 63, 64, 65, 66, 67, 68, 70, 72, 73, 74, 75, 76, 77, 78, 79, 80, 81, 82, 83, 84, 86, 88, 89, 90, 91, 93, 95, 96, 97, 98, 99, 100, 101, 102, 103, 104, 105, 108, 109, 110, 111, 112, 113, 114, 115, 119, 123, 124, 125, 126, 128, 134, 135, 136, 137, 138, 139, 141, 142, 144, 145, 146, 147, 148, 149, 150, 151. 152, 153, 154, 155, 156, 157, 158, 159, 160, 161, 162, 166, 167, 168, 169, 170, 171, 173, 174, 176, 177, 178, 180, 189, 192, 194, 195, 203, 204, 209, 216, 221, 223, 226, 227, 231, 234, 235, 236, 238, 240, 242, 244, 246, 247, 248, 249, 250, 251, 252, 256, 257, 258, 259, 261, 264, 265, 266, 267, 268, 269, 271, 272, 273, 274, 275, 276, 277, 278, 279, 280, 281, 282, 283, 284, 286, 287, 288, 289, 290, 291, 292, 295, 296, 297, 300, 301, 302, 303, 304 |
| PI3K γ | 1, 4, 5, 18, 38, 43, 60, 69, 169, 172, 196, 197, 198, 200, 201, 202, 204, 206, 207, 208, 209, 210, 211, 212, 213, 214, 215, 217, 218, 219, 220, 221, 222, 223, 225, 228, 230, 236, 237, 239, 245, 266, 285, 293, 294, 295, 296, 297, 298, 299, 300, 301, 302, 303, 304 | 17, 34, 35, 37, 38, 40, 42, 57, 61, 65, 91, 92, 94, 105, 107, 140, 164, 170, 175, 179, 184, 188, 190, 191, 193, 199, 203, 216, 224, 229, 232, 235, 241, 243, 244, 251, 253, 254, 255, 263, 264, 268, 270, 272, 276, 282, 287 | 2, 8, 9, 10, 11, 14, 15, 20, 22, 27, 28, 39, 41, 46, 47, 49, 51, 55, 58, 66, 70, 71, 73, 76, 78, 80, 93, 98, 99, 100, 103, 104, 106, 108, 109, 161, 162, 163, 165, 166, 180, 192, 205, 226, 227, 231, 233, 240, 242, 249, 250, 252, 256, 257, 259, 262, 265, 273, 274, 275, 278, 280, 286, 288, 291 | 3, 6, 7, 12, 13, 16, 19, 21, 23, 24, 25, 26, 29, 30, 31, 33, 36, 44, 45, 48, 50, 52, 53, 54, 56, 59, 62, 63, 64, 67, 68, 72, 74, 75, 11, 79, 81, 82, 83, 84, 86, 87, 88, 89, 90, 95, 96, 97, 101, 102, 142, 145, 146, 147, 148, 149, 150, 151, 152, 160, 167, 168, 171, 173, 174, 176, 177, 178. 183, 189, 194, 195, 234, 238, 246, 247, 248, 258, 260, 261, 267, 269, 271, 277, 279, 281, 283, 284, 289, 290, 292 |
| PI3K α | 6, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 54, 55, 56, 57, 58, 59, 60, 61, 62, 64, 65, 67, 68, 69, 70, 71, 72, | 3, 7, 63, 66, 84, 86, 89, 90, 97, 108, 113, 115, 152, 168, 171, 173, 189, 194, 296 | 53, 95, 101, 102, 145, 147, 149, 151, 177 | 142, 148, 150, 153, 154, 155, 156, 157, 158, 159, 176 |

TABLE 4-continued

In Vitro IC$_{50}$ data for selected compounds.

| IC50(nM) | +(greater than 10 microMolar) Compound No. | ++(less than 10 microMolar) Compound No. | +++(less than 1 microMolar Compound No. | ++++(less than 100 nM) Compound No. |
|---|---|---|---|---|
| | 73, 74, 79, 80, 81, 82, 83, 85, 87, 88, 91, 93, 96, 98, 99, 100, 103, 104, 105, 106, 107, 109, 110, 111, 112, 114, 140, 146, 160, 161, 162, 163, 164, 165, 166, 167, 169, 170, 172, 174, 175, 179, 180, 183, 184, 188, 190, 191, 192, 193, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 297, 298, 299, 300, 301, 302, 303, 304 | | | |
| PI3K β | 8, 9, 10, 11, 14, 21, 22, 24, 26, 27, 28, 29, 34, 35, 36, 37, 38, 39, 40, 41, 42, 43, 44, 46, 52, 54, 56, 57, 59, 60, 64, 68, 69, 70, 73, 76, 78, 79, 80, 87, 88, 91, 93, 98, 103, 104, 105, 107, 109, 112, 140, 146, 152, 162, 163, 164, 165, 166, 169, 170, 172, 175, 179, 180, 183, 184, 188, 190, 191, 192, 193, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 268, 270, 272, 273, 274, 276, 280, | 3, 12, 13, 23, 25, 53, 55, 58, 61, 63, 65, 67, 71, 72, 74, 75, 77, 81, 82, 83, 84, 85, 86, 96, 99, 106, 108, 110, 111, 113, 114, 115, 145, 147, 149, 151, 154, 158, 160, 161, 167, 168, 171, 173, 174, 177, 178, 194, 195, 267, 269, 271, 275, 277, 278, 279, 281, 282, 283, 284, 286, 288, 290, 291, 295, 297 | 7, 62, 66, 82, 89, 90, 95, 97, 100, 102, 150, 153, 159, 176, 189, 289, 292, 296 | 101, 142, 155, 156, 157 |

TABLE 4-continued

In Vitro IC$_{50}$ data for selected compounds.

| IC50(nM) | +(greater than 10 microMolar) Compound No. | ++(less than 10 microMolar) Compound No. | +++(less than 1 microMolar) Compound No. | ++++(less than 100 nM) Compound No. |
|---|---|---|---|---|
| | 285, 287, 293, 294, 298, 299, 300, 301, 302, 303, 304 | | | |
| B cell proliferation EC$_{50}$ (nM) | 38, 162, 205, 228, 229 | 1, 2, 5, 22, 26, 27, 39, 40, 43, 49, 57, 71, 87, 112, 200, 201, 202, 208, 209, 210, 211, 212, 213, 214, 215, 217, 218, 219, 220, 222, 223, 232, 233, 237, 262, 263, 293 | 4, 8, 9, 10, 11, 14, 15, 18, 19, 20, 21, 24, 25, 28, 29, 30, 31, 32, 34, 35, 36, 41, 42, 45, 46, 47, 50, 51, 61, 69, 70, 76, 77, 78, 79, 80, 85, 86, 91, 98, 100, 103, 104, 105, 106, 107, 110, 111, 114, 119, 124, 133, 135, 145, 152, 161, 162, 163, 169, 203, 204, 206, 207, 216, 221, 224, 225, 226, 230, 243, 245, 246, 251, 252, 253, 254, 256, 257, 260, 261, 264, 265, 272, 276, 287, 288 | 3, 6, 7, 12, 13, 16, 17, 23, 33, 37, 44, 48, 53, 54, 55, 62, 63, 66, 67, 68, 72, 73, 74, 75, 81, 82, 83, 84, 88, 89, 90, 93, 95, 96, 97, 99, 101, 102, 108, 109, 113, 115, 123, 125, 126, 128, 134, 136, 137, 138, 139, 141, 142, 144, 146, 147, 148, 149, 150, 151, 153, 154, 155, 156, 157, 158, 159, 160, 166, 167, 168, 170, 171, 173, 174, 176, 177, 178, 180, 189, 192, 194, 195, 199, 227, 231, 234, 235, 236, 238, 242, 244, 247, 248, 249, 250, 255, 258, 259, 266, 268, 271, 275, 277, 278, 279, 280, 281, 282, 283, 284, 286, 289, 290, 291, 292, 295, 296, 297 |

TABLE 5

Structures of the Compounds for the IC50 results described in Table 4.

Structure

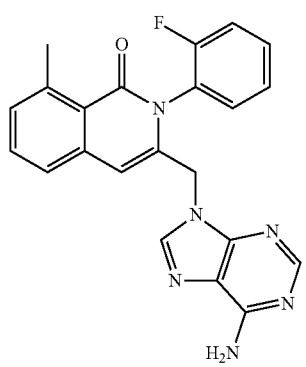

Compound 1

TABLE 5-continued

Structures of the Compounds for the IC50 results described in Table 4.

Structure

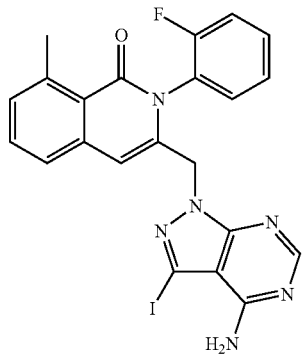

Compound 2

TABLE 5-continued
Structures of the Compounds for the IC50 results described in Table 4.
Structure
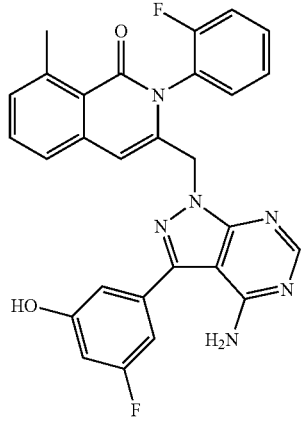
Compound 3
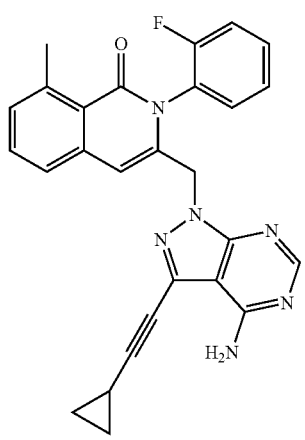
Compound 4
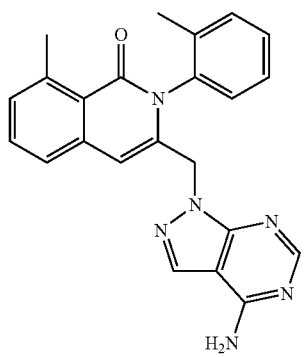
Compound 5
TABLE 5-continued
Structures of the Compounds for the IC50 results described in Table 4.
Structure
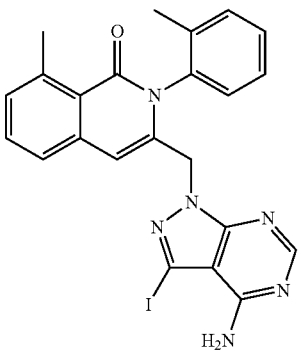
Compound 6
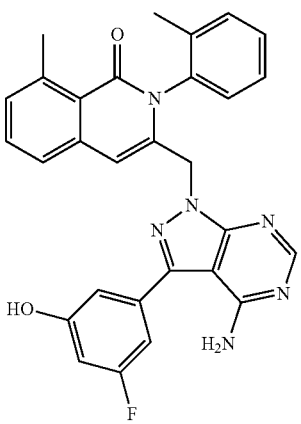
Compound 7
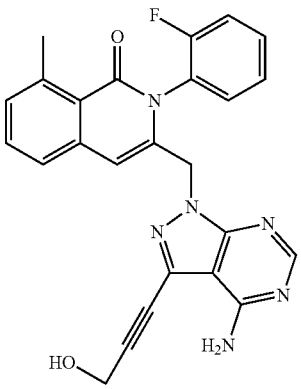
Compound 8

TABLE 5-continued

Structures of the Compounds for the IC50 results described in Table 4.

Structure

Compound 9

Compound 10

Compound 11

Compound 12

Compound 13

Compound 14

TABLE 5-continued

Structures of the Compounds for the IC50 results described in Table 4.

Structure

Compound 15

Compound 16

Compound 17

TABLE 5-continued

Structures of the Compounds for the IC50 results described in Table 4.

Structure

Compound 18

Compound 19

Compound 20

TABLE 5-continued
Structures of the Compounds for the IC50 results described in Table 4.
Structure
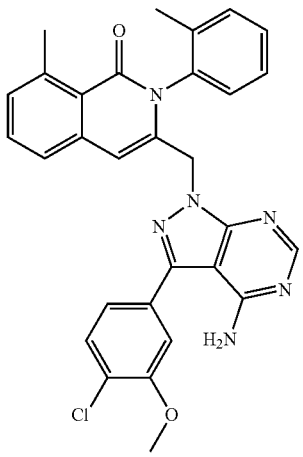 [SMILES: COc1ccc(-c2nn(Cc3cc4cccc(C)c4c(=O)n3-c3ccccc3C)c3ncnc(N)c23)cc1]
Compound 21
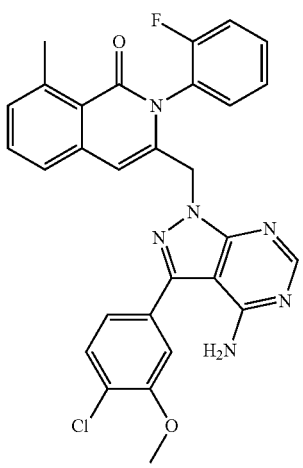
Compound 22
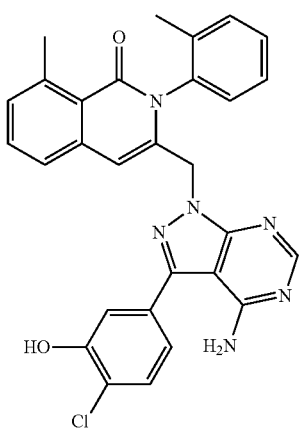
Compound 23
TABLE 5-continued
Structures of the Compounds for the IC50 results described in Table 4.
Structure
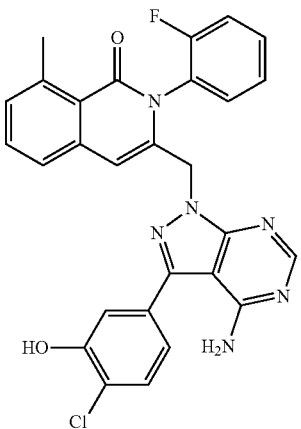
Compound 24
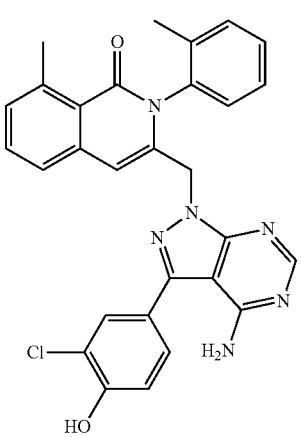
Compound 25
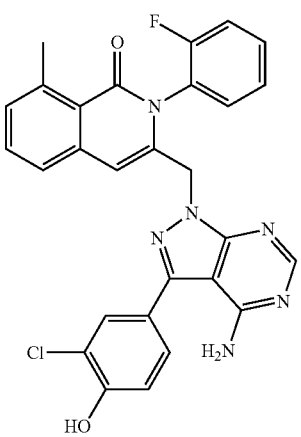
Compound 26

TABLE 5-continued
Structures of the Compounds for the IC50 results described in Table 4.
Structure
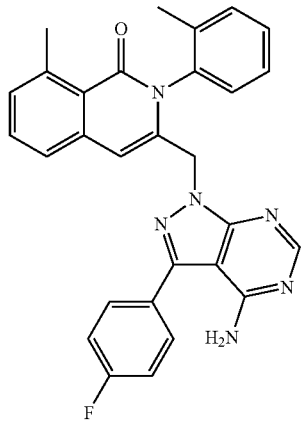
Compound 27
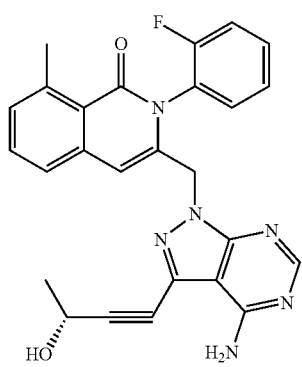
Compound 28
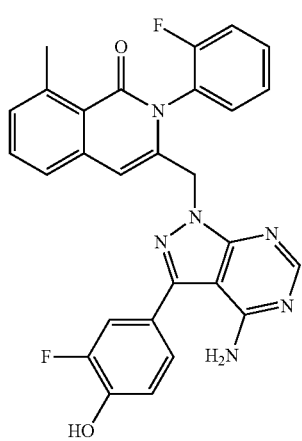
Compound 29
TABLE 5-continued
Structures of the Compounds for the IC50 results described in Table 4.
Structure
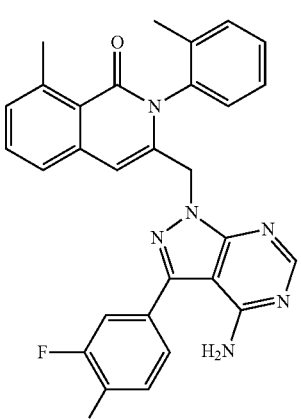
Compound 30
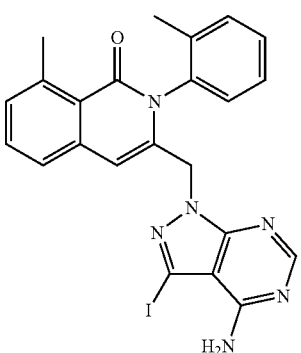
Compound 31
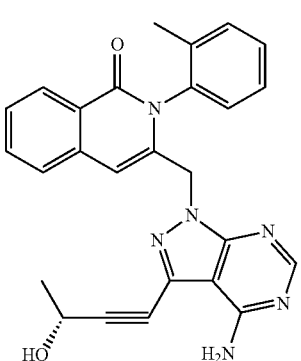
Compound 32

TABLE 5-continued
Structures of the Compounds for the IC50 results described in Table 4.
Structure
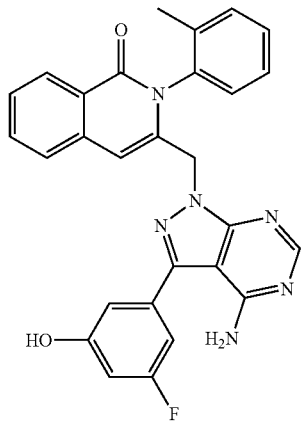
Compound 33
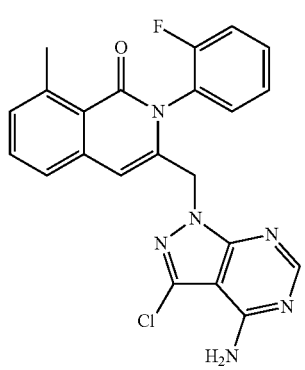
Compound 34
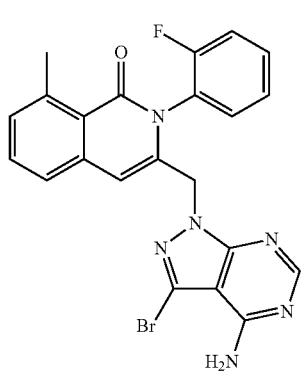
Compound 35
TABLE 5-continued
Structures of the Compounds for the IC50 results described in Table 4.
Structure
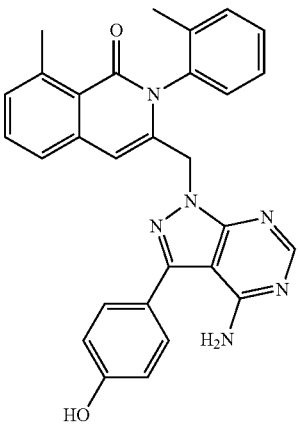
Compound 36
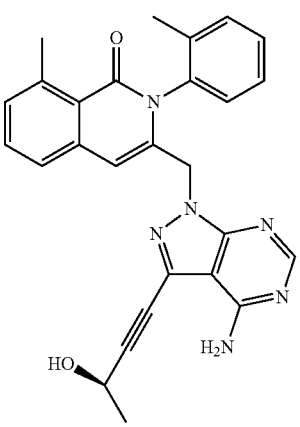
Compound 37
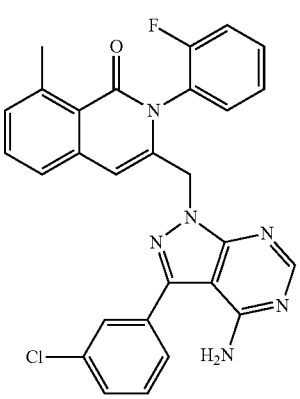
Compound 38

TABLE 5-continued
Structures of the Compounds for the IC50 results described in Table 4.
Structure
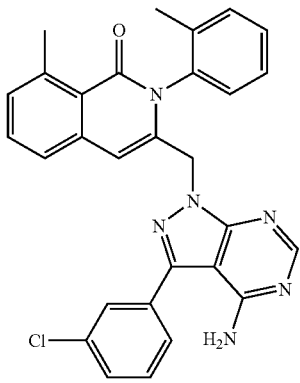
Compound 39
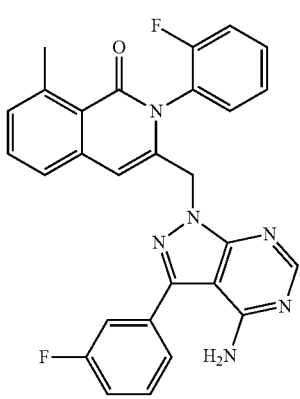
Compound 40
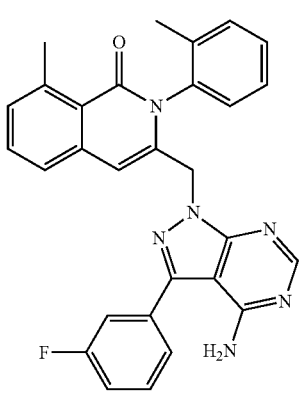
Compound 41
TABLE 5-continued
Structures of the Compounds for the IC50 results described in Table 4.
Structure
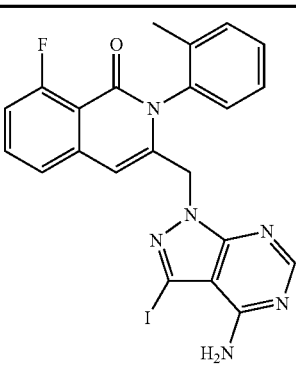
Compound 42
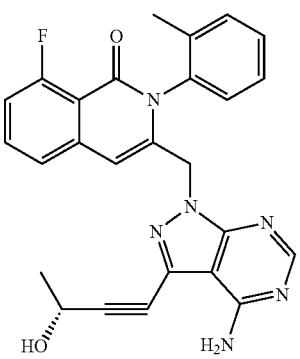
Compound 43
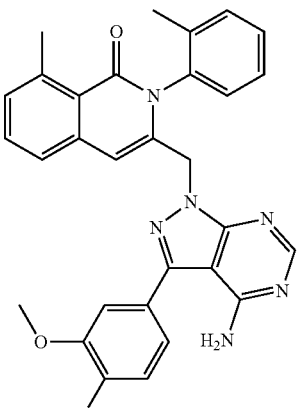
Compound 44

TABLE 5-continued
Structures of the Compounds for the IC50 results described in Table 4.
Structure
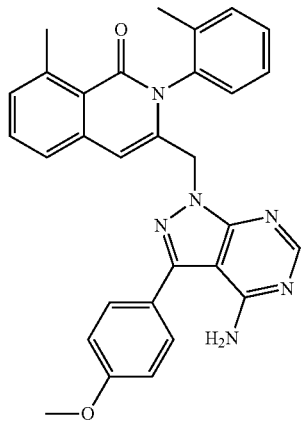
Compound 45
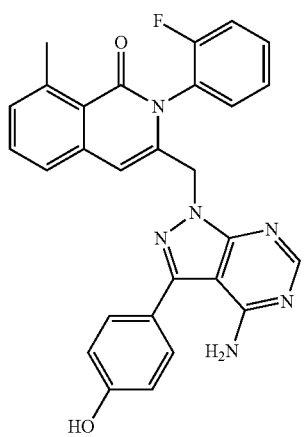
Compound 46
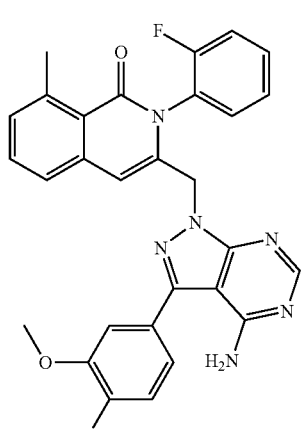
Compound 47
TABLE 5-continued
Structures of the Compounds for the IC50 results described in Table 4.
Structure
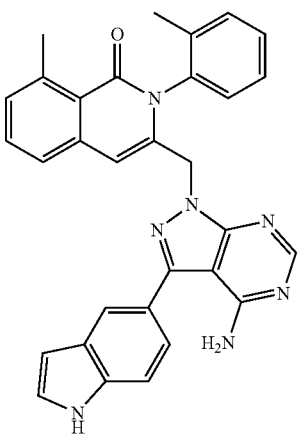
Compound 48
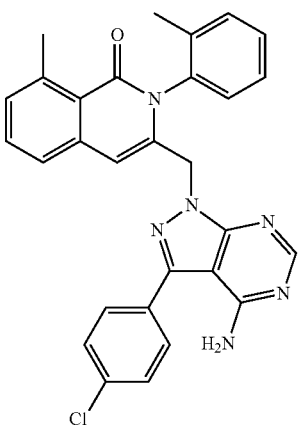
Compound 49
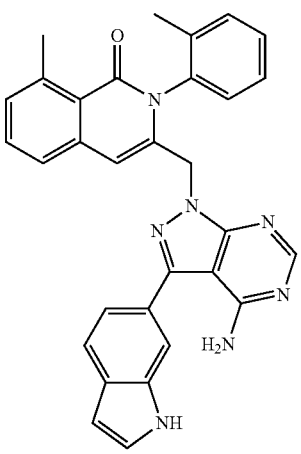
Compound 50

TABLE 5-continued
Structures of the Compounds for the IC50 results described in Table 4.
Structure
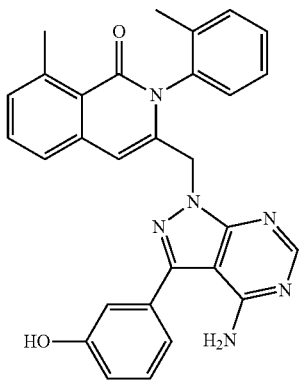
Compound 51
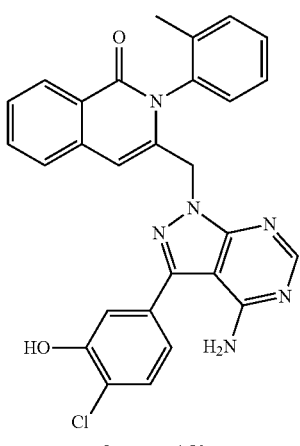
Compound 52
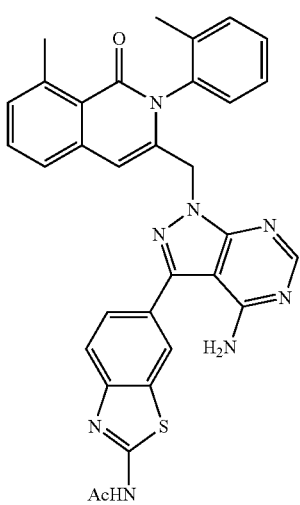
Compound 53
TABLE 5-continued
Structures of the Compounds for the IC50 results described in Table 4.
Structure
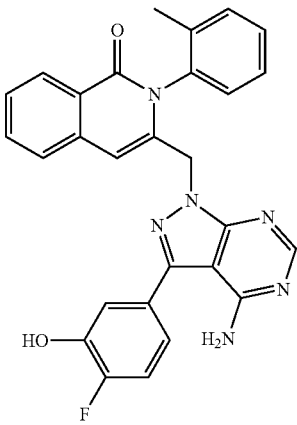
Compound 54
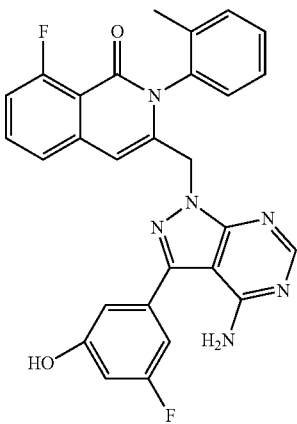
Compound 55
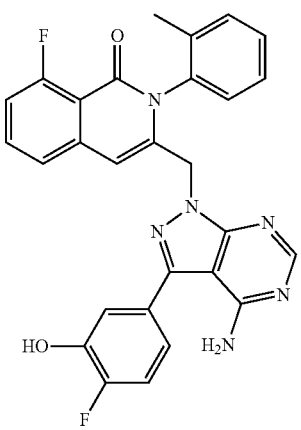
Compound 56

TABLE 5-continued
Structures of the Compounds for the IC50 results described in Table 4.
Structure
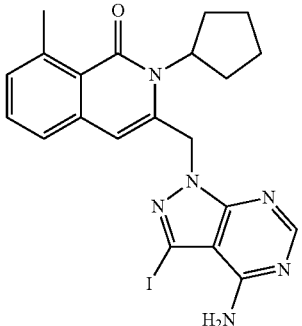
Compound 57
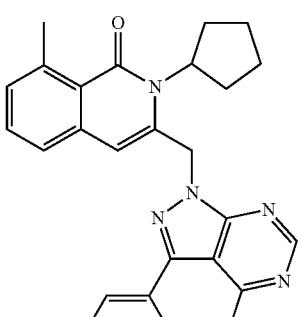
Compound 58
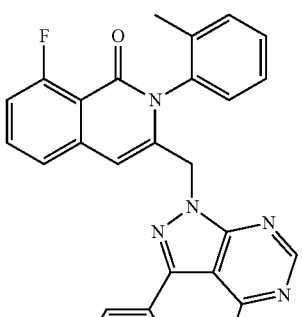
Compound 59
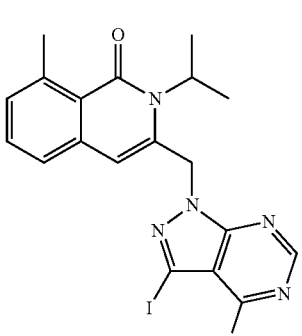
Compound 60
TABLE 5-continued
Structures of the Compounds for the IC50 results described in Table 4.
Structure
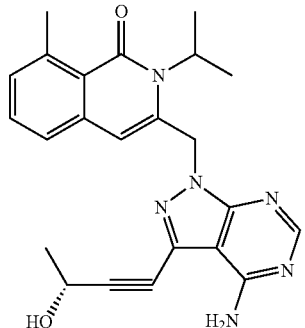
Compound 61
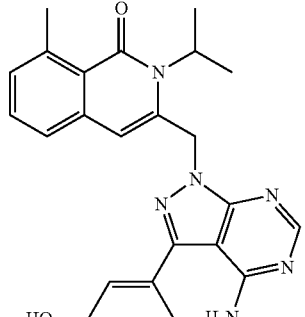
Compound 62
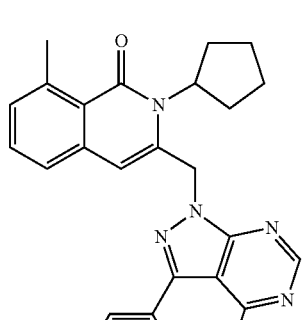
Compound 63

TABLE 5-continued
Structures of the Compounds for the IC50 results described in Table 4.
Structure
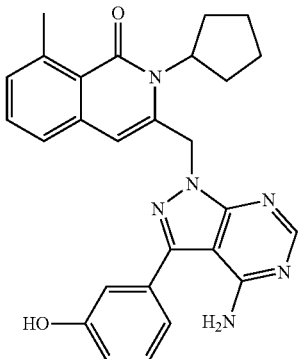
Compound 64
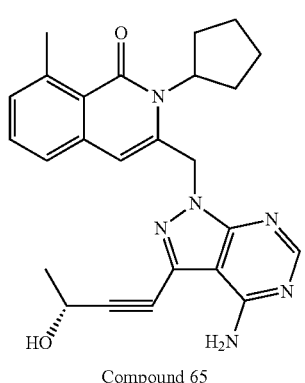 [SMILES: Cc1cccc2cc(Cn3nc(C#C[C@@H](C)O)c4c(N)ncnc43)n(C3CCCC3)c(=O)c12]
Compound 65
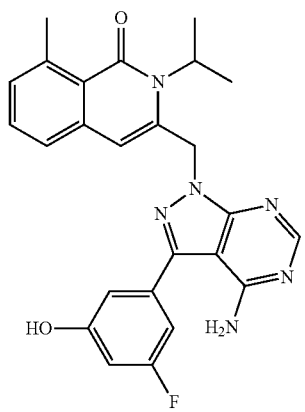
Compound 66
TABLE 5-continued
Structures of the Compounds for the IC50 results described in Table 4.
Structure
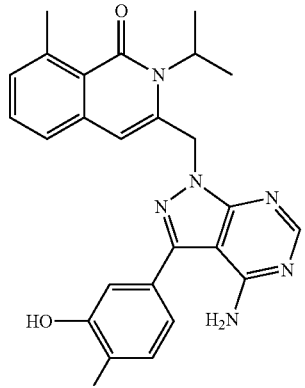
Compound 67
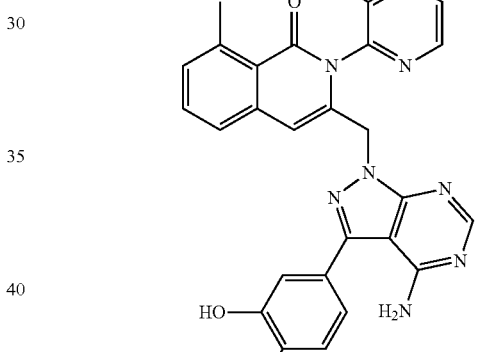
Compound 68
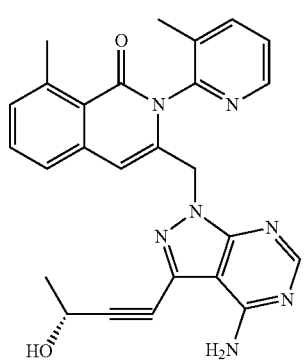
Compound 69

TABLE 5-continued
Structures of the Compounds for the IC50 results described in Table 4.
Structure
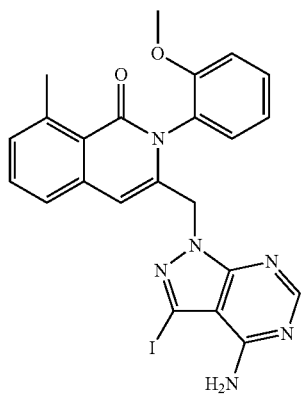
Compound 70
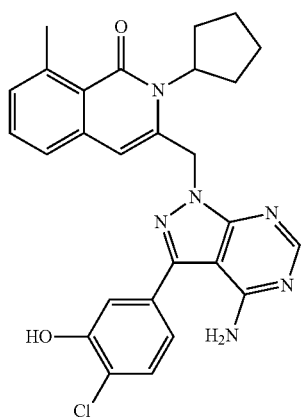
Compound 71
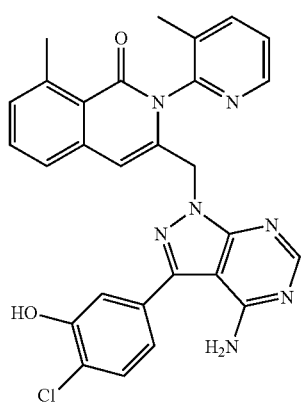
Compound 72
TABLE 5-continued
Structures of the Compounds for the IC50 results described in Table 4.
Structure
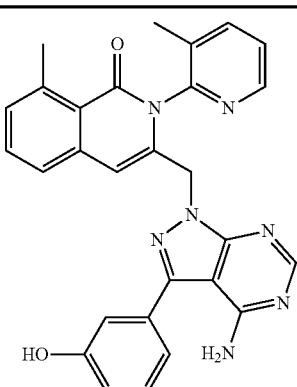
Compound 73
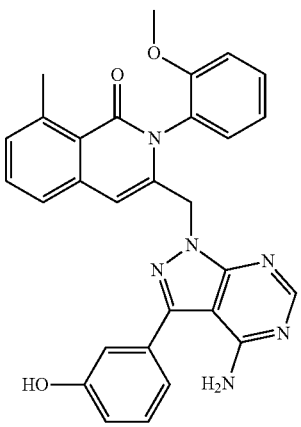
Compound 74
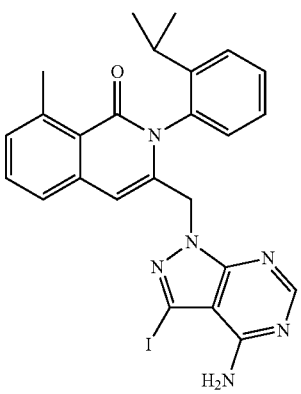
Compound 75

TABLE 5-continued

Structures of the Compounds for the IC50 results described in Table 4.

Compound 76

Compound 77

Compound 78

Compound 79

Compound 80

Compound 81

TABLE 5-continued
Structures of the Compounds for the IC50 results described in Table 4.
Structure
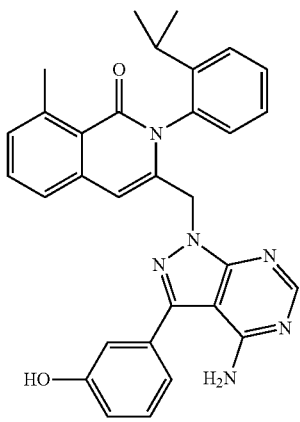
Compound 82
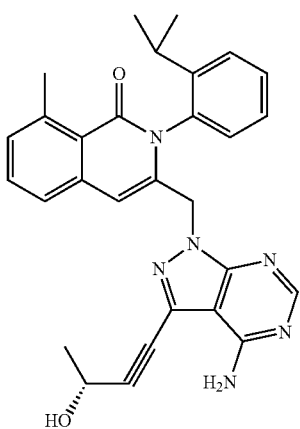
Compound 83
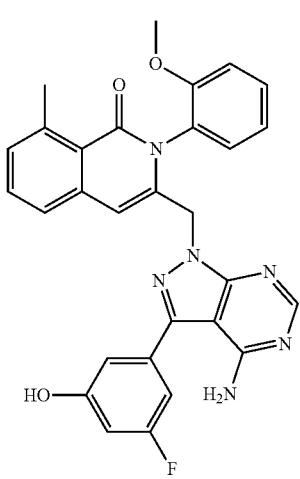
Compound 84
TABLE 5-continued
Structures of the Compounds for the IC50 results described in Table 4.
Structure
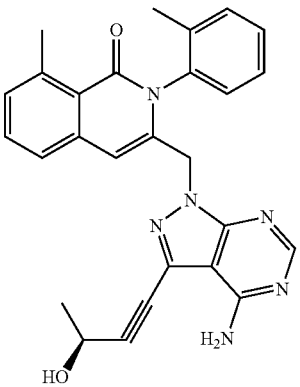
Compound 85
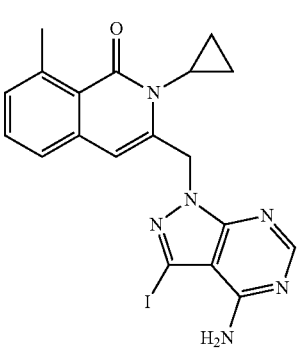
Compound 86
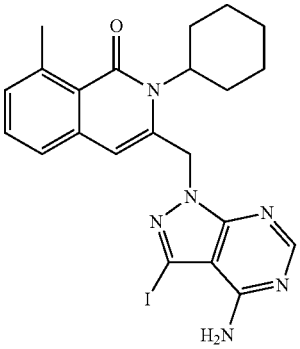
Compound 87

TABLE 5-continued

Structures of the Compounds for the IC50 results described in Table 4.

Structure

Compound 88

Compound 89

Compound 90

Compound 91

Compound 92

Compound 93

TABLE 5-continued
Structures of the Compounds for the IC50 results described in Table 4.
Structure
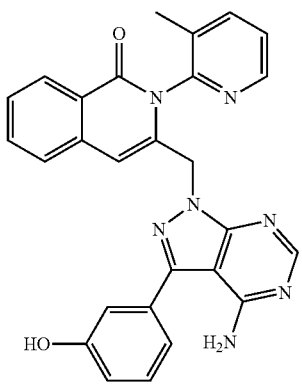
Compound 94
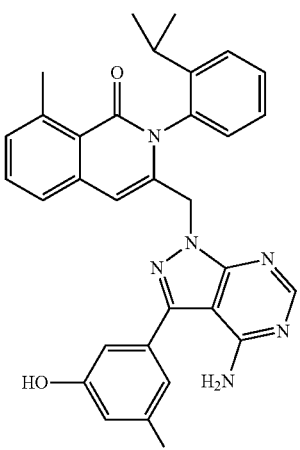
Compound 95
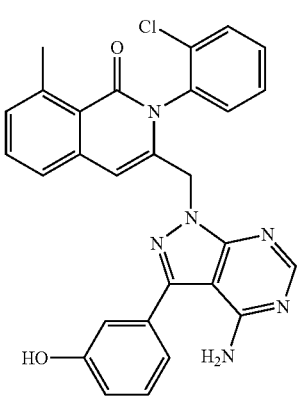
Compound 96
TABLE 5-continued
Structures of the Compounds for the IC50 results described in Table 4.
Structure
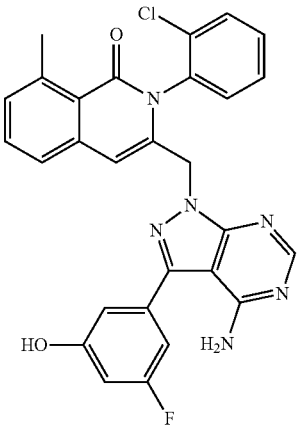
Compound 97
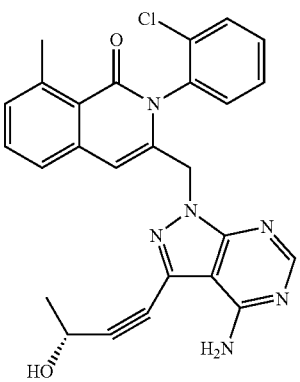
Compound 98
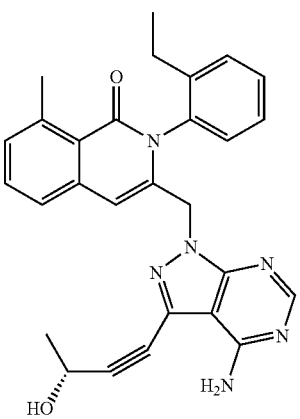
Compound 99

TABLE 5-continued
Structures of the Compounds for the IC50 results described in Table 4.
Structure
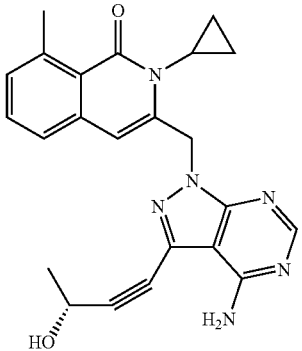
Compound 100
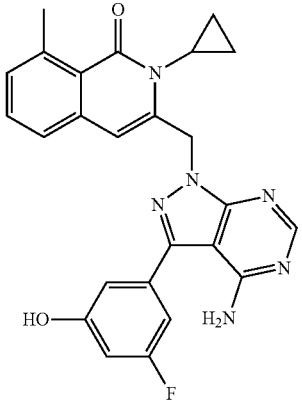
Compound 101
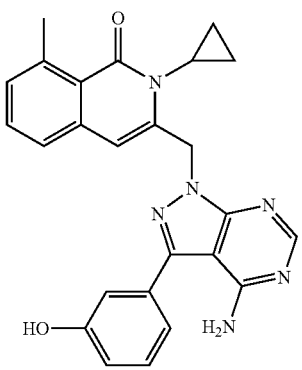
Compound 102
TABLE 5-continued
Structures of the Compounds for the IC50 results described in Table 4.
Structure
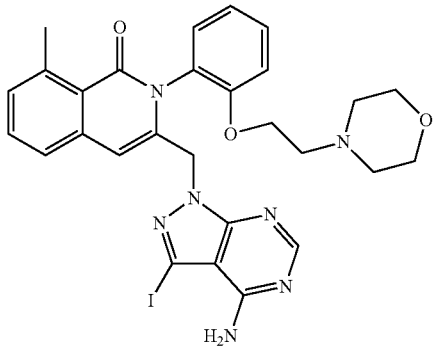
Compound 103
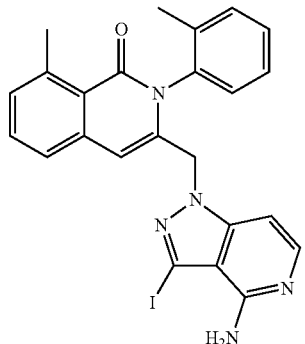
Compound 104
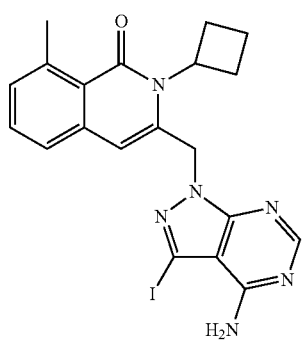
Compound 105
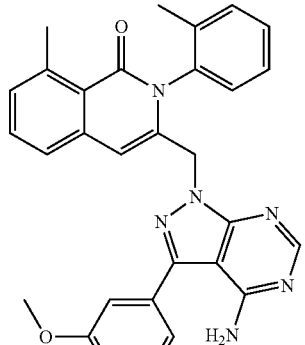
Compound 106

TABLE 5-continued
Structures of the Compounds for the IC50 results described in Table 4.
Structure
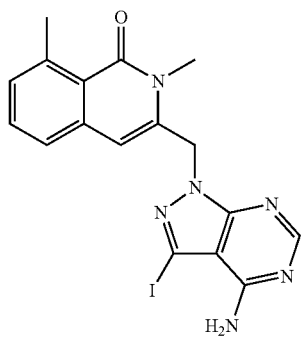
Compound 107
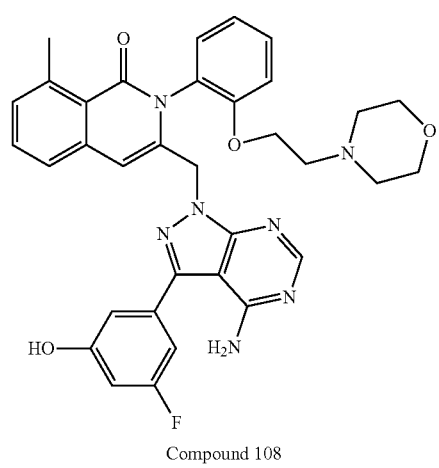 [SMILES: Cc1cccc2cc(Cn3nc(-c4cc(O)cc(F)c4)c4c(N)ncnc43)n(-c3ccccc3OCCN3CCOCC3)c(=O)c12]
Compound 108
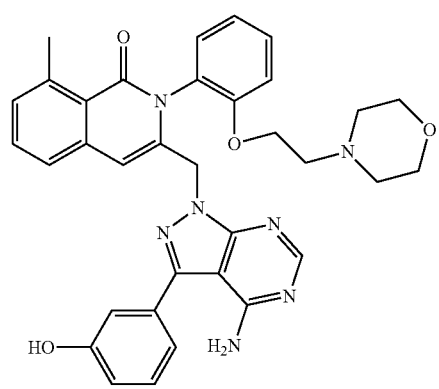
Compound 109
TABLE 5-continued
Structures of the Compounds for the IC50 results described in Table 4.
Structure
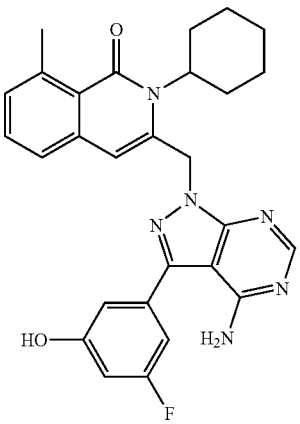
Compound 110
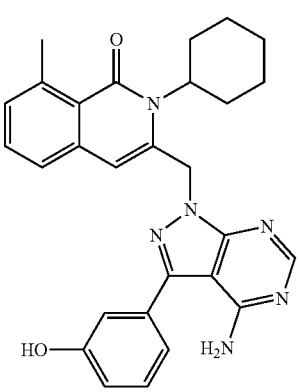
Compound 111
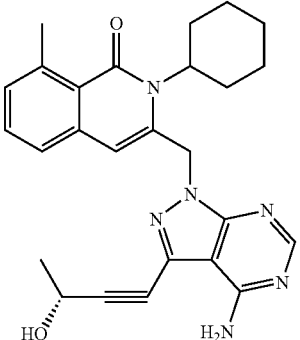
Compound 112

TABLE 5-continued
Structures of the Compounds for the IC50 results described in Table 4.
Structure
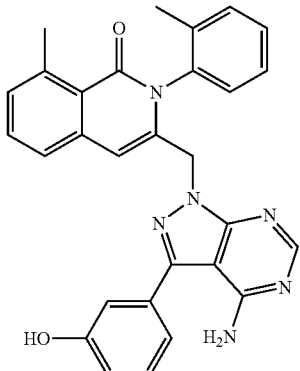
Compound 113
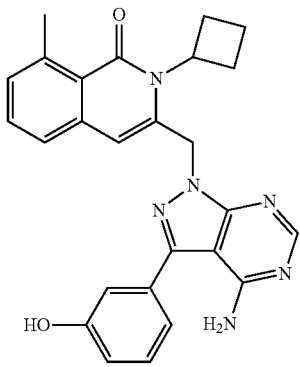
Compound 114
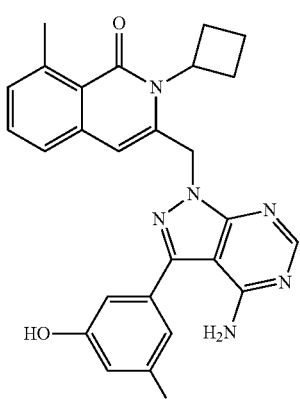
Compound 115
TABLE 5-continued
Structures of the Compounds for the IC50 results described in Table 4.
Structure
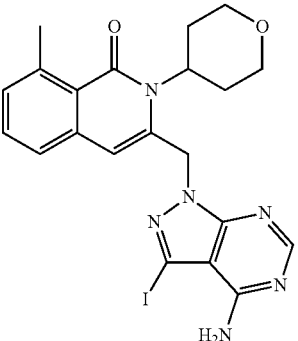
Compound 116
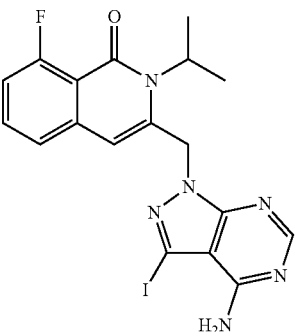
Compound 117
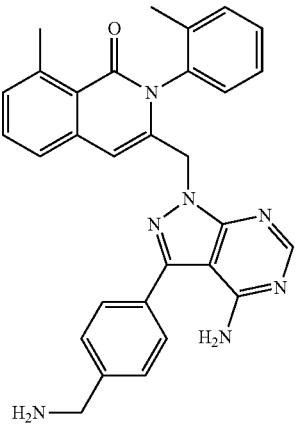
Compound 118

TABLE 5-continued
Structures of the Compounds for the IC50 results described in Table 4.
Structure
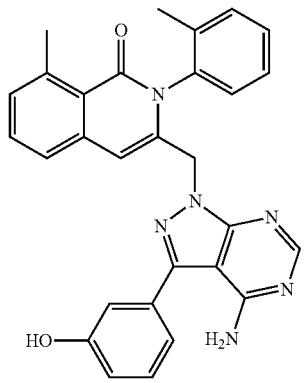
Compound 119
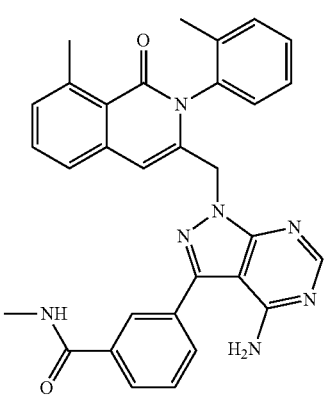
Compound 120
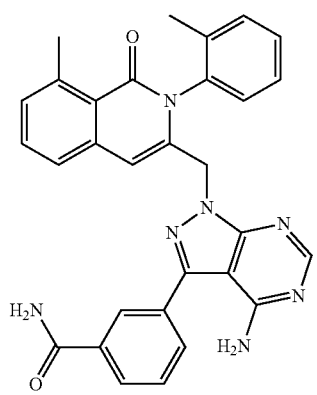
Compound 121
TABLE 5-continued
Structures of the Compounds for the IC50 results described in Table 4.
Structure
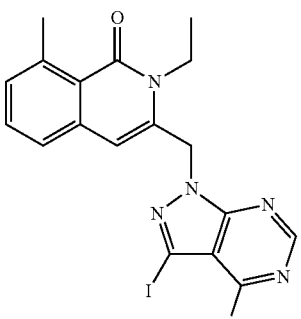
Compound 122
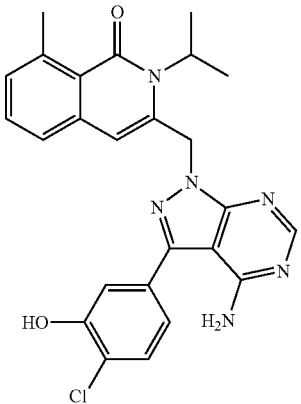
Compound 123
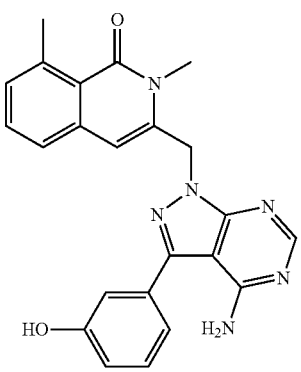
Compound 124

TABLE 5-continued
Structures of the Compounds for the IC50 results described in Table 4.
Structure
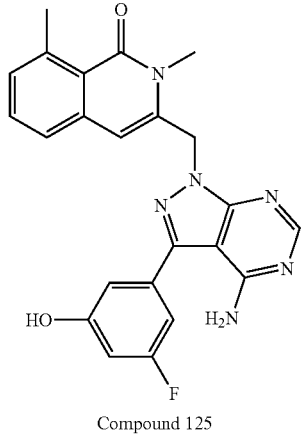 [SMILES: Cc1cccc2cc(Cn3nc(-c4cc(O)cc(F)c4)c4c(N)ncnc43)n(C)c(=O)c12]
Compound 125
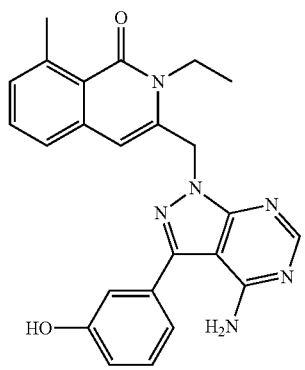
Compound 126
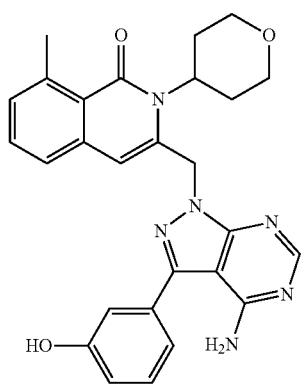
Compound 127
TABLE 5-continued
Structures of the Compounds for the IC50 results described in Table 4.
Structure
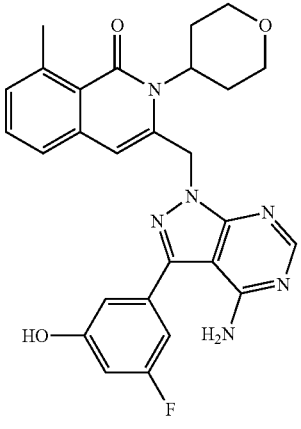
Compound 128
Compound 129
Compound 130

US 8,703,777 B2
263
TABLE 5-continued
Structures of the Compounds for the IC50 results described in Table 4.
Structure
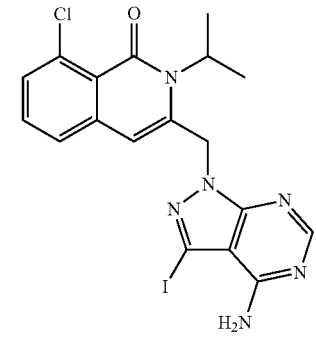
Compound 131
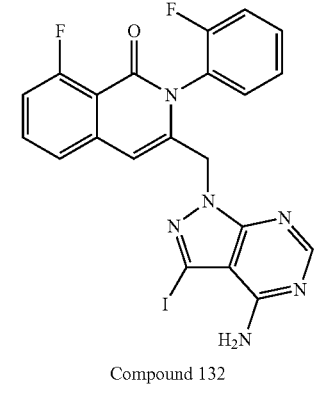 [SMILES: Nc1ncnc2c1c(I)nn2Cc1cc2cccc(F)c2c(=O)n1-c1ccccc1F]
Compound 132
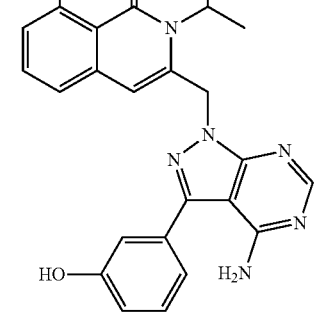
Compound 133
264
TABLE 5-continued
Structures of the Compounds for the IC50 results described in Table 4.
Structure
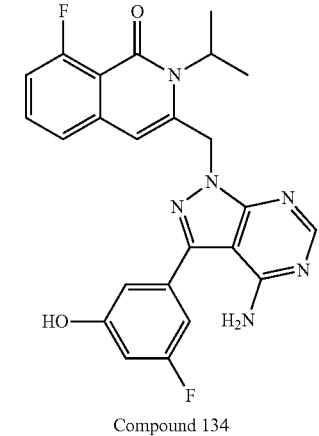 [SMILES: CC(C)n1c(Cn2nc(-c3cc(O)cc(F)c3)c3c(N)ncnc32)cc2cccc(Cl)c2c1=O]
Compound 134
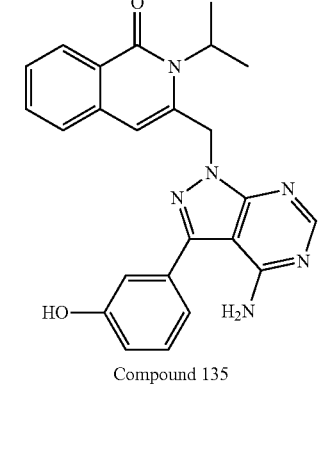
Compound 135
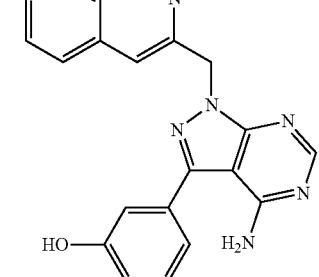
Compound 136

TABLE 5-continued
Structures of the Compounds for the IC50 results described in Table 4.
Structure
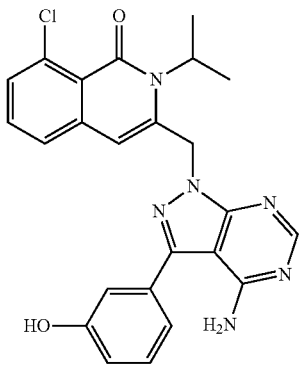
Compound 137
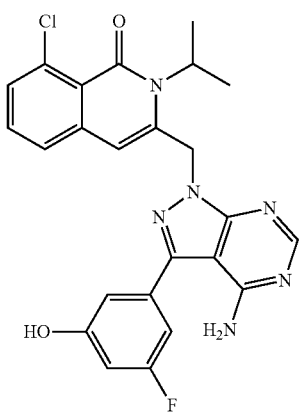
Compound 138
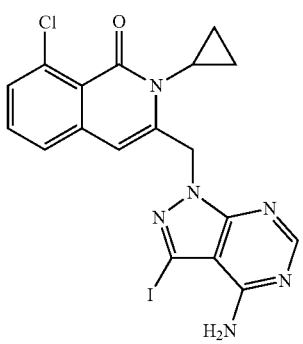
Compound 139
TABLE 5-continued
Structures of the Compounds for the IC50 results described in Table 4.
Structure
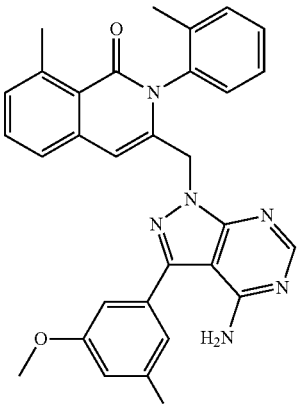
Compound 140
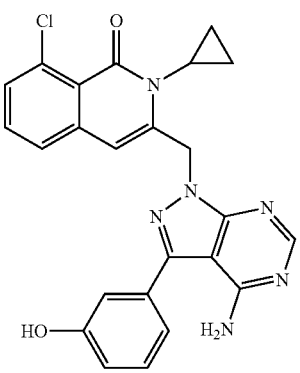
Compound 141
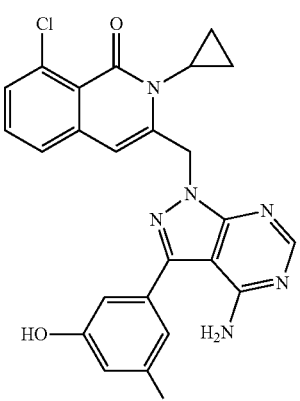
Compound 142

TABLE 5-continued
Structures of the Compounds for the IC50 results described in Table 4.
Structure
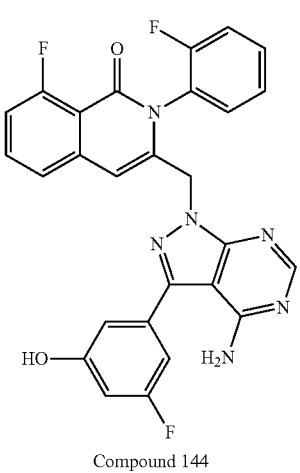 [SMILES: Nc1ncnc2c1c(-c1cc(O)cc(F)c1)nn2Cc1cc2cccc(F)c2c(=O)n1-c1ccccc1F]
Compound 143
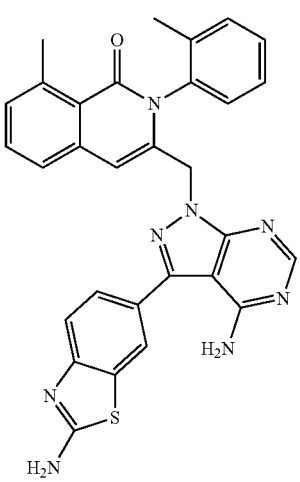
Compound 144
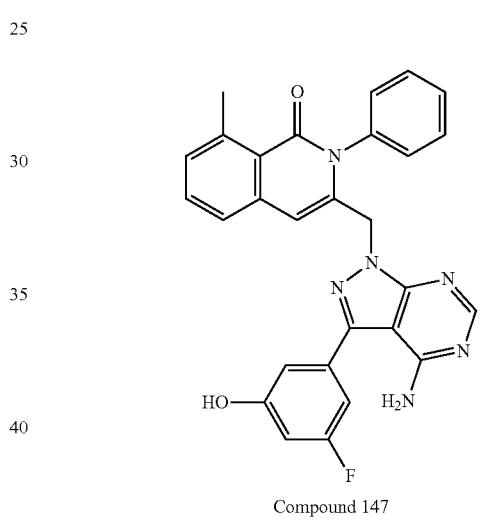
Compound 145
TABLE 5-continued
Structures of the Compounds for the IC50 results described in Table 4.
Structure
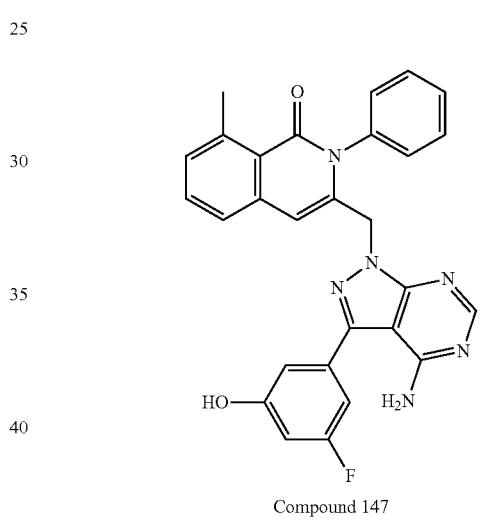
Compound 146
Compound 147
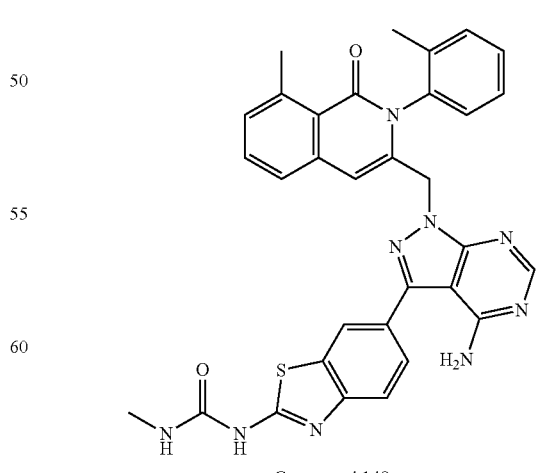
Compound 148

TABLE 5-continued
Structures of the Compounds for the IC50 results described in Table 4.
Structure
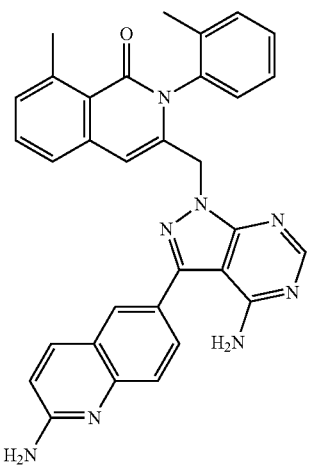
Compound 149
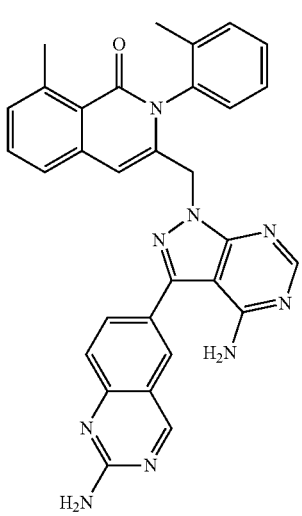
Compound 150
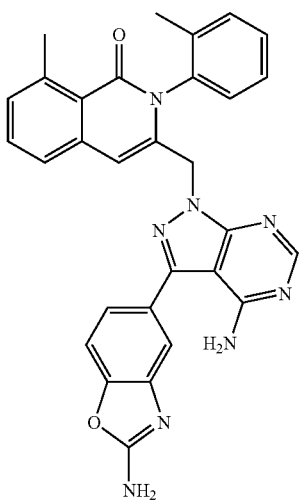
Compound 151
TABLE 5-continued
Structures of the Compounds for the IC50 results described in Table 4.
Structure
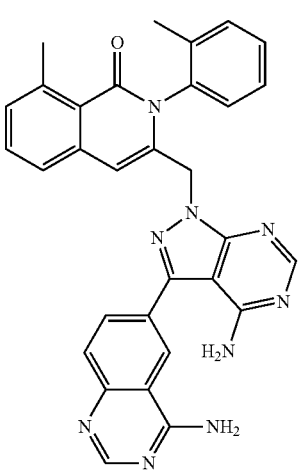
Compound 152
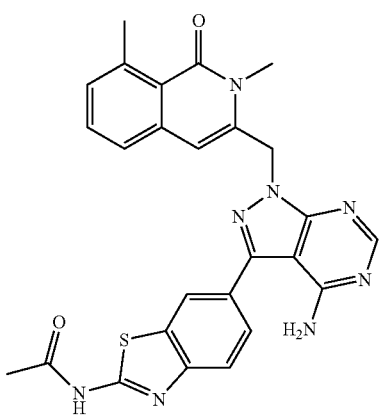
Compound 153
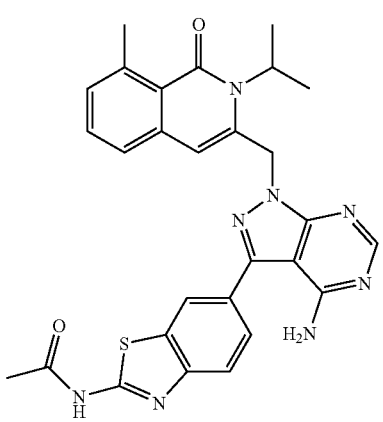
Compound 154

TABLE 5-continued
Structures of the Compounds for the IC50 results described in Table 4.
Structure
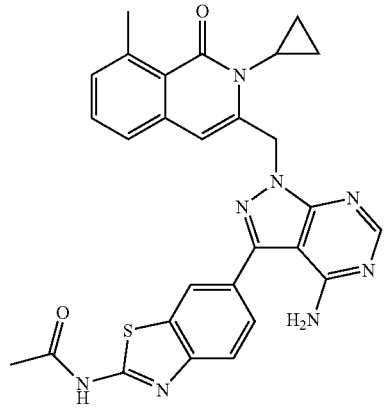
Compound 155
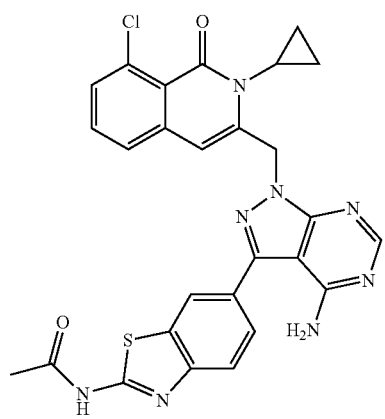
Compound 156
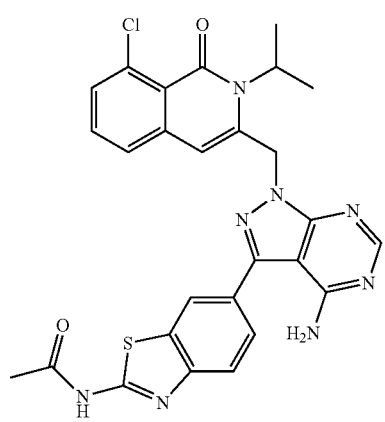
Compound 157
TABLE 5-continued
Structures of the Compounds for the IC50 results described in Table 4.
Structure
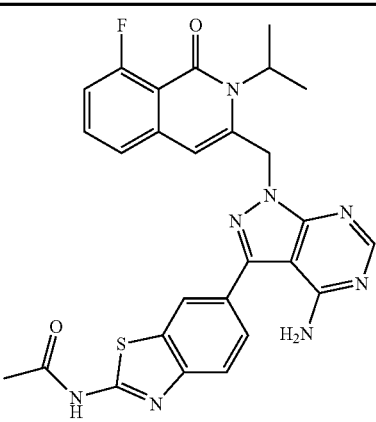
Compound 158
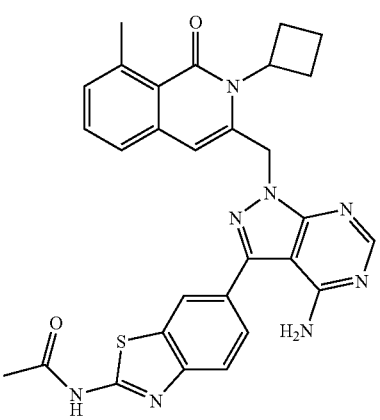
Compound 159
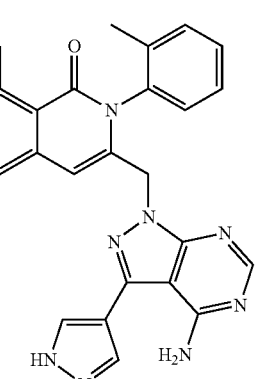
Compound 160

TABLE 5-continued
Structures of the Compounds for the IC50 results described in Table 4.
Structure
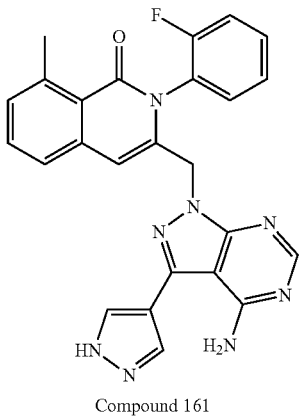 [SMILES: Cc1cccc2cc(Cn3nc(-c4cn[nH]c4)c4c(N)ncnc43)n(-c3ccccc3F)c(=O)c12]
Compound 161
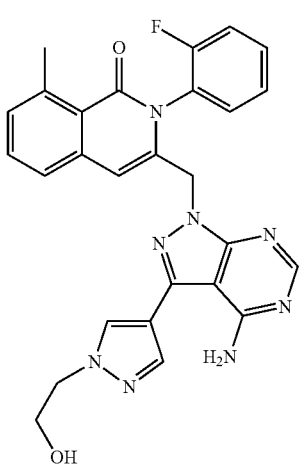
Compound 162
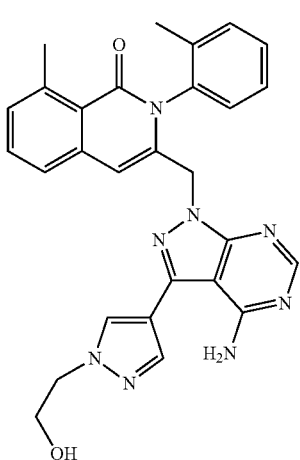
Compound 163
TABLE 5-continued
Structures of the Compounds for the IC50 results described in Table 4.
Structure
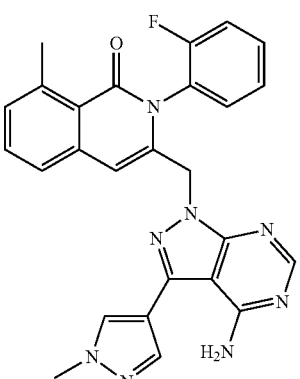
Compound 164
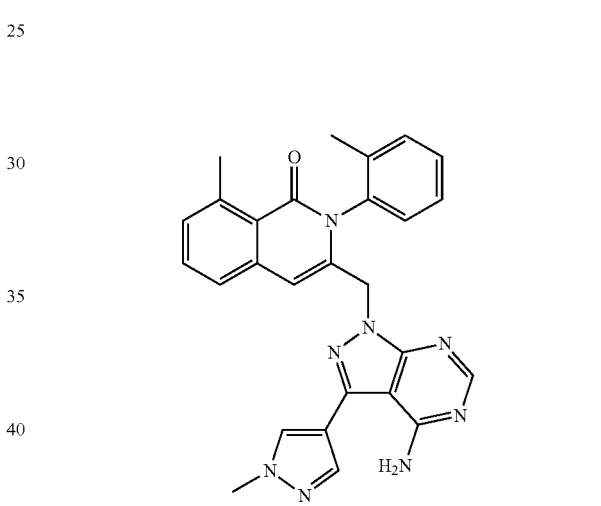
Compound 165
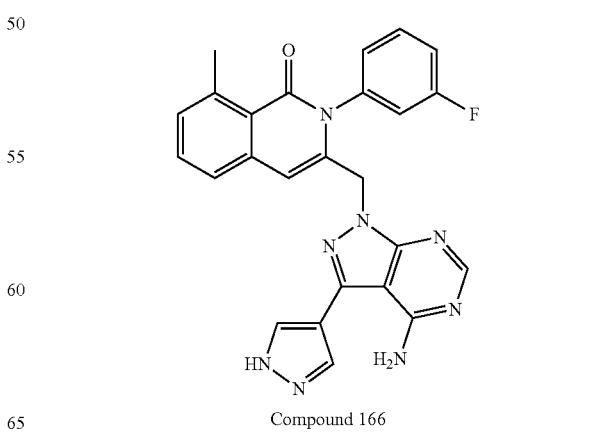
Compound 166

TABLE 5-continued
Structures of the Compounds for the IC50 results described in Table 4.
Structure
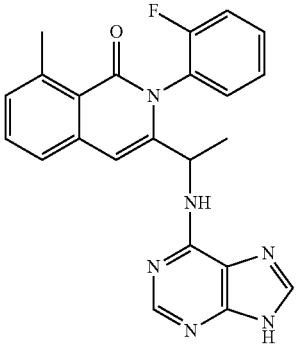
Compound 167
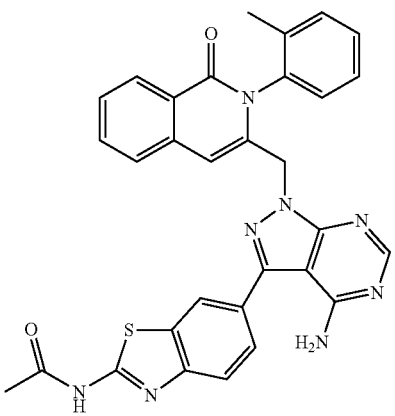
Compound 168
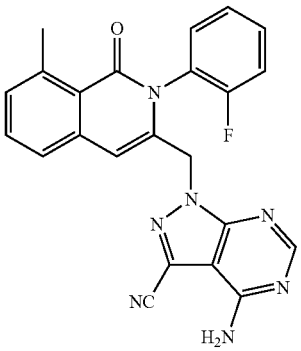
Compound 169
TABLE 5-continued
Structures of the Compounds for the IC50 results described in Table 4.
Structure
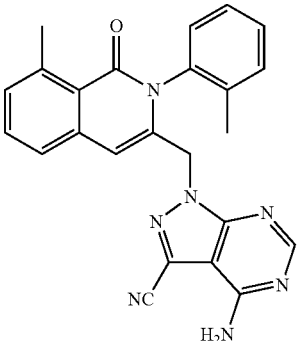
Compound 170
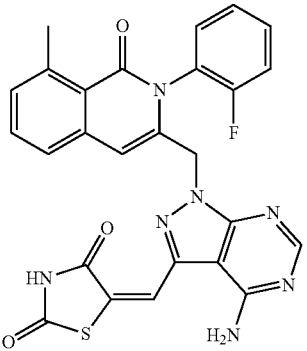
Compound 171
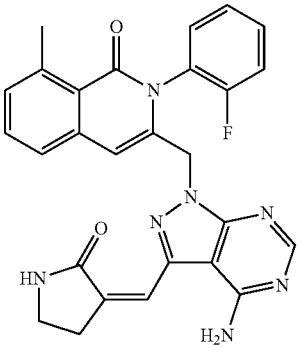
Compound 172
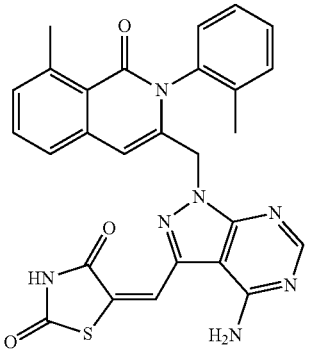
Compound 173

TABLE 5-continued
Structures of the Compounds for the IC50 results described in Table 4.
Structure
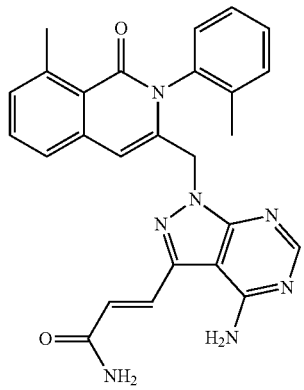
Compound 174
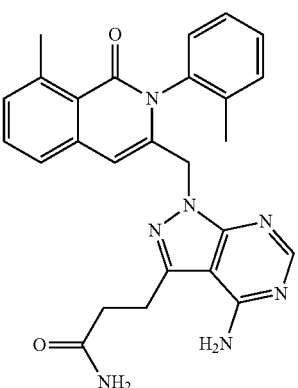
Compound 175
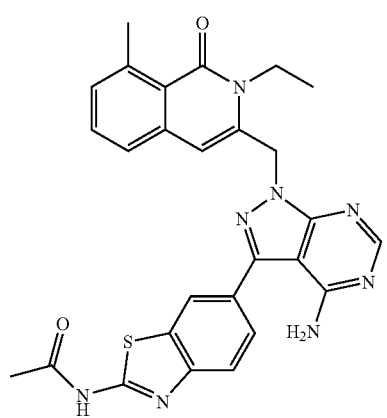
Compound 176
TABLE 5-continued
Structures of the Compounds for the IC50 results described in Table 4.
Structure
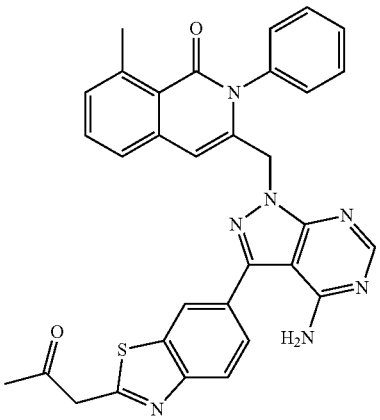
Compound 177
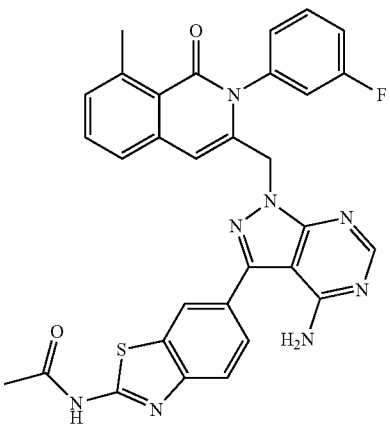
Compound 178
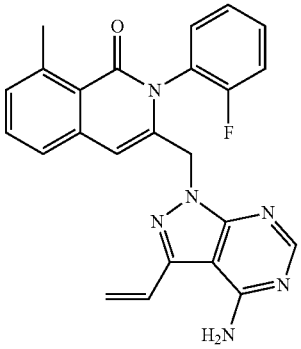
Compound 179

TABLE 5-continued
Structures of the Compounds for the IC50 results described in Table 4.
Structure
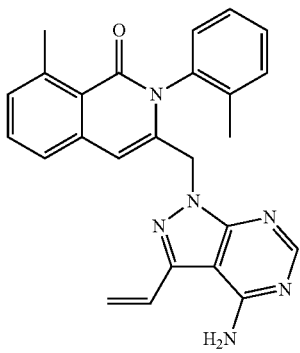
Compound 180
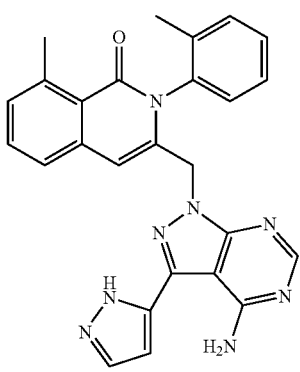
Compound 183
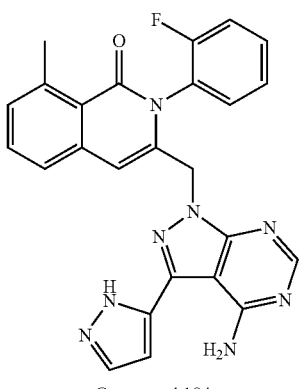
Compound 184
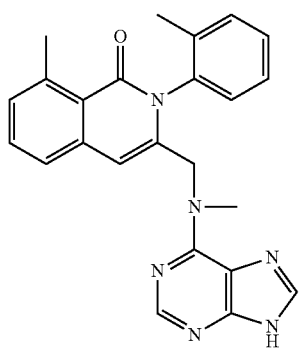
Compound 188
TABLE 5-continued
Structures of the Compounds for the IC50 results described in Table 4.
Structure
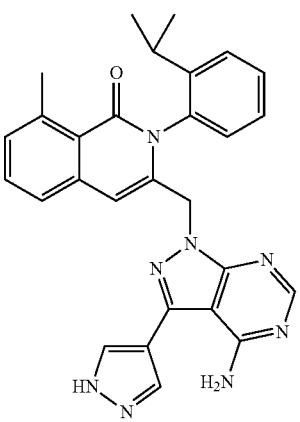
Compound 189
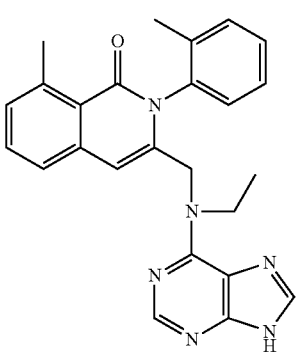
Compound 190
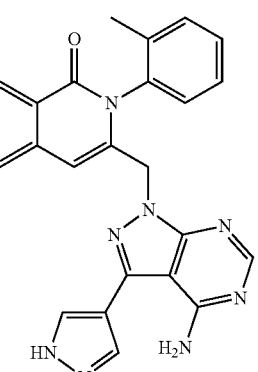
Compound 191

TABLE 5-continued
Structures of the Compounds for the IC50 results described in Table 4.
Structure
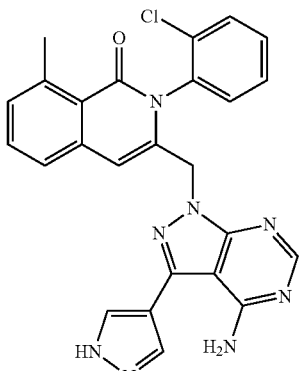
Compound 192
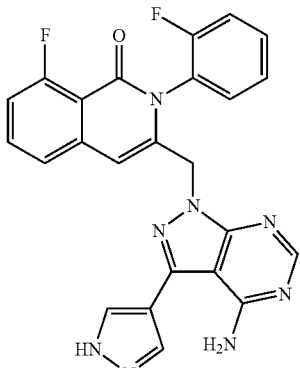
Compound 193
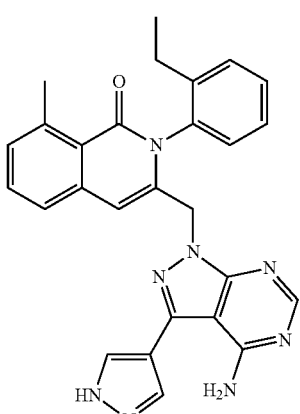
Compound 194
TABLE 5-continued
Structures of the Compounds for the IC50 results described in Table 4.
Structure
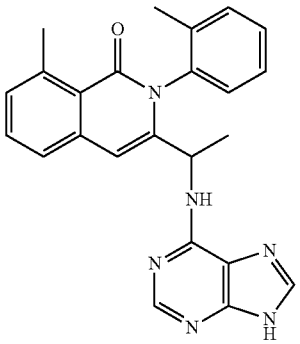
Compound 195
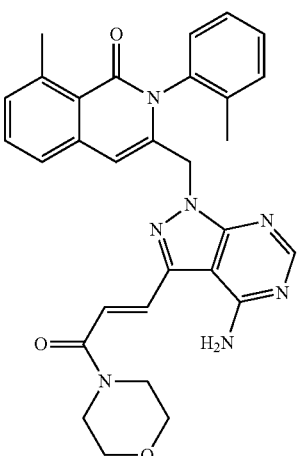
Compound 196
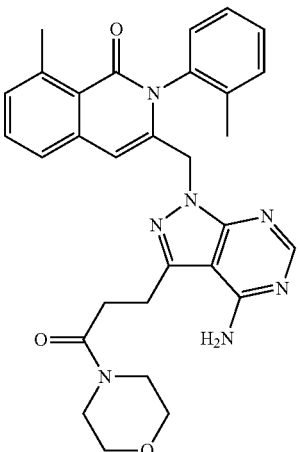
Compound 197

TABLE 5-continued
Structures of the Compounds for the IC50 results described in Table 4.
Structure
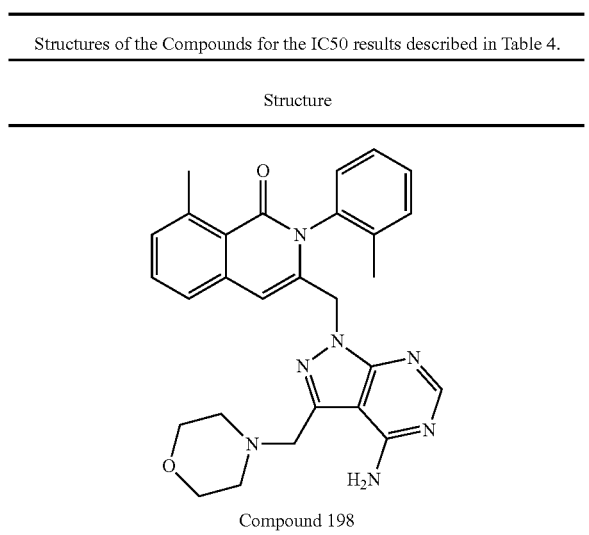
Compound 198
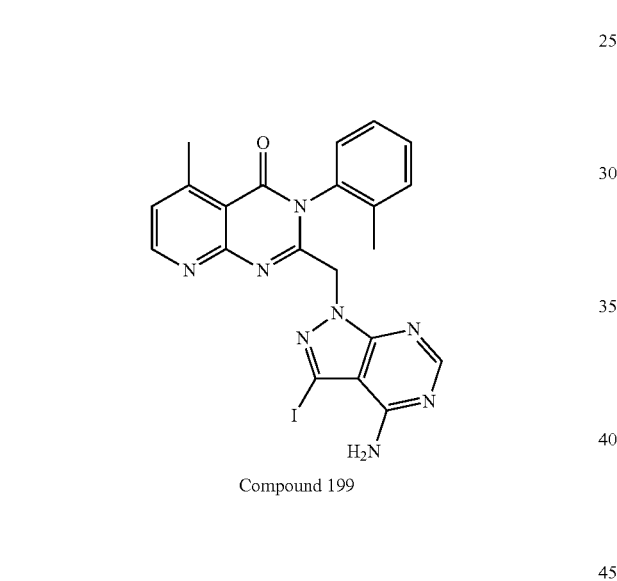
Compound 199
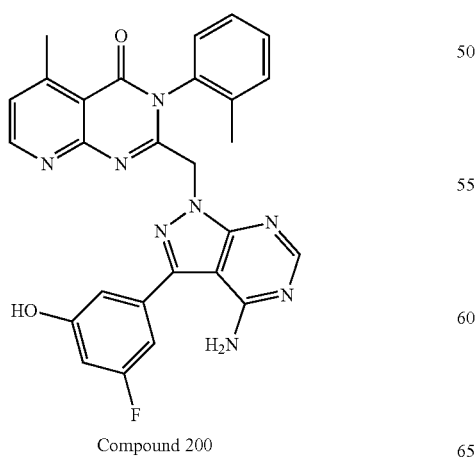
Compound 200
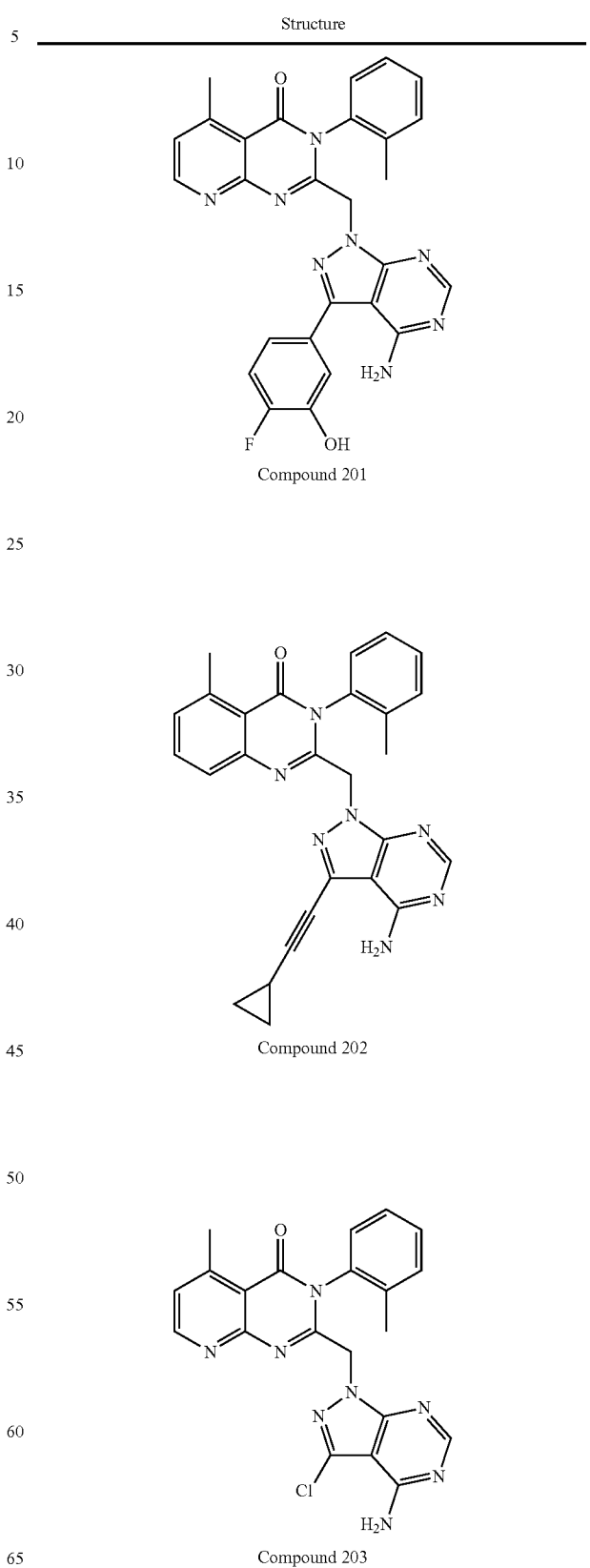
Compound 201
Compound 202
Compound 203

TABLE 5-continued
Structures of the Compounds for the IC50 results described in Table 4.
Structure
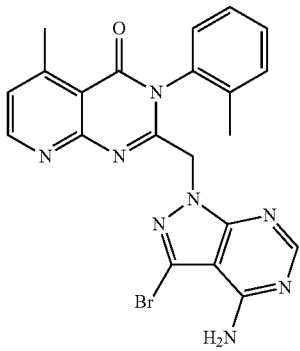
Compound 204
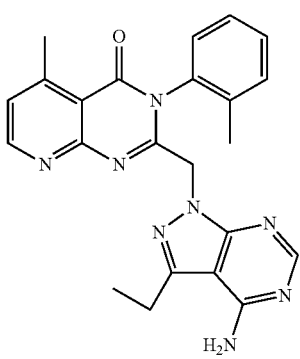
Compound 205
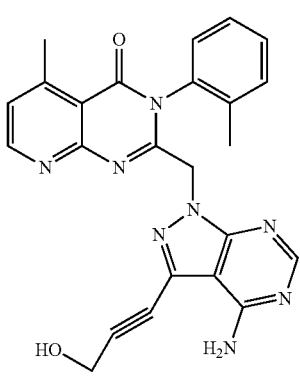
Compound 206
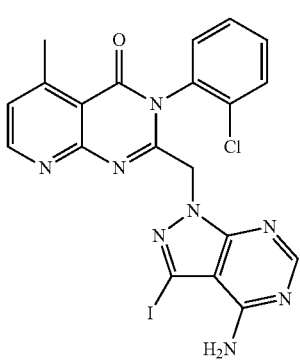
Compound 207
TABLE 5-continued
Structures of the Compounds for the IC50 results described in Table 4.
Structure
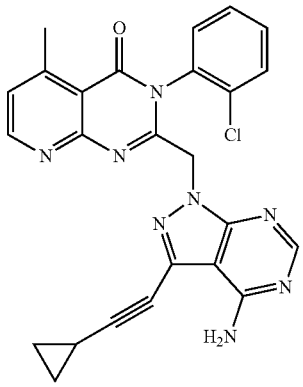
Compound 208
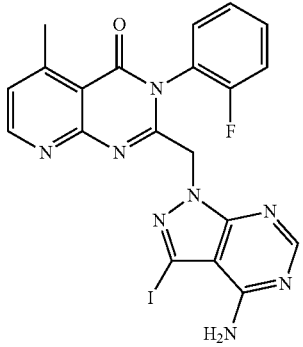
Compound 209
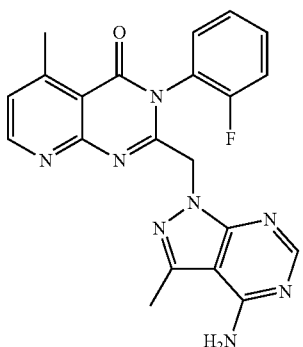
Compound 210

TABLE 5-continued
Structures of the Compounds for the IC50 results described in Table 4.
Structure
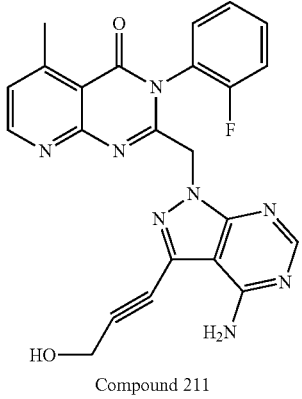 [SMILES: Cc1ccnc2nc(Cn3nc(C#CCO)c4c(N)ncnc43)n(-c3ccccc3F)c(=O)c12]
Compound 211
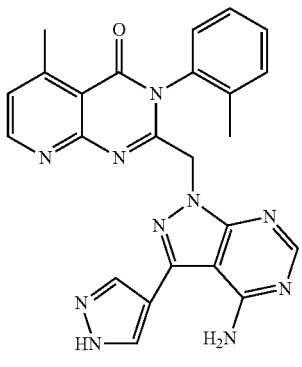
Compound 212
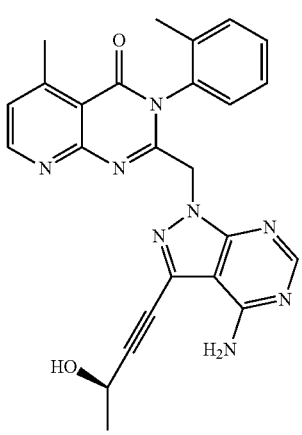
Compound 213
TABLE 5-continued
Structures of the Compounds for the IC50 results described in Table 4.
Structure
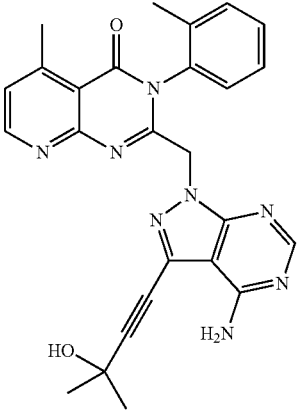
Compound 214
Compound 215
Compound 216

TABLE 5-continued
Structures of the Compounds for the IC50 results described in Table 4.
Structure
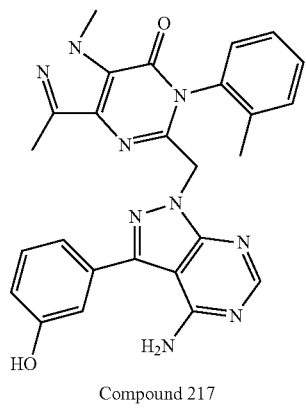 [SMILES: CNc1c(C(C)=N)nc(Cn2nc(-c3cccc(O)c3)c3c(N)ncnc32)n(-c2ccccc2C)c1=O]
Compound 217
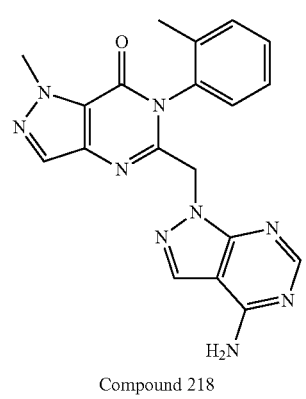 [SMILES: Cc1ccccc1-n1c(Cn2ncc3c(N)ncnc32)nc2cnn(C)c2c1=O]
Compound 218
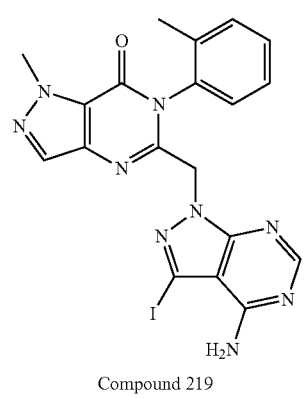 [SMILES: Cc1ccccc1-n1c(Cn2nc(I)c3c(N)ncnc32)nc2cnn(C)c2c1=O]
Compound 219
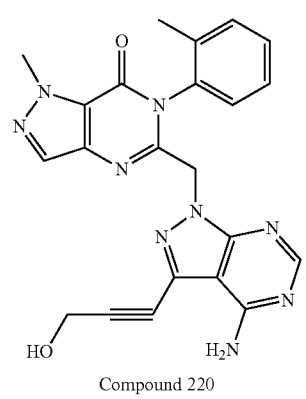 [SMILES: Cc1ccccc1-n1c(Cn2nc(C#CCO)c3c(N)ncnc32)nc2cnn(C)c2c1=O]
Compound 220
TABLE 5-continued
Structures of the Compounds for the IC50 results described in Table 4.
Structure
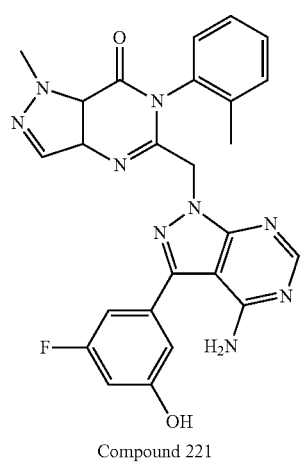 [SMILES: Cc1ccccc1N1C(=O)C2C(C=NN2C)N=C1Cn1nc(-c2cc(O)cc(F)c2)c2c(N)ncnc21]
Compound 221
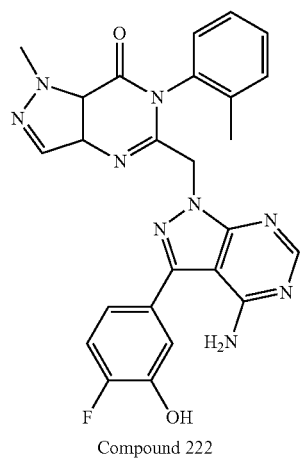 [SMILES: Cc1ccccc1N1C(=O)C2C(C=NN2C)N=C1Cn1nc(-c2ccc(F)c(O)c2)c2c(N)ncnc21]
Compound 222
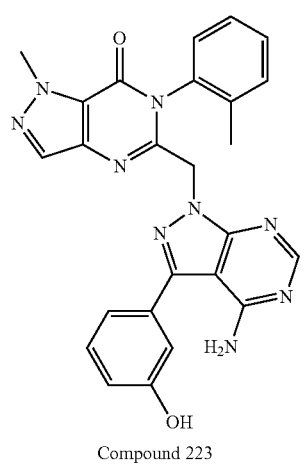 [SMILES: Cc1ccccc1-n1c(Cn2nc(-c3cccc(O)c3)c3c(N)ncnc32)nc2cnn(C)c2c1=O]
Compound 223

TABLE 5-continued

Structures of the Compounds for the IC50 results described in Table 4.

Structure

Compound 224

Compound 225

Compound 226

TABLE 5-continued

Structures of the Compounds for the IC50 results described in Table 4.

Structure

Compound 227

Compound 228

Compound 229

TABLE 5-continued
Structures of the Compounds for the IC50 results described in Table 4.
Structure
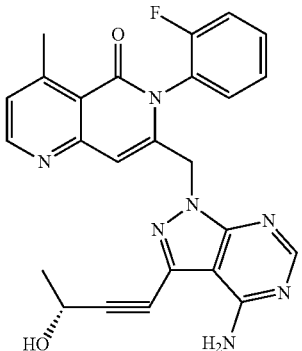
Compound 230
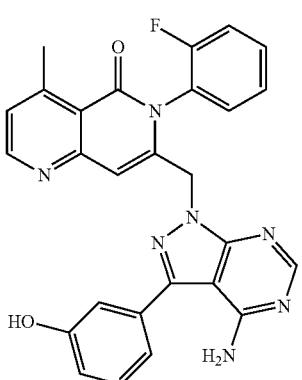
Compound 231
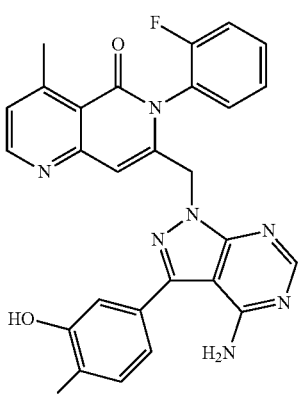
Compound 232
TABLE 5-continued
Structures of the Compounds for the IC50 results described in Table 4.
Structure
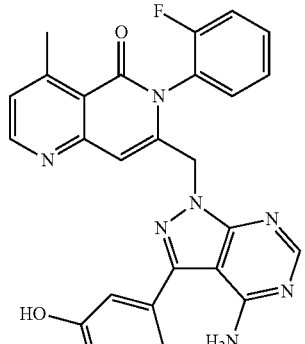
Compound 233
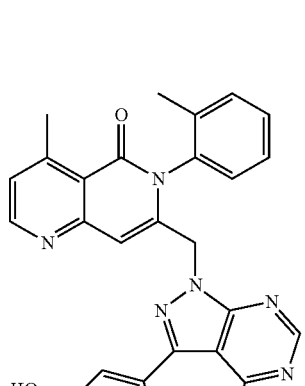
Compound 234
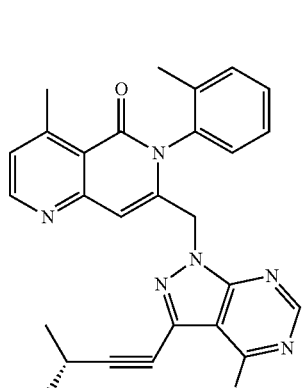
Compound 235

TABLE 5-continued
Structures of the Compounds for the IC50 results described in Table 4.
Structure
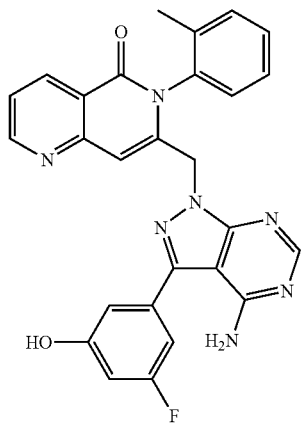
Compound 236
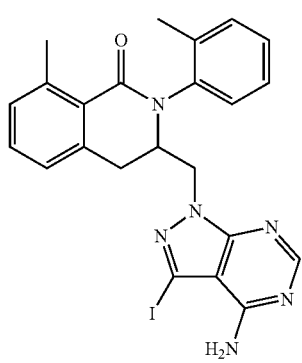
Compound 237
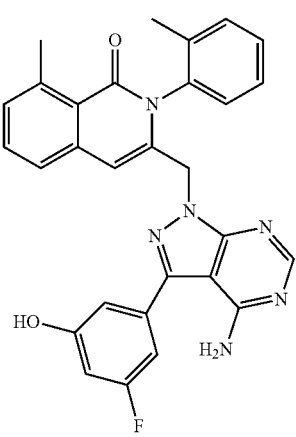
Compound 238
TABLE 5-continued
Structures of the Compounds for the IC50 results described in Table 4.
Structure
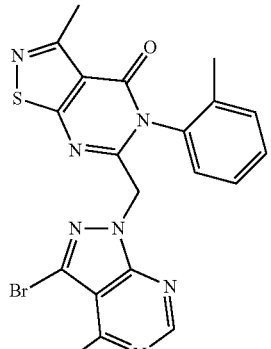
Compound 239
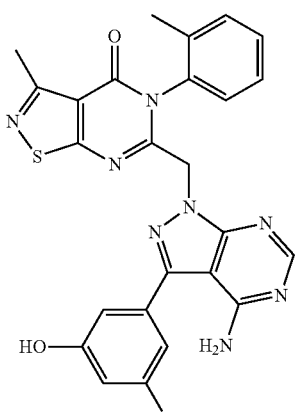
Compound 240
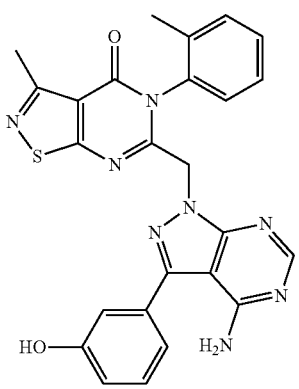
Compound 241

TABLE 5-continued
Structures of the Compounds for the IC50 results described in Table 4.
Structure
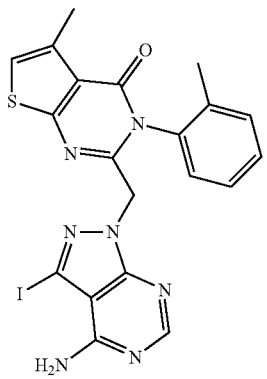
Compound 242
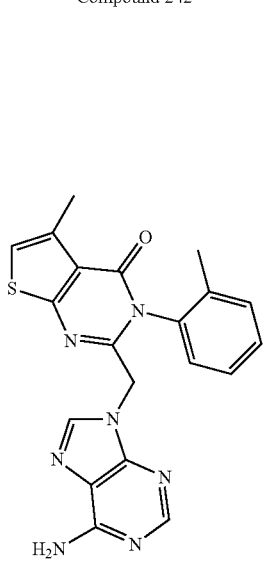
Compound 243
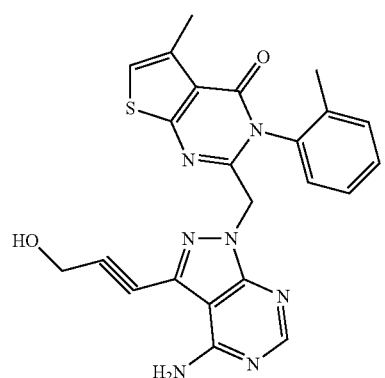
Compound 244
TABLE 5-continued
Structures of the Compounds for the IC50 results described in Table 4.
Structure
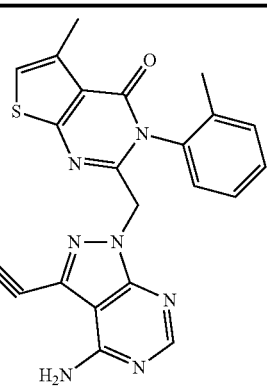
Compound 245
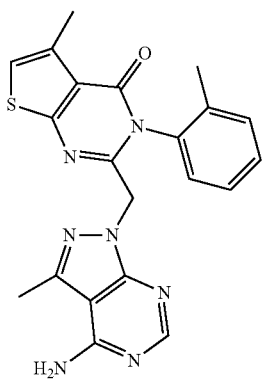
Compound 246
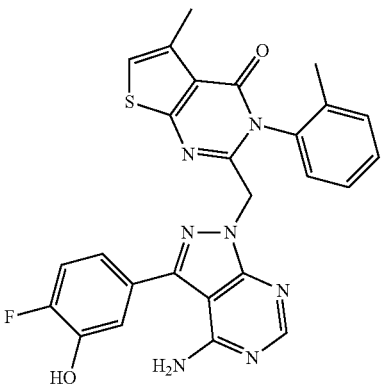
Compound 247

US 8,703,777 B2
299
TABLE 5-continued
Structures of the Compounds for the IC50 results described in Table 4.
Structure
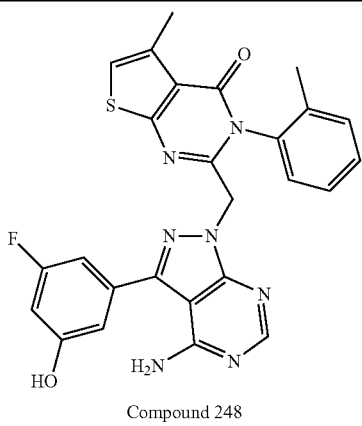
Compound 248
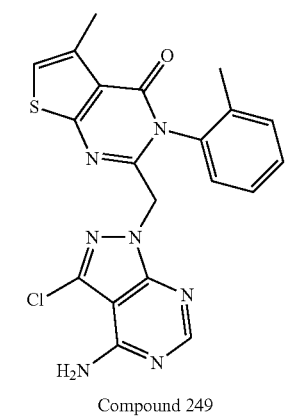 [SMILES: Cc1ccccc1-n1c(Cn2nc(Cl)c3c(N)ncnc32)nc2scc(C)c2c1=O]
Compound 249
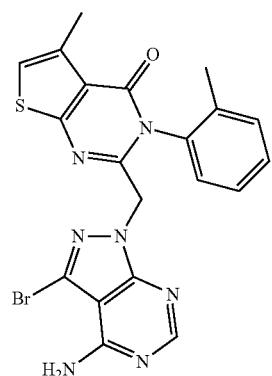
Compound 250
300
TABLE 5-continued
Structures of the Compounds for the IC50 results described in Table 4.
Structure
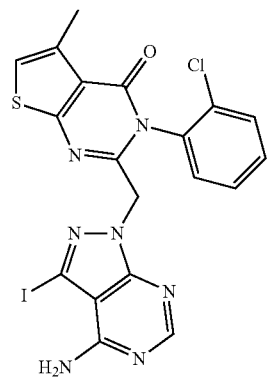
Compound 251
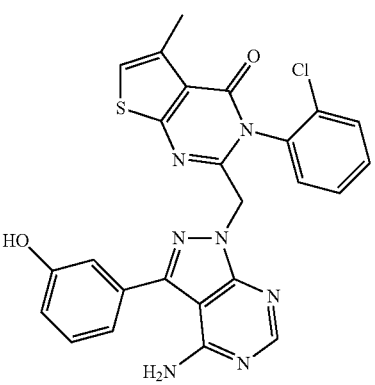
Compound 252
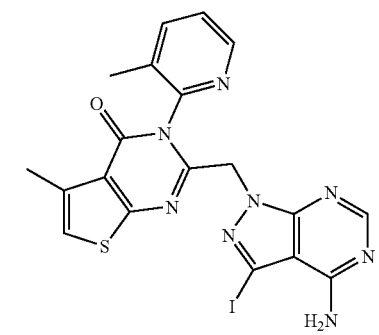
Compound 253

TABLE 5-continued
Structures of the Compounds for the IC50 results described in Table 4.
Structure
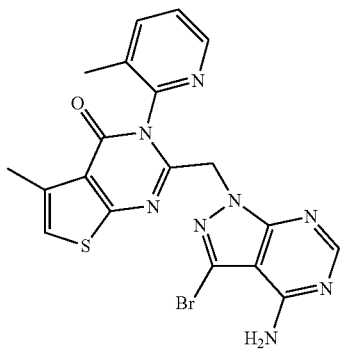
Compound 254
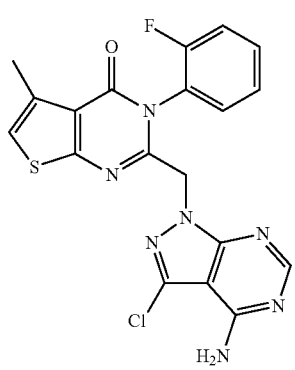
Compound 255
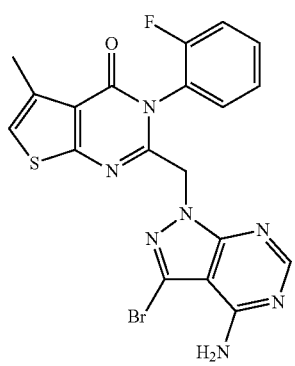
Compound 256
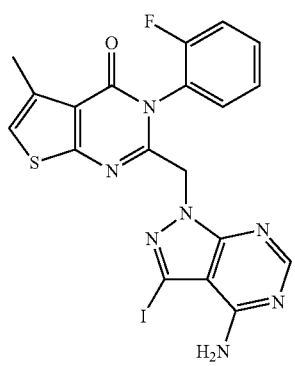
Compound 257
TABLE 5-continued
Structures of the Compounds for the IC50 results described in Table 4.
Structure
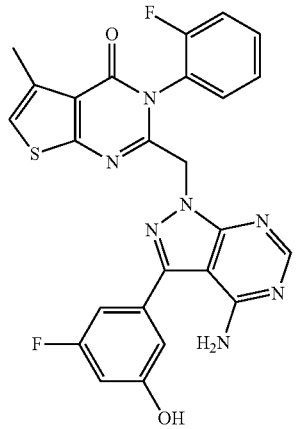
Compound 258
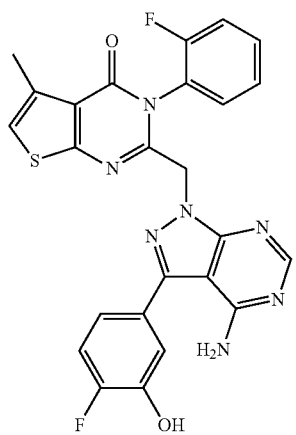
Compound 259
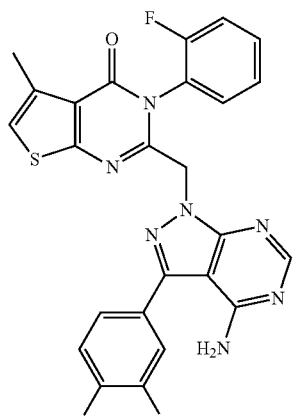
Compound 260

TABLE 5-continued
Structures of the Compounds for the IC50 results described in Table 4.
Structure
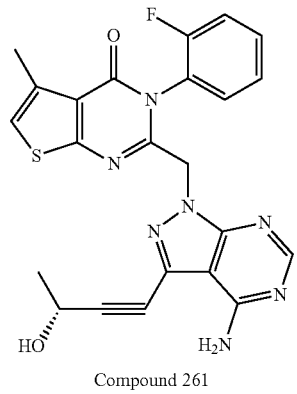 [SMILES: Cc1csc2nc(Cn3nc(C#C[C@@H](C)O)c4c(N)ncnc43)n(-c3ccccc3F)c(=O)c12]
Compound 261
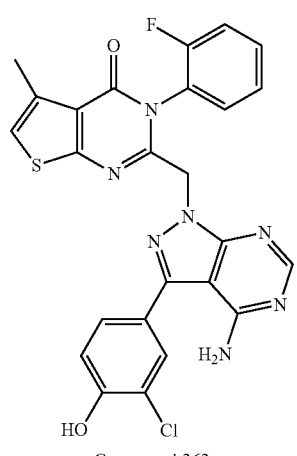
Compound 262
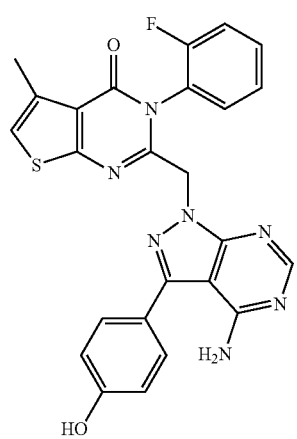
Compound 263
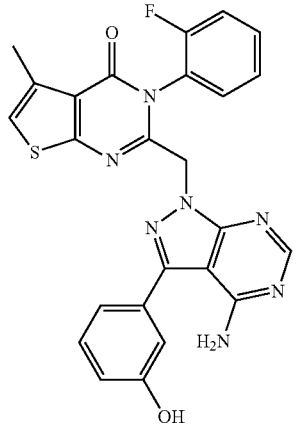
Compound 264
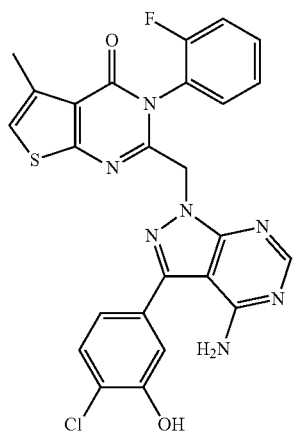
Compound 265
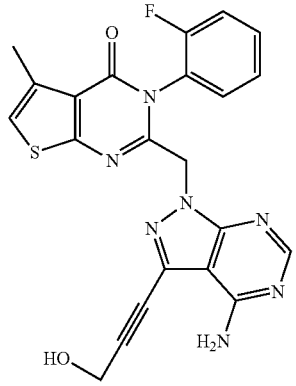
Compound 266

TABLE 5-continued
Structures of the Compounds for the IC50 results described in Table 4.
Structure
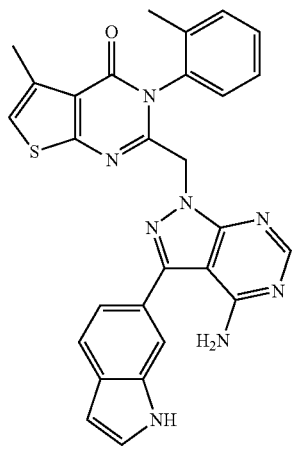
Compound 267
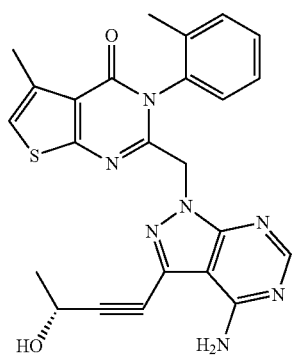
Compound 268
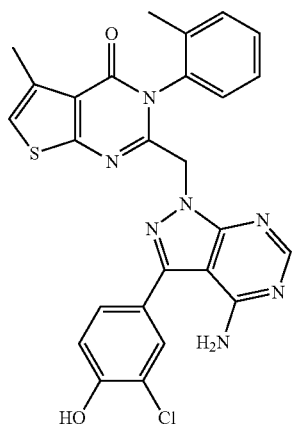
Compound 269
TABLE 5-continued
Structures of the Compounds for the IC50 results described in Table 4.
Structure
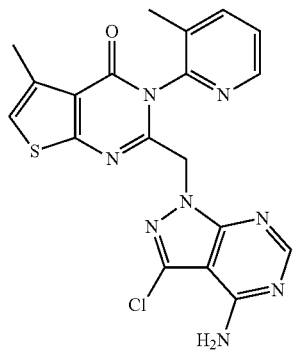
Compound 270
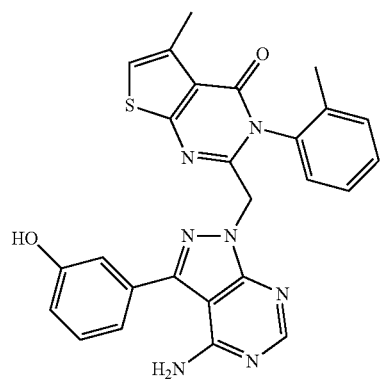
Compound 271
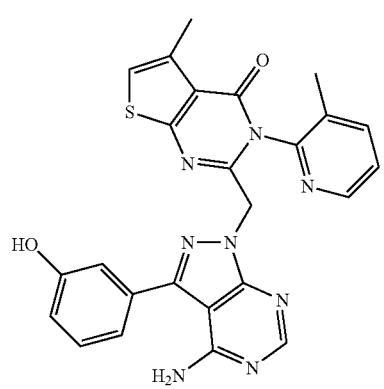
Compound 272

TABLE 5-continued
Structures of the Compounds for the IC50 results described in Table 4.
Structure
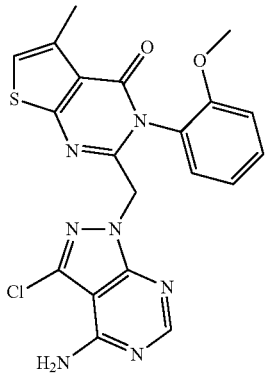
Compound 273
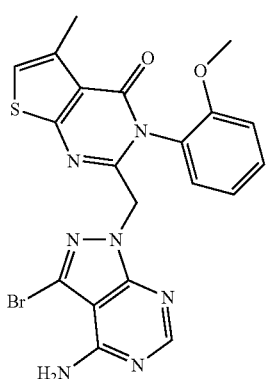
Compound 274
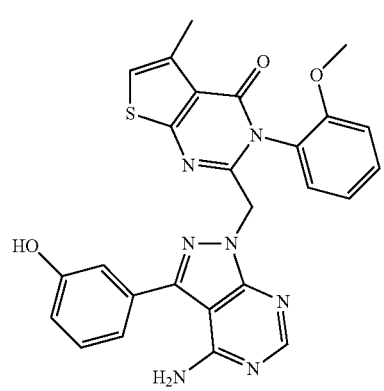
Compound 275
TABLE 5-continued
Structures of the Compounds for the IC50 results described in Table 4.
Structure
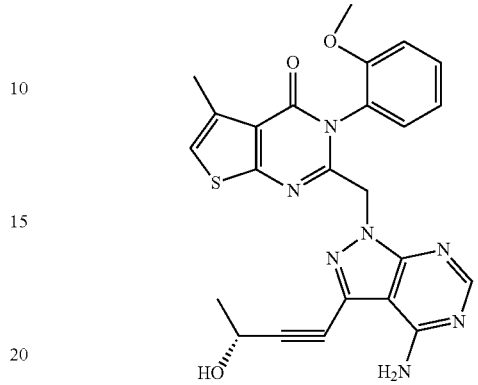
Compound 276
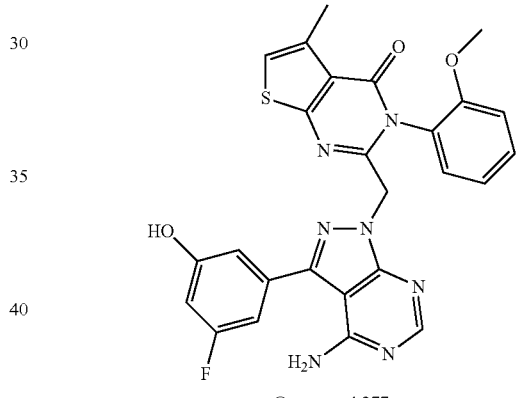
Compound 277
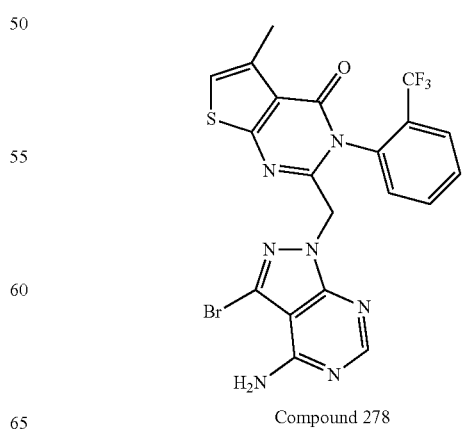
Compound 278

TABLE 5-continued
Structures of the Compounds for the IC50 results described in Table 4.
Structure
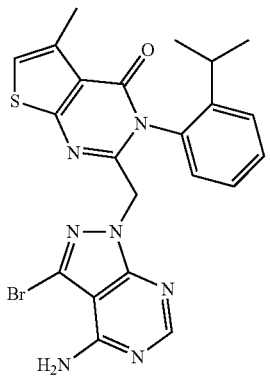
Compound 279
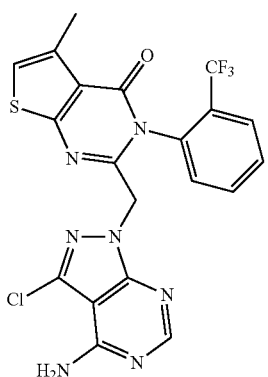
Compound 280
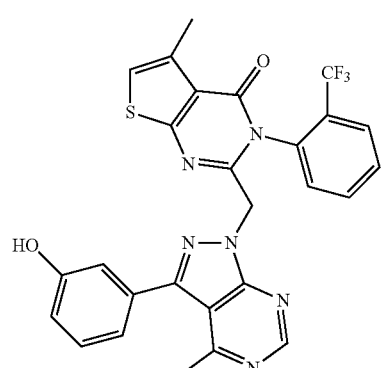
Compound 281
TABLE 5-continued
Structures of the Compounds for the IC50 results described in Table 4.
Structure
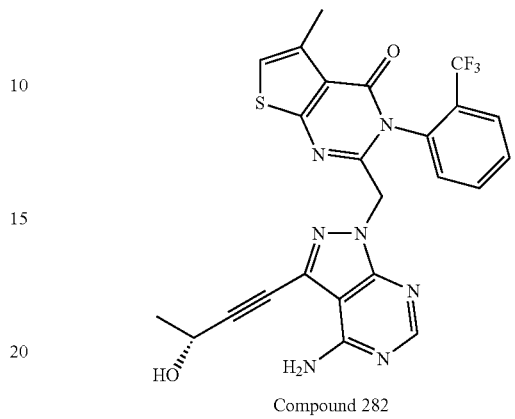
Compound 282
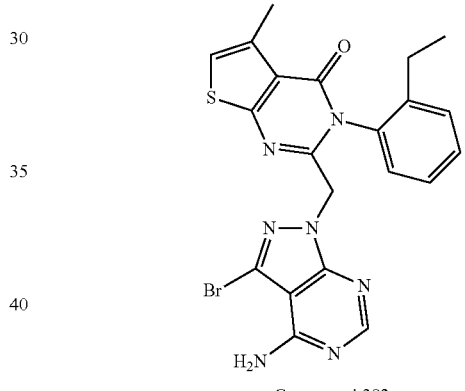
Compound 283
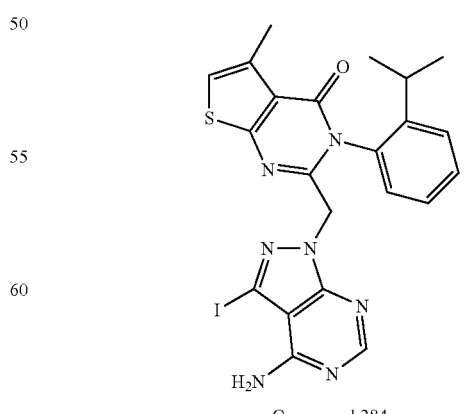
Compound 284

TABLE 5-continued
Structures of the Compounds for the IC50 results described in Table 4.
Structure
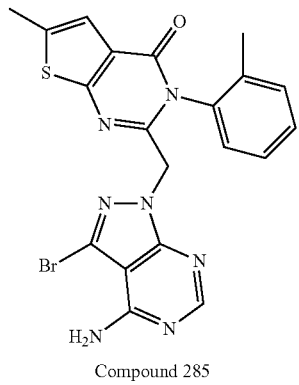 [SMILES: Cc1cc2c(=O)n(-c3ccccc3C)c(Cn3nc(Br)c4c(N)ncnc43)nc2s1]
Compound 285
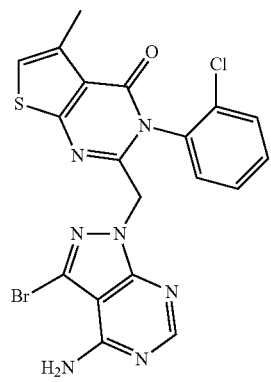
Compound 286
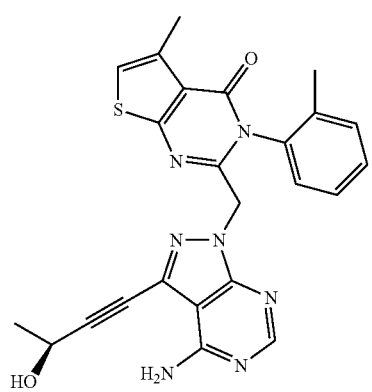
Compound 287
TABLE 5-continued
Structures of the Compounds for the IC50 results described in Table 4.
Structure
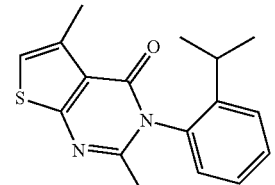
Compound 288
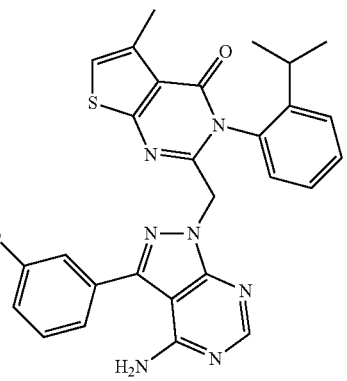
Compound 289
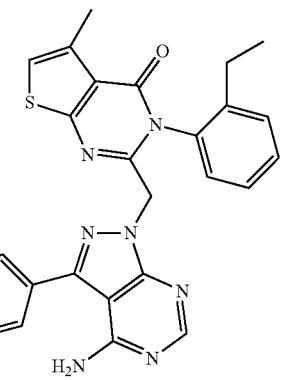
Compound 290

TABLE 5-continued
Structures of the Compounds for the IC50 results described in Table 4.
Structure
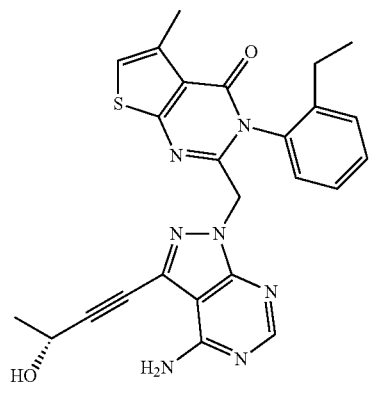
Compound 291
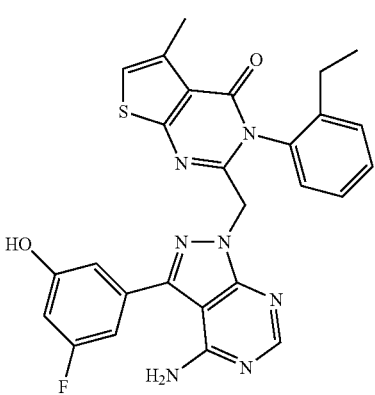
Compound 292
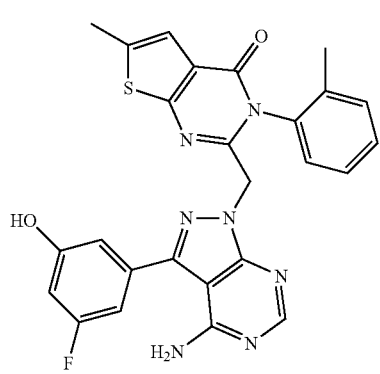
Compound 293
TABLE 5-continued
Structures of the Compounds for the IC50 results described in Table 4.
Structure
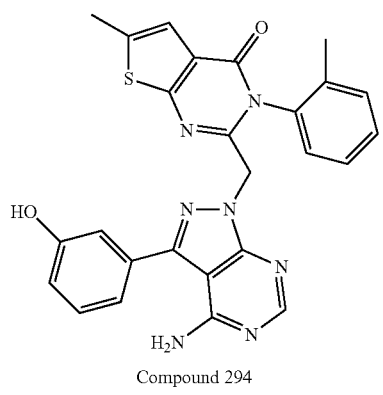 [SMILES: Cc1cc2c(=O)n(-c3ccccc3C)c(Cn3nc(-c4cccc(O)c4)c4c(N)ncnc43)nc2s1]
Compound 294
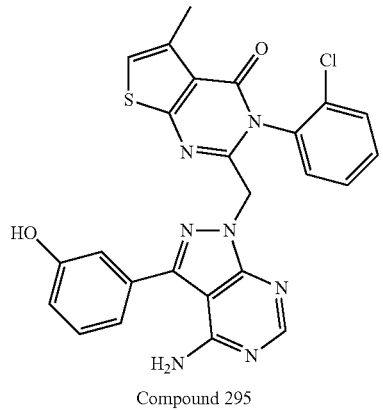 [SMILES: Cc1csc2nc(Cn3nc(-c4cccc(O)c4)c4c(N)ncnc43)n(-c3ccccc3Cl)c(=O)c12]
Compound 295
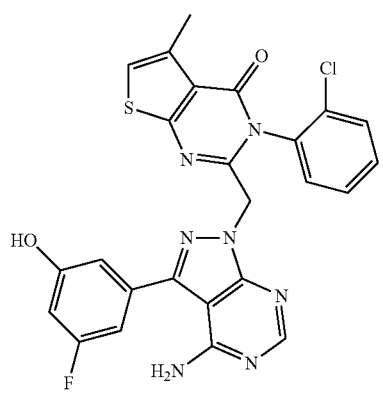
Compound 296

TABLE 5-continued
Structures of the Compounds for the IC50 results described in Table 4.
Structure
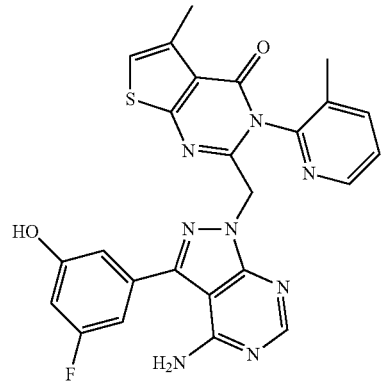
Compound 297
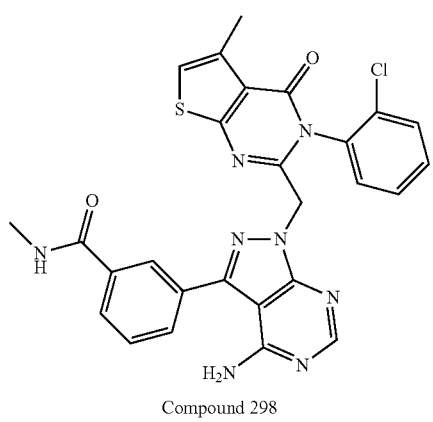 [SMILES: CNC(=O)c1cccc(-c2nn(Cc3nc4scc(C)c4c(=O)n3-c3ccccc3Cl)c3ncnc(N)c23)c1]
Compound 298
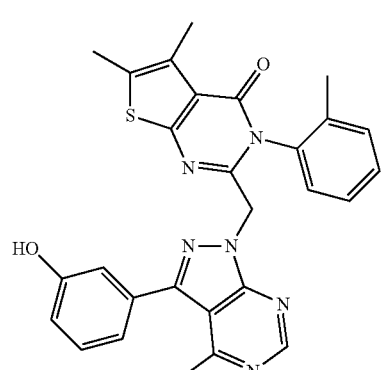
Compound 299
TABLE 5-continued
Structures of the Compounds for the IC50 results described in Table 4.
Structure
Compound 300
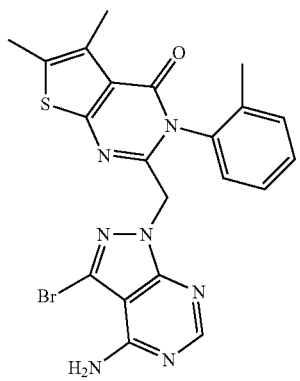
Compound 301
Compound 302

TABLE 5-continued

Structures of the Compounds for the IC50 results described in Table 4.

Structure

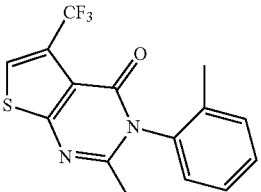

Compound 303

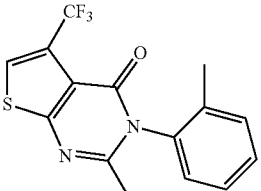

Compound 304

Example 16

Expression and Inhibition Assays of p110α/p85α, p110β/p85α, p110δ/p85α, and p110γ

Class I PI3-Ks can be either purchased (p110α/p85α, p110β/p85α, p110δ/p85α from Upstate, and p110γ from Sigma) or expressed as previously described (Knight et al., 2004). IC50 values are measured using either a standard TLC assay for lipid kinase activity (described below) or a high-throughput membrane capture assay. Kinase reactions are performed by preparing a reaction mixture containing kinase, inhibitor (2% DMSO final concentration), buffer (25 mM HEPES, pH 7.4, 10 mM MgCl2), and freshly sonicated phosphatidylinositol (100 μg/ml). Reactions are initiated by the addition of ATP containing 10 μCi of γ-32P-ATP to a final concentration 10 or 100 μM and allowed to proceed for 5 minutes at room temperature. For TLC analysis, reactions are then terminated by the addition of 105 μl 1N HCl followed by 160 μl CHCl3:MeOH (1:1). The biphasic mixture is vortexed, briefly centrifuged, and the organic phase is transferred to a new tube using a gel loading pipette tip precoated with CHCl3. This extract is spotted on TLC plates and developed for 3-4 hours in a 65:35 solution of n-propanol:1M acetic acid. The TLC plates are then dried, exposed to a phosphorimager screen (Storm, Amersham), and quantitated. For each compound, kinase activity is measured at 10-12 inhibitor concentrations representing two-fold dilutions from the highest concentration tested (typically, 200 μM). For compounds showing significant activity, IC50 determinations are repeated two to four times, and the reported value is the average of these independent measurements.

Other commercial kits or systems for assaying PI3-K activities are available. The commercially available kits or systems can be used to screen for inhibitors and/or agonists of PI3-Ks including but not limited to PI 3-Kinase α, β, δ, and γ. An exemplary system is PI3-Kinase (human) HTRF™ Assay from Upstate. The assay can be carried out according to the procedures suggested by the manufacturer. Briefly, the assay is a time resolved FRET assay that indirectly measures PIP3 product formed by the activity of a PI3-K. The kinase reaction is performed in a microtiter plate (e.g., a 384 well microtiter plate). The total reaction volume is approximately 20 ul per well. In the first step, each well receives 2 ul of test compound in 20% dimethylsulphoxide resulting in a 2% DMSO final concentration. Next, approximately 14.5 ul of a kinase/PIP2 mixture (diluted in 1× reaction buffer) is added per well for a final concentration of 0.25-0.3 ug/ml kinase and 10 uM PIP2. The plate is sealed and incubated for 15 minutes at room temperature. To start the reaction, 3.5 ul of ATP (diluted in 1× reaction buffer) is added per well for a final concentration of 10 uM ATP. The plate is sealed and incubated for 1 hour at room temperature. The reaction is stopped by adding 5 ul of Stop Solution per well and then 5 ul of Detection Mix is added per well. The plate is sealed, incubated for 1 hour at room temperature, and then read on an appropriate plate reader. Data is analyzed and IC50s are generated using GraphPad Prism 5.

Example 17

Expression and Inhibition Assays of Abl

The cross-activity or lack thereof of one or more compounds of the present invention against Abl kinase can be measured according to any procedures known in the art or methods disclosed below. The compounds described herein can be assayed in triplicate against recombinant full-length Abl or Abl (T315I) (Upstate) in an assay containing 25 mM HEPES, pH 7.4, 10 mM MgCl2, 200 μM ATP (2.5 μCi of γ-32P-ATP), and 0.5 mg/mL BSA. The optimized Abl peptide substrate EAIYAAPFAKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 18

Expression and Inhibition Assays of Hck

The cross-activity or lack thereof of one or more compounds of the present invention against Hck kinase can be measured according to any procedures known in the art or methods disclosed below. The compounds described herein can be assayed in triplicate against recombinant full-length Hck in an assay containing 25 mM HEPES, pH 7.4, 10 mM MgCl2, 200 μM ATP (2.5 μCi of γ-32P-ATP), and 0.5 mg/mL BSA. The optimized Src family kinase peptide substrate EIYGEFKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 19

Expression and Inhibition Assays of Inulsin Receptor (IR)

The cross-activity or lack thereof of one or more compounds of the present invention against IR receptor kinase can be measured according to any procedures known in the art or methods disclosed below. The compounds described herein can be assayed in triplicate against recombinant insulin receptor kinase domain (Upstate) in an assay containing 25 mM HEPES, pH 7.4, 10 mM MgCl2, 10 mM MnCl2, 200 µM ATP (2.5 µCi of γ-32P-ATP), and 0.5 mg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 20

Expression and Inhibition Assays of Src

The cross-activity or lack thereof of one or more compounds of the present invention against Src kinase can be measured according to any procedures known in the art or methods disclosed below. The compounds described herein can be assayed in triplicate against recombinant full-length Src or Src (T338I) in an assay containing 25 mM HEPES, pH 7.4, 10 mM MgCl2, 200 µM ATP (2.5 µCi of γ-32P-ATP), and 0.5 mg/mL BSA. The optimized Src family kinase peptide substrate EIYGEFKKK is used as phosphoacceptor (200 µM). Reactions are terminated by spotting onto phosphocellulose sheets, which are washed with 0.5% phosphoric acid (approximately 6 times, 5-10 minutes each). Sheets were dried and the transferred radioactivity quantitated by phosphorimaging.

Example 21

Expression and Inhibition Assays of DNA-PK (DNAK)

The cross-activity or lack thereof of one or more compounds of the present invention against DNAK kinase can be measured according to any procedures known in the art. DNA-PK can be purchased from Promega and assayed using the DNA-PK Assay System (Promega) according to the manufacturer's instructions.

Example 22

Expression and Inhibition Assays mTOR

The cross-activity or lack thereof of one or more compounds of the present invention against mTor can be measured according to any procedures known in the art or methods disclosed below. The compounds described herein can be tested against recombinant mTOR (Invitrogen) in an assay containing 50 mM HEPES, pH 7.5, 1 mM EGTA, 10 mM MgCl2, 2.5 mM, 0.01% Tween, 10 µM ATP (2.5 µCi of µ-32P-ATP), and 3 µg/mL BSA. Rat recombinant PHAS-1/4EBP1 (Calbiochem; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Other kits or systems for assaying mTOR activity are commercially available. For instance, one can use Invitrogen's LanthaScreen™ Kinase assay to test the inhibitors of mTOR disclosed herein. This assay is a time resolved FRET platform that measures the phosphorylation of GFP labeled 4EBP1 by mTOR kinase. The kinase reaction is performed in a white 384 well microtiter plate. The total reaction volume is 20 ul per well and the reaction buffer composition is 50 mM HEPES pH7.5, 0.01% Polysorbate 20, 1 mM EGTA, 10 mM MnCl2, and 2 mM DTT. In the first step, each well receives 2 ul of test compound in 20% dimethylsulphoxide resulting in a 2% DMSO final concentration. Next, 8 ul of mTOR diluted in reaction buffer is added per well for a 60 ng/ml final concentration. To start the reaction, 10 ul of an ATP/GFP-4EBP1 mixture (diluted in reaction buffer) is added per well for a final concentration of 10 uM ATP and 0.5 uM GFP-4EBP1. The plate is sealed and incubated for 1 hour at room temperature. The reaction is stopped by adding 10 ul per well of a Tb-anti-pT46 4EBP1 antibody/EDTA mixture (diluted in TR-FRET buffer) for a final concentration of 1.3 nM antibody and 6.7 mM EDTA. The plate is sealed, incubated for 1 hour at room temperature, and then read on a plate reader set up for LanthaScreen™ TR-FRET. Data is analyzed and IC50s are generated using GraphPad Prism 5.

Example 23

Expression and Inhibition Assays of Vascular Endothelial Growth Receptor

The cross-activity or lack thereof of one or more compounds of the present invention against VEGF receptor can be measured according to any procedures known in the art or methods disclosed below. The compounds described herein can be tested against recombinant KDR receptor kinase domain (Invitrogen) in an assay containing 25 mM HEPES, pH 7.4, 10 mM MgCl2, 0.1% BME, 10 µM ATP (2.5 µCi of µ-32P-ATP), and 3 µg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 24

Expression and Inhibition Assays of Ephrin Receptor B4 (EphB4)

The cross-activity or lack thereof of one or more compounds of the present invention against EphB4 can be measured according to any procedures known in the art or methods disclosed below. The compounds described herein can be tested against recombinant Ephrin receptor B4 kinase domain (Invitrogen) in an assay containing 25 mM HEPES, pH 7.4, 10 mM MgCl2, 0.1% BME, 10 µM ATP (2.5 µCi of µ-32P-ATP), and 3 µg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 25

Expression and Inhibition Assays of Epidermal Growth Factor Receptor (EGFR)

The cross-activity or lack thereof of one or more compounds of the present invention against EGFR kinase can be measured according to any procedures known in the art or methods disclosed below. The compounds described herein can be tested against recombinant EGF receptor kinase domain (Invitrogen) in an assay containing 25 mM HEPES, pH 7.4, 10 mM MgCl2, 0.1% BME, 10 µM ATP (2.5 µCi of µ-32P-ATP), and 3 µg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 26

Expression and Inhibition Assays of KIT Assay

The cross-activity or lack thereof of one or more compounds of the present invention against KIT kinase can be measured according to any procedures known in the art or methods disclosed below. The compounds described herein can be tested against recombinant KIT kinase domain (Invitrogen) in an assay containing 25 mM HEPES, pH 7.4, 10 mM MgCl2, 1 mM DTT, 10 mM MnCl2, 10 µM ATP (2.5 µCi of µ-32P-ATP), and 3 µg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 27

Expression and Inhibition Assays of RET

The cross-activity or lack thereof of one or more compounds of the present invention against RET kinase can be measured according to any procedures known in the art or methods disclosed below. The compounds described herein can be tested against recombinant RET kinase domain (Invitrogen) in an assay containing 25 mM HEPES, pH 7.4, 10 mM MgCl2, 2.5 mM DTT, 10 µM ATP (2.5 µCi of µ-32P-ATP), and 3 µg/mL BSA. The optimized Abl peptide substrate EAIYAAPFAKKK is used as phosphoacceptor (200 µM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 28

Expression and Inhibition Assays of Platelet Derived Growth Factor Receptor (PDGFR)

The cross-activity or lack thereof of one or more compounds of the present invention against PDGFR kinase can be measured according to any procedures known in the art or methods disclosed below. The compounds described herein can be tested against recombinant PDG receptor kinase domain (Invitrogen) in an assay containing 25 mM HEPES, pH 7.4, 10 mM MgCl2, 2.5 mM DTT, 10 µM ATP (2.5 µCi of µ-32P-ATP), and 3 µg/mL BSA. The optimized Abl peptide substrate EAIYAAPFAKKK is used as phosphoacceptor (200 µM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 29

Expression and Inhibition Assays of FMS-Related Tyrosine Kinase 3 (FLT-3)

The cross-activity or lack thereof of one or more compounds of the present invention against FLT-3 kinase can be measured according to any procedures known in the art or methods disclosed below. The compounds described herein can be tested against recombinant FLT-3 kinase domain (Invitrogen) in an assay containing 25 mM HEPES, pH 7.4, 10 mM MgCl2, 2.5 mM DTT, 10 µM ATP (2.5 µCi of µ-32P-ATP), and 3 µg/mL BSA. The optimized Abl peptide substrate EAIYAAPFAKKK is used as phosphoacceptor (200 µM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 30

Expression and Inhibition Assays of TEK Receptor Tyrosine Kinase (TIE2)

The cross-activity or lack thereof of one or more compounds of the present invention against TIE2 kinase can be measured according to any procedures known in the art or methods disclosed below. The compounds described herein can be tested against recombinant TIE2 kinase domain (Invitrogen) in an assay containing 25 mM HEPES, pH 7.4, 10 mM MgCl2, 2 mM DTT, 10 mM MnCl2, 10 µM ATP (2.5 µCi of µ-32P-ATP), and 3 µg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 31

B Cell Activation and Proliferation Assay

The ability of one or more subject compounds to inhibit B cell activation and proliferation is determined according to standard procedures known in the art. For example, an in vitro cellular proliferation assay is established that measures the metabolic activity of live cells. The assay is performed in a 96 well microtiter plate using Alamar Blue reduction. Balb/c splenic B cells are purified over a Ficoll-Paque™ PLUS gradient followed by magnetic cell separation using a MACS B cell Isolation Kit (Miletenyi). Cells are plated in 90 ul at 50,000 cells/well in B Cell Media (RPMI+10% FBS+Penn/Strep+50 uM bME+5 mM HEPES). A compound disclosed herein is diluted in B Cell Media and added in a 10 ul volume. Plates are incubated for 30 min at 37 C and 5% $CO_2$ (0.2% DMSO final concentration). A 50 ul B cell stimulation cocktail is then added containing either 10 ug/ml LPS or 5 ug/ml F(ab')2 Donkey anti-mouse IgM plus 2 ng/ml recombinant mouse IL4 in B Cell Media. Plates are incubated for 72 hours at 37° C. and 5% $CO_2$. A volume of 15 uL of Alamar Blue reagent is added to each well and plates are incubated for 5 hours at 37 C and 5% $CO_2$. Alamar Blue fluoresce is read at 560Ex/590Em, and IC50 or EC50 values are calculated using GraphPad Prism 5.

Example 32

Tumor Cell Line Proliferation Assay

The ability of one or more subject compounds to inhibit tumor cell line proliferation is determined according to standard procedures known in the art. For instance, an in vitro cellular proliferation assay can be performed to measure the metabolic activity of live cells. The assay is performed in a 96 well microtiter plate using Alamar Blue reduction. Human tumor cell lines are obtained from ATCC (e.g., MCF7, U-87 MG, MDA-MB-468, PC-3), grown to confluency in T75 flasks, trypsinized with 0.25% trypsin, washed one time with Tumor Cell Media (DMEM+10% FBS), and plated in 90 ul at 5,000 cells/well in Tumor Cell Media. A compound disclosed herein is diluted in Tumor Cell Media and added in a 10 ul volume. Plates are incubated for 72 hours at 37 C and 5% $CO_2$. A volume of 10 uL of Alamar Blue reagent is added to each well and plates are incubated for 3 hours at 37 C and 5% $CO_2$. Alamar Blue fluoresce is read at 560Ex/590Em, and IC50 values are calculated using GraphPad Prism 5.

Example 33

Antitumor Activity in Vivo

The compounds described herein can be evaluated in a panel of human and murine tumor models.
Paclitaxel-Refractory Tumor Models
1. Clinically-Derived Ovarian Carcinoma Model.
This tumor model is established from a tumor biopsy of an ovarian cancer patient. Tumor biopsy is taken from the patient.
The compounds described herein are administered to nude mice bearing staged tumors using an every 2 days×5 schedule.
2. A2780Tax Human Ovarian Carcinoma Xenograft (Mutated Tubulin).
A2780Tax is a paclitaxel-resistant human ovarian carcinoma model. It is derived from the sensitive parent A2780 line by co-incubation of cells with paclitaxel and verapamil, an MDR-reversal agent. Its resistance mechanism has been shown to be non-MDR related and is attributed to a mutation in the gene encoding the beta-tubulin protein.
The compounds described herein can be administered to mice bearing staged tumors on an every 2 days×5 schedule.
3. HCT116/VM46 Human Colon Carcinoma Xenograft (Multi-Drug Resistant).
HCT116/VM46 is an MDR-resistant colon carcinoma developed from the sensitive HCT116 parent line. In vivo, grown in nude mice, HCT116/VM46 has consistently demonstrated high resistance to paclitaxel.
The compounds described herein can be administered to mice bearing staged tumors on an every 2 days×5 schedule.
5. M5076 Murine Sarcoma Model
M5076 is a mouse fibrosarcoma that is inherently refractory to paclitaxel in vivo.
The compounds described herein can be administered to mice bearing staged tumors on an every 2 days×5 schedule.

One or more compounds of the invention can be used in combination other therapeutic agents in vivo in the multidrug resistant human colon carcinoma xenografts HCT/VM46 or any other model known in the art including those described herein.

Example 34

Microsome Stability Assay

The stability of one or more subject compounds is determined according to standard procedures known in the art. For example, stability of one or more subject compounds is established by an in vitro assay. In particular, an in vitro microsome stability assay is established that measures stability of one or more subject compounds when reacting with mouse, rat or human microsomes from liver. The microsome reaction with compounds is performed in 1.5 mL Eppendorf tube. Each tube contains 0.1 µL of 10.0 mg/ml NADPH; 75 µL of 20.0 mg/ml mouse, rat or human liver microsome; 0.4 µL of 0.2 M phosphate buffer, and 425 µL of dd$H_2O$, Negative control (without NADPH) tube contains 75 µL of 20.0 mg/ml mouse, rat or human liver microsome; 0.4 µL of 0.2 M phosphate buffer, and 525 µL of dd$H_2O$. The reaction is started by adding 1.0 µL of 10.0 mM tested compound. The reaction tubes are incubated at 37° C. 100 µL sample is collected into new Eppendorf tube containing 300 µL cold Methanol at 0, 5, 10, 15, 30 and 60 minutes of reaction. Samples are centrifuged at 15,000 rpm to remove protein. Supernatant of centrifuged sample is transferred to new tube. Concentration of stable compound after reaction with microsome in the supernatant is measured by Liquid Chromatography/Mass Spectrometry (LC-MS).

Example 35

Plasma Stability Assay

The stability of one or more subject compounds in plasma is determined according to standard procedures known in the art. See, e.g., Rapid Commun. Mass Spectrom., 10: 1019-1026. The following procedure is an HPLC-MS/MS assay using human plasma; other species including monkey, dog, rat, and mouse are also available. Frozen, heparinized human plasma is thawed in a cold water bath and spun for 10 minutes at 2000 rpm at 4° C. prior to use. A subject compound is added from a 400 µM stock solution to an aliquot of pre-warmed plasma to give a final assay volume of 400 µL (or 800 µL for half-life determination), containing 5 µM test compound and 0.5% DMSO. Reactions are incubated, with shaking, for 0 minutes and 60 minutes at 37° C., or for 0, 15, 30, 45 and 60 minutes at 37 C for half life determination. Reactions are stopped by transferring 50 µL of the incubation mixture to 200 µL of ice-cold acetonitrile and mixed by shaking for 5 minutes. The samples are centrifuged at 6000×g for 15 minutes at 4° C. and 120 µL of supernatant removed into clean tubes. The samples are then evaporated to dryness and submitted for analysis by HPLC-MS/MS.

Where desired, one or more control or reference compounds (5 µM) are tested simultaneously with the test compounds: one compound, propoxycaine, with low plasma stability and another compound, propantheline, with intermediate plasma stability.

Samples are reconstituted in acetonitrile/methanol/water (1/1/2, v/v/v) and analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 60 minutes relative to the amount remaining at time zero, expressed as percent, is reported as plasma stability. In case of half-life determination, the half-life is estimated from the slope of the initial linear range of the logarithmic curve of compound remaining (%) vs. time, assuming first order kinetics.

Example 36

Chemical Stability

The chemical stability of one or more subject compounds is determined according to standard procedures known in the art. The following details an exemplary procedure for ascertaining chemical stability of a subject compound. The default buffer used for the chemical stability assay is phosphate-buffered saline (PBS) at pH 7.4; other suitable buffers can be used. A subject compound is added from a 100 µM stock solution to an aliquot of PBS (in duplicate) to give a final assay volume of 400 µL, containing 5 µM test compound and 1% DMSO (for half-life determination a total sample volume of 700 µL is prepared). Reactions are incubated, with shaking, for 0 minutes and 24 hours at 37° C.; for half-life determination samples are incubated for 0, 2, 4, 6, and 24 hours. Reactions are stopped by adding immediately 100 µL of the incubation mixture to 100 µL of acetonitrile and vortexing for 5 minutes. The samples are then stored at −20° C. until analysis by HPLC-MS/MS. Where desired, a control compound or a reference compound such as chlorambucil (5 µM) is tested simultaneously with a subject compound of interest, as this compound is largely hydrolyzed over the course of 24 hours. Samples are analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 24 hours relative to the amount remaining at time zero, expressed as percent, is reported as chemical stability. In case of half-life determination, the half-life is estimated from the slope of the initial linear range of the logarithmic curve of compound remaining (%) vs. time, assuming first order kinetics.

Example 37

Akt Kinase Assay

Cells comprising components of the Akt/mTOR pathway, including but not limited to L6 myoblasts, B-ALL cells, B-cells, T-cells, leukemia cells, bone marrow cells, p190 transduced cells, phill adelphia chromosome positive cells (Ph+), and mouse embryonic fibroblasts, are typically grown in cell growth media such as DMEM supplemented with fetal bovine serum and/or antibiotics, and grown to confluency.

In order to compare the effect of one or more compounds disclosed herein on Akt activation, said cells are serum starved overnight and incubated with one or more compounds disclosed herein or about 0.1% DMSO for approximately 1 minute to about 1 hour prior to stimulation with insulin (e.g. 100 nM) for about 1 minutes to about 1 hour. Cells are lysed by scraping into ice cold lysis buffer containing detergents such as sodium dodecyl sulfate and protease inhibitors (e.g., PMSF). After contacting cells with lysis buffer, the solution is briefly sonicated, cleared by centrifugation, resolved by SDS-PAGE, transferred to nitrocellulose or PVDF and immunoblotted using antibodies to phospho-Akt S473, phospho-Akt T308, Akt, and β-actin (Cell Signaling Technologies).

The results demonstrate that one or more compounds of the present disclosure inhibit insulin stimulated phosphorylation of Akt at S473. Alternatively, some compounds disclosed herein additionally inhibit insulin stimulated phosphorylation of Akt at T308. Such class of compounds can inhibit Akt more effectively than rapamycin and may be indicative of mTORC2 inhibitors or inhibitors of upstream kinases such as PI3K or Akt.

Example 38

Kinase Signaling in Blood

PI3K/Akt/mTor signaling is measured in blood cells using the phosflow method (Methods Enzymol. 2007; 434:131-54). The advantage of this method is that it is by nature a single cell assay so that cellular heterogeneity can be detected rather than population averages. This allows concurrent distinction of signaling states in different populations defined by other markers. Phosflow is also highly quantitative. To test the effects of one or more compounds disclosed herein, unfractionated splenocytes, or peripheral blood mononuclear cells are stimulated with anti-CD3 to initiate T-cell receptor signaling. The cells are then fixed and stained for surface markers and intracellular phosphoproteins. It is expected that inhibitors disclosed herein inhibit anti-CD3 mediated phosphorylation of Akt-S473 and S6, whereas rapamycin inhibits S6 phosphorylation and enhances Akt phosphorylation under the conditions tested.

Similarly, aliquots of whole blood are incubated for 15 minutes with vehicle (e.g. 0.1% DMSO) or kinase inhibitors at various concentrations, before addition of stimuli to crosslink the T cell receptor (TCR) (anti-CD3 with secondary antibody) or the B cell receptor (BCR) using anti-kappa light chain antibody (Fab'2 fragments). After approximately 5 and 15 minutes, samples are fixed (e.g. with cold 4% paraformaldehyde) and used for phosflow. Surface staining is used to distinguish T and B cells using antibodies directed to cell surface markers that are known to the art. The level of phosphorylation of kinase substrates such as Akt and S6 are then measured by incubating the fixed cells with labeled antibodies specific to the phosphorylated isoforms of these proteins. The population of cells are then analyzed by flow cytometry.

Example 39

Colony Formation Assay

Murine bone marrow cells freshly transformed with a p190 BCR-Abl retrovirus (herein referred to as p190 transduced cells) are plated in the presence of various drug combinations in M3630 methylcellulose media for about 7 days with recombinant human IL-7 in about 30% serum, and the number of colonies formed is counted by visual examination under a microscope.

Alternatively, human peripheral blood mononuclear cells are obtained from Philadelphia chromosome positive (Ph+) and negative (Ph−) patients upon initial diagnosis or relapse. Live cells are isolated and enriched for CD19+ CD34+ B cell progenitors. After overnight liquid culture, cells are plated in methocult GF+H4435, Stem Cell Tehcnologies) supplemented with cytokines (IL-3, IL-6, IL-7, G-CSF, GM-CSF, CF, Flt3 ligand, and erythropoietin) and various concentrations of known chemotherapeutic agents in combination with either compounds of the present disclosure. Colonies are counted by microscopy 12-14 days later. This method can be used to test for evidence of additive or synergistic activity.

Example 40

In Vivo Effect of Kinase Inhibitors on Leukemic Cells

Female recipient mice are lethally irradiated from a γ source in two doses about 4 hr apart, with approximately 5Gy each. About 1 hr after the second radiation dose, mice are injected i.v. with about $1 \times 10^6$ leukemic cells (e.g. Ph+ human or murine cells, or p190 transduced bone marrow cells). These cells are administered together with a radioprotective dose of about $5 \times 10^6$ normal bone marrow cells from 3-5 week old donor mice. Recipients are given antibiotics in the water and monitored daily. Mice who become sick after about 14 days are euthanized and lymphoid organs are harvested for analysis. Kinase inhibitor treatment begins about 10 days after leukemic cell injection and continues daily until the mice become sick or a maximum of approximately 35 days post-transplant. Inhibitors are given by oral lavage.

Peripheral blood cells are collected approximately on day 10 (pre-treatment) and upon euthanization (post treatment), contacted with labeled anti-hCD4 antibodies and counted by flow cytometry. This method can be used to demonstrate that the synergistic effect of one or more compounds disclosed herein in combination with known chemotherapeutic agents significantly reduce leukemic blood cell counts as compared to treatment with known chemotherapeutic agents (e.g. Gleevec) alone under the conditions tested.

Example 41

Treatment of Lupus Disease Model Mice

Mice lacking the inhibitory receptor FcγRIIb that opposes PI3K signaling in B cells develop lupus with high penetrance. FcγRIIb knockout mice (R2KO, Jackson Labs) are considered a valid model of the human disease as some lupus patients show decreased expression or function of FcγRIIb (S. Bolland and J. V. Ravtech 2000. *Immunity* 12:277-285).

The R2KO mice develop lupus-like disease with antinuclear antibodies, glomerulonephritis and proteinurea within about 4-6 months of age. For these experiments, the rapamycin analogue RAD001 (available from LC Laboratories) is used as a benchmark compound, and administered orally. This compound has been shown to ameliorate lupus symptoms in the B6.Sle1z.Sle3z model (T. Wu et al. *J. Clin Invest.* 117:2186-2196).

Lupus disease model mice such as R2KO, BXSB or MLR/lpr are treated at about 2 months old, approximately for about two months. Mice are given doses of: vehicle, RAD001 at about 10 mg/kg, or compounds disclosed herein at approximately 1 mg/kg to about 500 mg/kg. Blood and urine samples are obtained at approximately throughout the testing period, and tested for antinuclear antibodies (in dilutions of serum) or protein concentration (in urine). Serum is also tested for anti-ssDNA and anti-dsDNA antibodies by ELISA. Animals are euthanized at day 60 and tissues harvested for measuring spleen weight and kidney disease. Glomerulonephritis is assessed in kidney sections stained with H&E. Other animals are studied for about two months after cessation of treatment, using the same endpoints.

This model established in the art can be employed to demonstrate that the kinase inhibitors disclosed herein can suppress or delay the onset of lupus symptoms in lupus disease model mice.

Example 42

Murine Bone Marrow Transplant Assay

Female recipient mice are lethally irradiated from a γ ray source. About 1 hr after the radiation dose, mice are injected with about 1×106 leukemic cells from early passage p190 transduced cultures (e.g. as described in *Cancer Genet Cytogenet.* 2005 August; 161(1):51-6). These cells are administered together with a radioprotective dose of approximately 5×106 normal bone marrow cells from 3-5 wk old donor mice. Recipients are given antibiotics in the water and monitored daily. Mice who become sick after about 14 days are euthanized and lymphoid organs harvested for flow cytometry and/or magnetic enrichment. Treatment begins on approximately day 10 and continues daily until mice become sick, or after a maximum of about 35 days post-transplant. Drugs are given by oral gavage (p.o.). In a pilot experiment a dose of chemotherapeutic that is not curative but delays leukemia onset by about one week or less is identified; controls are vehicle-treated or treated with chemotherapeutic agent, previously shown to delay but not cure leukemogenesis in this model (e.g. imatinib at about 70 mg/kg twice daily). For the first phase p190 cells that express eGFP are used, and post-mortem analysis is limited to enumeration of the percentage of leukemic cells in bone marrow, spleen and lymph node (LN) by flow cytometry. In the second phase, p190 cells that express a tailless form of human CD4 are used and the post-mortem analysis includes magnetic sorting of hCD4+ cells from spleen followed by immunoblot analysis of key signaling endpoints: p Akt-T308 and S473; pS6 and p4EBP-1. As controls for immunoblot detection, sorted cells are incubated in the presence or absence of kinase inhibitors of the present disclosure inhibitors before lysis. Optionally, "phosflow" is used to detect p Akt-S473 and pS6-S235/236 in hCD4-gated cells without prior sorting. These signaling studies are particularly useful if, for example, drug-treated mice have not developed clinical leukemia at the 35 day time point. Kaplan-Meier plots of survival are generated and statistical analysis done according to methods known in the art. Results from p190 cells are analyzed separated as well as cumulatively.

Samples of peripheral blood (100-200 µl) are obtained weekly from all mice, starting on day 10 immediately prior to commencing treatment. Plasma is used for measuring drug concentrations, and cells are analyzed for leukemia markers (eGFP or hCD4) and signaling biomarkers as described herein.

This general assay known in the art may be used to demonstrate that effective therapeutic doses of the compounds disclosed herein can be used for inhibiting the proliferation of leukemic cells.

Example 43

Cell Culture of Epithelial Cells of Ocular Origin

Ocular epithelial cells are obtained within 5 days postmortem post-mortem from corneas preserved under cold storage conditions in Optisol (Bausch and Lomb, Irvine, Calif.) or from corneal biopsy from living donors. The tissue is washed with phosphate-buffered saline and incubated in Dispase II (Roche Diagnostics, Basel, Switzerland) at 37° C. for 30 minutes, and the epithelial surface is gently scraped to separate the epithelium from the underlying stroma. The separated epithelium is then incubated and pipetted in trypsin-ethylenediaminetetraacetic acid to obtain a single cell suspension. The trypsin is then neutralized with corneal epithelium culture medium. Corneal epithelium culture medium is composed of Dulbecco modified Eagle medium:F12 basal media in a 2:1 ratio containing 10% irradiated fetal bovine serum, hydrocortisone 0.4 µg/mL, cholera toxin 0.1 nmol, recombinant human insulin 5 µg/mL, and epidermal growth factor 10 ng/mL, and the antimicrobials penicillin (100 IU/mL), streptomycin (100 µg/mL), and amphotericin B (0.25 µg/mL). Cells are maintained by sub-culturing at a 1:4 ratio after reaching 80% confluency. Ocular epithelial cells are screened for inhibition of proliferation or toxicity by contacting a test compound with the cells and assaying for viability using the commercially available MTF assay (Promega).

Example 44

Cell Culture of Endothelial Cells of Ocular Origin

All tissues are maintained at 4° C. in storage medium (Optisol; Chiron Vision, Irvine, Calif.) for less than 10 days before study. The tissue is rinsed three times with DMEM containing 50 mg/mL gentamicin and 1.25 mg/mL amphotericin B. The central cornea is removed by a trephine of 8-mm diameter. Afterward, the Descemet's membrane and corneal endothelial cells are stripped from the posterior surface of the peripheral corneoscleral tissue under a dissecting microscope and digested at 37° C. for 1.5 to 16 hours with 2 mg/mL collagenase A in supplemented hormonal epithelial medium (SHEM), which is made of an equal volume of HEPES-buffered DMEM and Ham's F12 supplemented with 5% FBS, 0.5% dimethyl sulfoxide, 2 ng/mL mouse EGF, 5 µg/mL insulin, 5 µg/mL transferrin, 5 ng/mL selenium, 0.5 µg/mL hydrocortisone, 1 nM cholera toxin, 50 µg/mL gentamicin, and 1.25 µg/mL amphotericin B. After digestion, HCECs formed aggregates, which are collected by centrifugation at 2000 rpm for 3 minutes to remove the digestion solution. As a control, Descemet's membrane strips are also digested in 10 mg/mL Dispase II in SHEM and trypsin/EDTA for up to 3 hours.

Preservation of Isolated HCEC Aggregates

The resultant aggregates of HCECs are preserved in KSFM with complete supplement (storage medium 1), DMEM/F12 with KSFM supplements (storage medium 2), or DMEM/F12 with SHEM supplements without FBS (storage medium 3). All these media are serum free, one of the major differences among them is the calcium concentration, which is 0.09 mM in storage medium 1, but is 1.05 mM in storage media 2 and 3. HCEC aggregates are stored in a tissue culture incubator at 37° C. for up to 3 weeks. Cell viability is determined (Live and Dead assay; Invitrogen) and also evaluated by subculturing them in SHEM.

Expansion of Isolated HCEC Aggregates

The resultant HCEC aggregates, either immediately after digestion or after a period of preservation in a storage medium, are then cultured in SHEM with or without additional growth factors such as 40 ng/mL bFGF, 0.1 mg/mL BPE, and 20 ng/mL NGF on a plastic dish under 37° C. and 5% CO2. The media are changed every 2 to 3 days. Some HCEC aggregates are pretreated with trypsin/EDTA at 37° C. for 10 minutes to dissociate endothelial cells before the aforementioned cultivation.

Immunostaining

HCEC aggregates are embedded in OCT and subjected to frozen sectioning. Cryosections of 4 µm are air-dried at room temperature (RT) for 30 minutes, and fixed in cold acetone for 10 minutes at −20° C. Sections used for immunostaining are rehydrated in PBS, and incubated in 0.2% Triton X-100 for 10 minutes. After three rinses with PBS for 5 minutes each and preincubation with 2% BSA to block nonspecific staining, the sections are incubated with anti-laminin 5, type IV collagen, perlecan, ZO-1, and connexin 43 (all at 1:100) antibodies for 1 hour. After three washes with PBS for 15 minutes, the sections are incubated with a FITC-conjugated secondary antibody (goat anti-rabbit or anti-mouse IgG at 1:100) for 45 minutes. After three additional PBS washes, each for 10 minutes, they are counterstained with propidium iodide (1:1000) or Hoechst 33342 (10 µg/mL), then mounted with an antifade solution and analyzed with a fluorescence microscope. HCECs cultured in 24-well plates or chamber slides are fixed in 4% paraformaldehyde for 15 minutes at RT and stained with anti-ZO-1 and connexin 43 antibodies as just described. For immunohistochemical staining of Ki67, endogenous peroxidase activity is blocked by 0.6% hydrogen peroxide for 10 minutes. Nonspecific staining is blocked by 1% normal goat serum for 30 minutes. Cells are then incubated with anti-Ki67 antibody (1:100) for 1 hour. After three washes with PBS for 15 minutes, cells are incubated with biotinylated rabbit anti-mouse IgG (1:100) for 30 minutes, followed by incubation with ABC reagent for 30 minutes. The reaction product is developed with DAB for 5 minutes and examined by light microscope.

Cell-Viability and TUNEL Assays

Cell-viability and terminal deoxyribonucleotidyl transferase-mediated FITC-linked dUTP nick-end DNA labeling (TUNEL) assays are used to determine living and apoptotic cells, respectively. HCEC aggregates are incubated with cell-viability assay reagents for 15 minutes at RT. Live cells are distinguished by green fluorescence staining of the cell cytoplasm, and dead cells are stained with red fluorescence in the nuclei. The TUNEL assay is performed according to the manufacturer's instructions. Briefly, cross-sections of HCEC aggregates are fixed in 4% paraformaldehyde for 20 minutes at RT and permeabilized with 1% Triton X-100. Samples are then incubated for 60 minutes at 37° C. with exogenous TdT and fluorescein-conjugated dUTP, for repair of nicked 3'-hydroxyl DNA ends. Cells are treated with DNase I as the positive control, whereas negative control cells are incubated with a buffer lacking the rTdT enzyme. The apoptotic nuclei are labeled with green fluorescence.

Example 45

Cell Culture of Retinal Cells

Eyes are cut in half along their equator and the neural retina is dissected from the anterior part of the eye in buffered saline solution, according to standard methods known in the art. Briefly, the retina, ciliary body, and vitreous are dissected away from the anterior half of the eye in one piece, and the retina is gently detached from the clear vitreous. Each retina is dissociated with papain (Worthington Biochemical Corporation, Lakewood, N.J.), followed by inactivation with fetal bovine serum (FBS) and addition of 134 Kunitz units/ml of DNaseI. The enzymatically dissociated cells are triturated and collected by centrifugation, resuspended in Dulbecco's modified Eagle's medium (DMEM)/F12 medium (Gibco BRL, Invitrogen Life Technologies, Carlsbad, Calif.) containing 25 µg/ml of insulin, 100 µg/ml of transferrin, 60 µM putrescine, 30 nM selenium, 20 nM progesterone, 100 U/ml of penicillin, 100 µg/ml of streptomycin, 0.05 M Hepes, and 10% FBS. Dissociated primary retinal cells are plated onto Poly-D-lysine- and Matrigel-(BD, Franklin Lakes, N.J.) coated glass coverslips that are placed in 24-well tissue culture plates (Falcon Tissue Culture Plates, Fisher Scientific, Pittsburgh, Pa.). Cells are maintained in culture for 5 days to one month in 0.5 ml of media (as above, except with only 1% FBS) at 37° C. and 5% CO2.

Immunocytochemistry Analysis

The retinal neuronal cells are cultured for 1, 3, 6, and 8 weeks in the presence and absence of test compounds of the present invention, and the cells are analyzed by immunohistochemistry at each time point. Immunocytochemistry analysis is performed according to standard techniques known in the art. Rod photoreceptors are identified by labeling with a rhodopsin-specific antibody (mouse monoclonal, diluted 1:500; Chemicon, Temecula, Calif.). An antibody to mid-weight neurofilament (NFM rabbit polyclonal, diluted 1:10,000, Chemicon) is used to identify ganglion cells; an antibody to β3-tubulin (G7121 mouse monoclonal, diluted 1:1000, Promega, Madison, Wis.) is used to generally identify interneurons and ganglion cells, and antibodies to calbindin (AB1778 rabbit polyclonal, diluted 1:250, Chemicon) and calretinin (AB5054 rabbit polyclonal, diluted 1:5000, Chemicon) are used to identify subpopulations of calbindin- and calretinin-expressing interneurons in the inner nuclear layer. Briefly, the retinal cell cultures are fixed with 4% paraformaldehyde (Polysciences, Inc, Warrington, Pa.) and/or ethanol, rinsed in Dulbecco's phosphate buffered saline (DPBS), and incubated with primary antibody for 1 hour at 37° C. The cells are then rinsed with DPBS, incubated with a secondary antibody (Alexa 488- or Alexa 568-conjugated secondary antibodies (Molecular Probes, Eugene, Oreg.)), and rinsed with DPBS. Nuclei are stained with 4',6-diamidino-2-phenylindole (DAN, Molecular Probes), and the cultures are rinsed with DPBS before removing the glass coverslips and mounting them with Fluoromount-G (Southern Biotech, Birmingham, Ala.) on glass slides for viewing and analysis.

Example 46

Matrigel Plug Angiogenesis Assay

Matrigel containing test compounds are injected subcutaneously or intraocularly, where it solidifies to form a plug. The plug is recovered after 7-21 days in the animal and examined histologically to determine the extent to which blood vessels have entered it. Angiogenesis is measured by quantification of the vessels in histologic sections. Alternatively, fluorescence measurement of plasma volume is performed using fluorescein isothiocyanate (FITC)-labeled dextran 150. The results are expected to indicate one or more compounds disclosed herein that inhibit angiogenesis and are thus expected to be useful in treating ocular disorders related to aberrant angiogenesis and/or vascular permeability.

Example 47

The Corneal Angiogenesis Assay

A pocket is made in the cornea, and a plug containing an angiogenesis inducing formulation (e.g. VEGF, FGF, or tumor cells), when introduced into this pocket, elicits the ingrowth of new vessels from the peripheral limbal vasculature. Slow-release materials such as ELVAX (ethylene vinyl copolymer) or Hydron are used to introduce angiogenesis inducing substances into the corneal pocket. Alternatively, a sponge material is used.

The effect of putative inhibitors on the locally induced (e.g., sponge implant) angiogenic reaction in the cornea (e.g., by FGF, VEGF, or tumor cells). The test compound is administered orally, systemically, or directly to the eye. Systemic administration is by bolus injection or, more effectively, by use of a sustained-release method such as implantation of osmotic pumps loaded with the test inhibitor. Administration to the eye is by any of the methods described herein including but not limited to eye drops, topical administration of a cream, emulsion, or gel, intravitreal injection.

The vascular response is monitored by direct observation throughout the course of the experiment using a stereomicroscope in mice. Definitive visualization of the corneal vasculature is achieved by administration of fluorochrome-labeled high-molecular weight dextran. Quantification is performed by measuring the area of vessel penetration, the progress of vessels toward the angiogenic stimulus over time, or in the case of fluorescence, histogram analysis or pixel counts above a specific (background) threshold.

The results are expected to indicate one or more compounds disclosed herein that inhibit angiogenesis and are thus expected to be useful in treating ocular disorders related to aberrant angiogenesis and/or vascular permeability.

Example 48

Microtiter-Plate Angiogenesis Assay

The assay plate is prepared by placing a collagen plug in the bottom of each well with 5-10 cell spheroids per collagen plug each spheroid containing 400-500 cells. Each collagen plug is covered with 1100 µl of storage medium per well and stored for future use (1-3 days at 37° C., 5% CO2). The plate is sealed with sealing. Test compounds are dissolved in 200 µl assay medium with at least one well including a VEGF positive control and at least one well without VEGF or test compound as a negative control. The assay plate is removed from the incubator and storage medium is carefully pipeted away. Assay medium containing the test compounds are pipeted onto the collagen plug. The plug is placed in a humidified incubator for (37° C., 5% CO2) 24-48 hours. Angiogenesis is quantified by counting the number of sprouts, measuring average sprout length, or determining cumulative sprout length. The assay can be preserved for later analysis by removing the assay medium, adding 1 ml of 10% paraformaldehyde in Hanks BSS per well, and storing at 4° C. The results are expected to identify compounds that inhibit angiogenesis in various cell types tested, including cells of ocular origin.

Example 49

TNP-Ficoll T-Cell Independent B-Cell Activation Assay

To test the effects of the compounds of the present invention in suppressing T cell independent antibody production, the TNP-Ficoll B-cell activation assay was used as described herein. Compounds of the present invention were dissolved in an appropriate vehicle (e.g. 5% 1-methyl-2-pyrrolidinone, 85% polyethylene glycol 400, 10% solutor). Compounds were administered orally approximately 1 hr before TNP-Ficoll treatment to 4-10 week old mice. To study the effects of the compounds on B-cell activation, one set of mice were grouped according to the following table:

| Group# | Mice/ group treated | Comp Group | Antigen injection at day-1 | | | Compound Administration from day-1 to day-7 | | |
|---|---|---|---|---|---|---|---|---|
| | | | TNP-F | Route | | (mg/kg) | Route | Regimen |
| 1 | 4 | Vehicle | Antigen only | 200 uL | ip | 0 | Po | BID for 7 days |
| 2 | 8 | — | Antigen only | (0.5 mg/ml) | | 0 | | |
| 3 | 8 | Compound #7 | reference | | | 30 | | |
| 4 | 8 | Compound #53 | Antigen + cmp | | | 1 | | |
| 5 | 8 | | | | | 3 | | |
| 6 | 8 | | | | | 10 | | |
| 7 | 8 | | | | | 30 | | |
| 8 | 8 | | | | | 60 | | |

Four animals in group 1, and eight animals in groups 2 to 7 were euthanized in CO2 2 hours after the last compound administration on day 7. Blood was immediately collected by cadio-puncture and kept at 37° C. for 1 hr to clot followed by overnight incubation at 4° C. to allow the clot to contract. The following day, serum was collected by decanting and centrifugation at 3000 rpm for 10 min. The collected serum was then frozen at −80° C. for future analysis.

Serum samples were analyzed for anti-TNP antibody titers by ELISA as described herein. TNP-BSA was coated onto a Nunc Maxisorb microtiter plate with 10 µl/well at a concentration of 10 µg/ml in phosphate buffered saline (PBS). The Maxisorb plate was incubated for 1.5 hours at room temperature and the solution was removed. 200 µl/well of blocking buffer (e.g. 1% BSA in PBS) was added to each well and incubated 1 hr at room temperature. The plate was washed once with 200 µl/well of PBS 0.05% Tween-20 (wash buffer). A 1:2 dilution of serum from each mouse in blocking buffer was added to each well in the first column (1) of the microtiter plate. The serum in each well of column 1 was then diluted 3-fold in blocking buffer and added to column 2. The serum in each well of column 2 was diluted 3-fold in blocking buffer and added to column 3. The procedure was repeated across the twelve columns of the microtiter plate. The microtiter plate was incubated 1 hr at room temperature. Serum was removed from the plate and the plate was washed three times with wash buffer. 100 µl/well of goat anti-mouse IgG3-HRP diluted 1:250 in blocking buffer was added to each well and incubated 1 hr at room temperature. The anti-mouse IgG3-HRP was removed from the microtiter plate and the plate was washed six times with wash buffer. HRP substrate (200 µl ABTS solution+30% H2O2+10 ml citrate buffer) was added to each well at 100 µl/well, incubated 2-20 minutes in the dark and the amount of anti-TNP IgG3 was determined spectrophotometrically at 405 nm. Similarly, anti-TNP IgM and total anti-TNP Ab were determined using anti-mouse IgM-HRP and anti-mouse Ig-HRP respectively.

Figure 2:
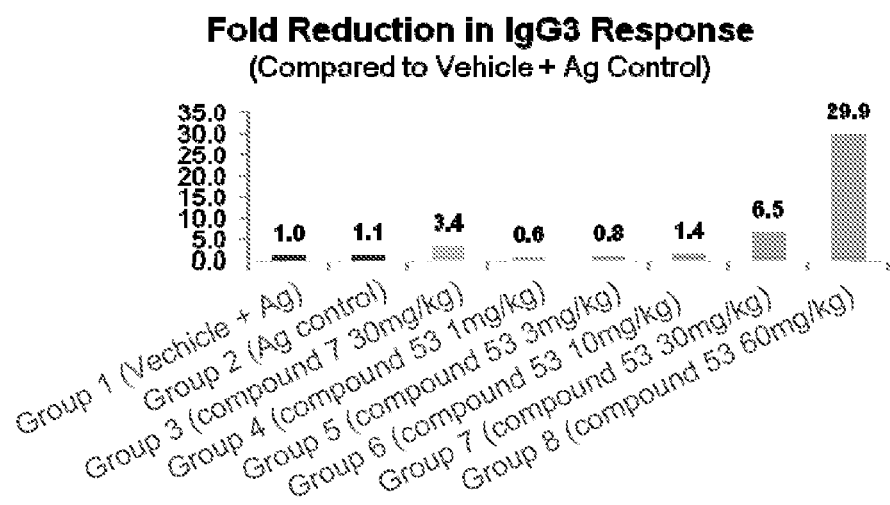
FIG. 2 depicts the fold reduction in TNP specific IgG3 response to antigens provided by compounds 7 and 53 of formula IV as compared to a vehicle control, when administered orally.

The results as shown in FIG. 2 further show that under the conditions tested compounds #7 and #53 exhibit 3.4 and 6.5-fold reductions respectively in IgG3 levels relative to vehicle control mice at a 30 mg/kg dose level. FIG. 2 further shows that compound #53 exhibits 29.9-fold reduction in IgG3 levels relative to vehicle control mice at a 60 mg/kg dose level under the conditions tested, Example 50

Rat Developing Type II Collagen Induced Arthritis Assay

In order to study the effects of the compounds of the present invention on the autoimmune disease arthritis, a collagen induced developing arthritis model was used. Female Lewis rats were given collagen injections at day 0. Bovine type II collagen was prepared as a 4 mg/ml solution in 0.01N acetic acid. Equal volumes of collagen and Freund's incomplete adjuvant were emulsified by hand mixing until a bead of the emulsified material held its form in water. Each rodent received a 300 µl injection of the mixture at each injection time spread over three subcutaneous sites on the back.

Oral compound administration began on day 0 and continued through day 16 with vehicle (5% NMP, 85% PEG 400, 10% Solutol) or compounds of the present invention in vehicle or control (e.g. methotrexate) at 12 hour intervals daily. Rats were weighed on days 0, 3, 6, 9-17 and caliper measurements of ankles taken on days 9-17. Final body weights were taken, and then the animals were euthanized on day 17. After euthanization, blood was drawn and hind paws and knees were removed. Blood was further processed for pharmacokinetics experiments as well as an anti-type II collagen antibody ELISA assay. Hind paws were weighed and then with the knees preserved in 10% formalin. The paws and knees were subsequently processed for microcopy. Livers, spleen and thymus were also weighed. Sciatic nerves were prepared for histopathology.

Knee and ankle joints were fixed for 1-2 days and decalcified for 4-5 days. Ankle joints were cut in half longitudinally, knees were cut in half along the frontal plane. Joints were then processed, embedded, sectioned and stained with toluidine blue. Scoring of the joints was done according to the following criteria:

Knee and Ankle Inflammation
0=Normal
1=Minimal infiltration of inflammatory cells in synovium/ periarticular tissue
2=Mild infiltration
3=Moderate infiltration with moderate edema
4=Marked infiltration with marked edema
5=Severe infiltration with severe edema
Ankle Pannus
0=Normal
1=Minimal infiltration of pannus in cartilage and subchondral bone
2=Mild infiltration (<¼ of tibia or tarsals at marginal zones)
3=Moderate infiltration (¼ to ⅓ of tibia or small tarsals affected at marginal zones)
4=Marked infiltration (½-¾ of tibia or tarsals affected at marginal zones)
5=Severe infiltration (>¾ of tibia or tarsals affected at marginal zones, severe distortion of overall architecture)

Knee Pannus
0=Normal
1=Minimal infiltration of pannus in cartilage and subchondral bone
2=Mild infiltration (extends over up to ¼ of surface or subchondral area of tibia or femur)
3=Moderate infiltration (extends over >¼ but <½ of surface or subchondral area of tibia or femur)
4=Marked infiltration (extends over ½ to ¾ of tibial or femoral surface)
5=Severe infiltration (covers >¾ of surface)
Cartilage Damage (Ankle, emphasis on small tarsals)
0=Normal
1=Minimal=minimal to mild loss of toluidine blue staining with no obvious chondrocyte loss or collagen disruption
2=Mild=mild loss of toluidine blue staining with focal mild (superficial) chondrocyte loss and/or collagen disruption
3=Moderate=moderate loss of toluidine blue staining with multifocal moderate (depth to middle zone) chondrocyte loss and/or collagen disruption, smaller tarsals affected to ½-¾ depth
4=Marked=marked loss of toluidine blue staining with multifocal marked (depth to deep zone) chondrocyte loss and/or collagen disruption, 1 or more small tarsals have full thickness loss of cartilage
5=Severe=severe diffuse loss of toluidine blue staining with multifocal severe (depth to tide mark) chondrocyte loss and/or collagen disruption
Cartilage Damage (Knee, emphasis on femoral condyles)
0=Normal
1=Minimal=minimal to mild loss of toluidine blue staining with no obvious chondrocyte loss or collagen disruption
2=Mild=mild loss of toluidine blue staining with focal mild (superficial) chondrocyte loss and/or collagen disruption
3=Moderate=moderate loss of toluidine blue staining with multifocal to diffuse moderate (depth to middle zone) chondrocyte loss and/or collagen disruption
4=Marked=marked loss of toluidine blue staining with multifocal to diffuse marked (depth to deep zone) chondrocyte loss and/or collagen disruption or single femoral surface with total or near total loss
5=Severe=severe diffuse loss of toluidine blue staining with multifocal severe (depth to tide mark) chondrocyte loss and/or collagen disruption on both femurs and/or tibias
Bone Resorption (Ankle)
0=Normal
1=Minimal=small areas of resorption, not readily apparent on low magnification, rare osteoclasts
2=Mild=more numerous areas of resorption, not readily apparent on low magnification, osteoclasts more numerous, <¼ of tibia or tarsals at marginal zones resorbed
3=Moderate=obvious resorption of medullary trabecular and cortical bone without full thickness defects in cortex, loss of some medullary trabeculae, lesion apparent on low magnification, osteoclasts more numerous, ¼ to ⅓ of tibia or tarsals affected at marginal zones
4=Marked=Full thickness defects in cortical bone, often with distortion of profile of remaining cortical surface, marked loss of medullary bone, numerous osteoclasts, ½-¾ of tibia or tarsals affected at marginal zones
5=Severe=Full thickness defects in cortical bone, often with distortion of profile of remaining cortical surface, marked loss of medullary bone, numerous osteoclasts, >¾ of tibia or tarsals affected at marginal zones, severe distortion of overall architecture
Bone Resorption (Knee)
0=Normal
1=Minimal=small areas of resorption, not readily apparent on low magnification, rare osteoclasts
2=Mild=more numerous areas of resorption, definite loss of subchondral bone involving ¼ of tibial or femoral surface (medial or lateral)
3=Moderate=obvious resorption of subchondral bone involving >¼ but <½ of tibial or femoral surface (medial or lateral)
4=Marked=obvious resorption of subchondral bone involving >½ but <¾ of tibial or femoral surface (medial or lateral)
5=Severe=distortion of entire joint due to destruction involving >¾ of tibial or femoral surface (medial or lateral)

Statistical analysis of body/paw weights, paw AUC parameters and histopathologic parameters were evaluated using a Student's t-test or other appropriate (ANOVA with post-test) with significance set at the 5% significance level. Percent inhibition of paw weight and AUC was calculated using the following formula:

$$\% \text{ Inhibition} = A - B/A \times 100$$

A=Mean Disease Control−Mean Normal
B=Mean Treated−Mean Normal

Figure 3:
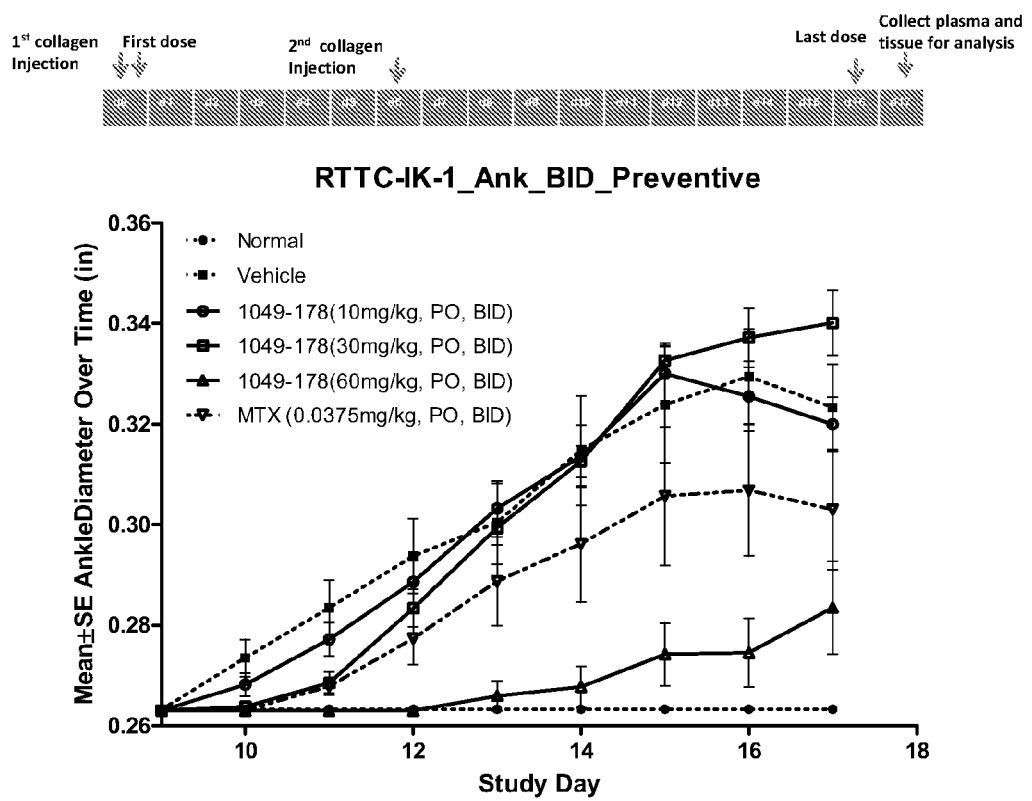
FIG. 3 depicts the dose-dependent effect of twice daily oral administration of compound 53 of formula IV in reducing the increase in ankle diameter over time in a collagen-induced developing arthritis model in rats. Also depicted are the results from non-arthritic control rats, arthritic control rats administered with a negative control vehicle, and arthritic control rats treated twice daily with methotrexate.

The results as shown in FIG. 3 demonstrate the effect of compound #53 at 10, 30, and 60 mg/kg dosages at 12 hour intervals on mean ankle diameter over time in a rat developing type II collagen induced arthritis model under the conditions tested. Relative to the vehicle alone control or to the methotrexate control, the compounds of the present invention exhibited a significant reduction in arthritis induced ankle diameter increase over time.

Figure 4:
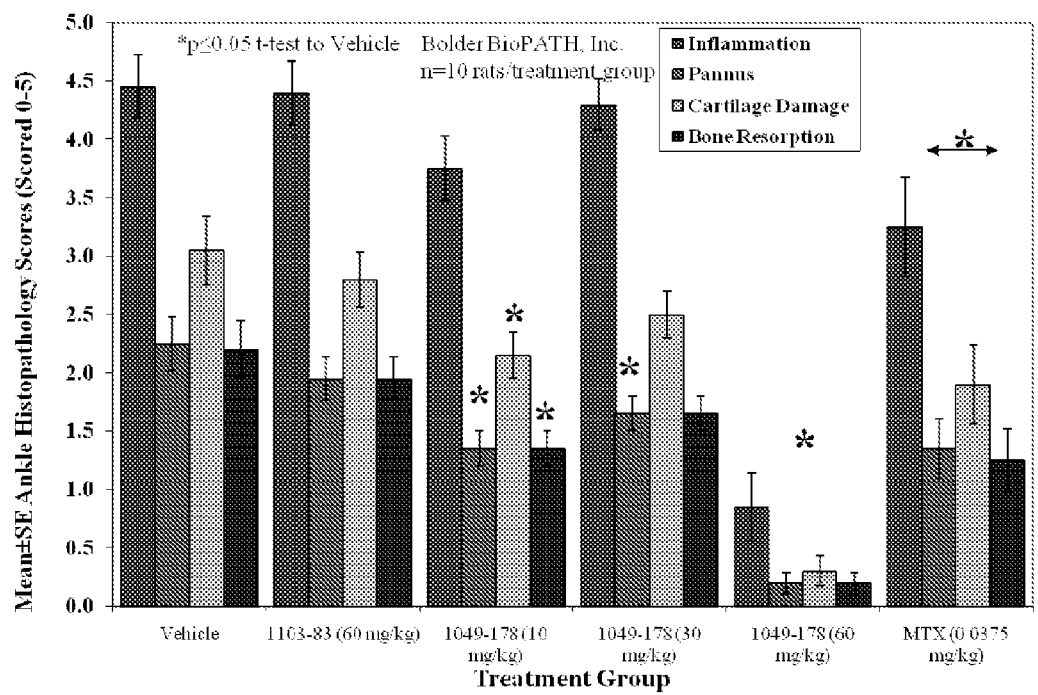
FIG. 4 depicts the dose-dependent effect of compounds 7 and 53 of formula IV in improving ankle histopathology when administered in a collagen-induced developing arthritis model in rats. Also depicted are the results from arthritic control rats administered with negative control vehicle or methotrexate.

The results as shown in FIG. 4 demonstrate the effect of compounds #7 and #53 on ankle histopathology in the categories of inflammation, pannus, cartilage damage, and bone resporption as previously described under the conditions tested. The results show a significant reduction in one or more categories by one of the compounds of the present invention (i.e. compound #53) under the conditions tested. FIG. 4 further shows that at 60 mg/kg, there is a statistically significant reduction in all categories of ankle histopathology for one of the compounds of the present invention (i.e. compound #53) under the conditions tested. This suggests that one or more compounds of the present invention may be useful for the treatment and reduction of arthritis disease symptoms.

Figure 5:
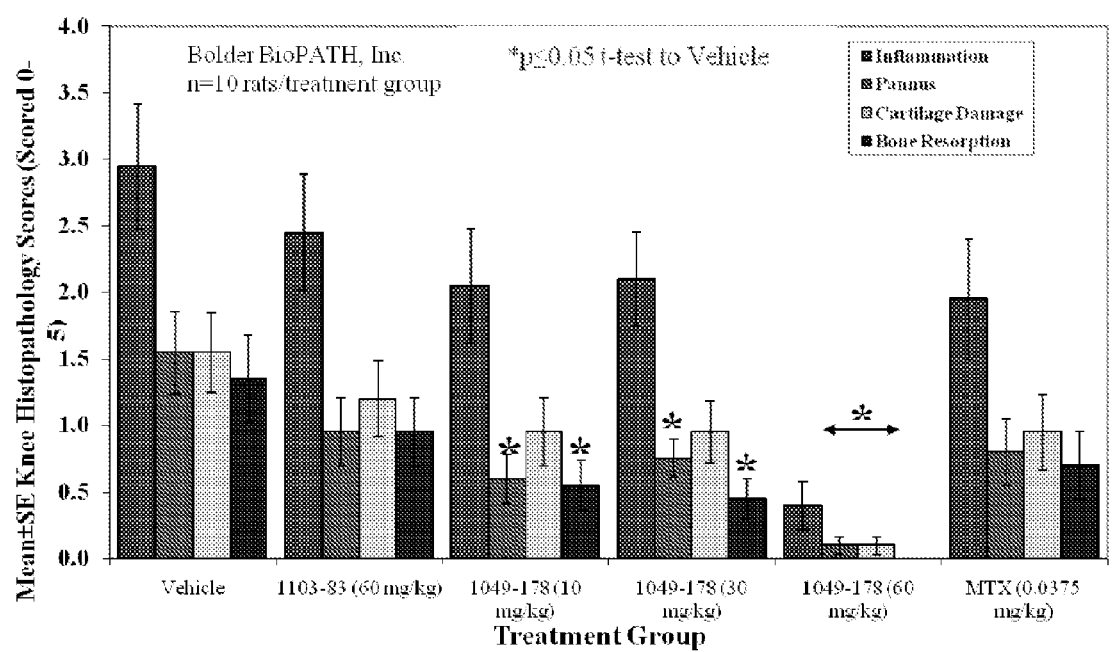
FIG. 5 depicts the dose-dependent effect of compounds 7 and 53 of formula IV in improving knee histopathology when administered in a collagen-induced developing arthritis model in rats. Also depicted are the results from arthritic control rats administered with negative control vehicle or positive control methotrexate.

The results as shown in FIG. 5 demonstrate the effect of compounds #7 and #53 on knee histopathology under the conditions tested. The results demonstrate a dose dependent reduction in knee histopathology. This suggests that one or more compounds of the present invention may be useful for the treatment and reduction of arthritis disease symptoms.

Figure 6:
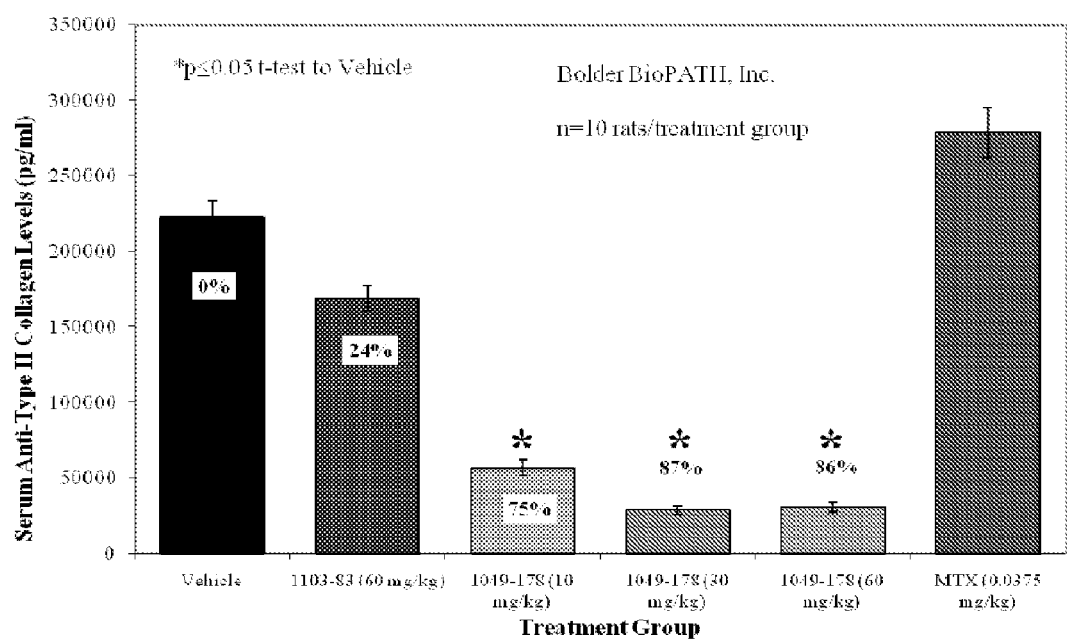
FIG. 6 depicts the dose-dependent effect of compounds 7 and 53 of formula IV in reducing the level of anti-type II collagen antibodies in vivo when administered to a collagen-induced developing arthritis rat model. Also depicted are the results from arthritic rats administered with negative control vehicle or methotrexate.

The results as shown in FIG. 6 demonstrate the effect of the compounds #7 and #53 on serum anti-type II collagen levels under the conditions tested. The results further show a significant reduction at 10, 20, and 60 mg/kg dosage levels of serum anti-type II collagen levels for compound #53, suggesting that one or more compounds of the present invention may not only be useful for the treatment and reduction of arthritis disease symptoms, but may also be useful for the inhibition of the autoimmune reaction itself.

Figure 7:
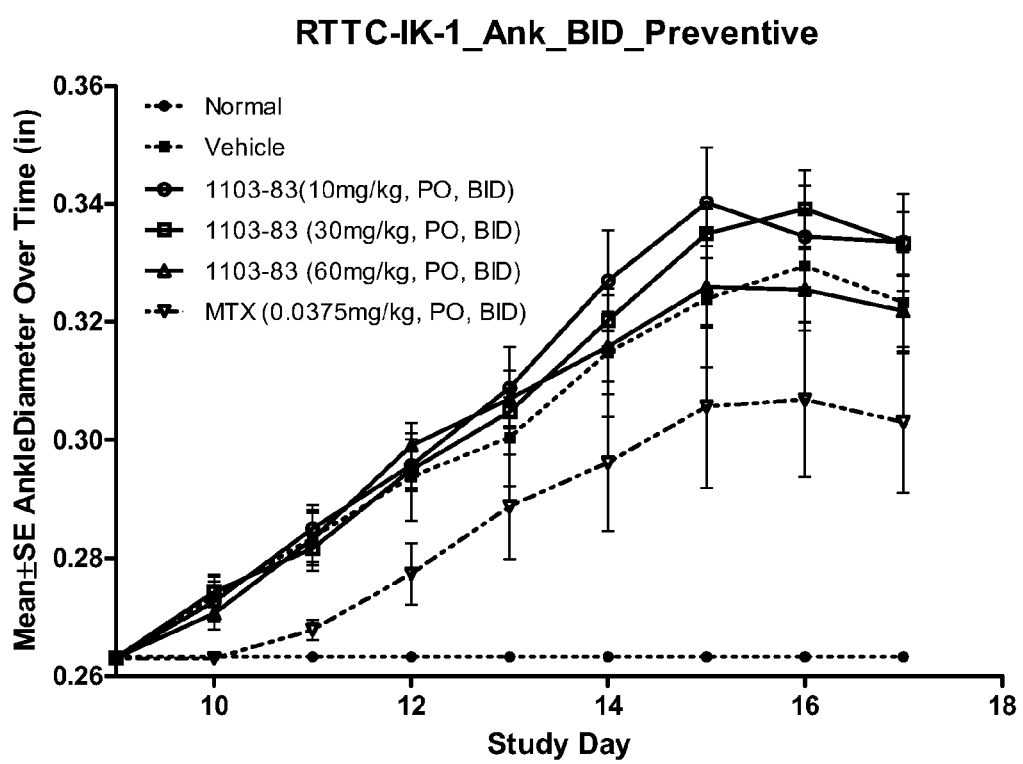
FIG. 7 depicts the dose-dependent effect of compound 7 of formula IV on improving ankle histopathology when administered in collagen-induced developing arthritis model in rats. Also depicted are the results from arthritic vehicle control rats and methotrexate-treated arthritic rats.

The results as shown in FIG. 7 demonstrate the effect of compound #7 at 10, 30, and 60 mg/kg dosages at 12 hour intervals on mean ankle diameter over time under the conditions tested. Relative to the vehicle alone control or to the methotrexate control, the compound exhibited a reduction in arthritis induced ankle diameter increase over time under the conditions tested.

Example 51

Rat Established Type II Collagen Induced Arthritis Assay

In order to examine the dose responsive efficacy of the compounds of the present invention in inhibiting the inflammation, cartilage destruction and bone resorption of 7 day established type II collagen induced arthritis in rats, compounds were administered orally daily or twice daily for 6 days.

Female Lewis rats were anesthetized and given collagen injections prepared and administered as described previously on day 0. On day 6, animals were anesthetized and given a second collagen injection. Caliper measurements of normal (pre-disease) right and left ankle joints were performed on day 9. On days 10-11, arthritis typically occurred and rats were randomized into treatment groups. Randomization was performed after ankle joint swelling was obviously established and there was good evidence of bilateral disease.

After an animal was selected for enrollment in the study, treatment was initiated by the oral route. Animals were given vehicle, control (Enbrel) or compound doses, twice daily or once daily (BID or QD respectively). Dosing was administered on days 1-6 using a volume of 2.5 ml/kg (BID) or 5 ml/kg (QD) for oral solutions. Rats were weighed on days 1-7 following establishment of arthritis and caliper measurements of ankles taken every day. Final body weights were taken on day 7 and animals were euthanized.

Figure 8:
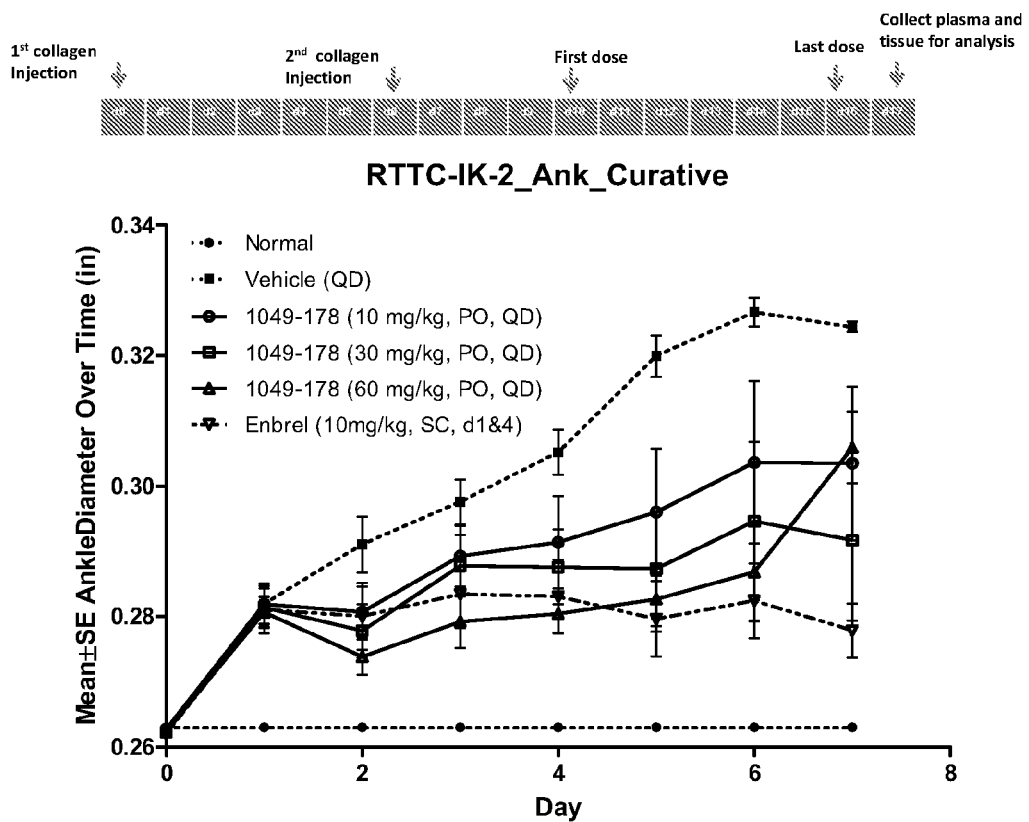
FIG. 8 depicts the dose-dependent effect of compound 53 of formula IV administered daily on ankle histopathology in a collagen-induced established arthritis model in rats. Also depicted are the results from arthritic arthritic vehicle control rats and Enbrel-treated arthritic rats.
Figure 9:
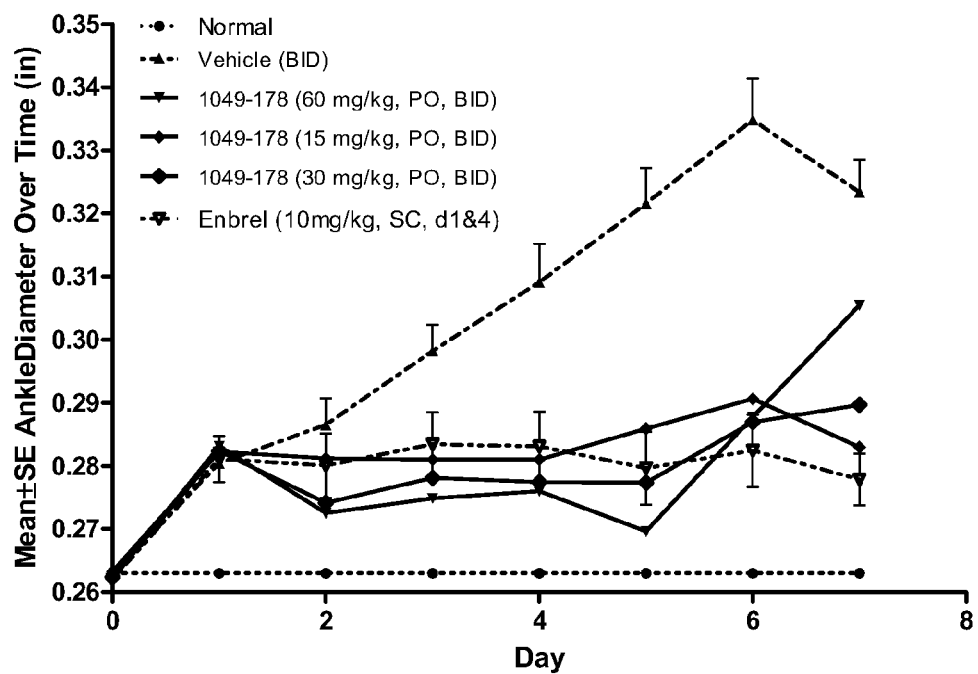
FIG. 9 depicts the dose-dependent effect of compound 53 of formula IV administered twice daily on ankle histopathology in a collagen-induced established arthritis model in rats. Also depicted are the results from arthritic vehicle control rats and Enbrel-treated arthritic rats.

The results as shown in FIG. 8 shows a significant reduction in mean ankle diameter increase over time for compound #53 with a once daily dosage under the conditions tested. The results in FIG. 9 further demonstrate a significant reduction in mean ankle diameter increase over time for compound #53 with a twice daily dosage under the conditions tested. This suggests that the compounds of the present invention may be useful for the treatment of autoimmune diseases such as arthritis.

Example 52

Adjuvant Induced Arthritis Assay

Intrathecal Catheterization of Rats

Isoflurane-anesthetized Lewis rats (200-250 g) were implanted with an intrathecal (IT) catheter. After a 6 d recovery period, all animals except those that appeared to have sensory or motor abnormalities (fewer than 5% of the total number) were used for experiments. For IT administration, 10 µl of drug or saline followed by 10 µl of isotonic saline was injected through the catheter.

Adjuvant Arthritis and Drug Treatment

Lewis rats were immunized at the base of the tail with 0.1 ml of complete Freund's adjuvant (CFA) on day 0 several days after catheter implantation (n=6/group). Drug (e.g. one or more compounds of the present invention or or vehicle) treatment was generally started on day 8 and continued daily until day 20. Clinical signs of arthritis generally begin on day 10, and paw swelling was determined every second day by water displacement plethysmometry.

Figure 10:
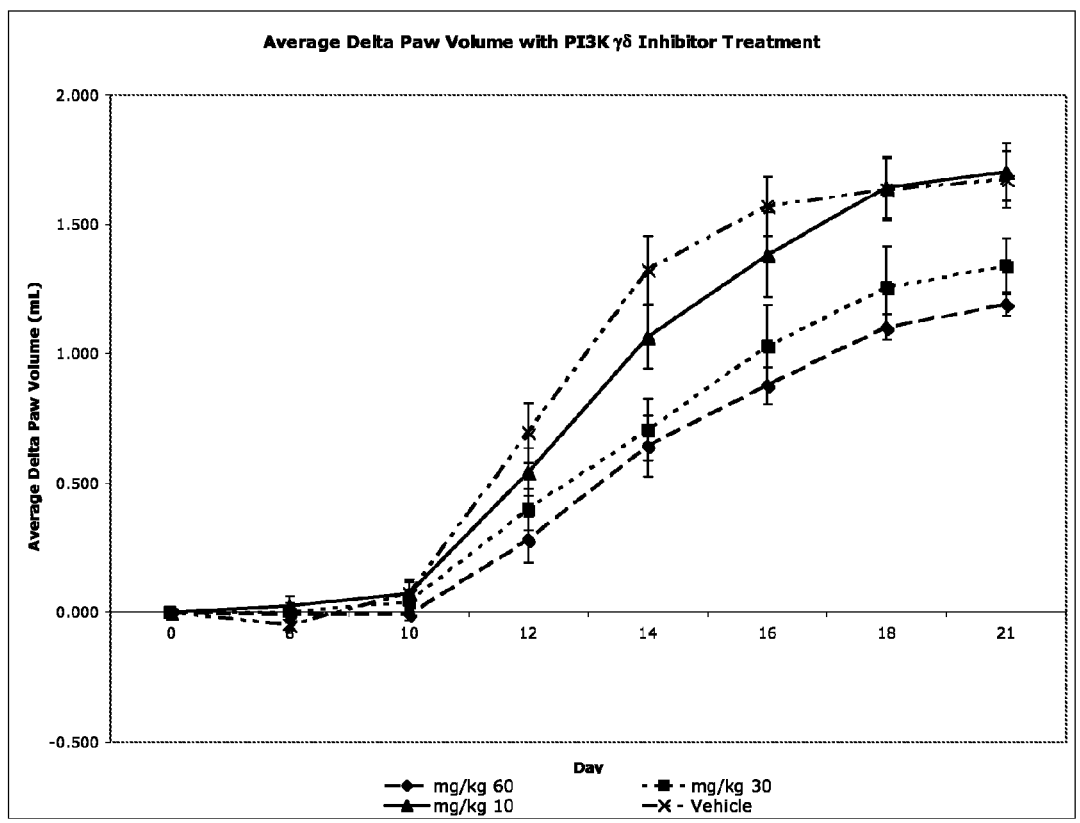
FIG. 10 depicts the dose-dependent effect of compound 53 of formula IV on the increase in average paw volume in an adjuvant induced arthritis model.

The results as depicted in FIG. 10 by the average change in paw volume under the dosage regimes indicated show that under the conditions tested, compound #53 shows a dose dependent reduction in the average paw volume increase as measured in this adjuvant induced arthritis model system. These results suggest that one or more of the compounds of the present invention may be useful for the treatment of one or more of the diseases or conditions described herein.

Figure 11:
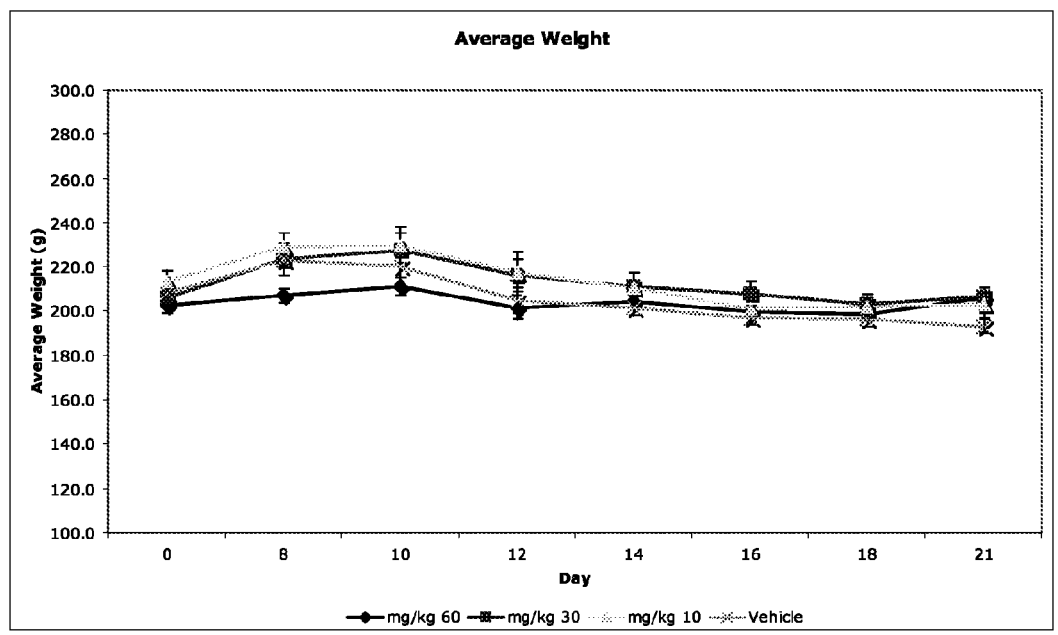
FIG. 11 depicts the effect of compound 53 of formula IV on the average weight over time of rats in an adjuvant induced arthritis model in rats.

The results as depicted in FIG. 11 show that compound #53 does not exhibit toxicity or other adverse reaction under the conditions tested as measured by a lack of weight loss.

Example 53

Rodent Pharmacokinetic Assay

In order to study the pharmacokinetics of the compounds of the present invention a set of 4-10 week old mice are grouped according to the following table:

| Group# | Mice/group | Compound treated | Compound Administration from day-1 to day-7 | | |
|---|---|---|---|---|---|
| | | | (mg/kg) | Route | Regimen |
| 1 | 3 | | 1 | Po | BID for 7 days |
| 2 | 3 | | 3 | | |
| 3 | 3 | | 10 | | |
| 4 | 3 | | 30 | | |
| 5 | 3 | | 60 | | |

Compounds of the present invention are dissolved in an appropriate vehicle (e.g. 5% 1-methyl-2-pyrrolidinone, 85% polyethylene glycol 400, 10% Solutor) and administered orally at 12 hour intervals daily. All animals are euthanized in $CO_2$ 2 hours after the final compound is administered. Blood is collected immediately and kept on ice for plasma isolation. Plasma is isolated by centrifuging at 5000 rpm for 10 minutes. Harvested plasma is frozen for pharmacokinetic detection.

The results are expected to demonstrate the pharmacokinetic parameters such as absorption, distribution, metabolism, excretion, and toxicity for the compounds of the present invention.

Example 54

Basotest™ Assay

The Basotest™ assay is performed using Orpegen Pharma Basotest™ reagent kit. Heparinized whole blood is pre-incubated with test compound or solvent at 37° C. for 20 min. Blood is then incubated with assay kit stimulation buffer (to prime cells for response) followed by allergen (dust mite extract or grass extract) for 20 min. The degranulation process is stopped by incubating the blood samples on ice. The cells are then labeled with anti-IgE-PE to detect basophilic granulocytes, and anti-gp53-FITC to detect gp53 (a glycoprotein expressed on activated basophils). After staining red blood cells are lysed by addition of Lysing Solution. Cells are washed, and analyzed by flow cytometry. Compounds 7 and 53 when tested in this assay inhibit allergen induced activation of basophilic granulocytes at sub micromolar range.

Example 55

Combination use of PI3Kδ Inhibitors and Agents that Inhibit IgE Production or Activity The compounds of the present invention may present synergistic or additive efficacy when administered in combination with agents that inhibit IgE production or activity. Agents that inhibit IgE production include, for example, one or more of TEI-9874, 2-(4-(6-cyclohexyloxy-2-naphtyloxy)phenylacetamide)benzoic acid, rapamycin, rapamycin analogs (i.e. rapalogs), TORC1 inhibitors, TORC2 inhibitors, and any other compounds that inhibit mTORC1 and mTORC2. Agents that inhibit IgE activity include, for example, anti-IgE antibodies such as Omalizumab and TNX-901.

One or more of the subject compounds capable of inhibiting PI3Kδ are efficacious in treatment of autoimmune and inflammatory disorders (AIID) for example rheumatoid arthritis. If any of the compounds causes an undesired level of IgE production, one may choose to administer it in combination with an agent that inhibits IgE production or IgE activity. Additionally, the administration of PI3Kδ or PI3Kδ/γ inhibitors of the present invention in combination with inhibitors of mTOR may also exhibit synergy through enhanced inhibition of the PI3K pathway. Various in vivo and in vitro models may be used to establish the effect of such combination treatment on AIID including but not limited to (a) in vitro B-cell antibody production assay, (b) in vivo TNP assay, and (c) rodent collagen induced arthritis model.

(a) B-Cell Assay

Mice are euthanized, and the spleens are removed and dispersed through a nylon mesh to generate a single-cell suspension. The splenocytes are washed (following removal of erythrocytes by osmotic shock) and incubated with anti-CD43 and anti-Mac-1 antibody-conjugated microbeads (Miltenyi Biotec). The bead-bound cells are separated from unbound cells using a magnetic cell sorter. The magnetized column retains the unwanted cells and the resting B cells are collected in the flow-through. Purified B-cells are stimulated with lipopolysaccharide or an anti-CD40 antibody and interleukin 4. Stimulated B-cells are treated with vehicle alone or with PI3Kδ inhibitors of the present invention such as compound 53 with and without mTOR inhibitors such as rapamycin, rapalogs, or mTORC1/C2 inhibitors. The results are expected to show that in the presence of mTOR inhibitors (e.g., rapamycin) alone, there is little to no substantial effect on IgG and IgE response. However, in the presence of PI3Kδ and mTOR inhibitors, the B-cells are expected to exhibit a decreased IgG response as compared to the B-cells treated with vehicle alone, and the B-cells are expected to exhibit a decreased IgE response as compared to the response from B-cells treated with PI3Kδ inhibitors alone.

(b) TNP Assay

Mice are immunized with TNP-Ficoll or TNP-KHL and treated with: vehicle, a PI3Kδ inhibitor, for example, compound 53 of the present invention, an mTOR inhibitor, for example rapamycin, or a PI3Kδ inhibitor in combination with an mTOR inhibitor such as rapamycin. Antigen-specific serum IgE is measured by ELISA using TNP-BSA coated plates and isotype specific labeled antibodies. It is expected that mice treated with an mTOR inhibitor alone exhibit little or no substantial effect on antigen specific IgG3 response and no statistically significant elevation in IgE response as compared to the vehicle control. It is also expected that mice treated with both PI3Kδ inhibitor and mTOR inhibitor exhibit a reduction in antigen specific IgG3 response as compared to the mice treated with vehicle alone. Additionally, the mice treated with both PI3Kδ inhibitor and mTOR inhibitor exhibit a decrease in IgE response as compared to the mice treated with PI3Kδ inhibitor alone.

(c) Rat Collagen Induced Arthritis Model

Female Lewis rats are anesthetized and given collagen injections prepared and administered as described previously on day 0. On day 6, animals are anesthetized and given a second collagen injection. Caliper measurements of normal (pre-disease) right and left ankle joints are performed on day 9. On days 10-11, arthritis typically occurs and rats are randomized into treatment groups. Randomization is performed after ankle joint swelling is obviously established and there is good evidence of bilateral disease.

After an animal is selected for enrollment in the study, treatment is initiated. Animals are given vehicle, PI3Kδ inhibitor, or PI3Kδ inhibitor in combination with rapamycin. Dosing is administered on days 1-6. Rats are weighed on days 1-7 following establishment of arthritis and caliper measurements of ankles taken every day. Final body weights are taken on day 7 and animals are euthanized.

It is expected that the combination treatment using PI3Kδ inhibitor and rapamycin provides greater efficacy than treatment with PI3Kδ inhibitor alone.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

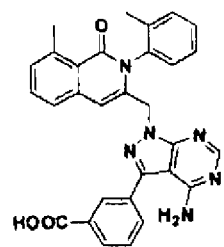

What is claimed is:

1. A compound of Formula IV:

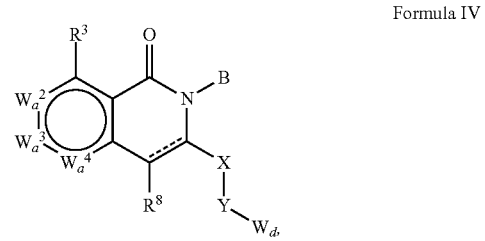

Formula IV or a pharmaceutically acceptable salt thereof, wherein $W_a^2$ is $CR^5$;

$W_a^3$ is $CR^6$;

$W_a^4$ is $CR^7$;

$W_d$ is

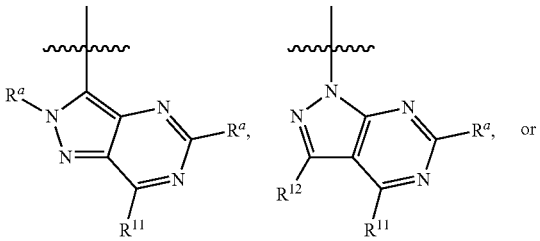

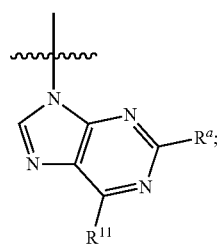

$R^a$ is hydrogen, halo, phosphate, urea, carbonate, alkyl, alkenyl, alkynyl, cycloalkyl, heteroalkyl, or heterocycloalkyl;

$R^{11}$ is hydrogen, alkyl, halo, amino, amido, hydroxy, or alkoxy;

$R^{12}$ is hydrogen, alkyl, cyano, alkynyl, alkenyl, halo, aryl, heteroaryl, heterocycloalkyl, cycloalkyl, amino, carboxylic acid, alkoxycarbonyl, or amido;

B is alkyl, amino, heteroalkyl, cycloalkyl, heterocycloalkyl, or a moiety of Formula II:

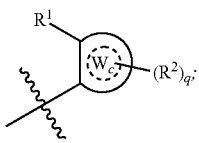

Formula II $W_c$ is aryl, heteroaryl, heterocycloalkyl, or cycloalkyl;

q is an integer of 0, 1, 2, 3, or 4;

X is a bond or —$(CH(R^9))_z$—;

Y is a bond, —O—, —S—, —S(═O)—, —S(═O)$_2$—, —N($R^9$)—, —C(═O)—$(CHR^9)_z$—, —C(═O)—, —N($R^9$)—C(═O)NH—, or —N($R^9$)C($R^9$)$_2$—;

each z is independently 1, 2, 3, or 4;

$R^1$ is hydrogen, alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, halo, cyano, hydroxy, nitro, phosphate, urea, or carbonate;

$R^2$ is alkyl, heteroalkyl, alkenyl, alkynyl, cycloalkyl, heterocycloalkyl, aryl, arylalkyl, heteroaryl, heteroarylalkyl, alkoxy, amido, amino, acyl, acyloxy, alkoxycarbonyl, sulfonamido, halo, cyano, hydroxy, or nitro;

$R^3$ is hydrogen, alkyl, alkenyl, alkynyl, cycloalkyl, heterocycloalkyl, alkoxy, amido, amino, acyl, acyloxy, alkoxycarbonyl, sulfonamido, halo, cyano, hydroxy, nitro, aryl, or heteroaryl;

$R^5$, $R^6$, $R^7$, and $R^8$ are independently hydrogen, $C_1$-$C_4$alkyl, $C_2$-$C_5$alkenyl, $C_2$-$C_5$alkynyl, $C_3$-$C_5$cycloalkyl, $C_1$-$C_4$heteroalkyl, $C_1$-$C_4$alkoxy, $C_1$-$C_4$amido, amino, acyl, $C_1$-$C_4$acyloxy, $C_1$-$C_4$sulfonamido, halo, cyano, hydroxy, or nitro; and each $R^9$ is independently hydrogen, $C_1$-$C_{10}$alkyl, $C_3$-$C_7$cycloalkyl, or $C_2$-$C_{10}$heteroalkyl.

2. The compound of claim 1, wherein the compound is of Formula V or Formula VI:

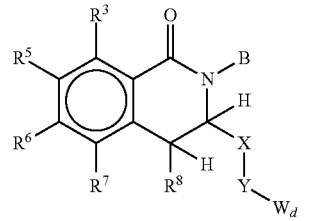

Formula V or

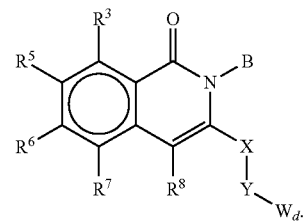

Formula VI

3. The compound of claim 1, wherein the compound is of Formula VII:

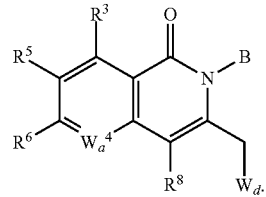

Formula VII

4. The compound of claim 1, wherein $R^1$ is selected from hydrogen, alkyl, and halo.

5. The compound of claim 4, wherein $R^1$ is hydrogen, methyl, isopropyl, or fluoro.

6. The compound of claim 1, wherein $R^3$ is —H, halo, alkyl, alkoxy, or cycloalkyl.

7. The compound of claim 6, wherein $R^3$ is —H, —CH$_3$, —CH$_2$CH$_3$, —CF$_3$, —Cl, or —F.

8. The compound of claim 7, wherein $R^3$ is methyl or chloro.

9. The compound of claim 1, wherein $R^5$ is H, —CN, —NH$_2$, $C_1$-$C_4$alkyl, $C_1$-$C_4$alkoxy, —CF$_3$, NO$_2$, or halo.

10. The compound of claim 1, wherein $R^6$ is H, —CN, —NH$_2$, $C_1$-$C_4$alkyl, $C_1$-$C_4$alkoxy, —CF$_3$, NO$_2$, or halo.

11. The compound of claim 1, wherein $R^7$ is H, —CN, —NH$_2$, $C_1$-$C_4$alkyl, $C_1$-$C_4$alkoxy, —CF$_3$, NO$_2$, or halo.

12. The compound of claim 1, wherein $R^8$ is H, —CN, —NH$_2$, $C_1$-$C_4$alkyl, $C_1$-$C_4$alkoxy, —CF$_3$, NO$_2$, or halo.

13. The compound of claim 1, wherein X is —CH$_2$— or —CH(CH$_3$)—.

14. The compound of claim 13, wherein —CH(CH$_3$)— is in an (S) stereochemical configuration.

15. The compound of claim 1, wherein X is —CH$_2$— and Y is a bond.

16. The compound of claim 1, wherein $W_c$ is aryl or heterocycloalkyl.

17. The compound of claim 1, wherein $W_d$ is 4-amino-1H-pyrazolo[3,4-d]pyrimidin-1-yl,
6-amino-9H-purin-9-yl, or
7-amino-2-methyl-2H-pyrazolo[4,3-d]pyrimidin-3-yl.

18. The compound of claim 1, wherein $W_d$ is

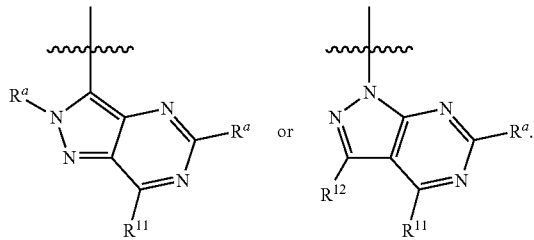

19. The compound of claim 18, wherein $W_d$ is

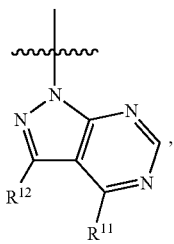

wherein $R^{11}$ is H, alkyl, halo, amino, amido, hydroxy, or alkoxy, and $R^{12}$ is H, alkyl, alkynyl, alkenyl, halo, aryl, heteroaryl, heterocycloalkyl, or cycloalkyl.

20. The compound of claim 19, wherein the compound is of Formula 6-A:

Formula 6-A

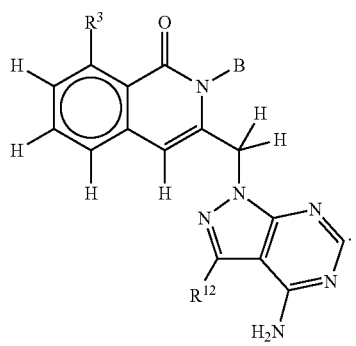

21. The compound of claim 20, wherein B is alkyl, amino, aryl, heteroalkyl, heteroaryl, heterocycloalkyl, or cycloalkyl.

22. The compound of claim 20, wherein B is aryl, alkyl, cycloalkyl, heteroaryl, or heterocycloalkyl.

23. The compound of claim 22, wherein B is optionally substituted phenyl, methyl, ethyl, isopropyl, cyclopropyl, cyclopentyl, optionally substituted pyridinyl, or tetrahydropyranyl.

24. The compound of claim 20, wherein B is a moiety of Formula II:

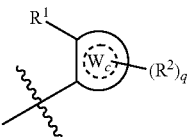

Formula II wherein $W_c$ is phenyl;

$R^1$ is H, —F, —Cl, —CN, —CH$_3$, isopropyl, —CF$_3$, —OCH$_3$, nitro, or phosphate;

$R^2$ is hydroxy or cyano; and q is an integer of 0 or 1.

25. The compound of claim 20, wherein $R^{12}$ is —I, —Br,

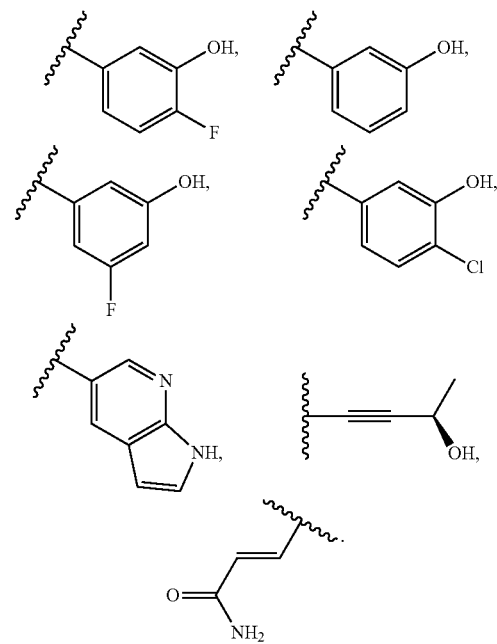

26. The compound of claim 25, wherein $R^{12}$ is

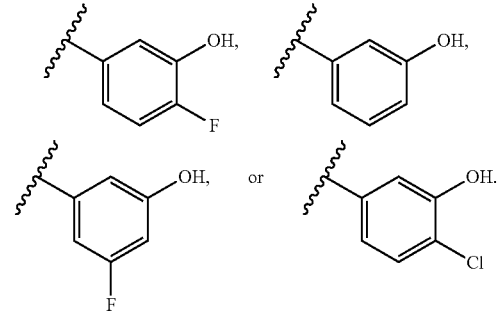

27. A pharmaceutical composition comprising a compound of claim 1, 19, or 20, or a pharmaceutically acceptable salt thereof, and one or more pharmaceutically acceptable excipients.

28. The compound of claim 1, wherein the compound is of Formula 2-A:

Formula 2-A

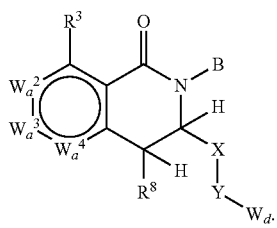

29. The compound of claim 1, wherein the compound is of Formula 2-B:

Formula 2-B

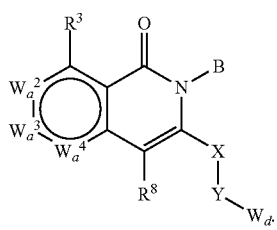

30. The compound of claim 20, or a pharmaceutically acceptable salt thereof, wherein the compound is:

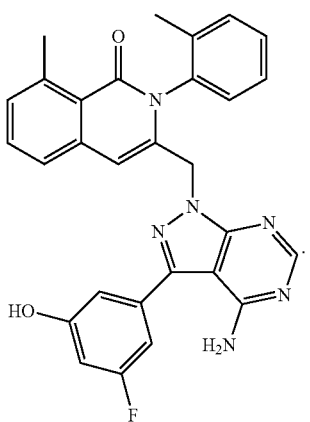 [SMILES: Cc1ccccc1-n1c(Cn2nc(-c3cc(O)cc(F)c3)c3c(N)ncnc32)cc2cccc(C)c2c1=O]

31. The compound of claim 20, or a pharmaceutically acceptable salt thereof, wherein the compound is:

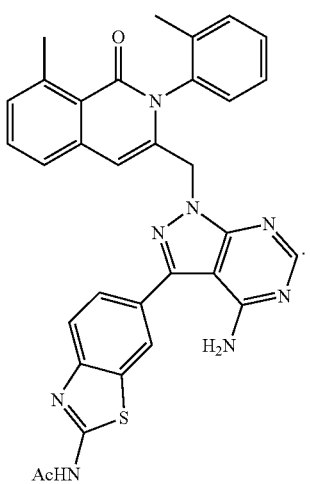 [SMILES: CC(=O)Nc1nc2ccc(-c3nn(Cc4cc5cccc(C)c5c(=O)n4-c4ccccc4C)c4ncnc(N)c34)cc2s1]

32. The compound of claim 2, or a pharmaceutically acceptable salt thereof, wherein the compound is:

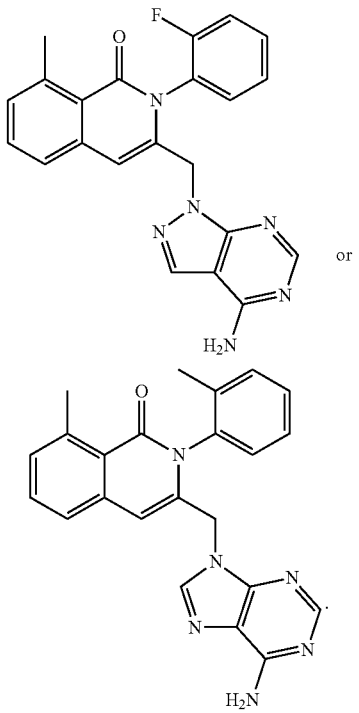

or

33. The compound of claim 18, or a pharmaceutically acceptable salt thereof, wherein the compound is:

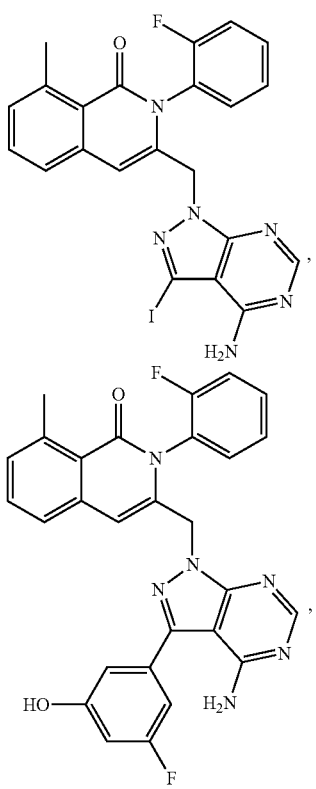

347
-continued
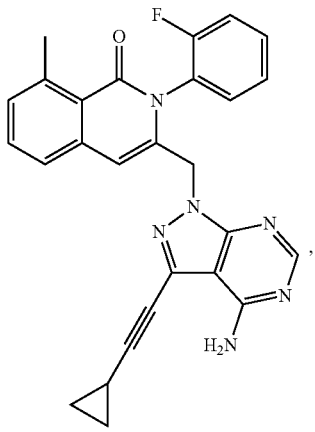
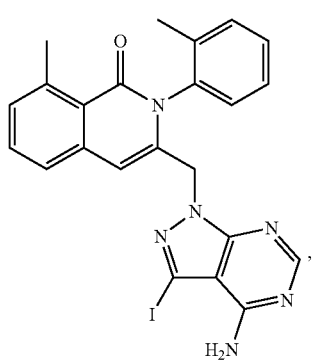
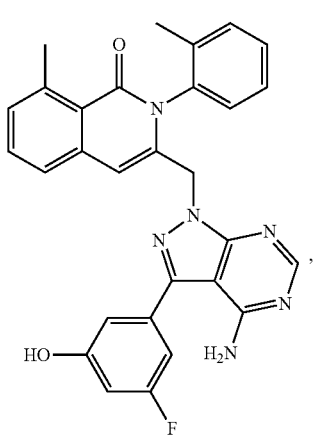
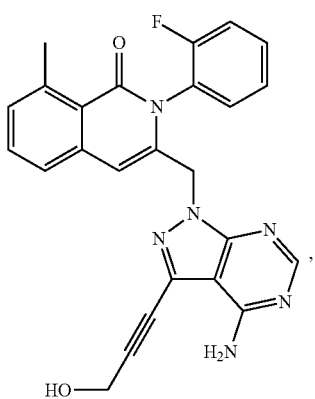
348
-continued
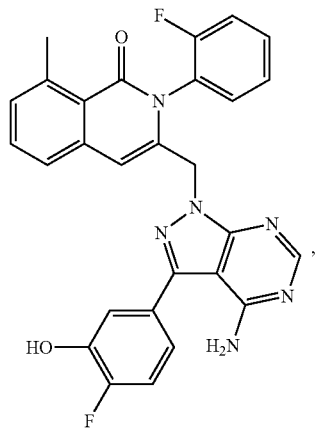
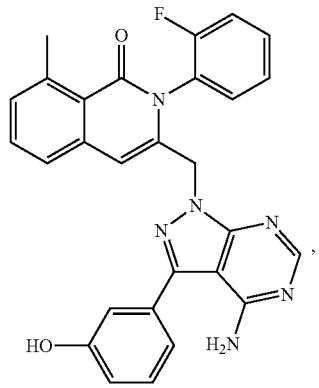
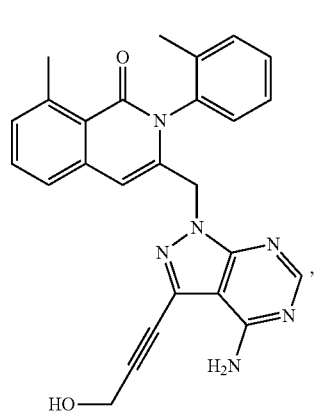
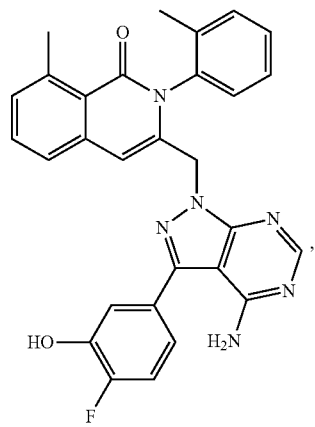

349
-continued
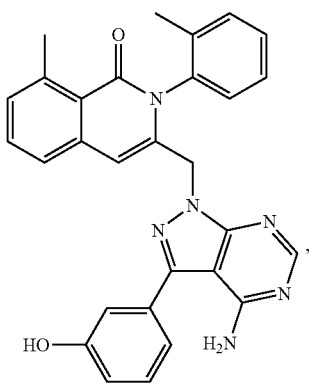
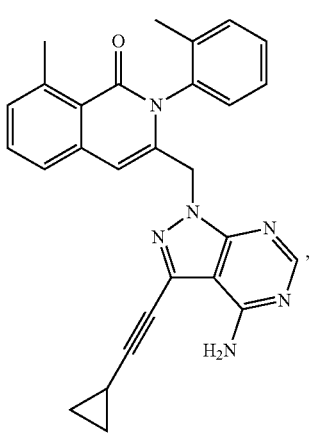
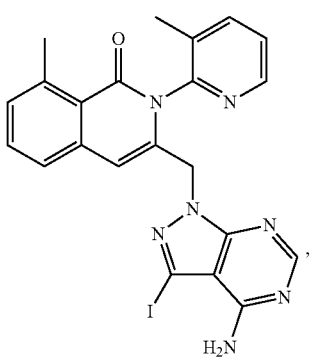
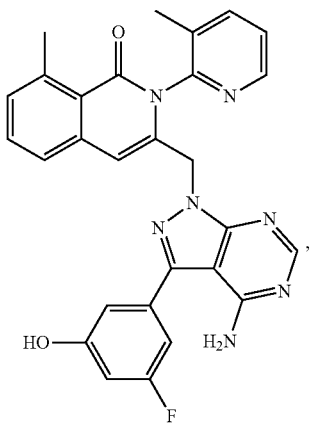
350
-continued
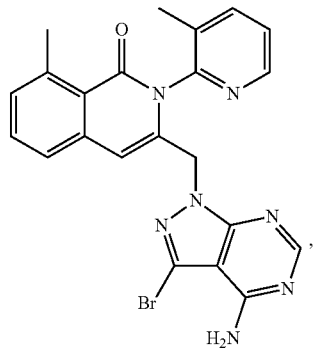
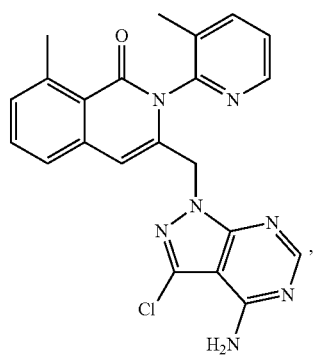
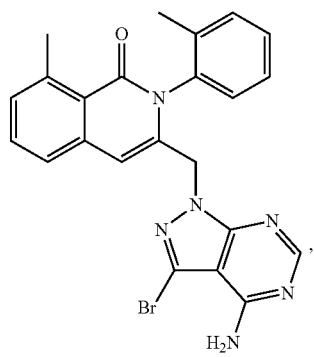
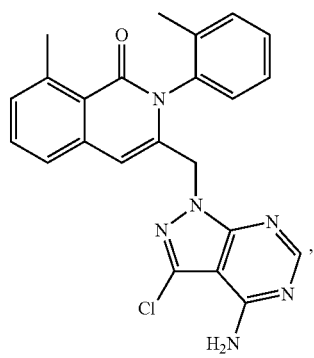

351
-continued
352
-continued
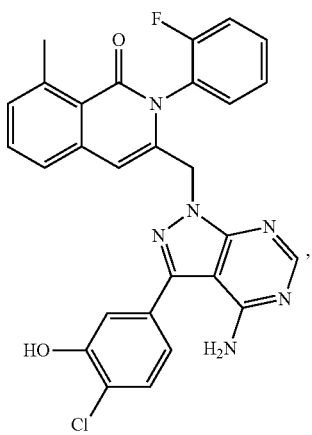
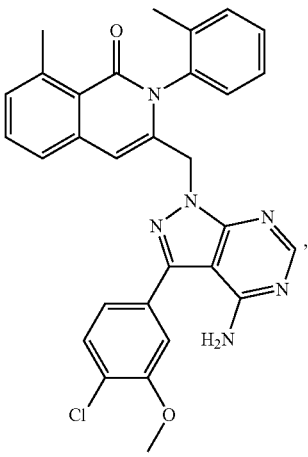
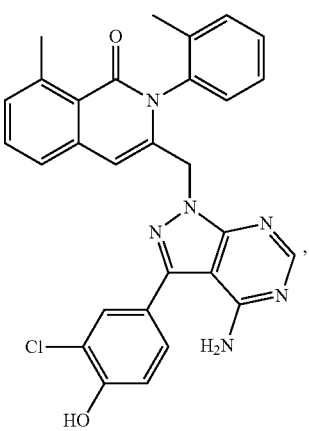
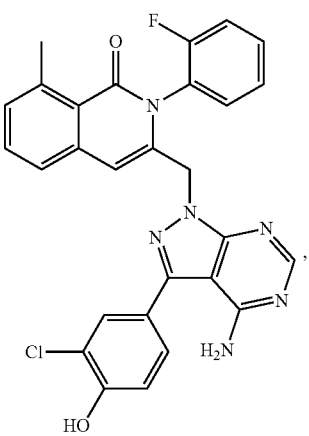
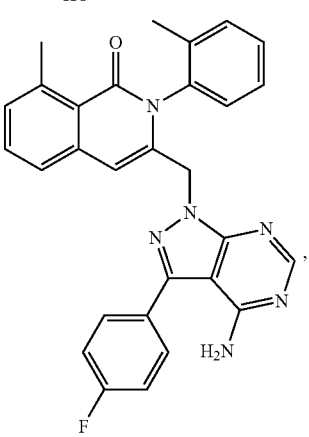

| 353 | 354 |
|---|---|
| -continued | -continued |
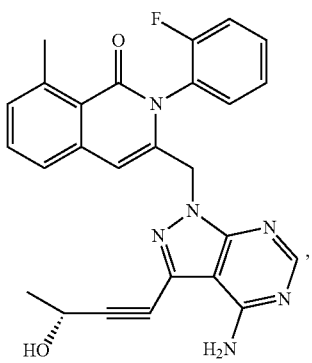
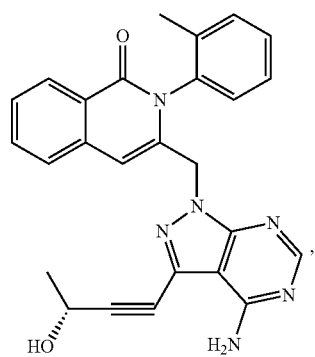

355
-continued
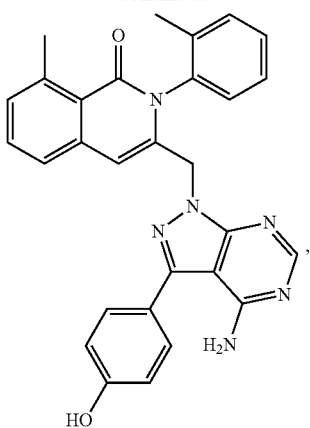
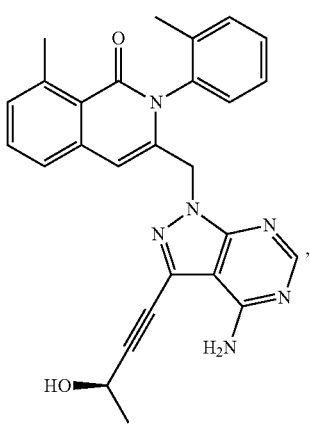
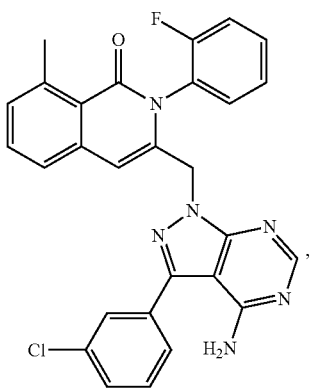
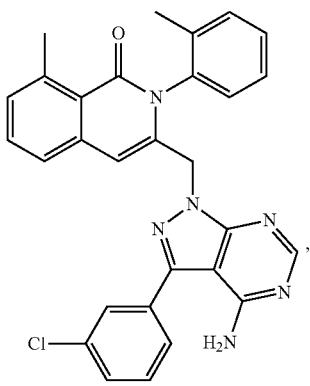
356
-continued
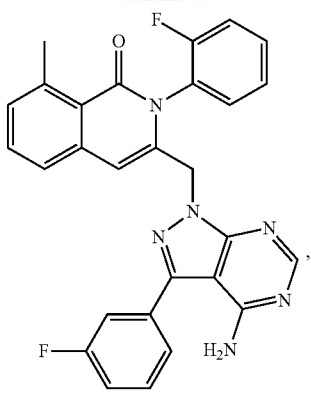
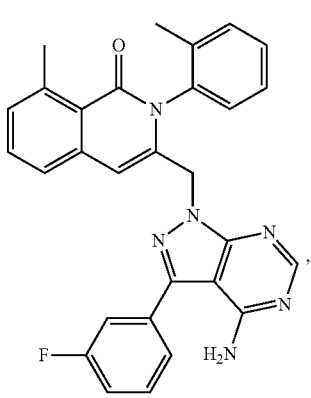
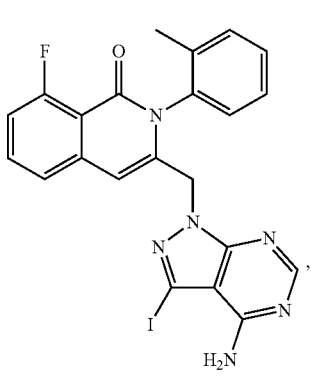
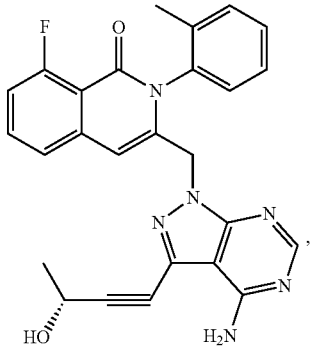

357
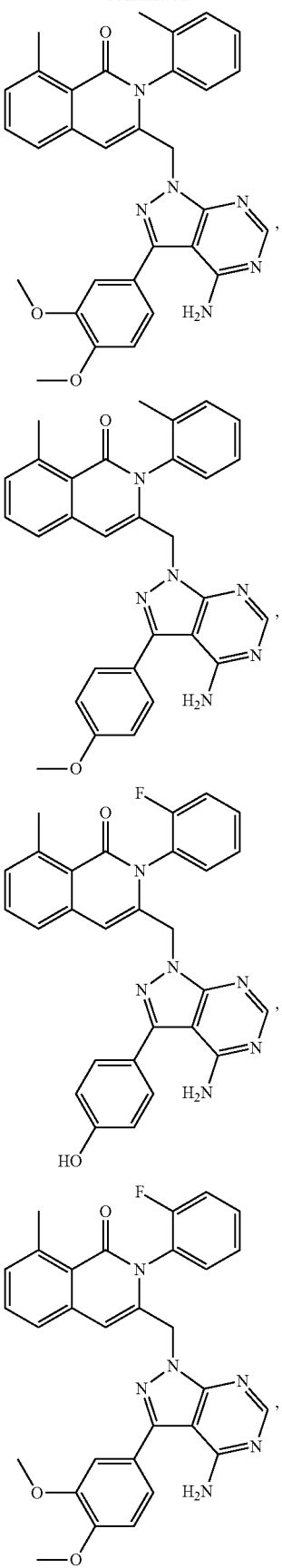
358
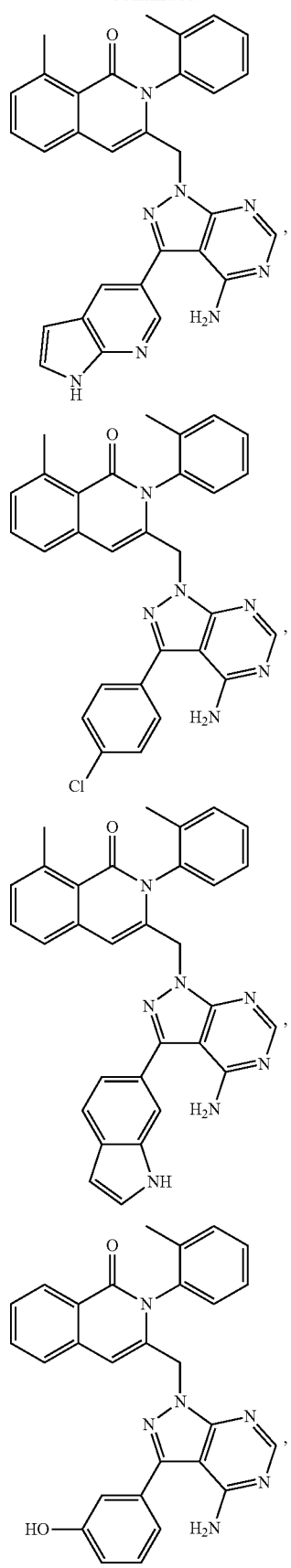

359
-continued
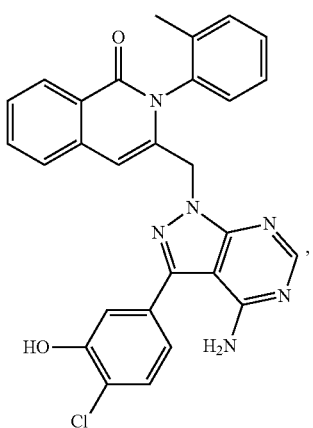
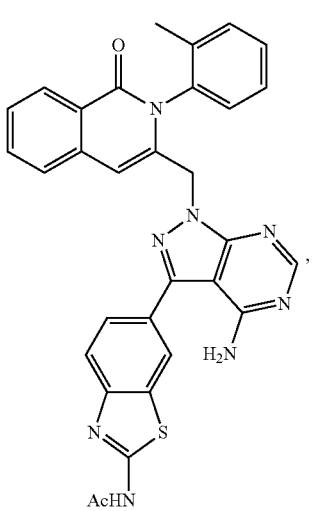
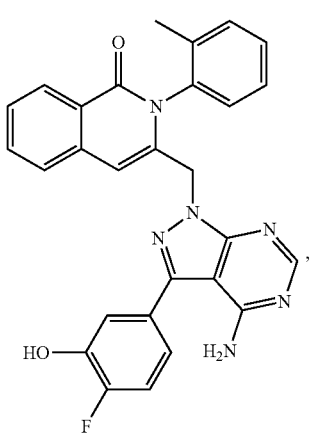
360
-continued
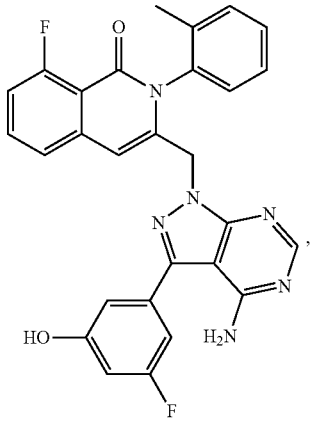
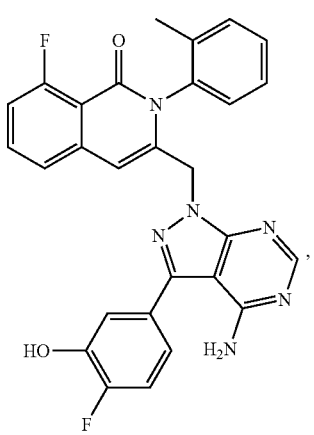
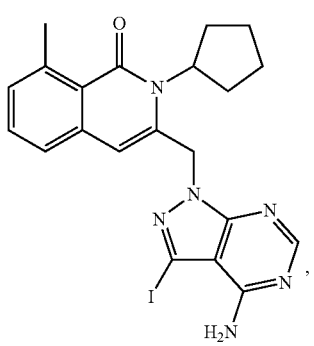
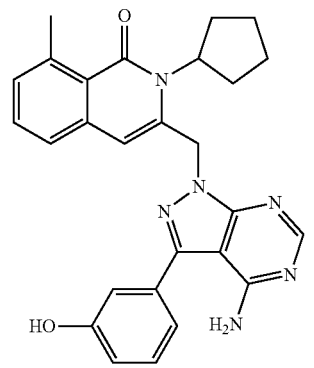

361
-continued
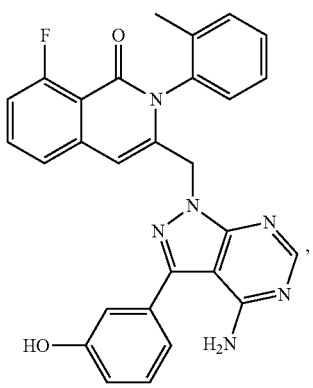,
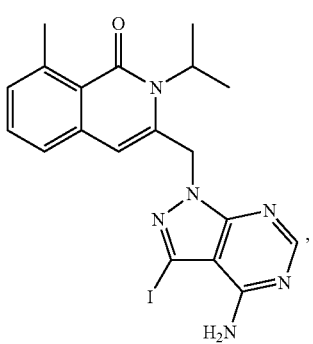,
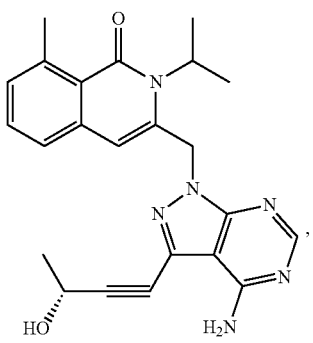,
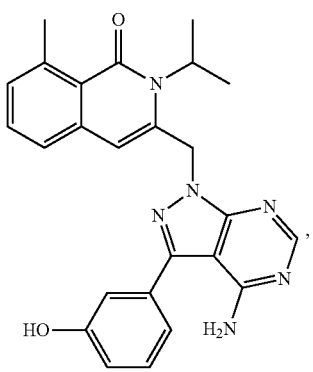,
362
-continued
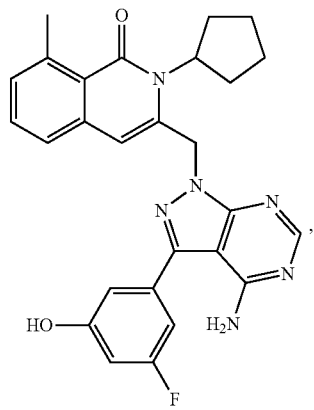,
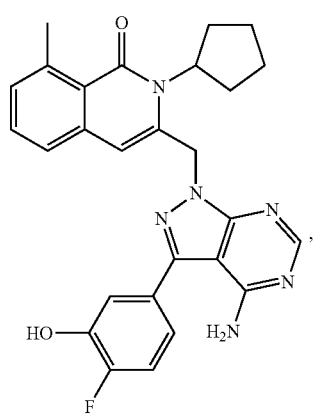,
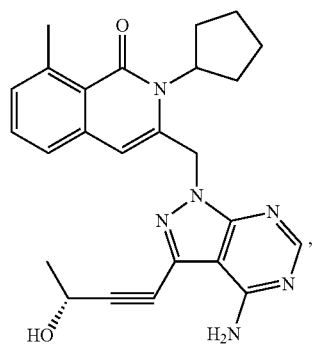,
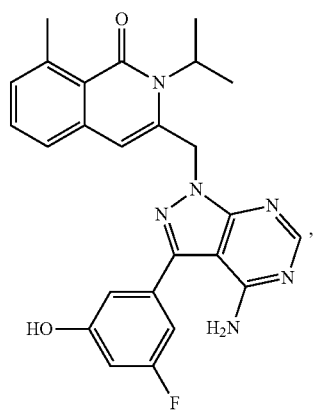, 363
-continued
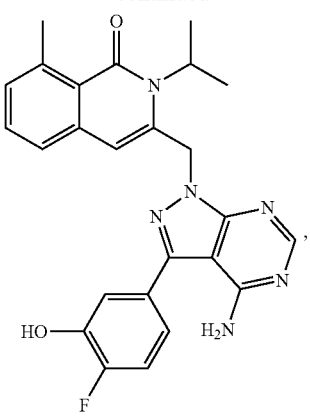
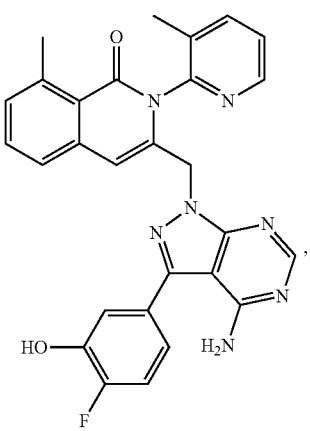
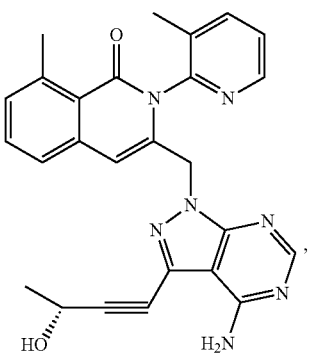
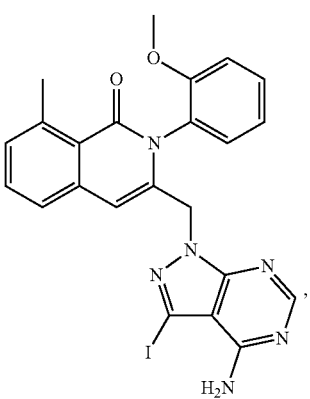
364
-continued
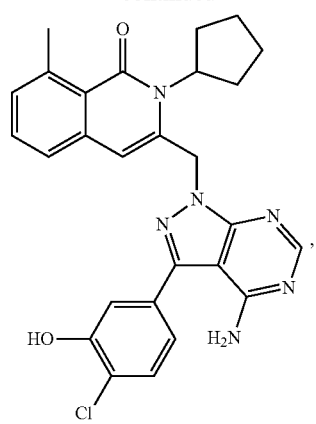
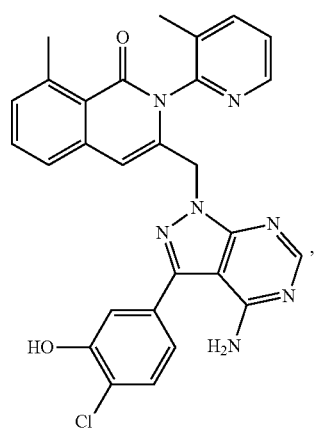
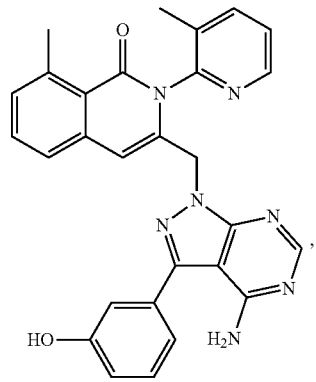
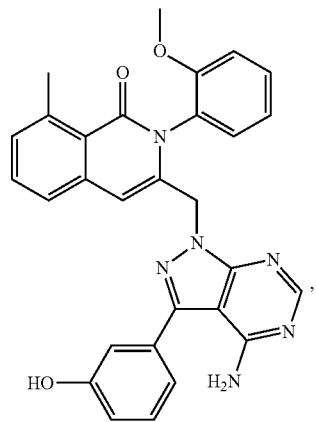

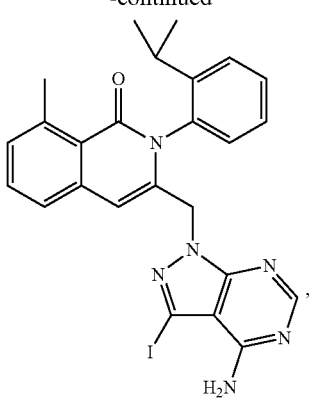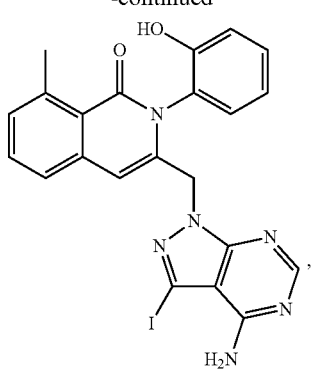

367
-continued
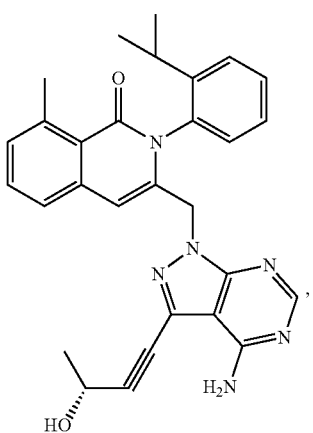
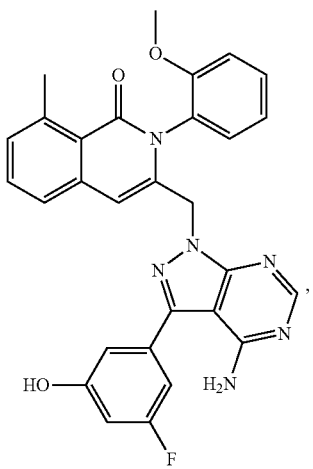
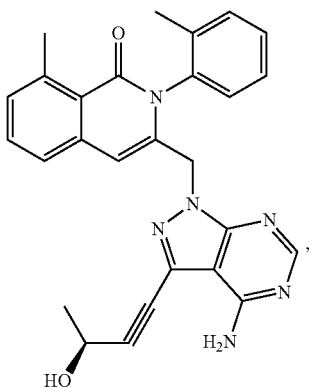
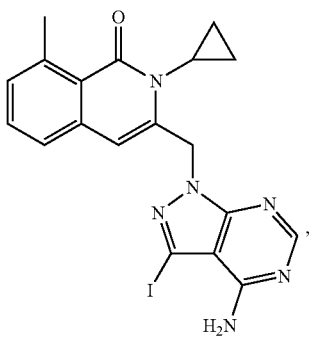
368
-continued
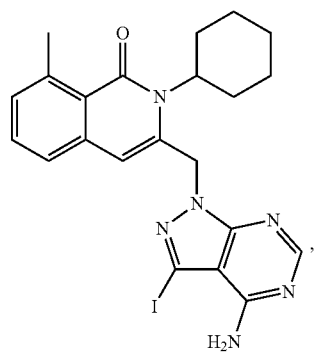
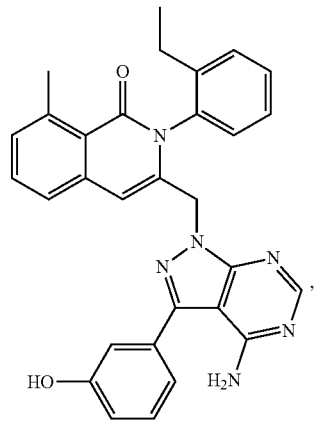
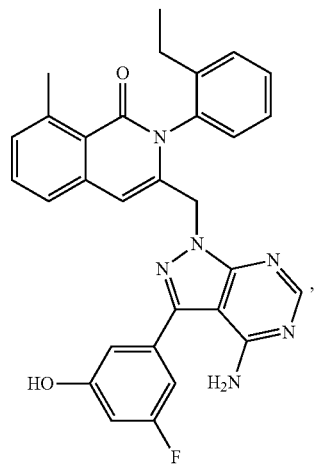
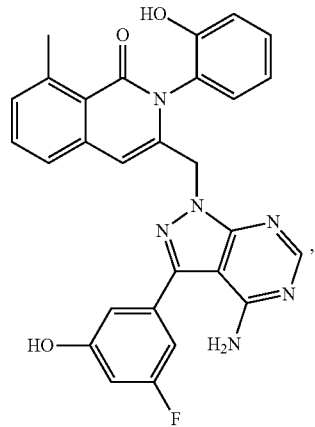

369
-continued
370
-continued
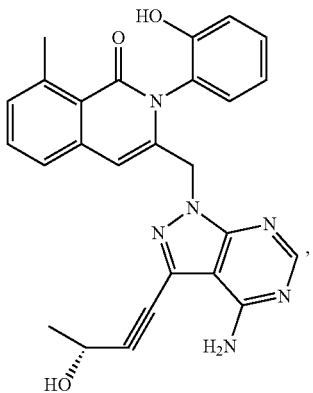
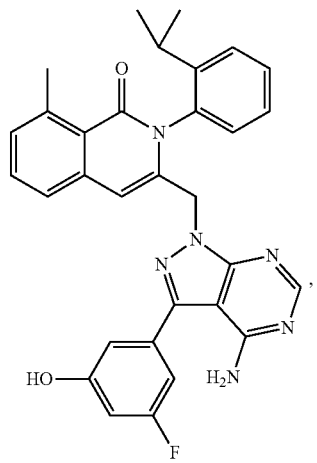

371
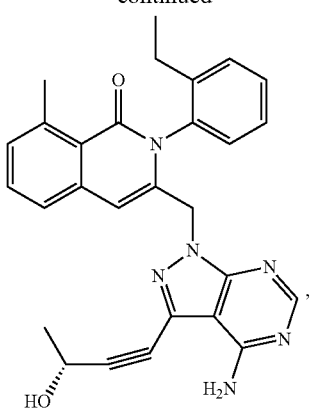
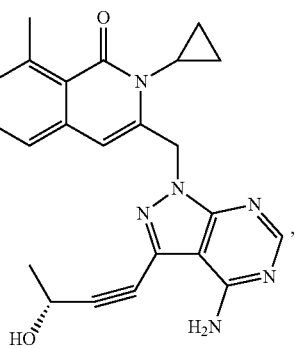
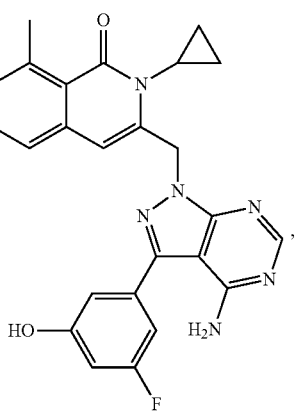
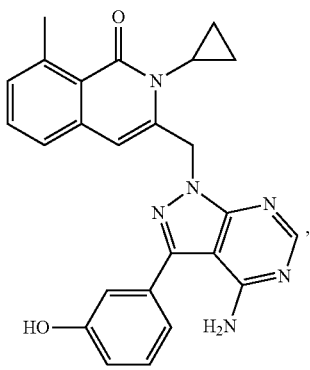
372
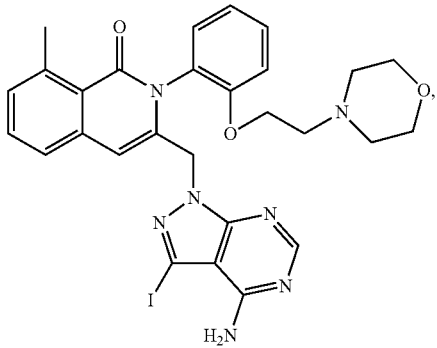
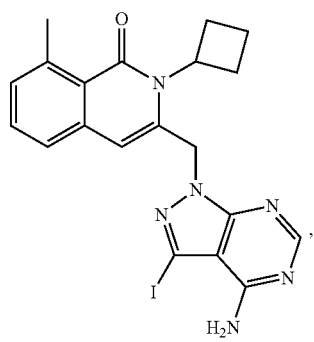
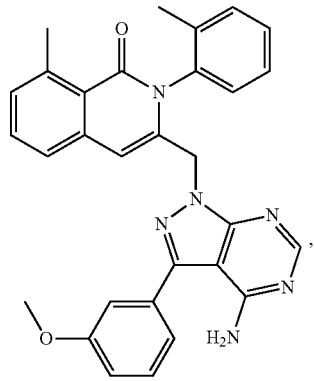
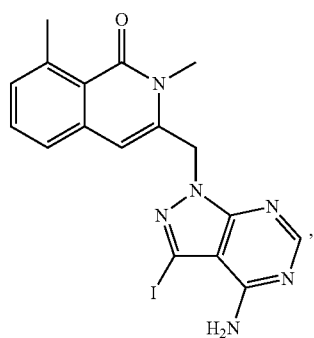

373
-continued
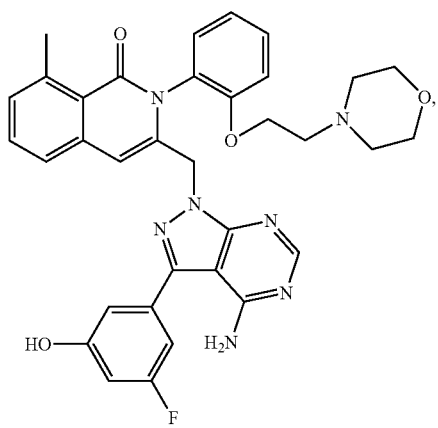
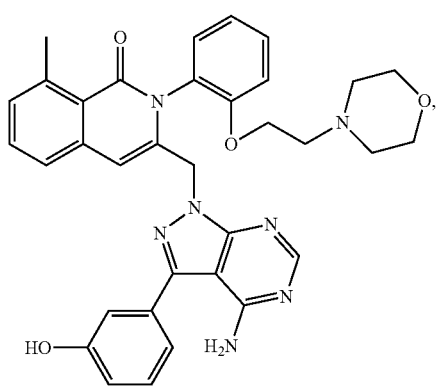
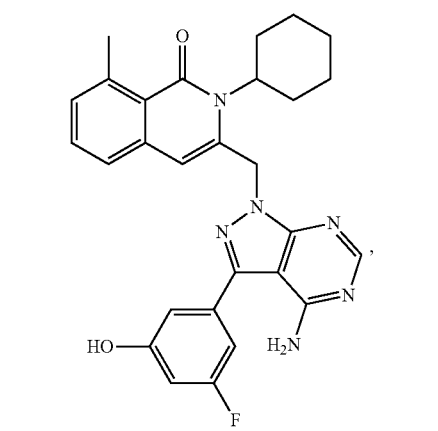
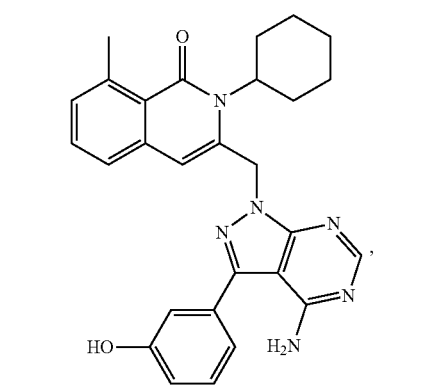
374
-continued
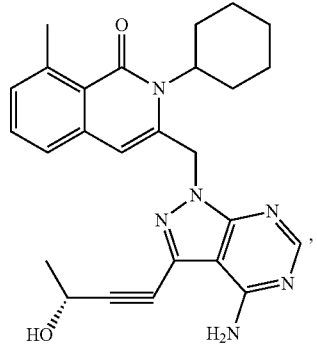
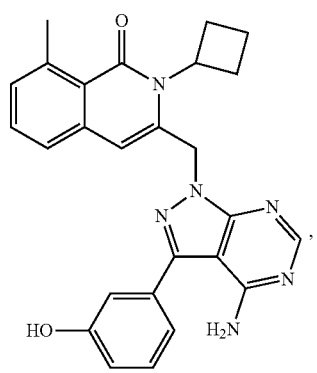
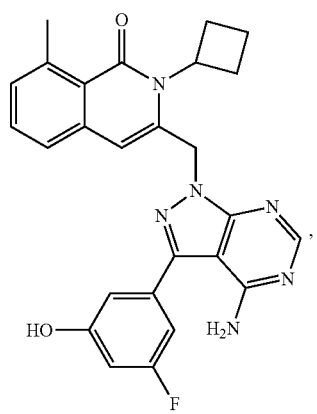
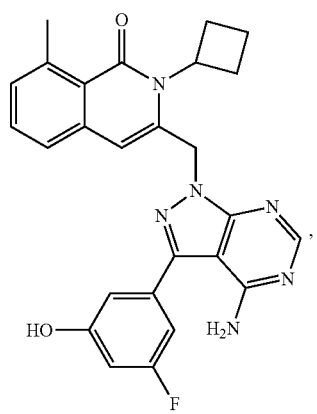

375
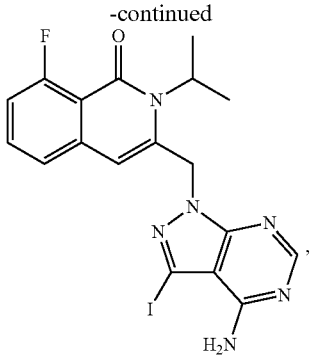
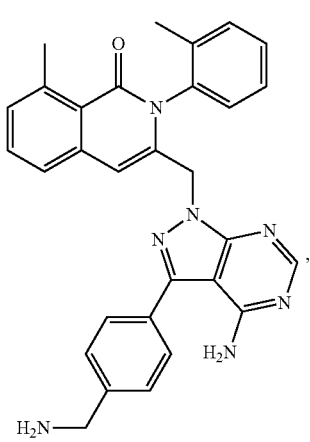
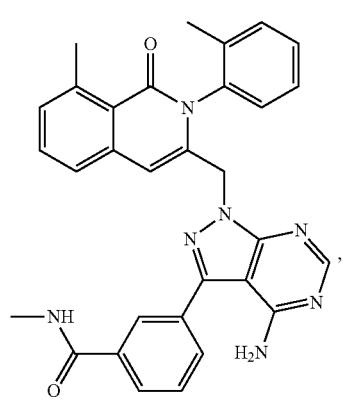
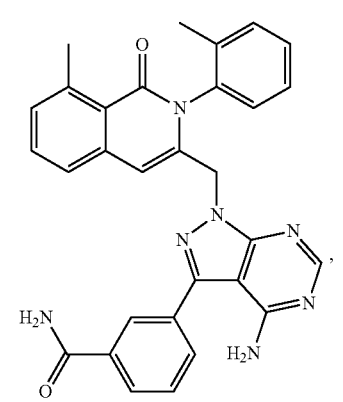
376
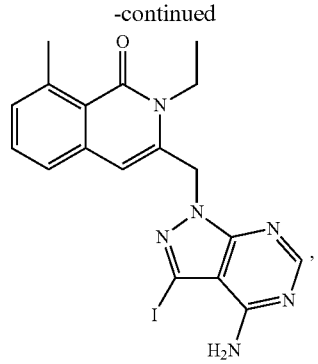
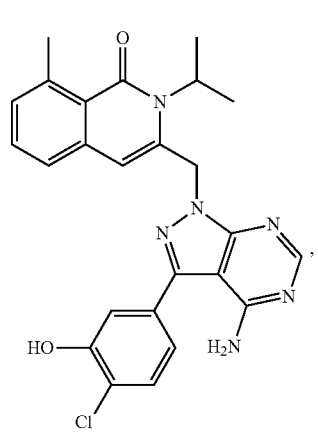
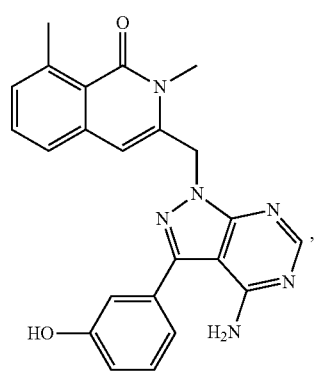
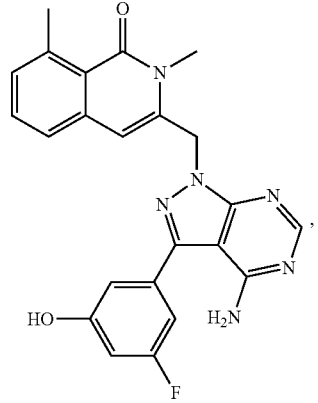

377
-continued
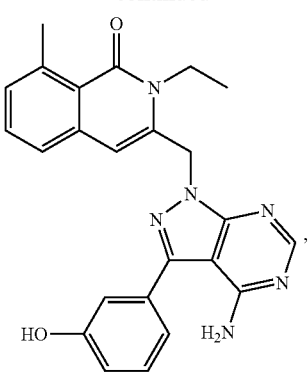
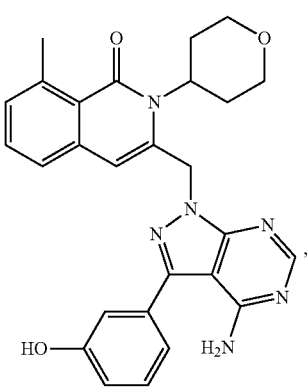
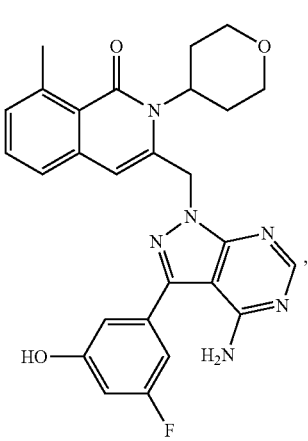
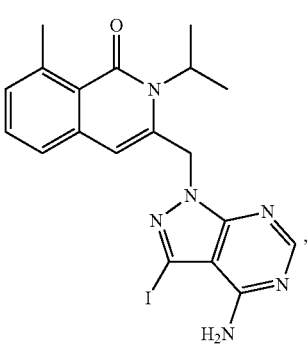
378
-continued
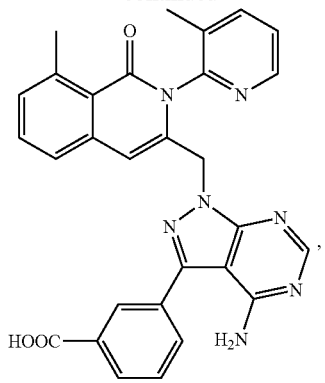
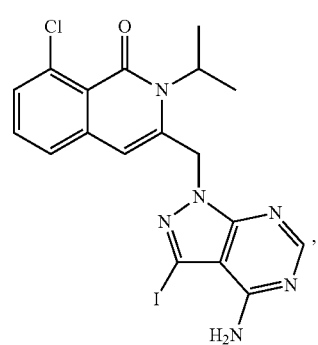
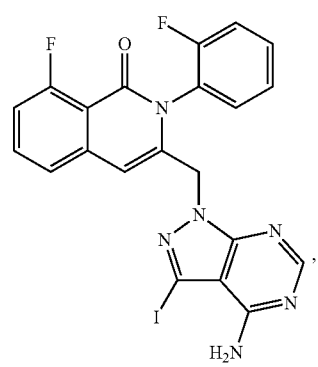
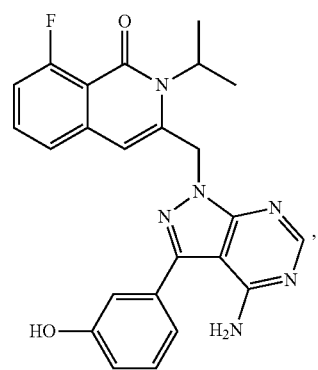

379                                    380
-continued                             -continued
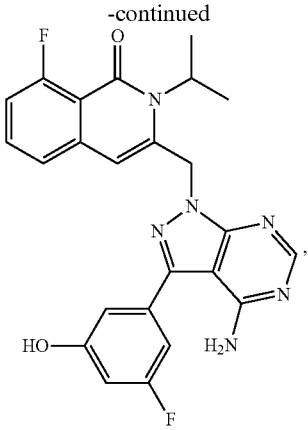      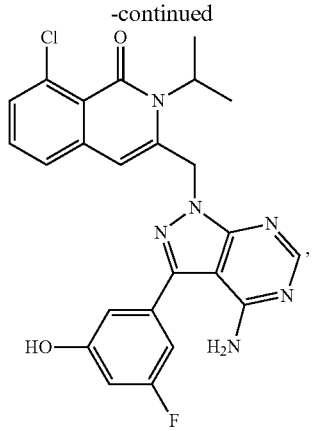
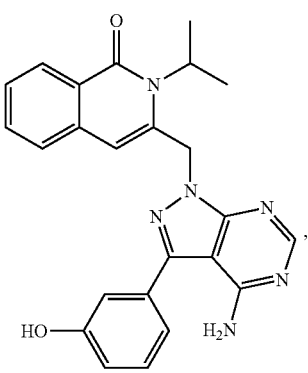      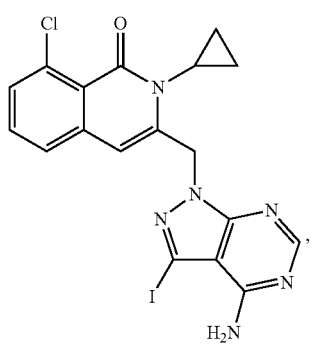
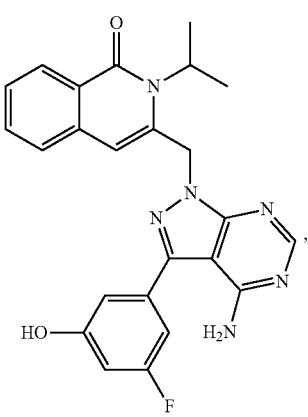      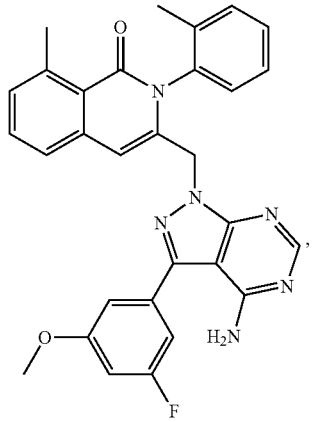
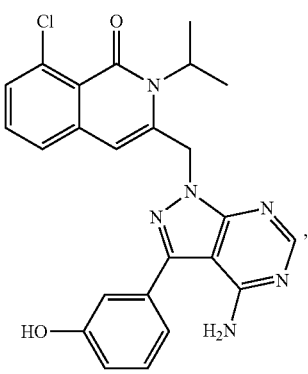      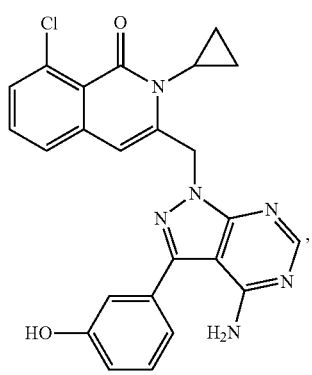

381
-continued
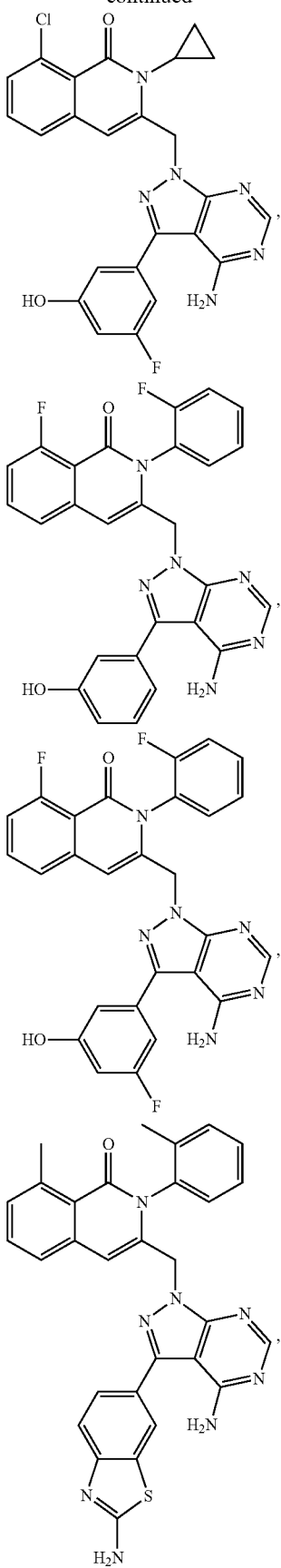
382
-continued
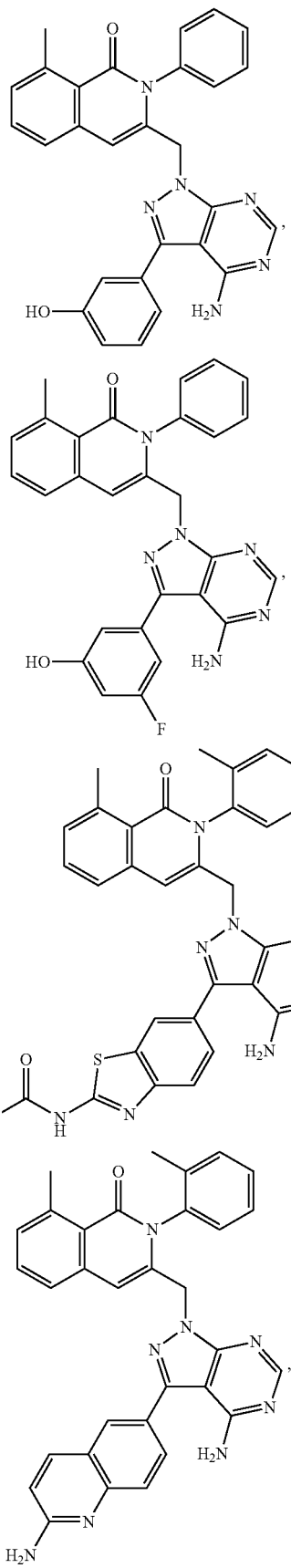

383
-continued
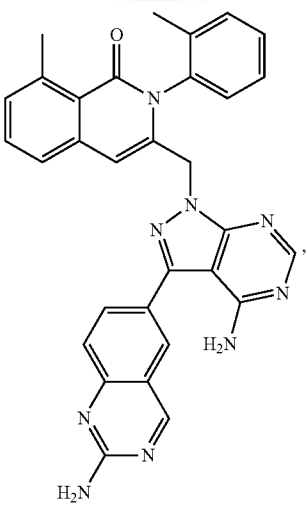
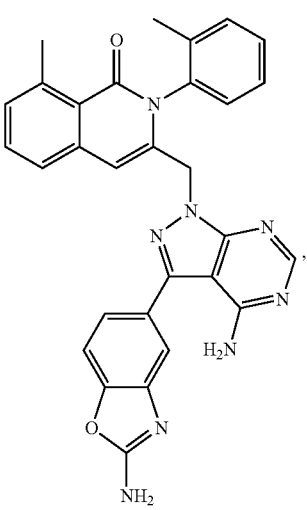
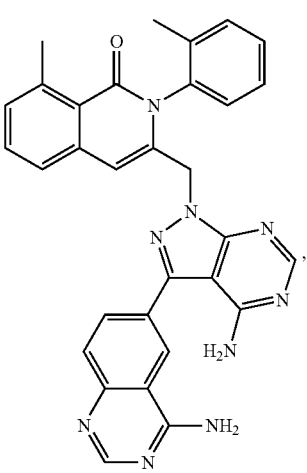
384
-continued
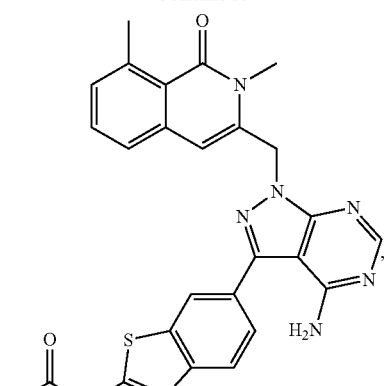
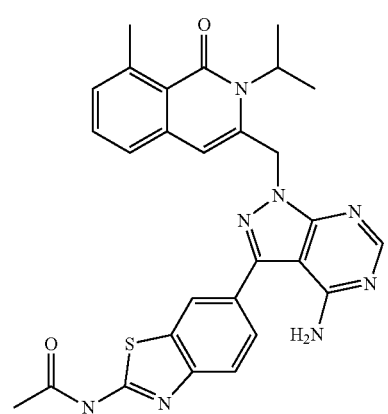
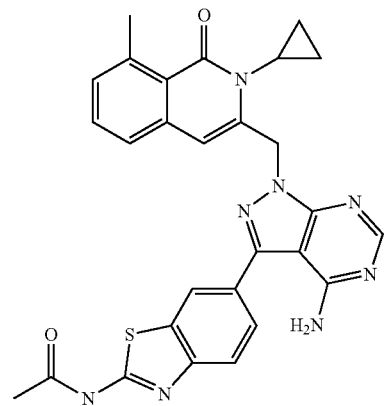
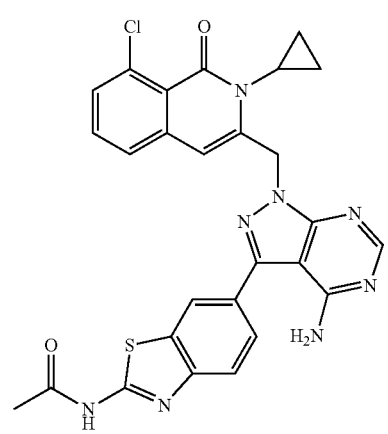

385
-continued
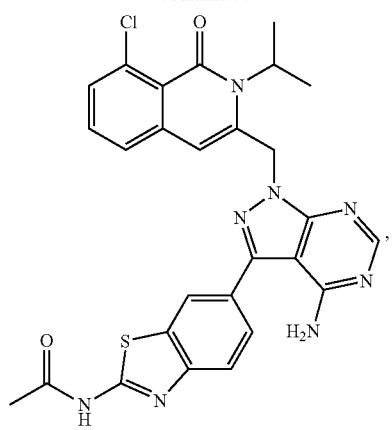
386
-continued
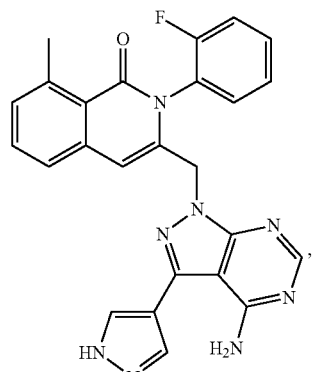
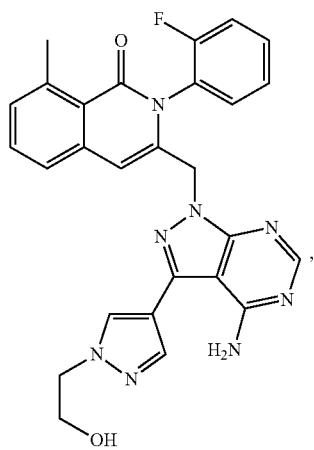
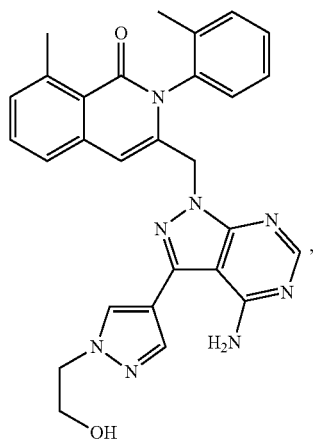
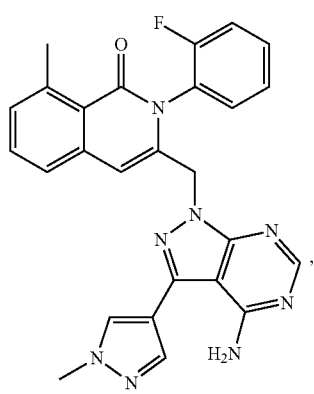

387
-continued
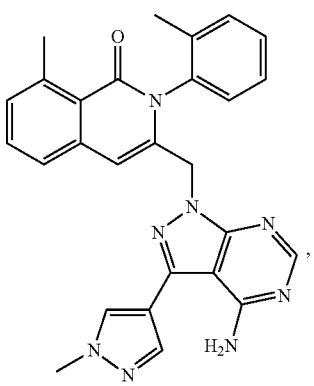
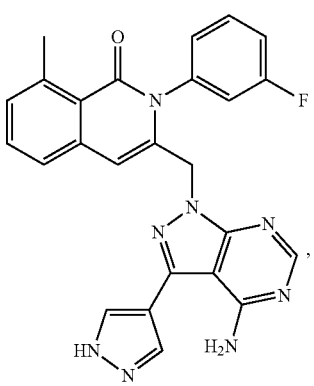
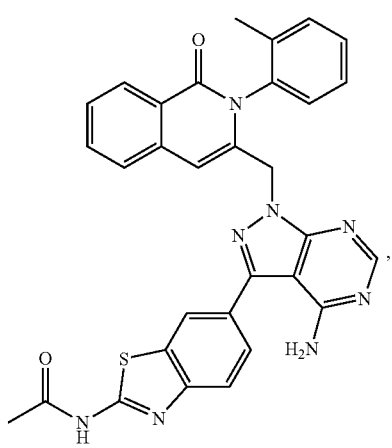
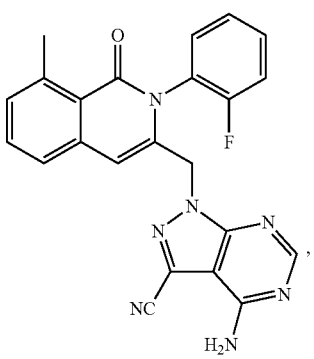
388
-continued
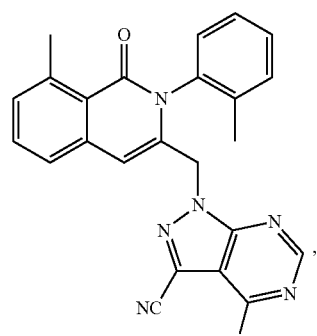
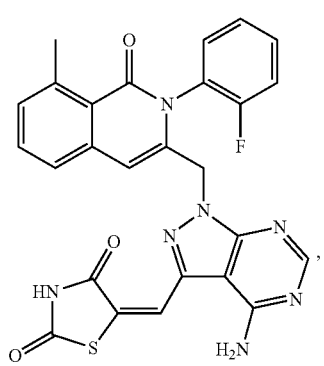
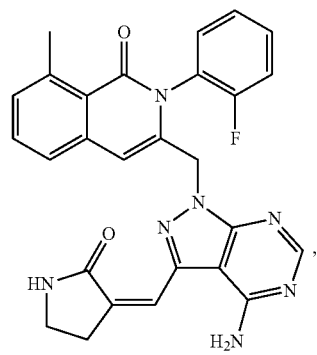
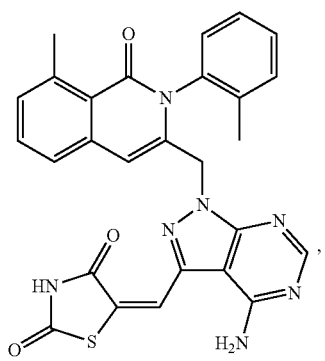

389
-continued
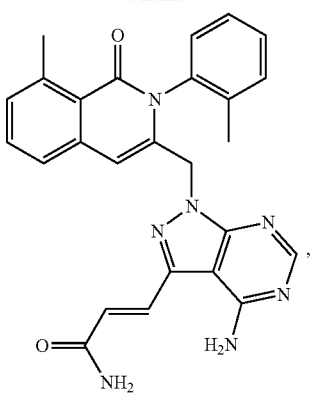
390
-continued
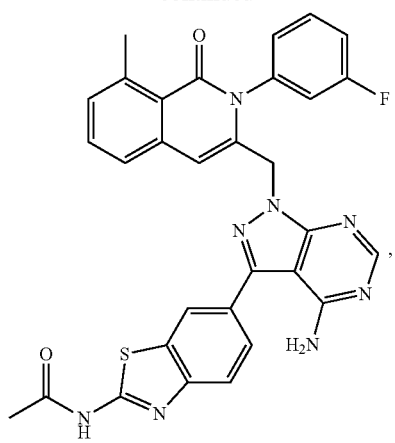
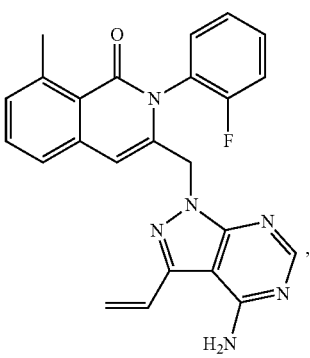
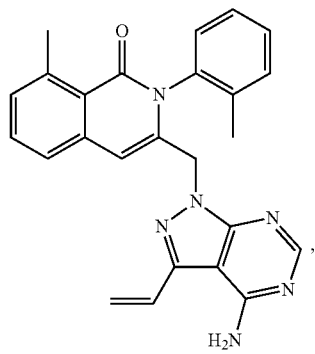
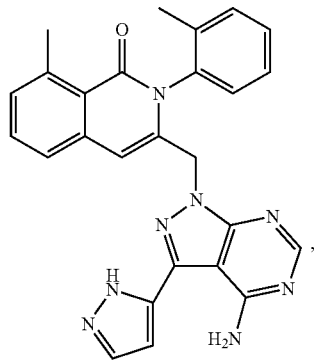

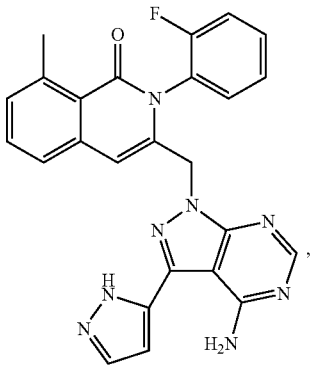
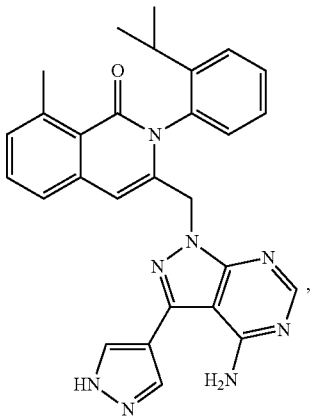
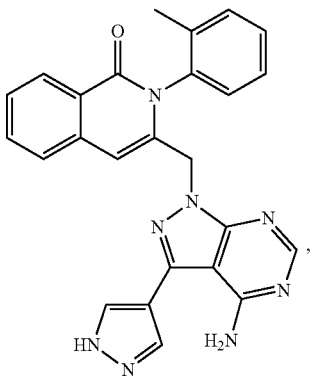
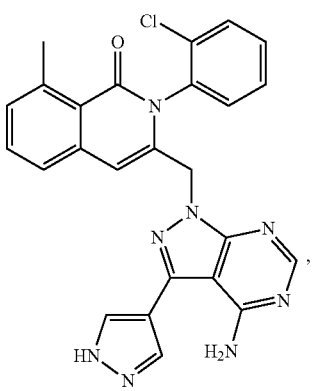
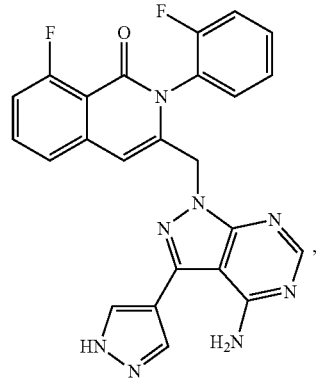
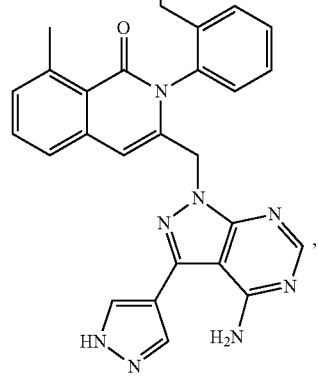
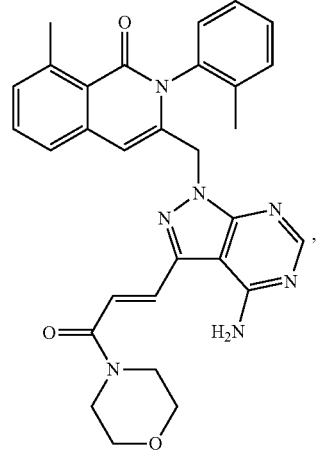
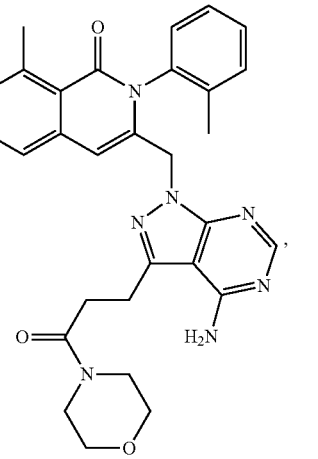
or -continued
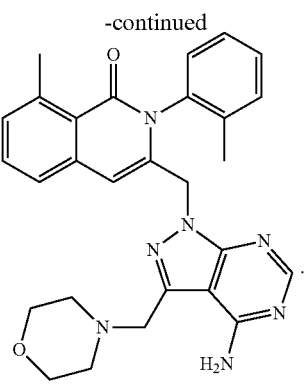
34. The compound of claim 28, or a pharmaceutically acceptable salt thereof, wherein the compound is:
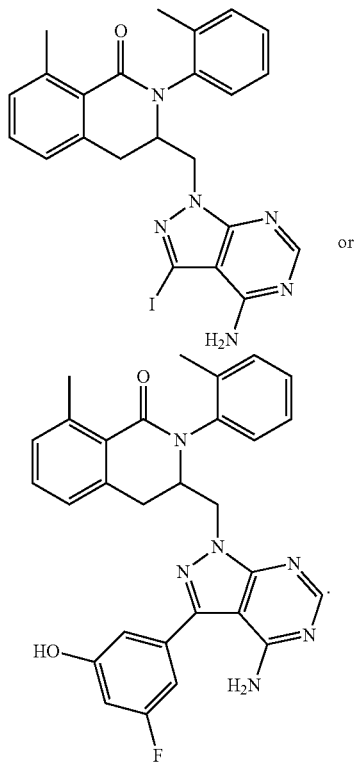
or
35. A compound or a pharmaceutically acceptable salt thereof, wherein the compound is:
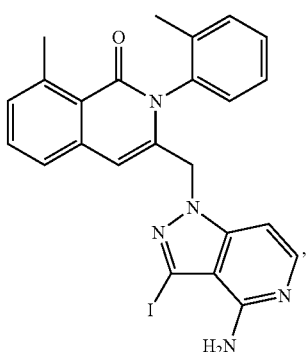
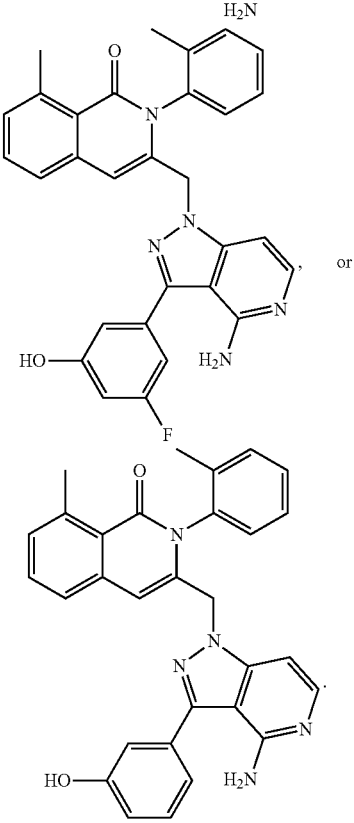
or
* * * * *

UNITED STATES PATENT AND TRADEMARK OFFICE
CERTIFICATE OF CORRECTION

PATENT NO. : 8,703,777 B2  
APPLICATION NO. : 12/811695  
DATED : April 22, 2014  
INVENTOR(S) : Ren et al.

Page 1 of 2

It is certified that error appears in the above-identified patent and that said Letters Patent is hereby corrected as shown below:

In the Claims

In column 344, Line 33-36 (part of claim 25), add the term "or" before the last structure in claim 25, to read:

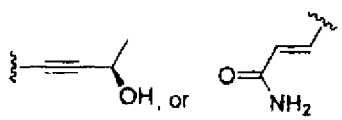

In column 346, Line 18-32 (part of claim 32), replace the structure of the first compound with:

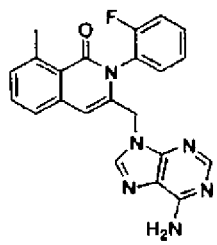

In column 360, Line 67 (part of claim 33), add a "," after the structure of the last compound.

In column 377, Line 54-67 (part of claim 33), replace the structure of the last compound with:

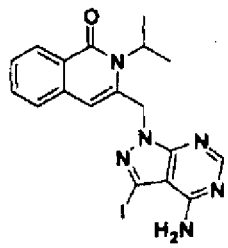

In column 378, Line 2-15 (part of claim 33), replace the structure of the first compound with:

Signed and Sealed this  
Twenty-fourth Day of February, 2015

Michelle K. Lee  
*Deputy Director of the United States Patent and Trademark Office*

CERTIFICATE OF CORRECTION (continued)
U.S. Pat. No. 8,703,777 B2